US008362068B2

(12) United States Patent
Dousson et al.

(10) Patent No.: US 8,362,068 B2
(45) Date of Patent: Jan. 29, 2013

(54) 5,5-FUSED ARYLENE OR HETEROARYLENE HEPATITIS C VIRUS INHIBITORS

(75) Inventors: Cyril B. Dousson, Canet (FR); David Dukhan, Saint Gely du Fesc (FR); Christophe Claude Parsy, Jacou (FR); Claire Pierra, Montarnaud (FR); Francois-Rene Alexandre, Montpellier (FR); Guillaume Brandt, Montpellier (FR); Daniel Da Costa, Saint Jean de Vedas (FR); Houcine Rahali, Saint Laurent des Arbres (FR); Jean-Laurent Paparin, Vendemian (FR); Michel Derock, Grabels (FR); Thierry Convard, Sathonay-Camp (FR); Dominique Surleraux, Wauthier-Braine (BE)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/972,254

(22) Filed: Dec. 17, 2010

(65) Prior Publication Data
US 2011/0150827 A1 Jun. 23, 2011

Related U.S. Application Data

(60) Provisional application No. 61/288,207, filed on Dec. 18, 2009, provisional application No. 61/371,634, filed on Aug. 6, 2010.

(51) Int. Cl.
| A61K 31/4184 | (2006.01) |
| A61K 31/4178 | (2006.01) |
| A61K 31/4025 | (2006.01) |
| A61K 31/381 | (2006.01) |
| C07D 235/04 | (2006.01) |
| C07D 409/14 | (2006.01) |
| C07D 495/04 | (2006.01) |

(52) U.S. Cl. ........ 514/443; 514/394; 514/397; 514/422; 548/304.7; 548/311.7; 548/526; 549/50
(58) Field of Classification Search ............... 514/394, 514/397, 422, 443; 548/304.7, 311.7, 526; 549/50
See application file for complete search history.

(56) References Cited

U.S. PATENT DOCUMENTS

| 4,368,190 A | 1/1983 | Shen et al. |
| 5,270,302 A | 12/1993 | Shiosaki et al. |
| 5,296,468 A | 3/1994 | Hoeger et al. |
| 5,382,569 A | 1/1995 | Cody et al. |
| 5,430,151 A | 7/1995 | Haebich et al. |
| 5,605,809 A | 2/1997 | Komoriya et al. |
| 5,618,792 A | 4/1997 | Gyorkos et al. |
| 5,652,219 A | 7/1997 | Bhatnagar |
| 5,714,342 A | 2/1998 | Komoriya et al. |
| 5,804,578 A | 9/1998 | Chakravarty et al. |
| 5,977,359 A | 11/1999 | Emonds-Alt et al. |
| 5,998,375 A | 12/1999 | Thogersen et al. |

(Continued)

FOREIGN PATENT DOCUMENTS

CA 2101316 9/1992

(Continued)

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*

(Continued)

Primary Examiner — Joseph Kosack
(74) Attorney, Agent, or Firm — Jones Day

(57) ABSTRACT

Provided herein are 5,5-fused heteroarylene hepatitis C virus inhibitor compounds, for example, of Formula I, IA, or IB, pharmaceutical compositions comprising the compounds, and processes of preparation thereof. Also provided are methods of their use for the treatment of an HCV infection in a host in need thereof.

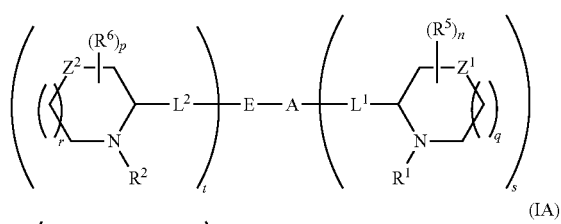

(I)

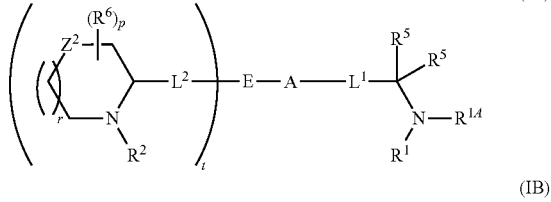

(IA)

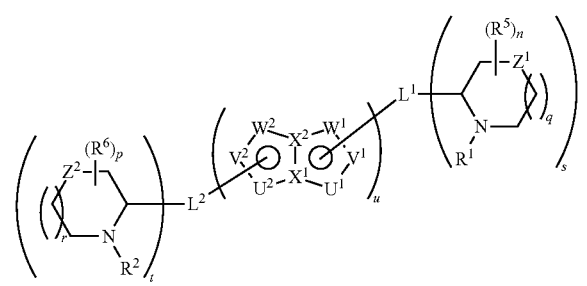

(IB)

53 Claims, No Drawings

U.S. PATENT DOCUMENTS

| | | | |
|---|---|---|---|
| 6,143,721 | A | 11/2000 | Janssen et al. |
| 6,214,799 | B1 | 4/2001 | Webber et al. |
| 6,525,024 | B1 | 2/2003 | Ternansky et al. |
| 6,596,687 | B1 | 7/2003 | Lin et al. |
| 6,737,420 | B2 | 5/2004 | Hom et al. |
| 6,906,037 | B2 | 6/2005 | Little et al. |
| 6,936,687 | B1 | 8/2005 | Komoriya et al. |
| 7,271,192 | B2 | 9/2007 | Sundermann et al. |
| 7,402,564 | B1 | 7/2008 | Schteingart et al. |
| 7,582,608 | B2 | 9/2009 | Bokvist et al. |
| 7,659,270 | B2 | 2/2010 | Bachand et al. |
| 7,759,495 | B2 | 7/2010 | Bachand et al. |
| 8,030,318 | B2 * | 10/2011 | Simmen et al. .......... 514/264.11 |
| 2003/0055037 | A1 | 3/2003 | DeLombaert et al. |
| 2005/0256056 | A1 | 11/2005 | North et al. |
| 2006/0240489 | A1 | 10/2006 | Wei et al. |
| 2007/0032417 | A1 | 2/2007 | Baell et al. |
| 2007/0042952 | A1 | 2/2007 | Dong |
| 2007/0167426 | A1 | 7/2007 | Siddiqui et al. |
| 2007/0197430 | A1 | 8/2007 | Baell et al. |
| 2008/0021066 | A1 | 1/2008 | Condon et al. |
| 2008/0044380 | A1 | 2/2008 | Bachand et al. |
| 2008/0050336 | A1 | 2/2008 | Bachand et al. |
| 2008/0070928 | A1 | 3/2008 | Nonoshita et al. |
| 2008/0085860 | A1 | 4/2008 | Bokvist et al. |
| 2008/0146500 | A1 | 6/2008 | Bokvist et al. |
| 2008/0194482 | A1 | 8/2008 | Zhang |
| 2008/0286758 | A1 | 11/2008 | Li et al. |
| 2008/0299075 | A1 | 12/2008 | Bachand et al. |
| 2008/0311075 | A1 | 12/2008 | Bachand et al. |
| 2008/0318845 | A1 | 12/2008 | Bokvist et al. |
| 2009/0041716 | A1 | 2/2009 | Kim et al. |
| 2009/0068140 | A1 | 3/2009 | Bachand et al. |
| 2009/0075907 | A1 | 3/2009 | Schteingart et al. |
| 2009/0118167 | A1 | 5/2009 | Bokvist et al. |
| 2009/0176822 | A1 | 7/2009 | Cohen et al. |
| 2009/0202478 | A1 | 8/2009 | Bachand et al. |
| 2009/0202483 | A1 | 8/2009 | Bachand et al. |
| 2009/0221630 | A1 | 9/2009 | Koehler et al. |
| 2009/0227521 | A1 | 9/2009 | Glas et al. |
| 2009/0233925 | A1 | 9/2009 | Bachand et al. |
| 2010/0068176 | A1 | 3/2010 | Belema et al. |
| 2010/0080772 | A1 | 4/2010 | Belema et al. |
| 2010/0158862 | A1 | 6/2010 | Kim et al. |
| 2010/0215616 | A1 | 8/2010 | Romine et al. |
| 2010/0215618 | A1 | 8/2010 | Carter et al. |
| 2010/0221216 | A1 | 9/2010 | Or et al. |
| 2010/0226882 | A1 | 9/2010 | Or et al. |
| 2010/0226883 | A1 | 9/2010 | Qiu et al. |
| 2010/0233122 | A1 | 9/2010 | Qiu et al. |
| 2010/0260715 | A1 | 10/2010 | Or et al. |
| 2010/0310512 | A1 | 12/2010 | Guo et al. |
| 2011/0172238 | A1 * | 7/2011 | Henderson et al. ....... 514/252.11 |

FOREIGN PATENT DOCUMENTS

| | | |
|---|---|---|
| JP | 2009-108152 | 5/2009 |
| WO | WO 93/00359 | 1/1993 |
| WO | WO 93/03058 | 2/1993 |
| WO | WO 93/04080 | 3/1993 |
| WO | WO 94/09031 | 4/1994 |
| WO | WO 94/22906 | 10/1994 |
| WO | WO 00/59867 | 10/2000 |
| WO | WO 03/033671 | 4/2003 |
| WO | WO 2005/016244 | 2/2005 |
| WO | WO 2005/032541 | 4/2005 |
| WO | WO 2006/133326 | 12/2006 |
| WO | WO 2007/056170 | 5/2007 |
| WO | WO 2007/070556 | 6/2007 |
| WO | WO 2007/070600 | 6/2007 |
| WO | WO 2007/080194 | 7/2007 |
| WO | WO 2008/017372 | 2/2008 |
| WO | WO 2008/021928 | 2/2008 |
| WO | WO 2008/045905 | 4/2008 |
| WO | WO 2008/077194 | 7/2008 |
| WO | WO 2008/079735 | 7/2008 |
| WO | WO 2008/134679 | 11/2008 |
| WO | WO 2008/144380 | 11/2008 |
| WO | WO 2009/000296 | 12/2008 |
| WO | WO 2009/000297 | 12/2008 |
| WO | WO 2009/020828 | 2/2009 |
| WO | WO 2009/094287 | 7/2009 |
| WO | WO 2009/102318 | 8/2009 |
| WO | WO 2009/102568 | 8/2009 |
| WO | WO 2009/102633 | 8/2009 |
| WO | WO 2009/102694 | 8/2009 |
| WO | WO 2009/143359 | 11/2009 |
| WO | WO 2009/143361 | 11/2009 |
| WO | WO 2010/017401 | 2/2010 |
| WO | WO 2010/065668 | 6/2010 |
| WO | WO 2010/065674 | 6/2010 |
| WO | WO 2010/065681 | 6/2010 |
| WO | WO 2010/091413 | 8/2010 |
| WO | WO 2010/096462 | 8/2010 |
| WO | WO 2010/096777 | 8/2010 |
| WO | WO 2010/099527 | 9/2010 |
| WO | WO 2010/132601 | 11/2010 |

OTHER PUBLICATIONS

Vippagunta et al. (Advanced Drug Delivery Reviews, 48 (2001), pp. 3-26.*

Boyer et al., "Pathogenesis, Diagnosis and Management of Hepatitis C," *J. Hepatol.* 2000, vol. 32(Suppl. 1), pp. 98-112.

Di Besceglie et al., "The Unmet Challenges of Hepatitis C," *Sci. Am.* 1999, vol. 281, pp. 80-85.

Fried et al., "Peginterferon alfa-2a Plus Ribavirin for Chronic Hepatitis C Virus Infection," *N. Engl. J. Med.* 2002, vol. 347, pp. 975-982.

Hadziyannis et al., "Peginterferon-α2a and Ribavirin Combination Therapy in Chronic Hepatitis C," *Ann. Intern. Med.* 2004, vol. 140, pp. 346-355.

Kato et al., "Molecular Cloning of the Human Hepatitis C Cirus Genome from Japanese Patients with Non-A, Non-B Hepatitis," *Proc. Natl. Acad. Sci. USA* 1990, vol. 87, pp. 9524-9528.

Kato, "Molecular Virology of Hepatitis C Virus," *Acta Medica Okayama* 2001, vol. 55, pp. 133-159.

Kuo et al., "An Assay for Circulating Antibodies to a Major Etiologic Virus of Human Non-A, Non-B Hepatitis," *Science* 1989, vol. 244, pp. 362-364.

Manns et al., "Peginterferon alfa-2b Plus Ribavirin Compared with Interferon alfa-2b Plus Ribavirin for Initial Treatment of Chronic Hepatitis C: a Randomised Trial," *Lancet* 2001, vol. 358, pp. 958-965.

Ndubaku et al., "Antagonism of c-IAP and XIAP Proteins is Required for Efficient Induction of Cell Death by Small-Molecule IAP Antagonists," *ACS Chem. Biol.* 2009, vol. 4, pp. 557-566.

Poynard et al., "Randomised Trial of Interferon α2b Plus Ribavirin for 48 Weeks or for 24 Weeks Versus Interferon α2b Plus Placebo for 48 Weeks for Treatment of Chronic Infection with Hepatitis C Virus," *Lancet* 1998, vol. 352, pp. 1426-1432.

Thomas, "Hepatitis C Epidemiology," *Curr. Top. Microbiol. Immunol.* 2000, vol. 242, pp. 25-41.

* cited by examiner

5,5-FUSED ARYLENE OR HETEROARYLENE HEPATITIS C VIRUS INHIBITORS

CROSS REFERENCE TO RELATED APPLICATIONS

This application claims priority under 35 U.S.C. §119(e) to U.S. Provisional Application Nos. 61/288,207, filed Dec. 18, 2009; and 61/371,634, filed Aug. 6, 2010; the disclosure of each of which is incorporated herein by reference in its entirety.

FIELD

Provided herein are 5,5-fused heteroarylene hepatitis C virus inhibitor compounds, pharmaceutical compositions comprising the compounds, and processes of preparation thereof. Also provided are methods of their use for the treatment of an HCV infection in a host in need thereof.

BACKGROUND

Hepatitis C virus (HCV) is known to cause at least 80% of posttransfusion hepatitis and a substantial proportion of sporadic acute hepatitis (Kuo et al., *Science* 1989, 244, 362-364; Thomas, *Curr. Top. Microbiol. Immunol.* 2000, 25-41). Preliminary evidence also implicates HCV in many cases of "idiopathic" chronic hepatitis, "cryptogenic" cirrhosis, and probably hepatocellular carcinoma unrelated to other hepatitis viruses, such as hepatitis B virus (Di Besceglie et al., *Scientific American,* 1999, October, 80-85; Boyer et al., *J. Hepatol.* 2000, 32, 98-112).

HCV is an enveloped virus containing a positive-sense single-stranded RNA genome of approximately 9.4 kb (Kato et al., *Proc. Natl. Acad. Sci. USA* 1990, 87, 9524-9528; Kato, *Acta Medica Okayama,* 2001, 55, 133-159). The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as an internal ribosome entry. This mechanism involves the binding of ribosomes to an RNA sequence known as the internal ribosome entry site (IRES). An RNA pseudoknot structure has recently been determined to be an essential structural element of the HCV IRES. Viral structural proteins include a nucleocapsid core protein (C) and two envelope glycoproteins, E1 and E2. HCV also encodes two proteinases, a zinc-dependent metalloproteinase encoded by the NS2-NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

Presently, the most effective HCV therapy employs a combination of alpha-interferon and ribavirin, leading to sustained efficacy in about 40% of patients (Poynard et al., *Lancet* 1998, 352, 1426-1432). Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load (Manns et al., *Lancet* 2001, 358, 958-965; Fried et al., *N. Engl. J. Med.* 2002, 347, 975-982; Hadziyannis et al., *Ann. Intern. Med.* 2004, 140, 346-355). Thus, there is a clear and unmet need to develop effective therapeutics for treatment of HCV infection.

SUMMARY OF THE DISCLOSURE

Provided herein is a compound of Formula I:

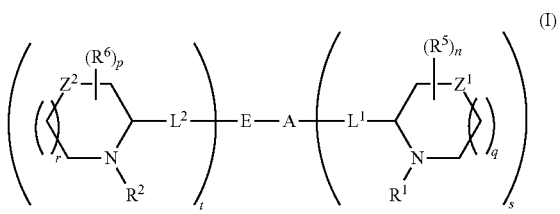

or a single enantiomer, a racemic mixture, a mixture of diastereomers, or an isotopic variant thereof; or a pharmaceutically acceptable salt, solvate, or prodrug thereof;

wherein:

s, t, A, and E are (i), (ii), or (iii):

(i) s is 1 or 2; t is 1; A is 5,5-fused heteroarylene; and E is $C_{2-6}$ alkynylene, $C_{3-7}$ cycloalkylene, $C_{6-14}$ arylene, $C_{2-6}$ alkynylene-$C_{6-14}$ arylene, or heteroarylene; with the proviso that E is not 5,6- or 6,6-fused arylene, $C_{2-6}$ alkynylene-5,6- or 6,6-fused arylene, or 5,6- or 6,6-fused heteroarylene;

(ii) s is 1 or 2; t is 0; A is 5,5-fused heteroarylene; and E is $C_{2-6}$ alkynylene-$R^{3a}$, $C_{3-7}$ cycloalkylene-$R^{3a}$, $C_{6-14}$ arylene-$R^{3a}$, or heteroarylene-$R^{3a}$, with the proviso that E is not 5,6- or 6,6-fused arylene-$R^{3a}$, or 5,6- or 6,6-fused heteroarylene-$R^{3a}$;

(iii) s is 0; t is 1; A is 5,5-fused heteroarylene-$R^{3a}$; E is $C_{2-6}$ alkynylene, $C_{3-7}$ cycloalkylene, $C_{6-14}$ arylene, or heteroarylene; with the proviso that E is not 5,6- or 6,6-fused arylene, or 5,6- or 6,6-fused heteroarylene;

each $R^1$ and $R^2$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, C(O)CH(N($R^{1c}$)C(O)N$R^{1b}R^{1d}$)$R^{1a}$, C(O)O$R^{1a}$, —C(O)N$R^{1b}R^{1c}$, —C(N$R^{1a}$)N$R^{1b}R^{1c}$, —P(O)(O$R^{1a}$)$R^{1d}$, CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or two $R^5$ or two $R^6$ that are attached to the same ring are linked together to form a bond, —O—, —N$R^7$—, —S—, $C_{1-6}$ alkylene, $C_{1-6}$ heteroalkylene, $C_{2-6}$ alkenylene, or $C_{2-6}$ heteroalkenylene;

each $L^1$ and $L^2$ is independently (a) a bond; (b) $C_{1-6}$ alkylene, $C_{2-6}$ alkenylene, $C_{2-6}$ alkynylene, $C_{3-7}$ cycloalkylene, $C_{6-14}$ arylene, $C_{6-14}$ arylene-heteroarylene, heteroarylene, heteroarylene-$C_{1-6}$ alkylene, heteroarylene-$C_{2-6}$ alkenylene, heteroarylene-$C_{2-6}$ alkynylene, or heterocyclylene; or (c) —C(O)—, —C(O)O—, —C(O)NR$^{1a}$—, —C(=NR$^{1a}$)NR$^{1c}$—, —O—, —OC(O)O—, —OC(O)NR$^{1a}$—, —OC(=NR$^{1a}$)NR$^{1c}$—, —OP(O)(OR$^{1a}$)—, —NR$^{1a}$—, —NR$^{1a}$C(O)NR$^{1c}$—, —NR$^{1a}$C(=NR$^{1b}$)NR$^{1c}$—, —NR$^{1a}$S(O)NR$^{1c}$—, —NR$^{1a}$S(O)$_2$NR$^{1c}$—, —S—, —S(O)—, —S(O)$_2$—, —S(O)NR$^{1a}$—, or —S(O)$_2$NR$^{1a}$—; with the proviso that the arylene and the arylene moiety of the $C_{6-14}$ arylene-heteroarylene are not 5,6- or 6,6-fused arylene, and the heteroarylene and the heteroarylene moiety in the $C_{6-14}$ arylene-heteroarylene, heteroarylene-$C_{1-6}$ alkylene, heteroarylene-$C_{2-6}$ alkenylene, and heteroarylene-$C_{2-6}$ alkynylene are not 5,6- or 6,6-fused heteroarylene;

each $Z^1$ and $Z^2$ is independently a bond, —O—, —S—, —S(O)—, —S(O$_2$)—, or —N(R$^7$)—;

each $R^7$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —P(O)(OR$^{1a}$)R$^{1d}$, —CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

each n and p is independently an integer of 0, 1, 2, 3, 4, 5, 6, or 7; and each q and r is independently an integer of 1, 2, 3, or 4;

wherein each alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, and heterocyclylene in $R^1$, $R^2$, $R^3$, $R^5$, $R^6$, $R^7$, $R^{1a}$, $R^{1b}$, $R^{1c}$, $R^{1d}$, A, E, $L^1$, or $L^2$ is optionally substituted with one or more substituents Q, where each Q is independently selected from (a) oxo, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^f$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Also provided herein is a compound of Formula I:

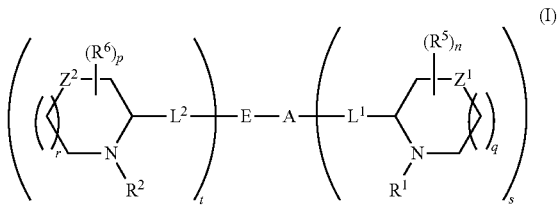

(I)

or a single enantiomer, a racemic mixture, a mixture of diastereomers, or an isotopic variant thereof; or a pharmaceutically acceptable salt, solvate, or prodrug thereof;

wherein:

s, t, A, and E are (i), (ii), or (iii):

(i) s is 1; t is 1; A is 5,5-fused heteroarylene; and E is $C_{2-6}$ alkynylene, $C_{6-14}$ arylene, or heteroarylene; with the proviso that E is not 5,6- or 6,6-fused arylene, or 5,6- or 6,6-fused heteroarylene;

(ii) s is 1; t is 0; A is 5,5-fused heteroarylene; and E is $C_{2-6}$ alkynylene-R$^{3a}$, $C_{6-14}$ arylene-R$^{3a}$, or heteroarylene-R$^{3a}$, with the proviso that E is not 5,6- or 6,6-fused arylene-R$^{3a}$, or 5,6- or 6,6-fused heteroarylene-R$^{3a}$;

(iii) s is 0; t is 1; A is 5,5-fused heteroarylene-R$^{3a}$; E is $C_{2-6}$ alkynylene, $C_{6-14}$ arylene, or heteroarylene; with the proviso that E is not 5,6- or 6,6-fused arylene, or 5,6- or 6,6-fused heteroarylene;

$R^1$ and $R^2$ are each independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)CH(NR$^{1b}$R$^{1c}$)R$^{1a}$, —C(O)CH(N(R$^{1c}$)C(O)R$^{1b}$)R$^{1a}$, —C(O)CH(N(R$^{1c}$)C(O)OR$^{1b}$)R$^{1a}$, —C(O)CH(N(R$^{1c}$)C(O)NR$^{1b}$R$^{1d}$)R$^{1a}$, —C(O)OR$^{1a}$, —C(O)NR$^{1b}$R$^{1c}$, —C(NR$^{1a}$)NR$^{1b}$R$^{1c}$, —P(O)(OR$^{1a}$)R$^{1d}$, —CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or two $R^5$ or two $R^6$ are linked together to form a bond, —O—, —NR$^7$—, —S—, $C_{1-6}$ alkylene, $C_{1-6}$ heteroalkylene, $C_{2-6}$ alkenylene, or $C_{2-6}$ heteroalkenylene;

$L^1$ and $L^2$ are each independently (a) a bond; (b) $C_{1-6}$ alkylene, $C_{2-6}$ alkenylene, $C_{2-6}$ alkynylene, $C_{3-7}$ cycloalkylene, $C_{6-14}$ arylene, heteroarylene, heteroarylene-$C_{1-6}$ alkylene, heteroarylene-$C_{2-6}$ alkenylene, heteroarylene-$C_{2-6}$ alkynylene, or heterocyclylene; or (c) —C(O)—, —C(O)O—, —C(O)NR$^{1a}$—, —C(=NR$^{1a}$)NR$^{1c}$—, —O—, —OC(O)O—, —OC(O)NR$^{1a}$—, —OC(=NR$^{1a}$)NR$^{1c}$—, —OP(O)(OR$^{1a}$)—, —NR$^{1a}$—, —NR$^{1a}$C(O)NR$^{1c}$—, —NR$^{1a}$C(=NR$^{1b}$)NR$^{1c}$—, —NR$^{1a}$S(O)NR$^{1c}$—, —NR$^{1a}$S(O)$_2$NR$^{1c}$—, —S—, —S(O)—, —S(O)$_2$—, —S(O)NR$^{1a}$—, or —S(O)$_2$NR$^{1a}$—;

$Z^1$ and $Z^2$ are each independently a bond, —O—, —S—, —S(O)—, —S(O$_2$)—, or —N(R$^7$)—;

each $R^7$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —P(O)(OR$^{1a}$)R$^{1d}$, —CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

n and p are each independently an integer of 0, 1, 2, 3, 4, 5, 6, or 7; and q and r are each independently an integer of 1, 2, 3, or 4;

wherein each alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, and heterocyclylene in $R^1$, $R^2$, $R^3$, $R^5$, $R^6$, $R^7$, $R^{1a}$, $R^{1b}$, $R^{1c}$, $R^{1d}$, A, E, $L^1$, or $L^2$ is optionally substituted with one or more substituents Q, where each Q is independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$;

wherein each Q$^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$) NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

Provided herein is a compound of Formula IA:

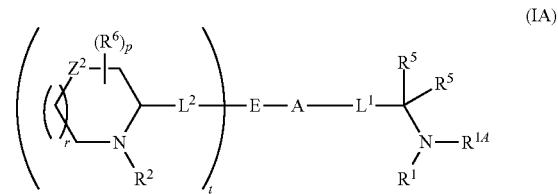

(IA)

or a single enantiomer, a racemic mixture, a mixture of diastereomers, or an isotopic variant thereof; or a pharmaceutically acceptable salt, solvate, or prodrug thereof;

wherein:

A is 5,5-fused arylene or 5,5-fused heteroarylene;

t and E are (i) or (ii):

(i) t is 1; and E is $C_{2-6}$ alkynylene, $C_{6-14}$ arylene, $C_{2-6}$ alkynylene-$C_{6-14}$ arylene, or heteroarylene; with the proviso that E is not 5,6- or 6,6-fused arylene, $C_{2-6}$ alkynylene-5,6- or 6,6-fused arylene, or 5,6- or 6,6-fused heteroarylene;

(ii) t is 0; and E is $C_{2-6}$ alkynylene-R$^{3a}$, $C_{6-14}$ arylene-R$^{3a}$, or heteroarylene-R$^{3a}$, with the proviso that E is not 5,6- or 6,6-fused arylene-R$^{3a}$, or 5,6- or 6,6-fused heteroarylene-R$^{3a}$;

$R^1$, $R^{1A}$, and $R^2$ are each independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)CH(NR$^{1b}$R$^{1c}$)R$^{1a}$, —C(O)CH(N(R$^{1c}$)C(O)R$^{1b}$)R$^{1a}$, —C(O)CH(N(R$^{1c}$)C(O)OR$^{1b}$)R$^{1a}$, —C(O)CH(N(R$^{1c}$)C(O)NR$^{1b}$R$^{1d}$)R$^{1a}$, —C(O)OR$^{1a}$, —C(O)NR$^{1b}$R$^{1c}$, —C(NR$^{1a}$)NR$^{1b}$R$^{1c}$, —P(O)(OR$^{1a}$)R$^{1d}$, —CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or two $R^5$ or two $R^6$ are linked together to form a bond, —O—, —NR$^7$—, —S—, $C_{1-6}$ alkylene, $C_{1-6}$ heteroalkylene, $C_{2-6}$ alkenylene, or $C_{2-6}$ heteroalkenylene;

$L^1$ and $L^2$ are each independently (a) a bond; (b) $C_{1-6}$ alkylene, $C_{2-6}$ alkenylene, $C_{2-6}$ alkynylene, $C_{3-7}$ cycloalkylene, $C_{6-14}$ arylene, $C_{6-14}$ arylene-heteroarylene, heteroarylene, heteroarylene-$C_{1-6}$ alkylene, heteroarylene-$C_{2-6}$ alkenylene, heteroarylene-$C_{2-6}$ alkynylene, or heterocyclylene; or (c) —C(O)—, —C(O)O—, —C(O)NR$^{1a}$, —C(=NR$^{1a}$)NR$^{1c}$—, —O—, —OC(O)O—, —OC(O) NR$^{1a}$—, —OC(=NR$^{1a}$)NR$^{1c}$—, —OP(O)(OR$^{1a}$)—, —NR$^{1a}$—, —NR$^{1a}$C(O)NR$^{1c}$—, —NR$^{1a}$C(=NR$^{1b}$) NR$^{1c}$—, —NR$^{1a}$S(O)NR$^{1c}$—, —NR$^{1a}$S(O)$_2$NR$^{1c}$—, —S—, —S(O)—, —S(O)$_2$—, —S(O)NR$^{1a}$—, or —S(O)$_2$NR$^{1a}$—;

Z$^2$ is a bond, —O—, —S—, —S(O)—, —S(O$_2$)—, or —N(R$^7$)—;

each R$^7$ is independently (a) hydrogen; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O) R$^{1d}$, —NR$^{1a}$C(O)OR$^{1d}$, —NR$^{1a}$C(O)NR$^{1b}$R$^{1c}$, —NR$^{1a}$C (=NR$^{1d}$)NR$^{1b}$R$^{1c}$, NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —P(O) (OR$^{1a}$)R$^{1d}$, —CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$;

each R$^{1a}$, R$^{1b}$, R$^{1c}$, and R$^{1d}$, is independently hydrogen, C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

p is an integer of 0, 1, 2, 3, 4, 5, 6, or 7; and r is an integer of 1, 2, 3, or 4;

wherein each alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, and heterocyclylene in R$^1$, R$^2$, R$^3$, R$^5$, R$^6$, R$^7$, R$^{1a}$, R$^{1b}$, R$^{1c}$, R$^{1d}$, A, E, L$^1$, or L$^2$ is optionally substituted with one or more substituents Q, where each Q is independently selected from (a) oxo, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$) NR$^b$R$^c$, —OR$^a$, —OC(O)R$^a$, —OC(O)OR$^a$, —OC(O) NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O) R$^d$, —NR$^a$C(O)OR$^d$, —NR$^a$C(O)NR$^b$R$^c$, —NR$^a$C(=NR$^d$) NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O) NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC (O)R$^e$, —OC(O)OR$^e$, —OC(O)NR$^f$R$^g$, —OC(=NR$^e$) NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O) OR$^f$, —NR$^e$C(O)NR$^f$R$^g$, —NR$^e$C(=NR$^h$)NR$^f$R$^g$, —NR$^e$S (O)R$^h$, —NR$^e$S(O)$_2$R$^h$, —NR$^e$S(O)NR$^f$R$^g$, —NR$^e$S(O)$_2$ NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

Provided herein is a compound of Formula IA:

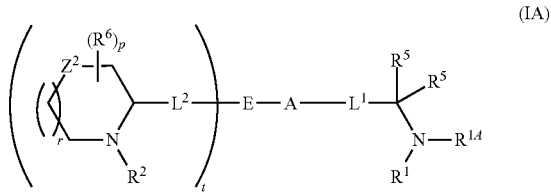

(IA)

or a single enantiomer, a racemic mixture, a mixture of diastereomers, or an isotopic variant thereof; or a pharmaceutically acceptable salt, solvate, or prodrug thereof;

wherein:

A is 5,5-fused arylene or 5,5-fused heteroarylene;

t and E are (i) or (ii):

(i) t is 1; and E is C$_{2-6}$ alkynylene, C$_{6-14}$ arylene, or heteroarylene; with the proviso that E is not 5,6- or 6,6-fused arylene, or 5,6- or 6,6-fused heteroarylene;

(ii) t is 0; and E is C$_{2-6}$ alkynylene-R$^{3a}$, C$_{6-14}$ arylene-R$^{3a}$, or heteroarylene-R$^{3a}$, with the proviso that E is not 5,6- or 6,6-fused arylene-R$^{3a}$, or 5,6- or 6,6-fused heteroarylene-R$^{3a}$;

R$^1$, R$^{1A}$, and R$^2$ are each independently (a) hydrogen; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (c) —C(O) R$^{1a}$, —C(O)CH(NR$^{1b}$R$^{1c}$)R$^{1a}$, —C(O)CH(N(R$^c$)C(O)R$^{1b}$) R$^{1a}$, —C(O)CH(N(R$^{1c}$)C(O)OR$^{1b}$)R$^{1a}$, —C(O)CH(N(R$^{1c}$) C(O)NR$^{1b}$R$^{1d}$)R$^{1a}$, —C(O)OR$^{1a}$, —C(O)NR$^{1b}$R$^{1c}$, —C(NR$^{1a}$)NR$^{1b}$R$^{1c}$, —P(O)(OR$^{1a}$)R$^{1d}$, —CH$_2$P(O)(OR$^{1a}$) R$^{1d}$, —S(O)R$^{1a}$, —S(O)$_2$R$^{1a}$, —S(O)NR$^{1b}$R$^{1c}$, or —S(O)$_2$NR$^{1b}$R$^{1e}$;

each R$^{3a}$ is independently hydrogen or R$^3$;

each R$^3$, R$^5$, and R$^6$ is independently (a) cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C (O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$ S(O)$_2$NR$^{1b}$R$^{1c}$, —SR$^{1a}$, —S(O)R$^{1a}$, —S(O)$_2$R$^{1a}$, —S(O) NR$^{1b}$R$^{1c}$, or —S(O)$_2$NR$^{1b}$R$^{1c}$; or two R$^5$ or two R$^6$ are linked together to form a bond, —O—, —NR$^7$—, —S—, C$_{1-6}$ alkylene, C$_{1-6}$ heteroalkylene, C$_{2-6}$ alkenylene, or C$_{2-6}$ heteroalkenylene;

L$^1$ and L$^2$ are each independently (a) a bond; (b) C$_{1-6}$ alkylene, C$_{2-6}$ alkenylene, C$_{2-6}$ alkynylene, C$_{3-7}$ cycloalkylene, C$_{6-14}$ arylene, heteroarylene, heteroarylene-C$_{1-6}$ alkylene, heteroarylene-C$_{2-6}$ alkenylene, heteroarylene-C$_{2-6}$ alkynylene, or heterocyclylene; or (c) —C(O)—, —C(O)O—, —C(O)NR$^{1a}$—, —C(=NR$^{1a}$)NR$^{1c}$—, —O—, —OC(O) O—, —OC(O)NR$^{1a}$—, —OC(=NR$^{1a}$)NR$^{1c}$—, —OP(O) (OR$^{1a}$)—, —NR$^{1a}$—, —NR$^{1a}$C(O)NR$^{1c}$—, —NR$^{1a}$C (=NR$^{1b}$)NR$^{1c}$—, —NR$^{1a}$S(O)NR$^{1c}$—, —NR$^{1a}$ S(O)$_2$NR$^{1c}$—, —S—, —S(O)—, —S(O)$_2$—, —S(O) NR$^{1a}$—, or —S(O)$_2$NR$^{1a}$—;

Z$^2$ is a bond, —O—, —S—, —S(O)—, —S(O$_2$)—, or —N(R)—;

each $R^7$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

p is an integer of 0, 1, 2, 3, 4, 5, 6, or 7; and r is an integer of 1, 2, 3, or 4;

wherein each alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, and heterocyclylene in $R^1$, $R^2$, $R^3$, $R^5$, $R^6$, $R^7$, $R^{1a}$, $R^{1b}$, $R^{1c}$, $R^{1d}$, A, E, $L^1$, or $L^2$ is optionally substituted with one or more substituents Q, where each Q is independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Provided herein is a compound of Formula IB:

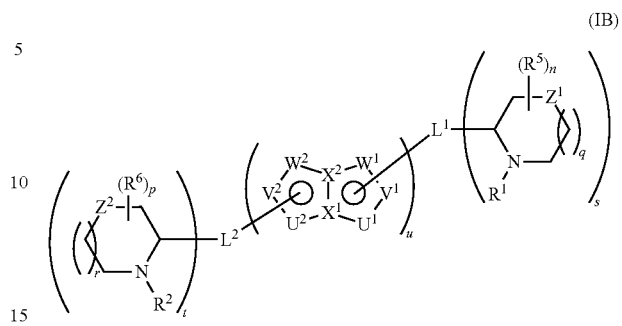

(IB)

or a single enantiomer, a racemic mixture, a mixture of diastereomers, or an isotopic variant thereof; or a pharmaceutically acceptable salt, solvate, or prodrug thereof;
wherein:
$U^1, U^2, V^1, V^2, W^1$, and $W^2$ are each independently C, N, O, S, C$R^{3a}$, or N$R^{3a}$;
$X^1$ and $X^2$ are each independently C or N;
each $R^1$ and $R^2$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, —C(O)CH(N($R^{1c}$)C(O)N$R^{1b}R^{1c}$)$R^{1a}$, —C(O)O$R^{1a}$, —C(O)N$R^{1b}R^{1c}$, —C(N$R^{1a}$)N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;

each $R^{3a}$ is independently hydrogen or $R^3$;
each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-44}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or two $R^5$ or two $R^6$ that are attached to the same ring are linked together to form a bond, —O—, —N$R^7$—, —S—, $C_{1-6}$ alkylene, $C_{1-6}$ heteroalkylene, $C_{2-6}$ alkenylene, or $C_{2-6}$ heteroalkenylene;

$L^1$ and $L^2$ are each independently selected from:
a bond,

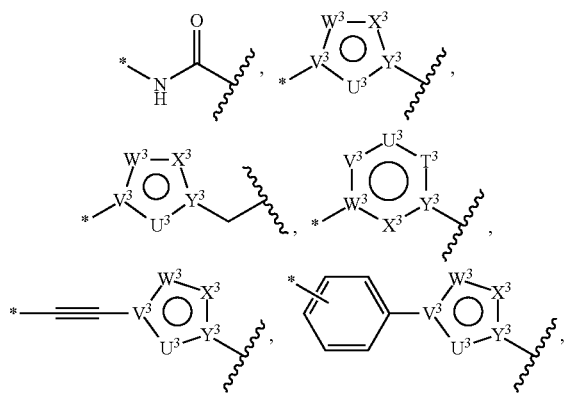

-continued

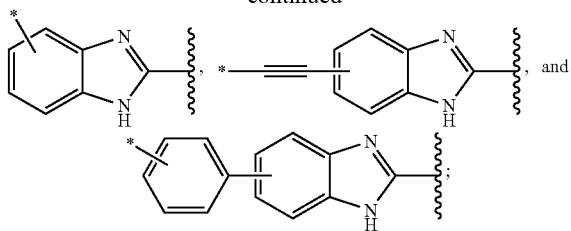

wherein each moiety is optionally substituted with one, two, three, or four R³; the star (*) on each moiety represents the point of attachment thought which the moiety is connected to U¹, U², V¹, V², W¹, or W² of

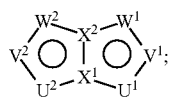

and the zigzag line ( ) on each moiety represents the point of attachment through which the moiety is connected to

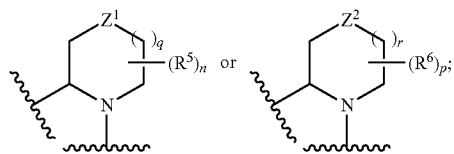

and wherein T³ is a bond, C, N, O, S, CR³ᵃ, or NR³ᵃ; U³, V³, W³, and X³ are each independently C, N, O, S, CR³ᵃ, or NR³ᵃ; and Y³ is C or N;

each Z¹ and Z² is independently a bond, —O—, —S—, —S(O)—, —S(O₂)—, or —N(R⁷)—;

each R⁷ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R¹ᵃ, —C(O)OR¹ᵃ, —C(O)NR¹ᵇR¹ᶜ, —C(NR¹ᵃ)NR¹ᵇR¹ᶜ, —OR¹ᵃ, —OC(O)R¹ᵃ, —OC(O)OR¹ᵃ, —OC(O)NR¹ᵇR¹ᶜ, —OC(NR¹ᵃ)NR¹ᵇR¹ᶜ, —OS(O)R¹ᵃ, —OS(O)₂R¹ᵃ, —OS(O)NR¹ᵇR¹ᶜ, —OS(O)₂NR¹ᵇR¹ᶜ, —NR¹ᵇR¹ᶜ, —NR¹ᵃC(O)R¹ᵈ, —NR¹ᵃC(O)OR¹ᵈ, —NR¹ᵃC(O)NR¹ᵇR¹ᶜ, —NR¹ᵃC(=NR¹ᵈ)NR¹ᵇR¹ᶜ, —NR¹ᵃS(O)R¹ᵈ, —NR¹ᵃS(O)₂R¹ᵈ, —NR¹ᵃS(O)NR¹ᵇR¹ᶜ, —NR¹ᵃS(O)₂NR¹ᵇR¹ᶜ, —P(O)(OR¹ᵃ)R¹ᵈ, —CH₂P(O)(OR¹ᵃ)R¹ᵈ, —S(O)R¹ᵃ, —S(O)₂R¹ᵃ, —S(O)NR¹ᵇR¹ᶜ, or —S(O)₂NR¹ᵇR¹ᶜ;

each R¹ᵃ, R¹ᵇ, R¹ᶜ, and R¹ᵈ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R¹ᵃ and R¹ᶜ together with the C and N atoms to which they are attached form heterocyclyl; or R¹ᵇ and R¹ᶜ together with the N atom to which they are attached form heterocyclyl;

each n and p is independently an integer of 0, 1, 2, 3, 4, 5, 6, or 7;

each q and r is independently an integer of 1, 2, 3, or 4;

s and t are each independently an integer of 0, 1, or 2; and u is an integer of 1 or 2;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more substituents Q, where each Q is independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Qᵃ; and (c) —C(O)Rᵃ, —C(O)ORᵃ, —C(O)NRᵇRᶜ, —C(NRᵃ)NRᵇRᶜ, —ORᵃ, —OC(O)Rᵃ, —OC(O)ORᵃ, —OC(O)NRᵇRᶜ, —OC(=NRᵃ)NRᵇRᶜ, —OS(O)Rᵃ, —OS(O)₂Rᵃ, —OS(O)NRᵇRᶜ, —OS(O)₂NRᵇRᶜ, —NRᵇRᶜ, —NRᵃC(O)Rᵈ, —NRᵃC(O)ORᵈ, —NRᵃC(O)NRᵇRᶜ, —NRᵃC(=NRᵈ)NRᵇRᶜ, —NRᵃS(O)Rᵈ, —NRᵃS(O)₂Rᵈ, —NRᵃS(O)NRᵇRᶜ, —NRᵃS(O)₂NRᵇRᶜ, —SRᵃ, —S(O)Rᵃ, —S(O)₂Rᵃ, —S(O)NRᵇRᶜ, and —S(O)₂NRᵇRᶜ, wherein each Rᵃ, Rᵇ, Rᶜ, and Rᵈ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Qᵃ; or (iii) Rᵇ and Rᶜ together with the N atom to which they are attached form heterocyclyl, optionally substituted with one or more, in one embodiment, one, two, three, or four, substituents Qᵃ;

wherein each Qᵃ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)Rᵉ, —C(O)ORᵉ, —C(O)NRᶠRᵍ, —C(NRᵉ)NRᶠRᵍ, —ORᵉ, —OC(O)Rᵉ, —OC(O)ORᵉ, —OC(O)NRᶠRᵍ, —OC(=NRᵉ)NRᶠRᵍ, —OS(O)Rᵉ, —OS(O)₂Rᵉ, —OS(O)NRᶠRᵍ, —OS(O)₂NRᶠRᵍ, —NRᶠRᵍ, —NRᵉC(O)Rʰ, —NRᵉC(O)ORᶠ, —NRᵉC(O)NRᶠRᵍ, —NRᵉC(=NRʰ)NRᶠRᵍ, —NRᵉS(O)Rʰ, —NRᵉS(O)₂Rʰ, —NRᵉS(O)NRᶠRᵍ, —NRᵉS(O)₂NRᶠRᵍ, —SRᵉ, —S(O)Rᵉ, —S(O)₂Rᵉ, —S(O)NRᶠRᵍ, and —S(O)₂NRᶠRᵍ; wherein each Rᵉ, Rᶠ, Rᵍ, and Rʰ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) Rᶠ and Rᵍ together with the N atom to which they are attached form heterocyclyl.

Provided herein are pharmaceutical compositions comprising a compound disclosed herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof; in combination with one or more pharmaceutically acceptable excipients or carriers.

Further provided herein is a method for treating or preventing an HCV infection, which comprises administering to a subject a therapeutically effective amount of a compound disclosed herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof.

Additionally provided herein is a method for treating, preventing, or ameliorating one or more symptoms of a liver disease or disorder associated with an HCV infection, comprising administering to a subject a therapeutically effective amount of a compound disclosed herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof.

Provided herein is a method for inhibiting replication of a virus in a host, which comprises administering to the host a therapeutically effective amount of a compound disclosed herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The term "host" refers to a unicellular or multicellular organism in which a virus can replicate, including, but not limited to, a cell, cell line, and animal, such as a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "$IC_{50}$" or "$EC_{50}$" refers an amount, concentration, or dosage of a compound that is required for 50% inhibition of a maximal response in an assay that measures such response.

The term "$CC_{50}$" refers an amount, concentration, or dosage of a compound that results in 50% reduction of the viability of a host. In certain embodiments, the $CC_{50}$ of a compound is the amount, concentration, or dosage of the compound that is required to reduce the viability of cells treated with the compound by 50%, in comparison with cells untreated with the compound.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "alkyl" refers to a linear or branched saturated monovalent hydrocarbon radical, wherein the alkyl may optionally be substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkylene" refers to a linear or branched saturated divalent hydrocarbon radical, wherein the alkylene may optionally be substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms).

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —$CH_2O$—, —$CH_2OCH_2$—, —$CH_2CH_2O$—, —$CH_2NH$—, —$CH_2NHCH_2$—, —$CH_2CH_2NH$—, —$CH_2S$—, —$CH_2SCH_2$—, and —$CH_2CH_2S$—. In certain embodiments, heteroalkylene may also be optionally substituted with one or more substituents Q as described herein.

The term "alkenyl" refers to a linear or branched monovalent hydrocarbon radical, which contains one or more, in one embodiment, one to five, in another embodiment, one, carbon-carbon double bond(s). The alkenyl may be optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one to five, in another embodiment, one, carbon-carbon double bond(s). The alkenylene may be optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "heteroalkenylene" refers to a linear or branched divalent hydrocarbon radical, which contains one or more, in one embodiment, one to five, in another embodiment, one, carbon-carbon double bond(s), and which contains one or more heteroatoms each independently selected from O, S, and N in the hydrocarbon chain. The heteroalkenylene may be optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH=CHO—, —CH=CHOCH₂—, —CH=CHCH₂O—, —CH=CHS—, —CH=CHSCH₂—, —CH=CHCH₂S—, or —CH=CHCH₂NH—.

The term "alkynyl" refers to a linear or branched monovalent hydrocarbon radical, which contains one or more, in one embodiment, one to five, in another embodiment, one, carbon-carbon triple bond(s). The alkynyl may be optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH₃) and propargyl (—CH₂C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "alkynylene" refers to a linear or branched divalent hydrocarbon radical, which contains one or more, in one embodiment, one to five, in another embodiment, one, carbon-carbon triple bond(s). The alkynylene may be optionally substituted with one or more substituents Q as described herein. For example, $C_{2-6}$ alkynylene refers to a linear unsaturated divalent hydrocarbon radical of 2 to 6 carbon atoms or a branched unsaturated divalent hydrocarbon radical of 3 to 6 carbon atoms. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene, propynylene (including all isomeric forms, e.g., 1-propynylene and propargylene), butynylene (including all isomeric forms, e.g., 1-butyn-1-ylene and 2-butyn-1-ylene), pentynylene (including all isomeric forms, e.g., 1-pentyn-1-ylene and 1-methyl-2-butyn-1-ylene), and hexynylene (including all isomeric forms, e.g., 1-hexyn-1-ylene).

The term "cycloalkyl" refers to a cyclic monovalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "cycloalkylene" refers to a cyclic divalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene (e.g., 1,1-cyclopropylene and 1,2-cyclopropylene), cyclobutylene (e.g., 1,1-cyclobutylene, 1,2-cyclobutylene, or 1,3-cyclobutylene), cyclopentylene (e.g., 1,1-cyclopentylene, 1,2-cyclopentylene, or 1,3-cyclopentylene), cyclohexylene (e.g., 1,1-cyclohexylene, 1,2-cyclohexylene, 1,3-cyclohexylene, or 1,4-cyclohexylene), cycloheptylene (e.g., 1,1-cycloheptylene, 1,2-cycloheptylene, 1,3-cycloheptylene, or 1,4-cycloheptylene), decalinylene, and adamantylene.

The term "aryl" refers to a monovalent monocyclic aromatic group and/or monovalent polycyclic aromatic group that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted with one or more substituents Q as described herein.

The term "arylene" refers to a divalent monocyclic aromatic group and/or divalent polycyclic aromatic group that contain at least one aromatic carbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydronaphthylene (tetralinylene). In certain embodiments, arylene may be optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, aralkyl are optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, and N in the ring. Heteroaryl groups are bonded to the rest of a molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted with one or more substituents Q as described herein.

The term "heteroarylene" refers to a divalent monocyclic aromatic group or divalent polycyclic aromatic group that contain at least one aromatic ring, wherein at least one aromatic ring contains one or more heteroatoms independently selected from O, S, and N in the ring. Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroarylene groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroarylene may also be optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted with one or more substituents Q as described herein.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, heterocyclic may also be optionally substituted with one or more substituents Q as described herein.

The term "halogen", "halide" or "halo" refers to fluorine, chlorine, bromine, and/or iodine.

The term "optionally substituted" is intended to mean that a group or substituent, such as an alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, or heterocyclylene group, may be substituted with one or more substituents Q, each of which is independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (b) oxo (=O), halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$) NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O) R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) R$^b$ and R$^c$ together with the N atom to which they are attached form heteroaryl or heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O) OR$^h$, —NR$^e$C(O)NR$^f$R$^g$, —NR$^e$C(=NR$^h$)NR$^f$R$^g$, —NR$^e$S (O)R$^h$, —NR$^e$S(O)$_2$R$^h$, —NR$^e$S(O)NR$^f$R$^g$, —NR$^e$S(O)$_2$ NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N) nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I) iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{13}$C, as example, or any nitrogen can be $^{15}$N, as example, and any oxygen can be $^{18}$O, where feasible according to the judgment of one of skill. In certain embodiments, an "isotopic variant" of a compound contains unnatural proportions of deuterium.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a single enantiomer, a racemic mixture, a mixture of diastereomers, or an isotopic variant thereof; or a pharmaceutically acceptable salt, solvate, or prodrug thereof"

has the same meaning as the phrase "a single enantiomer, a racemic mixture, a mixture of diastereomers, or an isotopic variant of the compound referenced therein; or a pharmaceutically acceptable salt, solvate, or prodrug of the compound referenced therein, or a single enantiomer, a racemic mixture, a mixture of diastereomers, or an isotopic variant of the compound referenced therein."

Compounds

HCV has a single positive-stranded RNA genome having about 9.6 kb in length that encodes a large polyprotein having about 3010 amino acids. This precursor polyprotein is then processed into a range of structural proteins, including core protein, C, and envelope glycoproteins, E1 and E2; and nonstructural proteins, including NS2, NS3, NS4A, NS4B, NS5A, and NS5B, by host signal peptidases and two viral proteases, NS2-3 and NS3. The nonstructural protein 5A (NS5A) is a multifunctional protein essential for HCV replication. Because of its vital role in viral replication, HCV NS5A protein has been actively pursued as a drug target for developing anti-HCV therapy.

In one embodiment, provided herein is a compound of Formula I:

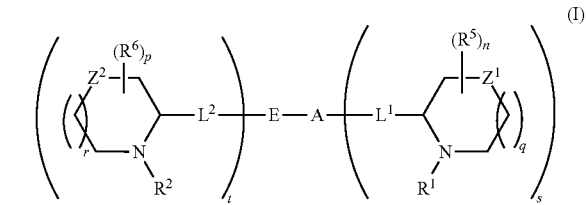

or a single enantiomer, a racemic mixture, a mixture of diastereomers, or an isotopic variant thereof; or a pharmaceutically acceptable salt, solvate, or prodrug thereof;

wherein:

s, t, A, and E are (i), (ii), or (iii):

(i) s is 1 or 2; t is 1; A is 5,5-fused heteroarylene; and E is $C_{2-6}$ alkynylene, $C_{3-7}$ cycloalkylene, $C_{6-14}$ arylene, $C_{2-6}$ alkynylene-$C_{6-14}$ arylene, or heteroarylene; with the proviso that E is not 5,6- or 6,6-fused arylene, $C_{2-6}$ alkynylene-5,6- or 6,6-fused arylene, or 5,6- or 6,6-fused heteroarylene;

(ii) s is 1 or 2; t is 0; A is 5,5-fused heteroarylene; and E is $C_{2-6}$ alkynylene-$R^{3a}$, $C_{3-7}$ cycloalkylene-$R^{3a}$, $C_{6-14}$ arylene-$R^{3a}$, or heteroarylene-$R^{3a}$, with the proviso that E is not 5,6- or 6,6-fused arylene-$R^{3a}$, or 5,6- or 6,6-fused heteroarylene-$R^{3a}$;

(iii) s is 0; t is 1; A is 5,5-fused heteroarylene-$R^{3a}$; E is $C_{2-6}$ alkynylene, $C_{3-7}$ cycloalkylene, $C_{6-14}$ arylene, or heteroarylene; with the proviso that E is not 5,6- or 6,6-fused arylene, or 5,6- or 6,6-fused heteroarylene;

each $R^1$ and $R^2$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(NR$^{1b}$R$^{1c}$)$R^{1a}$, —C(O)CH(N(R$^{1c}$)C(O)$R^{1b}$)$R^{1a}$, —C(O)CH(N(R$^{1c}$)C(O)O$R^{1b}$)$R^{1a}$, —C(O)CH(N(R$^{1c}$)C(O) NR$^{1b}$R$^{1d}$)$R^{1a}$, —C(O)O$R^{1a}$, —C(O)NR$^{1b}$R$^{1c}$, —C(NR$^{1a}$) NR$^{1b}$R$^{1c}$, —P(O)(O$R^{1a}$)$R^{1d}$, CH$_2$P(O)(O$R^{1a}$)$R^{1d}$, S(O)$R^{1a}$, —S(O)$_2$R$^{1a}$, —S(O)NR$^{1b}$R$^{1c}$, or —S(O)$_2$NR$^{1b}$R$^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(NR$^{1a}$)NR$^{1b}$R$^{1c}$, —OR$^{1a}$, —OC(O)$R^{1a}$, —OC(O)O$R^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or two R$^5$ or two R$^6$ that are attached to the same ring are linked together to form a bond, —O—, —NR$^7$—, —S—, C$_{1-6}$ alkylene, C$_{1-6}$ heteroalkylene, C$_{2-6}$ alkenylene, or C$_{2-6}$ heteroalkenylene;

each L$^1$ and L$^2$ is independently (a) a bond; (b) C$_{1-6}$ alkylene, C$_{2-6}$ alkenylene, C$_{2-6}$ alkynylene, C$_{3-7}$ cycloalkylene, C$_{6-14}$ arylene, C$_{6-14}$ arylene-heteroarylene, heteroarylene, heteroarylene-C$_{1-6}$ alkylene, heteroarylene-C$_{2-6}$ alkenylene, heteroarylene-C$_{2-6}$ alkynylene, or heterocyclylene; or (c) —C(O)—, —C(O)O—, —C(O)NR$^{1a}$—, —C(=NR$^{1a}$)NR$^{1c}$—, —O—, —OC(O)O—, —OC(O)NR$^{1a}$—, —OC(=NR$^{1a}$)NR$^{1c}$—, —OP(O)(OR$^{1a}$)—, —NR$^{1a}$—, —NR$^{1a}$C(O)NR$^{1c}$—, —NR$^{1a}$C(=NR$^{1b}$)NR$^{1c}$—, —NR$^{1a}$S(O)NR$^{1c}$NR$^{1a}$S(O)$_2$NR$^{1c}$—, —S—, —S(O)—, —S(O)$_2$—, —S(O)NR$^{1a}$—, or —S(O)$_2$NR$^{1a}$—; with the proviso that the arylene and the arylene moiety of the C$_{6-14}$ arylene-heteroarylene are not 5,6- or 6,6-fused arylene, and the heteroarylene and the heteroarylene moiety in the C$_{6-14}$ arylene-heteroarylene, heteroarylene-C$_{1-6}$ alkylene, heteroarylene-C$_{2-6}$ alkenylene, and heteroarylene-C$_{2-6}$ alkynylene are not 5,6- or 6,6-fused heteroarylene;

each Z$^1$ and Z$^2$ is independently a bond, —O—, —S—, —S(O)—, —S(O$_2$)—, or —N(R$^7$)—;

each R$^7$ is independently (a) hydrogen; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —P(O)(OR$^{1a}$)R$^{1d}$, —CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$;

each R$^{1a}$, R$^{1b}$, R$^{1c}$, and R$^{1d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

each n and p is independently an integer of 0, 1, 2, 3, 4, 5, 6, or 7; and each q and r is independently an integer of 1, 2, 3, or 4;

wherein each alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, and heterocyclylene in R$^1$, R$^2$, R$^3$, R$^5$, R$^6$, R$^7$, R$^{1a}$, R$^{1b}$, R$^{1c}$, R$^{1d}$, A, E, L$^1$, or L$^2$ is optionally substituted with one or more substituents Q, where each Q is independently selected from (a) oxo, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^b$, —NR$^e$C(O)OR$^f$, —NR$^e$C(O)NR$^f$R$^g$, —NR$^e$C(=NR$^h$)NR$^f$R$^g$, —NR$^e$S(O)R$^b$, —NR$^e$S(O)$_2$R$^b$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In another embodiment, provided herein is a compound of Formula I:

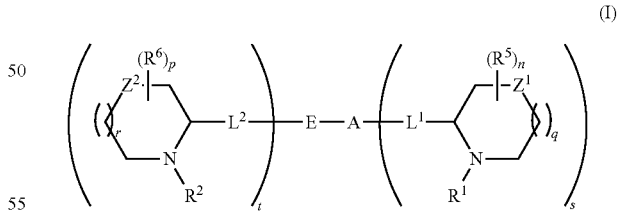

(I)

or a single enantiomer, a racemic mixture, a mixture of diastereomers, or an isotopic variant thereof; or a pharmaceutically acceptable salt, solvate, or prodrug thereof;

wherein:

s, t, A, and E are (i), (ii), or (iii):

(i) s is 1; t is 1; A is 5,5-fused heteroarylene; and E is C$_{2-6}$ alkynylene, C$_{6-14}$ arylene, or heteroarylene; with the proviso that E is not 5,6- or 6,6-fused arylene, or 5,6- or 6,6-fused heteroarylene;

(ii) s is 1; t is 0; A is 5,5-fused heteroarylene; and E is $C_{2-6}$ alkynylene-$R^{3a}$, $C_{6-14}$ arylene-$R^{3a}$, or heteroarylene-$R^{3a}$, with the proviso that E is not 5,6- or 6,6-fused arylene-$R^{3a}$, or 5,6- or 6,6-fused heteroarylene-$R^{3a}$;

(iii) s is 0; t is 1; A is 5,5-fused heteroarylene-$R^{3a}$; E is $C_{2-6}$ alkynylene, $C_{6-14}$ arylene, or heteroarylene; with the proviso that E is not 5,6- or 6,6-fused arylene, or 5,6- or 6,6-fused heteroarylene;

$R^1$ and $R^2$ are each independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, —C(O)CH(N($R^{1c}$)C(O)N$R^{1b}R^{1d}$)$R^{1a}$, —C(O)O$R^{1a}$, —C(O)N$R^{1b}R^{1c}$, —C(N$R^{1a}$)N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or two $R^5$ or two $R^6$ are linked together to form a bond, —O—, —N$R^7$—, —S—, $C_{1-6}$ alkylene, $C_{1-6}$ heteroalkylene, $C_{2-6}$ alkenylene, or $C_{2-6}$ heteroalkenylene;

$L^1$ and $L^2$ are each independently (a) a bond; (b) $C_{1-6}$ alkylene, $C_{2-6}$ alkenylene, $C_{2-6}$ alkynylene, $C_{3-7}$ cycloalkylene, $C_{6-14}$ arylene, heteroarylene, heteroarylene-$C_{1-6}$ alkylene, heteroarylene-$C_{2-6}$ alkenylene, heteroarylene-$C_{2-6}$ alkynylene, or heterocyclylene; or (c) —C(O)—, —C(O)O—, —C(O)N$R^{1a}$—, —C(=N$R^{1a}$)N$R^{1c}$—, —O—, —OC(O) O—, —OC(O)N$R^{1a}$—, —OC(=N$R^{1a}$)N$R^{1c}$—, —OP(O)(O$R^{1a}$)—, —N$R^{1a}$—, —N$R^{1a}$C(O)N$R^{1c}$—, —N$R^{1a}$C(=N$R^{1b}$)N$R^{1c}$—, —N$R^{1a}$S(O)N$R^{1c}$—, —N$R^{1a}$S(O)$_2$N$R^{1c}$—, —S—, —S(O)—, —S(O)$_2$—, —S(O)N$R^{1a}$—, or —S(O)$_2$N$R^{1a}$—;

$Z^1$ and $Z^2$ are each independently a bond, —O—, —S—, —S(O)—, —S(O$_2$)—, or —N($R^7$)—;

each $R^7$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, N$R^{1b}R^{1c}$, N$R^{1a}$C(O)$R^{1d}$, N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —P(O)(O$R^{1a}$)$R^{1d}$, CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

n and p are each independently an integer of 0, 1, 2, 3, 4, 5, 6, or 7; and q and r are each independently an integer of 1, 2, 3, or 4;

wherein each alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, and heterocyclylene in $R^1$, $R^2$, $R^3$, $R^5$, $R^6$, $R^7$, $R^{1a}$, $R^{1b}$, $R^{1c}$, $R^{1d}$, A, E, $L^1$, or $L^2$ is optionally substituted with one or more substituents Q, where each Q is independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^e$, and —S(O)$_2$N$R^bR^e$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In one embodiment, the arylene and the arylene moiety of the $C_{6-14}$ arylene-heteroarylene of $L^1$ or $L^2$ in Formula I are not 5,6- or 6,6-fused arylene, and the heteroarylene and the heteroarylene moiety in the $C_{6-14}$ arylene-heteroarylene, heteroarylene-$C_{1-6}$ alkylene, heteroarylene-$C_{2-6}$ alkenylene, and heteroarylene-$C_{2-6}$ alkynylene of $L^1$ or $L^2$ in Formula I are not 5,6- or 6,6-fused heteroarylene.

In yet another embodiment, provided herein is a compound of Formula II:

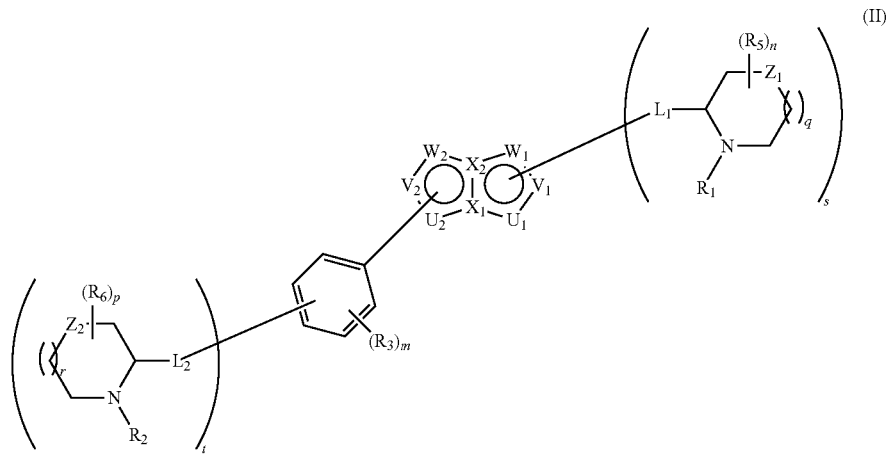

(II)

or a single enantiomer, a racemic mixture, a mixture of diastereomers, or an isotopic variant thereof; or a pharmaceutically acceptable salt, solvate, or prodrug thereof;
wherein:
$R^1$, $R^2$, $R^3$, $R^5$, $R^6$, $L^1$, $L^2$, $Z^1$, $L^2$, $Z^1$, $Z^2$, n, p, q, r, s, and t are each as defined herein;
$U^1$, $U^2$, $V^1$, $V^2$, $W^1$, and $W^2$ are each independently C, N, O, S, $CR^{3a}$, or $NR^{3a}$; where $R^{3a}$ is as defined herein;
$X^1$ and $X^2$ are each independently C or N; and
m is an integer of 0, 1, 2, 3, or 4;
wherein the bonds between $U^1$ and $V^1$, $U^1$ and $X^1$, $V^1$ and $W^1$, $W^1$ and $X^2$, $U^2$ and $V^2$, $U^2$ and $X^1$, $V^2$ and $W^2$, $W^2$ and $X^2$, and $X^1$ and $X^2$ are each a single or double bond.

In yet another embodiment, provided herein is a compound of Formula III:

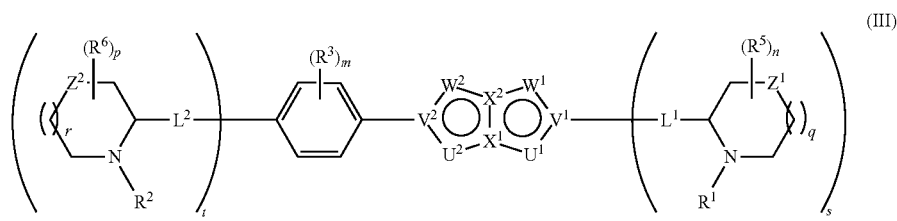

(III)

or a single enantiomer, a racemic mixture, a mixture of diastereomers, or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In one embodiment, provided herein is a compound of Formula IIIa:

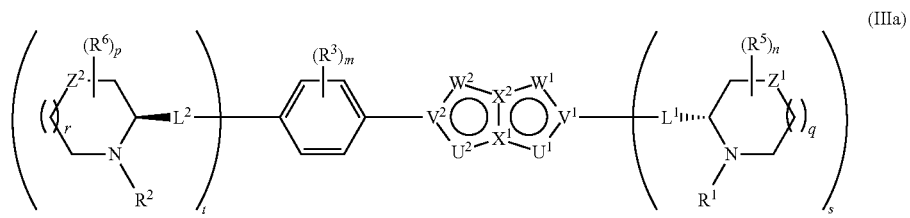

(IIIa)

or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $Z^1$, $Z^2$, m, n, p, q, r, s, and t are each as defined herein.

In another embodiment, provided herein is a compound of Formula IIIb:

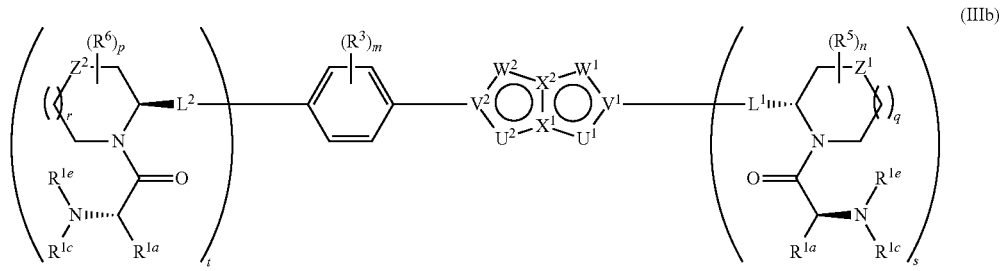

(IIIb)

or an isotopic variant thereof; or a pharmaceutically acceptable salt, solvate, or prodrug thereof; wherein $R^{1a}$, $R^{1c}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein; and each $R^{1e}$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1b}$, —C(O)O$R^{1b}$, or —C(O)N$R^{1b}R^{1d}$, where $R^{1b}$ and $R^{1d}$ are each as defined herein.

In yet another embodiment, provided herein is a compound of Formula IIIc:

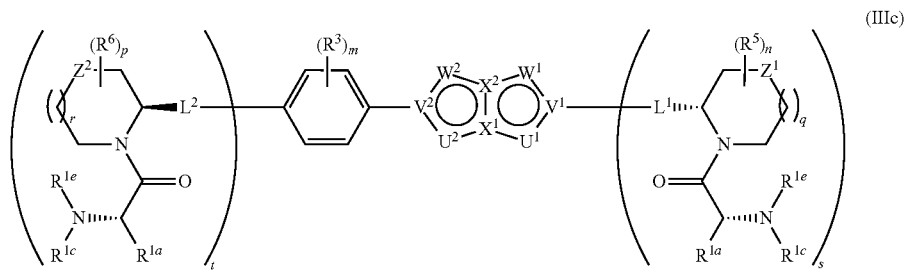

(IIIc)

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In Formula II, III, IIIa, IIIb, or IIIc, in one embodiment, $U^1$ and $X^2$ are N, $U^2$ is S, $W^1$ and $W^2$ are CH, and $V^1$, $V^2$, and $X^1$ are C; in another embodiment, $U^1$ is S, $U^2$ and $X^2$ are N, $W^1$ and $W^2$ are CH, and $V^1$, $V^2$, and $X^1$ are C; in yet another embodiment, $U^1$ and $X^2$ are N, $U^2$ is O, $W^1$ and $W^2$ are CH, and $V^1$, $V^2$, and $X^1$ are C; in yet another embodiment, $U^1$ is O, $U^2$ and $X^2$ are N, $W^1$ and $W^2$ are CH, and $V^1$, $V^2$, and $X^1$ are C; in yet another embodiment, $U^1$ is S, $U^2$ and $W^1$ are CH, $W^2$ is $NR^{3a}$, and $V^1$, $V^2$, $X^1$, and $X^2$ are C; in yet another embodiment, $U^1$ is $NR^{3a}$, $U^2$ and $W^1$ are CH, $W^2$ is S, and $V^1$, $V^2$, $X^1$, and $X^2$ are C; in yet another embodiment, $U^1$ is $NR^{3a}$, $U^2$ is S, $W^1$ is CH, $W^2$ is N, and $V^1$, $V^2$, $X^1$, and $X^2$ are C; in still another embodiment, $U^1$ is S, $U^2$ is $NR^{3a}$, $W^1$ is N, $W^2$ is CH, and $V^1$, $V^2$, $X^1$, and $X^2$ are C; where each $R^{3a}$ is as defined herein.

In Formula II, III, IIIa, IIIb, or IIIc, in one embodiment, $U^1$ and $X^2$ are N, $U^2$ is S, $V^1$, $V^2$, and $X^1$ are C, and $W^1$ and $W^2$ are each independently $CR^{3a}$; in another embodiment, $U^1$ is S, $U^2$ and $X^2$ are N, $V^1$, $V^2$, and $X^1$ are C, and $W^1$ and $W^2$ are each independently $CR^{3a}$; in yet another embodiment, $U^1$ and $X^2$ are N, $U^2$ is O, $V^1$, $V^2$, and $X^1$ are C, and $W^1$ and $W^2$ are each independently $CR^{3a}$; in yet another embodiment, $U^1$ is O, $U^2$ and $X^2$ are N, $V^1$, $V^2$, and $X^1$ are C, and $W^1$ and $W^2$ are each independently $CR^{3a}$; in yet another embodiment, $U^1$ is $NR^{3a}$, $U^2$ is S, $V^1$, $V^2$, $X^1$, and $X^2$ are C, $W^1$ is $CR^{3a}$, and $W^2$ is N; in yet another embodiment, $U^1$ and $W^2$ are each independently $CR^{3a}$, $U^2$ is S, $V^1$, $V^2$, $X^1$, and $X^2$ are C, $W^1$ is $NR^{3a}$; in yet another embodiment, $U^1$ is S, $U^2$ and $W^1$ are each independently $CR^{3a}$, $V^1$, $V^2$, $X^1$, and $X^2$ are C, $W^2$ is $NR^{3a}$; in yet another embodiment, $U^1$ and $W^2$ are each independently $CR^{3a}$, $U^2$ is O, $V^1$, $V^2$, $X^1$, and $X^2$ are C, $W^1$ is $NR^{3a}$; in yet another embodiment, $U^1$ and $W^2$ are N, $U^2$ and $W^1$ are S, $V^1$, $V^2$, $X^1$, and $X^2$ are C; in yet another embodiment, $U^1$ and $W^2$ are S, $U^2$ and $W^1$ are each independently $CR^{3a}$, $V^1$, $V^2$, $X^1$, and $X^2$ are C; in yet another embodiment, $U^1$ and $X^2$ are N, $U^2$ is $NR^{3a}$, $V^1$, $V^2$, and $X^1$ are C, and $W^1$ and $W^2$ are each independently $CR^{3a}$; in yet another embodiment, $U^1$ is S, $U^2$ is $NR^{3a}$, $V^1$, $V^2$, $X^1$, and $X^2$ are C, and $W^1$ and $W^2$ are each independently $CR^{3a}$; in still another embodiment, $U^1$, $W^2$, and $X^1$ are N, $U^2$ is $CR^{3a}$, $V^1$, $V^2$, and $X^2$ are C, and $W^1$ is S; wherein each $R^{3a}$ is as defined herein.

In yet another embodiment, provided herein is a compound of Formula IV:

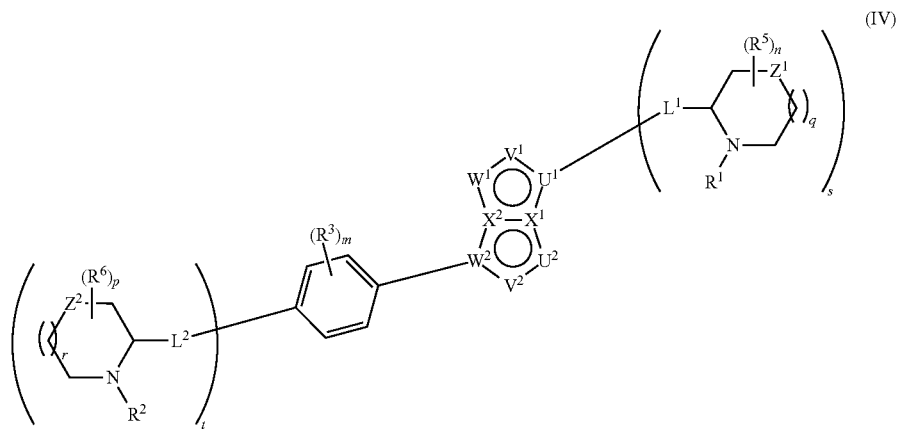

or a single enantiomer, a racemic mixture, a mixture of diastereomers, or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In one embodiment, provided herein is a compound of Formula IVa:

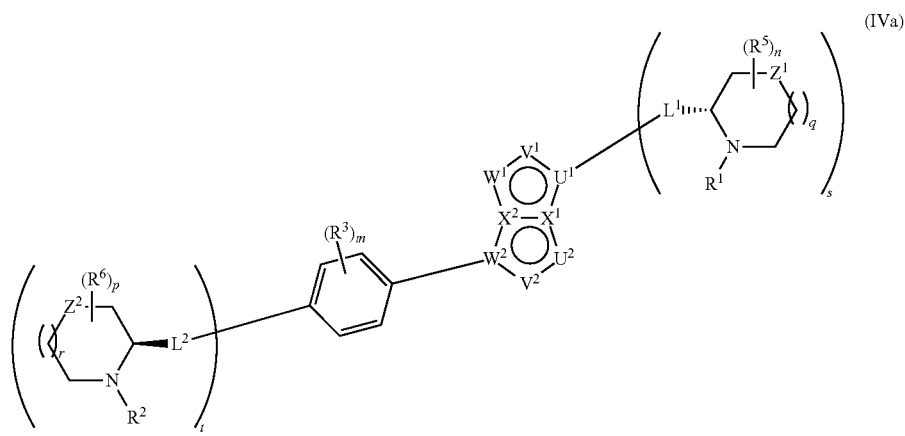

or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $Z^1$, $Z^2$, m, n, p, q, r, s, and t are each as defined herein.

In another embodiment, provided herein is a compound of Formula IVb:

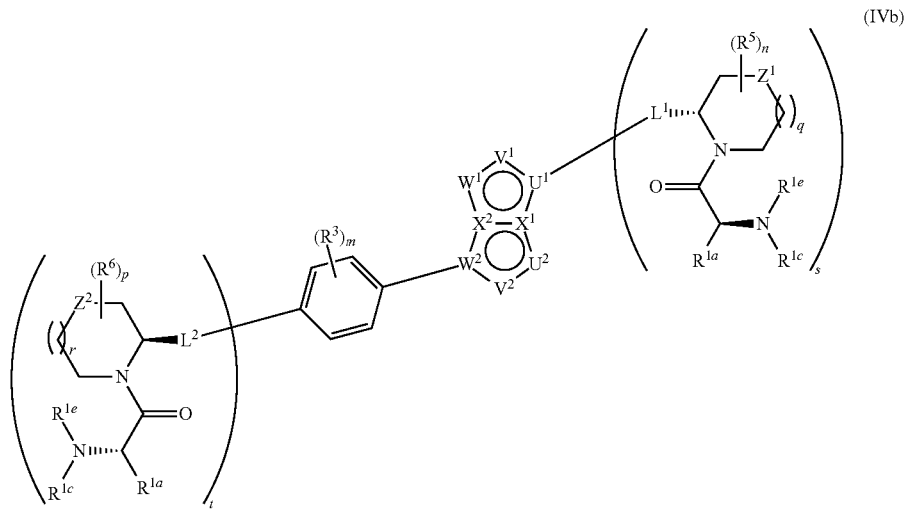

(IVb)

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In yet another embodiment, provided herein is a compound of Formula IVc:

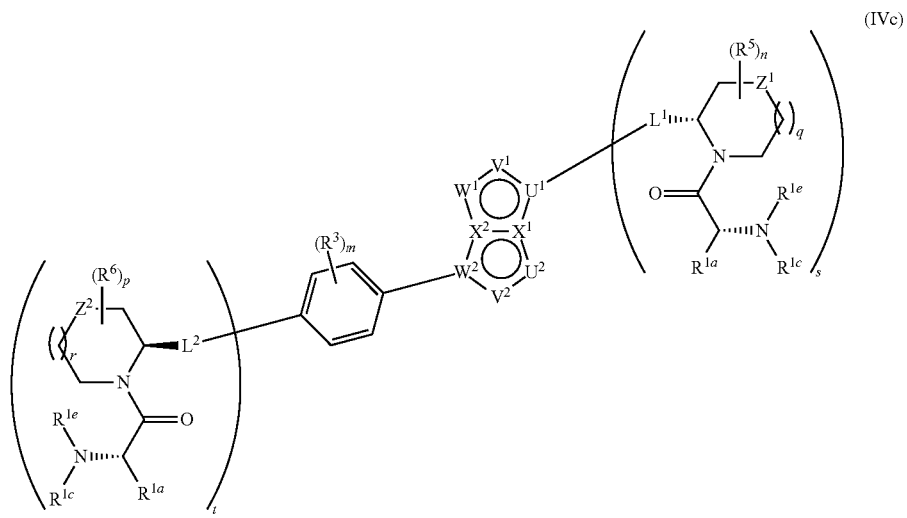

(IVc)

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In Formula II, IV, IVa, IVb, or IVc, in one embodiment, $U^1$, $W^2$, $X^1$, and $X^2$ are C, $U^2$ and $W^1$ are S, and $V^1$ and $V^2$ are CH; in another embodiment, $U^1$, $W^2$, $X^1$, and $X^2$ are C, $U^2$ and $W^1$ are CH, and $V^1$ and $V^2$ are N; in yet another embodiment, $U^1$, $X^1$, and $X^2$ are C, $U^2$, $V^1$, and $V^2$ are CH, $W^1$ is S, and $W^2$ is N; in still another embodiment, $U^1$ is N, $U^2$ is S, $V^1$, $V^2$, and $W^1$ are CH, and $W^2$, $X^1$, and $X^2$ are C.

In II, IV, IVa, IVb, or IVc, in one embodiment, $U^1$, $X^1$, and $X^2$ are C, $V^1$, $V^2$, $U^2$ are each independently $CR^{3a}$, $W^1$ is S, and $W^2$ is N; in another embodiment, $U^1$, $W^2$, $X^1$, and $X^2$ are C, $U^2$ and $W^1$ are S, and $V^1$ and $V^2$ are each independently $CR^{3a}$; in yet another embodiment, $U^1$, $W^2$, $X^1$, and $X^2$ are C, $U^2$ is $NR^{3a}$, $V^1$ and $V^2$ are each independently $CR^{3a}$, and $W^1$ is S; in yet another embodiment, $U^1$, $W^2$, $X^1$, and $X^2$ are C, $U^2$ is $NR^{3a}$, $V^1$ and $V^2$ are each independently $CR^{3a}$, and $W^1$ is O; in yet another embodiment, $U^1$, $W^2$, $X^1$, and $X^2$ are C, $U^2$ is S, $V^1$ and $V^2$ are each independently $CR^{3a}$, and $W^1$ is $NR^{3a}$; in yet another embodiment, $U^1$ and $X^1$ are C, $U^2$, $V^1$, and $V^2$ are each independently $CR^{3a}$, $W^1$, $W^2$, and $X^2$ are N; in yet another embodiment, $U^1$, $W^2$, $X^1$, and $X^2$ are C, $U^2$ and $W^2$ are each independently $CR^{3a}$, $V^1$ and $V^2$ are N; in still another embodiment, $U^1$ is N, $U^2$ is S, $V^1$, $V^2$, and $W^1$ are each independently $CR^{3a}$, $W^2$, $X^1$, and $X^2$ are C; wherein each $R^{3a}$ is as defined herein.

In yet another embodiment, provided herein is a compound of Formula V:

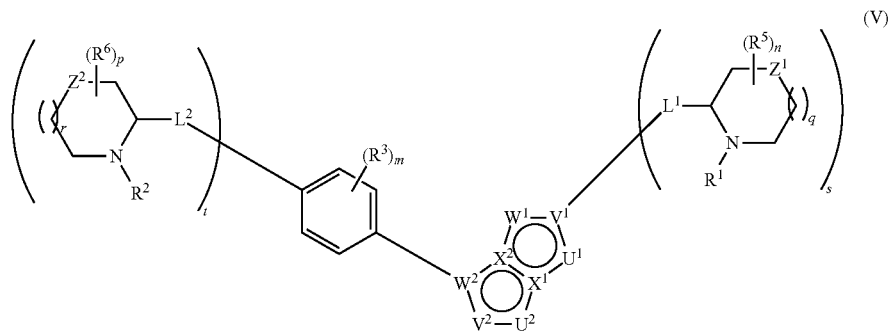

(V)

or a single enantiomer, a racemic mixture, a mixture of diastereomers, or an isotopic variant thereof; or a pharmaceutically acceptable salt, solvate, or prodrug thereof;

wherein $R^1$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In one embodiment, provided herein is a compound of Formula Va:

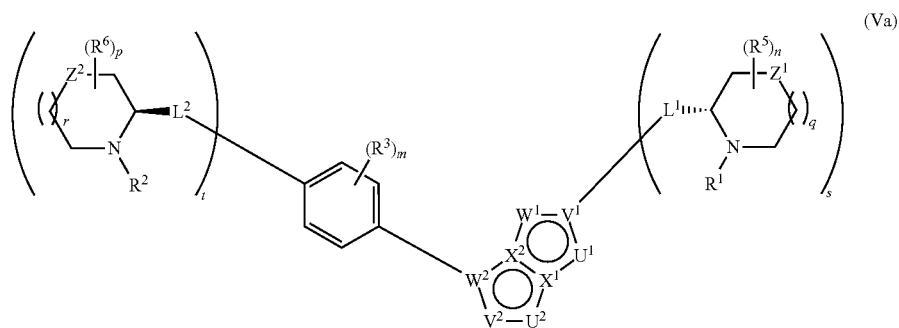

(Va)

or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $Z^1$, $Z^2$, m, n, p, q, r, s, and t are each as defined herein.

In another embodiment, provided herein is a compound of Formula Vb:

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In yet another embodiment, provided herein is a compound of Formula Vc:

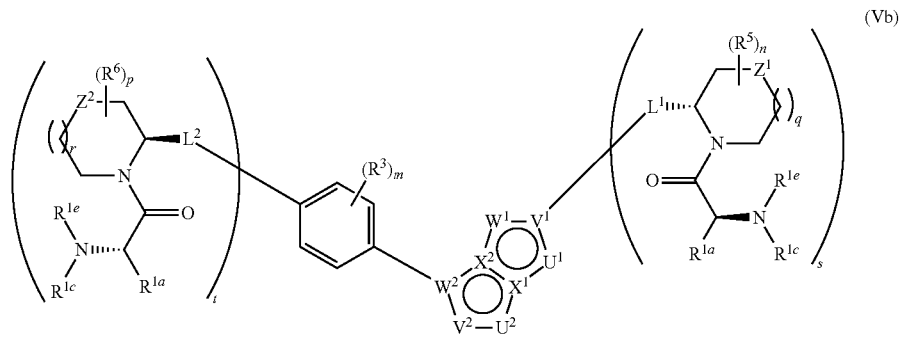

(Vb)

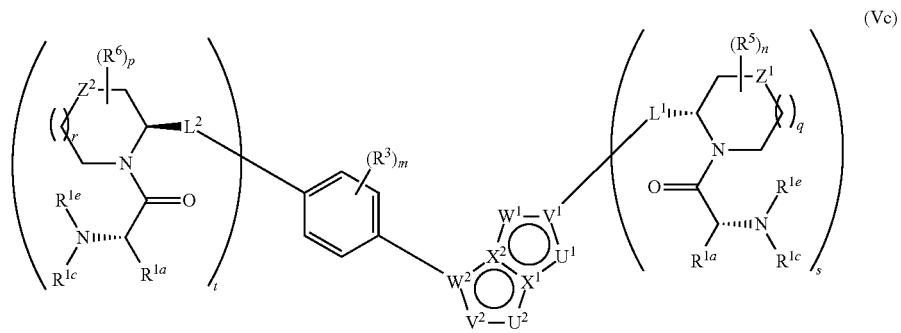

(Vc)

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In Formula II, V, Va, Vb, or Vc, in one embodiment, $U^1$ is S, $U^2$, $V^2$, and $W^1$ are CH, $V^1$, $X^1$, and $X^2$ are C, and $W^2$ is N; in another embodiment, $U^1$ and $V^2$ are CH, $U^2$ and $W^1$ are S, and $V^1$, $W^2$, $X^1$, and $X^2$ are C.

In Formula II, V, Va, Vb, or Vc, in one embodiment, $U^1$ and $V^2$ are each independently $CR^{3a}$, $U^2$ and $W^1$ are S, and $V^1$, $W^2$, $X^1$, and $X^2$ are C; in another embodiment, $U^1$ and $V^2$ are each independently $CR^{3a}$, $U^2$ is S, $V^1$, $W^2$, $X^1$, and $X^2$ are C, and $W^1$ is $NR^{3a}$; in yet another embodiment, $U^1$ and $X^2$ are N, $U^2$ is S, $V^1$, $W^2$, and $X^1$ are C, and $V^2$ and $W^1$ are each independently $CR^{3a}$; wherein each $R^{3a}$ is as defined herein.

In yet another embodiment, provided herein is a compound of Formula VI:

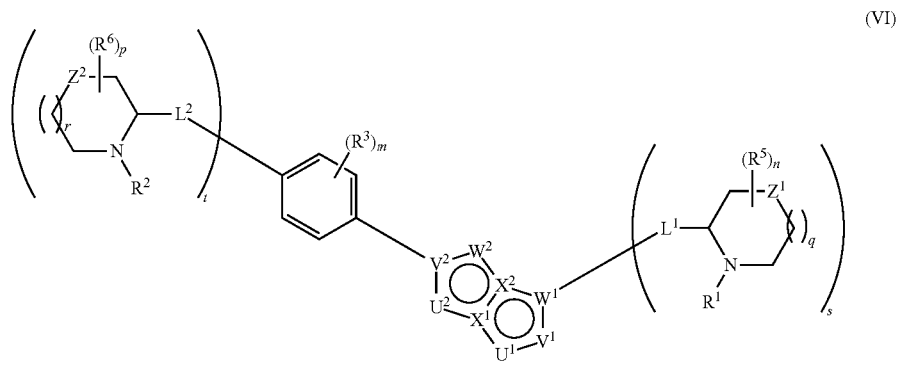

(VI)

or a single enantiomer, a racemic mixture, a mixture of diastereomers, or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In one embodiment, provided herein is a compound of Formula VIa:

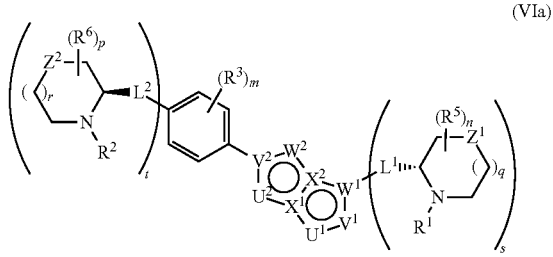

(VIa)

or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $Z^1$, $Z^2$, m, n, p, q, r, s, and t are each as defined herein.

In another embodiment, provided herein is a compound of Formula VIb:

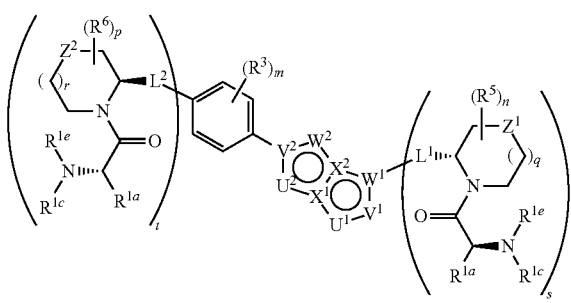

(VIb)

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In yet another embodiment, provided herein is a compound of Formula VIc:

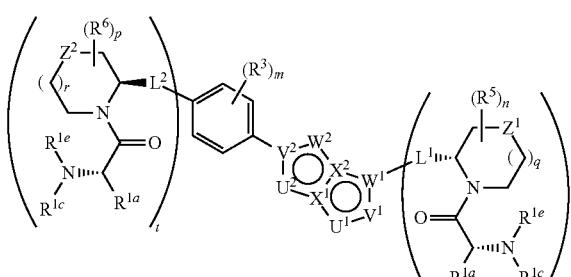

(VIc)

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In Formula II, VI, VIa, VIb, or VIc, in one embodiment, $U^1$, $V^1$, and $W^2$ are CH, $U^2$ is S, $V^2$, $X^1$, and $X^2$ are C, and $W^1$ is N; in another embodiment, $U^1$ and $W^2$ are S, $U^2$ and $V^1$ are CH, and $V^2$, $W^1$, $X^1$, and $X^2$ are C.

In Formula II, VI, VIa, VIb, or VIc, in one embodiment, $U^1$ and $W^2$ are S, $U^2$ and $V^1$ are each independently $CR^{3a}$, and $V^2$, $W^1$, $X^1$, and $X^2$ are C; in another embodiment, $U^1$ is S, $U^2$ and $X^2$ are N, $V^1$ and $W^2$ are each independently $CR^{3a}$, and $V^2$, $W^1$, and $X^1$ are C; in yet another embodiment, $U^1$ is S, $U^2$ and $V^1$ are each independently $CR^{3a}$, $V^2$, $W^1$, $X^1$, and $X^2$ are C; and $W^2$ is $NR^{3a}$; wherein each $R^{3a}$ is as defined herein.

In yet another embodiment, provided herein is a compound of Formula VII:

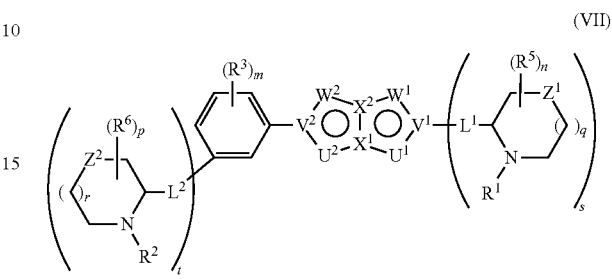

(VII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In one embodiment, provided herein is a compound of Formula VIIa:

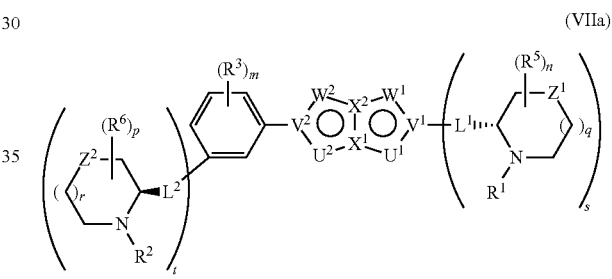

(VIIa)

or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $Z^1$, $Z^2$, m, n, p, q, r, s, and t are each as defined herein.

In another embodiment, provided herein is a compound of Formula VIIb:

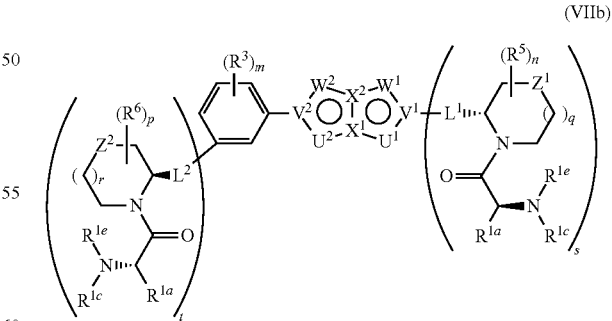

(VIIb)

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In yet another embodiment, provided herein is a compound of Formula VIIc:

(VIIc)

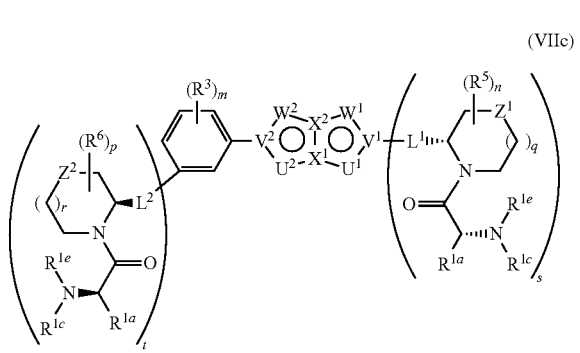

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In Formula II, VII, VIIa, VIIb, or VIIc, in one embodiment, $U^1$ and $X^2$ are N, $U^2$ is S, $V^1$, $V^2$, and $X^1$ are C, and $W^1$ and $W^2$ are each independently $CR^{3a}$; in another embodiment, $U^1$ is S, $U^2$ and $X^2$ are N, $V^1$, $V^2$, and $X^1$ are C, and $W^1$ and $W^2$ are each independently $CR^{3a}$; in yet another embodiment, $U^1$ and $X^2$ are N, $U^2$ is O, $V^1$, $V^2$, and $X^1$ are C, and $W^1$ and $W^2$ are each independently $CR^{3a}$; in yet another embodiment, $U^1$ is O, $U^2$ and $X^2$ are N, $V^1$, $V^2$, and $X^1$ are C, and $W^1$ and $W^2$ are each independently $CR^{3a}$; in yet another embodiment, $U^1$ is $NR^{3a}$, $U^2$ is S, $V^1$, $V^2$, $X^1$, and $X^2$ are C, $W^1$ is $CR^{3a}$, and $W^2$ is N; in yet another embodiment, $U^1$ and $W^2$ are each independently $CR^{3a}$, $U^2$ is S, $V^1$, $V^2$, $X^1$, and $X^2$ are C, $W^1$ is $NR^{3a}$; in yet another embodiment, $U^1$ is S, $U^2$ and $W^1$ are each independently $CR^{3a}$, $V^1$, $V^2$, $X^1$, and $X^2$ are C, $W^2$ is $NR^{3a}$; in yet another embodiment, $U^1$ and $W^2$ are each independently $CR^{3a}$, $U^2$ is O, $V^1$, $V^2$, $X^1$, and $X^2$ are C, $W^1$ is $NR^{3a}$; in yet another embodiment, $U^1$ and $W^2$ are N, $U^2$ and $W^1$ are S, $V^1$, $V^2$, $X^1$, and $X^2$ are C; in yet another embodiment, $U^1$ and $W^2$ are S, $U^2$ and $W^1$ are each independently $CR^{3a}$, $V^1$, $V^2$, $X^1$, and $X^2$ are C; in yet another embodiment, $U^1$ and $X^2$ are N, $U^2$ is $NR^{3a}$, $V^1$, $V^2$, and $X^1$ are C, and $W^1$ and $W^2$ are each independently $CR^{3a}$; in yet another embodiment, $U^1$ is S, $U^2$ is $NR^{3a}$, $V^1$, $V^2$, $X^1$, and $X^2$ are C, and $W^1$ and $W^2$ are each independently $CR^{3a}$; in still another embodiment, $U^1$, $W^2$, and $X^1$ are N, $U^2$ is $CR^{3a}$, $V^1$, $V^2$, and $X^2$ are C, and $W^1$ is S; wherein each $R^{3a}$ is as defined herein.

In yet another embodiment, provided herein is a compound of Formula VIII:

(VIII)

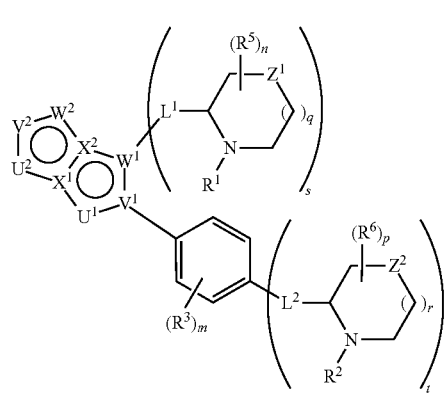

or a single enantiomer, a racemic mixture, a mixture of diastereomers, or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In one embodiment, provided herein is a compound of Formula VIIIa:

(VIIIa)

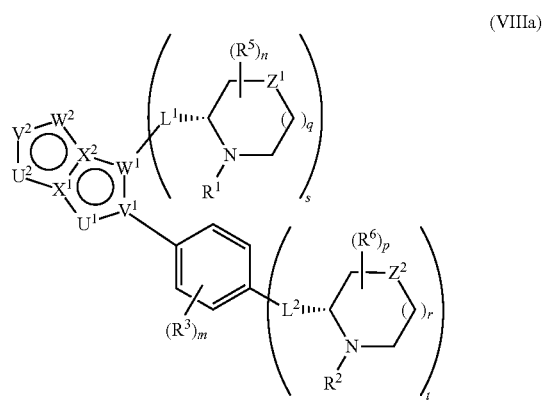

or an isotopic variant thereof; or a pharmaceutically acceptable salt, solvate, or prodrug thereof; wherein $R^1$, $R^2$, $R^3$, $R^5$, $R^6$, $L^1$, $L^2$, $U^1$, $U^2$, $V^1$, $V^2$, $W^1$, $W^2$, $Z^1$, $Z^2$, m, n, p, q, r, s, and t are each as defined herein.

In another embodiment, provided herein is a compound of Formula VIIIb:

(VIIIb)

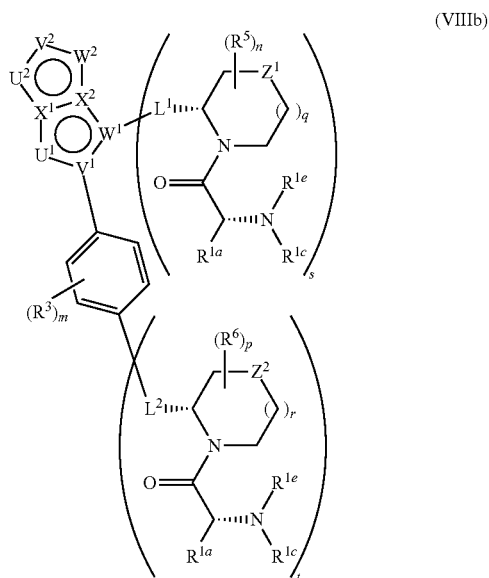

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In yet another embodiment, provided herein is a compound of Formula VIIIc:

(VIIIc)

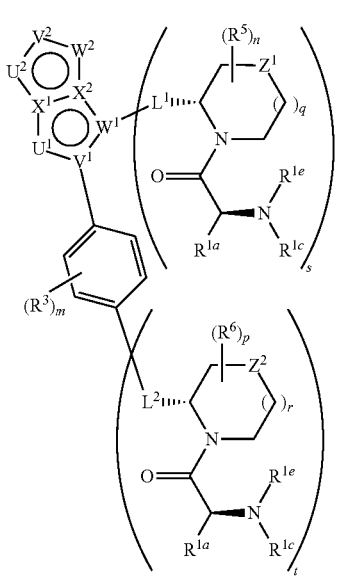

or an isotopic variant thereof; or a pharmaceutically acceptable salt, solvate, or prodrug thereof; wherein $R^{1a}$, $R^{1c}$, $R^{1e}$, $R^3$, $R^5$, $R^6$, $L^1$, $L^2$, $U^1$, $U^2$, $V^1$, $V^2$, $W^1$, $W^2$, $X^1$, $X^2$, $Z^1$, $Z^2$, m, n, p, q, r, s, and t are each as defined herein.

In Formula II, VIII, VIIIa, VIIIb, or VIIIc, in one embodiment, $U^1$ and $X^2$ are N, $U^2$ is S, $V^1$, $W^1$, and $X^1$ are C, and $V^2$ and $W^2$ are each independently $CR^{3a}$; in another embodiment, $U^1$ is S, $U^2$ and $X^2$ are N, $V^1$, $W^1$, and $X^1$ are C, and $V^2$ and $W^2$ are each independently $CR^{3a}$, wherein each $R^{3a}$ is as defined herein.

In yet another embodiment, provided herein is a compound of Formula IX:

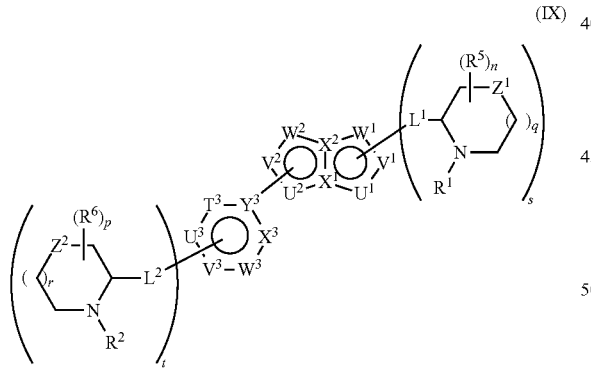

(IX)

or a single enantiomer, a racemic mixture, a mixture of diastereomers, or an isotopic variant thereof; or a pharmaceutically acceptable salt, solvate, or prodrug thereof;
wherein:
$R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein;
$T^3$ is a bond, C, N, O, S, $CR^{3a}$, or $NR^{3a}$; where $R^{3a}$ is as defined herein;
$U^3$, $V^3$, $W^3$, and $X^3$ are each independently C, N, O, S, $CR^{3a}$, or $NR^{3a}$; where $R^{3a}$ is as defined herein; and
$Y^3$ is C or N.

In yet another embodiment, provided herein is a compound of Formula X:

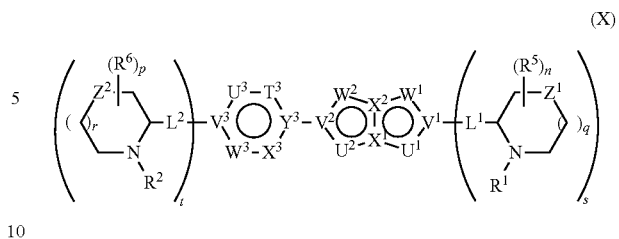

(X)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^1$, $T^3$, $U^1$, $U^2$, $U^3$, $V^1$, $V^{12}$, $V^3$, $W^1$, $W^2$, $W^3$, $X^1$, $X^2$, $X^3$, $Y^3$, $Z^1$, $Z^2$, n, p, q, r, s, and t are each as defined herein.

In one embodiment, provided herein is a compound of Formula Xa:

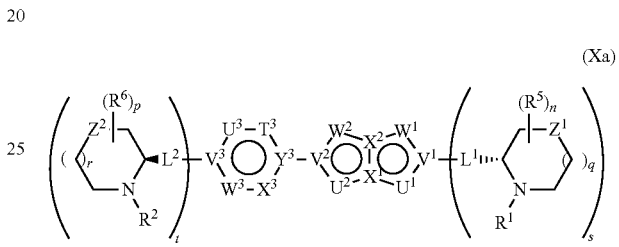

(Xa)

or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In another embodiment, provided herein is a compound of Formula Xb:

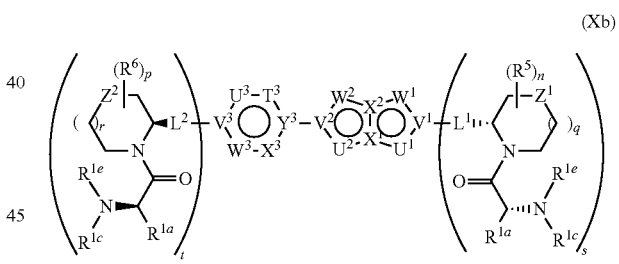

(Xb)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In yet another embodiment, provided herein is a compound of Formula Xc:

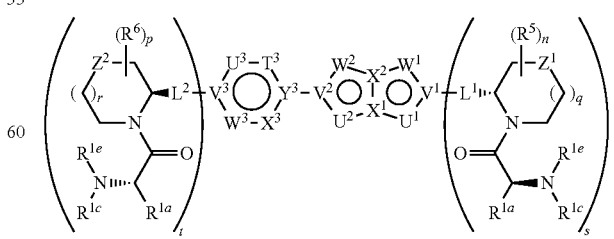

(Xc)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In Formula IX, X, Xa, Xb, or Xc, in one embodiment, $U^1$ and $X^2$ are N, $U^2$ is S, $V^1$, $V^2$, and $X^1$ are C, and $W^1$ and $W^2$ are each independently $CR^{3a}$; in another embodiment, $U^1$ is S, $U^2$ and $X^2$ are N, $V^1$, $V^2$, and $X^1$ are C, and $W^1$ and $W^2$ are each independently $CR^{3a}$; in yet another embodiment, $U^1$ and $X^2$ are N, $U^2$ is O, $V^1$, $V^2$, and $X^1$ are C, and $W^1$ and $W^2$ are each independently $CR^{3a}$; in yet another embodiment, $U^1$ is O, $U^2$ and $X^2$ are N, $V^1$, $V^2$, and $X^1$ are C, and $W^1$ and $W^2$ are each independently $CR^{3a}$; in yet another embodiment, $U^1$ is $NR^{3a}$, $U^2$ is S, $V^1$, $V^2$, $X^1$, and $X^2$ are C, $W^1$ is $CR^{3a}$, and $W^2$ is N; in yet another embodiment, $U^1$ and $W^2$ are each independently $CR^{3a}$, $U^2$ is S, $V^1$, $V^2$, $X^1$, and $X^2$ are C, $W^1$ is $NR^{3a}$; in yet another embodiment, $U^1$ is S, $U^2$ and $W^1$ are each independently $CR^{3a}$, $V^1$, $V^2$, $X^1$, and $X^2$ are C, $W^2$ is $NR^{3a}$; in yet another embodiment, $U^1$ and $W^2$ are each independently $CR^{3a}$, $U^2$ is O, $V^1$, $V^2$, $X^1$, and $X^2$ are C, $W^1$ is $NR^{3a}$; in yet another embodiment, $U^1$ and $W^2$ are N, $U^2$ and $W^1$ are S, $V^1$, $V^2$, $X^1$, and $X^2$ are C; in yet another embodiment, $U^1$ and $W^2$ are S, $U^2$ and $W^1$ are each independently $CR^{3a}$, $V^1$, $V^2$, $X^1$, and $X^2$ are C; in yet another embodiment, $U^1$ and $X^2$ are N, $U^2$ is $NR^{3a}$, $V^1$, $V^2$, and $X^1$ are C, and $W^1$ and $W^2$ are each independently $CR^{3a}$; in yet another embodiment, $U^1$ is S, $U^2$ is $NR^{3a}$, $V^1$, $V^2$, $X^1$, and $X^2$ are C, and $W^1$ and $W^2$ are each independently $CR^{3a}$; in still another embodiment, $U^1$, $W^2$, and $X^1$ are N, $U^2$ is $CR^{3a}$, $V^1$, $V^2$, and $X^2$ are C, and $W^1$ is S; wherein each $R^{3a}$ is as defined herein.

In Formula IX, X, Xa, Xb, or Xc, in one embodiment, $T^3$, $U^3$, $W^3$, and $X^3$ are each independently $CR^{3a}$, $V^3$ and $Y^3$ are C; in another embodiment, $T^3$ is a bond; in yet another embodiment, $T^3$ is a bond, $U^3$ is $NR^{3a}$, $V^3$ and $Y^3$ are C, $W^3$ is N, and $X^3$ is $CR^{3a}$; in yet another embodiment, $T^3$ is a bond, $U^3$, $W^3$, and $X^3$ are each independently $CR^{3a}$, $V^3$ is C, and $Y^3$ are N; in yet another embodiment, $T^3$ is a bond, $U^3$ is S, $V^3$ and $Y^3$ are C, $W^3$ is $CR^{3a}$, and $X^3$ is N; in yet another embodiment, $T^3$ is a bond, $U^3$ is S, $V^3$ and $Y^3$ are C, $W^3$ is N, and $X^3$ is $CR^{3a}$; in yet another embodiment, $T^3$ is a bond, $U^3$ is N, $V^3$ and $Y^3$ are C, $W^3$ is $NR^{3a}$, and $X^3$ is $CR^{3a}$; wherein each $R^{3a}$ is as defined herein.

In yet another embodiment, provided herein is a compound of Formula XI:

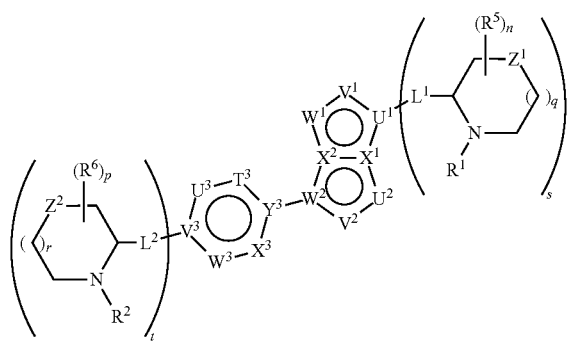

(XI)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In one embodiment, provided herein is a compound of Formula XIa:

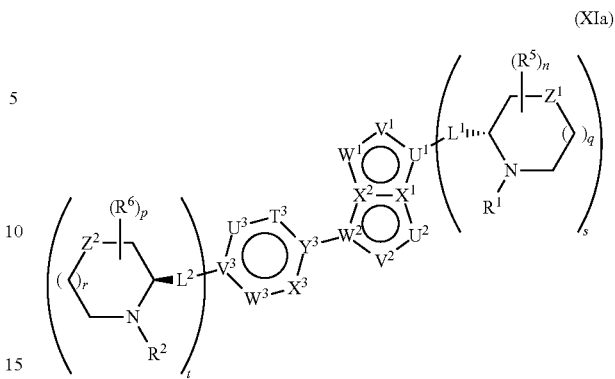

(XIa)

or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In another embodiment, provided herein is a compound of Formula XIb:

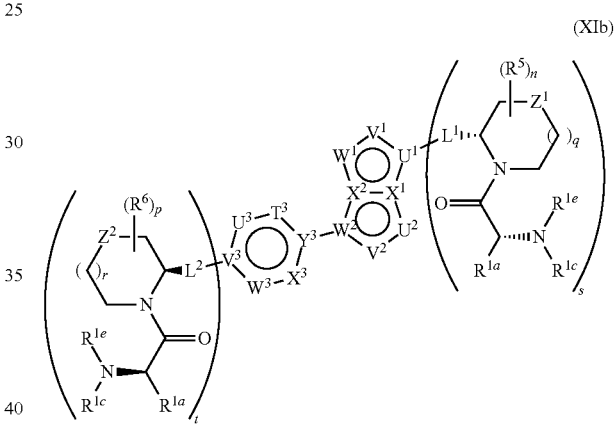

(XIb)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In yet another embodiment, provided herein is a compound of Formula XIc:

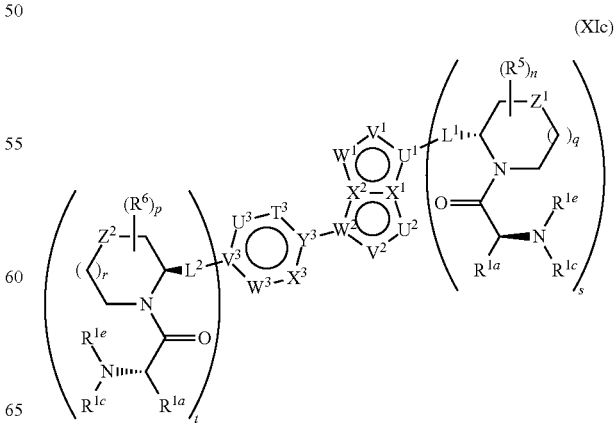

(XIc)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In IX, XI, XIa, XIb, or XIc, in one embodiment, $U^1$, $X^1$, and $X^2$ are C, $V^1$, $V^2$, $U^2$ are each independently $CR^{3a}$, $W^1$ is S, and $W^2$ is N; in another embodiment, $U^1$, $W^2$, $X^1$, and $X^2$ are C, $U^2$ and $W^1$ are S, and $V^1$ and $V^2$ are each independently $CR^{3a}$; in $X^1$, yet another embodiment, $U^1$, $W^2$, A and $X^2$ are C, $U^2$ is $NR^{3a}$, $V^1$ and $V^2$ are each independently $CR^{3a}$, and $W^1$ is S; in yet another embodiment, $U^1$, $W^2$, $X^1$, and $X^2$ are C, $U^2$ is $NR^{3a}$, $V^1$ and $V^2$ are each independently $CR^{3a}$, and $W^1$ is O; in yet another embodiment, $U^1$, $W^2$, $X^1$, and $X^2$ are C, $U^2$ is S, $V^1$ and $V^2$ are each independently $CR^{3a}$, and $W^1$ is $NR^{3a}$; in yet another embodiment, $U^1$ and $X^1$ are C, $U^2$, $V^1$, and $V^2$ are each independently $CR^{3a}$, $W^1$, $W^2$, and $X^2$ are N; in yet another embodiment, $U^1$, $W^2$, $X^1$, and $X^2$ are C, $U^2$ and $W^2$ are each independently $CR^{3a}$, $V^1$ and $V^2$ are N; in still another embodiment, $U^1$ is N, $U^2$ is S, $V^1$, $V^2$, and $W^1$ are each independently $CR^{3a}$, $W^2$, $X^1$, and $X^2$ are C; wherein each $R^{3a}$ is as defined herein.

In Formula IX, $X^1$, XIa, XIb, or XIc, in one embodiment, $T^3$, $U^3$, $W^3$, and $X^3$ are each independently $CR^{3a}$, $V^3$ and $Y^3$ are C; in another embodiment, $T^3$ is a bond; in yet another embodiment, $T^3$ is a bond, $U^3$ is $NR^{3a}$, $V^3$ and $Y^3$ are C, $W^3$ is N, and $X^3$ is $CR^{3a}$; in yet another embodiment, $T^3$ is a bond, $U^3$, $W^3$, and $X^3$ are each independently $CR^{3a}$, $V^3$ is C, and $Y^3$ are N; in yet another embodiment, $T^3$ is a bond, $U^3$ is S, $V^3$ and $Y^3$ are C, $W^3$ is $CR^{3a}$, and $X^3$ is N; in yet another embodiment, $T^3$ is a bond, $U^3$ is S, $V^3$ and $Y^3$ are C, $W^3$ is N, and $X^3$ is $CR^{3a}$; in yet another embodiment, $T^3$ is a bond, $U^3$ is N, $V^3$ and $Y^3$ are C, $W^3$ is $NR^{3a}$, and $X^3$ is $CR^{3a}$; wherein each $R^{3a}$ is as defined herein.

In yet another embodiment, provided herein is a compound of Formula XII:

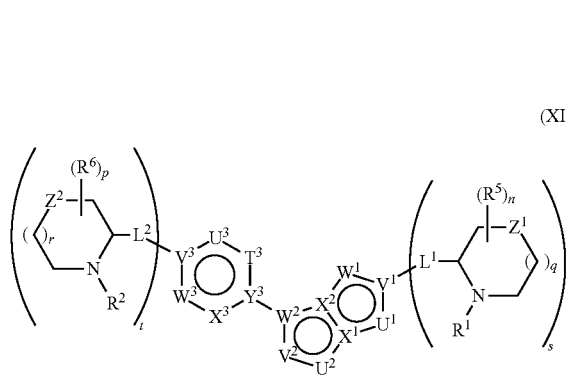

(XII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In one embodiment, provided herein is a compound of Formula XIIa:

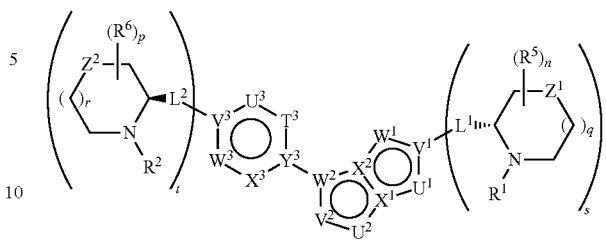

(XIIa)

or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In another embodiment, provided herein is a compound of Formula XIIb:

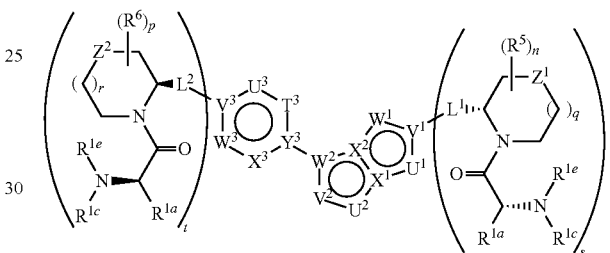

(XIIb)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In yet another embodiment, provided herein is a compound of Formula XIIc:

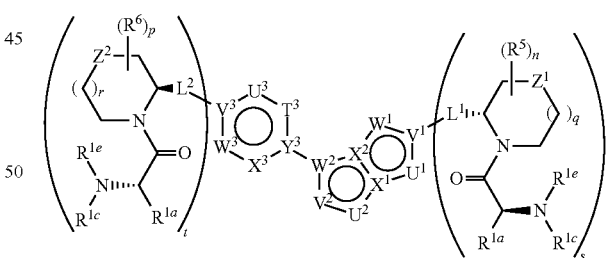

(XIIc)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In Formula IX, XII, XIIa, XIIb, or XIIc, in one embodiment, $U^1$ and $V^2$ are each independently $CR^{3a}$, $U^2$ and $W^1$ are S, and $V^1$, $W^2$, $X^1$, and $X^2$ are C; in another embodiment, $U^1$ and $V^2$ are each independently $CR^{3a}$, $U^2$ is S, $V^1$, $W^2$, $X^1$, and $X^2$ are C, and $W^1$ is $NR^{3a}$; in yet another embodiment, $U^1$ and $X^2$ are N, $U^2$ is S, $V^1$, $W^2$, and $X^1$ are C, and $V^2$ and $W^1$ are each independently $CR^{3a}$; wherein each $R^{3a}$ is as defined herein.

In Formula IX, XII, XIIa, XIIb, or XIIc, in one embodiment, $T^3$, $U^3$, $W^3$, and $X^3$ are each independently $CR^{3a}$, $V^3$ and $Y^3$ are C; in another embodiment, $T^3$ is a bond; in yet another embodiment, $T^3$ is a bond, $U^3$ is $NR^{3a}$, $V^3$ and $Y^3$ are C, $W^3$ is N, and $X^3$ is $CR^{3a}$; in yet another embodiment, $T^3$ is a bond, $U^3$, $W^3$, and $X^3$ are each independently $CR^{3a}$, $V^3$ is C, and $Y^3$ are N; in yet another embodiment, $T^3$ is a bond, $U^3$ is S, $V^3$ and $Y^3$ are C, $W^3$ is $CR^{3a}$, and $X^3$ is N; in yet another embodiment, $T^3$ is a bond, $U^3$ is S, $V^3$ and $Y^3$ are C, $W^3$ is N, and $X^3$ is $CR^{3a}$; in yet another embodiment, $T^3$ is a bond, $U^3$ is N, $V^3$ and $Y^3$ are C, $W^3$ is $NR^{3a}$, and $X^3$ is $CR^{3a}$; wherein each $R^{3a}$ is as defined herein.

In yet another embodiment, provided herein is a compound of Formula XIII:

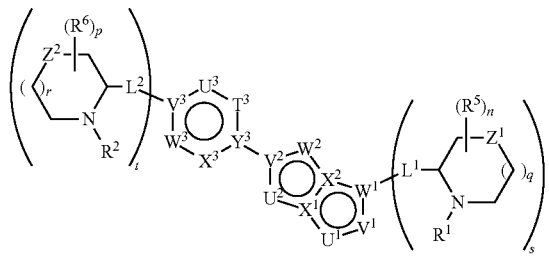

(XIII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In one embodiment, provided herein is a compound of Formula XIIIa:

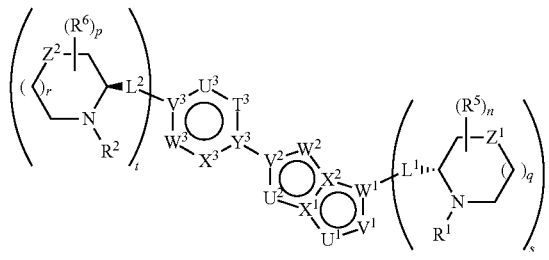

(XIIIa)

or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In another embodiment, provided herein is a compound of Formula XIIIb:

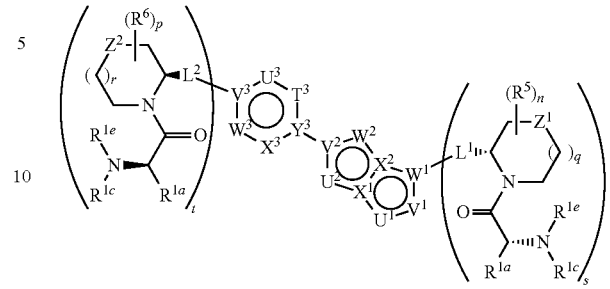

(XIIIb)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In yet another embodiment, provided herein is a compound of Formula XIIIc:

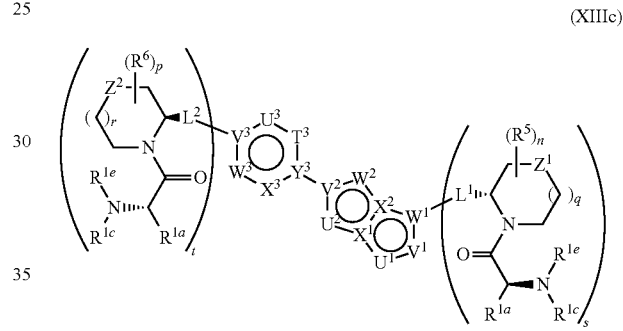

(XIIIc)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In Formula IX, XIII, XIIIa, XIIIb, or XIIIc, in one embodiment, $U^1$ and $W^2$ are S, $U^2$ and $V^1$ are each independently $CR^{3a}$, and $V^2$, $W^1$, $X^1$, and $X^2$ are C; in another embodiment, $U^1$ is S, $U^2$ and $X^2$ are N, $V^1$ and $W^2$ are each independently $CR^{3a}$, and $V^2$, $W^1$, and $X^1$ are C; in yet another embodiment, $U^1$ is S, $U^2$ and $V^1$ are each independently $CR^{3a}$, $V^2$, $W^1$, $X^1$, and $X^2$ are C; and $W^2$ is $NR^{3a}$; wherein each $R^{3a}$ is as defined herein.

In Formula IX, XIII, XIIIa, XIIIb, or XIIIc, in one embodiment, $T^3$, $U^3$, $W^3$, and $X^3$ are each independently $CR^{3a}$, $V^3$ and $Y^3$ are C; in another embodiment, $T^3$ is a bond; in yet another embodiment, $T^3$ is a bond, $U^3$ is $NR^{3a}$, $V^3$ and $Y^3$ are C, $W^3$ is N, and $X^3$ is $CR^{3a}$; in yet another embodiment, $T^3$ is a bond, $U^3$, $W^3$, and $X^3$ are each independently $CR^{3a}$, $V^3$ is C, and $Y^3$ are N; in yet another embodiment, $T^3$ is a bond, $U^3$ is S, $V^3$ and $Y^3$ are C, $W^3$ is $CR^{3a}$, and $X^3$ is N; in yet another embodiment, $T^3$ is a bond, $U^3$ is S, $V^3$ and $Y^3$ are C, $W^3$ is N, and $X^3$ is $CR^{3a}$; in yet another embodiment, $T^3$ is a bond, $U^3$ is N, $V^3$ and $Y^3$ are C, $W^3$ is $NR^{3a}$, and $X^3$ is $CR^{3a}$; wherein each $R^{3a}$ is as defined herein.

In yet another embodiment, provided herein is a compound of Formula XIV:

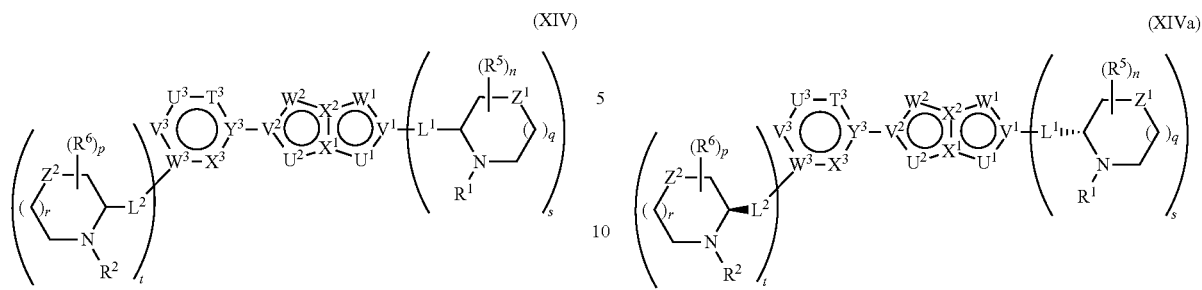

(XIV)

(XIVa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In one embodiment, provided herein is a compound of Formula XIVa:

or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In another embodiment, provided herein is a compound of Formula XIVb:

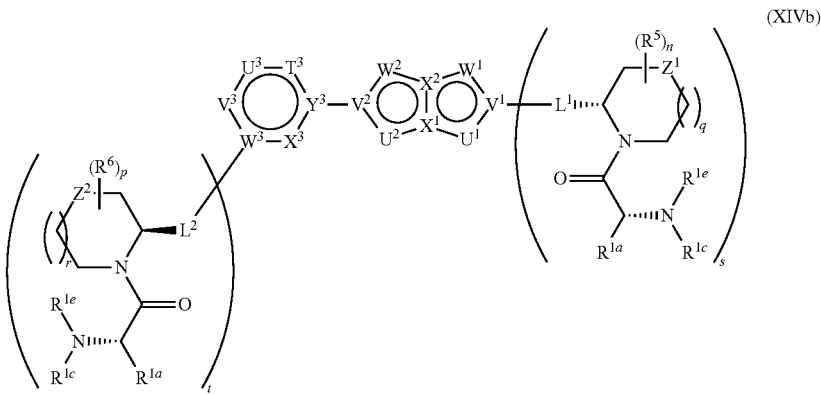

(XIVb)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In yet another embodiment, provided herein is a compound of Formula XIVc:

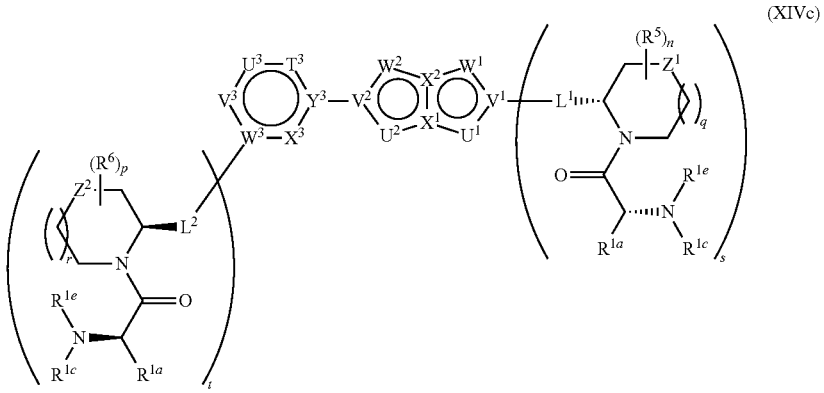

(XIVc)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In Formula IX, XIV, XIVa, XIVb, or XIVc, in one embodiment, $U^1$ and $X^2$ are N, $U^2$ is S, $V^1$, $V^2$, and $X^1$ are C, and $W^1$ and $W^2$ are each independently $CR^{3a}$; in another embodiment, $U^1$ is S, $U^2$ and $X^2$ are N, $V^1$, $V^2$, and $X^1$ are C, and $W^1$ and $W^2$ are each independently $CR^{3a}$; in yet another embodiment, $U^1$ and $X^2$ are N, $U^2$ is O, $V^1$, $V^2$, and $X^1$ are C, and $W^1$ and $W^2$ are each independently $CR^{3a}$; in yet another embodiment, $U^1$ is O, $U^2$ and $X^2$ are N, $V^1$, $V^2$, and $X^1$ are C, and $W^1$ and $W^2$ are each independently $CR^{3a}$; in yet another embodiment, $U^1$ is $NR^{3a}$, $U^2$ is S, $V^1$, $V^2$, $X^1$, and $X^2$ are C, $W^1$ is $CR^{3a}$, and $W^2$ is N; in yet another embodiment, $U^1$ and $W^2$ are each independently $CR^{3a}$, $U^2$ is S, $V^1$, $V^2$, $X^1$, and $X^2$ are C, $W^1$ is $NR^{3a}$; in yet another embodiment, $U^1$ is S, $U^2$ and $W^1$ are each independently $CR^{3a}$, $V^1$, $V^2$, $X^1$, and $X^2$ are C, $W^2$ is $NR^{3a}$; in yet another embodiment, $U^1$ and $W^2$ are each independently $CR^{3a}$, $U^2$ is O, $V^1$, $V^2$, $X^1$, and $X^2$ are C, $W^1$ is $NR^{3a}$; in yet another embodiment, $U^1$ and $W^2$ are N, $U^2$ and $W^1$ are S, $V^1$, $V^2$, $X^1$, and $X^2$ are C; in yet another embodiment, $U^1$ and $W^2$ are S, $U^2$ and $W^1$ are each independently $CR^{3a}$, $V^1$, $V^2$, $X^1$, and $X^2$ are C; in yet another embodiment, $U^1$ and $X^2$ are N, $U^2$ is $NR^{3a}$, $V^1$, $V^2$, and $X^1$ are C, and $W^1$ and $W^2$ are each independently $CR^{3a}$; in yet another embodiment, $U^1$ is S, $U^2$ is $NR^{3a}$, $V^1$, $V^2$, $X^1$, and $X^2$ are C, and $W^1$ and $W^2$ are each independently $CR^{3a}$; in still another embodiment, $U^1$, $W^2$, and $X^1$ are N, $U^2$ is $CR^{3a}$, $V^1$, $V^2$, and $X^2$ are C, and $W^1$ is S; wherein each $R^{3a}$ is as defined herein.

In Formula IX, XIV, XIVa, XIVb, or XIVc, in one embodiment, $T^3$, $U^3$, $V^3$, and $X^3$ are each independently $CR^{3a}$, $W^3$ and $Y^3$ are C; in another embodiment, $T^3$ is a bond; wherein each $R^{3a}$ is as defined herein.

In yet another embodiment, provided herein is a compound of Formula XV:

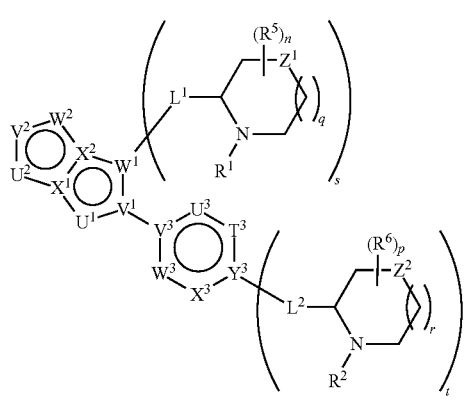

(XV)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In one embodiment, provided herein is a compound of Formula XVa:

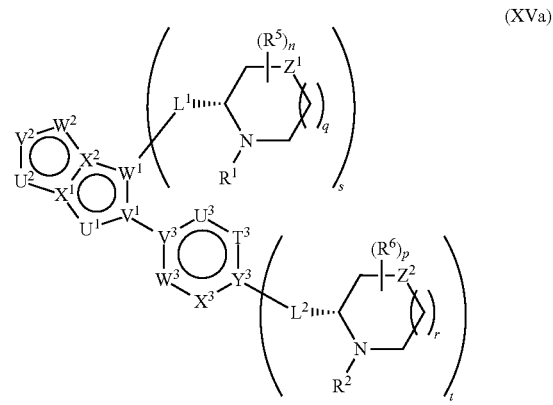

(XVa)

or an isotopic variant thereof; or a pharmaceutically acceptable salt, solvate, or prodrug thereof; wherein $R^1$, $R^2$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In another embodiment, provided herein is a compound of Formula XVb:

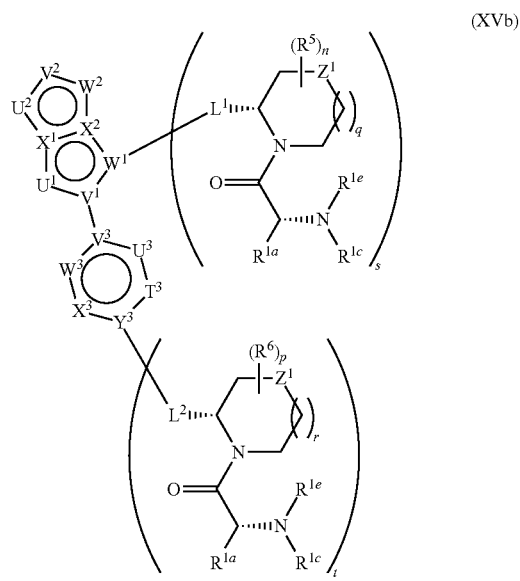

(XVb)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In yet another embodiment, provided herein is a compound of Formula XVc:

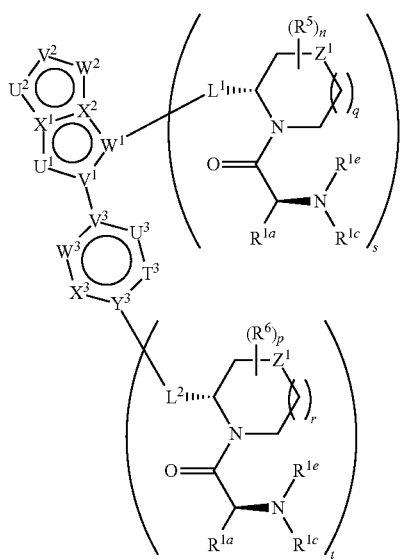

(XVc)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, n, p, q, r, s, and t are each as defined herein.

In Formula IX, XV, XVa, XVb, or XVc, in one embodiment, $U^1$ and $X^2$ are N, $U^2$ is S, $V^1$, $W^1$, and $X^1$ are C, and $V^2$ and $W^2$ are each independently $CR^{3a}$; in another embodiment, $U^1$ is S, $U^2$ and $X^2$ are N, $V^1$, $W^1$, and $X^1$ are C, and $V^2$ and $W^2$ are each independently $CR^{3a}$, wherein each $R^{3a}$ is as defined herein.

In Formula IX, XV, XVa, XVb, or XVc, in one embodiment, $T^3$, $U^3$, $W^3$, and $X^3$ are each independently $CR^{3a}$, $V^3$ and $Y^3$ are C; in another embodiment, $T^3$ is a bond; in yet another embodiment, $T^3$ is a bond, $U^3$ is $NR^{3a}$, $V^3$ and $Y^3$ are C, $W^3$ is N, and $X^3$ is $CR^{3a}$; in yet another embodiment, $T^3$ is a bond, $U^3$, $W^3$, and $X^3$ are each independently $CR^{3a}$, $V^3$ is C, and $Y^3$ are N; in yet another embodiment, $T^3$ is a bond, $U^3$ is S, $V^3$ and $Y^3$ are C, $W^3$ is $CR^{3a}$, and $X^3$ is N; in yet another embodiment, $T^3$ is a bond, $U^3$ is S, $V^3$ and $Y^3$ are C, $W^3$ is N, and $X^3$ is $CR^{3a}$; in yet another embodiment, $T^3$ is a bond, $U^3$ is N, $V^3$ and $Y^3$ are C, $W^3$ is $NR^{3a}$, and $X^3$ is $CR^{3a}$; wherein each $R^{3a}$ is as defined herein.

In yet another embodiment, provided herein is a compound of Formula XVI:

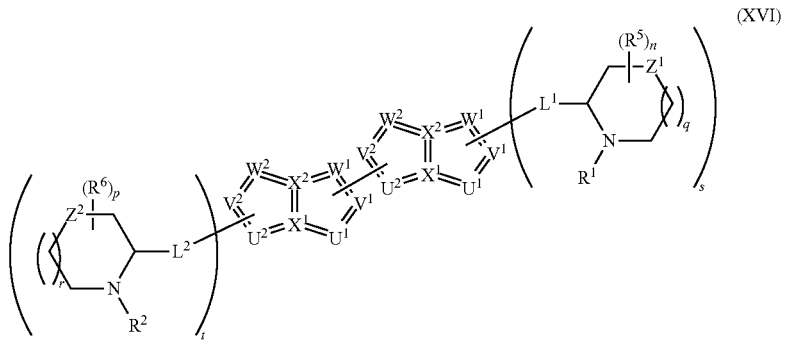

(XVI)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In yet another embodiment, provided herein is a compound of Formula XVII:

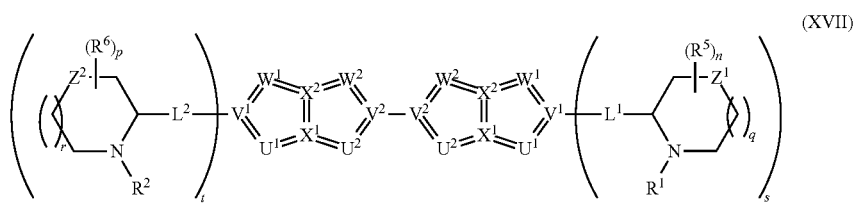

(XVII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In one embodiment, provided herein is a compound of Formula XVIIa:

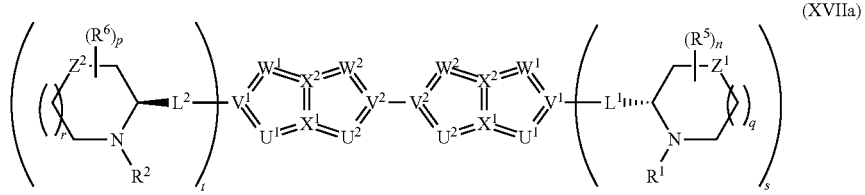

(XVIIa)

or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In another embodiment, provided herein is a compound of Formula XVIIb:

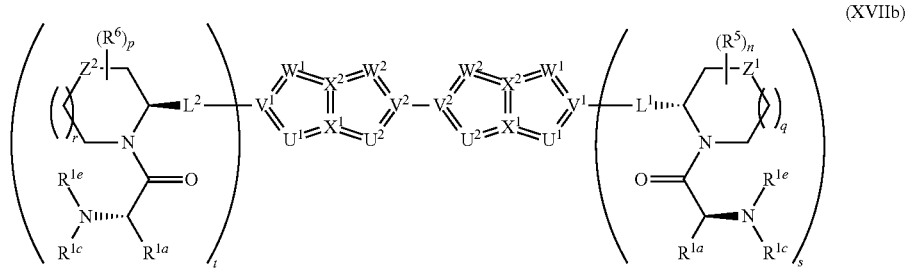

(XVIIb)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In yet another embodiment, provided herein is a compound of Formula XVIIIc:

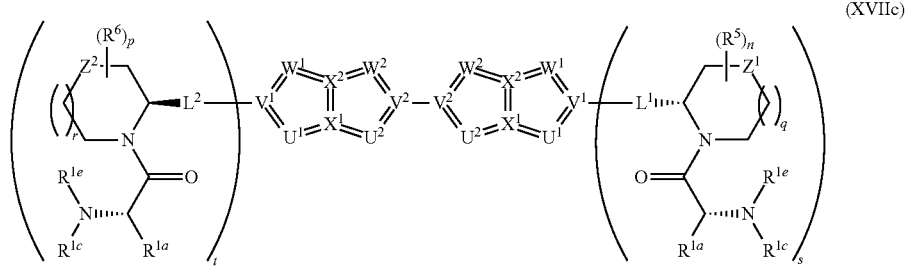

(XVIIc)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In Formula II, XVI, XVII, XVIIa, XVIIb, or XVIIc, in one embodiment, $U^1$ and $X^2$ are N, $U^2$ is S, $W^1$ and $W^2$ are CH, and $V^1$, $V^2$, and $X^1$ are C; in another embodiment, $U^1$ is S, $U^2$ and $X^2$ are N, $W^1$ and $W^2$ are CH, and $V^1$, $V^2$, and $X^1$ are C; in yet another embodiment, $U^1$ and $X^2$ are N, $U^2$ is O, $W^1$ and $W^2$ are CH, and $V^1$, $V^2$, and $X^1$ are C; in yet another embodiment, $U^1$ is O, $U^2$ and $X^2$ are N, $W^1$ and $W^2$ are CH, and $V^1$, $V^2$, and $X^1$ are C; in yet another embodiment, $U^1$ is S, $U^2$ and $W^1$ are CH, $W^2$ is $NR^{3a}$, and $V^1$, $V^2$, $X^1$, and $X^2$ are C; in yet another embodiment, $U^1$ is $NR^{3a}$, $U^2$ and $W^1$ are CH, $W^2$ is S, and $V^1$, $V^2$, $X^1$, and $X^2$ are C; in yet another embodiment, $U^1$ is $NR^{3a}$, $U^2$ is S, $W^1$ is CH, $W^2$ is N, and $V^1$, $V^2$, $X^1$, and $X^2$ are C; in still another embodiment, $U^1$ is S, $U^2$ is $NR^{3a}$, $W^1$ is N, $W^2$ is CH, and $V^1$, $V^2$, $X^1$, and $X^2$ are C; where each $R^{3a}$ is as defined herein.

In Formula II, XVI, XVII, XVIIa, XVIIb, or XVIIc, in one embodiment, $U^1$ and $X^2$ are N, $U^2$ is S, $V^1$, $V^2$, and $X^1$ are C, and $W^1$ and $W^2$ are each independently $CR^{3a}$; in another embodiment, $U^1$ is S, $U^2$ and $X^2$ are N, $V^1$, $V^2$, and $X^1$ are C, and $W^1$ and $W^2$ are each independently $CR^{3a}$; in yet another embodiment, $U^1$ and $X^2$ are N, $U^2$ is O, $V^1$, $V^2$, and $X^1$ are C, and $W^1$ and $W^2$ are each independently $CR^{3a}$; in yet another embodiment, $U^1$ is O, $U^2$ and $X^2$ are N, $V^1$, $V^2$, and $X^1$ are C, and $W^1$ and $W^2$ are each independently $CR^{3a}$; in yet another embodiment, $U^1$ is $NR^{3a}$, $U^2$ is S, $V^1$, $V^2$, $X^1$, and $X^2$ are C, $W^1$ is $CR^{3a}$, and $W^2$ is N; in yet another embodiment, $U^1$ and $W^2$ are each independently $CR^{3a}$, $U^2$ is S, $V^1$, $V^2$, $X^1$, and $X^2$ are C, $W^1$ is $NR^{3a}$; in yet another embodiment, $U^1$ is S, $U^2$ and $W^1$ are each independently $CR^{3a}$, $V^1$, $V^2$, $X^1$, and $X^2$ are C, $W^2$ is $NR^{3a}$; in yet another embodiment, $U^1$ and $W^2$ are each independently $CR^{3a}$, $U^2$ is O, $V^1$, $V^2$, $X^1$, and $X^2$ are C, $W^1$ is $NR^{3a}$; in yet another embodiment, $U^1$ and $W^2$ are N, $U^2$ and $W^1$ are S, $V^1$, $V^2$, $X^1$, and $X^2$ are C; in yet another embodiment, $U^1$ and $W^2$ are S, $U^2$ and $W^1$ are each independently $CR^{3a}$, $V^1$, $V^2$, $X^1$, and $X^2$ are C; in yet another embodiment, $U^1$ and $X^2$ are N, $U^2$ is $NR^{3a}$, $V^1$, $V^2$, and $X^1$ are C, and $W^1$ and $W^2$ are each independently $CR^{3a}$; in yet another embodiment, $U^1$ is S, $U^2$ is $NR^{3a}$, $V^1$, $V^2$, $X^1$, and $X^2$ are C, and $W^1$ and $W^2$ are each independently $CR^{3a}$; in still another embodiment, $U^1$, $W^2$, and $X^1$ are N, $U^2$ is $CR^{3a}$, $V^1$, $V^2$, and $X^2$ are C, and $W^1$ is S; wherein each $R^{3a}$ is as defined herein.

In yet another embodiment, provided herein is a compound of Formula XVIII:

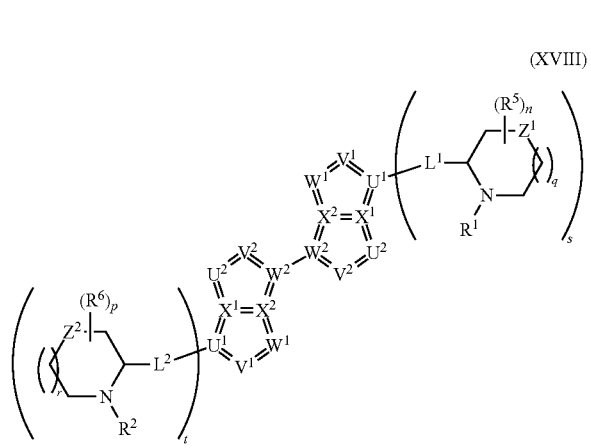

(XVIII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In yet another embodiment, provided herein is a compound of Formula XVIIIa:

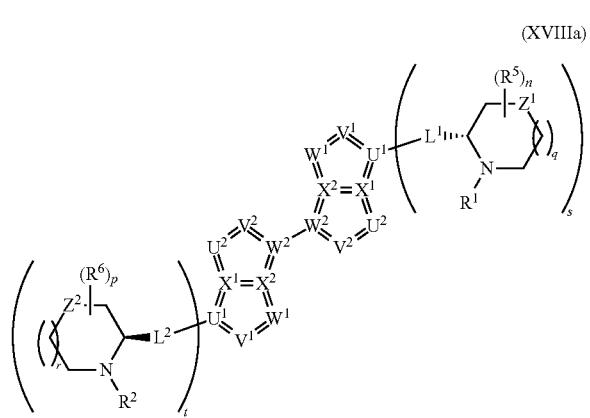

(XVIIIa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In another embodiment, provided herein is a compound of Formula XVIIIb:

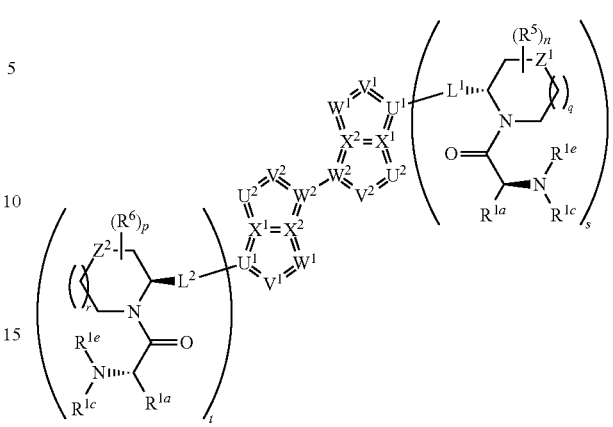

(XVIIIb)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In yet another embodiment, provided herein is a compound of Formula XVIIIc:

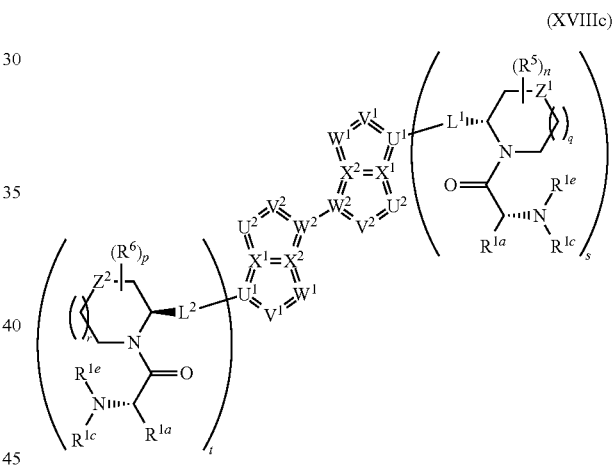

(XVIIIc)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In Formula II, XVI, XVIII, XVIIIa, XVIIIb, or XVIIIc, in one embodiment, $U^1$, $W^2$, $X^1$, and $X^2$ are C, $U^2$ and $W^1$ are S, and $V^1$ and $V^2$ are CH; in another embodiment, $U^1$, $W^2$, $X^1$, and $X^2$ are C, $U^2$ and $W^1$ are CH, and $V^1$ and $V^2$ are N; in yet another embodiment, $U^1$, $X^1$, and $X^2$ are C, $U^2$, $V^1$, and $V^2$ are CH, $W^1$ is S, and $W^2$ is N; in still another embodiment, $U^1$ is N, $U^2$ is S, $V^1$, $V^2$, and $W^1$ are CH, and $W^2$, $X^1$, and $X^2$ are C.

In Formula II, XVI, XVIII, XVIIIa, XVIIIb, or XVIIIc, in one embodiment, $U^1$, $X^1$, and $X^2$ are C, $V^1$, $V^2$, $U^2$ are each independently $CR^{3a}$, $W^1$ is S, and $W^2$ is N; in another embodiment, $U^1$, $W^2$, $X^1$, and $X^2$ are C, $U^2$ and $W^1$ are S, and $V^1$ and $V^2$ are each independently $CR^{3a}$; in yet another embodiment, $U^1$, $W^2$, $X^1$, and $X^2$ are C, $U^2$ is $NR^{3a}$, $V^1$ and $V^2$ are each independently $CR^{3a}$, and $W^1$ is S; in yet another embodiment, $U^1$, $W^2$, $X^1$, and $X^2$ are C, $U^2$ is $NR^{3a}$, $V^1$ and $V^2$ are each independently $CR^{3a}$, and $W^1$ is O; in yet another embodiment, $U^1$, $W^2$, $X^1$, and $X^2$ are C, $U^2$ is S, $V^1$ and $V^2$ are each independently $CR^{3a}$, and $W^1$ is $NR^{3a}$; in yet another embodiment, $U^1$ and $X^1$ are C, $U^2$, $V^1$, and $V^2$ are each independently $CR^{3a}$, $W^1$, $W^2$, and $X^2$ are N; in yet another embodiment, $U^1$, $W^2$, $X^1$, and $X^2$ are C, $U^2$ and $W^2$ are each independently $CR^{3a}$, $V^1$ and $V^2$ are N; in still another embodiment, $U^1$ is N, $U^2$ is S, $V^1$, $V^2$, and $W^1$ are each independently $CR^{3a}$, $W^2$, $X^1$, and $X^2$ are C; wherein each $R^{3a}$ is as defined herein.

In yet another embodiment, provided herein is a compound of Formula XIX:

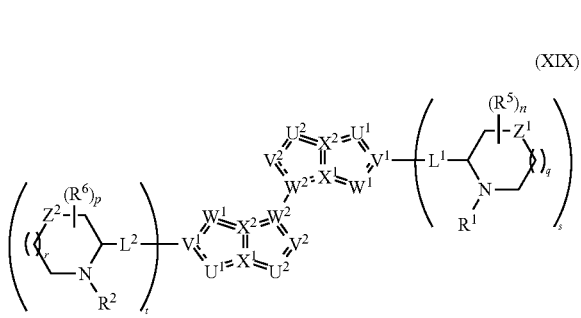

(XIX)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In yet another embodiment, provided herein is a compound of Formula XIXa:

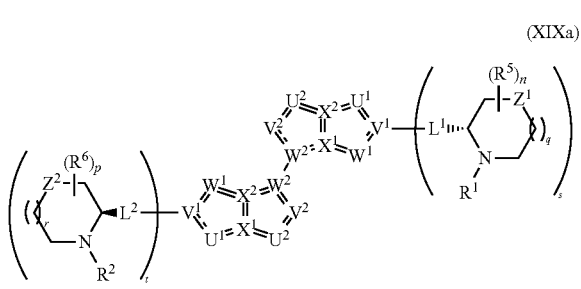

(XIXa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In another embodiment, provided herein is a compound of Formula XIXb:

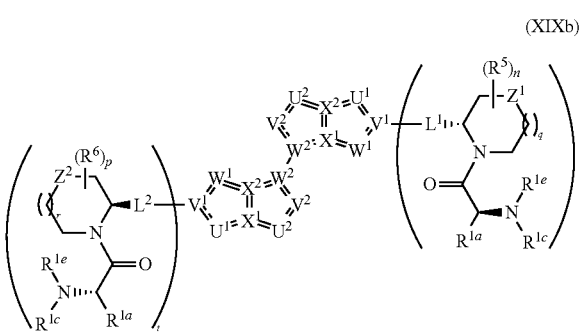

(XIXb)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In yet another embodiment, provided herein is a compound of Formula XIXc:

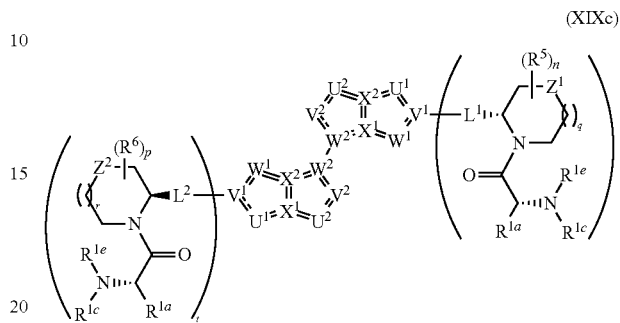

(XIXc)

or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, and t are each as defined herein.

In Formula II, XVI, XIX, XIXa, XIXb, or XIXc, in one embodiment, $U^1$ is S, $U^2$, $V^2$, and $W^1$ are CH, $V^1$, $X^1$, and $X^2$ are C, and $W^2$ is N; in another embodiment, $U^1$ and $V^2$ are CH, $U^2$ and $W^1$ are S, and $V^1$, $W^2$, $X^1$, and $X^2$ are C.

In Formula II, XVI, XIX, XIXa, XIXb, or XIXc, in one embodiment, $U^1$ and $V^2$ are each independently $CR^{3a}$, $U^2$ and $W^1$ are S, and $V^1$, $W^2$, $X^1$, and $X^2$ are C; in another embodiment, $U^1$ and $V^2$ are each independently $CR^{3a}$, $U^2$ is S, $V^1$, $W^2$, $X^1$, and $X^2$ are C, and $W^1$ is $NR^{3a}$; in yet another embodiment, $U^1$ and $X^2$ are N, $U^2$ is S, $V^1$, $W^2$, and $X^1$ are C, and $V^2$ and $W^1$ are each independently $CR^{3a}$; wherein each $R^{3a}$ is as defined herein.

In yet another embodiment, provided herein is a compound of Formula XX:

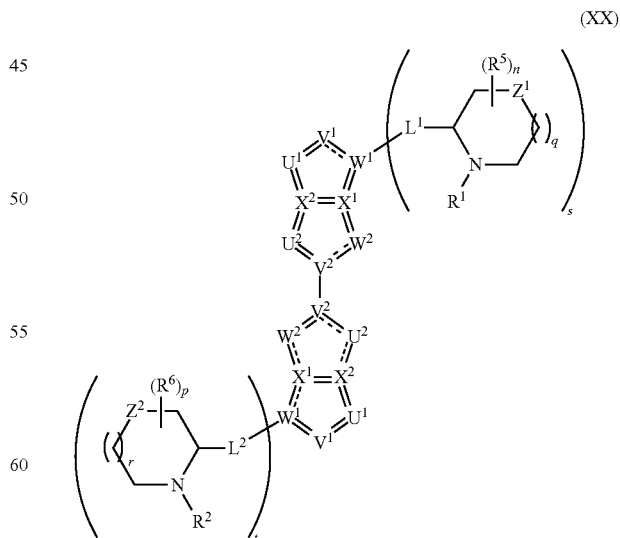

(XX)

or a single enantiomer, a racemic mixture, a mixture of diastereomers, or an isotopic variant thereof; or a pharmaceutically acceptable salt, solvate, or prodrug thereof; wherein $R^1$, $R^2, R^5, R^6, L^1, L^2, U^1, U^2, V^1, V^2, W^1, W^2, X^1, X^2, Z^1, Z^2$, n, p, q, r, s, and t are each as defined herein.

In one embodiment, provided herein is a compound of Formula XXa:

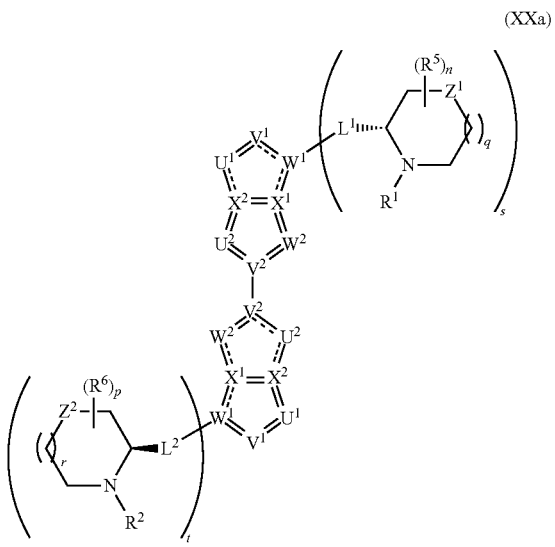

(XXa)

or an isotopic variant thereof; or a pharmaceutically acceptable salt, solvate, or prodrug thereof; wherein $R^1, R^2, R^5, R^6, L^1, L^2, U^1, U^2, V^1, V^2, W^1, W^2, X^1, X^2, Z^1, Z^2$, n, p, q, r, s, and t are each as defined herein.

In another embodiment, provided herein is a compound of Formula XIb:

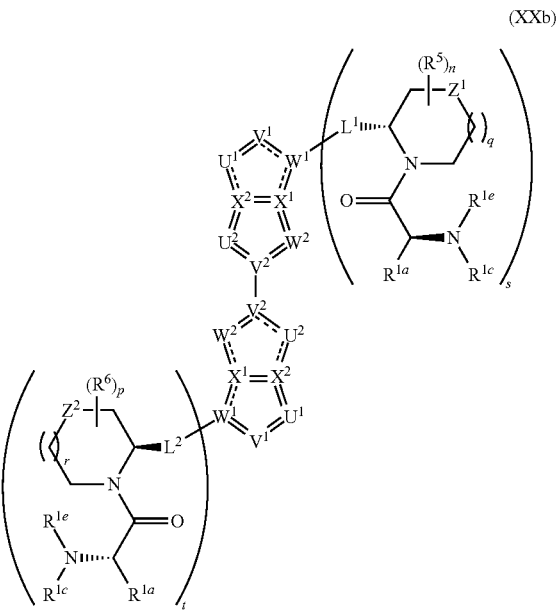

(XXb)

or an isotopic variant thereof; or a pharmaceutically acceptable salt, solvate, or prodrug thereof; wherein $R^{1a}, R^{1c}, R^{1e}, R^5, R^6, L^1, L^2, U^1, U^2, V^1, V^2, W^1, W^2, X^1, X^2, Z^1, Z^2$, n, p, q, r, s, and t are each as defined herein.

In yet another embodiment, provided herein is a compound of Formula XXc:

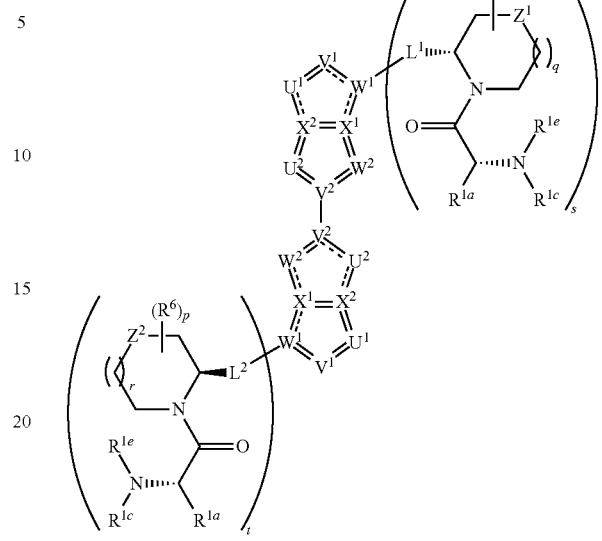

(XXc)

or an isotopic variant thereof; or a pharmaceutically acceptable salt, solvate, or prodrug thereof; wherein $R^{1a}, R^{1c}, R^{1e}, R^5, R^6, L^1, L^2, U^1, U^2, V^1, V^2, W^1, W^2, X^1, X^2, Z^1, Z^2$, n, p, q, r, s, and t are each as defined herein.

In Formula II, XVI, XX, XXa, XXb, or XXc, in one embodiment, $U^1, V^1$, and $W^2$ are CH, $U^2$ is S, $V^2, X^1$, and $X^2$ are C, and $W^1$ is N; in another embodiment, $U^1$ and $W^2$ are S, $U^2$ and $V^1$ are CH, and $V^2, W^1, X^1$, and $X^2$ are C.

In Formula II, XVI, XX, XXa, XXb, or XXc, in one embodiment, $U^1$ and $W^2$ are S, $U^2$ and $V^1$ are each independently $CR^{3a}$, and $V^2, W^1, X^1$, and $X^2$ are C; in another embodiment, $U^1$ is S, $U^2$ and $X^2$ are N, $V^1$ and $W^2$ are each independently $CR^{3a}$, and $V^2, W^1$, and $X^1$ are C; in yet another embodiment, $U^1$ is S, $U^2$ and $V^1$ are each independently $CR^{3a}$, $V^2, W^1, X^1$, and $X^2$ are C; and $W^2$ is $NR^{3a}$; wherein each $R^{3a}$ is as defined herein.

In another embodiment, each divalent moiety

is independently selected from the group consisting of:

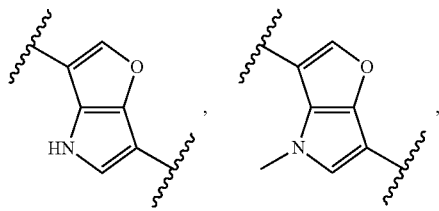

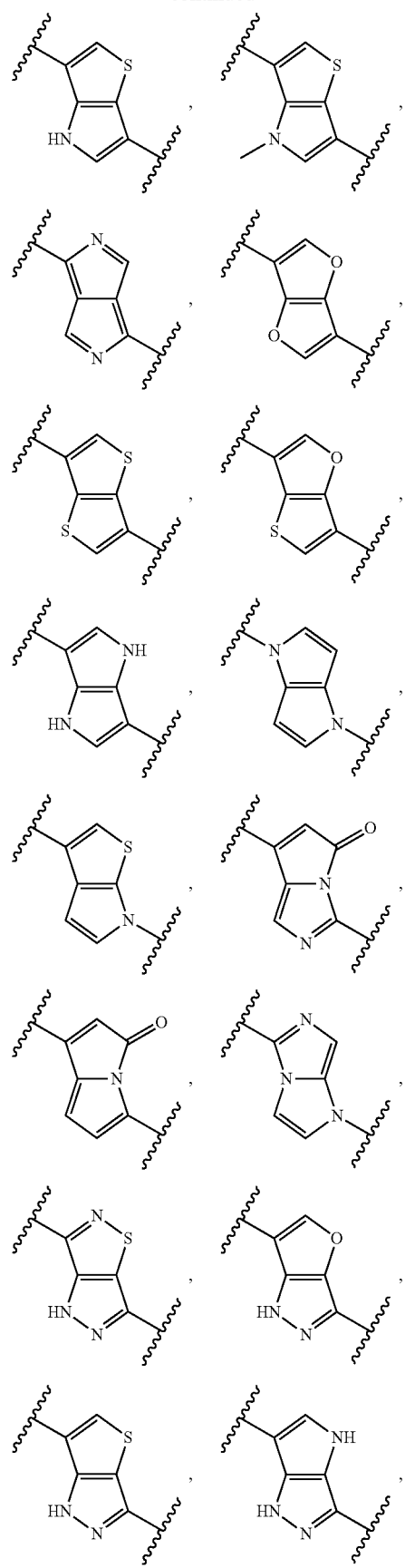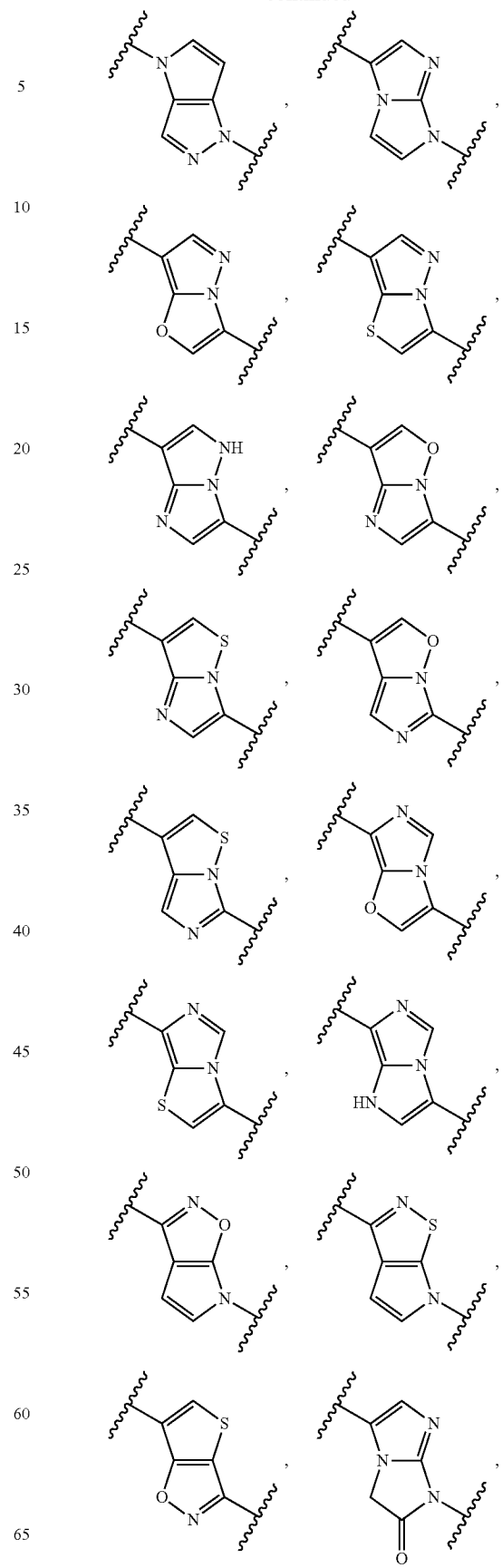

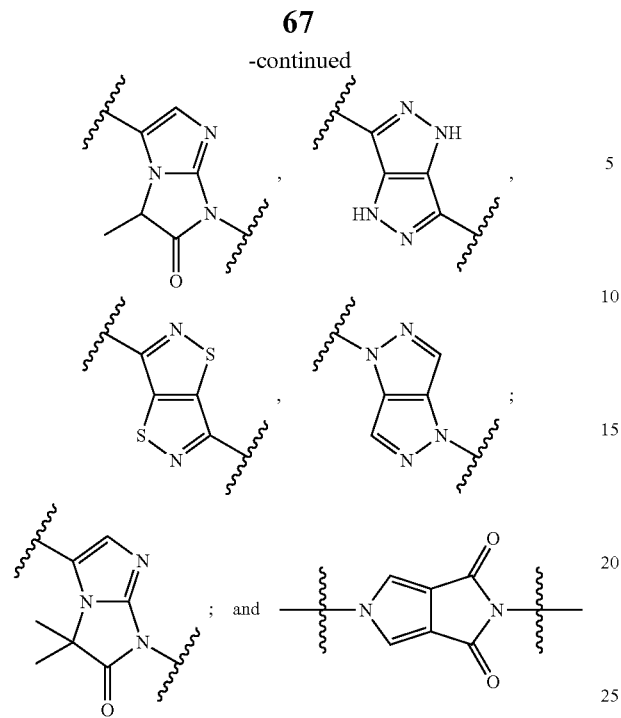

wherein each divalent moiety is optionally substituted with one, two, three, or four $R^3$ groups.

In yet another embodiment, provided herein is a compound of Formula XXI:

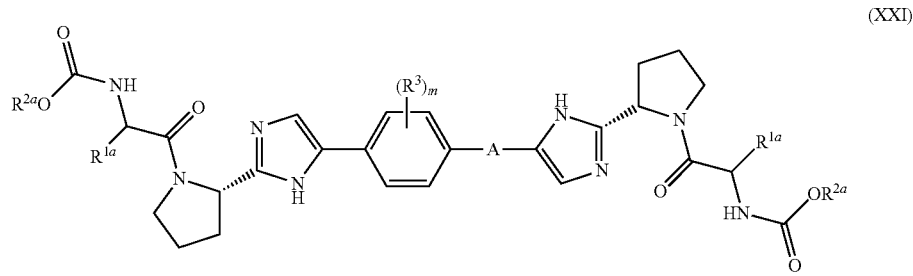

(XXI)

or an isotopic variant thereof; or a pharmaceutically acceptable salt, solvate, or prodrug thereof; wherein $R^{1a}$, $R^3$, A, and m are each as defined herein; each $R^{2a}$ is independently (i) hydrogen; or (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more, in one embodiment, one, two, or three substituents Q.

In yet another embodiment, provided herein is a compound of Formula XXII:

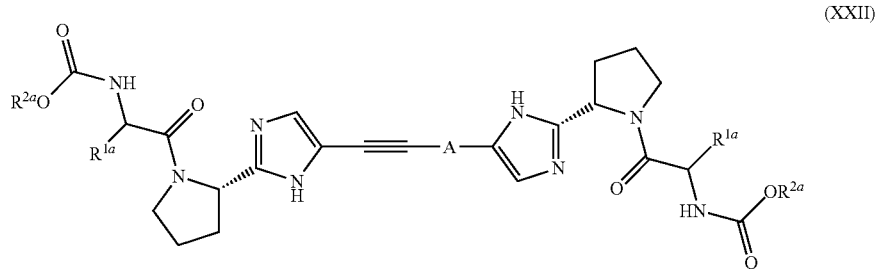

(XXII)

or an isotopic variant thereof; or a pharmaceutically acceptable salt, solvate, or prodrug thereof; wherein $R^{1a}$, $R^{2a}$, $R^3$, A and m are each as defined herein.

In one embodiment, A in Formula XXI or XXII is selected from:

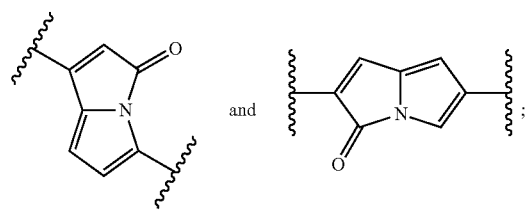 [SMILES: *C1=CC(=O)n2c(*)ccc21 ; *C1=Cc2cc(*)cn2C1=O]

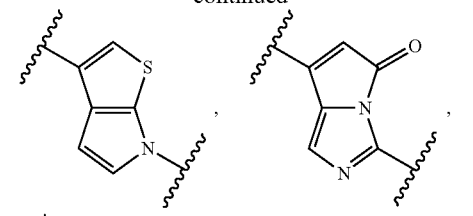

wherein each divalent moiety is optionally substituted with one, two, three, or four, in one embodiment, one or two, $R^3$ groups, where $R^3$ is as defined herein. In certain embodiments, each $R^3$ is independently oxo, chloro, fluoro, nitro, amino, methyl, trifluoromethyl, cyclohexyl, phenyl, or methoxy.

In another embodiment, A in Formula XXI or XXII is selected from:

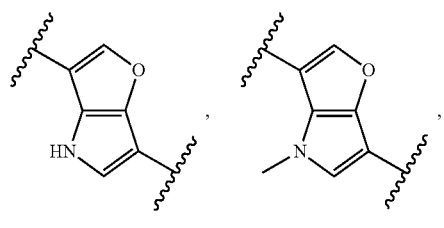

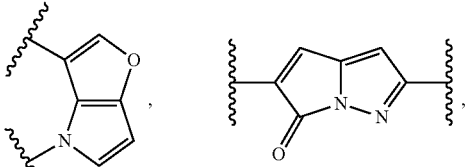

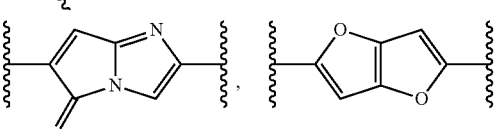

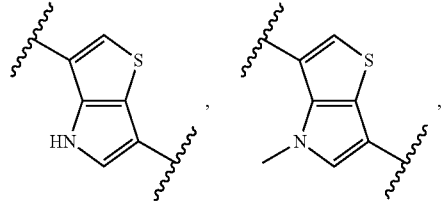

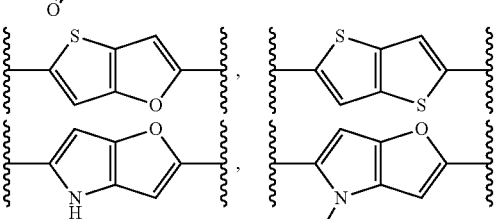

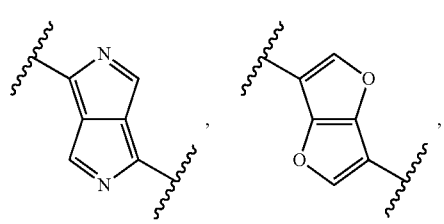

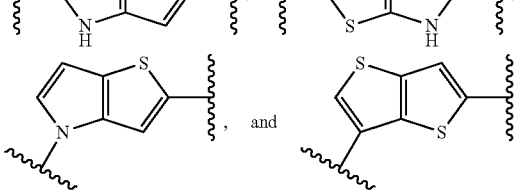

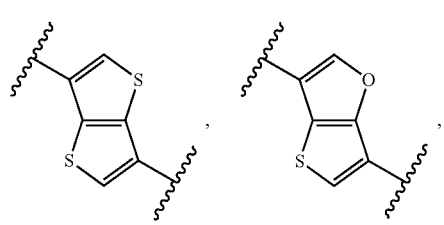

wherein each divalent moiety is optionally substituted with one, two, three, or four, in one embodiment, one or two, $R^3$ groups, where $R^3$ is as defined herein. In certain embodiments, each $R^3$ is independently oxo, chloro, fluoro, nitro, amino, methyl, trifluoromethyl, cyclohexyl, phenyl, or methoxy.

In yet another embodiment, A in Formula XXI or XXII is selected from:

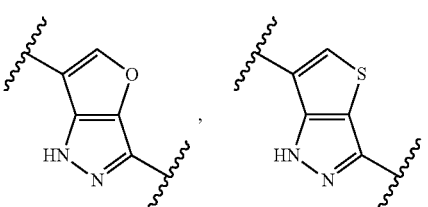

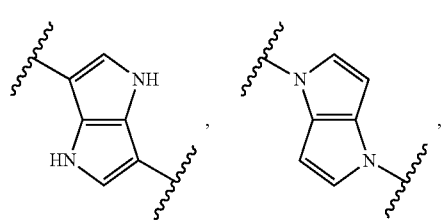

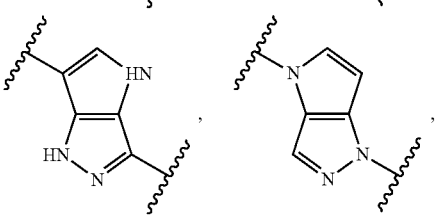

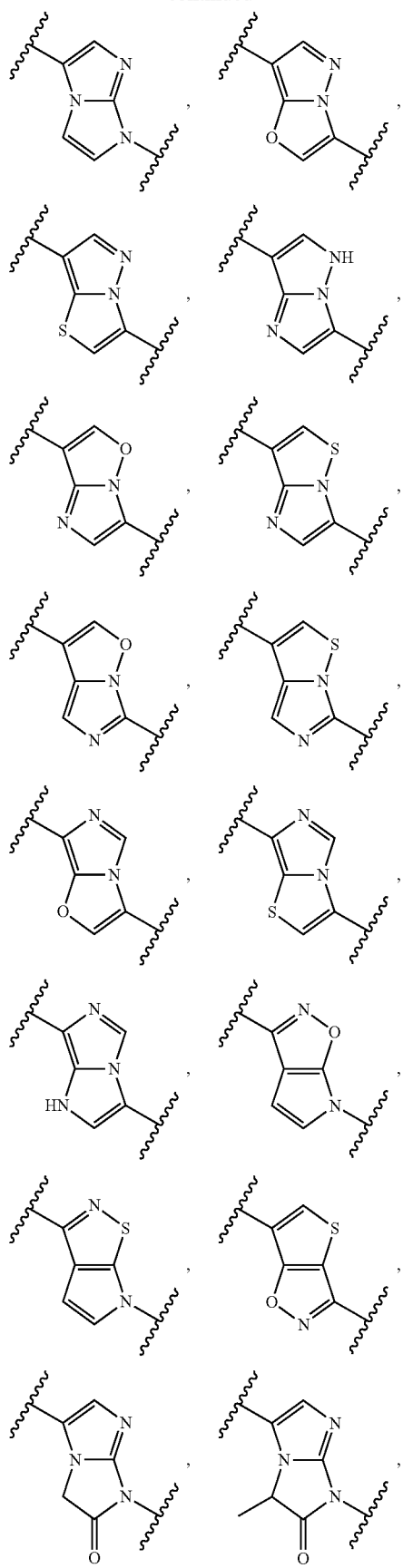
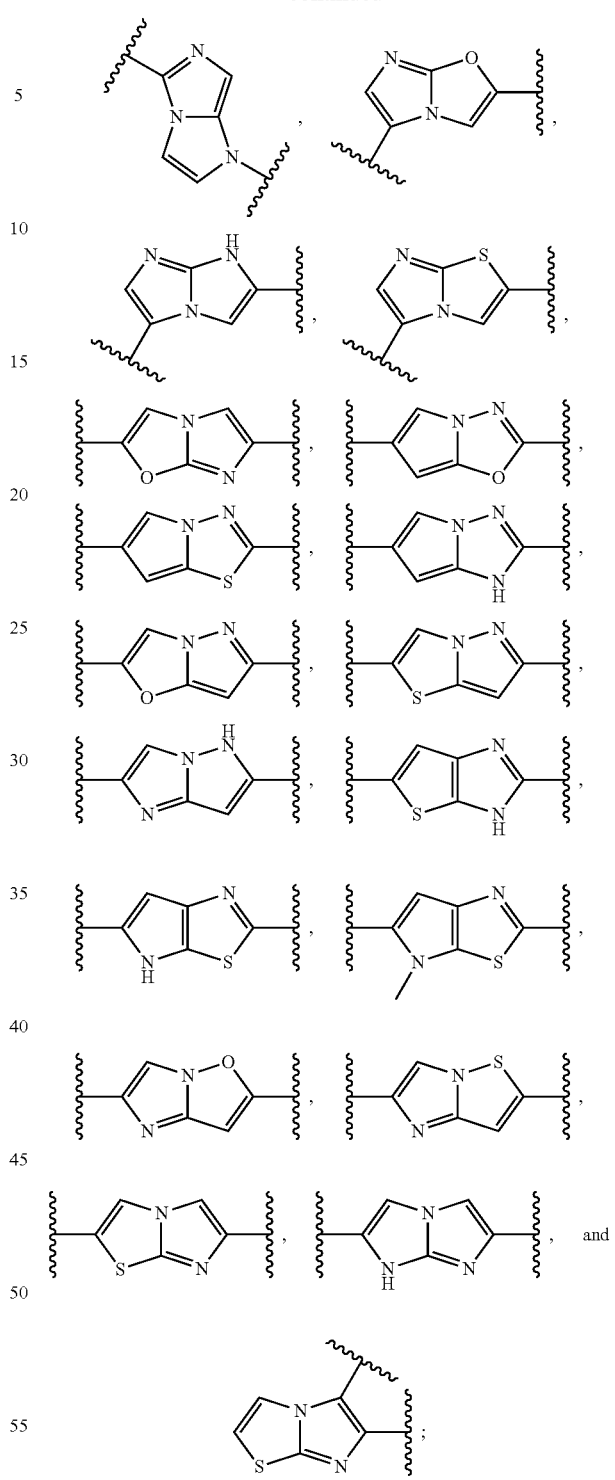
wherein each divalent moiety is optionally substituted with one, two, three, or four, in one embodiment, one or two, $R^3$ groups, where $R^3$ is as defined herein. In certain embodiments, each $R^3$ is independently oxo, chloro, fluoro, nitro, amino, methyl, trifluoromethyl, cyclohexyl, phenyl, or methoxy.
In still another embodiment, A in Formula XXI or XXII is selected from:

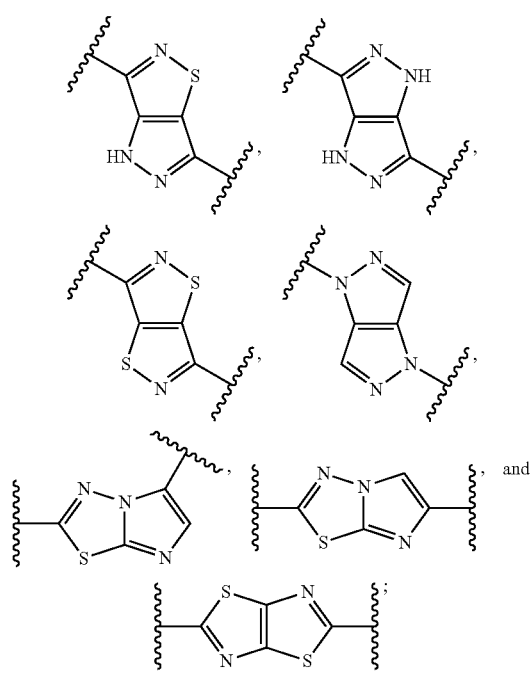

wherein each divalent moiety is optionally substituted with one, two, three, or four, in one embodiment, one or two, R³ groups, where R³ is as defined herein. In certain embodiments, each R³ is independently oxo, chloro, fluoro, nitro, amino, methyl, trifluoromethyl, cyclohexyl, phenyl, or methoxy.

In yet another embodiment, provided herein is a compound of Formula XXIII:

(XXIII)

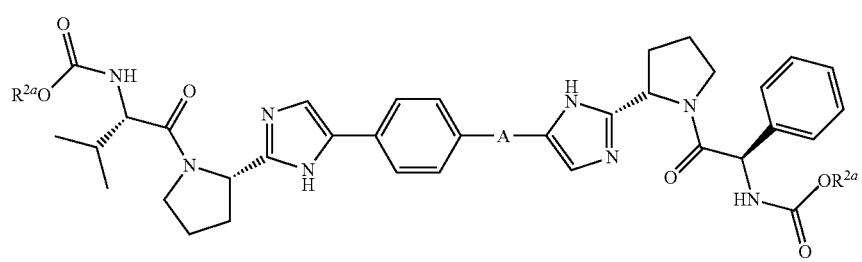

or an isotopic variant thereof; or a pharmaceutically acceptable salt, solvate, or prodrug thereof; wherein R²ᵃ is defined herein; and A is selected from the group consisting of:

(i)

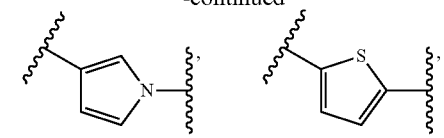

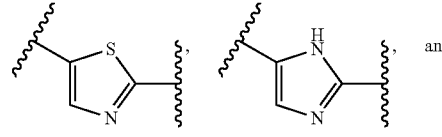

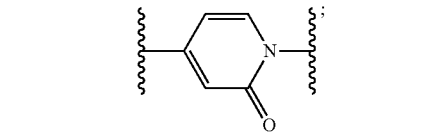

(ii)

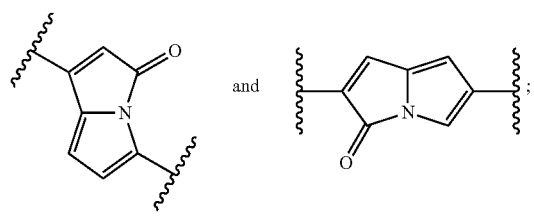

(iii)

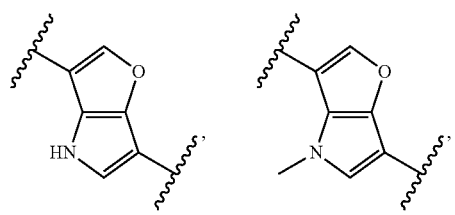

-continued

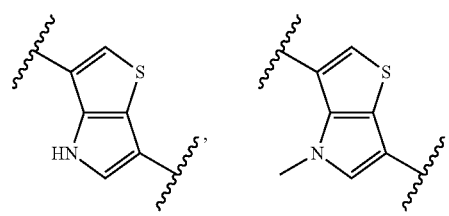

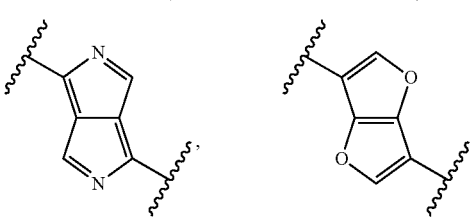

-continued
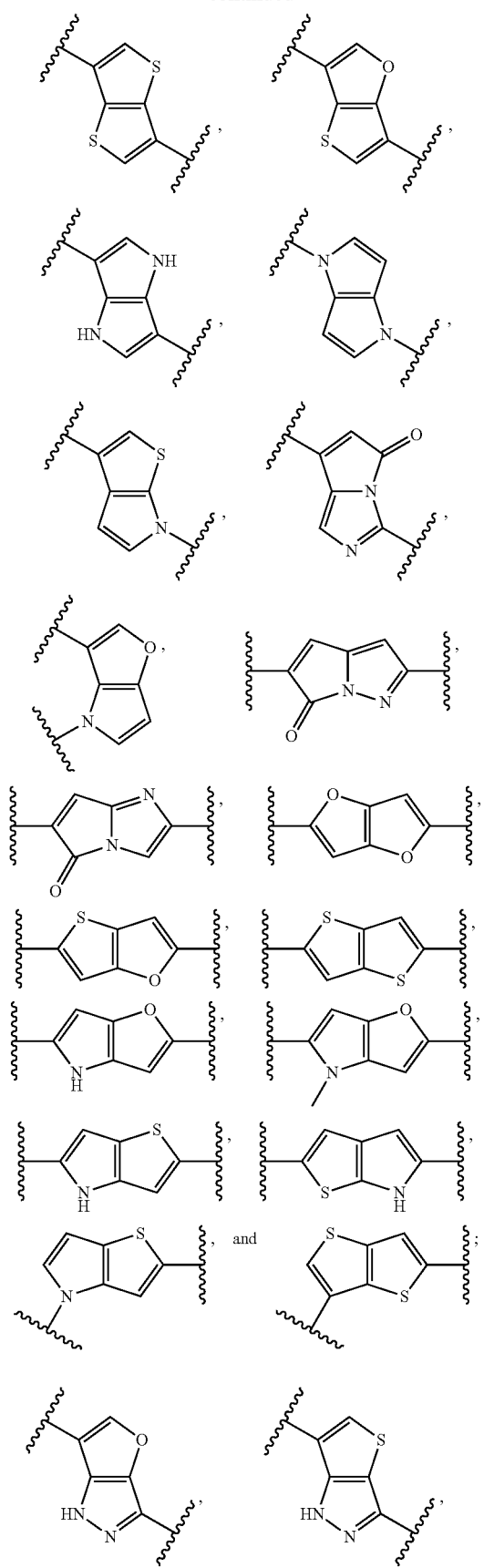
-continued
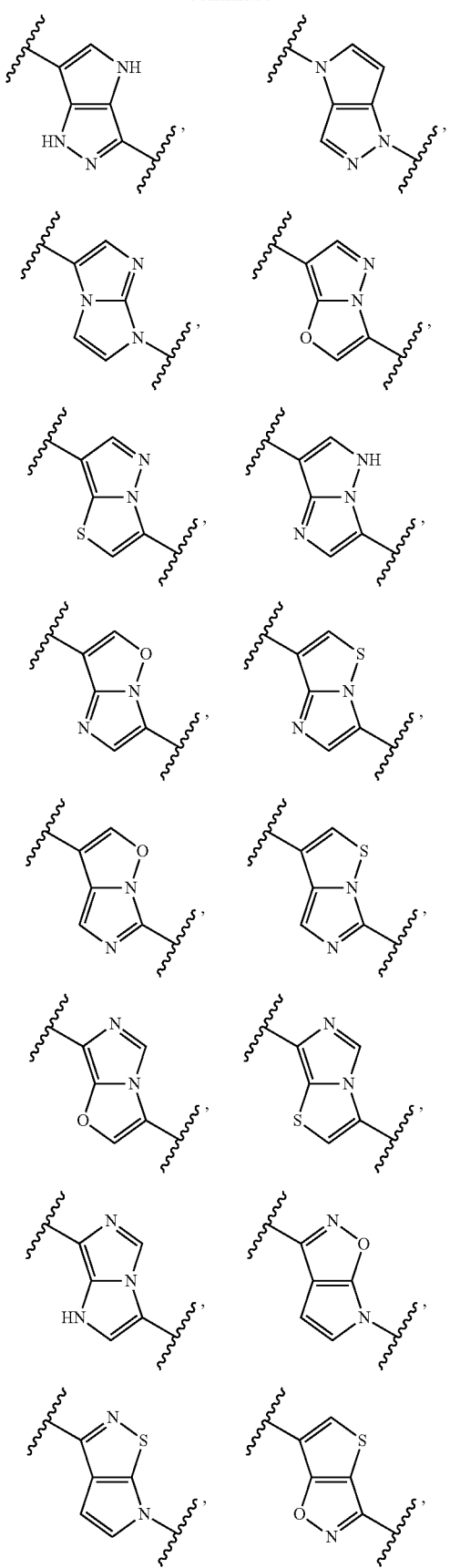

-continued

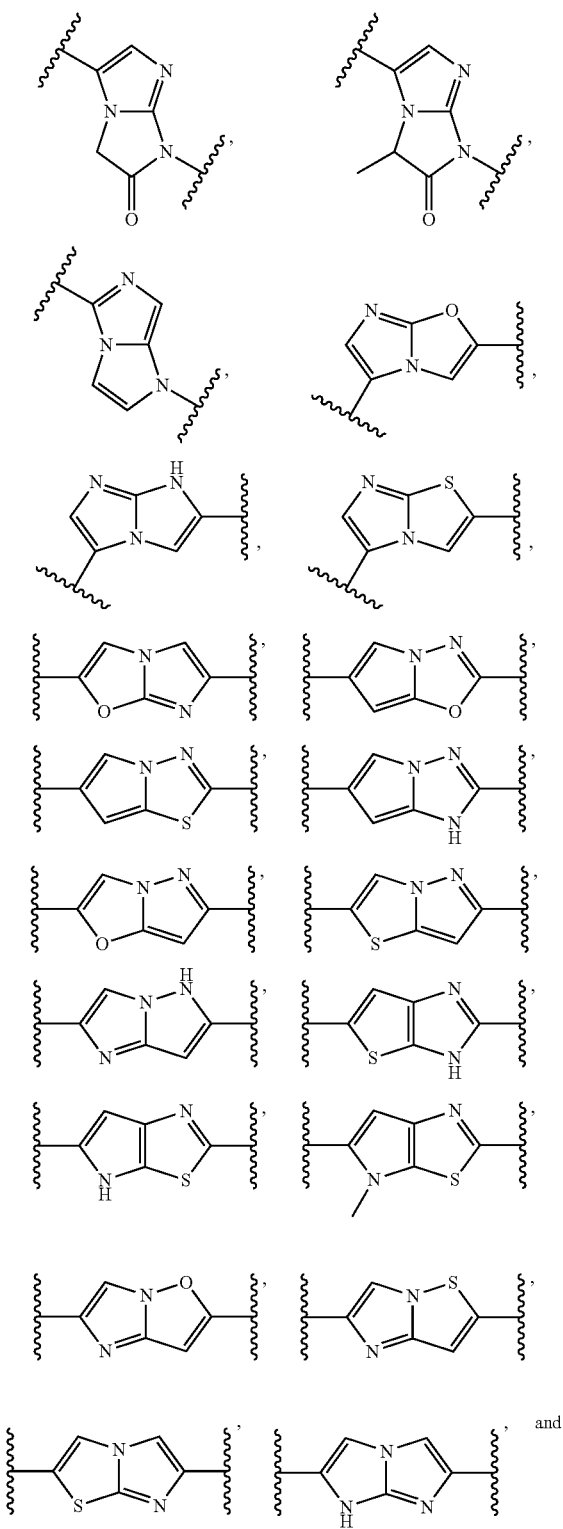

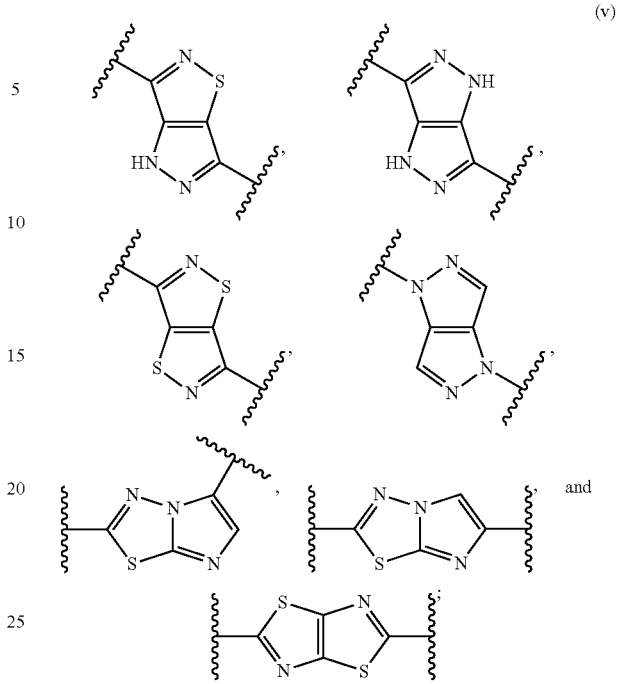

wherein each divalent moiety is optionally substituted with one to four $R^3$ groups.

In one embodiment, provided herein is a compound of Formula IA:

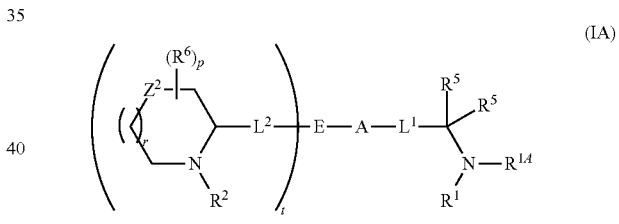

or a single enantiomer, a racemic mixture, a mixture of diastereomers, or an isotopic variant thereof; or a pharmaceutically acceptable salt, solvate, or prodrug thereof;

wherein:

A is 5,5-fused arylene or 5,5-fused heteroarylene;

t and E are (i) or (ii):

(i) t is 1; and E is $C_{2-6}$ alkynylene, $C_{6-14}$ arylene, $C_{2-6}$ alkynylene-$C_{6-14}$ arylene, or heteroarylene; with the proviso that E is not 5,6- or 6,6-fused arylene, $C_{2-6}$ alkynylene-5,6- or 6,6-fused arylene, or 5,6- or 6,6-fused heteroarylene;

(ii) t is 0; and E is $C_{2-6}$ alkynylene-$R^{3a}$, $C_{6-14}$ arylene-$R^{3a}$, or heteroarylene-$R^{3a}$, with the proviso that E is not 5,6- or 6,6-fused arylene-$R^{3a}$, or 5,6- or 6,6-fused heteroarylene-$R^{3a}$;

$R^1$, $R^{1A}$, and $R^2$ are each independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, C(O)CH(N($R^{1c}$)C(O)N$R^{1b}R^{1d}$)$R^{1a}$, C(O)O$R^{1a}$, —C(O)N$R^{1b}R^{1c}$, —C(N$R^{1a}$)N$R^{1b}R^{1c}$, —P(O)(O$R^{1a}$)$R^{1d}$, $CH_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or two $R^5$ or two $R^6$ are linked together to form a bond, —O—, —N$R^7$—, —S—, $C_{1-6}$ alkylene, $C_{1-6}$ heteroalkylene, $C_{2-6}$ alkenylene, or $C_{2-6}$ heteroalkenylene;

$L^1$ and $L^2$ are each independently (a) a bond; (b) $C_{1-6}$ alkylene, $C_{2-6}$ alkenylene, $C_{2-6}$ alkynylene, $C_{3-7}$ cycloalkylene, $C_{6-14}$ arylene, $C_{6-14}$ arylene-heteroarylene, heteroarylene, heteroarylene-$C_{1-6}$ alkylene, heteroarylene-$C_{2-6}$ alkenylene, heteroarylene-$C_{2-6}$ alkynylene, or heterocyclylene; or (c) —C(O)—, —C(O)O—, —C(O)N$R^{1a}$—, C(=N$R^{1a}$)N$R^{1c}$—, —O—, —OC(O)O—, —OC(O)N$R^{1a}$—, —OC(=N$R^{1a}$)N$R^{1c}$—, —OP(O)(O$R^{1a}$)—, —N$R^{1a}$—, —N$R^{1a}$C(O)N$R^{1c}$—, —N$R^{1a}$C(=N$R^{1b}$)N$R^{1c}$—, —N$R^{1a}$S(O)N$R^{1c}$—, —N$R^{1a}$S(O)$_2$N$R^{1c}$—, —S—, —S(O)—, —S(O)$_2$—, —S(O)N$R^{1a}$—, or —S(O)$_2$N$R^{1a}$—;

$Z^2$ is a bond, —O—, —S—, —S(O)—, —S(O$_2$)—, or —N($R^7$)—;

each $R^7$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

p is an integer of 0, 1, 2, 3, 4, 5, 6, or 7; and r is an integer of 1, 2, 3, or 4;

wherein each alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, and heterocyclylene in $R^1$, $R^2$, $R^3$, $R^5$, $R^6$, $R^7$, $R^{1a}$, $R^{1b}$, $R^{1c}$, $R^{1d}$, A, E, $L^1$, or $L^2$ is optionally substituted with one or more substituents Q, where each Q is independently selected from (a) oxo, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein is a compound of Formula IA:

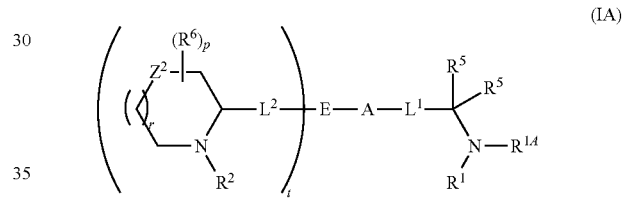

(IA)

or a single enantiomer, a racemic mixture, a mixture of diastereomers, or an isotopic variant thereof; or a pharmaceutically acceptable salt, solvate, or prodrug thereof;

wherein:

A is 5,5-fused arylene or 5,5-fused heteroarylene;

t and E are (i) or (ii):

(i) t is 1; and E is $C_{2-6}$ alkynylene, $C_{6-14}$ arylene, or heteroarylene; with the proviso that E is not 5,6- or 6,6-fused arylene, or 5,6- or 6,6-fused heteroarylene;

(ii) t is 0; and E is $C_{2-6}$ alkynylene-$R^{3a}$, $C_{6-14}$ arylene-$R^{3a}$, or heteroarylene-$R^{3a}$, with the proviso that E is not 5,6- or 6,6-fused arylene-$R^{3a}$, or 5,6- or 6,6-fused heteroarylene-$R^{3a}$;

$R^1$, $R^{1A}$, and $R^2$ are each independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, —C(O)CH(N($R^{1c}$)C(O)N$R^{1b}R^{1d}$)$R^{1a}$, —C(O)O$R^{1a}$, —C(O)N$R^{1b}R^{1c}$, —C(N$R^{1a}$)N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or two R$^5$ or two R$^6$ are linked together to form a bond, —O—, —NR$^7$—, —S—, $C_{1-6}$ alkylene, $C_{1-6}$ heteroalkylene, $C_{2-6}$ alkenylene, or $C_{2-6}$ heteroalkenylene;

L$^1$ and L$^2$ are each independently (a) a bond; (b) $C_{1-6}$ alkylene, $C_{2-6}$ alkenylene, $C_{2-6}$ alkynylene, $C_{3-7}$ cycloalkylene, $C_{6-14}$ arylene, heteroarylene, heteroarylene-$C_{1-6}$ alkylene, heteroarylene-$C_{2-6}$ alkenylene, heteroarylene-$C_{2-6}$ alkynylene, or heterocyclylene; or (c) —C(O)—, —C(O)O—, —C(O)NR$^{1a}$—, —C(=NR$^{1a}$)NR$^{1c}$—, —O—, —OC(O)O—, —OC(O)NR$^{1a}$—, —OC(=NR$^{1a}$)NR$^{1c}$—, —OP(O)(OR$^{1a}$)—, —NR$^{1a}$—, —NR$^{1a}$C(O)NR$^{1c}$—, —NR$^{1a}$C(=NR$^{1b}$)NR$^{1c}$—, —NR$^{1a}$S(O)NR$^{1c}$—, —NR$^{1a}$S(O)$_2$NR$^{1c}$—, —S—, —S(O)—, —S(O)$_2$—, —S(O)NR$^{1a}$—, or —S(O)$_2$NR$^{1a}$—;

Z$^2$ is a bond, —O—, —S—, —S(O)—, —S(O$_2$)—, or —N(R$^7$)—;

each R$^7$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —P(O)(OR$^{1a}$)R$^{1d}$, —CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$;

each R$^{1a}$, R$^{1b}$, R$^{1c}$, and R$^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

p is an integer of 0, 1, 2, 3, 4, 5, 6, or 7; and r is an integer of 1, 2, 3, or 4;

wherein each alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, and heterocyclylene in R$^1$, R$^2$, R$^3$, R$^5$, R$^6$, R$^7$, R$^{1a}$, R$^{1b}$, R$^{1c}$, R$^{1d}$, A, E, L$^1$, or L$^2$ is optionally substituted with one or more substituents Q, where each Q is independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$;

wherein each Q$^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

In yet another embodiment, provided herein is a compound of Formula IIA:

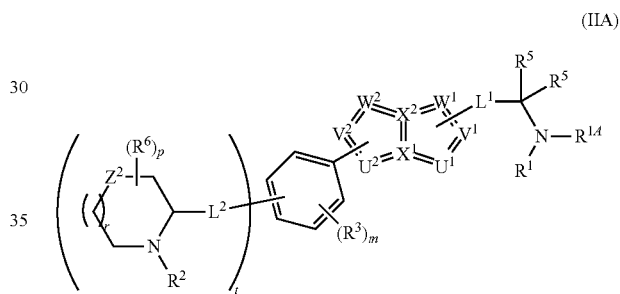

(IIA)

or a single enantiomer, a racemic mixture, a mixture of diastereomers, or an isotopic variant thereof; or a pharmaceutically acceptable salt, solvate, or prodrug thereof; wherein R$^1$, R$^{14}$, R$^2$, R$^3$, R$^5$, R$^6$, L$^1$, L$^2$, U$^1$, U$^2$, V$^1$, V$^2$, W$^1$, W$^2$, X$^1$, X$^2$, Z$^2$, p, r, and t are each as defined herein.

In yet another embodiment, provided herein is a compound of Formula IIIA:

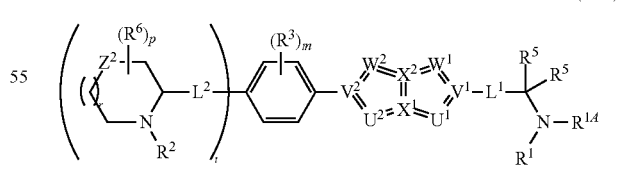

(IIIA)

or a single enantiomer, a racemic mixture, a mixture of diastereomers, or an isotopic variant thereof; or a pharmaceutically acceptable salt, solvate, or prodrug thereof; wherein R$^1$, R$^{14}$, R$^2$, R$^3$, R$^5$, R$^6$, L$^1$, L$^2$, U$^1$, U$^2$, V$^1$, V$^2$, W$^1$, W$^2$, X$^1$, X$^2$, Z$^2$, p, r, and t are each as defined herein.

In one embodiment, provided herein is a compound of Formula IIIAa:

(IIIAa)

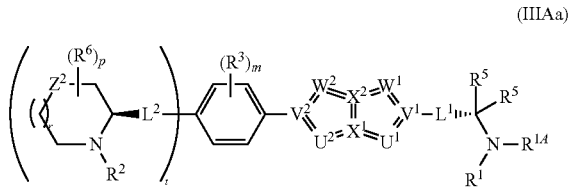

or an isotopic variant thereof; or a pharmaceutically acceptable salt, solvate, or prodrug thereof; wherein $R^1$, $R^{1A}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In another embodiment, provided herein is a compound of Formula IIIAb:

(IIIAb)

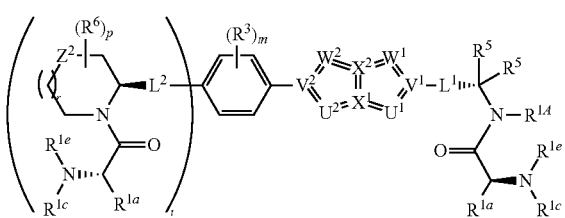

or an isotopic variant thereof; or a pharmaceutically acceptable salt, solvate, or prodrug thereof; wherein $R^{1a}$, $R^{1c}$, $R^{1e}$, $R^{1A}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula IIIAc:

(IIIAc)

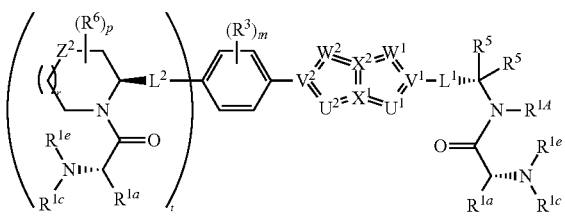

or an isotopic variant thereof; or a pharmaceutically acceptable salt, solvate, or prodrug thereof; wherein $R^{1a}$, $R^{1c}$, $R^{1e}$, $R^{1A}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula IVA:

(IVA)

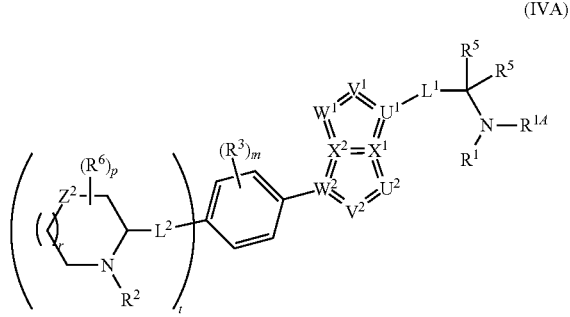

or a single enantiomer, a racemic mixture, a mixture of diastereomers, or an isotopic variant thereof; or a pharmaceutically acceptable salt, solvate, or prodrug thereof; wherein $R^1$, $R^{1A}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In one embodiment, provided herein is a compound of Formula IVAa:

(IVAa)

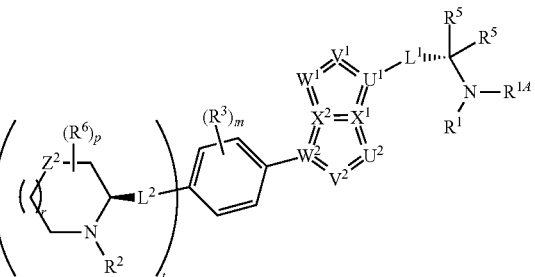

or an isotopic variant thereof; or a pharmaceutically acceptable salt, solvate, or prodrug thereof; wherein $R^1$, $R^{1A}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In another embodiment, provided herein is a compound of Formula IVAb:

(IVAb)

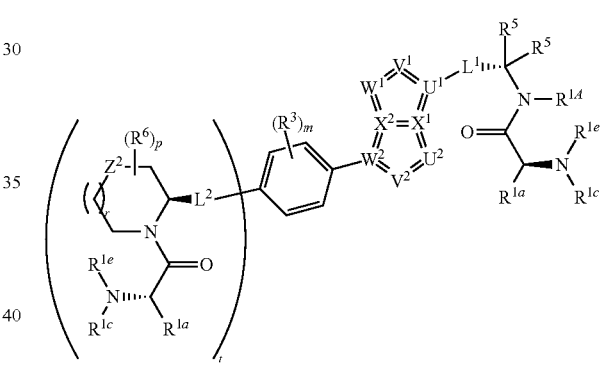

or an isotopic variant thereof; or a pharmaceutically acceptable salt, solvate, or prodrug thereof; wherein $R^{1a}$, $R^{1c}$, $R^{1e}$, $R^{1A}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula IVAc:

(IVAc)

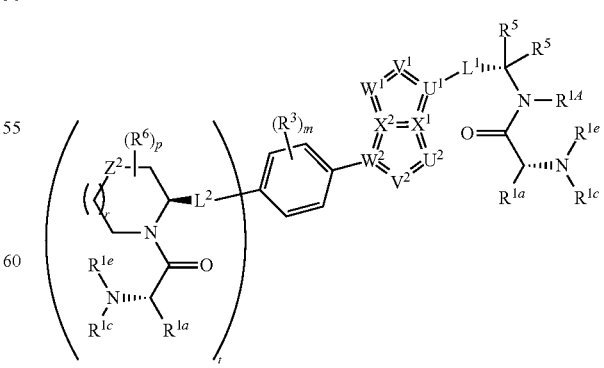

or an isotopic variant thereof; or a pharmaceutically acceptable salt, solvate, or prodrug thereof; wherein $R^{1a}$, $R^{1c}$, $R^{1e}$, $R^{1A}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula VA:

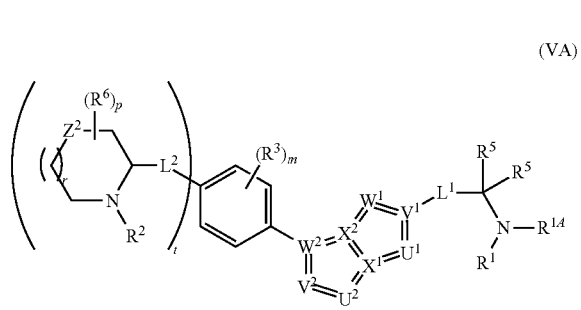

(VA)

or a single enantiomer, a racemic mixture, a mixture of diastereomers, or an isotopic variant thereof; or a pharmaceutically acceptable salt, solvate, or prodrug thereof; wherein $R^1$, $R^{1A}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In one embodiment, provided herein is a compound of Formula VAa:

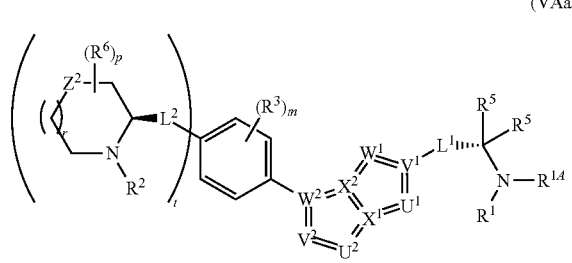

(VAa)

or an isotopic variant thereof; or a pharmaceutically acceptable salt, solvate, or prodrug thereof; wherein $R^1$, $R^{1A}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In another embodiment, provided herein is a compound of Formula VAb:

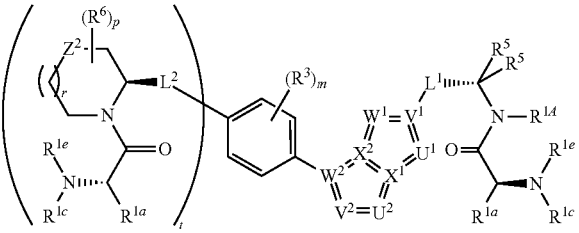

(VAb)

or an isotopic variant thereof; or a pharmaceutically acceptable salt, solvate, or prodrug thereof; wherein $R^{1a}$, $R^{1c}$, $R^{1e}$, $R^{1A}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula VAc:

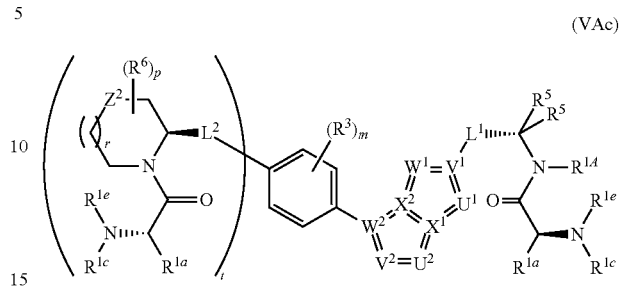

(VAc)

or an isotopic variant thereof; or a pharmaceutically acceptable salt, solvate, or prodrug thereof; wherein $R^{1a}$, $R^{1c}$, $R^{1e}$, $R^{1A}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula VIA:

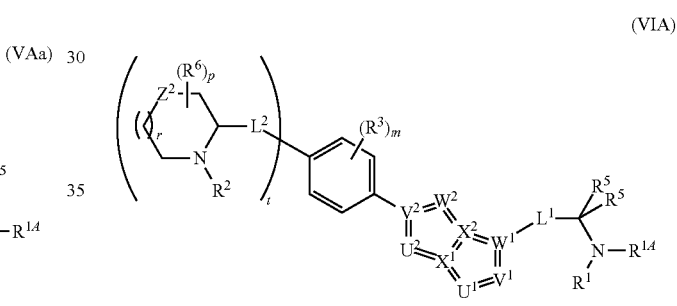

(VIA)

or a single enantiomer, a racemic mixture, a mixture of diastereomers, or an isotopic variant thereof; or a pharmaceutically acceptable salt, solvate, or prodrug thereof; wherein $R^1$, $R^{1A}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In one embodiment, provided herein is a compound of Formula VIAa:

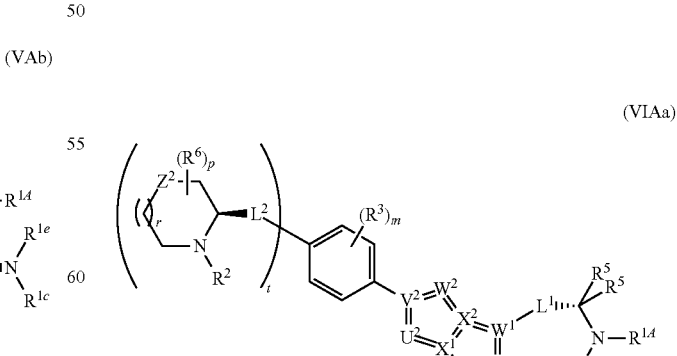

(VIAa)

or an isotopic variant thereof; or a pharmaceutically acceptable salt, solvate, or prodrug thereof; wherein $R^1$, $R^{14}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In another embodiment, provided herein is a compound of Formula VIAb:

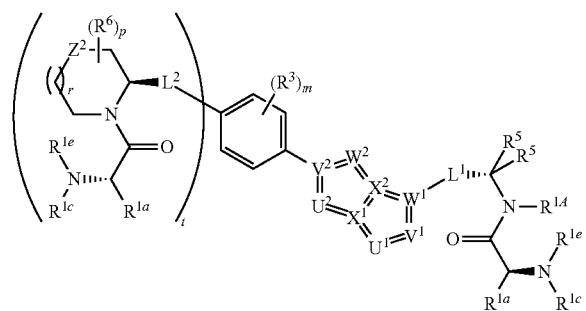

(VIAb)

or an isotopic variant thereof; or a pharmaceutically acceptable salt, solvate, or prodrug thereof; wherein $R^{1a}$, $R^{1c}$, $R^{1e}$, $R^{14}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula VIAc:

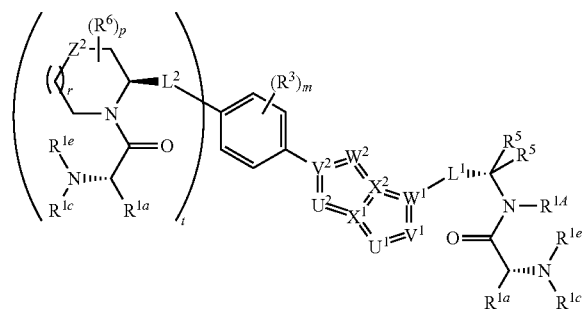

(VIAc)

or an isotopic variant thereof; or a pharmaceutically acceptable salt, solvate, or prodrug thereof; wherein $R^{1a}$, $R^{1c}$, $R^{1e}$, $R^{14}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula VIIA:

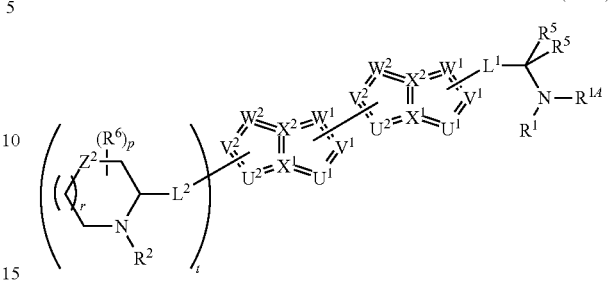

(VIIA)

or a single enantiomer, a racemic mixture, a mixture of diastereomers, or an isotopic variant thereof; or a pharmaceutically acceptable salt, solvate, or prodrug thereof; wherein $R^1$, $R^{14}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula VIIIA:

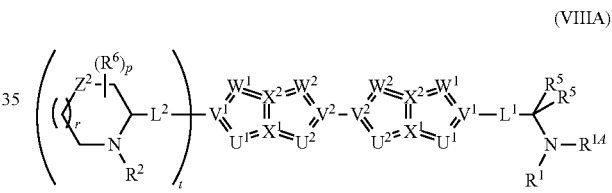

(VIIIA)

or a single enantiomer, a racemic mixture, a mixture of diastereomers, or an isotopic variant thereof; or a pharmaceutically acceptable salt, solvate, or prodrug thereof; wherein $R^1$, $R^{14}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In one embodiment, provided herein is a compound of Formula VIIIAa:

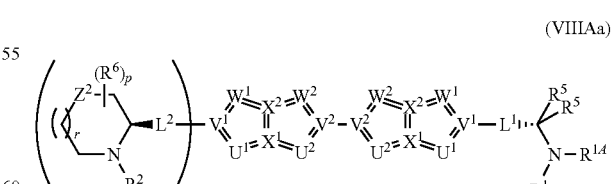

(VIIIAa)

or an isotopic variant thereof; or a pharmaceutically acceptable salt, solvate, or prodrug thereof; wherein $R^1$, $R^{14}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In another embodiment, provided herein is a compound of Formula VIIIAb:

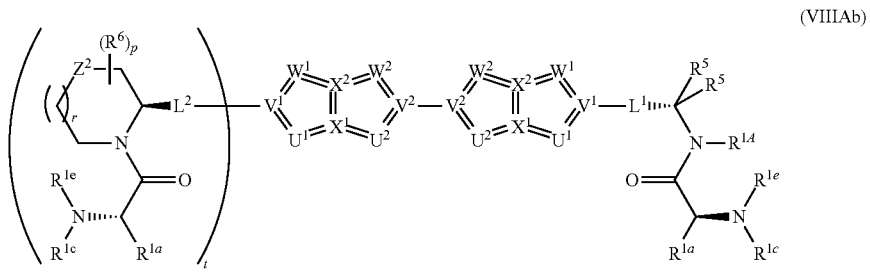

(VIIIAb)

or an isotopic variant thereof; or a pharmaceutically acceptable salt, solvate, or prodrug thereof; wherein $R^{1a}$, $R^{1c}$, $R^{1e}$, $R^{14}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula VIIIAc:

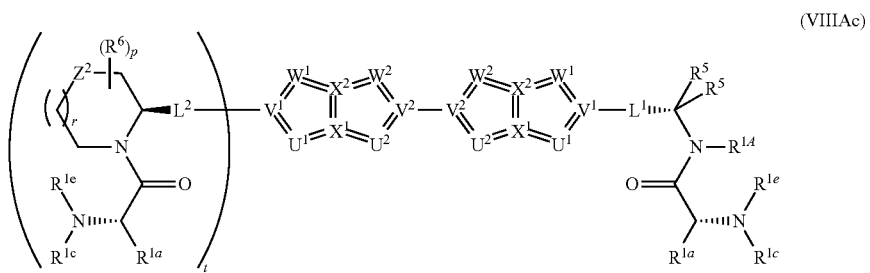

(VIIIAc)

or an isotopic variant thereof; or a pharmaceutically acceptable salt, solvate, or prodrug thereof; wherein $R^{1a}$, $R^{1c}$, $R^{1e}$, $R^{14}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula IXA:

In yet another embodiment, provided herein is a compound of Formula IXAa:

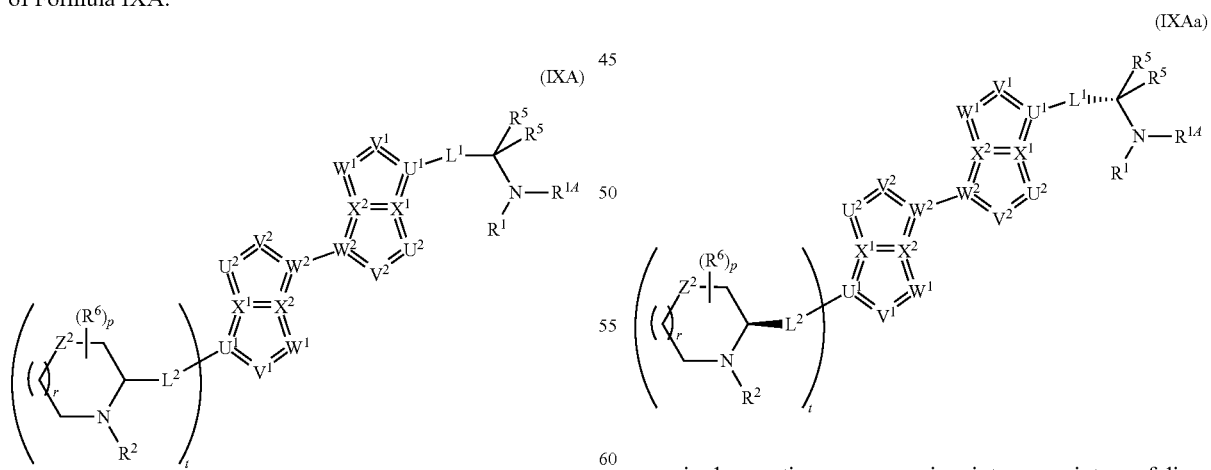

(IXA)

(IXAa)

or a single enantiomer, a racemic mixture, a mixture of diastereomers, or an isotopic variant thereof; or a pharmaceutically acceptable salt, solvate, or prodrug thereof; wherein $R^1$, $R^{14}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

or a single enantiomer, a racemic mixture, a mixture of diastereomers, or an isotopic variant thereof; or a pharmaceutically acceptable salt, solvate, or prodrug thereof; wherein $R^1$, $R^{14}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In another embodiment, provided herein is a compound of Formula IXAb:

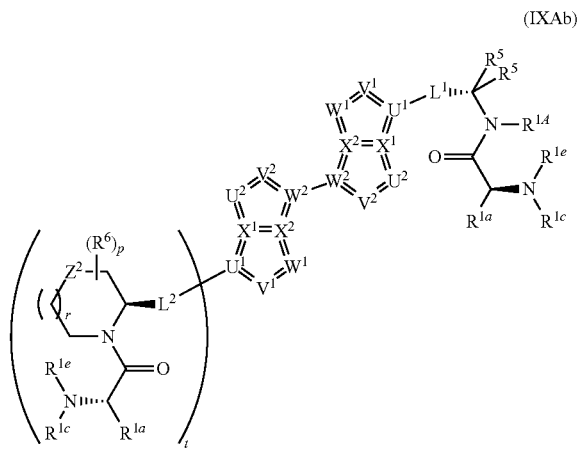

(IXAb)

or an isotopic variant thereof; or a pharmaceutically acceptable salt, solvate, or prodrug thereof; wherein $R^{1a}$, $R^{1c}$, $R^{1e}$, $R^{14}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula IXAc:

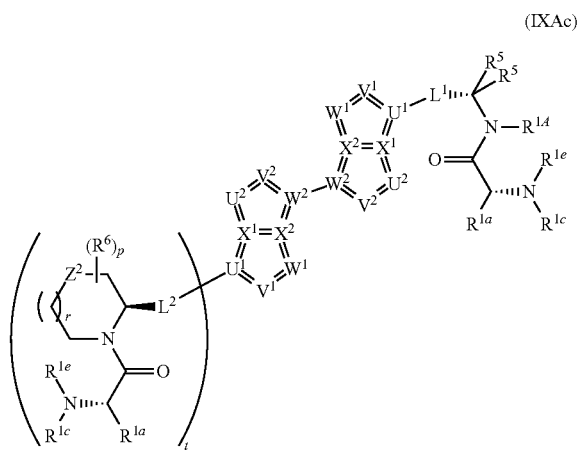

(IXAc)

or an isotopic variant thereof; or a pharmaceutically acceptable salt, solvate, or prodrug thereof; wherein $R^{1a}$, $R^{1c}$, $R^{1e}$, $R^{14}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula XA:

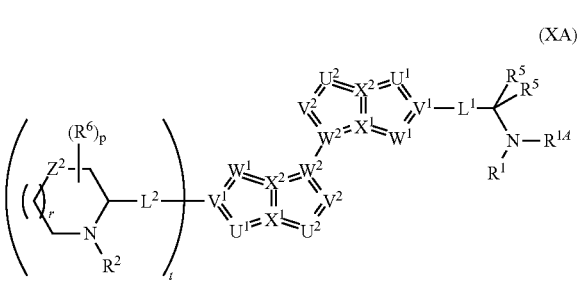

(XA)

or a single enantiomer, a racemic mixture, a mixture of diastereomers, or an isotopic variant thereof; or a pharmaceutically acceptable salt, solvate, or prodrug thereof; wherein $R^1$, $R^{1a}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula XAa:

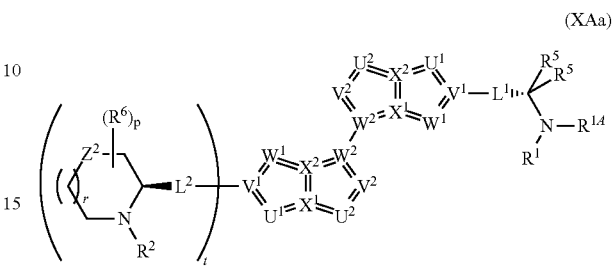

(XAa)

or a single enantiomer, a racemic mixture, a mixture of diastereomers, or an isotopic variant thereof; or a pharmaceutically acceptable salt, solvate, or prodrug thereof; wherein $R^1$, $R^{1a}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In another embodiment, provided herein is a compound of Formula XAb:

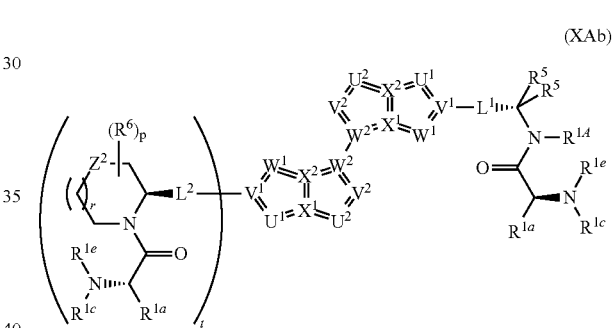

(XAb)

or an isotopic variant thereof; or a pharmaceutically acceptable salt, solvate, or prodrug thereof; wherein $R^{1a}$, $R^{1c}$, $R^{1e}$, $R^{14}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula XAc:

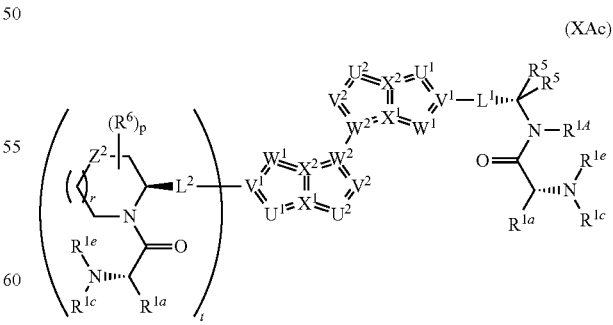

(XAc)

or an isotopic variant thereof; or a pharmaceutically acceptable salt, solvate, or prodrug thereof; wherein $R^{1a}$, $R^{1c}$, $R^{1e}$, $R^{14}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula XIA:

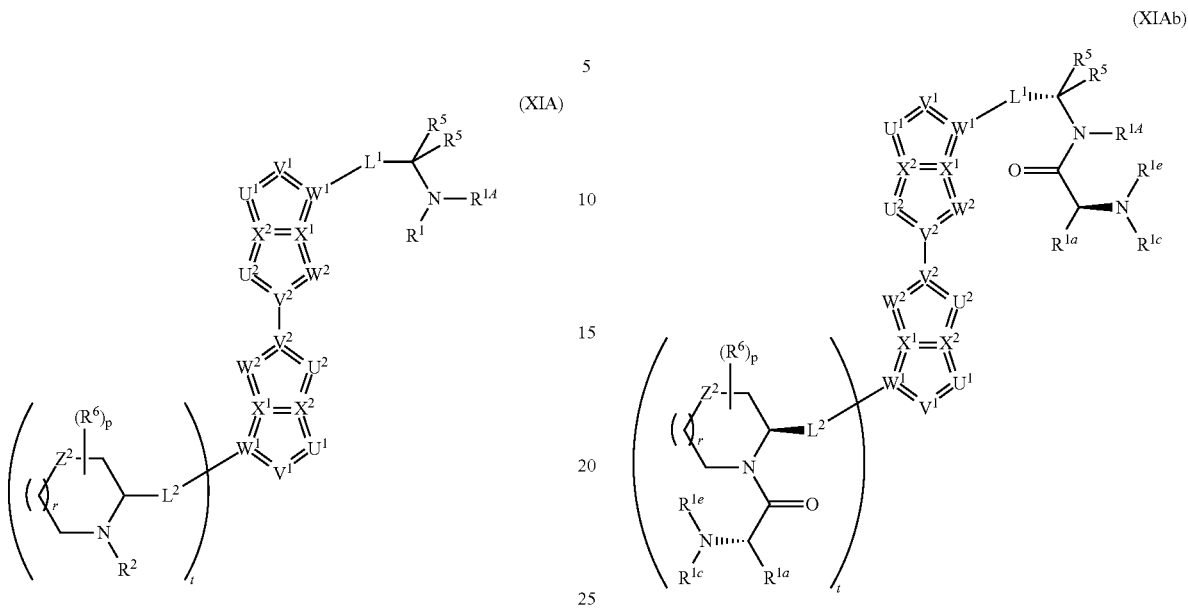

or a single enantiomer, a racemic mixture, a mixture of diastereomers, or an isotopic variant thereof; or a pharmaceutically acceptable salt, solvate, or prodrug thereof; wherein $R^1$, $R^{1A}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In one embodiment, provided herein is a compound of Formula XIAa:

or an isotopic variant thereof; or a pharmaceutically acceptable salt, solvate, or prodrug thereof; wherein $R^1$, $R^{1A}$, $R^2$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In another embodiment, provided herein is a compound of Formula XIAb:

or an isotopic variant thereof; or a pharmaceutically acceptable salt, solvate, or prodrug thereof; wherein $R^{1a}$, $R^{1c}$, $R^{1e}$, $R^{1A}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In yet another embodiment, provided herein is a compound of Formula XIAc:

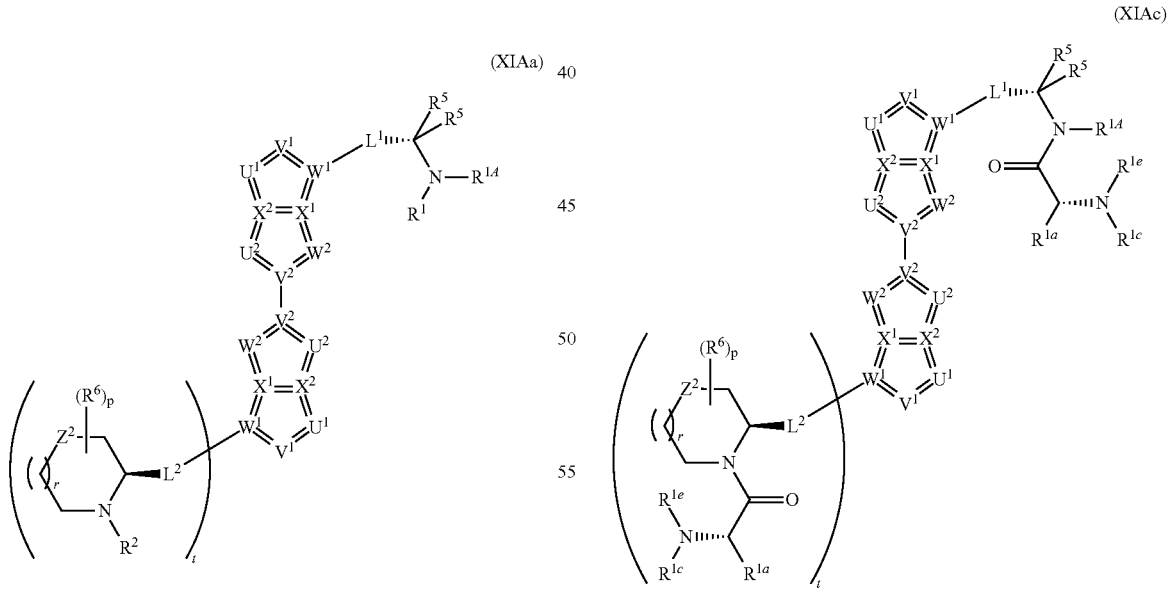

or an isotopic variant thereof; or a pharmaceutically acceptable salt, solvate, or prodrug thereof; wherein $R^{1a}$, $R^{1c}$, $R^{1e}$, $R^{1A}$, $R^3$, $R^5$, $R^6$, $L^1$, $L^2$, $U^1$, $U^2$, $V^1$, $V^2$, $W^1$, $W^2$, $X^1$, $X^2$, $Z^2$, p, r, and t are each as defined herein.

In one embodiment, provided herein is a compound of Formula IB:

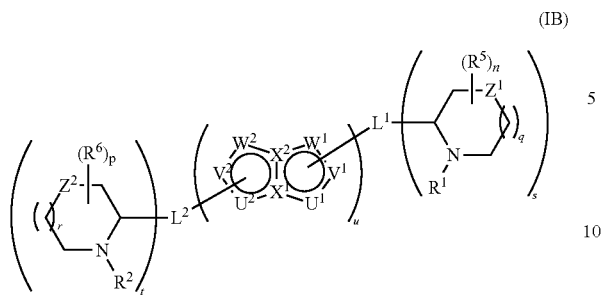

(IB)

or a single enantiomer, a racemic mixture, a mixture of diastereomers, or an isotopic variant thereof; or a pharmaceutically acceptable salt, solvate, or prodrug thereof;
wherein:
$U^1$, $U^2$, $V^1$, $V^2$, $W^1$, and $W^2$ are each independently C, N, O, S, $CR^{3a}$, or $NR^{3a}$;

$X^1$ and $X^2$ are each independently C or N;

each $R^1$ and $R^2$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH($NR^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, —C(O)CH(N($R^{1c}$)C(O)N$R^{1b}R^{1d}$)$R^{1a}$, —C(O)O$R^{1a}$, —C(O)N$R^{1b}R^{1c}$, —C($NR^{1a}$)N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2$$R^{1a}$, —S(O)N$R^{1b}R^{1c}$, or —S(O)$_2$N$R^{1b}R^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C($NR^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=$NR^{1a}$)N$R^{1b}R^{1c}$, —OS(O)$R^{1a}$, —OS(O)$_2$$R^{1a}$, —OS(O)N$R^{1b}R^{1c}$, —OS(O)$_2$N$R^{1b}R^{1c}$, —N$R^{1b}R^{1c}$, —$NR^{1a}$C(O)$R^{1d}$, —$NR^{1a}$C(O)O$R^{1d}$, —$NR^{1a}$C(O)N$R^{1b}R^{1c}$, —$NR^{1a}$C(=$NR^{1d}$)N$R^{1b}R^{1c}$, —$NR^{1a}$S(O)$R^{1d}$, —$NR^{1a}$S(O)$_2$$R^{1d}$, —$NR^{1a}$S(O)N$R^{1b}R^{1c}$, —$NR^{1a}$S(O)$_2$N$R^{1b}R^{1c}$, —$SR^{1a}$, —S(O)$R^{1a}$, —S(O)$_2$$R^{1a}$, —S(O)N$R^{1b}R^{1c}$, or —S(O)$_2$N$R^{1b}R^{1c}$; or two $R^5$ or two $R^6$ that are attached to the same ring are linked together to form a bond, —O—, —$NR^7$—, —S—, $C_{1-6}$ alkylene, $C_{1-6}$ heteroalkylene, $C_{2-6}$ alkenylene, or $C_{2-6}$ heteroalkenylene;

$L^1$ and $L^2$ are each independently selected from:
a bond,

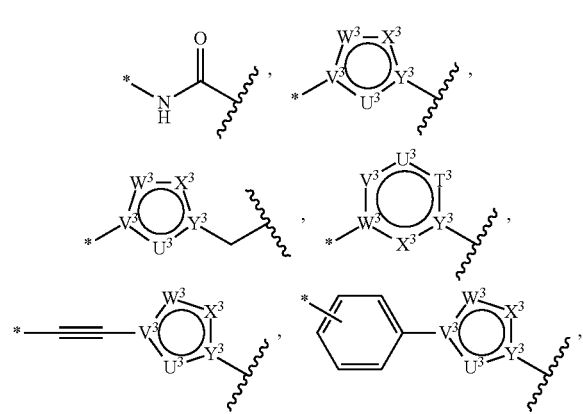

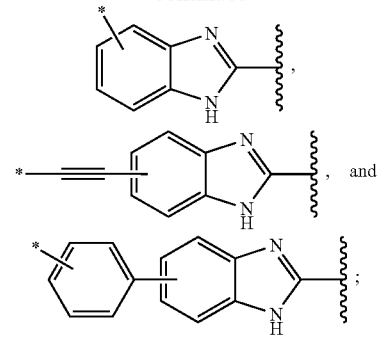

wherein each moiety is optionally substituted with one, two, three, or four $R^3$; the star (*) on each moiety represents the point of attachment thought which the moiety is connected to $U^1$, $U^2$, $V^1$, $V^2$, $W^1$, or $W^2$ of

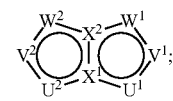

and the zigzag line ( ) on each moiety represents the point of attachment through which the moiety is connected to

and wherein $T^3$ is a bond, C, N, O, S, $CR^{3a}$, or $NR^{3a}$; $U^3$, $V^3$, $W^3$, and $X^3$ are each independently C, N, O, S, $CR^{3a}$, or $NR^{3a}$; and $Y^3$ is C or N;

each $Z^1$ and $Z^2$ is independently a bond, —O—, —S—, —S(O)—, —S(O$_2$)—, or —N($R^7$)—;

each $R^7$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C($NR^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=$NR^{1a}$)N$R^{1b}R^{1c}$, —OS(O)$R^{1a}$, —OS(O)$_2$$R^{1a}$, —OS(O)N$R^{1b}R^{1c}$, —OS(O)$_2$N$R^{1b}R^{1c}$, —N$R^{1b}R^{1c}$, —$NR^{1a}$C(O)$R^{1d}$, —$NR^{1a}$C(O)O$R^{1d}$, —$NR^{1a}$C(O)N$R^{1b}R^{1c}$, —$NR^{1a}$C(=$NR^{1d}$)N$R^{1b}R^{1c}$, —$NR^{1a}$S(O)$R^{1d}$, —$NR^{1a}$S(O)$_2$$R^{1d}$, —$NR^{1a}$S(O)N$R^{1b}R^{1c}$, —$NR^{1a}$S(O)$_2$N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2$$R^{1a}$, —S(O)N$R^{1b}R^{1c}$, or —S(O)$_2$N$R^{1b}R^{1c}$;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

each n and p is independently an integer of 0, 1, 2, 3, 4, 5, 6, or 7;

each q and r is independently an integer of 1, 2, 3, or 4;

s and t are each independently an integer of 0, 1, or 2; and u is an integer of 1 or 2;

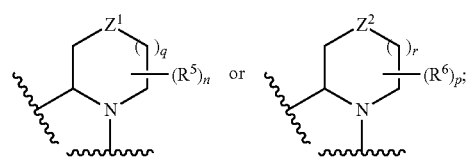

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more substituents Q, where each Q is independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$;

wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

In certain embodiments, $L^1$ and $L^2$ are each independently selected from:

a bond,

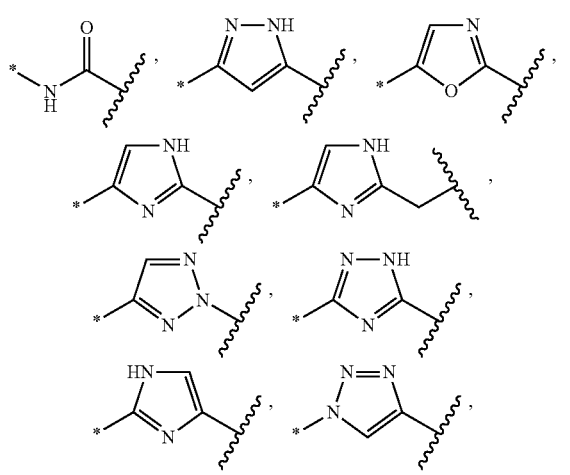

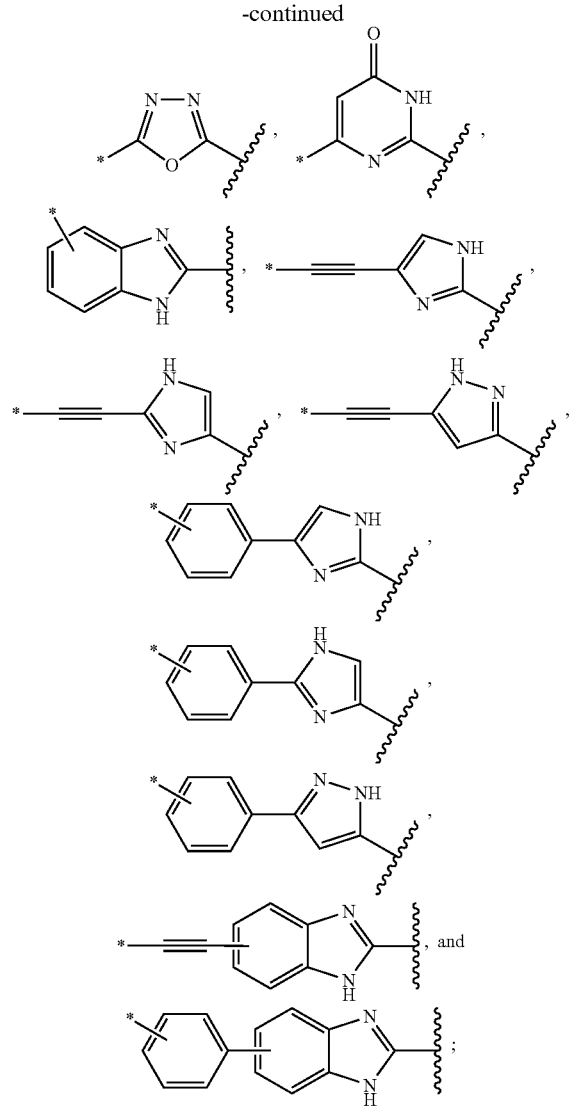

wherein each moiety is optionally substituted with one, two, three, or four R$^3$; the star (*) on each moiety represents the point of attachment thought which the moiety is connected to $U^1$, $U^2$, $V^1$, $V^2$, $W^1$, or $W^2$ of

and the zigzag line ( ) on each moiety represents the point of attachment through which the moiety is connected to

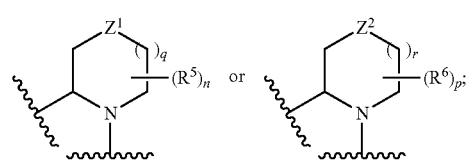

where each $R^3$ is as defined herein.

In certain embodiments, $L^1$ and $L^2$ are each independently selected from:

a bond,

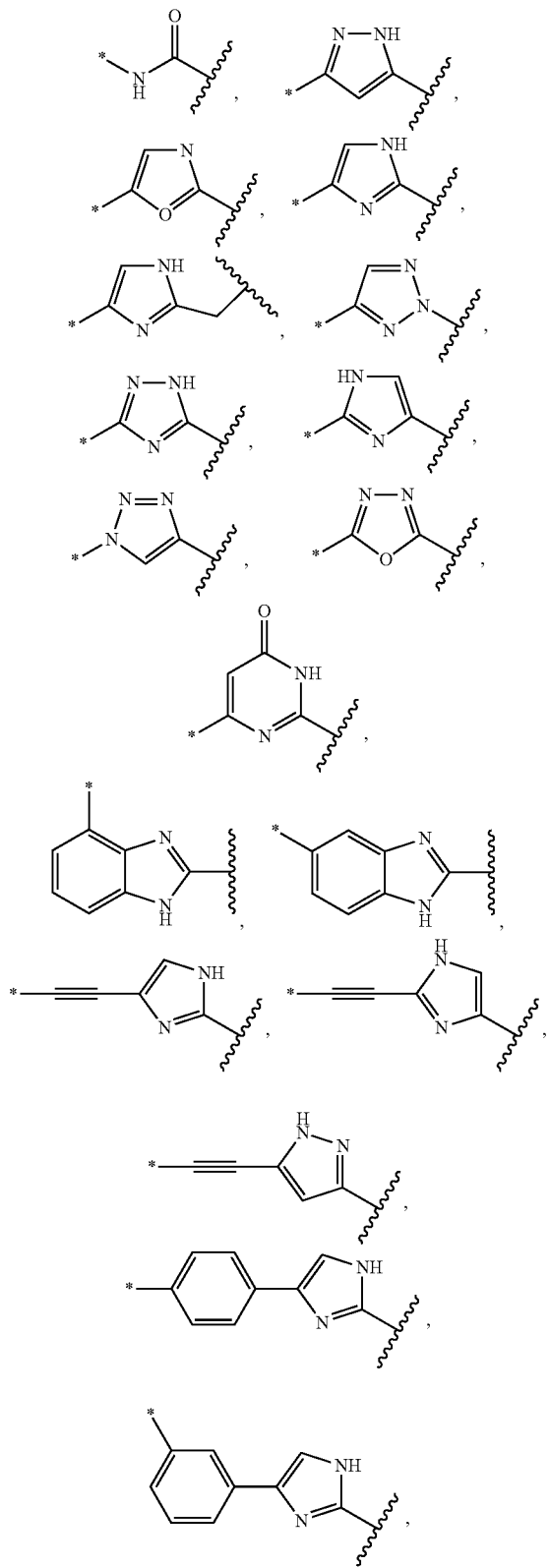

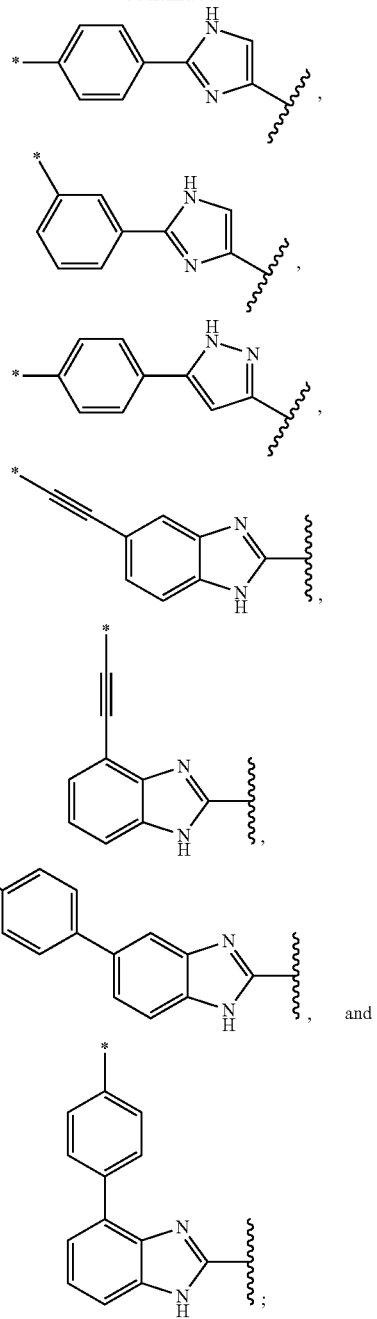

wherein each moiety is optionally substituted with one, two, three, or four $R^3$; the star (*) on each moiety represents the point of attachment thought which the moiety is connected to $U^1$, $U^2$, $V^1$, $V^2$, $W^1$, or $W^2$ of

and the zigzag line (  ) on each moiety represents the point of attachment through which the moiety is connected to

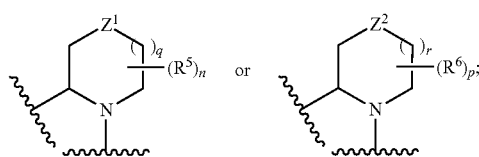

where each $R^3$ is as defined herein.

In one embodiment, provided herein is a compound of Formula IBa:

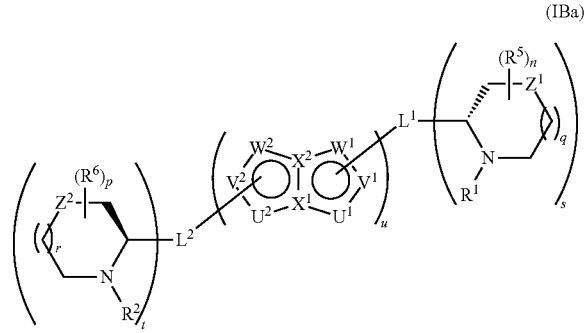

(IBa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In another embodiment, provided herein is a compound of Formula IBb:

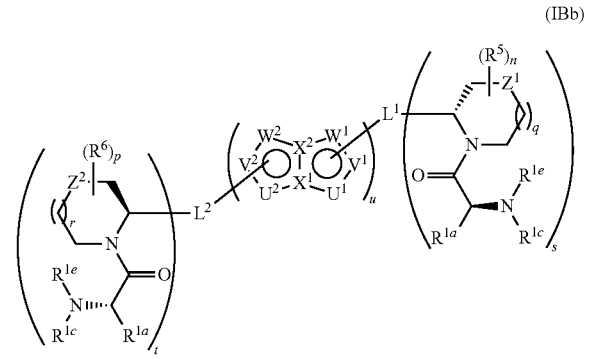

(IBb)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In yet another embodiment, provided herein is a compound of Formula IBc:

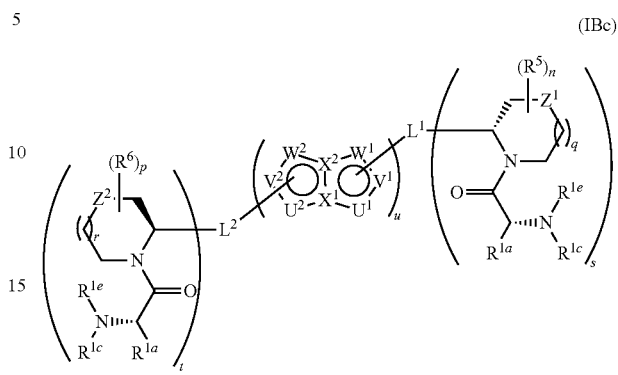

(IBc)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In another embodiment, provided herein is a compound of Formula IIB:

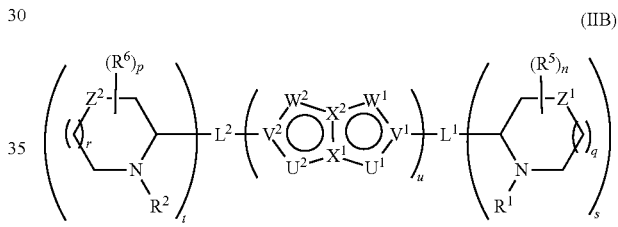

(IIB)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $W^1$, $W^2$, $X^1$, $X^2$, $Z^1$, $Z^2$, n, p, q, r, s, t, and u are each as defined herein; and $V^1$ and $V^2$ are each independently C or N.

In one embodiment, provided herein is a compound of Formula IIBa:

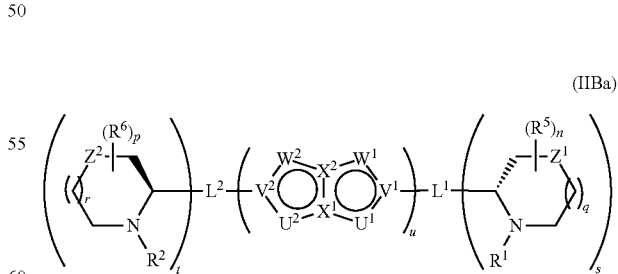

(IIBa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In another embodiment, provided herein is a compound of Formula IIBb:

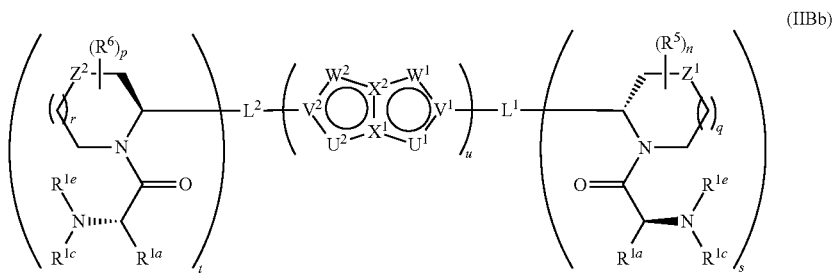

(IIBb)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In yet another embodiment, provided herein is a compound of Formula IIBc:

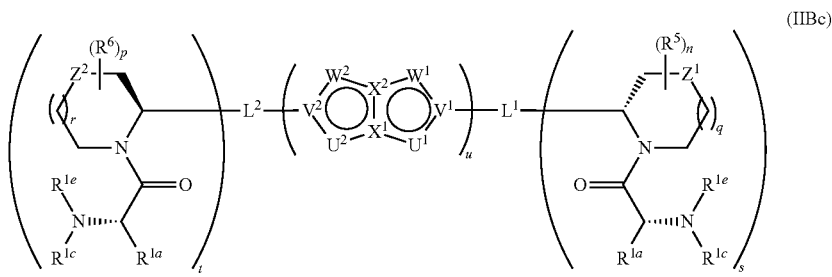

(IIBc)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In Formula IB, IIB, IIBa, IIBb, or IIBc, in one embodiment, $U^1$ and $X^2$ are N, $U^2$ is S, $V^1$, $V^2$, and $X^1$ are C, and $W^1$ and $W^2$ are each independently $CR^{3a}$; in another embodiment, $U^1$ is S, $U^2$ and $X^2$ are N, $V^1$, $V^2$, and $X^1$ are C, and $W^1$ and $W^2$ are each independently $CR^{3a}$; in yet another embodiment, $U^1$ and $X^2$ are N, $U^2$ is O, $V^1$, $V^2$, and $X^1$ are C, and $W^1$ and $W^2$ are each independently $CR^{3a}$; in yet another embodiment, $U^1$ is O, $U^2$ and $X^2$ are N, $V^1$, $V^2$, and $X^1$ are C, and $W^1$ and $W^2$ are each independently $CR^{3a}$; in yet another embodiment, $U^1$ is $NR^{3a}$, $U^2$ is S, $V^1$, $V^2$, $X^1$, and $X^2$ are C, $W^1$ is $CR^{3a}$, and $W^2$ is N; in yet another embodiment, $U^1$ and $W^2$ are each independently $CR^{3a}$, $U^2$ is S, $V^1$, $V^2$, $X^1$, and $X^2$ are C, $W^1$ is $NR^{3a}$; in yet another embodiment, $U^1$ is S, $U^2$ and $W^1$ are each independently $CR^{3a}$, $V^1$, $V^2$, $X^1$, and $X^2$ are C, $W^2$ is $NR^{3a}$; in yet another embodiment, $U^1$ and $W^2$ are each independently $CR^{3a}$, $U^2$ is O, $V^1$, $V^2$, $X^1$, and $X^2$ are C, $W^1$ is $NR^{3a}$; in yet another embodiment, $U^1$ and $W^2$ are N, $U^2$ and $W^1$ are S, $V^1$, $V^2$, $X^1$, and $X^2$ are C; in yet another embodiment, $U^1$ and $W^2$ are S, $U^2$ and $W^1$ are each independently $CR^{3a}$, $V^1$, $V^2$, $X^1$, and $X^2$ are C; in yet another embodiment, $U^1$ and $X^2$ are N, $U^2$ is $NR^{3a}$, $V^1$, $V^2$, and $X^1$ are C, and $W^1$ and $W^2$ are each independently $CR^{3a}$; in yet another embodiment, $U^1$ is S, $U^2$ is $NR^{3a}$, $V^1$, $V^2$, $X^1$, and $X^2$ are C, and $W^1$ and $W^2$ are each independently $CR^{3a}$; in still another embodiment, $U^1$, $W^2$, and $X^1$ are N, $U^2$ is $CR^{3a}$, $V^1$, $V^2$, and $X^2$ are C, and $W^1$ is S; wherein each $R^{3a}$ is as defined herein.

In yet another embodiment, provided herein is a compound of Formula IIIB:

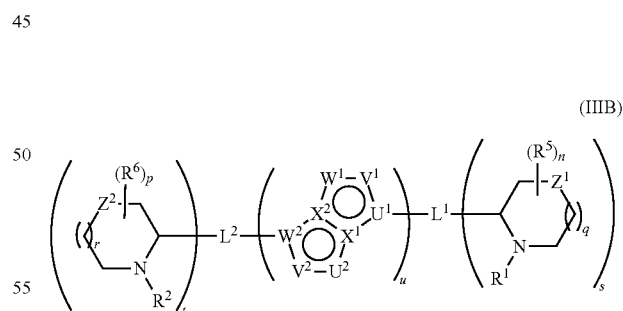

(IIIB)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^2$, $V^1$, $V^2$, $W^1$, $X^1$, $X^2$, $Z^1$, $Z^2$, n, p, q, r, s, t, and u are each as defined herein; and $U^1$ and $W^2$ are each independently C or N.

In one embodiment, provided herein is a compound of Formula IIIBa:

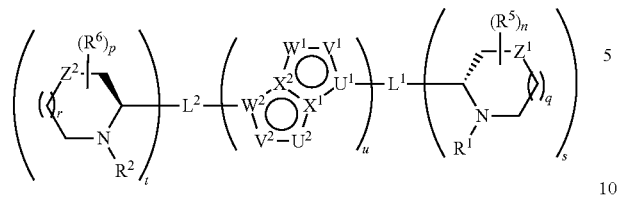
(IIIBa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In another embodiment, provided herein is a compound of Formula IIIBb:

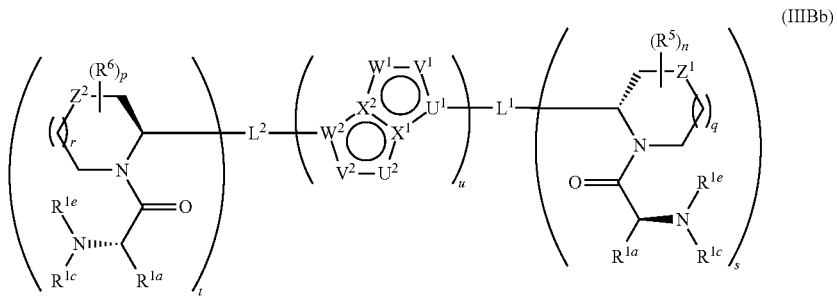
(IIIBb)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In yet another embodiment, provided herein is a compound of Formula IIIBc:

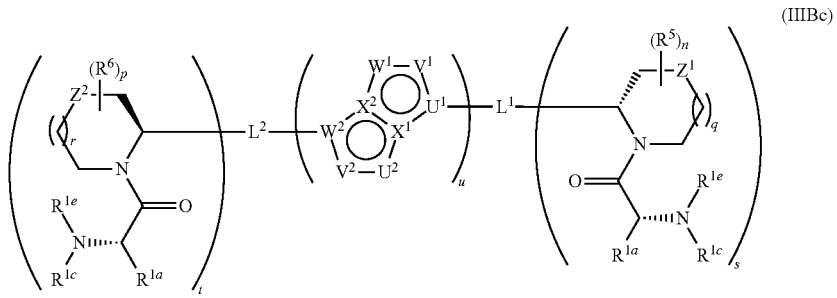
(IIIBc)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In yet another embodiment, provided herein is a compound of Formula IIIBd:

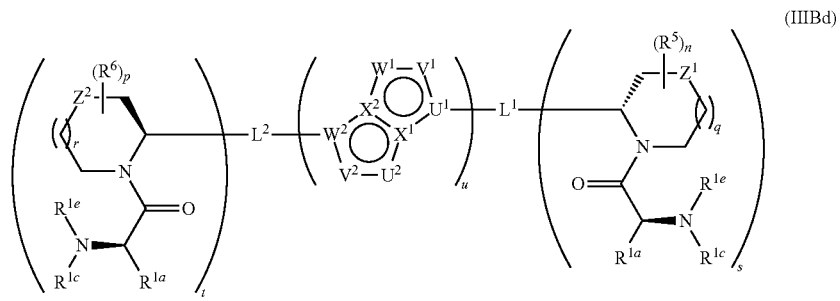

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In IB, IIIB, IIIBa, IIIBb, IIIBc, or IIIBd, in one embodiment, $U^1$, $X^1$, and $X^2$ are C, $V^1$, $V^2$, $U^2$ are each independently $CR^{3a}$, $W^1$ is S, and $W^2$ is N; in another embodiment, $U^1$, $W^2$, $X^1$, and $X^2$ are C, $U^2$ and $W^1$ are S, and $V^1$ and $V^2$ are each independently $CR^{3a}$; in yet another embodiment, $U^1$, $W^2$, $X^1$, and $X^2$ are C, $U^2$ is $NR^{3a}$, $V^1$ and $V^2$ are each independently $CR^{3a}$, and $W^1$ is S; in yet another embodiment, $U^1$, $W^2$, $X^1$, and $X^2$ are C, $U^2$ is $NR^{3a}$, $V^1$ and $V^2$ are each independently $CR^{3a}$, and $W^1$ is O; in yet another embodiment, $U^1$, $W^2$, $X^1$, and $X^2$ are C, $U^2$ is S, $V^1$ and $V^2$ are each independently $CR^{3a}$, and $W^1$ is $NR^{3a}$; in yet another embodiment, $U^1$ and $X^1$ are C, $U^2$, $V^1$, and $V^2$ are each independently $CR^{3a}$, $W^1$, $W^2$, and $X^2$ are N; in yet another embodiment, $U^1$, $W^2$, $X^1$, and $X^2$ are C, $U^2$ and $W^2$ are each independently $CR^{3a}$, $V^1$ and $V^2$ are N; in still another embodiment, $U^1$ is N, $U^2$ is S, $V^1$, $V^2$, and $W^1$ are each independently $CR^{3a}$, $W^2$, $X^1$, and $X^2$ are C; wherein each $R^{3a}$ is as defined herein.

In yet another embodiment, provided herein is a compound of Formula IVB:

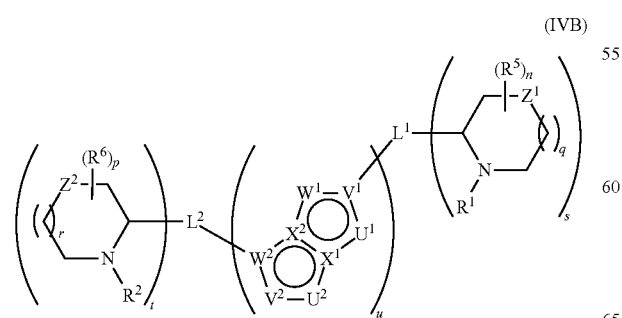

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $X^1$, $X^2$, $Z^1$, $Z^2$, n, p, q, r, s, t, and u are each as defined herein; and $V^1$ and $W^2$ are each independently C or N.

In one embodiment, provided herein is a compound of Formula IVBa:

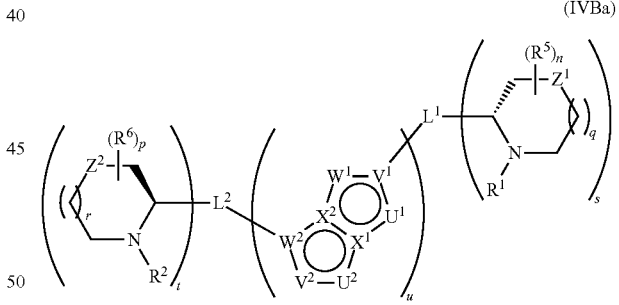

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In another embodiment, provided herein is a compound of Formula IVBb:

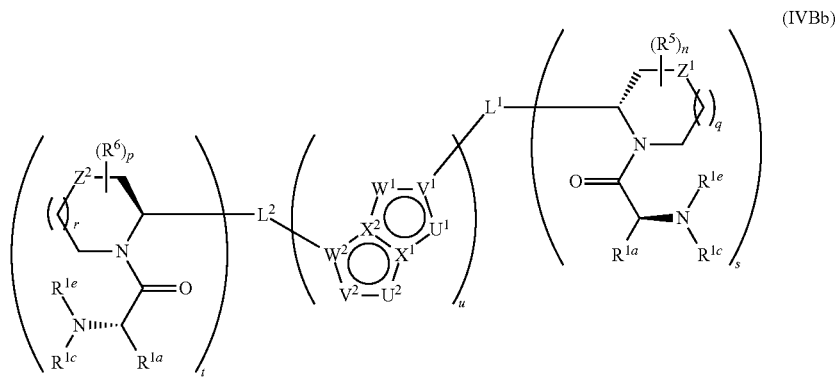

(IVBb)

or a single enantiomer, a racemic mixture, a mixture of diastereomers, or an isotopic variant thereof; or a pharmaceutically acceptable salt, solvate, or prodrug thereof; wherein $R^{1a}, R^{1c}, R^{1e}, R^5, R^6, L^1, L^2, U^1, U^2, V^1, V^2, W^1, W^2, X^1, X^2, Z^1, Z^2$, n, p, q, r, s, t, and u are each as defined herein.

In yet another embodiment, provided herein is a compound of Formula IVBc:

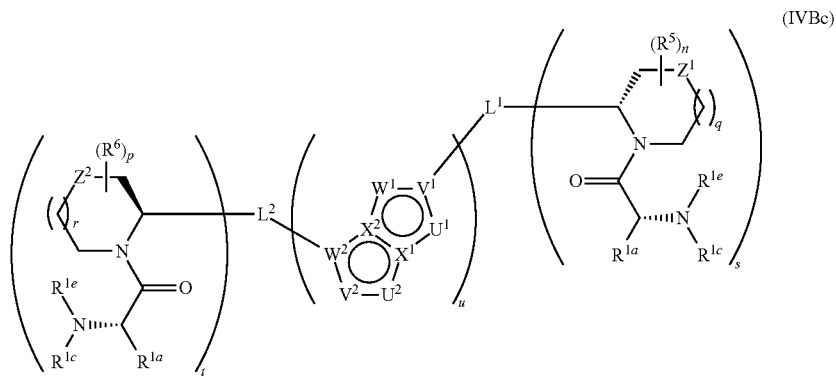

(IVBc)

or a single enantiomer, a racemic mixture, a mixture of diastereomers, or an isotopic variant thereof; or a pharmaceutically acceptable salt, solvate, or prodrug thereof; wherein $R^{1a}, R^{1c}, R^{1e}, R^5, R^6, L^1, L^2, U^1, U^2, V^1, V^2, W^1, W^2, X^1, X^2, Z^1, Z^2$, n, p, q, r, s, t, and u are each as defined herein.

In Formula IB, IVB, IVBa, IVBb, or IVBc, in one embodiment, $U^1$ and $V^2$ are each independently $CR^{3a}$, $U^2$ and $W^1$ are S, and $V^1, W^2, X^1$, and $X^2$ are C; in another embodiment, $U^1$ and $V^2$ are each independently $CR^{3a}$, $U^2$ is S, $V^1, W^2, X^1$, A and $X^2$ are C, and $W^1$ is $NR^{3a}$; in yet another embodiment, $U^1$ and $X^2$ are N, $U^2$ is S, $V^1, W^2$, and $X^1$ are C, and $V^2$ and $W^1$ are each independently $CR^{3a}$; wherein each $R^{3a}$ is as defined herein.

In yet another embodiment, provided herein is a compound of Formula VB:

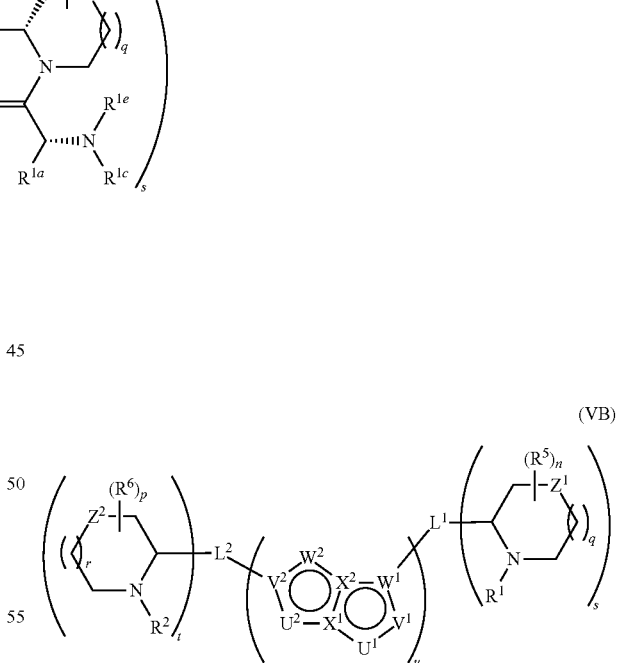

(VB)

or a single enantiomer, a racemic mixture, a mixture of diastereomers, or an isotopic variant thereof; or a pharmaceutically acceptable salt, solvate, or prodrug thereof; wherein $R^1$, $R^2, R^5, R^6, L^1, L^2, U^1, U^2, V^1, W^2, X^1, X^2, Z^1, Z^2$, n, p, q, r, s, t, and u are each as defined herein; and $V^2$ and $W^1$ are each independently C or N.

In one embodiment, provided herein is a compound of Formula VBa:

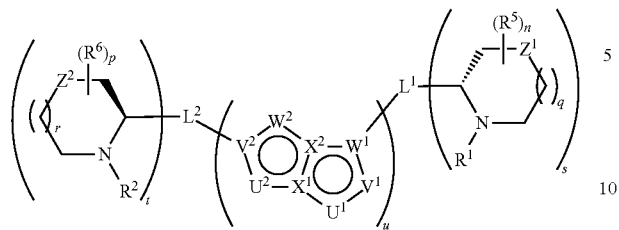

(VBa)

or a single enantiomer, a racemic mixture, a mixture of mastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In another embodiment, provided herein is a compound of Formula VBb:

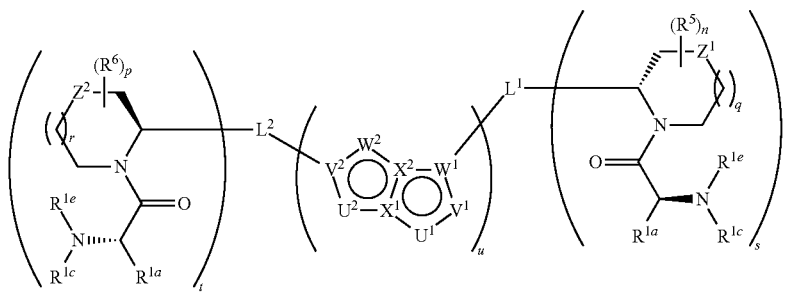

(VBb)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In yet another embodiment, provided herein is a compound of Formula VBc:

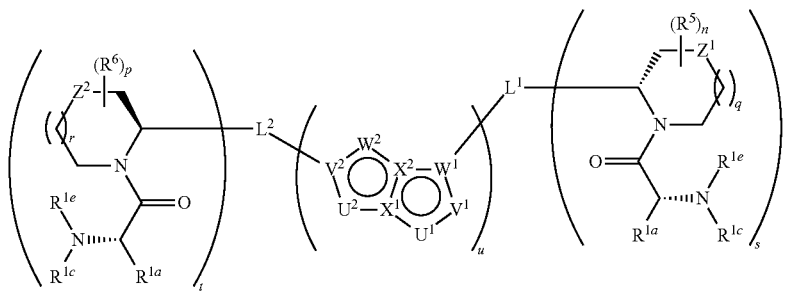

(VBc)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In Formula IB, VB, VBa, VBb, or VBc, in one embodiment, $U^1$ and $W^2$ are S, $U^2$ and $V^1$ are each independently $CR^{3a}$, and $V^2$, $W^1$, $X^1$, and $X^2$ are C; in another embodiment, $U^1$ is S, $U^2$ and $X^2$ are N, $V^1$ and $W^2$ are each independently $CR^{3a}$, and $V^2$, $W^1$, and $X^1$ are C; in yet another embodiment, $U^1$ is S, $U^2$ and $V^1$ are each independently $CR^{3a}$, $V^2$, $W^1$, $X^1$, and $X^2$ are C; and $W^2$ is $NR^{3a}$; wherein each $R^{3a}$ is as defined herein.

In still another embodiment, provided herein is a compound of Formula VIB:

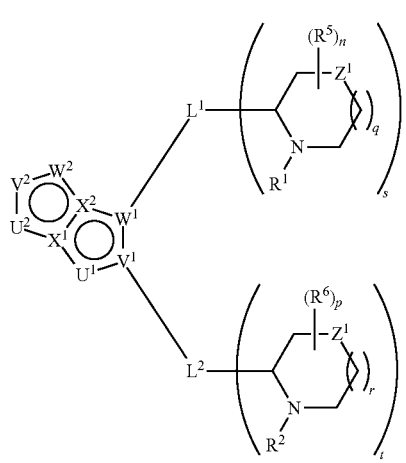

(VIB)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^2$, $W^2$, $X^1$, $X^2$, $Z^1$, $Z^2$, n, p, q, r, s, t, and u are each as defined herein; and $V^1$ and $W^1$ are each independently C or N.

In one embodiment, provided herein is a compound of Formula VIBa:

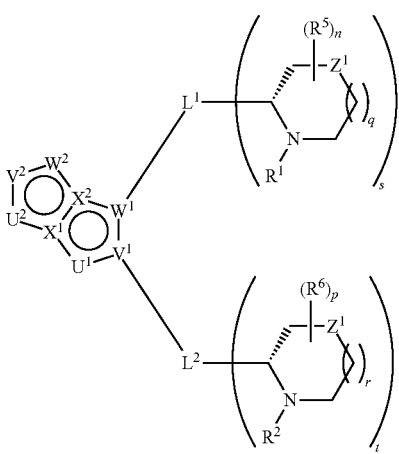

(VIBa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In another embodiment, provided herein is a compound of Formula VIBb:

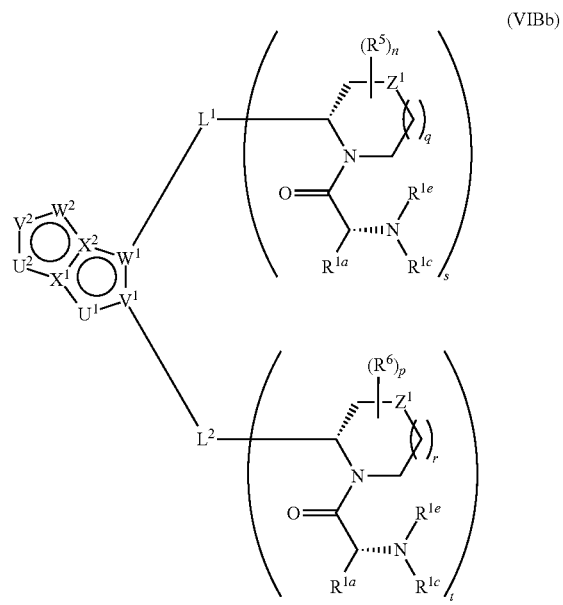

(VIBb)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In yet another embodiment, provided herein is a compound of Formula VIBc:

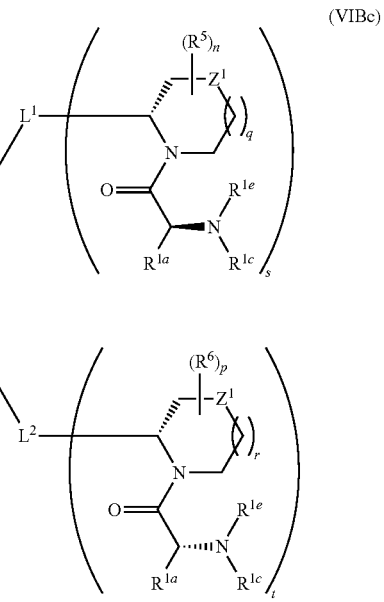

(VIBc)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $Z^1$, $Z^2$, n, p, q, r, s, t, and u are each as defined herein. In Formula IB, VIB, VIBa, VIBb, or VIBc, in one embodiment, $U^1$ and $X^2$ are N, $U^2$ is S, $V^1$, $W^1$, and $X^1$ are C, and $V^2$ and $W^2$ are each independently $CR^{3a}$; in another embodiment, $U^1$ is S, $U^2$ and $X^2$ are N, $V^1$, $W^1$, and $X^1$ are C, and $V^2$ and $W^2$ are each independently $CR^{3a}$, wherein each $R^{3a}$ is as defined herein.

In still another embodiment, provided herein is a compound of Formula AA:

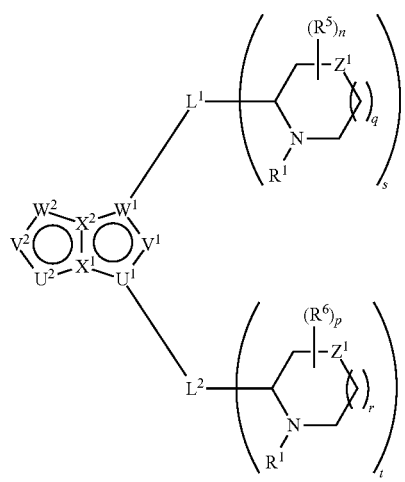

(AA)

wherein $R^1$, $R^2$, $R^5$, $R^6$, $L^1$, $L^2$, $U^2$, $V^1$, $V^2$, $W^2$, $X^1$, $X^2$, $Z^1$, $Z^2$, n, p, q, r, s, t, and u are each as defined herein; and $U^1$ and $W^1$ are each independently C or N.

In one embodiment, provided herein is a compound of Formula AAa:

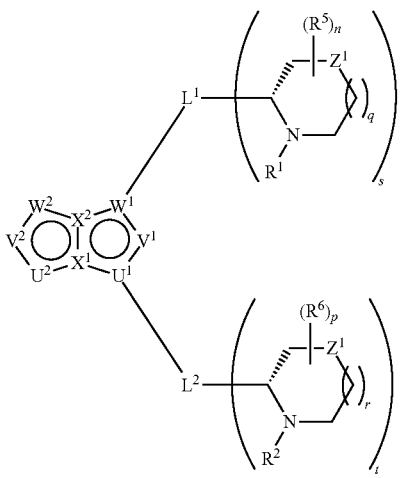

(AAa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In another embodiment, provided herein is a compound of Formula AAb:

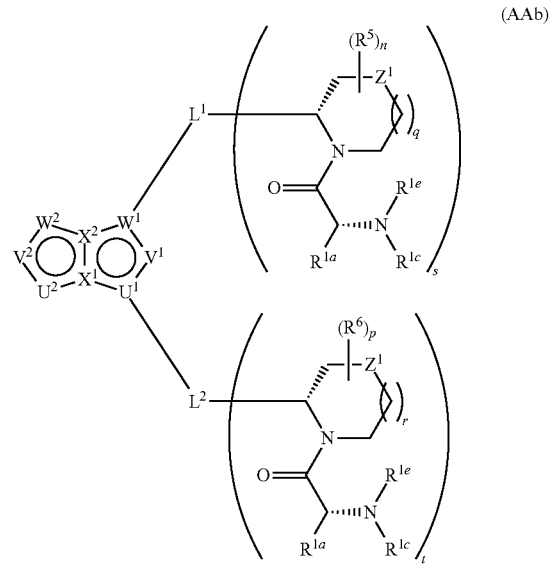

(AAb)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $X^1$, $X^2$, $Z^1$, $Z^2$, n, p, q, r, s, t, and u are each as defined herein.

In yet another embodiment, provided herein is a compound of Formula AAc:

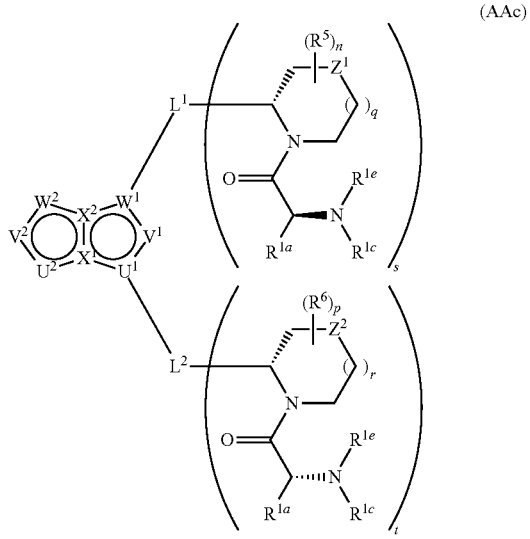

(AAc)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $U^1$, $U^2$, $V^1$, $V^2$, $W^1$, $W^2$, $Z^1$, $Z^2$, n, p, q, r, s, t, and u are each as defined herein.

In yet another embodiment, provided herein is a compound of Formula IC:

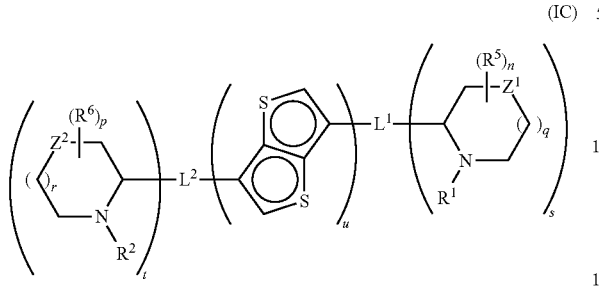

(IC)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $Z^1$, $Z^2$, n, p, q, r, s, t, and u are each as defined herein.

In one embodiment, provided herein is a compound of Formula ICa:

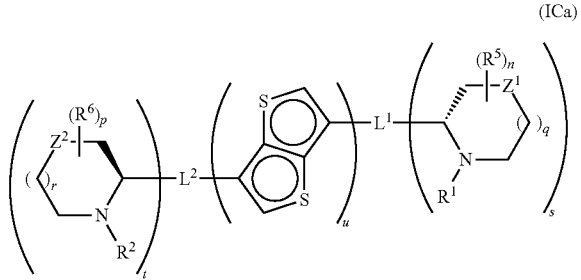

(ICa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $L^2$, $Z^1$, $Z^2$, n, p, q, r, s, t, and u are each as defined herein.

In another embodiment, provided herein is a compound of Formula ICb:

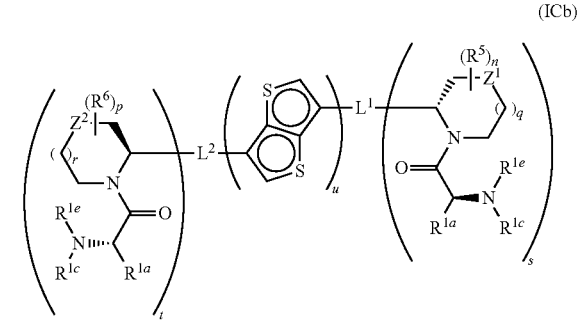

(ICb)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $Z^1$, $Z^2$, n, p, q, r, s, t, and u are each as defined herein.

In yet another embodiment, provided herein is a compound of Formula ICc:

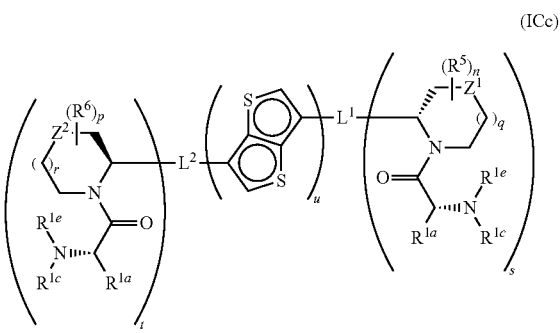

(ICc)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $Z^1$, $Z^2$, n, p, q, r, s, t, and u are each as defined herein.

In yet another embodiment, provided herein is a compound of Formula ICd:

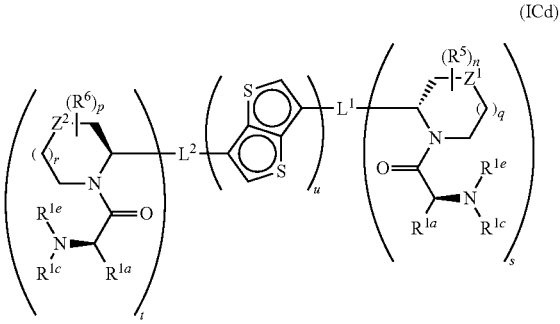

(ICd)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $L^2$, $Z^1$, $Z^2$, n, p, q, r, s, t, and u are each as defined herein.

In yet another embodiment, provided herein is a compound of Formula IIC:

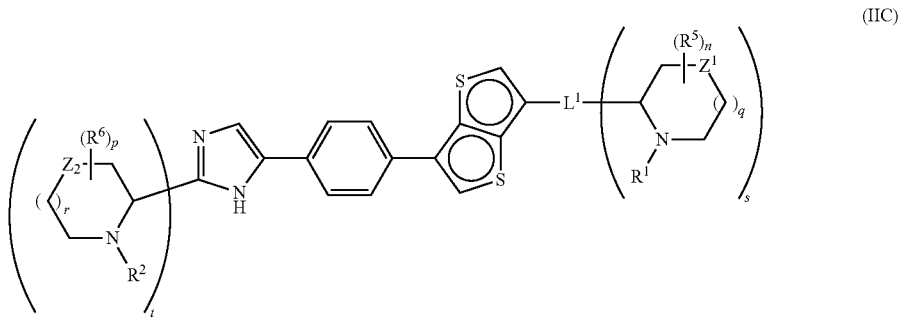

(IIC)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $Z^1$, $Z^2$, n, p, q, r, s, and t are each as defined herein.

In one embodiment, provided herein is a compound of Formula IICa:

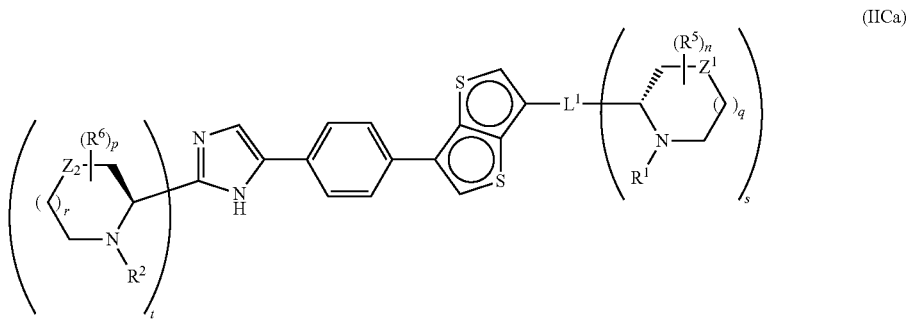

(IICa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^5$, $R^6$, $L^1$, $Z^1$, $Z^2$, n, p, q, r, s, and t are each as defined herein.

In another embodiment, provided herein is a compound of Formula IICb:

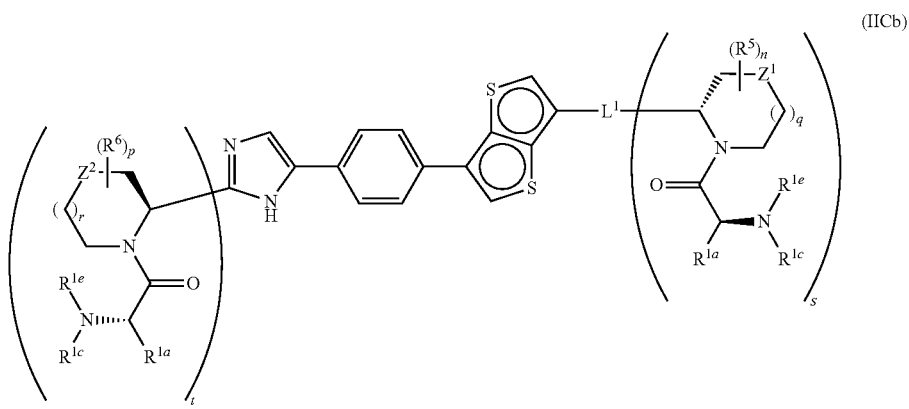

(IICb)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $Z^1$, $Z^2$, n, p, q, r, s, and t are each as defined herein.

In yet another embodiment, provided herein is a compound of Formula IICc:

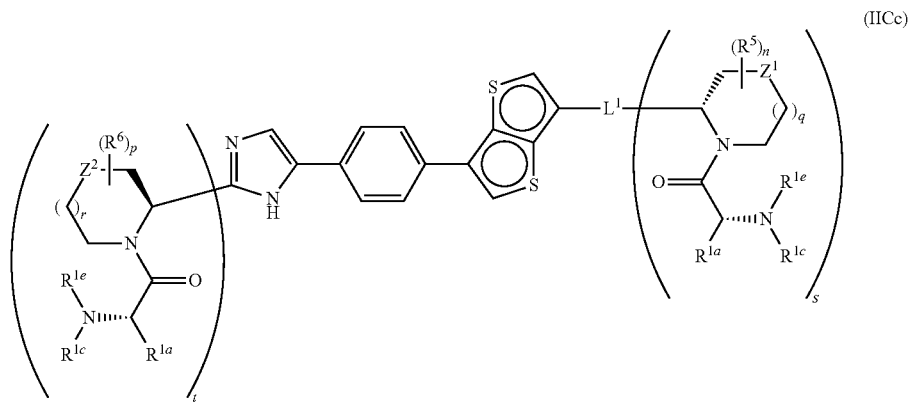

(IICc)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $Z^1$, $Z^2$, n, p, q, r, s, and t are each as defined herein.

In yet another embodiment, provided herein is a compound of Formula IICd:

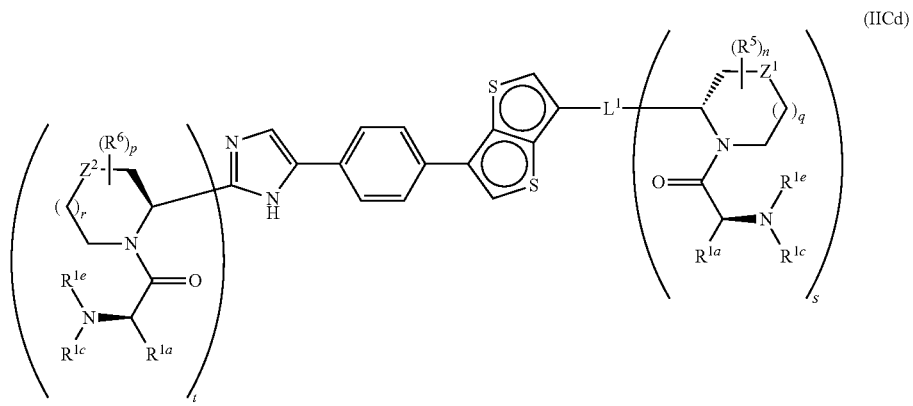

(IICd)

or a single enantiomer, a racemic mixture, a mixture of diastereomers, or an isotopic variant thereof; or a pharmaceutically acceptable salt, solvate, or prodrug thereof; wherein $R^{1a}$, $R^{1c}$, $R^{1e}$, $R^5$, $R^6$, $L^1$, $Z^1$, $Z^2$, n, p, q, r, s, and t are each as defined herein.

The groups, $R^1$, $R^{1A}$, $R^{1a}$, $R^{1b}$, $R^{1c}$, $R^{1e}$, $R^2$, $R^3$, $R^{3a}$, $R^5$, $R^6$, $L^1$, $L^2$, $T^3$, $U^1$, $U^2$, $U^3$, $V^1$, $V^2$, $V^3$, $W^1$, $W^2$, $W^3$, $X^1$, $X^2$, $X^3$, $Y^3$, $Z^1$, $Z^2$, m, n, p, q, r, s, and t in formulae described herein, including Formulae I to XXIII, IIIa to VIIIa, Xa to XVa, XVIIa to XXa, IIIb to VIIIb, Xb to XVb, XVIIb to XXb, IIIc to VIIIc, Xc to XVc, XVIIc to XXc, IA to XIA, IIIAa to VIAa, VIIIAa to XIAa, IIIAb to VIAb, VIIIAb to XIAb, IIIAc to VIAc, VIIIAc to XIAc, IB to VIB, IBa to VIBa, IBb to VIBb, IBc to VIBc, IIIBd, ICa to ICd, IIC to IICd, and AA, AAa, AAb, and AAc are further defined herein. All combinations of the embodiments provided herein for such groups are within the scope of this disclosure.

In certain embodiments, $R^1$ is hydrogen. In certain embodiments, $R^1$ is $C_{1-6}$ alkyl, optionally substituted with one or more substituents Q. In certain embodiments, $R^1$ is $C_{2-6}$ alkenyl, optionally substituted with one or more substituents Q. In certain embodiments, $R^1$ is $C_{2-6}$ alkynyl, optionally substituted with one or more substituents Q. In certain embodiments, $R^1$ is $C_{3-7}$ cycloalkyl, optionally substituted with one or more substituents Q. In certain embodiments, $R^1$ is $C_{6-14}$ aryl, optionally substituted with one or more substituents Q. In certain embodiments, $R^1$ is $C_{7-15}$ aralkyl, optionally substituted with one or more substituents Q. In certain embodiments, $R^1$ is heteroaryl, optionally substituted with one or more substituents Q. In certain embodiments, $R^1$ is heterocyclyl, optionally substituted with one or more substituents Q.

In certain embodiments, $R^1$ is —C(O)$R^{1a}$, wherein $R^{1a}$ is as defined herein. In certain embodiments, $R^1$ is —C(O)CH(NR$^{1b}$R$^{1c}$)R$^{1a}$, wherein R$^{1a}$, R$^{1b}$, and R$^{1c}$ are each as defined herein. In certain embodiments, $R^1$ is —C(O)CH[N(C(O)R$^{1b}$)R$^{1c}$]R$^{1a}$, wherein R$^{1a}$, R$^{1b}$, and R$^{1c}$ are each as defined herein. In certain embodiments, $R^1$ is —C(O)CH[N(C(O)OR$^{1b}$)R$^{1c}$]R$^{1a}$, wherein R$^{1a}$, R$^{1b}$, and R$^{1c}$ are each as defined herein. In certain embodiments, $R^1$ is —C(O)CH[N(C(O)NR$^{1b}$R$^{1d}$)R$^{1c}$]R$^{1a}$, wherein R$^{1a}$, R$^{1b}$, R$^{1c}$, and R$^{1d}$ are each as defined herein. In certain embodiments, $R^1$ is —C(O)OR$^{1a}$, wherein R$^{1a}$ is as defined herein. In certain embodiments, $R^1$ is —C(O)NR$^{1b}$R$^{1c}$, wherein R$^{1b}$ and R$^{1c}$ are each as defined herein. In certain embodiments, $R^1$ is —C(NR$^{1a}$)NR$^{1b}$R$^{1c}$, wherein R$^{1a}$, R$^{1b}$, and R$^{1c}$ are each as defined herein. In certain embodiments, $R^1$ is —P(O)(OR$^{1a}$)R$^{1d}$, wherein R$^{1a}$ and R$^{1d}$ are each as defined herein. In certain embodiments, $R^1$ is —CH$_2$P(O)(OR$^{1a}$)R$^{1d}$, wherein R$^{1a}$ and R$^{1d}$ are each as defined herein. In certain embodiments, $R^1$ is —S(O)R$^{1a}$, wherein R$^{1a}$ is as defined herein. In certain embodiments, $R^1$ is —S(O)$_2$R$^{1a}$, wherein R$^{1a}$ is as defined herein. In certain embodiments, $R^1$ is —S(O)NR$^{1b}$R$^{1c}$, wherein R$^{1b}$ and R$^{1c}$ are each as defined herein. In certain embodiments, $R^1$ is —S(O)$_2$NR$^{1b}$R$^{1c}$, wherein R$^{1b}$ and R$^{1c}$ are each as defined herein.

In certain embodiments, $R^{1A}$ is hydrogen. In certain embodiments, $R^{1A}$ is $C_{1-6}$ alkyl, optionally substituted with one or more substituents Q. In certain embodiments, $R^{1A}$ is $C_{2-6}$ alkenyl, optionally substituted with one or more substituents Q. In certain embodiments, $R^{1A}$ is $C_{2-6}$ alkynyl, optionally substituted with one or more substituents Q. In certain embodiments, $R^{1A}$ is $C_{3-7}$ cycloalkyl, optionally substituted with one or more substituents Q. In certain embodiments, $R^{1A}$ is $C_{6-14}$ aryl, optionally substituted with one or more substituents Q. In certain embodiments, $R^{1A}$ is $C_{7-15}$ aralkyl, optionally substituted with one or more substituents Q. In certain embodiments, $R^{1A}$ is heteroaryl, optionally substituted with one or more substituents Q. In certain embodiments, $R^{1A}$ is heterocyclyl. In certain embodiments, $R^{1A}$ is —C(O)R$^{1a}$, wherein R$^{1a}$ is as defined herein. In certain embodiments, $R^{1A}$ is —C(O)OR$^{1a}$, wherein R$^{1a}$ is as defined herein. In certain embodiments, $R^{1A}$ is —C(O)NR$^{1b}$R$^{1c}$, wherein R$^{1b}$ and R$^{1c}$ are each as defined herein. In certain embodiments, $R^{1A}$ is —C(NR$^{1a}$)NR$^{1b}$R$^{1c}$, wherein R$^{1a}$, R$^{1b}$, and R$^{1c}$ are each as defined herein. In certain embodiments, $R^{1A}$ is —P(O)(OR$^{1a}$)R$^{1d}$, wherein R$^{1a}$ and R$^{1d}$ are each as defined herein. In certain embodiments, $R^{1A}$ is —CH$_2$P(O)(OR$^{1a}$)R$^{1d}$, wherein R$^{1a}$ and R$^{1d}$ are each as defined herein. In certain embodiments, $R^{1A}$ is —S(O)R$^{1a}$, wherein R$^{1a}$ is as defined herein. In certain embodiments, $R^{1A}$ is S(O)$_2$R$^{1a}$, wherein R$^{1a}$ is as defined herein. In certain embodiments, $R^{1A}$ is —S(O)NR$^{1b}$R$^{1c}$, wherein R$^{1b}$ and R$^{1c}$ are each as defined herein. In certain embodiments, $R^{1A}$ is —S(O)$_2$NR$^{1b}$R$^{1c}$, wherein R$^{1b}$ and R$^{1c}$ are each as defined herein.

In certain embodiments, $R^2$ is hydrogen. In certain embodiments, $R^2$ is $C_{1-6}$ alkyl, optionally substituted with one or more substituents Q. In certain embodiments, $R^2$ is $C_{2-6}$ alkenyl, optionally substituted with one or more substituents Q. In certain embodiments, $R^2$ is $C_{2-6}$ alkynyl, optionally substituted with one or more substituents Q. In certain embodiments, $R^2$ is $C_{3-7}$ cycloalkyl, optionally substituted with one or more substituents Q. In certain embodiments, $R^2$ is $C_{6-14}$ aryl, optionally substituted with one or more substituents Q. In certain embodiments, $R^2$ is $C_{7-15}$ aralkyl, optionally substituted with one or more substituents Q. In certain embodiments, $R^2$ is heteroaryl, optionally substituted with one or more substituents Q. In certain embodiments, $R^2$ is heterocyclyl, optionally substituted with one or more substituents Q.

In certain embodiments, $R^2$ is —C(O)R$^{1a}$, wherein R$^{1a}$ is as defined herein. In certain embodiments, $R^2$ is —C(O)CH(NR$^{1b}$R$^{1c}$)R$^{1a}$, wherein R$^{1a}$R$^{1b}$, and R$^{1c}$ are each as defined herein. In certain embodiments, $R^2$ is —C(O)CH[N(C(O)R$^{1b}$)R$^{1c}$]R$^{1a}$, wherein R$^{1a}$, R$^{1b}$, and R$^{1c}$ are each as defined herein. In certain embodiments, $R^2$ is —C(O)CH[N(C(O)OR$^{1b}$)R$^{1c}$]R$^{1a}$, wherein R$^{1a}$, R$^{1b}$, and R$^{1c}$ are each as defined herein. In certain embodiments, $R^2$ is —C(O)CH[N(C(O)NR$^{1b}$R$^{1d}$)R$^{1c}$]R$^{1a}$, wherein R$^{1a}$, R$^{1b}$, R$^{1c}$, and R$^{1d}$ are each as defined herein. In certain embodiments, $R^2$ is —C(O)OR$^{1a}$, wherein R$^{1a}$ is as defined herein. In certain embodiments, $R^2$ is —C(O)NR$^{1b}$R$^{1c}$, wherein R$^{1b}$ and R$^{1c}$ are each as defined herein. In certain embodiments, $R^2$ is —C(NR$^{1a}$)NR$^{1b}$R$^{1c}$, wherein R$^{1a}$, R$^{1b}$, and R$^{1c}$ are each as defined herein. In certain embodiments, $R^2$ is —P(O)(OR$^{1a}$)R$^{1d}$, wherein R$^{1a}$ and R$^{1d}$ are each as defined herein. In certain embodiments, $R^2$ is —CH$_2$P(O)(OR$^{1a}$)R$^{1d}$, wherein R$^{1a}$ and R$^{1d}$ are each as defined herein. In certain embodiments, $R^2$ is —S(O)R$^{1a}$, wherein R$^{1a}$ is as defined herein. In certain embodiments, $R^2$ is —S(O)$_2$R$^{1a}$, wherein R$^{1a}$ is as defined herein. In certain embodiments, $R^2$ is —S(O)NR$^{1b}$R$^{1c}$, wherein R$^{1b}$ and R$^{1c}$ are each as defined herein. In certain embodiments, $R^2$ is —S(O)$_2$NR$^{1b}$R$^{1c}$, wherein R$^{1b}$ and R$^{1c}$ are each as defined herein.

In certain embodiments, $R^1$ and $R^2$ are each independently selected from 2(R)-(dimethylamino)propionyl, 2-(methoxycarbonylamino)propionyl, 2(R)-(methoxy-carbonylamino)propionyl, 2-(ethoxycarbonylamino)propionyl, 2(R)-(methoxycarbonyl-amino)-3-methoxy-propionyl, 2(R)-(methoxycarbonylamino)-3-aminocarbonyl-propionyl, 2-(methoxycarbonylamino)-2-methylpropionyl, 2(R)-(methoxycarbonylamino)-3(R)-hydroxy-butanoyl, 2(R)-(methoxycarbonylamino)-3(S)-hydroxybutanoyl, 2(R)-(methoxycarbonyl-amino)-3-methylbutanoyl, 2(S)-(methoxycarbonylamino)-3-methylbutanoyl, 2(R)-(ethoxycarbonyl-amino)-3-methylbutanoyl, 2(S)-(ethoxycarbonylamino)-3-methylbutanoyl, 2(R)-(isoproxycarbonyl-amino)-3-methylbutanoyl, 2(S)-(isopropoxycarbonylamino)-3-methylbutanoyl, 2(R)-(tert-butoxycarbonylamino)-3-methylbutanoyl, 2(S)-(tert-butoxycarbonylamino)-3-methylbutanoyl, 2(R)-(methoxycarbonylamino)-3-hydroxy-3-methylbutanoyl, 2-(methoxycarbonylamino)-2-cyclopropyl-acetyl, 2-(methoxycarbonylamino)pentanoyl, 2-(methoxycarbonylamino)pent-4-enoyl, 1-(methoxycarbonylamino)cyclopropylcarbonyl, 1-(methoxycarbonylamino)-cyclobutylcarbonyl, 1-(methoxycarbonylamino)-cyclopentyl-carbonyl, 2(R)-(methoxycarbonylamino)-2-phenylacetyl, 2(R)-(ethoxycarbonylamino)-2-phenylacetyl, 2(R)-(isopropoxycarbonylamino)-2-phenylacetyl, 2(R)-(tert-butoxycarbonylamino)-2-phenylacetyl, 2(S)-(tert-butoxycarbonylamino)-2-phenylacetyl, 2(R)-(methoxycarbonyl-amino)-2-(2-chlorophenyl)acetyl, 2(R)-(dimethylamino)-2-phenylacetyl, 2-(dimethylamino)-2-(4-nitrophenyl)acetyl, 2-(dimethylamino)-2-(2-fluorophenyl)acetyl, 2(R)-(dimethylamino)-2-(2-fluorophenyl)acetyl, 2(S)-(dimethylamino)-2-(2-fluorophenyl)acetyl, 2-(dimethyl-amino)-2-(3-fluorophenyl)acetyl, 2-(dimethylamino)-2-(2-chlorophenyl)acetyl, 2(R)-(dimethylamino)-2-(2-chlorophenyl)acetyl, 2-(dimethylamino)-2-(3-chlorophenyl)acetyl, 2-(dimethylamino)-2-(4-chlorophenyl)acetyl, 2-(dimethylamino)-2-(2-trifluoromethyl-phenyl)acetyl, 2-(dimethyl-amino)-2-(3-trifluoromethylphenyl)acetyl, 2-(dimethylamino)-2-(thien-2-yl)acetyl, 2-(dimethylamino)-2-(thien-3-yl)acetyl, 2-(dimethylamino)-2-(2-methylthiazol-4-yl)acetyl, 2-(dimethylamino)-2-(benzothien-3-yl)acetyl, 2-(dimethylamino)-2-(2-methyl-benzothiazol-5-yl)acetyl, 2-(dimethylamino)-2-(benzoisoxazol-3-yl)acetyl, 2-(dimethylamino)-2-(quinolin-3-yl)acetyl, 2(R)-(diethylamino)-2-phenylacetyl, 2(R)-(methylethylamino)-2-phenylacetyl, 2-(dimethylamino)-2-naphth-1-ylacetyl, 2(R)-(pyrrolidin-1-yl)-2-phenylacetyl, 2-(3(S)-fluoropyrrolidin-1-yl)-2-phenylacetyl, 2(R)-(morpholin-4-yl)-2-phenylacetyl, 2(R)-(piperidin-1-yl)-2-phenylacetyl, 2(R)-(piperidin-1-yl)-2-(2-fluorophenyl)acetyl, 2-(4-hydroxy-piperidin-1-yl)-2-phenylacetyl, 2-(4-phenylpiperidin-1-yl)-2-phenylacetyl, 2(R)-(4-hydroxy-4-methylpiperidin-1-yl)-2-phenylacetyl, 2(R)-(4-hydroxy-4-phenylpiperidin-1-yl)-2-phenylacetyl, 2-(3-oxopiperazin-1-yl)-2-phenylacetyl, 2-(4-methylpiperazin-1-yl)-2-phenylacetyl, 2-(dimethylamino)-2-(pyridin-2-yl)acetyl, 2-(dimethylamino)-2-(pyridin-3-yl)acetyl, 2-(dimethylamino)-2-(pyridin-4-yl)acetyl, 2-(dimethylamino)-2-(6-chloropyridin-3-yl)acetyl, 2-(2-dimethylaminomethyl)phenylacetyl, 2-(2-pyrrolin-1-ylmethyl)phenylacetyl, 2-(2-piperidin-1-ylmethyl)phenylacetyl, 2-(2-morpholin-4-ylmethyl)phenylacetyl, 2-(2-(4-methylpiperazin-1-ylmethyl)phenylacetyl, 1-methylpyrrolidine-2(R)-carbonyl, 1-methyl-4(R)-fluoro-pyrrolidine-2(R)-carbonyl, 2-(R)-(methylaminoarbonylamino)-2-phenylacetyl, 2-(R)-(ethylaminoarbonylamino)-2-phenylacetyl, 2(R)-(cyclopentylaminoarbonylamino)-2-phenylacetyl, 2(R)-(dimethylaminoarbonylamino)-2-phenylacetyl, (N,N-benzylmethyl-amino)acetyl, and 2-(N,N-benzylmethylamino)-3-methylbutanoyl. Further examples of $R^1$ and $R^2$ can be found, e.g., in U.S. Pat. Appl. Publ. Nos. 2009/0202478 and 2009/0202483; and International Pat. Appl. Nos. WO 2008/144380 and WO 2009/102694, the disclosure of each of which is incorporated herein by reference in its entirety.

In certain embodiments, $R^{1a}$ is hydrogen. In certain embodiments, $R^{1a}$ is $C_{1-6}$ alkyl, optionally substituted with one or more substituents Q. In certain embodiments, $R^{1a}$ is $C_{1-6}$ alkyl, optionally substituted with one or more substituents, where each substituent is independently selected from hydroxyl, mercapto, methylthio, amino, carboxy, carbamoyl, guanidino, phenyl, hydroxyphenyl, imidazolyl, or indolyl. In certain embodiments, $R^{1a}$ is $C_{1-6}$ alkyl, optionally substituted with one or more substituents, each of which is independently selected from hydroxyl, mercapto, methylthio, amino, carboxy, carbamoyl, guanidino, phenyl, hydroxyphenyl, imidazolyl, or indolyl. In certain embodiments, $R^{1a}$ is methyl, ethyl, propyl, or butyl, each optionally substituted with one or more substituents Q. In certain embodiments, $R^{1a}$ is methyl, ethyl, propyl, or butyl, each optionally substituted with one or more substituents, where each substituent is independently selected from hydroxyl, mercapto, methylthio, amino, carboxy, carbamoyl, guanidino, phenyl, hydroxyphenyl, imidazolyl, or indolyl. In certain embodiments, $R^{1a}$ is methyl, isopropyl, 2-methylpropyl, 1-methylpropyl, 2-methylthioethyl, benzyl, 3-indolylmethyl, hydroxymethyl, 1-hydroxyethyl, mercaptomethyl, 4-hydroxybenzyl, carbamoylmethyl, 2-carbamoylethyl, carboxymethyl, 2-carboxyethyl, 4-aminobutyl, 3-guanidinopropyl, or 4-imidazolylmethyl.

In certain embodiments, $R^{1a}$ is $C_{2-6}$ alkenyl, optionally substituted with one or more substituents Q. In certain embodiments, $R^{1a}$ is $C_{2-6}$ alkynyl, optionally substituted with one or more substituents Q. In certain embodiments, $R^{1a}$ is $C_{3-7}$ cycloalkyl, optionally substituted with one or more substituents Q. In certain embodiments, $R^{1a}$ is $C_{6-14}$ aryl, optionally substituted with one or more substituents Q. In certain embodiments, $R^{1a}$ is phenyl, optionally substituted with one or more substituents Q. In certain embodiments, $R^{1a}$ is $C_{7-15}$ aralkyl, optionally substituted with one or more substituents Q. In certain embodiments, $R^{1a}$ is benzyl or hydroxybenzyl. In certain embodiments, $R^{1a}$ is benzyl or 4-hydroxybenzyl. In certain embodiments, $R^{1a}$ is heteroaryl, optionally substituted with one or more substituents Q. In certain embodiments, $R^{1a}$ is heterocyclyl, optionally substituted with one or more substituents Q.

In certain embodiments, $R^{1b}$ is hydrogen. In certain embodiments, $R^{1b}$ is $C_{1-6}$ alkyl, optionally substituted with one or more substituents Q. In certain embodiments, $R^{1b}$ is $C_{2-6}$ alkenyl, optionally substituted with one or more substituents Q. In certain embodiments, $R^{1b}$ is $C_{2-6}$ alkynyl, optionally substituted with one or more substituents Q. In certain embodiments, $R^{1b}$ is $C_{3-7}$ cycloalkyl, optionally substituted with one or more substituents Q. In certain embodiments, $R^{1b}$ is $C_{6-14}$ aryl, optionally substituted with one or more substituents Q. In certain embodiments, $R^{1b}$ is $C_{7-15}$ aralkyl, optionally substituted with one or more substituents Q. In certain embodiments, $R^{1b}$ is heteroaryl, optionally substituted with one or more substituents Q. In certain embodiments, $R^{1b}$ is heterocyclyl, optionally substituted with one or more substituents Q.

In certain embodiments, $R^{1c}$ is hydrogen. In certain embodiments, $R^{1c}$ is $C_{1-6}$ alkyl, optionally substituted with one or more substituents Q. In certain embodiments, $R^{1c}$ is methyl. In certain embodiments, $R^{1c}$ is $C_{2-6}$ alkenyl, optionally substituted with one or more substituents Q. In certain embodiments, $R^{1c}$ is $C_{2-6}$ alkynyl, optionally substituted with one or more substituents Q. In certain embodiments, $R^{1c}$ is $C_{3-7}$ cycloalkyl, optionally substituted with one or more substituents Q. In certain embodiments, $R^{1c}$ is $C_{6-14}$ aryl, optionally substituted with one or more substituents Q. In certain embodiments, $R^{1c}$ is $C_{7-15}$ aralkyl, optionally substituted with one or more substituents Q. In certain embodiments, $R^{1c}$ is heteroaryl, optionally substituted with one or more substituents Q. In certain embodiments, $R^{1c}$ is heterocyclyl, optionally substituted with one or more substituents Q.

In certain embodiments, $R^{1a}$ and $R^{1c}$ together with the C and N atoms to which they are attached form heterocyclyl, in one embodiment, pyrrolidinyl, in another embodiment, 2-pyrrolidinyl, each optionally substituted with one or more substituents Q.

In certain embodiments, $R^{1b}$ and $R^{1c}$ together with the N atom to which they are attached form heterocyclyl, optionally substituted with one or more substituents Q.

In certain embodiments, $R^{1d}$ is hydrogen. In certain embodiments, $R^{1d}$ is $C_{1-6}$ alkyl, optionally substituted with one or more substituents Q. In certain embodiments, $R^{1d}$ is methyl. In certain embodiments, $R^{1d}$ is $C_{2-6}$ alkenyl, optionally substituted with one or more substituents Q. In certain embodiments, $R^{1d}$ is $C_{2-6}$ alkynyl, optionally substituted with one or more substituents Q. In certain embodiments, $R^{1d}$ is $C_{3-7}$ cycloalkyl, optionally substituted with one or more substituents Q. In certain embodiments, $R^{1d}$ is $C_{6-14}$ aryl, optionally substituted with one or more substituents Q. In certain embodiments, $R^{1d}$ is $C_{7-15}$ aralkyl, optionally substituted with one or more substituents Q. In certain embodiments, $R^{1d}$ is heteroaryl, optionally substituted with one or more substituents Q. In certain embodiments, $R^{1d}$ is heterocyclyl, optionally substituted with one or more substituents Q.

In certain embodiments, $R^{1e}$ is hydrogen. In certain embodiments, $R^{1e}$ is $C_{1-6}$ alkyl, optionally substituted with one or more substituents Q. In certain embodiments, $R^{1e}$ is $C_{2-6}$ alkenyl, optionally substituted with one or more substituents Q. In certain embodiments, $R^{1e}$ is $C_{2-6}$ alkynyl, optionally substituted with one or more substituents Q. In certain embodiments, $R^{1e}$ is $C_{3-7}$ cycloalkyl, optionally substituted with one or more substituents Q. In certain embodiments, $R^{1e}$ is $C_{6-14}$ aryl, optionally substituted with one or more substituents Q. In certain embodiments, $R^{1e}$ is $C_{7-15}$ aralkyl, optionally substituted with one or more substituents Q. In certain embodiments, $R^{1e}$ is heteroaryl, optionally substituted with one or more substituents Q. In certain embodiments, $R^{1e}$ is heterocyclyl, each optionally substituted with one or more substituents Q. In certain embodiments, $R^{1e}$ is —C(O)$R^{1a}$, wherein $R^{1a}$ is as defined herein. In certain embodiments, $R^{1e}$ is —C(O)O$R^{1a}$, wherein $R^{1a}$ is as defined herein. In certain embodiments, $R^{1e}$ is —C(O)O—$C_{1-6}$ alkyl, optionally substituted with one or more substituents Q. In certain embodiments, $R^{1e}$ is methoxycarbonyl or butoxycarbonyl. In certain embodiments, $R^{1e}$ is ethoxycarbonyl or propoxycarbonyl. In certain embodiments, $R^{1e}$ is isopropoxycarbonyl. In certain embodiments, $R^{1e}$ is isobutoxycarbonyl. In certain embodiments, $R^{1e}$ is t-butoxycarbonyl. In certain embodiments, $R^{1e}$ is C(O)NR$^{1b}$R$^{1d}$, wherein $R^{1b}$ and $R^{1d}$ are each as defined herein.

In certain embodiments, $R^{3a}$ is hydrogen. In certain embodiments, $R^{3a}$ is $R^3$, which is as defined herein. In certain embodiments, $R^{3a}$ is hydrogen, chloro, fluoro, nitro, amino, methyl, trifluoromethyl, phenyl, or methoxy.

In certain embodiments, $R^3$ is oxo. In certain embodiments, $R^3$ is cyano. In certain embodiments, $R^3$ is halo. In certain embodiments, $R^3$ is nitro. In certain embodiments, $R^3$ is $C_{1-6}$ alkyl, optionally substituted with one or more substituents Q. In certain embodiments, $R^3$ is methyl, optionally substituted with one or more substituents Q. In certain embodiments, $R^3$ is $C_{2-6}$ alkenyl, optionally substituted with one or more substituents Q. In certain embodiments, $R^3$ is $C_{2-6}$ alkynyl, optionally substituted with one or more substituents Q. In certain embodiments, $R^3$ is $C_{3-7}$ cycloalkyl, optionally substituted with one or more substituents Q. In certain embodiments, $R^3$ is cyclohexyl, optionally substituted with one or more substituents Q. In certain embodiments, $R^3$ is cyclohexyl. In certain embodiments, $R^3$ is $C_{6-14}$ aryl, optionally substituted with one or more substituents Q. In certain embodiments, $R^3$ is $C_{7-15}$ aralkyl, optionally substituted with one or more substituents Q. In certain embodiments, $R^3$ is heteroaryl, optionally substituted with one or more substituents Q. In certain embodiments, $R^3$ is heterocyclyl, optionally substituted with one or more substituents Q. In certain embodiments, $R^3$ is —C(O)$R^{1a}$, where $R^{1a}$ is as defined herein. In certain embodiments, $R^3$ is —C(O)O$R^{1a}$, where $R^{1a}$ is as defined herein. In certain embodiments, $R^3$ is —C(O)OCH$_3$. In certain embodiments, $R^3$ is —C(O)NR$^{1b}$R$^{1c}$, where $R^{1b}$ and $R^{1c}$ are each as defined herein. In certain embodiments, $R^3$ is —C(NR$^{1a}$)NR$^{1b}$R$^{1c}$, where $R^{1a}$, $R^{1b}$, and $R^{1c}$ are each as defined herein. In certain embodiments, $R^3$ is —O$R^{1a}$, where $R^{1a}$ is as defined herein. In certain embodiments, $R^3$ is —OH. In certain embodiments, $R^3$ is —OC(O)$R^{1a}$, where $R^{1a}$ is as defined herein. In certain embodiments, $R^3$ is —OC(O)O$R^{1a}$, where $R^{1a}$ is as defined herein. In certain embodiments, $R^3$ is —OC(O)NR$^{1b}$R$^{1c}$, where $R^{1b}$ and $R^{1c}$ are each as defined herein. In certain embodiments, $R^3$ is —OC(=NR$^{1a}$)NR$^{1b}$R$^{1c}$, where $R^{1a}$, $R^{1b}$, and $R^{1c}$ are each as defined herein. In certain embodiments, $R^3$ is —OS(O)$R^{1a}$, where $R^{1a}$ is as defined herein. In certain embodiments, $R^3$ is —OS(O)$_2$R$^{1a}$, where $R^{1a}$ is as defined herein. In certain embodiments, $R^3$ is —OS(O)NR$^{1b}$R$^{1c}$, where $R^{1b}$ and $R^{1c}$ are each as defined herein. In certain embodiments, $R^3$ is —OS(O)$_2$NR$^{1b}$R$^{1c}$, where $R^{1b}$ and $R^{1c}$ are each as defined herein. In certain embodiments, $R^3$ is —NR$^{1b}$R$^{1c}$, where $R^{1b}$ and $R^{1c}$ are each as defined herein. In certain embodiments, $R^3$ is —NR$^{1a}$C(O)$R^{1d}$, where $R^{1a}$ and $R^{1d}$ are each as defined herein. In certain embodiments, $R^3$ is —NR$^{1a}$C(O)O$R^{1d}$, where $R^{1a}$ and $R^{1d}$ are each as defined herein. In certain embodiments, $R^3$ is —NR$^{1a}$C(O)NR$^{1b}$R$^{1c}$, where $R^{1a}$, $R^{1b}$, and $R^{1c}$ are each as defined herein. In certain embodiments, $R^3$ is —NR$^{1a}$C(=NR$^{1d}$)NR$^{1b}$R$^{1c}$, where $R^{1a}$, $R^{1b}$, $R^{1c}$, and $R^{1d}$ are each as defined herein. In certain embodiments, $R^3$ is —NR$^{1a}$S(O)$R^{1d}$, where $R^{1a}$ and $R^{1d}$ are each as defined herein. In certain embodiments, $R^3$ is —NR$^{1a}$S(O)$_2$R$^{1d}$, where $R^{1a}$ and $R^{1d}$ are each defined herein. In certain embodiments, $R^3$ is —NR$^{1a}$S(O)NR$^{1b}$R$^{1c}$, where $R^{1a}$, $R^{1b}$, and $R^{1c}$ are each as defined herein. In certain embodiments, $R^3$ is —NR$^{1a}$S(O)$_2$NR$^{1b}$R$^{1c}$, where $R^{1a}R^{1b}$, and $R^{1c}$ are each as defined herein. In certain embodiments, $R^3$ is —S$R^{1a}$, where $R^{1a}$ is as defined herein. In certain embodiments, $R^3$ is —S(O)$R^{1a}$, where $R^{1a}$ is as defined herein. In certain embodiments, $R^3$ is —S(O)$_2$R$^{1a}$, where $R^{1a}$ is as defined herein. In certain embodiments, $R^3$ is —S(O)NR$^{1b}$R$^{1c}$, where $R^{1b}$ and $R^{1c}$ are each as defined herein. In certain embodiments, $R^3$ is —S(O)$_2$NR$^{1b}$R$^{1c}$, where $R^{1b}$ and $R^{1c}$ are each as defined herein. In certain embodiments, $R^3$ is chloro, fluoro, nitro, amino, methyl, trifluoromethyl, phenyl, or methoxy.

In certain embodiments, $R^5$ is cyano. In certain embodiments, $R^5$ is halo. In certain embodiments, $R^5$ is nitro. In certain embodiments, $R^5$ is $C_{1-6}$ alkyl, optionally substituted with one or more substituents Q. In certain embodiments, $R^5$ is $C_{2-6}$ alkenyl, optionally substituted with one or more substituents Q. In certain embodiments, $R^5$ is $C_{2-6}$ alkynyl, optionally substituted with one or more substituents Q. In certain embodiments, $R^5$ is $C_{3-7}$ cycloalkyl, optionally substituted with one or more substituents Q. In certain embodiments, $R^5$ is $C_{6-14}$ aryl, optionally substituted with one or more substituents Q. In certain embodiments, $R^5$ is $C_{7-15}$ aralkyl, optionally substituted with one or more substituents Q. In certain embodiments, $R^5$ is heteroaryl, optionally substituted with one or more substituents Q. In certain embodiments, $R^5$ is heterocyclyl, optionally substituted with one or more substituents Q. In certain embodiments, $R^5$ is —C(O)$R^{1a}$, where $R^{1a}$ is as defined herein. In certain embodiments, $R^5$ is —C(O)O$R^{1a}$, where $R^{1a}$ is as defined herein. In certain embodiments, $R^5$ is —C(O)NR$^{1b}$R$^{1c}$, where $R^{1b}$ and $R^{1c}$ are each as defined herein. In certain embodiments, $R^5$ is —C(NR$^{1a}$)NR$^{1b}$R$^{1c}$, where $R^{1a}$, $R^{1b}$, and $R^{1c}$ are each as defined herein. In certain embodiments, $R^5$ is —O$R^{1a}$, where $R^{1a}$ is as defined herein. In certain embodiments, $R^5$ is —OC(O)$R^{1a}$, where $R^{1a}$ is as defined herein. In certain embodiments, $R^5$ is —OC(O)O$R^{1a}$, where $R^{1a}$ is as defined herein. In certain embodiments, $R^5$ is —OC(O)NR$^{1b}$R$^{1c}$, where $R^{1b}$ and $R^{1c}$ are each as defined herein. In certain embodiments, $R^5$ is —OC(=NR$^{1a}$)NR$^{1b}$R$^{1c}$, where $R^{1a}R^{1b}$, and $R^{1c}$ are each as defined herein. In certain embodiments, $R^5$ is —OS(O)$R^{1a}$, where $R^{1a}$ is as defined herein. In certain embodiments, $R^5$ is —OS(O)$_2$R$^{1a}$, where $R^{1a}$ is as defined herein. In certain embodiments, $R^5$ is —OS(O)NR$^{1b}$R$^{1c}$, where $R^{1b}$ and $R^{1c}$ are each as defined herein. In certain embodiments, $R^5$ is —OS(O)$_2$NR$^{1b}$R$^{1c}$, where $R^{1b}$ and $R^{1c}$ are each as defined herein. In certain embodiments, $R^5$ is —NR$^{1b}$R$^{1c}$, where $R^{1b}$ and $R^{1c}$ are each as defined herein. In certain embodiments, $R^5$ is —NR$^{1a}$C(O)$R^{1d}$, where $R^{1a}$ and $R^{1d}$ are each as defined herein. In certain embodiments, $R^5$ is —NR$^{1a}$C(O)O$R^{1d}$, where $R^{1a}$ and $R^{1d}$ are each as defined herein. In certain embodiments, $R^5$ is —NR$^{1a}$C(O)NR$^{1b}$R$^{1c}$, where $R^{1a}$, $R^{1b}$, and $R^{1c}$ are each as defined herein. In certain embodiments, $R^5$ is —NR$^{1a}$C(=NR$^{1d}$)NR$^{1b}$R$^{1c}$, where $R^{1a}$, $R^{1b}$, $R^{1c}$, and $R^{1d}$ are each as defined herein. In certain embodiments, $R^5$ is —NR$^{1a}$S(O)$R^{1d}$, where $R^{1a}$ and $R^{1d}$ are each as defined herein. In certain embodiments, $R^5$ is —NR$^{1a}$S(O)$_2$R$^{1d}$, where $R^{1a}$ and $R^{1d}$ are each defined herein. In certain embodiments, $R^5$ is —NR$^{1a}$S(O)NR$^{1b}$R$^{1c}$, where $R^{1a}$, $R^{1b}$, and $R^{1c}$ are each as defined herein. In certain embodiments, $R^5$ is —NR$^{1a}$S(O)$_2$NR$^{1b}$R$^{1c}$, where $R^{1a}$, $R^{1b}$, and $R^{1c}$ are each as defined herein. In certain embodiments, $R^5$ is —S$R^{1a}$, where $R^{1a}$ is as defined herein. In certain embodiments, $R^5$ is —S(O)$R^{1a}$, where $R^{1a}$ is as defined herein. In certain embodiments, $R^5$ is —S(O)$_2$R$^{1a}$, where $R^{1a}$ is as defined herein. In certain embodiments, $R^5$ is —S(O)NR$^{1b}$R$^{1c}$, where $R^{1b}$ and $R^{1c}$ are each as defined herein. In certain embodiments, $R^5$ is —S(O)$_2$NR$^{1b}$R$^{1c}$, where $R^{1b}$ and $R^{1c}$ are each as defined herein.

In certain embodiments, two $R^5$ are linked together to form a bond. In certain embodiments, two $R^5$ are linked together to form —O—. In certain embodiments, two $R^5$ are linked together to form —NR$^7$—, where $R^7$ is as defined herein. In certain embodiments, two $R^5$ are linked together to form —S—. In certain embodiments, two $R^5$ are linked together to form $C_{1-6}$ alkylene, optionally substituted with one or more substituents Q. In certain embodiments, two $R^5$ are linked together to form methylene, ethylene, or propylene, each optionally substituted with one or more substituents Q. In certain embodiments, two $R^5$ are linked together to form $C_{1-6}$ heteroalkylene, optionally substituted with one or more substituents Q. In certain embodiments, two $R^5$ are linked together to form $C_{2-6}$ alkenylene, optionally substituted with one or more substituents Q. In certain embodiments, two $R^5$ are linked together to form $C_{2-6}$ heteroalkenylene, optionally substituted with one or more substituents Q. In certain embodiments, two $R^5$ are linked together to form a fused ring. In certain embodiments, two $R^5$ are linked together to form a bridged ring. In certain embodiments, two $R^5$ are linked together to form a spiro ring.

In certain embodiments, $R^6$ is cyano. In certain embodiments, $R^6$ is halo. In certain embodiments, $R^6$ is nitro. In certain embodiments, $R^6$ is $C_{1-6}$ alkyl, optionally substituted with one or more substituents Q. In certain embodiments, $R^6$ is $C_{2-6}$ alkenyl, optionally substituted with one or more substituents Q. In certain embodiments, $R^6$ is $C_{2-6}$ alkynyl, optionally substituted with one or more substituents Q. In certain embodiments, $R^6$ is $C_{3-7}$ cycloalkyl, optionally substituted with one or more substituents Q. In certain embodiments, $R^6$ is $C_{6-14}$ aryl, optionally substituted with one or more substituents Q. In certain embodiments, $R^6$ is $C_{7-15}$ aralkyl, optionally substituted with one or more substituents Q. In certain embodiments, $R^6$ is heteroaryl, optionally substituted with one or more substituents Q. In certain embodiments, $R^6$ is heterocyclyl, optionally substituted with one or more substituents Q. In certain embodiments, $R^6$ is —C(O)$R^{1a}$, where $R^{1a}$ is as defined herein. In certain embodiments, $R^6$ is —C(O)O$R^{1a}$, where $R^{1a}$ is as defined herein. In certain embodiments, $R^6$ is —C(O)N$R^{1b}R^{1c}$, where $R^{1b}$ and $R^{1c}$ are each as defined herein. In certain embodiments, $R^6$ is —C(N$R^{1a}$)N$R^{1b}R^{1c}$, where $R^{1a}$, $R^{1b}$, and $R^{1c}$ are each as defined herein. In certain embodiments, $R^6$ is —O$R^{1a}$, where $R^{1a}$ is as defined herein. In certain embodiments, $R^6$ is —OC(O)$R^{1a}$, where $R^{1a}$ is as defined herein. In certain embodiments, $R^6$ is —OC(O)O$R^{1a}$, where $R^{1a}$ is as defined herein. In certain embodiments, $R^6$ is —OC(O)N$R^{1b}R^{1c}$, where $R^{1b}$ and $R^{1c}$ are each as defined herein. In certain embodiments, $R^6$ is —OC(=N$R^{1a}$)N$R^{1b}R^{1c}$, where $R^{1a}$, $R^{1b}$, and $R^{1c}$ are each as defined herein. In certain embodiments, $R^6$ is —OS(O)$R^{1a}$, where $R^{1a}$ is as defined herein. In certain embodiments, $R^6$ is —OS(O)$_2$$R^{1a}$, where $R^{1a}$ is as defined herein. In certain embodiments, $R^6$ is —OS(O)N$R^{1b}R^{1c}$, where $R^{1b}$ and $R^{1c}$ are each as defined herein. In certain embodiments, $R^6$ is —OS(O)$_2$N$R^{1b}R^{1c}$, where $R^{1b}$ and $R^{1c}$ are each as defined herein. In certain embodiments, $R^6$ is —N$R^{1b}R^{1c}$, where $R^{1b}$ and $R^{1c}$ are each as defined herein. In certain embodiments, $R^6$ is —N$R^{1a}$C(O)$R^{1d}$, where $R^{1a}$ and $R^{1d}$ are each as defined herein. In certain embodiments, $R^6$ is —N$R^{1a}$C(O)O$R^{1d}$, where $R^{1a}$ and $R^{1d}$ are each as defined herein. In certain embodiments, $R^6$ is —N$R^{1a}$C(O)N$R^{1b}R^{1c}$, where $R^{1a}$, $R^{1b}$, and $R^{1c}$ are each as defined herein. In certain embodiments, $R^6$ is —N$R^{1a}$C(=N$R^{1d}$)N$R^{1b}R^{1c}$, where $R^{1a}$, $R^{1b}$, $R^{1c}$, and $R^{1d}$ are each as defined herein. In certain embodiments, $R^6$ is —N$R^{1a}$S(O)$R^{1d}$, where $R^{1a}$ and $R^{1d}$ are each as defined herein. In certain embodiments, $R^6$ is —N$R^{1a}$S(O)$_2$$R^{1d}$, where $R^{1a}$ and $R^{1d}$ are each defined herein. In certain embodiments, $R^6$ is —N$R^{1a}$S(O)N$R^{1b}R^{1c}$, where $R^{1a}$, $R^{1b}$, and $R^{1c}$ are each as defined herein. In certain embodiments, $R^6$ is —N$R^{1a}$S(O)$_2$N$R^{1b}R^{1c}$, where $R^{1a}$, $R^{1b}$, and $R^{1c}$ are each as defined herein. In certain embodiments, $R^6$ is —S$R^{1a}$, where $R^{1a}$ is as defined herein. In certain embodiments, $R^6$ is —S(O)$R^{1a}$, where $R^{1a}$ is as defined herein. In certain embodiments, $R^6$ is —S(O)$_2$$R^{1a}$, where $R^{1a}$ is as defined herein. In certain embodiments, $R^6$ is —S(O)N$R^{1b}R^{1c}$, where $R^{1b}$ and $R^{1c}$ are each as defined herein. In certain embodiments, $R^6$ is —S(O)$_2$N$R^{1b}R^{1c}$, where $R^{1b}$ and $R^{1c}$ are each as defined herein.

In certain embodiments, two $R^6$ are linked together to form a bond. In certain embodiments, two $R^6$ are linked together to form —O—. In certain embodiments, two $R^6$ are linked together to form —N$R^7$—, where $R^7$ is as defined herein. In certain embodiments, two $R^6$ are linked together to form —S—. In certain embodiments, two $R^6$ are linked together to form $C_{1-6}$ alkylene, optionally substituted with one or more substituents Q. In certain embodiments, two $R^6$ are linked together to form methylene, ethylene, or propylene, each optionally substituted with one or more substituents Q. In certain embodiments, two $R^6$ are linked together to form $C_{1-6}$ heteroalkylene, optionally substituted with one or more substituents Q. In certain embodiments, two $R^6$ are linked together to form $C_{2-6}$ alkenylene, optionally substituted with one or more substituents Q. In certain embodiments, two $R^6$ are linked together to form $C_{2-6}$ heteroalkenylene, optionally substituted with one or more substituents Q. In certain embodiments, two $R^6$ are linked together to form a fused ring. In certain embodiments, two $R^6$ are linked together to form a bridged ring. In certain embodiments, two $R^6$ are linked together to form a spiro ring.

In certain embodiments, A is 5,5-fused heteroarylene, optionally substituted with one or more substituents $R^3$, wherein $R^3$ is as defined herein. In certain embodiments, A is thieno[3,2-b]thienylene, pyrrolo[3,4-c]pyrrolylene, 4H-thieno[3,2-b]pyrrolylene, 6H-thieno[2,3-b]pyrrolylene, imidazo[2,1-b]oxazolylene, imidazo[2,1-b]thiazolylene, or 4H-pyrrolo[3,2-d]thiazolylene, each optionally substituted with one or more substituents $R^3$, wherein $R^3$ is as defined herein. In certain embodiments, A is thieno[3,2-b]thien-2,6-ylene, thieno[3,2-b]thien-3,6-ylene, pyrrolo[3,4-c]pyrrol-1,4-ylene, 4H-thieno[3,2-b]pyrrol-2,5-ylene, 6H-thieno[2,3-b]pyrrol-3,6-ylene, imidazo[2,1-b]oxazol-2,6-ylene, imidazo[2,1-b]thiazol-2,6-ylene, or 4H-pyrrolo[3,2-d]thiazol-2,5-ylene, each optionally substituted with one or more substituents $R^3$, wherein $R^3$ is as defined herein.

In certain embodiments, A is 3H-pyrrolizinylene, 4H-furo[3,2-b]pyrrolylene, furo[3,2-b]furanylene, 1,4-dihydropyrrolo[3,2-b]pyrrolylene, 5H-pyrrolo[1,2-c]imidazolylene, 4H-furo[3,2-b]pyrrolylene, 6H-pyrrolo[1,2-b]pyrazolylene, 5H-pyrrolo[1,2-a]imidazolylene, thieno[3,2-b]furanylene, 1H-furo[3,2-c]pyrazolylene, 1H-thieno[3,2-c]pyrazolylene, 1,4-dihydropyrrolo[3,2-c]pyrazolylene, 1H-imidazo[1,2-a]imidazolylene, pyrazolo[5,1-b]oxazolylene, pyrazolo[5,1-b]thiazolylene, 5H-imidazo[1,2-b]pyrazolylene, imidazo[1,2-b]isoxazolylene, imidazo[1,2-b]isothiazolylene, imidazo[1,5-b]isoxazolylene, imidazo[1,5-b]isothiazolylene, imidazo[5,1-b]oxazolylene, imidazo[5,1-b]thiazolylene, 1H-imidazo[1,5-a]imidazolylene, 6H-pyrrolo[3,2-d]isoxazolylene, 6H-pyrrolo[3,2-d]isothiazolylene, pyrrolo[2,1-b][1,3,4]oxadiazolylene, pyrrolo[2,1-b][1,3,4]thiadiazolylene, 1H-pyrrolo[1,2-b][1,2,4]triazolylene, 3H-furo[2,3-d]imidazolylene, 3H-thieno[2,3-d]imidazolylene, 3,4-dihydropyrrolo[2,3-d]imidazolylene, furo[3,2-d]thiazolylene, thieno[3,2-d]thiazolylene, 4H-pyrrolo[3,2-d]thiazolylene, 4H-pyrazolo[3,4-d]isoxazolylene, 4H-pyrazolo[3,4-d]isothiazolylene, 1,4-dihydropyrazolo[4,3-c]pyrazolylene, isoxazolo[5,4-d]isoxazolylene, isothiazolo[5,4-d]isothiazolylene, imidazo[2,1-b][1,3,4]thiadiazolylene, 1H-imidazo[1,5-a]imidazolylene, imidazo[2,1-b]oxazolylene, imidazo[2,1-b]thiazolylene, 1H-imidazo[1,2-a]imidazolylene, 1H-imidazo[1,2-a]imidazolylene, thieno[3,2-b]furanylene, or thiazolo[5,4-d]thiazolylene, each optionally substituted with one or more substituents $R^3$, wherein $R^3$ is as defined herein.

In certain embodiments, A is imidazo[2,1-b]thiazol-5,6-ylene, 3H-pyrrolizin-1,5-ylene, 3H-pyrrolizin-2,6-ylene, 4H-furo[3,2-b]pyrrol-2,5-ylene, 4H-furo[3,2-b]pyrrol-3,6-ylene, furo[3,2-b]furan-2,5-ylene, furo[3,2-b]furan-3,6-ylene, 1,4-dihydropyrrolo[3,2-b]pyrrol-2,5-ylene, 1,4-dihydropyrrolo[3,2-b]pyrrol-3,6-ylene, 5H-pyrrolo[1,2-c] imidazol-3,7-ylene, 4H-furo[3,2-b]pyrrol-2,4-ylene, 4H-furo[3,2-b]pyrrol-2,5-ylene, 4H-furo[3,2-b]pyrrol-3,4-ylene, 4H-furo[3,2-b]pyrrol-3,6-ylene, 6H-pyrrolo[1,2-b]pyrazol-2,5-ylene, 5H-pyrrolo[1,2-a]imidazol-2,6-ylene, 5H-pyrrolo[1,2-a]imidazol-3,7-ylene, thieno[3,2-b]furan-2,5-ylene, thieno[3,2-b]furan-3,6-ylene, 1H-furo[3,2-c]pyrazol-3,6-ylene, 1H-thieno[3,2-c]pyrazol-3,6-ylene, 1,4-dihydropyrrolo[3,2-c]pyrazol-3,6-ylene, 1H-imidazo[1,2-a]imidazol-2,6-ylene, pyrazolo[5,1-b]oxazol-2,6-ylene, pyrazolo[5,1-b]oxazol-3,7-ylene, pyrazolo[5,1-b]thiazol-2,6-ylene, pyrazolo[5,1-b]thiazol-3,7-ylene, 5H-imidazo[1,2-b]pyrazol-2,6-ylene, 5H-imidazo[1,2-b]pyrazol-3,7-ylene, imidazo[1,2-b]isoxazol-2,6-ylene, imidazo[1,2-b]isoxazol-3,7-ylene, imidazo[1,2-b]isothiazol-2,6-ylene, imidazo[1,2-b]isothiazol-3,7-ylene, imidazo[1,5-b]isoxazol-3,7-ylene, imidazo[1,5-b]isothiazol-3,6-ylene, imidazo[5,1-b]oxazol-3,7-ylene, imidazo[5,1-b]thiazol-3,7-ylene, 1H-imidazo[1,5-a]imidazol-3,7-ylene, 6H-pyrrolo[3,2-d]isoxazol-3,6-ylene, 6H-pyrrolo[3,2-d]isothiazol-3,6-ylene, pyrrolo[2,1-b][1,3,4]oxadiazol-2,6-ylene, pyrrolo[2,1-b][1,3,4]thiadiazol-2,6-ylene, 1H-pyrrolo[1,2-b][1,2,4]triazol-1,5-ylene, 1H-pyrrolo[1,2-b][1,2,4]triazol-2,6-ylene, 3H-furo[2,3-d]imidazol-2,5-ylene, 3H-furo[2,3-d]imidazol-3,6-ylene, 3H-thieno[2,3-d]imidazol-2,5-ylene, 3H-thieno[2,3-d]imidazol-3,6-ylene, 3,4-dihydropyrrolo[2,3-d]imidazol-2,5-ylene, 3,4-dihydropyrrolo[2,3-d]imidazol-3,6-ylene, furo[3,2-d]thiazol-2,5-ylene, thieno[3,2-d]thiazol-2,5-ylene, 4H-pyrrolo[3,2-d]thiazol-2,5-ylene, 4H-pyrazolo[3,4-d]isoxazol-3,6-ylene, 4H-pyrazolo[3,4-d]isothiazol-3,6-ylene, 1,4-dihydropyrazolo[4,3-c]pyrazol-1,4-ylene, 1,4-dihydropyrazolo[4,3-c]pyrazol-3,6-ylene, isoxazolo[5,4-d]isoxazol-3,6-ylene, isothiazolo[5,4-d]isothiazol-3,6-ylene, imidazo[2,1-b][1,3,4]thiadiazol-2,5-ylene, imidazo[2,1-b][1,3,4]thiadiazol-2,6-ylene, 6H-pyrrolo[3,2-d]isoxazol-3,6-ylene, 1H-imidazo[1,5-a]imidazol-1,5-ylene, imidazo[2,1-b]oxazol-2,5-ylene, imidazo[2,1-b]thiazol-2,5-ylene, 1H-imidazo[1,2-a]imidazol-2,5-ylene, 1H-imidazo[1,2-a]imidazol-1,5-ylene, thieno[3,2-b]furan-3,6-ylene, or thiazolo[5,4-d]thiazol-2,5-ylene, each optionally substituted with one or more substituents R³, wherein R³ is as defined herein.

In certain embodiments, A is selected from:

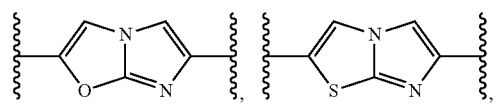

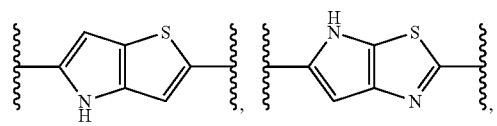

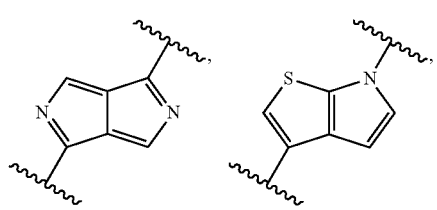

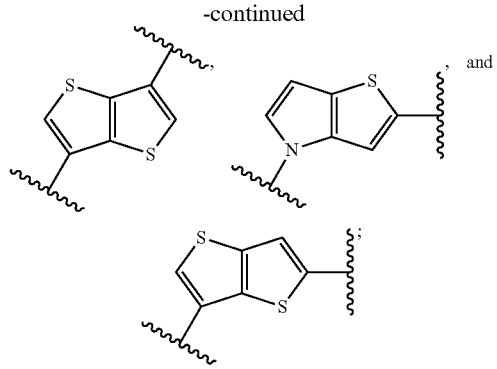

wherein each divalent moiety is optionally substituted with one, two, three, or four, in one embodiment, one or two, R³ groups, where R³ is as defined herein. In certain embodiments, each R³ is independently chloro, fluoro, nitro, amino, methyl, trifluoromethyl, phenyl, or methoxy.

In certain embodiments, A or the divalent moiety

is selected from:

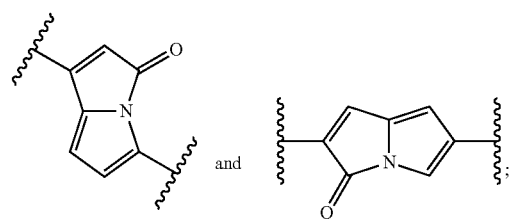 [SMILES: *C1=CC(=O)n2c(*)ccc21 ; *C1=Cc2cc(*)cn2C1=O]

wherein each divalent moiety is optionally substituted with one, two, three, or four, in one embodiment, one or two, R³ groups, where R³ is as defined herein. In certain embodiments, each R³ is independently oxo, chloro, fluoro, nitro, amino, methyl, trifluoromethyl, cyclohexyl, phenyl, or methoxy.

In certain embodiments, A or the divalent moiety

is selected from:

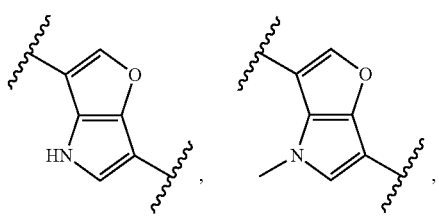

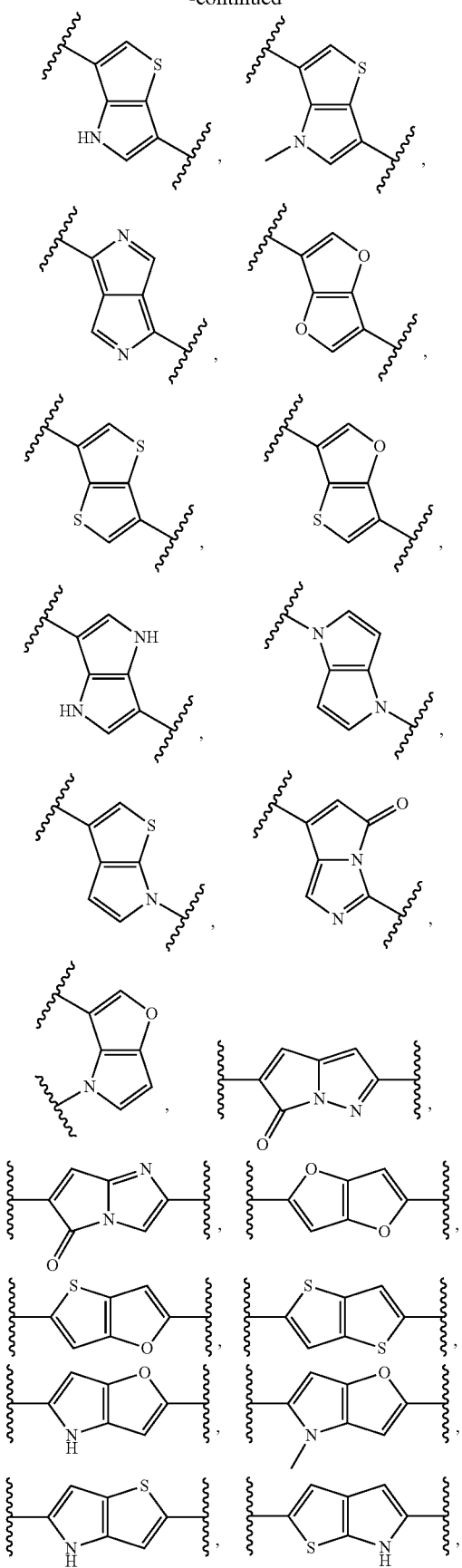
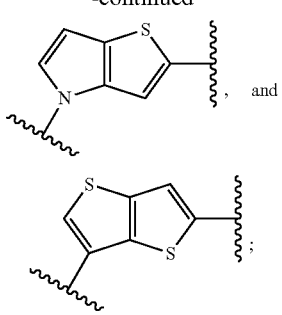
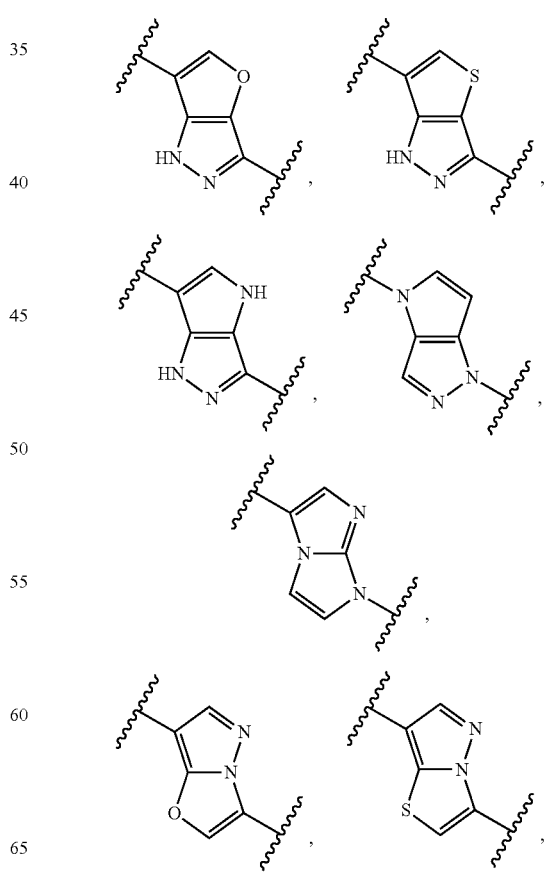
wherein each divalent moiety is optionally substituted with one, two, three, or four, in one embodiment, one or two, $R^3$ groups, where $R^3$ is as defined herein. In certain embodiments, each $R^3$ is independently oxo, chloro, fluoro, nitro, amino, methyl, trifluoromethyl, cyclohexyl, phenyl, or methoxy.
In certain embodiments, A or the divalent moiety
is selected from:

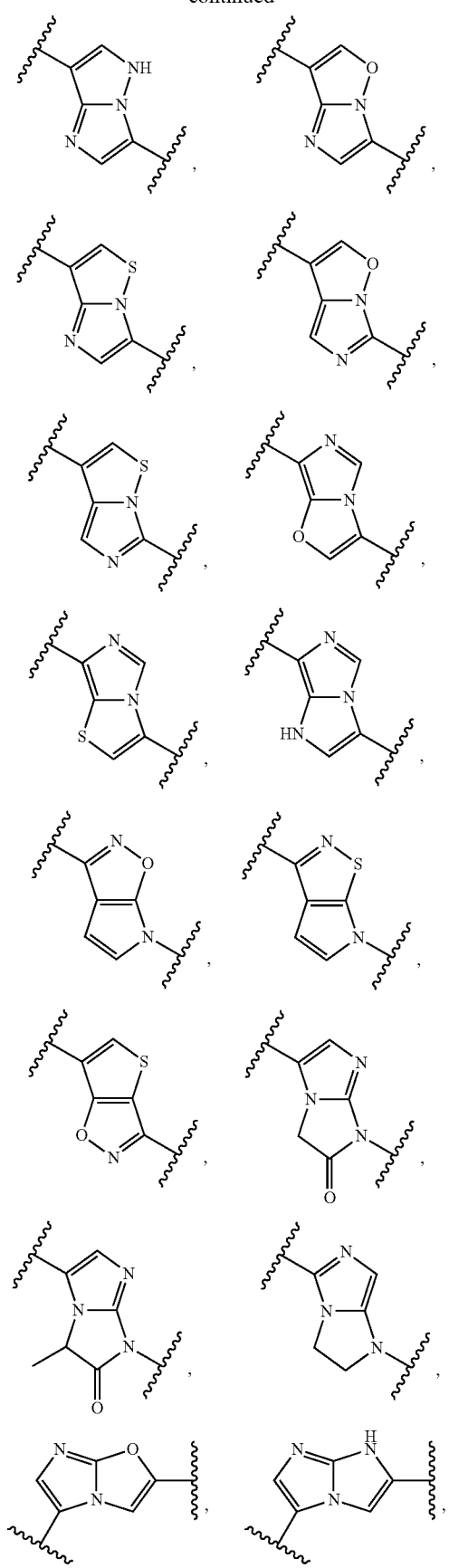
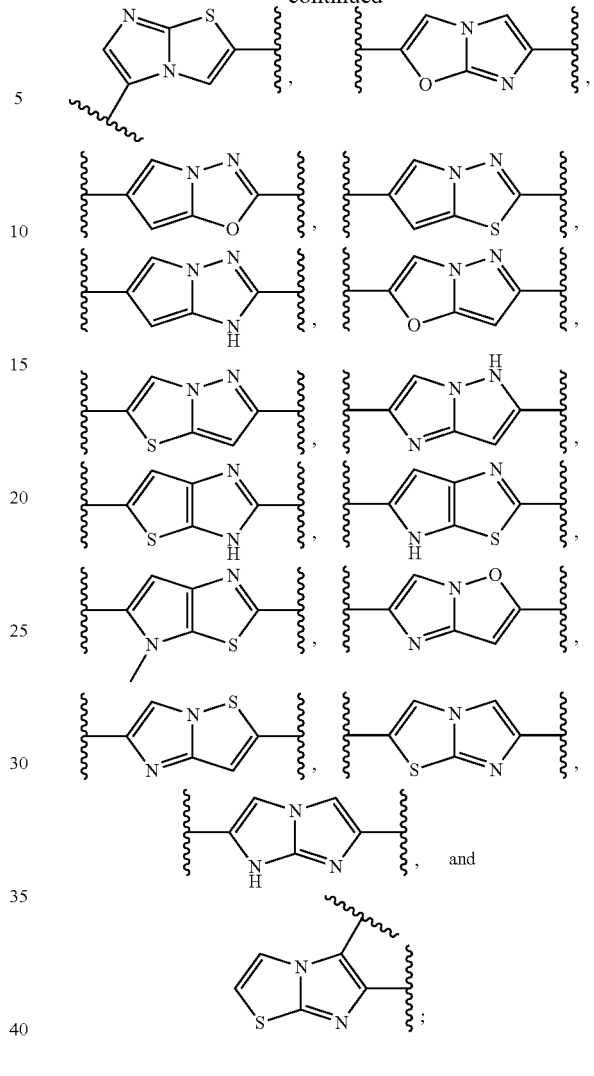
wherein each divalent moiety is optionally substituted with one, two, three, or four, in one embodiment, one or two, $R^3$ groups, where $R^3$ is as defined herein. In certain embodiments, each $R^3$ is independently oxo, chloro, fluoro, nitro, amino, methyl, trifluoromethyl, cyclohexyl, phenyl, or methoxy.
In certain embodiments, A or the divalent moiety
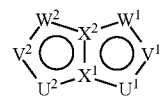
is selected from:
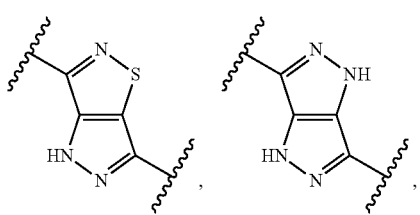

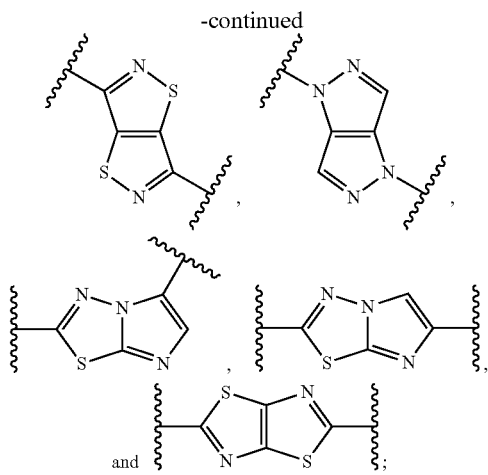

wherein each divalent moiety is optionally substituted with one, two, three, or four, in one embodiment, one or two, $R^3$ groups, where $R^3$ is as defined herein. In certain embodiments, each $R^3$ is independently oxo, chloro, fluoro, nitro, amino, methyl, trifluoromethyl, cyclohexyl, phenyl, or methoxy.

In certain embodiments, A is 5,5-fused heteroarylene-$R^{3a}$, optionally substituted with one or more substituents $R^3$, where $R^{3a}$ and $R^3$ are each as defined herein. In certain embodiments, A is thieno[3,2-b]thienylene-$R^{3a}$, pyrrolo[3,4-c]pyrrolylene-$R^{3a}$, 4H-thieno[3,2-b]pyrrolylene-$R^{3a}$, 6H-thieno[2,3-b]pyrrolylene-$R^{3a}$, imidazo[2,1-b]oxazolylene-$R^{3a}$, imidazo[2,1-b]thiazolylene-$R^{3a}$, or 4H-pyrrolo[3,2-d]thiazolylene-$R^{3a}$, each optionally substituted with one or more substituents $R^3$, where $R^{3a}$ and $R^3$ are each as defined herein. In certain embodiments, A is thieno[3,2-b]thienyl, pyrrolo[3,4-c]pyrrolyl, 4H-thieno[3,2-b]pyrrolyl, 6H-thieno[2,3-b]pyrrolyl, imidazo[2,1-b]oxazolyl, imidazo[2,1-b]thiazolyl, or 4H-pyrrolo[3,2-d]thiazolyl, each optionally substituted with one or more substituents $R^3$, where $R^3$ is as defined herein. In certain embodiments, A is thieno[3,2-b]thien-3,6-ylene-$R^{3a}$, pyrrolo[3,4-c]pyrrol-1,4-ylene-$R^{3a}$, 4H-thieno[3,2-b]pyrrol-2,5-ylene-$R^{3a}$, 6H-thieno[2,3-b]pyrrol-3,6-ylene-$R^{3a}$, imidazo[2,1-b]oxazol-2,6-ylene-$R^{3a}$, imidazo[2,1-b]thiazol-2,6-ylene-$R^{3a}$, or 4H-pyrrolo[3,2-d]thiazol-2,5-ylene-$R^{3a}$, each optionally substituted with one or more substituents $R^3$, where $R^{3a}$ and $R^3$ are each as defined herein.

In certain embodiments, A is 3H-pyrrolizinylene-$R^{3a}$, 4H-furo[3,2-b]pyrrolylene-$R^{3a}$, furo[3,2-b]furanylene-$R^{3a}$, 1,4-dihydropyrrolo[3,2-b]pyrrolylene-$R^{3a}$, 5H-pyrrolo[1,2-c]imidazolylene-$R^{3a}$, 4H-furo[3,2-b]pyrrolylene-$R^{3a}$, 6H-pyrrolo[1,2-b]pyrazolylene-$R^{3a}$, 5H-pyrrolo[1,2-a]imidazolylene-$R^{3a}$, thieno[3,2-b]furanylene-$R^{3a}$, 1H-furo[3,2-c]pyrazolylene-$R^{3a}$, 1H-thieno[3,2-c]pyrazolylene-$R^{3a}$, 1,4-dihydropyrrolo[3,2-c]pyrazolylene-$R^{3a}$, 1H-imidazo[1,2-a]imidazolylene-$R^{3a}$, pyrazolo[5,1-b]oxazolylene-$R^{3a}$, pyrazolo[5,1-b]thiazolylene-$R^{3a}$, 5H-imidazo[1,2-b]pyrazolylene-$R^{3a}$, imidazo[1,2-b]isoxazolylene-$R^{3a}$, imidazo[1,2-b]isothiazolylene-$R^{3a}$, imidazo[1,5-b]isoxazolylene-$R^{3a}$, imidazo[1,5-b]isothiazolylene-$R^{3a}$, imidazo[5,1-b]oxazolylene-$R^{3a}$, imidazo[5,1-b]thiazolylene-$R^{3a}$, 1H-imidazo[1,5-a]imidazolylene-$R^{3a}$, 6H-pyrrolo[3,2-d]isoxazolylene-$R^{3a}$, 6H-pyrrolo[3,2-d]isothiazolylene-$R^{3a}$, pyrrolo[2,1-b][1,3,4]oxadiazolylene-$R^{3a}$, pyrrolo[2,1-b][1,3,4]thiadiazolylene-$R^{3a}$, 1H-pyrrolo[1,2-b][1,2,4]triazolylene-$R^{3a}$, 3H-furo[2,3-d]imidazolylene-$R^{3a}$, 3H-thieno[2,3-d]imidazolylene-$R^{3a}$, 3,4-dihydropyrrolo[2,3-d]imidazolylene-$R^{3a}$, furo[3,2-d]thiazolylene-$R^{3a}$, thieno[3,2-d]thiazolylene-$R^{3a}$, 4H-pyrrolo[3,2-d]thiazolylene-$R^{3a}$, 4H-pyrazolo[3,4-d]isoxazolylene-$R^{3a}$, 4H-pyrazolo[3,4-d]isothiazolylene-$R^{3a}$, 1,4-dihydropyrazolo[4,3-c]pyrazolylene-$R^{3a}$, isoxazolo[5,4-d]isoxazolylene-$R^{3a}$, isothiazolo[5,4-d]isothiazolylene-$R^{3a}$, imidazo[2,1-b][1,3,4]thiadiazolylene-$R^{3a}$, 1H-imidazo[1,5-a]imidazolylene-$R^{3a}$, imidazo[2,1-b]oxazolylene-$R^{3a}$, imidazo[2,1-b]thiazolylene-$R^{3a}$, 1H-imidazo[1,2-a]imidazolylene-$R^{3a}$, 1H-imidazo[1,2-a]imidazolylene-$R^{3a}$, thieno[3,2-b]furanylene-$R^{3a}$, or thiazolo[5,4-d]thiazolylene-$R^{3a}$, each optionally substituted with one or more substituents $R^3$, wherein $R^3$ is as defined herein.

In certain embodiments, A is imidazo[2,1-b]thiazol-5,6-ylene-$R^{3a}$, 3H-pyrrolizin-1,5-ylene-$R^{3a}$, 3H-pyrrolizin-2,6-ylene-$R^{3a}$, 4H-furo[3,2-b]pyrrol-2,5-ylene-$R^{3a}$, 4H-furo[3,2-b]pyrrol-3,6-ylene-$R^{3a}$, furo[3,2-b]furan-2,5-ylene-$R^{3a}$, furo[3,2-b]furan-3,6-ylene-$R^{3a}$, 1,4-dihydropyrrolo[3,2-b]pyrrol-2,5-ylene-$R^{3a}$, 1,4-dihydropyrrolo[3,2-b]pyrrol-3,6-ylene-$R^{3a}$, 5H-pyrrolo[1,2-c]imidazol-3,7-ylene-$R^{3a}$, 4H-furo[3,2-b]pyrrol-2,4-ylene-$R^{3a}$, 4H-furo[3,2-b]pyrrol-2,5-ylene-$R^{3a}$, 4H-furo[3,2-b]pyrrol-3,4-ylene-$R^{3a}$, 4H-furo[3,2-b]pyrrol-3,6-ylene-$R^{3a}$, 6H-pyrrolo[1,2-b]pyrazol-2,5-ylene-$R^{3a}$, 5H-pyrrolo[1,2-a]imidazol-2,6-ylene-$R^{3a}$, 5H-pyrrolo[1,2-a]imidazol-3,7-ylene-$R^{3a}$, thieno[3,2-b]furan-2,5-ylene-$R^{3a}$, thieno[3,2-b]furan-3,6-ylene-$R^{3a}$, 1H-furo[3,2-c]pyrazol-3,6-ylene-$R^{3a}$, 1H-thieno[3,2-c]pyrazol-3,6-ylene-$R^{3a}$, 1,4-dihydropyrrolo[3,2-c]pyrazol-3,6-ylene-$R^{3a}$, 1H-imidazo[1,2-a]imidazol-2,6-ylene-$R^{3a}$, pyrazolo[5,1-b]oxazol-2,6-ylene-$R^{3a}$, pyrazolo[5,1-b]oxazol-3,7-ylene-$R^{3a}$, pyrazolo[5,1-b]thiazol-2,6-ylene-$R^{3a}$, pyrazolo[5,1-b]thiazol-3,7-ylene-$R^{3a}$, 5H-imidazo[1,2-b]pyrazol-2,6-ylene-$R^{3a}$, 5H-imidazo[1,2-b]pyrazol-3,7-ylene-$R^{3a}$, imidazo[1,2-b]isoxazol-2,6-ylene-$R^{3a}$, imidazo[1,2-b]isoxazol-3,7-ylene-$R^{3a}$, imidazo[1,2-b]isothiazol-2,6-ylene-$R^{3a}$, imidazo[1,2-b]isothiazol-3,7-ylene-$R^{3a}$, imidazo[1,5-b]isoxazol-3,7-ylene-$R^{3a}$, imidazo[1,5-b]isothiazol-3,6-ylene-$R^{3a}$, imidazo[5,1-b]oxazol-3,7-ylene-$R^{3a}$, imidazo[5,1-b]thiazol-3,7-ylene-$R^{3a}$, 1H-imidazo[1,5-a]imidazol-3,7-ylene-$R^{3a}$, 6H-pyrrolo[3,2-d]isoxazol-3,6-ylene-$R^{3a}$, 6H-pyrrolo[3,2-d]isothiazol-3,6-ylene-$R^{3a}$, pyrrolo[2,1-b][1,3,4]oxadiazol-2,6-ylene-$R^{3a}$, pyrrolo[2,1-b][1,3,4]thiadiazol-2,6-ylene-$R^{3a}$, 1H-pyrrolo[1,2-b][1,2,4]triazol-1,5-ylene-$R^{3a}$, 1H-pyrrolo[1,2-b][1,2,4]triazol-2,6-ylene-$R^{3a}$, 3H-furo[2,3-d]imidazol-2,5-ylene-$R^{3a}$, 3H-furo[2,3-d]imidazol-3,6-ylene-$R^{3a}$, 3H-thieno[2,3-d]imidazol-2,5-ylene-$R^{3a}$, 3H-thieno[2,3-d]imidazol-3,6-ylene-$R^{3a}$, 3,4-dihydropyrrolo[2,3-d]imidazol-2,5-ylene-$R^{3a}$, 3,4-dihydropyrrolo[2,3-d]imidazol-3,6-ylene-$R^{3a}$, furo[3,2-d]thiazol-2,5-ylene-$R^{3a}$, thieno[3,2-d]thiazol-2,5-ylene-$R^{3a}$, 4H-pyrrolo[3,2-d]thiazol-2,5-ylene-$R^{3a}$, 4H-pyrazolo[3,4-d]isoxazol-3,6-ylene-$R^{3a}$, 4H-pyrazolo[3,4-d]isothiazol-3,6-ylene-$R^{3a}$, 1,4-dihydropyrazolo[4,3-c]pyrazol-1,4-ylene-$R^{3a}$, 1,4-dihydropyrazolo[4,3-c]pyrazol-3,6-ylene-$R^{3a}$, isoxazolo[5,4-d]isoxazol-3,6-ylene-$R^{3a}$, isothiazolo[5,4-d]isothiazol-3,6-ylene-$R^{3a}$, imidazo[2,1-b][1,3,4]thiadiazol-2,5-ylene-$R^{3a}$, imidazo[2,1-b][1,3,4]thiadiazol-2,6-ylene-$R^{3a}$, 6H-pyrrolo[3,2-d]isoxazol-3,6-ylene-$R^{3a}$, 1H-imidazo[1,5-a]imidazol-1,5-ylene-$R^{3a}$, imidazo[2,1-b]oxazol-2,5-ylene-$R^{3a}$, imidazo[2,1-b]thiazol-2,5-ylene-$R^{3a}$, 1H-imidazo[1,2-a]imidazol-2,5-ylene-$R^{3a}$, 1H-imidazo[1,2-a]imidazol-1,5-ylene-$R^{3a}$, thieno[3,2-b]furan-3,6-ylene-$R^{3a}$, or thiazolo[5,4-d]thiazol-2,5-ylene-$R^{3a}$, each optionally substituted with one or more substituents $R^3$, wherein $R^3$ is as defined herein.

In certain embodiments, E is $C_{2-6}$ alkynylene, optionally substituted with one or more substituents $R^3$, wherein $R^3$ is as defined herein. In certain embodiments, E is ethynylene. In certain embodiments, E is $C_{3-7}$ cycloalkylene, optionally substituted with one or more substituents $R^3$, wherein $R^3$ is as defined herein. In certain embodiments, E is cyclohexylene, optionally substituted with one or more substituents $R^3$, wherein $R^3$ is as defined herein. In certain embodiments, E is $C_{6-14}$ arylene, optionally substituted with one or more substituents $R^3$, wherein $R^3$ is as defined herein. In certain embodiments, E is monocyclic arylene, optionally substituted with one or more substituents $R^3$, wherein $R^3$ is as defined herein. In certain embodiments, E is phenylene, optionally substituted with one or more substituents $R^3$, wherein $R^3$ is as defined herein. In certain embodiments, E is bicyclic arylene, optionally substituted with one or more substituents $R^3$, wherein $R^3$ is as defined herein. In certain embodiments, E is $C_{2-6}$ alkynylene-$C_{6-14}$ arylene, optionally substituted with one or more substituents $R^3$, wherein $R^3$ is as defined herein. In certain embodiments, E is ethynylene-$C_{6-14}$ arylene, optionally substituted with one or more substituents $R^3$, wherein $R^3$ is as defined herein. In certain embodiments, E is ethynylene-phenylene, optionally substituted with one or more substituents $R^3$, wherein $R^3$ is as defined herein. In certain embodiments, E is ethynylene-1,4-phenylene, optionally substituted with one or more substituents $R^3$, wherein $R^3$ is as defined herein.

In certain embodiments, E is heteroarylene, optionally substituted with one or more substituents $R^3$, wherein $R^3$ is as defined herein. In certain embodiments, E is monocyclic heteroarylene, optionally substituted with one or more substituents $R^3$, wherein $R^3$ is as defined herein. In certain embodiments, E is 5-membered heteroarylene, optionally substituted with one or more substituents $R^3$, wherein $R^3$ is as defined herein. In certain embodiments, E is furanylene, isothiazolylene, isoxazolylene, imidazolylene, thienylene, or thiazolylene, each optionally substituted with one or more substituents $R^3$, wherein $R^3$ is as defined herein. In certain embodiments, E is thiazol-2,5-ylene, optionally substituted with one or more substituents $R^3$, wherein $R^3$ is as defined herein. In certain embodiments, E is 6-membered heteroarylene, optionally substituted with one or more substituents $R^3$, wherein $R^3$ is as defined herein. In certain embodiments, E is bicyclic heteroarylene, optionally substituted with one or more substituents $R^3$, wherein $R^3$ is as defined herein. In certain embodiments, E is 5,5-fused heteroarylene, optionally substituted with one or more substituents $R^3$, wherein $R^3$ is as defined herein. In certain embodiments, E is thieno[3,2-b]thienylene, pyrrolo[3,4-c]pyrrolylene, 4H-thieno[3,2-b]pyrrolylene, 6H-thieno[2,3-b]pyrrolylene, imidazo[2,1-b]oxazolylene, imidazo[2,1-b]thiazolylene, or 4H-pyrrolo[3,2-d]thiazolylene, each optionally substituted with one or more substituents $R^3$, wherein $R^3$ is as defined herein. In certain embodiments, E is thieno[3,2-b]thien-2,6-ylene, thieno[3,2-b]thien-3,6-ylene, pyrrolo[3,4-c]pyrrol-1,4-ylene, 4H-thieno[3,2-b]pyrrol-2,5-ylene, 6H-thieno[2,3-b]pyrrol-3,6-ylene, imidazo[2,1-b]oxazol-2,6-ylene, imidazo[2,1-b]thiazol-2,6-ylene, or 4H-pyrrolo[3,2-d]thiazol-2,5-ylene, each optionally substituted with one or more substituents $R^3$, wherein $R^3$ is as defined herein.

In certain embodiments, E is 3H-pyrrolizinylene, 4H-furo[3,2-b]pyrrolylene, furo[3,2-b]furanylene, 1,4-dihydropyrrolo[3,2-b]pyrrolylene, 5H-pyrrolo[1,2-c]imidazolylene, 4H-furo[3,2-b]pyrrolylene, 6H-pyrrolo[1,2-b]pyrazolylene, 5H-pyrrolo[1,2-a]imidazolylene, thieno[3,2-b]furanylene, 1H-furo[3,2-c]pyrazolylene, 1H-thieno[3,2-c]pyrazolylene, 1,4-dihydropyrrolo[3,2-c]pyrazolylene, 1H-imidazo[1,2-a]imidazolylene, pyrazolo[5,1-b]oxazolylene, pyrazolo[5,1-b]thiazolylene, 5H-imidazo[1,2-b]pyrazolylene, imidazo[1,2-b]isoxazolylene, imidazo[1,2-b]isothiazolylene, imidazo[1,5-b]isoxazolylene, imidazo[1,5-b]isothiazolylene, imidazo[5,1-b]oxazolylene, imidazo[5,1-b]thiazolylene, 1H-imidazo[1,5-a]imidazolylene, 6H-pyrrolo[3,2-d]isoxazolylene, 6H-pyrrolo[3,2-d]isothiazolylene, pyrrolo[2,1-b][1,3,4]oxadiazolylene, pyrrolo[2,1-b][1,3,4]thiadiazolylene, 1H-pyrrolo[1,2-b][1,2,4]triazolylene, 3H-furo[2,3-d]imidazolylene, 3H-thieno[2,3-d]imidazolylene, 3,4-dihydropyrrolo[2,3-d]imidazolylene, furo[3,2-d]thiazolylene, thieno[3,2-d]thiazolylene, 4H-pyrrolo[3,2-d]thiazolylene, 4H-pyrazolo[3,4-d]isoxazolylene, 4H-pyrazolo[3,4-d]isothiazolylene, 1,4-dihydropyrazolo[4,3-c]pyrazolylene, isoxazolo[5,4-d]isoxazolylene, isothiazolo[5,4-d]isothiazolylene, imidazo[2,1-b][1,3,4]thiadiazolylene, 1H-imidazo[1,5-a]imidazolylene, imidazo[2,1-b]oxazolylene, imidazo[2,1-b]thiazolylene, 1H-imidazo[1,2-a]imidazolylene, 1H-imidazo[1,2-a]imidazolylene, thieno[3,2-b]furanylene, or thiazolo[5,4-d]thiazolylene, each optionally substituted with one or more substituents $R^3$, wherein $R^3$ is as defined herein.

In certain embodiments, E is imidazo[2,1-b]thiazol-5,6-ylene, 3H-pyrrolizin-1,5-ylene, 3H-pyrrolizin-2,6-ylene, 4H-furo[3,2-b]pyrrol-2,5-ylene, 4H-furo[3,2-b]pyrrol-3,6-ylene, furo[3,2-b]furan-2,5-ylene, furo[3,2-b]furan-3,6-ylene, 1,4-dihydropyrrolo[3,2-b]pyrrol-2,5-ylene, 1,4-dihydropyrrolo[3,2-b]pyrrol-3,6-ylene, 5H-pyrrolo[1,2-c]imidazol-3,7-ylene, 4H-furo[3,2-b]pyrrol-2,4-ylene, 4H-furo[3,2-b]pyrrol-2,5-ylene, 4H-furo[3,2-b]pyrrol-3,4-ylene, 4H-furo[3,2-b]pyrrol-3,6-ylene, 6H-pyrrolo[1,2-b]pyrazol-2,5-ylene, 5H-pyrrolo[1,2-a]imidazol-2,6-ylene, 5H-pyrrolo[1,2-a]imidazol-3,7-ylene, thieno[3,2-b]furan-2,5-ylene, thieno[3,2-b]furan-3,6-ylene, 1H-furo[3,2-c]pyrazol-3,6-ylene, 1H-thieno[3,2-c]pyrazol-3,6-ylene, 1,4-dihydropyrrolo[3,2-c]pyrazol-3,6-ylene, 1H-imidazo[1,2-a]imidazol-2,6-ylene, pyrazolo[5,1-b]oxazol-2,6-ylene, pyrazolo[5,1-b]oxazol-3,7-ylene, pyrazolo[5,1-b]thiazol-2,6-ylene, pyrazolo[5,1-b]thiazol-3,7-ylene, 5H-imidazo[1,2-b]pyrazol-2,6-ylene, 5H-imidazo[1,2-b]pyrazol-3,7-ylene, imidazo[1,2-b]isoxazol-2,6-ylene, imidazo[1,2-b]isoxazol-3,7-ylene, imidazo[1,2-b]isothiazol-2,6-ylene, imidazo[1,2-b]isothiazol-3,7-ylene, imidazo[1,5-b]isoxazol-3,7-ylene, imidazo[1,5-b]isothiazol-3,6-ylene, imidazo[5,1-b]oxazol-3,7-ylene, imidazo[5,1-b]thiazol-3,7-ylene, 1H-imidazo[1,5-a]imidazol-3,7-ylene, 6H-pyrrolo[3,2-d]isoxazol-3,6-ylene, 6H-pyrrolo[3,2-d]isothiazol-3,6-ylene, pyrrolo[2,1-b][1,3,4]oxadiazol-2,6-ylene, pyrrolo[2,1-b][1,3,4]thiadiazol-2,6-ylene, 1H-pyrrolo[1,2-b][1,2,4]triazol-1,5-ylene, 1H-pyrrolo[1,2-b][1,2,4]triazol-2,6-ylene, 3H-furo[2,3-d]imidazol-2,5-ylene, 3H-furo[2,3-d]imidazol-3,6-ylene, 3H-thieno[2,3-d]imidazol-2,5-ylene, 3H-thieno[2,3-d]imidazol-3,6-ylene, 3,4-dihydropyrrolo[2,3-d]imidazol-2,5-ylene, 3,4-dihydropyrrolo[2,3-d]imidazol-3,6-ylene, furo[3,2-d]thiazol-2,5-ylene, thieno[3,2-d]thiazol-2,5-ylene, 4H-pyrrolo[3,2-d]thiazol-2,5-ylene, 4H-pyrazolo[3,4-d]isoxazol-3,6-ylene, 4H-pyrazolo[3,4-d]isothiazol-3,6-ylene, 1,4-dihydropyrazolo[4,3-c]pyrazol-1,4-ylene, 1,4-dihydropyrazolo[4,3-c]pyrazol-3,6-ylene, isoxazolo[5,4-d]isoxazol-3,6-ylene, isothiazolo[5,4-d]isothiazol-3,6-ylene, imidazo[2,1-b][1,3,4]thiadiazol-2,5-ylene, imidazo[2,1-b][1,3,4]thiadiazol-2,6-ylene, 6H-pyrrolo[3,2-d]isoxazol-3,6-ylene, 1H-imidazo[1,5-a]imidazol-1,5-ylene, imidazo[2,1-b]oxazol-2,5-ylene, imidazo[2,1-b]thiazol-2,5-ylene, 1H-imidazo[1,2-a]imidazol-2,5-ylene, 1H-imidazo[1,2-a]imidazol-1,5-ylene, thieno[3,2-b]furan-3,6-ylene, or thiazolo[5,4-d]thiazol-2,5-ylene, each optionally substituted with one or more substituents $R^3$, wherein $R^3$ is as defined herein.

In certain embodiments, E is 3H-pyrrolizinylene-R$^{3a}$, 4H-furo[3,2-b]pyrrolylene-R$^{3a}$, furo[3,2-b]furanylene-R$^{3a}$, 1,4-dihydropyrrolo[3,2-b]pyrrolylene-R$^{3a}$, 5H-pyrrolo[1,2-c]imidazolylene-R$^{3a}$, 4H-furo[3,2-b]pyrrolylene-R$^{3a}$, 6H-pyrrolo[1,2-b]pyrazolylene-R$^{3a}$, 5H-pyrrolo[1,2-a]imidazolylene-R$^{3a}$, thieno[3,2-b]furanylene-R$^{3a}$, 1H-furo[3,2-c]pyrazolylene-R$^{3a}$, 1H-thieno[3,2-c]pyrazolylene-R$^{3a}$, 1,4-dihydropyrrolo[3,2-c]pyrazolylene-R$^{3a}$, 1H-imidazo[1,2-a]imidazolylene-R$^{3a}$, pyrazolo[5,1-b]oxazolylene-R$^{3a}$, pyrazolo[5,1-b]thiazolylene-R$^{3a}$, 5H-imidazo[1,2-b]pyrazolylene-R$^{3a}$, imidazo[1,2-b]isoxazolylene-R$^{3a}$, imidazo[1,2-b]isothiazolylene-R$^{3a}$, imidazo[1,5-b]isoxazolylene-R$^{3a}$, imidazo[1,5-b]isothiazolylene-R$^{3a}$, imidazo[5,1-b]oxazolylene-R$^{3a}$, imidazo[5,1-b]thiazolylene-R$^{3a}$, 1H-imidazo[1,5-a]imidazolylene-R$^{3a}$, 6H-pyrrolo[3,2-d]isoxazolylene-R$^{3a}$, 6H-pyrrolo[3,2-d]isothiazolylene-R$^{3a}$, pyrrolo[2,1-b][1,3,4]oxadiazolylene-R$^{3a}$, pyrrolo[2,1-b][1,3,4]thiadiazolylene-R$^{3a}$, 1H-pyrrolo[1,2-b][1,2,4]triazolylene-R$^{3a}$, 3H-furo[2,3-d]imidazolylene-R$^{3a}$, 3H-thieno[2,3-d]imidazolylene-R$^{3a}$, 3,4-dihydropyrrolo[2,3-d]imidazolylene-R$^{3a}$, furo[3,2-d]thiazolylene-R$^{3a}$, thieno[3,2-d]thiazolylene-R$^{3a}$, 4H-pyrrolo[3,2-d]thiazolylene-R$^{3a}$, 4H-pyrazolo[3,4-d]isoxazolylene-R$^{3a}$, 4H-pyrazolo[3,4-d]isothiazolylene-R$^{3a}$, 1,4-dihydropyrazolo[4,3-c]pyrazolylene-R$^{3a}$, isoxazolo[5,4-d]isoxazolylene-R$^{3a}$, isothiazolo[5,4-d]isothiazolylene-R$^{3a}$, imidazo[2,1-b][1,3,4]thiadiazolylene-R$^{3a}$, 1H-imidazo[1,5-a]imidazolylene-R$^{3a}$, imidazo[2,1-b]oxazolylene-R$^{3a}$, imidazo[2,1-b]thiazolylene-R$^{3a}$, 1H-imidazo[1,2-a]imidazolylene-R$^{3a}$, 1H-imidazo[1,2-a]imidazolylene-R$^{3a}$, thieno[3,2-b]furanylene-R$^{3a}$, or thiazolo[5,4-d]thiazolylene-R$^{3a}$, each optionally substituted with one or more substituents R$^3$, wherein R$^3$ is as defined herein.

In certain embodiments, E is imidazo[2,1-b]thiazol-5,6-ylene-R$^{3a}$, 3H-pyrrolizin-1,5-ylene-R$^{3a}$, 3H-pyrrolizin-2,6-ylene-R$^{3a}$, 4H-furo[3,2-b]pyrrol-2,5-ylene-R$^{3a}$, 4H-furo[3,2-b]pyrrol-3,6-ylene-R$^{3a}$, furo[3,2-b]furan-2,5-ylene-R$^{3a}$, furo[3,2-b]furan-3,6-ylene-R$^{3a}$, 1,4-dihydropyrrolo[3,2-b]pyrrol-2,5-ylene-R$^{3a}$, 1,4-dihydropyrrolo[3,2-b]pyrrol-3,6-ylene-R$^{3a}$, 5H-pyrrolo[1,2-c]imidazol-3,7-ylene-R$^{3a}$, 4H-furo[3,2-b]pyrrol-2,4-ylene-R$^{3a}$, 4H-furo[3,2-b]pyrrol-2,5-ylene-R$^{3a}$, 4H-furo[3,2-b]pyrrol-3,4-ylene-R$^{3a}$, 4H-furo[3,2-b]pyrrol-3,6-ylene-R$^{3a}$, 6H-pyrrolo[1,2-b]pyrazol-2,5-ylene-R$^{3a}$, 5H-pyrrolo[1,2-a]imidazol-2,6-ylene-R$^{3a}$, 5H-pyrrolo[1,2-a]imidazol-3,7-ylene-R$^{3a}$, thieno[3,2-b]furan-2,5-ylene-R$^{3a}$, thieno[3,2-b]furan-3,6-ylene-R$^{3a}$, 1H-furo[3,2-c]pyrazol-3,6-ylene-R$^{3a}$, 1H-thieno[3,2-c]pyrazol-3,6-ylene-R$^{3a}$, 1,4-dihydropyrrolo[3,2-c]pyrazol-3,6-ylene-R$^{3a}$, 1H-imidazo[1,2-a]imidazol-2,6-ylene-R$^{3a}$, pyrazolo[5,1-b]oxazol-2,6-ylene-R$^{3a}$, pyrazolo[5,1-b]oxazol-3,7-ylene-R$^{3a}$, pyrazolo[5,1-b]thiazol-2,6-ylene-R$^{3a}$, pyrazolo[5,1-b]thiazol-3,7-ylene-R$^{3a}$, 5H-imidazo[1,2-b]pyrazol-2,6-ylene-R$^{3a}$, 5H-imidazo[1,2-b]pyrazol-3,7-ylene-R$^{3a}$, imidazo[1,2-b]isoxazol-2,6-ylene-R$^{3a}$, imidazo[1,2-b]isoxazol-3,7-ylene-R$^{3a}$, imidazo[1,2-b]isothiazol-2,6-ylene-R$^{3a}$, imidazo[1,2-b]isothiazol-3,7-ylene-R$^{3a}$, imidazo[1,5-b]isoxazol-3,7-ylene-R$^{3a}$, imidazo[1,5-b]isothiazol-3,6-ylene-R$^{3a}$, imidazo[5,1-b]oxazol-3,7-ylene-R$^{3a}$, imidazo[5,1-b]thiazol-3,7-ylene-R$^{3a}$, 1H-imidazo[1,5-a]imidazol-3,7-ylene-R$^{3a}$, 6H-pyrrolo[3,2-d]isoxazol-3,6-ylene-R$^{3a}$, 6H-pyrrolo[3,2-d]isothiazol-3,6-ylene-R$^{3a}$, pyrrolo[2,1-b][1,3,4]oxadiazol-2,6-ylene-R$^{3a}$, pyrrolo[2,1-b][1,3,4]thiadiazol-2,6-ylene-R$^{3a}$, 1H-pyrrolo[1,2-b][1,2,4]triazol-1,5-ylene-R$^{3a}$, 1H-pyrrolo[1,2-b][1,2,4]triazol-2,6-ylene-R$^{3a}$, 3H-furo[2,3-d]imidazol-2,5-ylene-R$^{3a}$, 3H-furo[2,3-d]imidazol-3,6-ylene-R$^{3a}$, 3H-thieno[2,3-d]imidazol-2,5-ylene-R$^{3a}$, 3H-thieno[2,3-d]imidazol-3,6-ylene-R$^{3a}$, 3,4-dihydropyrrolo[2,3-d]imidazol-2,5-ylene-R$^{3a}$, 3,4-dihydropyrrolo[2,3-d]imidazol-3,6-ylene-R$^{3a}$, furo[3,2-d]thiazol-2,5-ylene-R$^{3a}$, thieno[3,2-d]thiazol-2,5-ylene-R$^{3a}$, 4H-pyrrolo[3,2-d]thiazol-2,5-ylene-R$^{3a}$, 4H-pyrazolo[3,4-d]isoxazol-3,6-ylene-R$^{3a}$, 4H-pyrazolo[3,4-d]isothiazol-3,6-ylene-R$^{3a}$, 1,4-dihydropyrazolo[4,3-c]pyrazol-1,4-ylene-R$^{3a}$, 1,4-dihydropyrazolo[4,3-c]pyrazol-3,6-ylene-R$^{3a}$, isoxazolo[5,4-d]isoxazol-3,6-ylene-R$^{3a}$, isothiazolo[5,4-d]isothiazol-3,6-ylene-R$^{3a}$, imidazo[2,1-b][1,3,4]thiadiazol-2,5-ylene-R$^{3a}$, imidazo[2,1-b][1,3,4]thiadiazol-2,6-ylene-R$^{3a}$, 6H-pyrrolo[3,2-d]isoxazol-3,6-ylene-R$^{3a}$, 1H-imidazo[1,5-a]imidazol-1,5-ylene-R$^{3a}$, imidazo[2,1-b]oxazol-2,5-ylene-R$^{3a}$, imidazo[2,1-b]thiazol-2,5-ylene-R$^{3a}$, 1H-imidazo[1,2-a]imidazol-2,5-ylene-R$^{3a}$, 1H-imidazo[1,2-a]imidazol-1,5-ylene-R$^{3a}$, thieno[3,2-b]furan-3,6-ylene-R$^{3a}$, or thiazolo[5,4-d]thiazol-2,5-ylene-R$^{3a}$, each optionally substituted with one or more substituents R$^3$, wherein R$^3$ is as defined herein.

In certain embodiments, E is selected from:

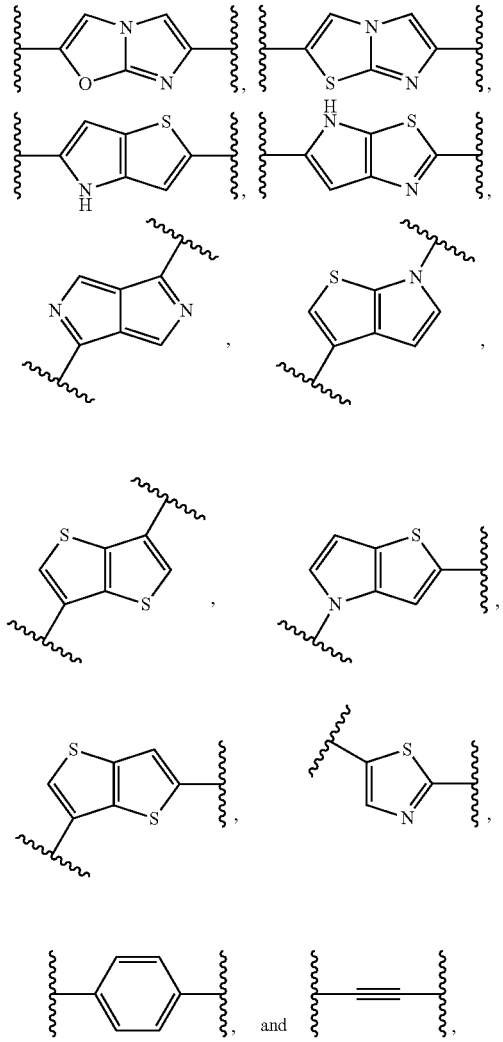

wherein each divalent moiety is optionally substituted with one, two, three, or four, in one embodiment, one or two, R$^3$ groups, where R$^3$ is as defined herein. In certain embodiments, each R$^3$ is independently chloro, fluoro, nitro, amino, methyl, trifluoromethyl, phenyl, or methoxy.

In certain embodiments, E is selected from:

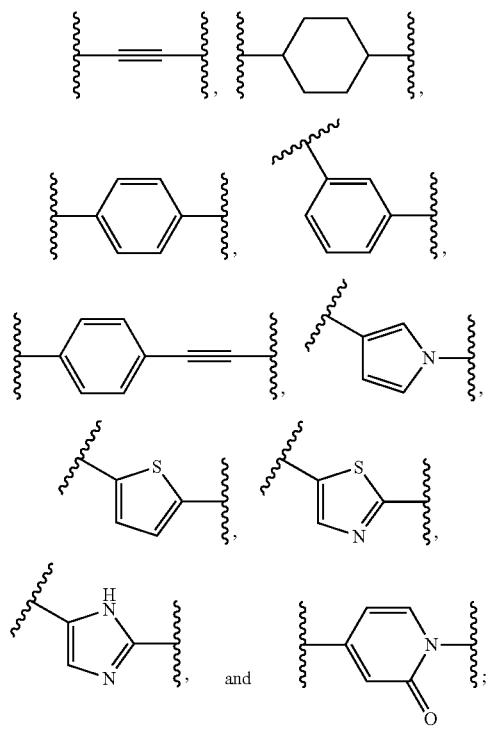

wherein each divalent moiety is optionally substituted with one, two, three, or four, in one embodiment, one or two, R³ groups, where R³ is as defined herein. In certain embodiments, each R³ is independently oxo, chloro, fluoro, nitro, hydroxy, amino, methyl, trifluoromethyl, cyclohexyl, phenyl, methoxy, or methoxycarbonyl.

In certain embodiments, E or the divalent moiety

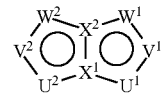

is selected from:

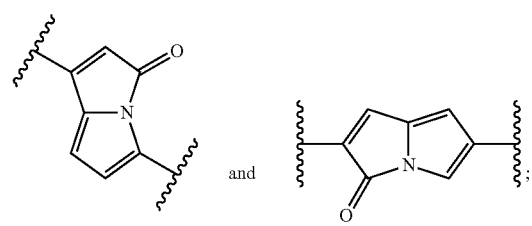 [SMILES: *C1=CC(=O)n2c(*)ccc21 ; *C1=Cc2cc(*)cn2C1=O]

wherein each divalent moiety is optionally substituted with one, two, three, or four, in one embodiment, one or two, R³ groups, where R³ is as defined herein. In certain embodiments, each R³ is independently oxo, chloro, fluoro, nitro, hydroxy, amino, methyl, trifluoromethyl, cyclohexyl, phenyl, methoxy, or methoxycarbonyl.

In certain embodiments, E or the divalent moiety

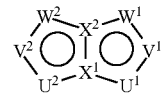

is selected from:

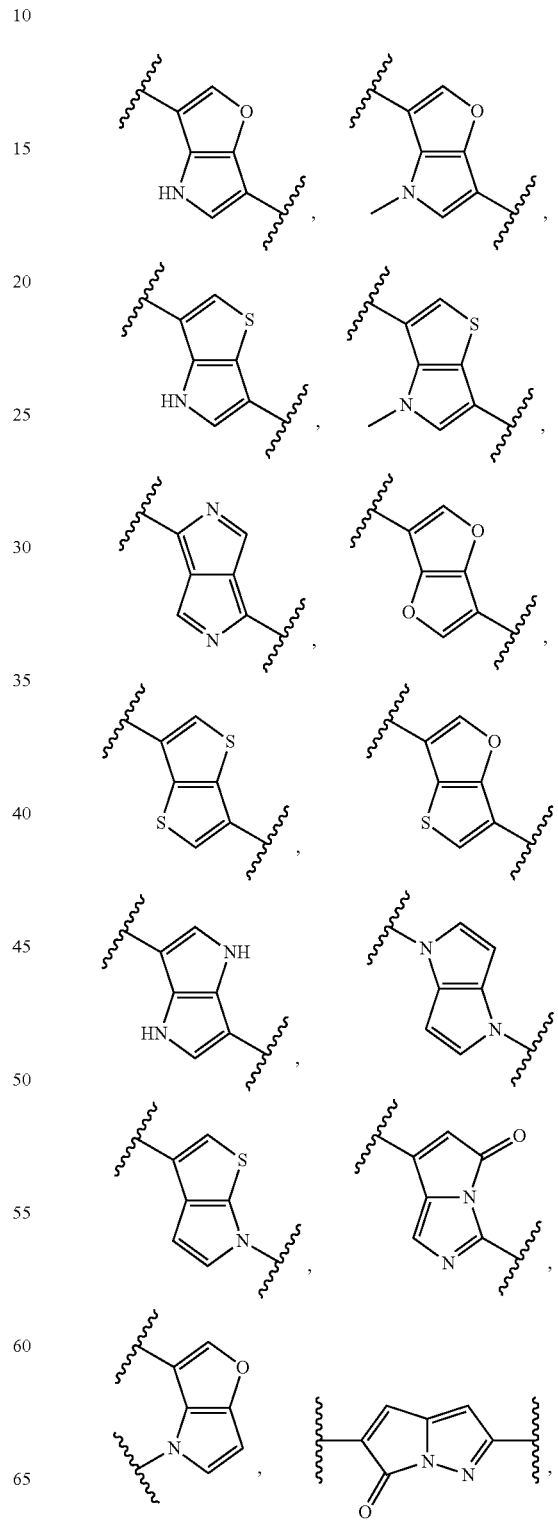

-continued

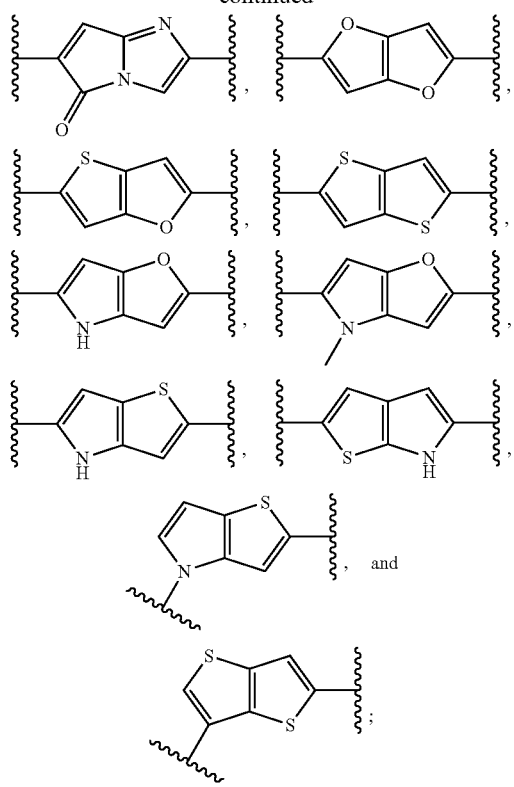

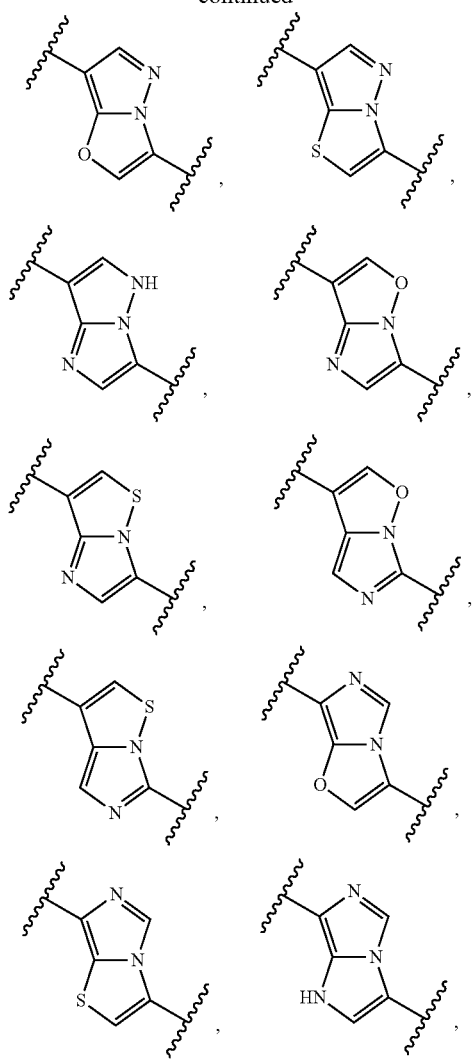

wherein each divalent moiety is optionally substituted with one, two, three, or four, in one embodiment, one or two, $R^3$ groups, where $R^3$ is as defined herein. In certain embodiments, each $R^3$ is independently oxo, chloro, fluoro, nitro, hydroxy, amino, methyl, trifluoromethyl, cyclohexyl, phenyl, methoxy, or methoxycarbonyl.

In certain embodiments, E or the divalent moiety

is selected from:

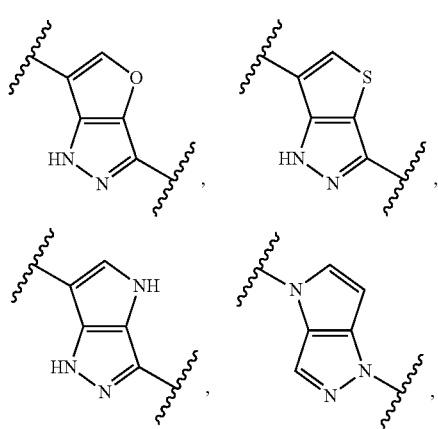

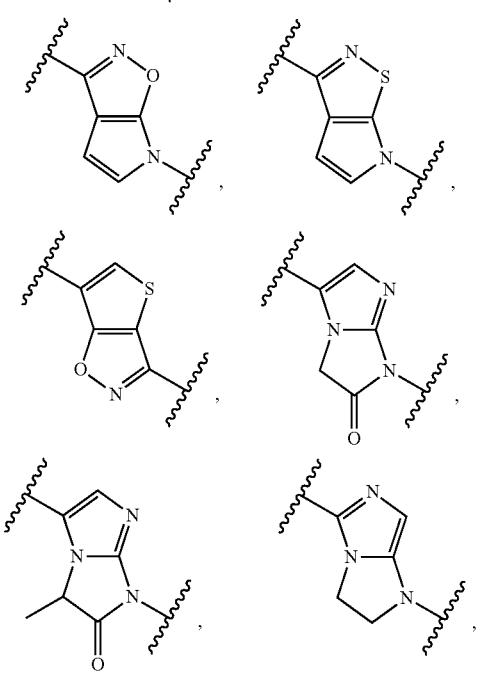

-continued

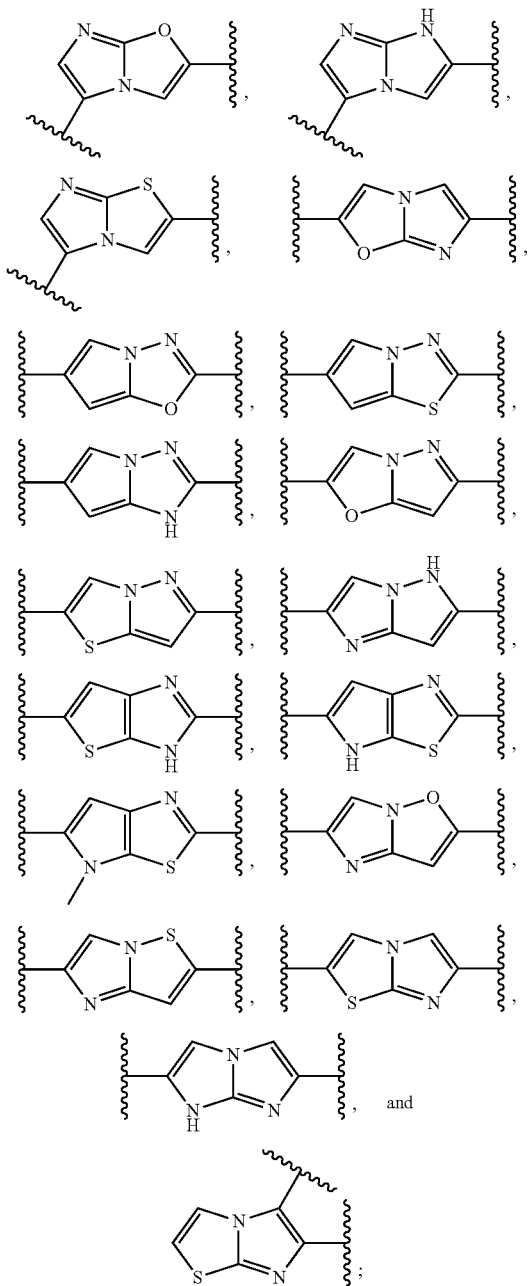

wherein each divalent moiety is optionally substituted with one, two, three, or four, in one embodiment, one or two, $R^3$ groups, where $R^3$ is as defined herein. In certain embodiments, each $R^3$ is independently oxo, chloro, fluoro, nitro, hydroxy, amino, methyl, trifluoromethyl, cyclohexyl, phenyl, methoxy, or methoxycarbonyl.

In certain embodiments, E or the divalent moiety

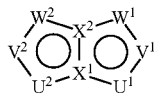

is selected from:

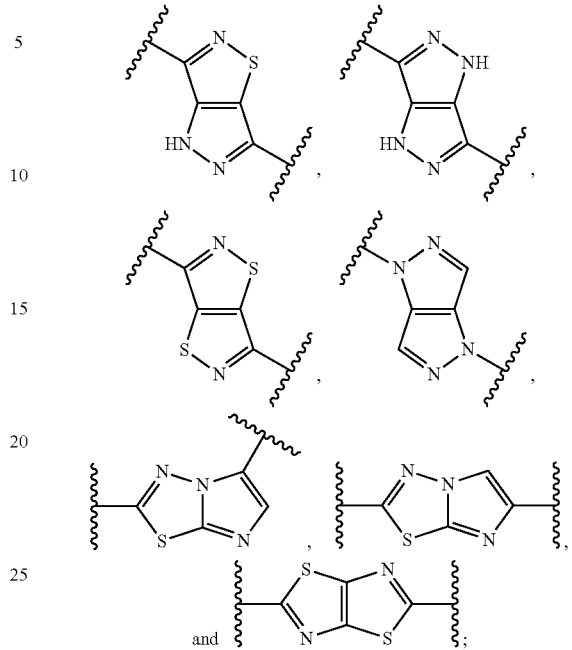

wherein each divalent moiety is optionally substituted with one, two, three, or four, in one embodiment, one or two, $R^3$ groups, where $R^3$ is as defined herein. In certain embodiments, each $R^3$ is independently oxo, chloro, fluoro, nitro, hydroxy, amino, methyl, trifluoromethyl, cyclohexyl, phenyl, methoxy, or methoxycarbonyl.

In certain embodiments, E is $C_{2-6}$ alkynylene-$R^{3a}$, optionally substituted with one or more substituents $R^3$, where $R^{3a}$ and $R^3$ are each as defined herein. In certain embodiments, E is ethynylene-$R^{3a}$, where $R^{3a}$ is as defined herein. In certain embodiments, E is phenylethynyl. In certain embodiments, E is $C_{3-7}$ cycloalkylene-$R^{3a}$, optionally substituted with one or more substituents $R^3$, wherein $R^3$ is as defined herein. In certain embodiments, E is cyclohexylene-$R^{3a}$, optionally substituted with one or more substituents $R^3$, wherein $R^3$ is as defined herein. In certain embodiments, E is $C_{6-14}$ arylene-$R^{3a}$, optionally substituted with one or more substituents $R^3$, where $R^{3a}$ and $R^3$ are each as defined herein. In certain embodiments, E is monocyclic arylene-$R^{3a}$, optionally substituted with one or more substituents $R^3$, where $R^{3a}$ and $R^3$ are each as defined herein. In certain embodiments, E is phenylene-$R^{3a}$, optionally substituted with one or more substituents $R^3$, where $R^{3a}$ and $R^3$ are each as defined herein. In certain embodiments, E is phenyl or aminophenyl. In certain embodiments, E is 4-aminophenyl. In certain embodiments, E is bicyclic arylene-$R^{3a}$, optionally substituted with one or more substituents $R^3$, where $R^{3a}$ and $R^3$ are each as defined herein. In certain embodiments, E is $C_{2-6}$ alkynylene-$C_{6-14}$ arylene-$R^{3a}$, optionally substituted with one or more substituents $R^3$, wherein $R^3$ is as defined herein. In certain embodiments, E is ethynylene-$C_{6-14}$ arylene-$R^{3a}$, optionally substituted with one or more substituents $R^3$, wherein $R^3$ is as defined herein. In certain embodiments, E is ethynylene-phenylene-$R^{3a}$, optionally substituted with one or more substituents $R^3$, wherein $R^3$ is as defined herein. In certain embodiments, E is ethynylene-1,4-phenylene-$R^{3a}$, optionally substituted with one or more substituents $R^3$, wherein $R^3$ is as defined herein.

In certain embodiments, E is heteroarylene-$R^{3a}$, optionally substituted with one or more substituents $R^3$, where $R^{3a}$ and $R^3$ are each as defined herein. In certain embodiments, E is monocyclic heteroarylene-$R^{3a}$, optionally substituted with one or more substituents $R^3$, where $R^{3a}$ and $R^3$ are each as defined herein. In certain embodiments, E is 5-membered heteroarylene-$R^{3a}$, optionally substituted with one or more substituents $R^3$, where $R^{3a}$ and $R^3$ are each as defined herein. In certain embodiments, E is furanylene-$R^{3a}$, isothiazolylene-$R^{3a}$, isoxazolylene-$R^{3a}$, imidazolylene-$R^{3a}$, thienylene-$R^{3a}$, or thiazolylene-$R^{3a}$, each optionally substituted with one or more substituents $R^3$, where $R^{3a}$ and $R^3$ are each as defined herein. In certain embodiments, E is thiazol-2,5-ylene-$R^{3a}$, optionally substituted with one or more substituents $R^3$, where $R^{3a}$ and $R^3$ are each as defined herein. In certain embodiments, E is 6-membered heteroarylene-$R^{3a}$, optionally substituted with one or more substituents $R^3$, where $R^{3a}$ and $R^3$ are each as defined herein. In certain embodiments, E is bicyclic heteroarylene-$R^{3a}$, optionally substituted with one or more substituents $R^3$, where $R^{3a}$ and $R^3$ are each as defined herein.

In certain embodiments, E is 5,5-fused heteroarylene-$R^{3a}$, optionally substituted with one or more substituents $R^{3a}$, where $R^{3a}$ and $R^3$ are each as defined herein. In certain embodiments, E is thieno[3,2-b]thienylene-$R^{3a}$, pyrrolo[3,4-c]pyrrolylene-$R^{3a}$, 4H-thieno[3,2-b]pyrrolylene-$R^{3a}$, 6H-thieno[2,3-b]pyrrolylene-$R^{3a}$, imidazo[2,1-b]oxazolylene-$R^{3a}$, imidazo[2,1-b]thiazolylene-$R^{3a}$, or 4H-pyrrolo[3,2-d]thiazolylene-$R^{3a}$, each optionally substituted with one or more additional substituents $R^3$, where $R^{3a}$ and $R^3$ are each as defined herein. In certain embodiments, E is thieno[3,2-b]thienyl, pyrrolo[3,4-c]pyrrolyl, 4H-thieno[3,2-b]pyrrolyl, 6H-thieno[2,3-b]pyrrolyl, imidazo[2,1-b]oxazolyl, imidazo[2,1-b]thiazolyl, or 4H-pyrrolo[3,2-d]thiazolyl, each optionally substituted with one or more substituents $R^3$, where $R^3$ is as defined herein. In certain embodiments, E is thieno[3,2-b]thien-3,6-ylene-$R^{3a}$, pyrrolo[3,4-c]pyrrol-1,4-ylene-$R^{3a}$, 4H-thieno[3,2-b]pyrrol-2,5-ylene-$R^{3a}$, 6H-thieno[2,3-b]pyrrol-3,6-ylene-$R^{3a}$, imidazo[2,1-b]oxazol-2,6-ylene-$R^{3a}$, imidazo[2,1-b]thiazol-2,6-ylene-$R^{3a}$, or 4H-pyrrolo[3,2-d]thiazol-2,5-ylene-$R^{3a}$, each optionally substituted with one or more substituents $R^3$, where $R^{3a}$ and $R^3$ are each as defined herein.

In certain embodiments, $L^1$ is a bond. In certain embodiments, $L^1$ is not a bond. In certain embodiments, $L^1$ is $C_{1-6}$ alkylene, optionally substituted with one or more substituents Q. In certain embodiments, $L^1$ is $C_{2-6}$ alkenylene, optionally substituted with one or more substituents Q. In certain embodiments, $L^1$ is $C_{2-6}$ alkynylene, optionally substituted with one or more substituents Q. In certain embodiments, $L^1$ is $C_{3-7}$ cycloalkylene, optionally substituted with one or more substituents Q. In certain embodiments, $L^1$ is $C_{6-14}$ arylene, optionally substituted with one or more substituents Q. In certain embodiments, $L^1$ is $C_{6-14}$ arylene-heteroarylene, optionally substituted with one or more substituents Q. In certain embodiments, $L^1$ is phenyl-heteroarylene, optionally substituted with one or more substituents Q. In certain embodiments, $L^1$ is phenyl-imidazolylene, optionally substituted with one or more substituents Q. In certain embodiments, $L^1$ is heteroarylene, optionally substituted with one or more substituents Q. In certain embodiments, $L^1$ is five- or six-membered heteroarylene, each optionally substituted with one or more substituents Q. In certain embodiments, $L^1$ is pyrazolylene, imidazolylene, or triazolylene, each optionally substituted with one or more substituents Q. In certain embodiments, $L^1$ is not thiazolylene. In certain embodiments, $L^1$ is pyrazolylene, imidazolylene, oxazolylene, 1,3,4-oxadiazolylene, 1,2,3-triazolylene, or 1,2,4-triazolylene, each optionally substituted with one or more substituents Q. In certain embodiments, $L^1$ is pyrazol-3,5-ylene, oxazol-2,5-ylene, imidazol-2,4-ylene, 1,3,4-oxadiazol-2,5-ylene, 1,2,3-triazol-1,4-ylene, 1,2,3-triazol-2,4-ylene, or 1,2,4-triazol-3,5-ylene, each optionally substituted with one or more substituents Q. In certain embodiments, $L^1$ is heteroarylene-$C_{1-6}$ alkylene, optionally substituted with one or more substituents Q. In certain embodiments, $L^1$ is imidazolylene-methylene, optionally substituted with one or more substituents Q. In certain embodiments, $L^1$ is imidazol-2,4-ylene-methylene, optionally substituted with one or more substituents Q. In certain embodiments, $L^1$ is heteroarylene-$C_{2-6}$ alkenylene, optionally substituted with one or more substituents Q. In certain embodiments, $L^1$ is heteroarylene-$C_{2-6}$ alkynylene, optionally substituted with one or more substituents Q. In certain embodiments, $L^1$ is heterocyclylene; optionally substituted with one or more substituents Q.

In certain embodiments, $L^1$ is —C(O)—. In certain embodiments, $L^1$ is —C(O)O—. In certain embodiments, $L^1$ is —C(O)$NR^{1a}$—, where $R^{1a}$ is as defined herein. In certain embodiments, $L^1$ is —C(O)NH—. In certain embodiments, $L^1$ is —C(=$NR^{1a}$)$NR^{1c}$—, where $R^{1a}$ and $R^{1c}$ are each as defined herein. In certain embodiments, $L^1$ is —O—. In certain embodiments, $L^1$ is —OC(O)O—. In certain embodiments, $L^1$ is —OC(O)$NR^{1a}$—, where $R^{1a}$ is as defined herein. In certain embodiments, $L^1$ is —OC(=$NR^{1a}$)$NR^{1c}$—, where $R^{1a}$ and $R^{1c}$ are each as defined herein. In certain embodiments, $L^1$ is —OP(O)(O$R^{1a}$)—, where $R^{1a}$ is as defined herein. In certain embodiments, $L^1$ is —$NR^{1a}$—, where $R^{1a}$ is as defined herein. In certain embodiments, $L^1$ is —$NR^{1a}$C(O)$NR^{1c}$—, where $R^{1a}$ and $R^{1c}$ are each as defined herein. In certain embodiments, $L^1$ is —$NR^{1a}$C(=$NR^{1b}$)$NR^{1c}$—, where $R^{1a}$, $R^{1b}$, and $R^{1c}$ are each as defined herein. In certain embodiments, $L^1$ is —$NR^{1a}$S(O)$NR^{1c}$—, where $R^{1a}$ and $R^{1c}$ are each as defined herein. In certain embodiments, $L^1$ is —$NR^{1a}$S(O)$_2NR^{1c}$—, where $R^{1a}$ and $R^{1c}$ are each as defined herein. In certain embodiments, $L^1$ is —S—. In certain embodiments, $L^1$ is —S(O)—. In certain embodiments, $L^1$ is —S(O)$_2$—. In certain embodiments, $L^1$ is —S(O)$NR^{1a}$—, where $R^{1a}$ is as defined herein. In certain embodiments, $L^1$ is —S(O)$_2NR^{1a}$—, where $R^{1a}$ is as defined herein.

In certain embodiments, the arylene and the arylene moiety of the $C_{6-14}$ arylene-heteroarylene of $L^1$ are not 5,6- or 6,6-fused arylene. In certain embodiments, the heteroarylene and the heteroarylene moiety in the $C_{6-14}$ arylene-heteroarylene, heteroarylene-$C_{1-6}$ alkylene, heteroarylene-$C_{2-6}$ alkenylene, and heteroarylene-$C_{2-6}$ alkynylene of $L^1$ are not 5,6- or 6,6-fused heteroarylene.

In certain embodiments, $L^2$ is a bond. In certain embodiments, $L^2$ is not a bond. In certain embodiments, $L^2$ is $C_{1-6}$ alkylene, optionally substituted with one or more substituents Q. In certain embodiments, $L^2$ is $C_{2-6}$ alkenylene, optionally substituted with one or more substituents Q. In certain embodiments, $L^2$ is $C_{2-6}$ alkynylene, optionally substituted with one or more substituents Q. In certain embodiments, $L^2$ is $C_{3-7}$ cycloalkylene, optionally substituted with one or more substituents Q. In certain embodiments, $L^2$ is $C_{6-14}$ arylene, optionally substituted with one or more substituents Q. In certain embodiments, $L^2$ is $C_{6-14}$ arylene-heteroarylene, optionally substituted with one or more substituents Q. In certain embodiments, $L^2$ is phenyl-heteroarylene, optionally substituted with one or more substituents Q. In certain embodiments, $L^2$ is phenyl-imidazolylene, optionally substituted with one or more substituents Q. In certain embodiments, $L^2$ is heteroarylene, optionally substituted with one or more substituents Q. In certain embodiments, $L^2$ is five- or six-membered heteroarylene, each optionally substituted with one or more substituents Q. In certain embodiments, L² is pyrazolylene, imidazolylene, or triazolylene, each optionally substituted with one or more substituents Q. In certain embodiments, L¹ is not thiazolylene. In certain embodiments, L² is pyrazolylene, oxazolylene, imidazolylene, 1,3,4-oxadiazolylene, 1,2,3-triazolylene, or 1,2,4-triazolylene, each optionally substituted with one or more substituents Q. In certain embodiments, L² is pyrazol-3,5-ylene, oxazol-2,5-ylene, imidazol-2,4-ylene, 1,3,4-oxadiazol-2,5-ylene, 1,2,3-triazol-1,4-ylene, 1,2,3-triazol-2,4-ylene, or 1,2,4-triazol-3,5-ylene, each optionally substituted with one or more substituents Q. In certain embodiments, L² is heteroarylene-C₁₋₆ alkylene, optionally substituted with one or more substituents Q. In certain embodiments, L² is imidazolylene-methylene, optionally substituted with one or more substituents Q. In certain embodiments, L² is imidazol-2,4-ylene-methylene, optionally substituted with one or more substituents Q. In certain embodiments, L² is heteroarylene-C₂₋₆ alkenylene, optionally substituted with one or more substituents Q. In certain embodiments, L² is heteroarylene-C₂₋₆ alkynylene, optionally substituted with one or more substituents Q. In certain embodiments, L² is heterocyclylene; optionally substituted with one or more substituents Q.

In certain embodiments, L² is —C(O)—. In certain embodiments, L² is —C(O)O—. In certain embodiments, L² is —C(O)NR¹ᵃ—, where R¹ᵃ is as defined herein. In certain embodiments, L² is —C(O)NH—. In certain embodiments, L² is —C(=NR¹ᵃ)NR¹ᶜ—, where R¹ᵃ and R¹ᶜ are each as defined herein. In certain embodiments, L² is —O—. In certain embodiments, L² is —OC(O)O—. In certain embodiments, L² is —OC(O)NR¹ᵃ—, where R¹ᵃ is as defined herein. In certain embodiments, L² is —OC(=NR¹ᵃ)NR¹ᶜ—, where R¹ᵃ and R¹ᶜ are each as defined herein. In certain embodiments, L² is —OP(O)(OR¹ᵃ)—, where R¹ᵃ is as defined herein. In certain embodiments, L² is —NR¹ᵃ—, where R¹ᵃ is as defined herein. In certain embodiments, L² is —NR¹ᵃC(O)NR¹ᶜ—, where R¹ᵃ and R¹ᶜ are each as defined herein. In certain embodiments, L² is —NR¹ᵃC(=NR¹ᵇ)NR¹ᶜ, where R¹ᵃ, R¹ᵇ, and R¹ᶜ are each as defined herein. In certain embodiments, L² is —NR¹ᵃS(O)NR¹ᶜ—, where R¹ᵃ and R¹ᶜ are each as defined herein. In certain embodiments, L² is —NR¹ᵃS(O)₂NR¹ᶜ—, where R¹ᵃ and R¹ᶜ are each as defined herein. In certain embodiments, L² is —S—. In certain embodiments, L² is —S(O)—. In certain embodiments, L² is —S(O)₂—. In certain embodiments, L² is —S(O)NR¹ᵃ—, where R¹ᵃ is as defined herein. In certain embodiments, L² is —S(O)₂NR¹ᵃ—, where R¹ᵃ is as defined herein.

In certain embodiments, the arylene and the arylene moiety of the C₆₋₁₄ arylene-heteroarylene of L² are not 5,6- or 6,6-fused arylene. In certain embodiments, the heteroarylene and the heteroarylene moiety in the C₆₋₁₄ arylene-heteroarylene, heteroarylene-C₁₋₆ alkylene, heteroarylene-C₂₋₆ alkenylene, and heteroarylene-C₂₋₆ alkynylene of L² are not 5,6- or 6,6-fused heteroarylene.

In certain embodiments, L¹ and L² are each independently selected from:

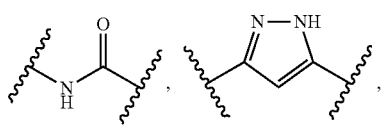

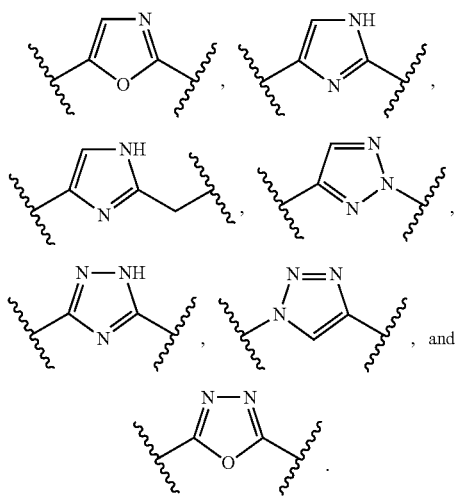

In certain embodiments, L¹ and L² are each independently selected from:

a bond,

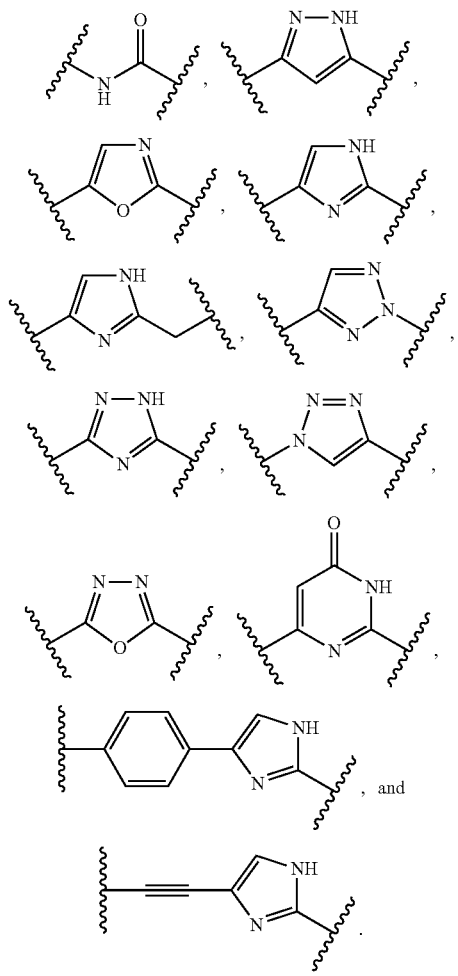

In certain embodiments, $L^1$ and $L^2$ are each independently selected from:

a bond,

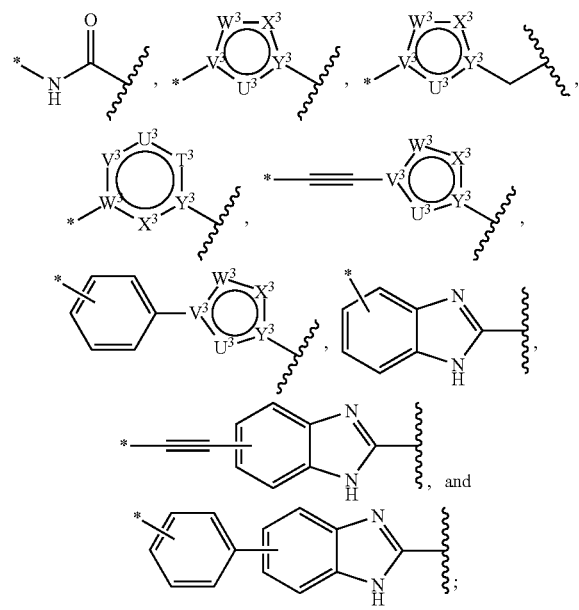

, and

;

wherein each moiety is optionally substituted with one, two, three, or four $R^3$; the star (*) on each moiety represents the point of attachment thought which the moiety is connected to $U^1$, $U^2$, $V^1$, $V^2$, $W^1$, or $W^2$ of

;

and the zigzag line (⟩) on each moiety represents the point of attachment through which the moiety is connected to

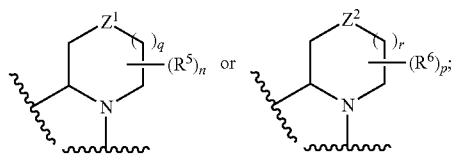

and wherein $T^3$ is a bond, C, N, O, S, $CR^{3a}$, or $NR^{3a}$; $U^3$, $V^3$, $W^3$, and $X^3$ are each independently C, N, O, S, $CR^{3a}$, or $NR^{3a}$; and $Y^3$ is C or N; where each $R^{3a}$ and $R^3$ is as defined herein.

In certain embodiments, $L^1$ and $L^2$ are each independently selected from:

a bond,

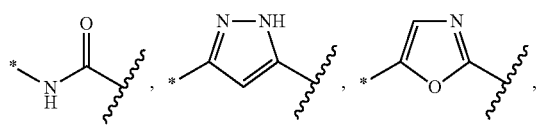

,

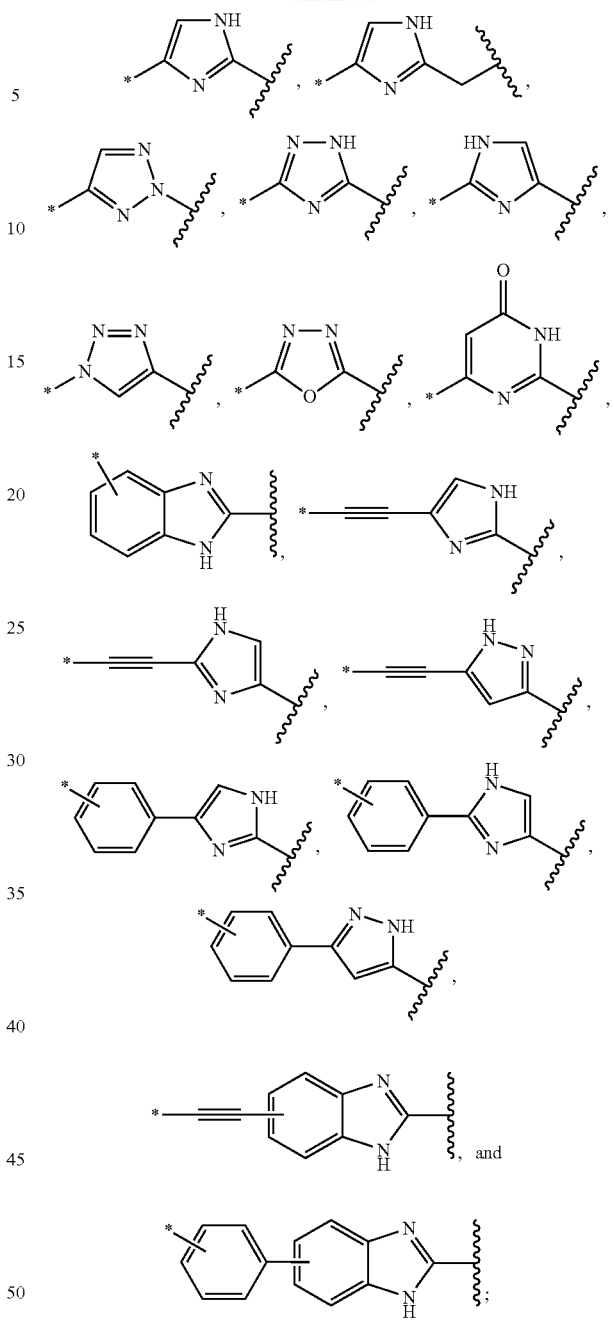

;

wherein each moiety is optionally substituted with one, two, three, or four $R^3$; the star (*) on each moiety represents the point of attachment thought which the moiety is connected to $U^1$, $U^2$, $V^1$, $V^2$, $W^1$, or $W^2$ of

;

and the zigzag line (⟩) on each moiety represents the point of attachment through which the moiety is connected to

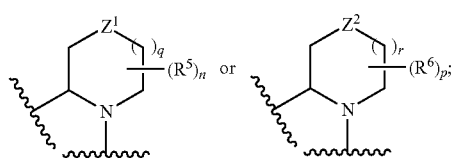

where each R³ is as defined herein.

In certain embodiments, L¹ and L² are each independently selected from:

a bond,

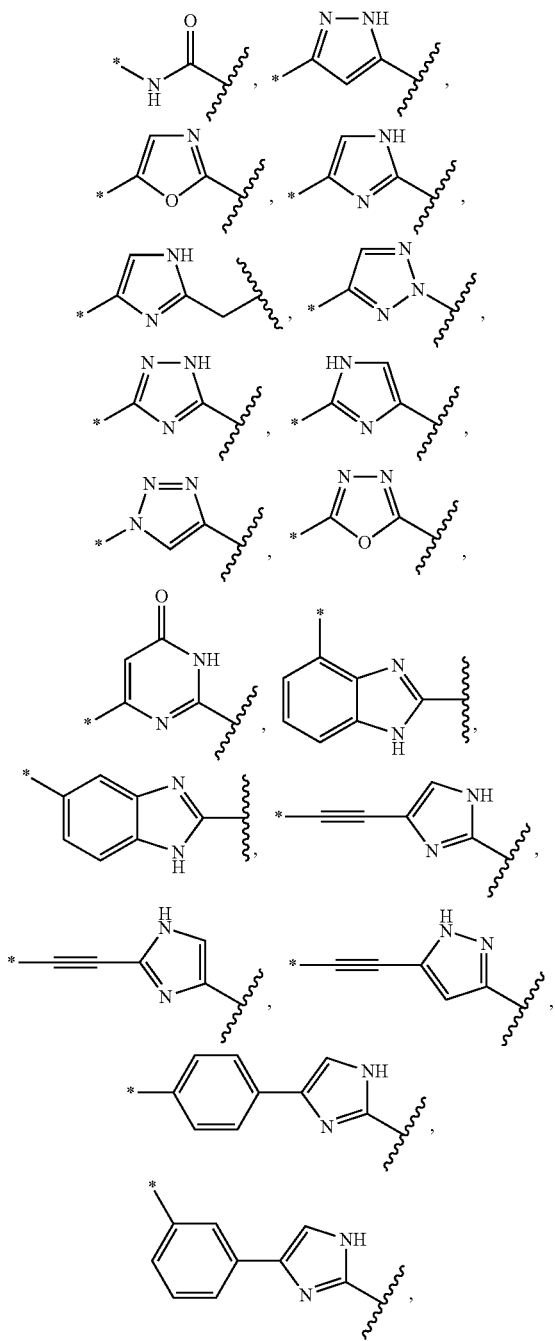

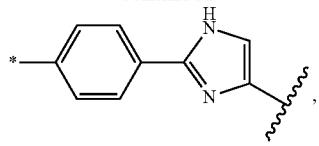

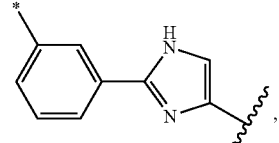

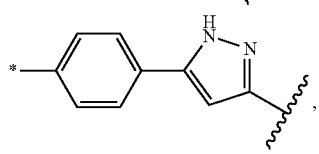

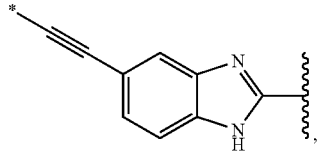

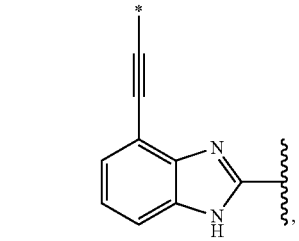

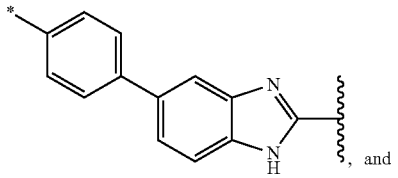

, and

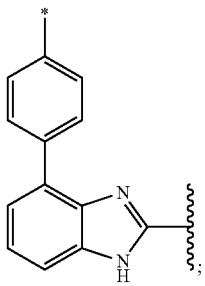

;

wherein each moiety is optionally substituted with one, two, three, or four $R^3$; the star (*) on each moiety represents the point of attachment thought which the moiety is connected to $U^1$, $U^2$, $V^1$, $V^2$, $W^1$, or $W^2$ of

and the zigzag line ( ) on each moiety represents the point of attachment through which the moiety is connected to

[Structure showing two piperidine-like rings with Z¹ and Z² substituents, (R⁵)ₙ and (R⁶)ₚ groups, with q and r ring sizes]

where each $R^3$ is as defined herein.

In certain embodiments, $T^3$ is a bond. In certain embodiments, $T^3$ is C. In certain embodiments, $T^3$ is N. In certain embodiments, $T^3$ is O. In certain embodiments, $T^3$ is S. In certain embodiments, $T^3$ is $CR^{3a}$, wherein $R^{3a}$ is as defined herein. In certain embodiments, $T^3$ is CH. In certain embodiments, $T^3$ is $NR^{3a}$, wherein $R^{3a}$ is as defined herein. In certain embodiments, $T^3$ is NH.

In certain embodiments, $U^1$ is C. In certain embodiments, $U^1$ is N. In certain embodiments, $U^1$ is O. In certain embodiments, $U^1$ is S. In certain embodiments, $U^1$ is $CR^{3a}$, wherein $R^{3a}$ is as defined herein. In certain embodiments, $U^1$ is CH. In certain embodiments, $U^1$ is $NR^{3a}$, wherein $R^{3a}$ is as defined herein. In certain embodiments, $U^1$ is NH.

In certain embodiments, $U^2$ is C. In certain embodiments, $U^2$ is N. In certain embodiments, $U^2$ is O. In certain embodiments, $U^2$ is S. In certain embodiments, $U^2$ is $CR^{3a}$, wherein $R^{3a}$ is as defined herein. In certain embodiments, $U^2$ is CH. In certain embodiments, $U^2$ is $NR^{3a}$, wherein $R^{3a}$ is as defined herein. In certain embodiments, $U^2$ is NH.

In certain embodiments, $U^3$ is C. In certain embodiments, $U^3$ is N. In certain embodiments, $U^3$ is O. In certain embodiments, $U^3$ is S. In certain embodiments, $U^3$ is $CR^{3a}$, wherein $R^{3a}$ is as defined herein. In certain embodiments, $U^3$ is CH. In certain embodiments, $U^3$ is $NR^{3a}$, wherein $R^{3a}$ is as defined herein. In certain embodiments, $U^3$ is NH.

In certain embodiments, $V^1$ is C. In certain embodiments, $V^1$ is N. In certain embodiments, $V^1$ is O. In certain embodiments, $V^1$ is S. In certain embodiments, $V^1$ is $CR^{3a}$, wherein $R^{3a}$ is as defined herein. In certain embodiments, $V^1$ is CH. In certain embodiments, $V^1$ is $NR^{3a}$, wherein $R^{3a}$ is as defined herein. In certain embodiments, $V^1$ is NH.

In certain embodiments, $V^2$ is C. In certain embodiments, $V^2$ is N. In certain embodiments, $V^2$ is O. In certain embodiments, $V^2$ is S. In certain embodiments, $V^2$ is $CR^{3a}$, wherein $R^{3a}$ is as defined herein. In certain embodiments, $V^2$ is CH. In certain embodiments, $V^2$ is $NR^{3a}$, wherein $R^{3a}$ is as defined herein. In certain embodiments, $V^2$ is NH.

In certain embodiments, $V^3$ is C. In certain embodiments, $V^3$ is N. In certain embodiments, $V^3$ is O. In certain embodiments, $V^3$ is S. In certain embodiments, $V^3$ is $CR^{3a}$, wherein $R^{3a}$ is as defined herein. In certain embodiments, $V^3$ is CH. In certain embodiments, $V^3$ is $NR^{3a}$, wherein $R^{3a}$ is as defined herein. In certain embodiments, $V^3$ is NH.

In certain embodiments, $W^1$ is C. In certain embodiments, $W^1$ is N. In certain embodiments, $W^1$ is O. In certain embodiments, $W^1$ is S. In certain embodiments, $W^1$ is $CR^{3a}$, wherein $R^{3a}$ is as defined herein. In certain embodiments, $W^1$ is CH. In certain embodiments, $W^1$ is $NR^{3a}$, wherein $R^{3a}$ is as defined herein. In certain embodiments, $W^1$ is NH.

In certain embodiments, $W^2$ is C. In certain embodiments, $W^2$ is N. In certain embodiments, $W^2$ is O. In certain embodiments, $W^2$ is S. In certain embodiments, $W^2$ is $CR^{3a}$, wherein $R^{3a}$ is as defined herein. In certain embodiments, $W^2$ is CH. In certain embodiments, $W^2$ is $NR^{3a}$, wherein $R^{3a}$ is as defined herein. In certain embodiments, $W^2$ is NH.

In certain embodiments, $W^3$ is C. In certain embodiments, $W^3$ is N. In certain embodiments, $W^3$ is O. In certain embodiments, $W^3$ is S. In certain embodiments, $W^3$ is $CR^{3a}$, wherein $R^{3a}$ is as defined herein. In certain embodiments, $W^3$ is CH. In certain embodiments, $W^3$ is $NR^{3a}$, wherein $R^{3a}$ is as defined herein. In certain embodiments, $W^3$ is NH.

In certain embodiments, $X^1$ is C. In certain embodiments, $X^1$ is N.

In certain embodiments, $X^2$ is C. In certain embodiments, $X^2$ is N.

In certain embodiments, $X^3$ is C. In certain embodiments, $X^3$ is N. In certain embodiments, $X^3$ is O. In certain embodiments, $X^3$ is S. In certain embodiments, $X^3$ is $CR^{3a}$, wherein $R^{3a}$ is as defined herein. In certain embodiments, $X^3$ is CH. In certain embodiments, $X^3$ is $NR^{3a}$, wherein $R^{3a}$ is as defined herein. In certain embodiments, $X^3$ is NH.

In certain embodiments, $Y^3$ is C. In certain embodiments, $Y^3$ is N.

In certain embodiments, $Z^1$ is a bond. In certain embodiments, $Z^1$ is —O—. In certain embodiments, $Z^1$ is —S—. In certain embodiments, $Z^1$ is —S(O)—. In certain embodiments, $Z^1$ is —S(O$_2$)—. In certain embodiments, $Z^1$ is —N(R$^7$)—, where $R^7$ is as defined herein. In certain embodiments, $Z^1$ is —NH—. In certain embodiments, $Z^1$ is —N(C(O)R$^{1a}$)—, where $R^{1a}$ is as defined herein. In certain embodiments, $Z^1$ is —N(C(O)C$_{1-6}$ alkyl)-. In certain embodiments, $Z^1$ is —N(C(O)CH$_3$)—.

In certain embodiments, $Z^2$ is a bond. In certain embodiments, $Z^2$ is —O—. In certain embodiments, $Z^2$ is —S—. In certain embodiments, $Z^2$ is —S(O)—. In certain embodiments, $Z^2$ is —S(O$_2$)—. In certain embodiments, $Z^2$ is —N(R$^7$)—, where $R^7$ is as defined herein. In certain embodiments, $Z^2$ is —NH—. In certain embodiments, $Z^2$ is —N(C(O)R$^{1a}$)—, where $R^{1a}$ is as defined herein. In certain embodiments, $Z^2$ is —N(C(O)C$_{1-6}$ alkyl)-. In certain embodiments, $Z^2$ is —N(C(O)CH$_3$)—.

In certain embodiments, m is 0. In certain embodiments, m is 1. In certain embodiments, m is 2. In certain embodiments, m is 3. In certain embodiments, m is 4.

In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7.

In certain embodiments, p is 0. In certain embodiments, p is 1. In certain embodiments, p is 2. In certain embodiments, p is 3. In certain embodiments, p is 4. In certain embodiments, p is 5. In certain embodiments, p is 6. In certain embodiments, p is 7.

In certain embodiments, q is 1. In certain embodiments, q is 2. In certain embodiments, q is 3. In certain embodiments, q is 4. In certain embodiments, q is an integer of 2, 3, or 4.

In certain embodiments, r is 1. In certain embodiments, r is 2. In certain embodiments, r is 3. In certain embodiments, r is 4. In certain embodiments, r is an integer of 2, 3, or 4.

In certain embodiments, s is 0 and t is 1. In certain embodiments, s is 1 and t is 0. In certain embodiments, s and t are both 1. In certain embodiments, s is 2 and t is 1. In certain embodiments, s is 2 and t is 0.

In certain embodiments, u is 1. In certain embodiments, u is 2.

In certain embodiments, the moiety

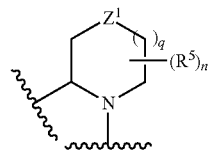

has the structure of:

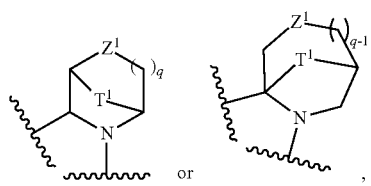

wherein $Z^1$ and q are each as defined herein; and each $T^1$ is independently a bond, —O—, —NR$^7$—, —S—, $C_{1-6}$ alkylene, $C_{1-6}$ heteroalkylene, $C_{2-6}$ alkenylene, or $C_{2-6}$ heteroalkenylene, where $R^7$ is as defined herein.

In certain embodiments, the moiety

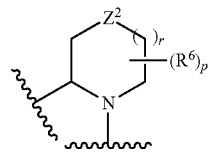

has the structure of:

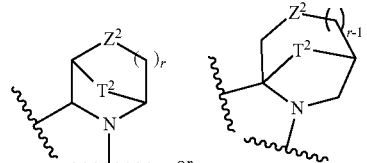

wherein $Z^2$ and r are each as defined herein; and each $T^2$ is independently a bond, —O—, —NR$^7$—, —S—, $C_{1-6}$ alkylene, $C_{1-6}$ heteroalkylene, $C_{2-6}$ alkenylene, or $C_{2-6}$ heteroalkenylene, where $R^7$ is as defined herein.

In one embodiment, the moiety

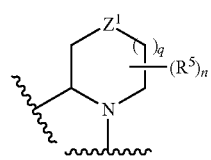

has the structure of

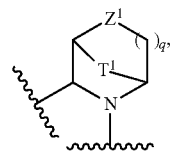

and the moiety

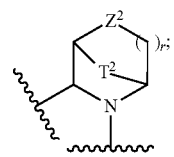

has the structure of

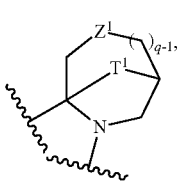

wherein $T^1$, $T^2$ $Z^1$, $Z^2$, q, and r are each as defined herein.

In another embodiment, the moiety

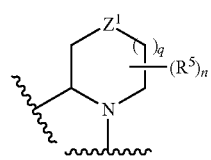

has the structure of

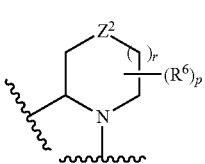

and the moiety

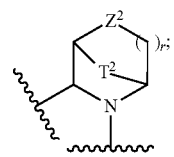

has the structure of

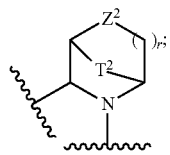

wherein $T^1$, $T^2$ $Z^1$, $Z^2$, q, and r are each as defined herein.

In yet another embodiment, the moiety

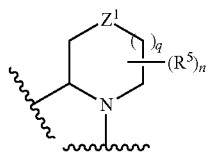

has the structure of

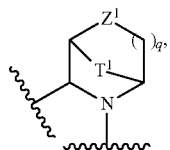

and the moiety

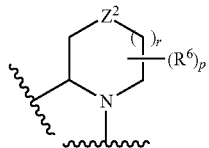

has the structure of

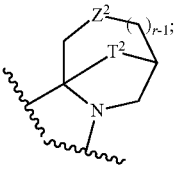

wherein $T^1$, $T^2$ $Z^1$, $Z^2$, q, and r are each as defined herein.

In still another embodiment, the moiety

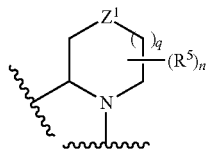

has the structure of

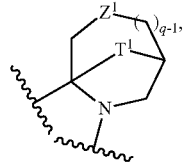

and the moiety

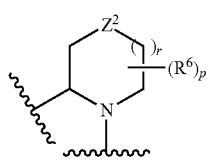

has the structure of

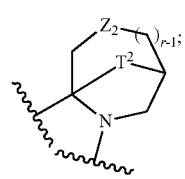

wherein $T^1$, $T^2$ $Z^1$, $Z^2$, q, and r are each as defined herein.

In certain embodiments, $T^1$ is a bond. In certain embodiments, $T^1$ is —O—. In certain embodiments, $T^1$ is —$NR^7$—, where $R^7$ is as defined herein. In certain embodiments, $T^1$ is —S—. In certain embodiments, $T^1$ is $C_{1-6}$ alkylene, optionally substituted with one or more substituents Q. In certain embodiments, $T^1$ is methylene or ethylene. In certain embodiments, $T^1$ is $C_{1-6}$ heteroalkylene, optionally substituted with one or more substituents Q. In certain embodiments, $T^1$ is $C_{2-6}$ alkenylene, optionally substituted with one or more substituents Q. In certain embodiments, $T^1$ is $C_{2-6}$ heteroalkenylene, optionally substituted with one or more substituents Q. In certain embodiments, each $T^1$ is independently —O—, —$NR^7$—, —S—, $C_{1-6}$ alkylene, $C_{1-6}$ heteroalkylene, $C_{2-6}$ alkenylene, or $C_{2-6}$ heteroalkenylene, where $R^7$ is as defined herein.

In certain embodiments, $T^2$ is a bond. In certain embodiments, $T^2$ is —O—. In certain embodiments, $T^2$ is —$NR^7$—, where $R^7$ is as defined herein. In certain embodiments, $T^2$ is —S—. In certain embodiments, $T^2$ is $C_{1-6}$ alkylene, optionally substituted with one or more substituents Q. In certain embodiments, $T^2$ is methylene or ethylene. In certain embodiments, $T^2$ is $C_{1-6}$ heteroalkylene, optionally substituted with one or more substituents Q. In certain embodiments, $T^2$ is $C_{2-6}$ alkenylene, optionally substituted with one or more substituents Q. In certain embodiments, $T^2$ is $C_{2-6}$ heteroalkenylene, optionally substituted with one or more substituents Q. In certain embodiments, each $T^2$ is independently —O—, —$NR^7$—, —S—, $C_{1-6}$ alkylene, $C_{1-6}$ heteroalkylene, $C_{2-6}$ alkenylene, or $C_{2-6}$ heteroalkenylene, where $R^7$ is as defined herein.

In certain embodiments, the moieties
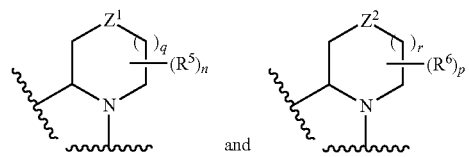
and
are each independently selected from:
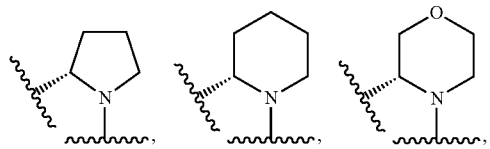
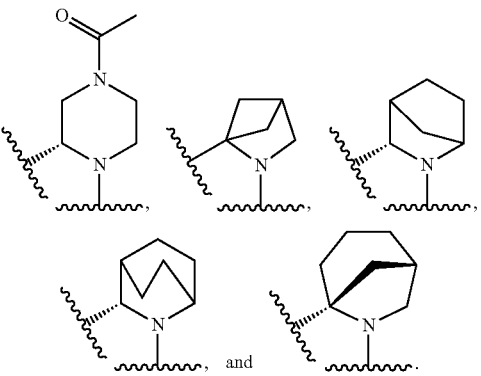
In one embodiment, provided herein is a compound selected from the group consisting of:
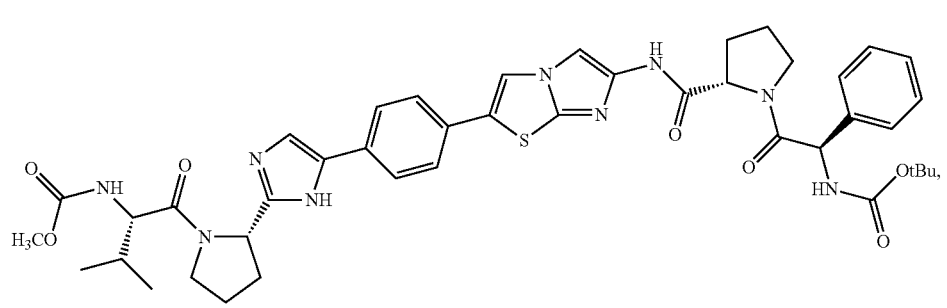
A1
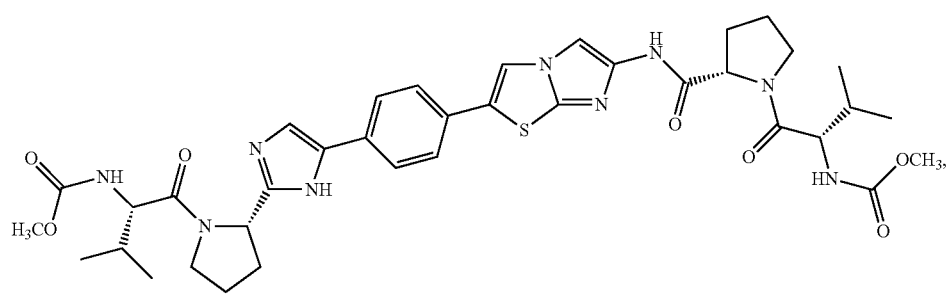
A2
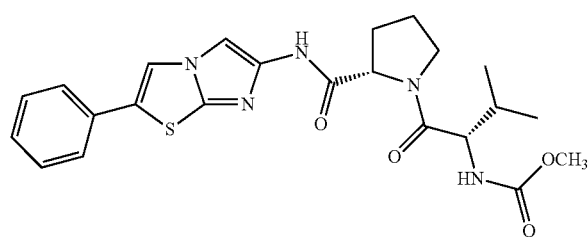
A3
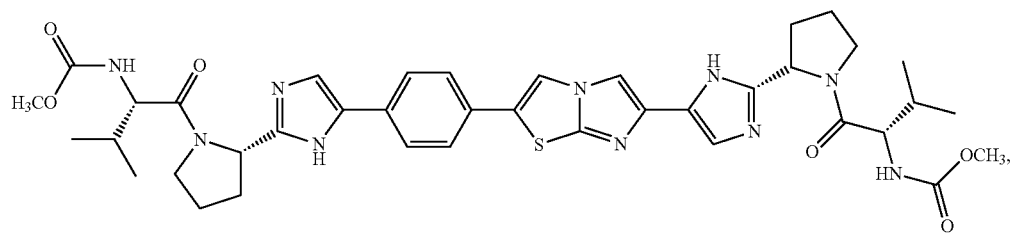
A4

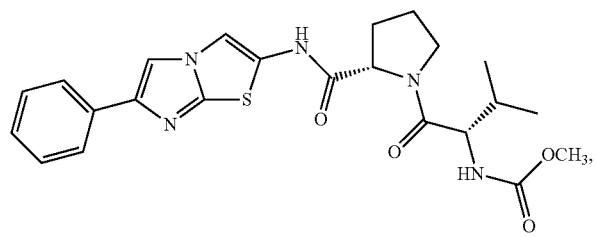
A5
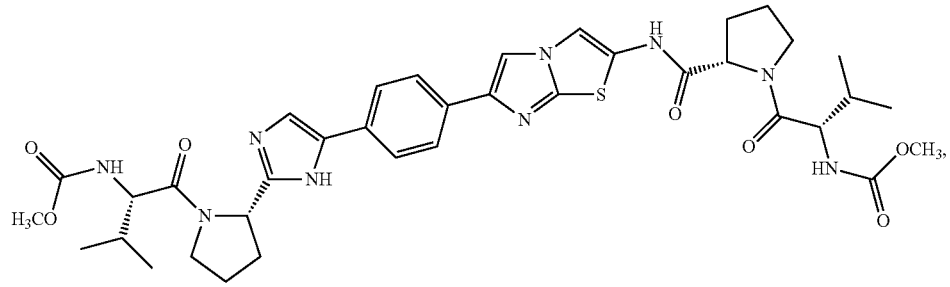
A6
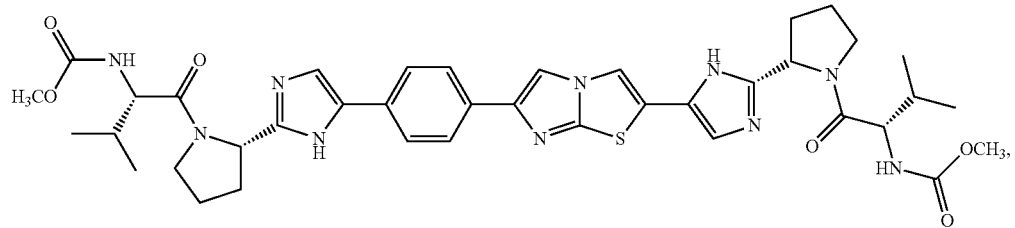
A7
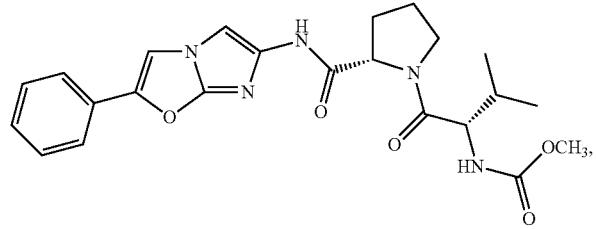
A8
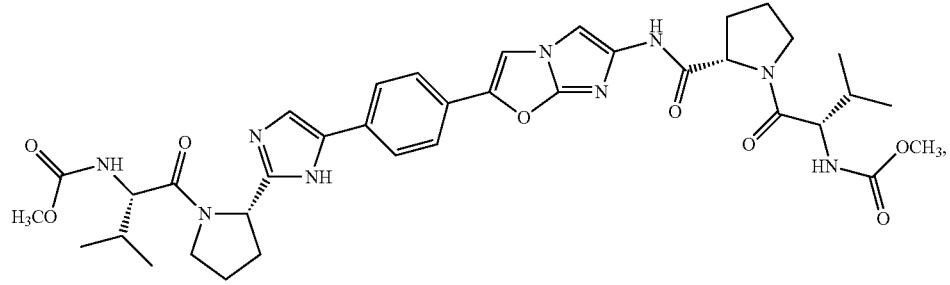
A9
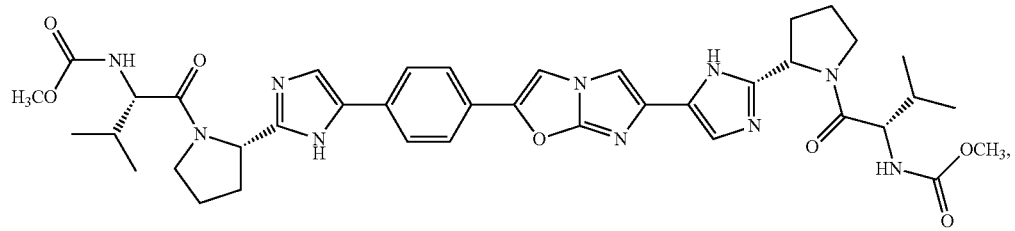
A10

-continued
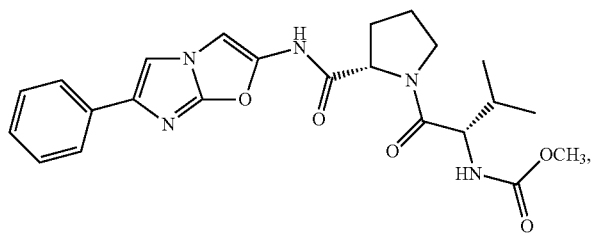
A11
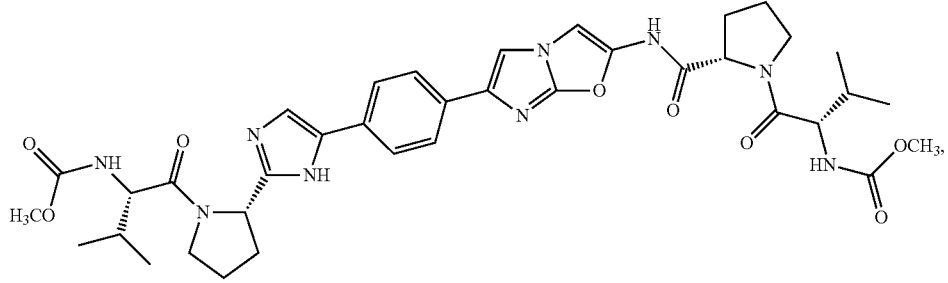
A12
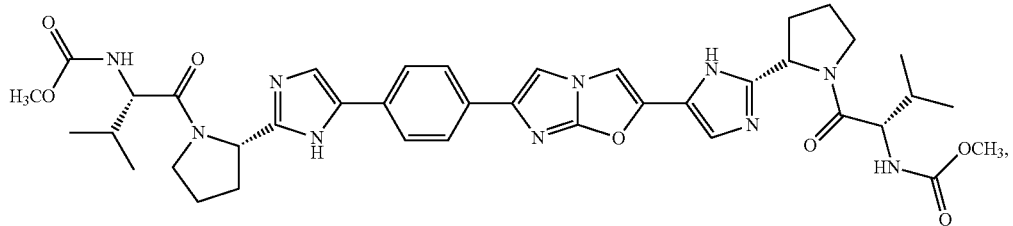
A13
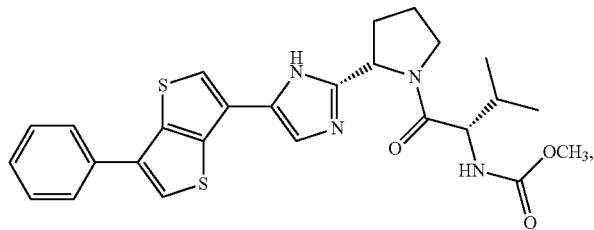
A14
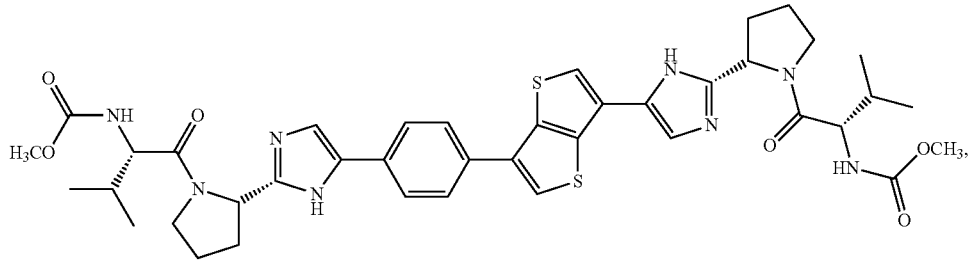
A15
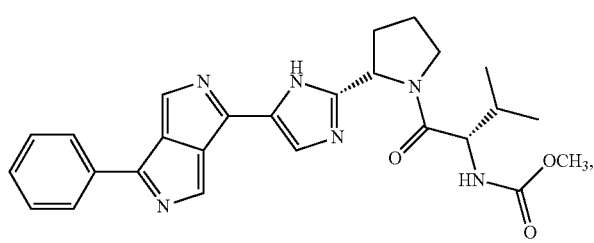
A16

-continued
A17
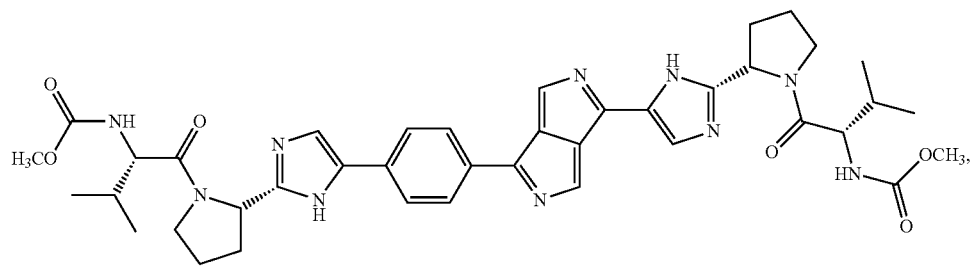
A18
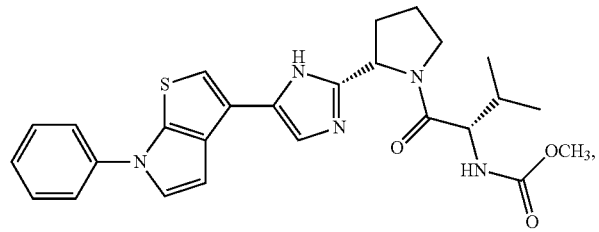
A19
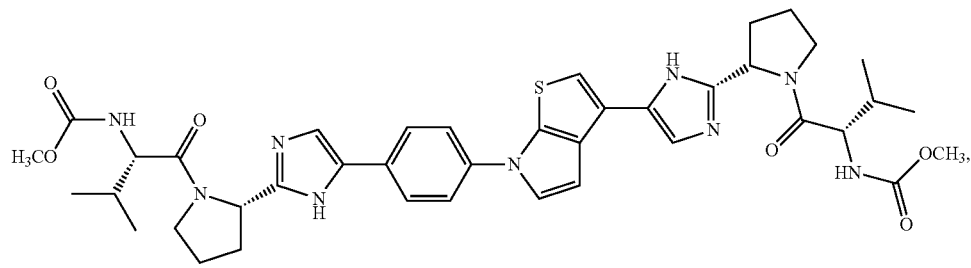
A20
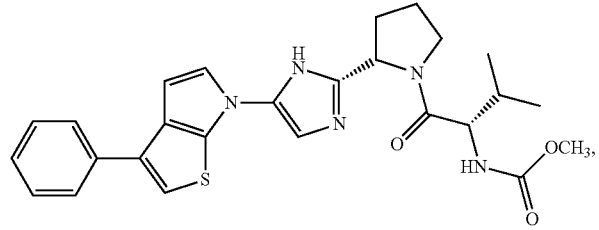
A21
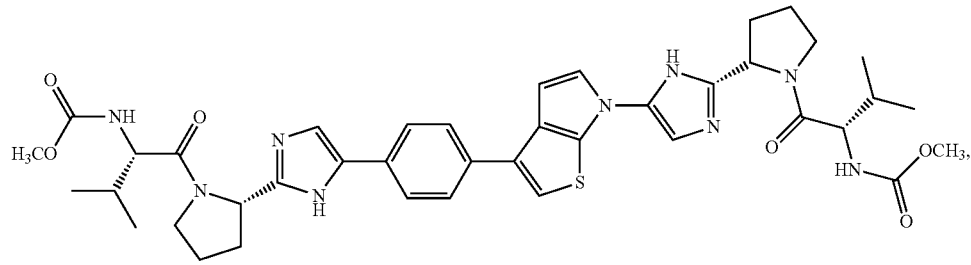
A22
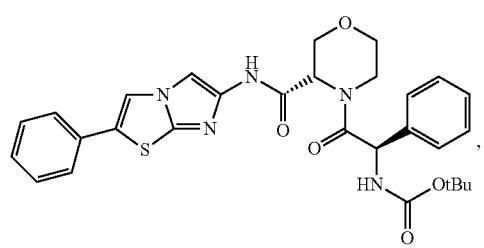
A23
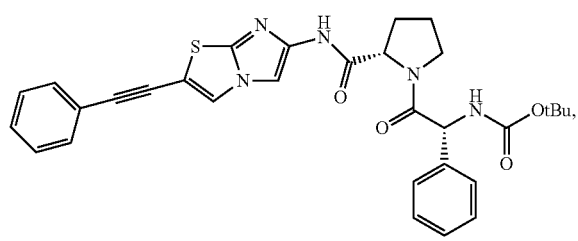

-continued
A24
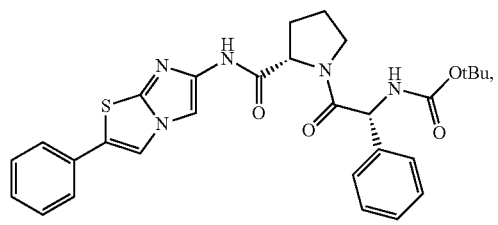
A25
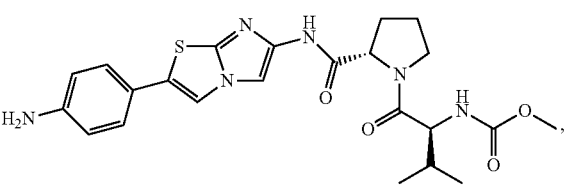
A26
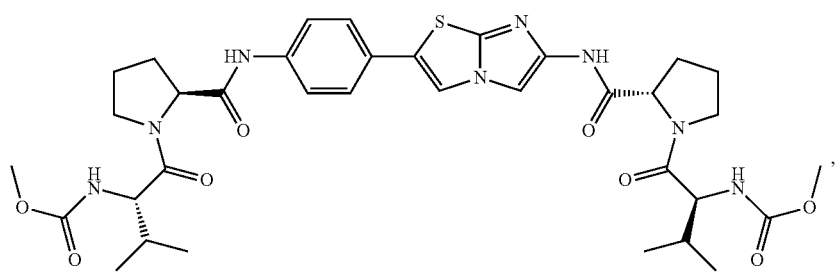
A27
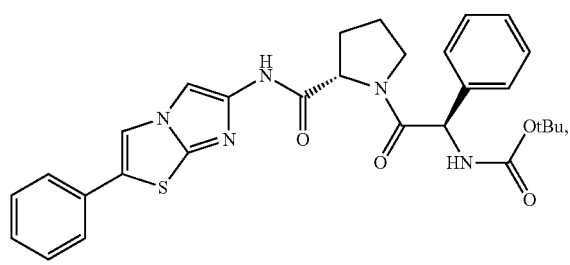
A28
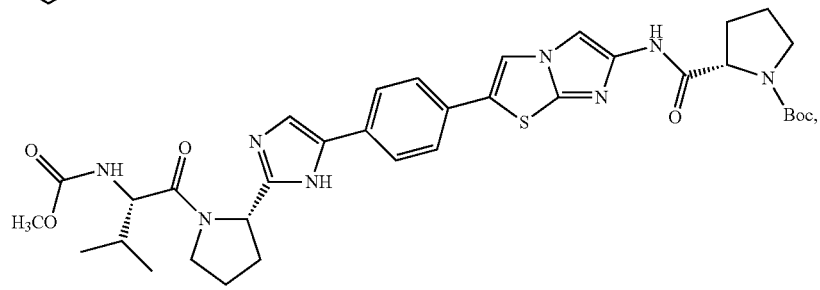
A29
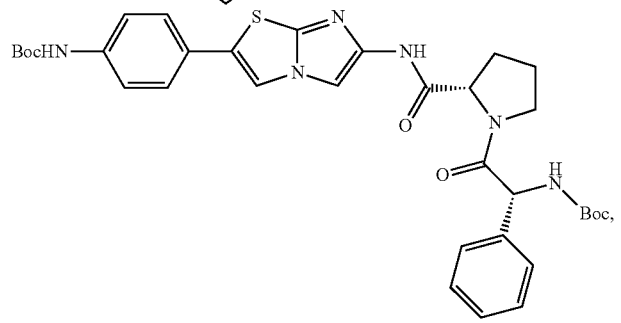
A30
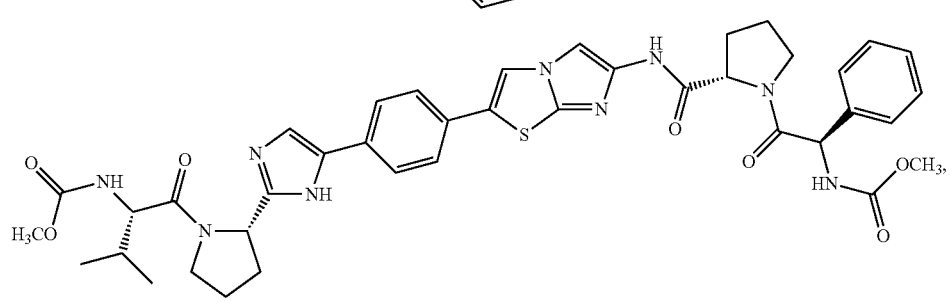

-continued
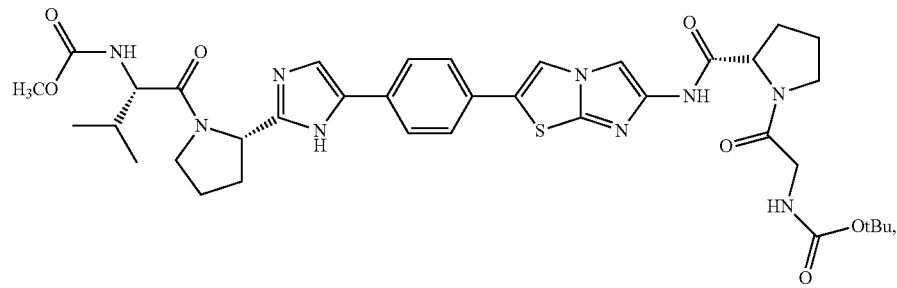
A31
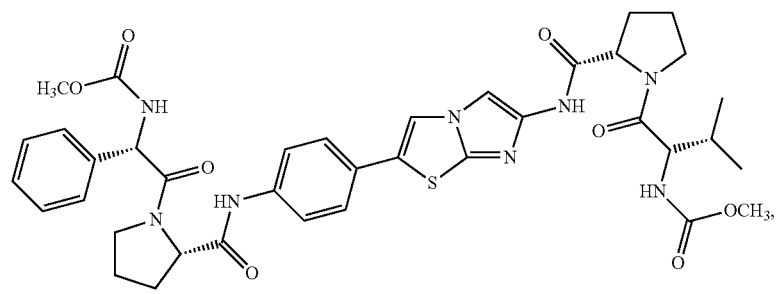
A32
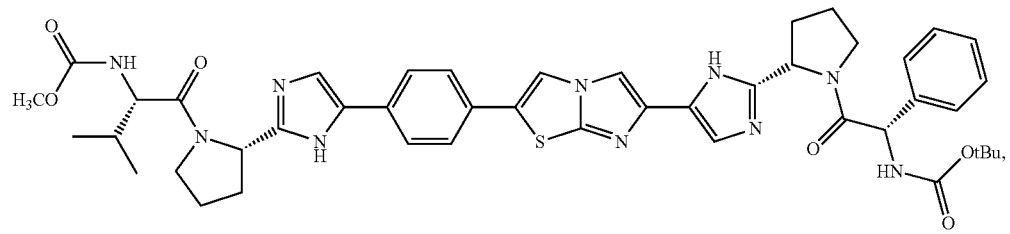
A33
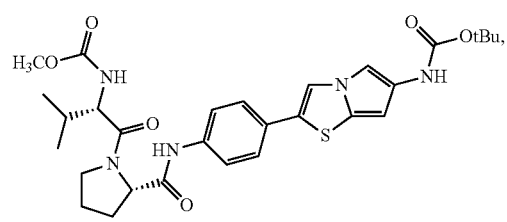
A34
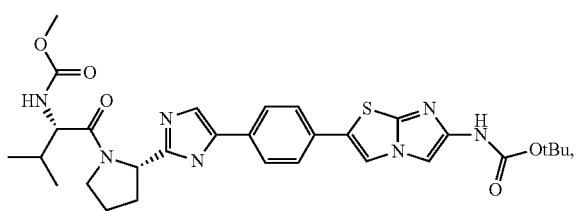
A35
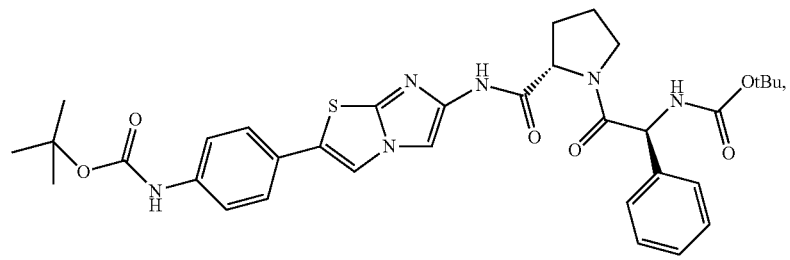
A36

-continued
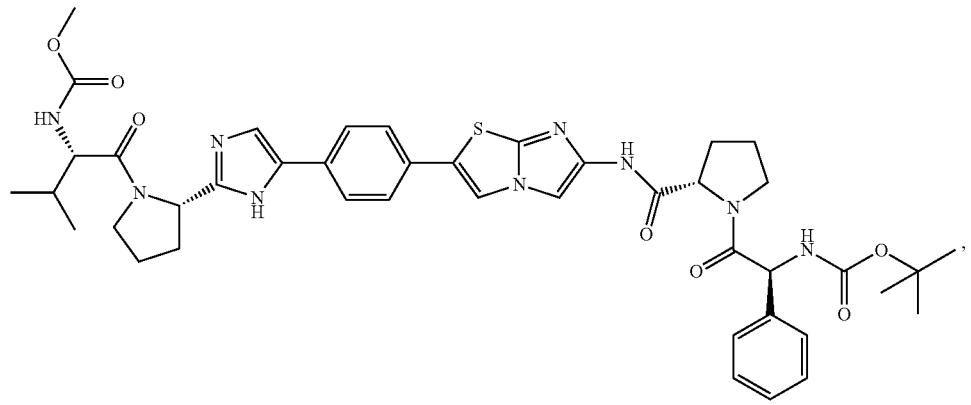
A37
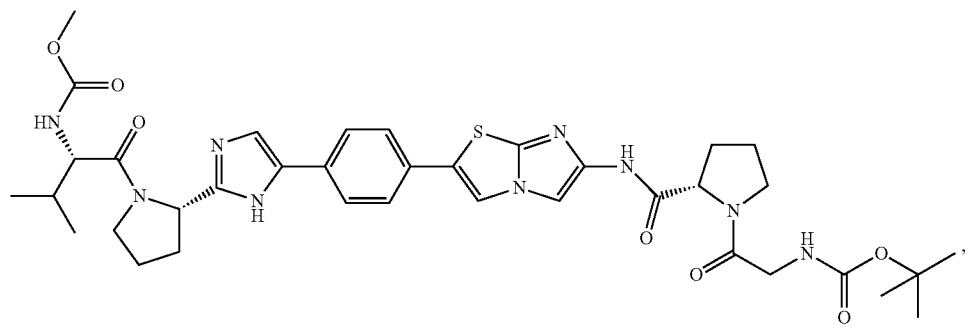
A38
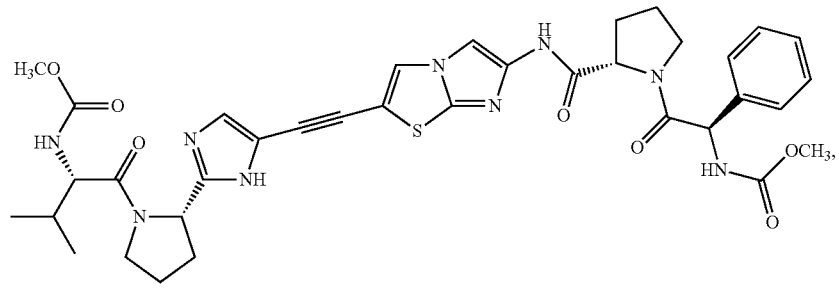
A39
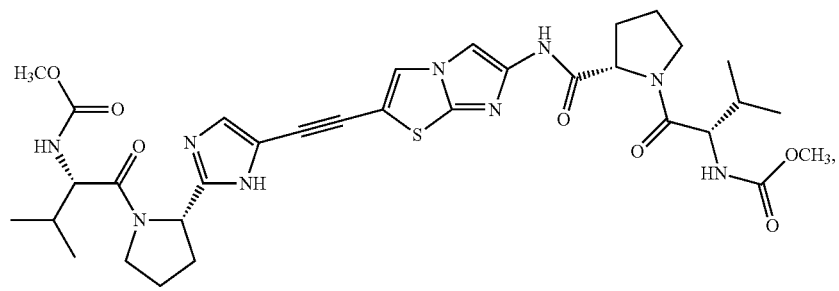
A40
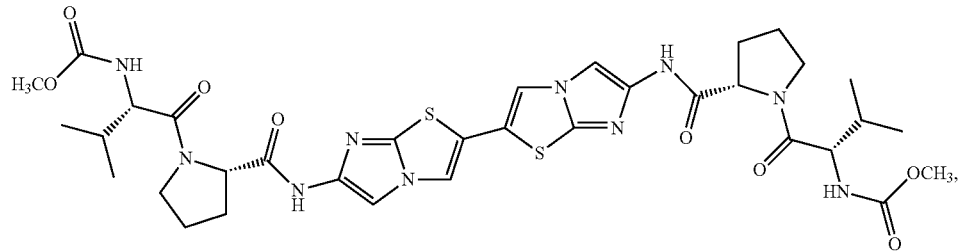
A41

-continued
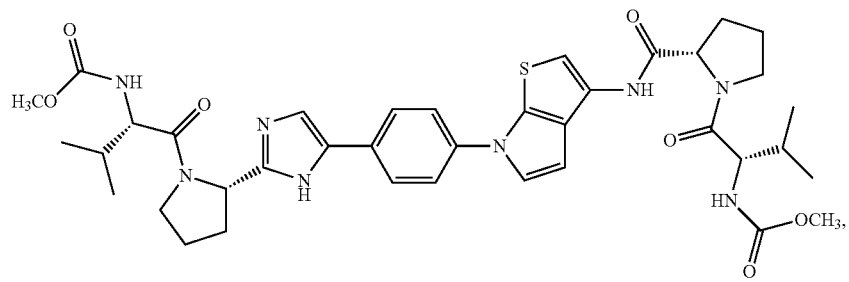
A42
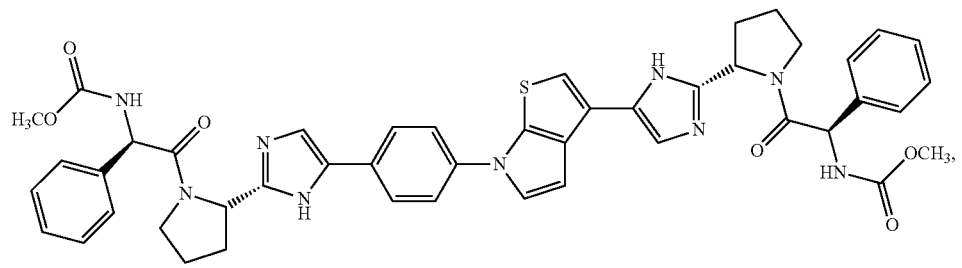
A43
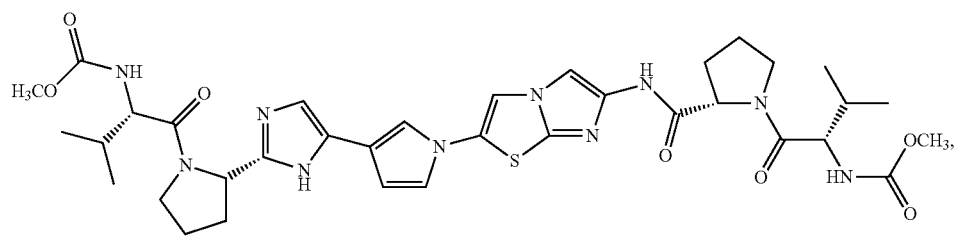
A44
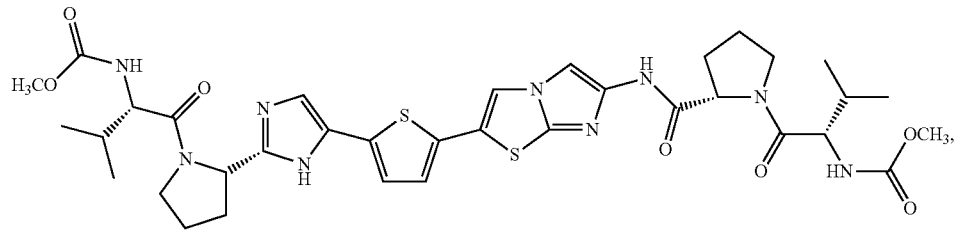
A45
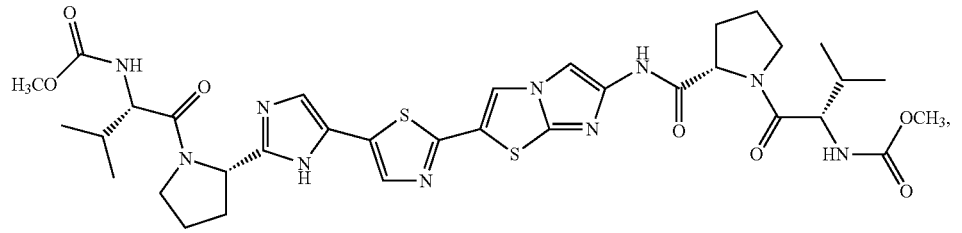
A46
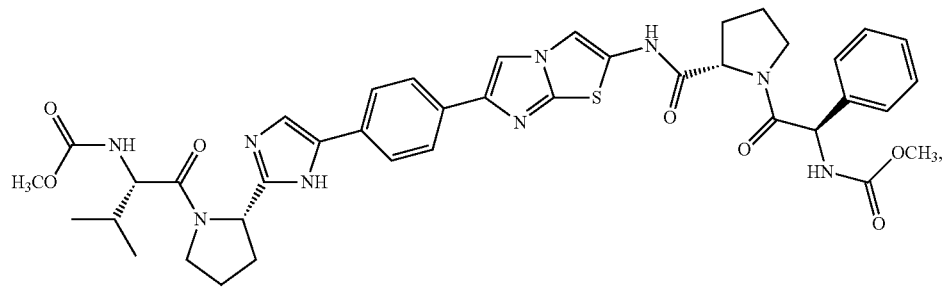
A47

-continued
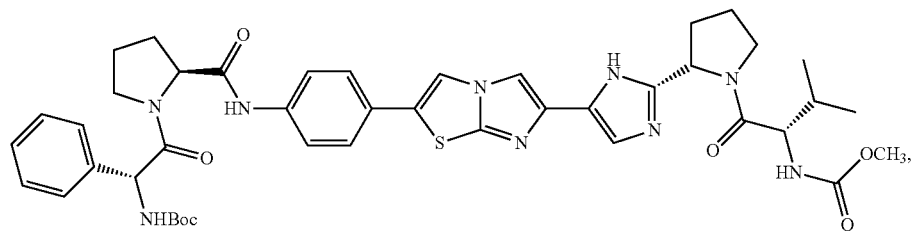
A48
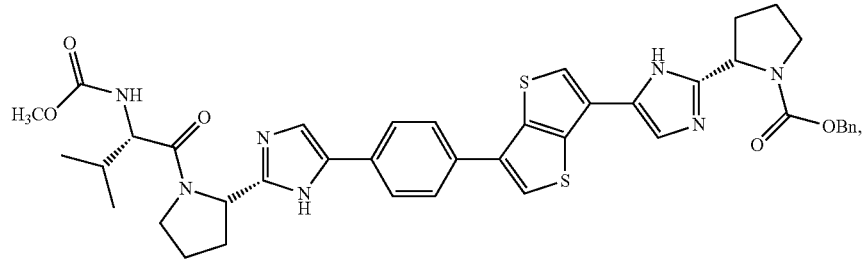
A49
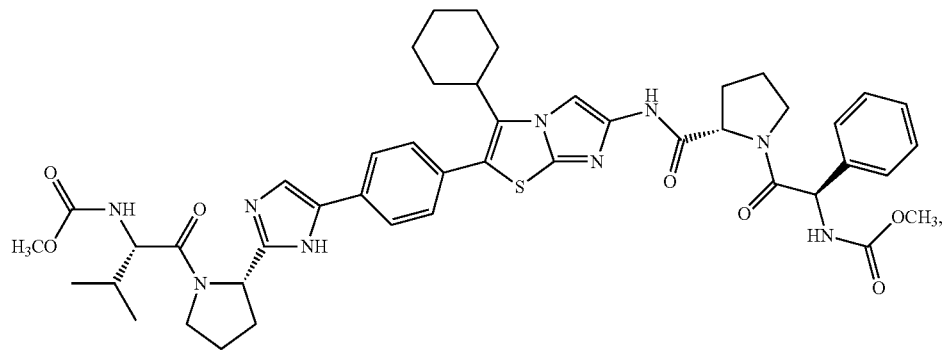
A50
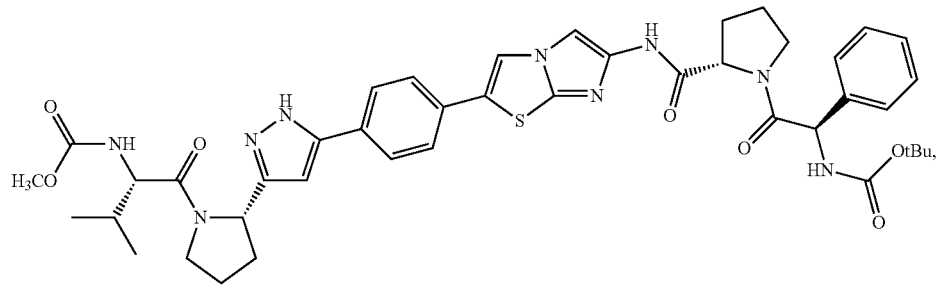
A51
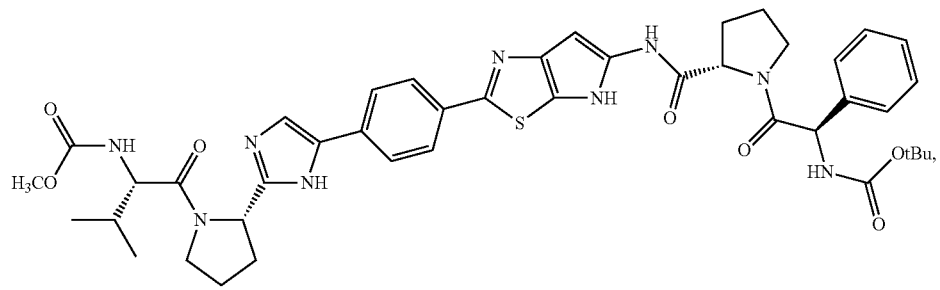
A52

-continued
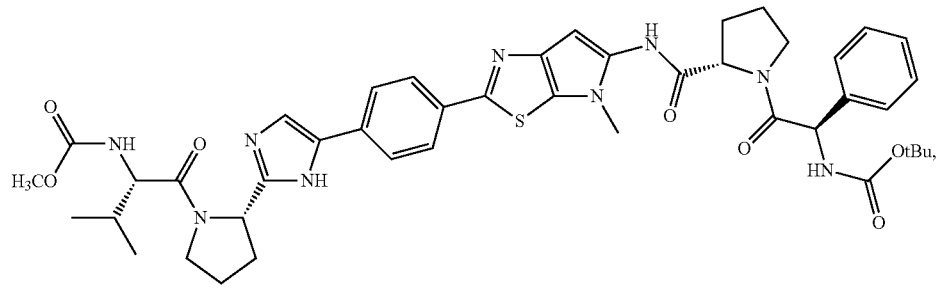
A53
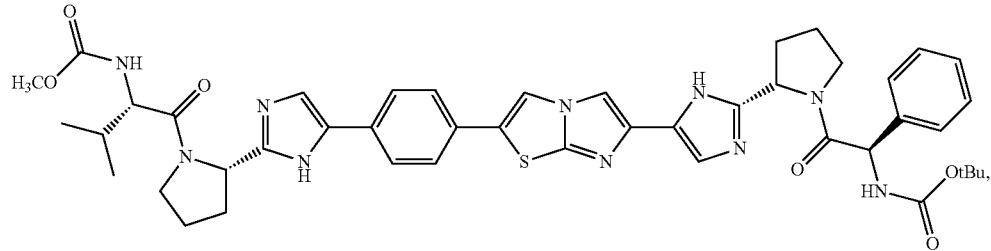
A54
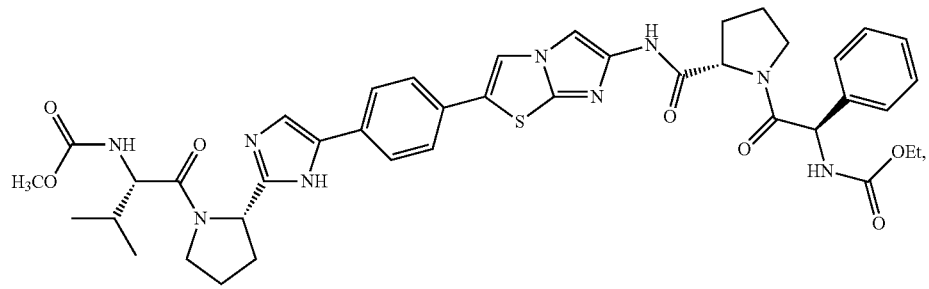
A55
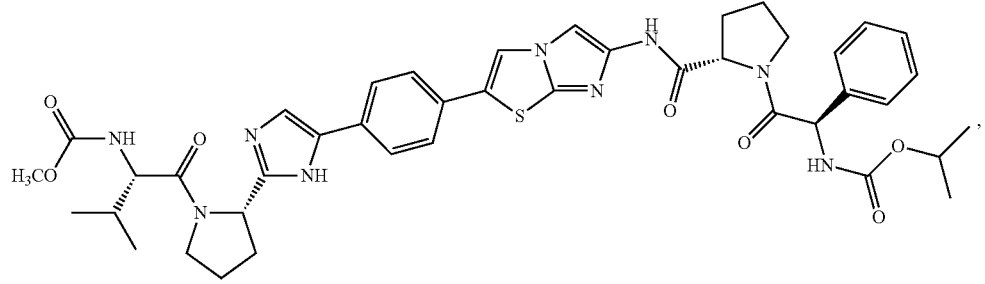
A56
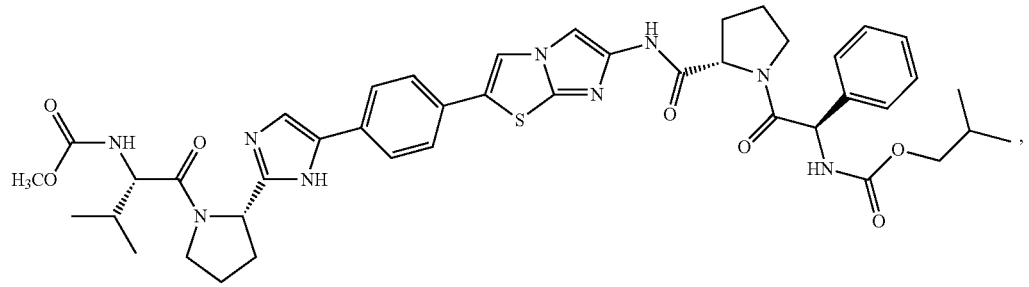
A57

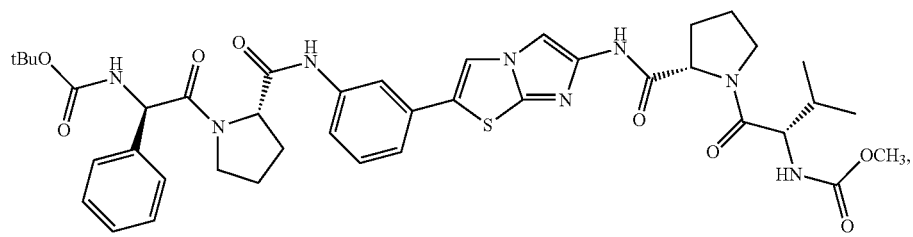
A58
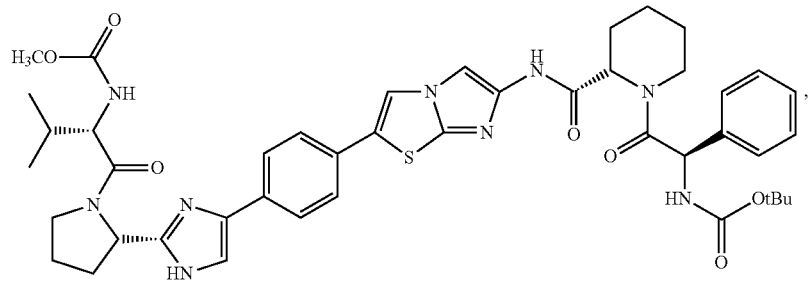
A59
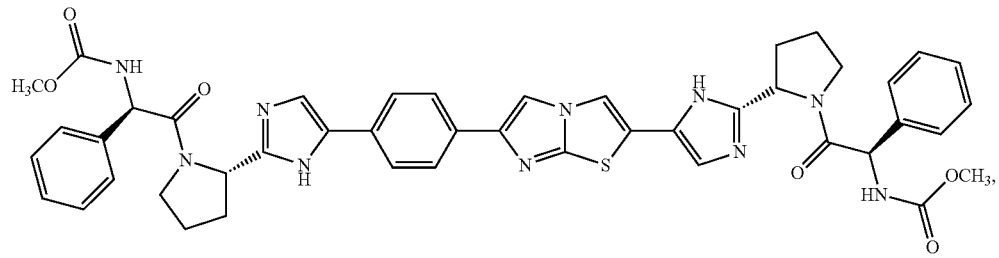
A60
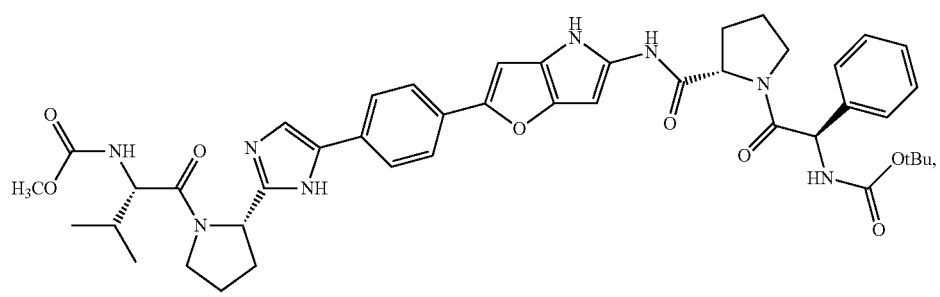
A61
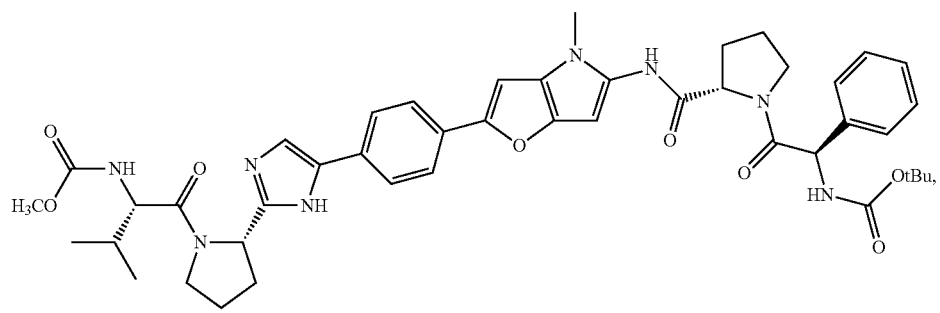
A62

A63
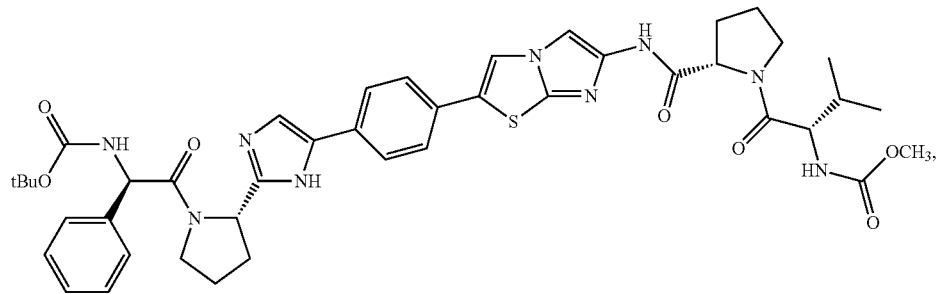
A64
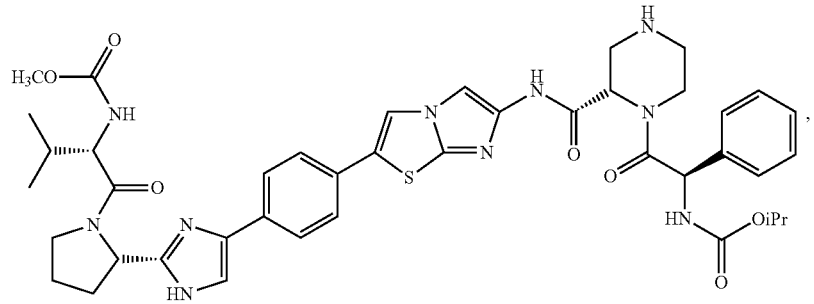
A65
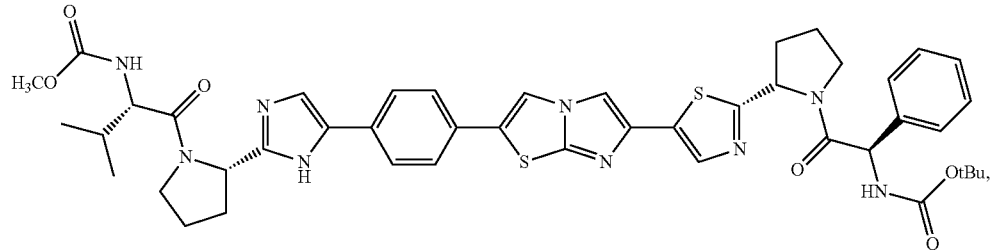
A66
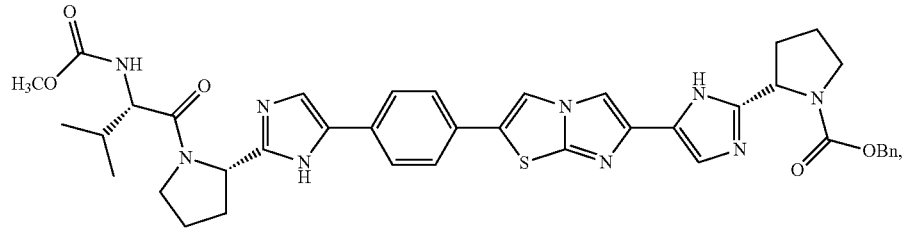
A67
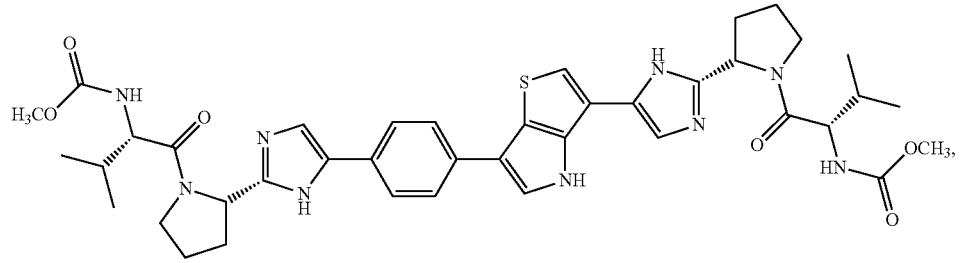

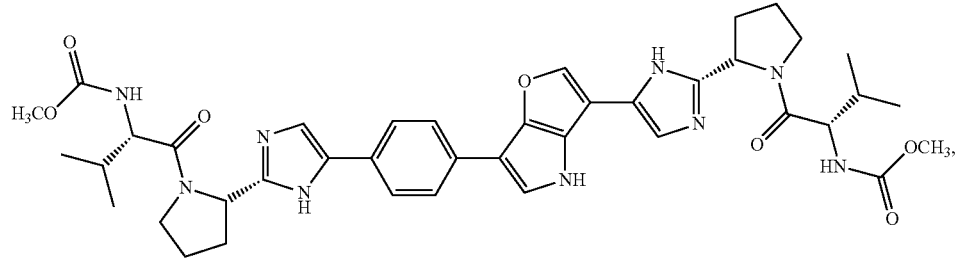
A68
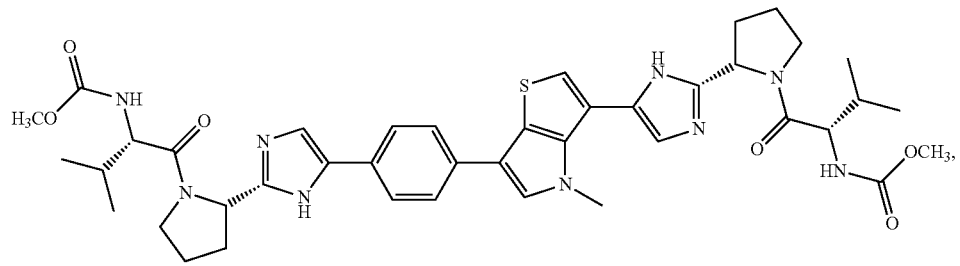
A69
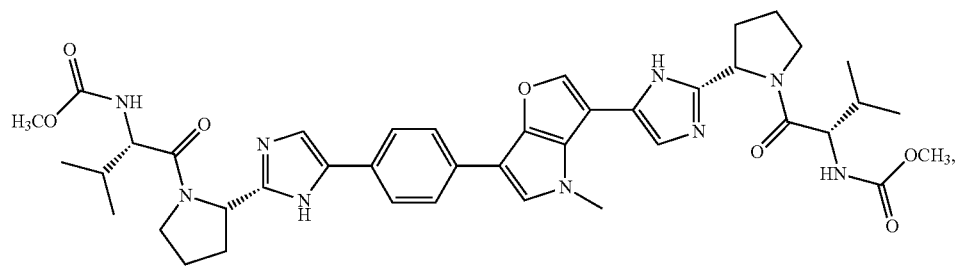
A70
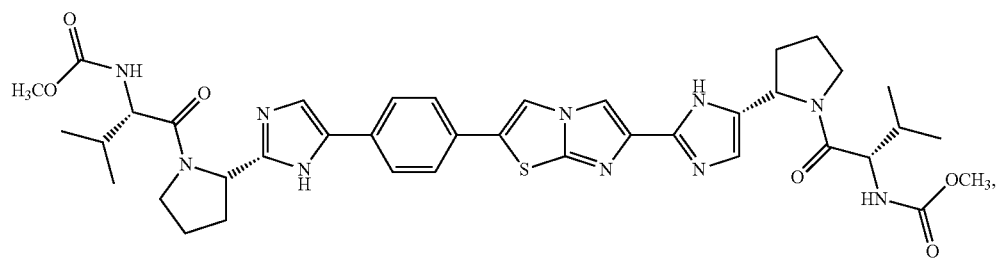
A71
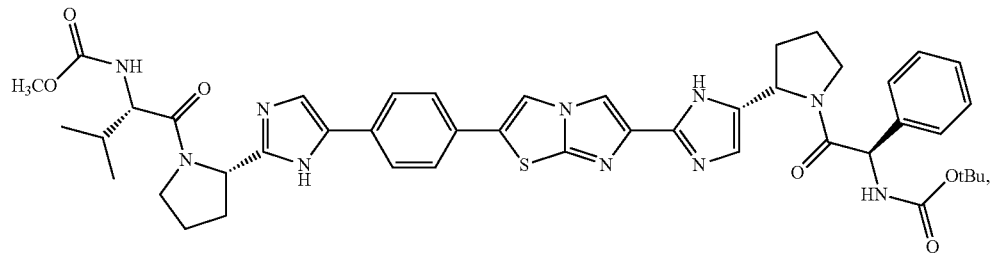
A72
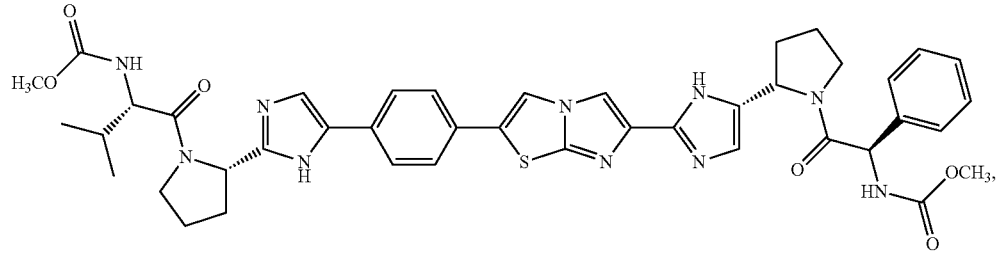
A73

-continued
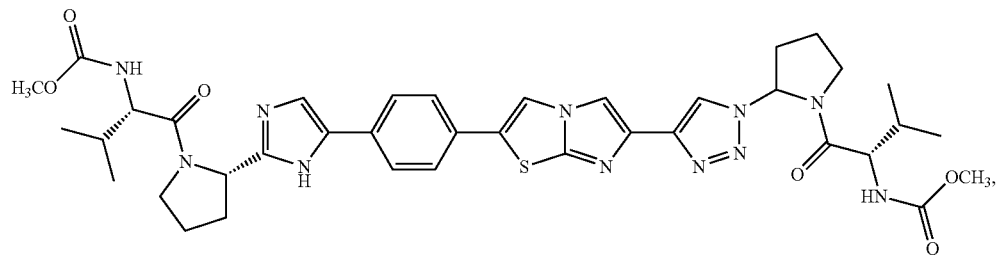 A74
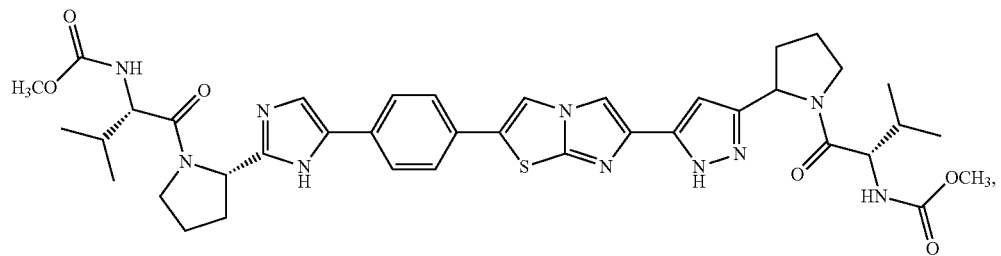 A75
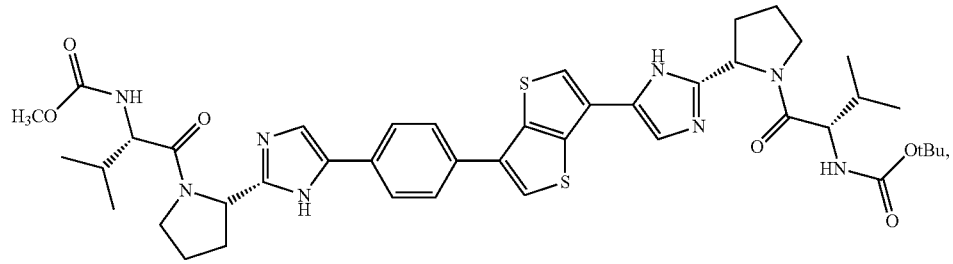 A76
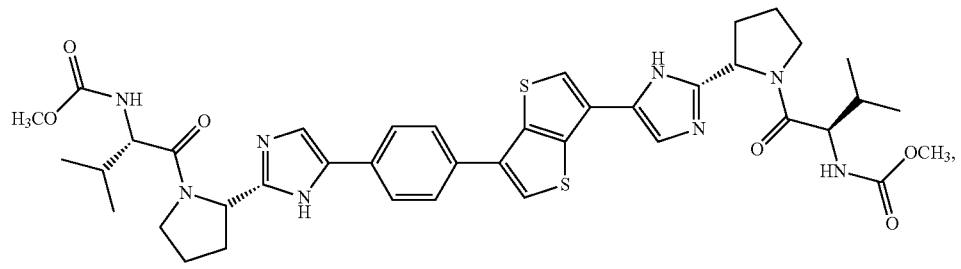 A77
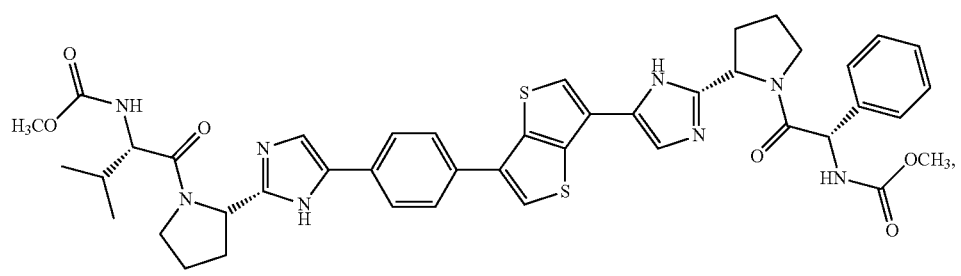 A78
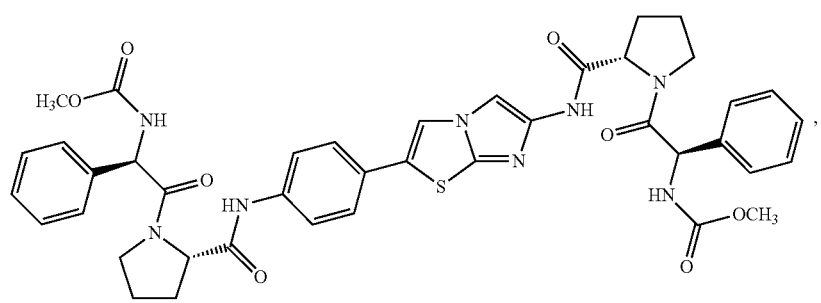 A79

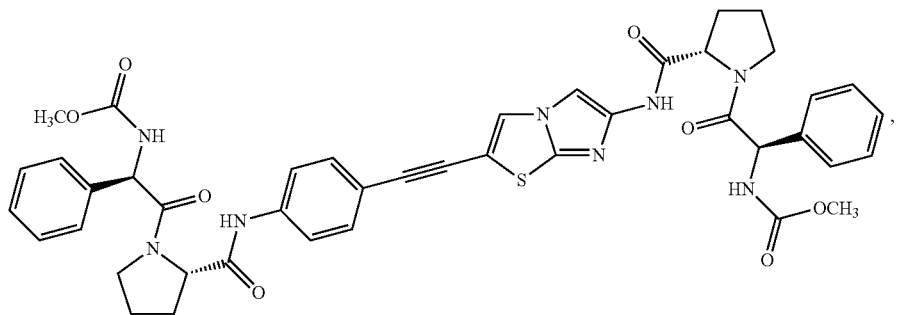
A80
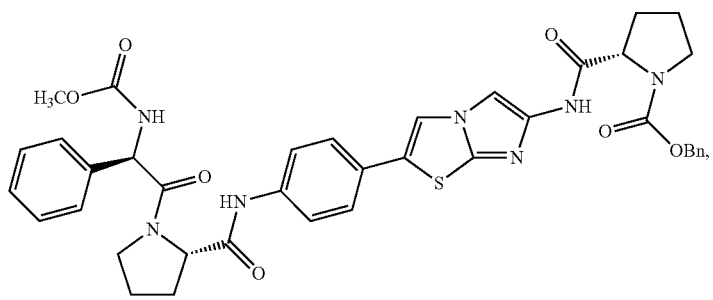
A81
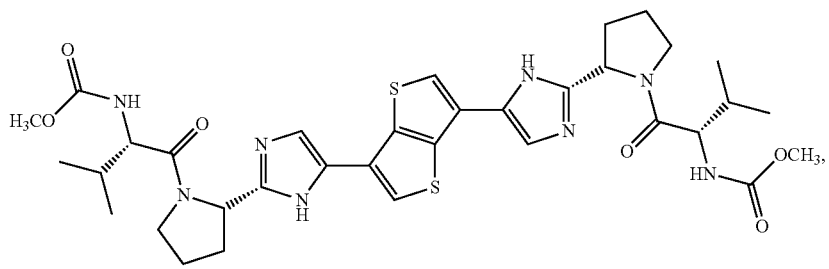
A82
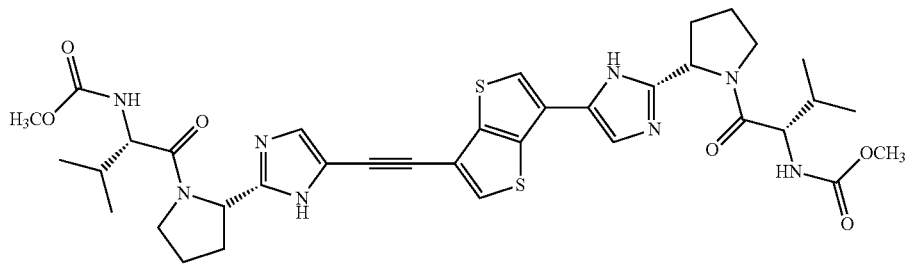
A83
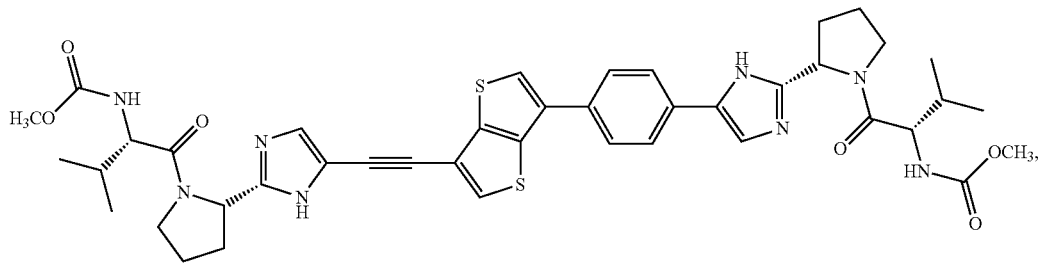
A84

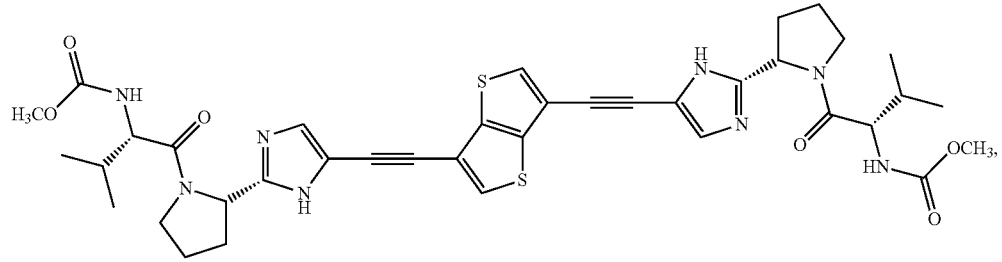
A85
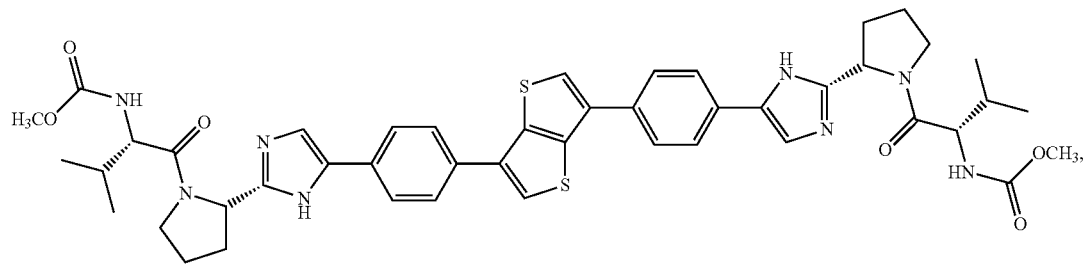
A86
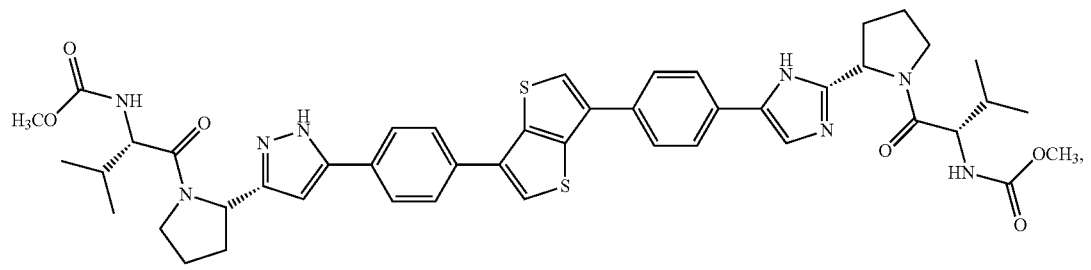
A87
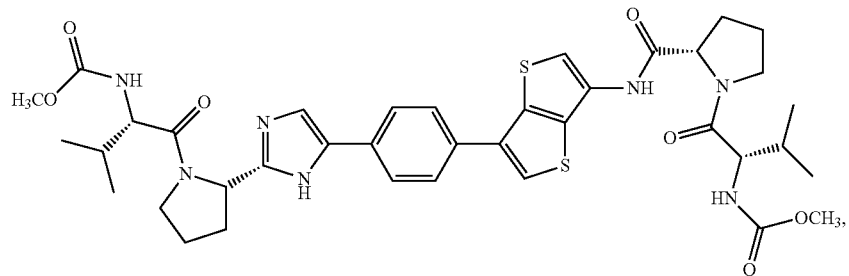
A88
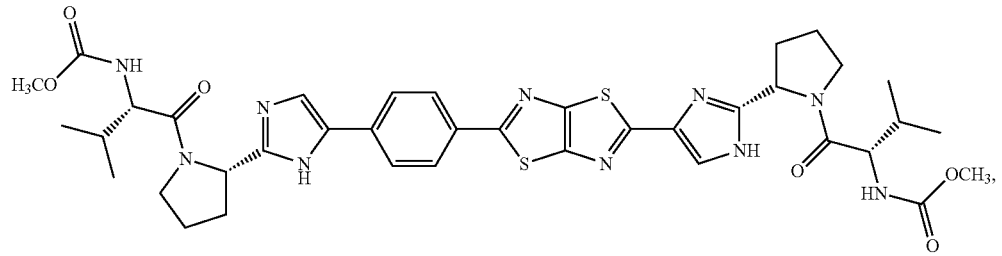
A89
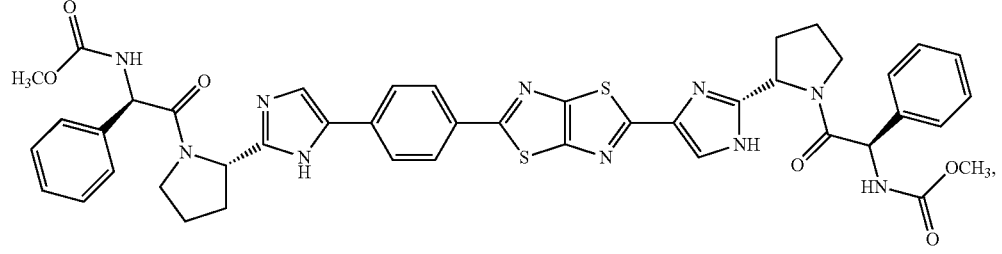
A90

-continued
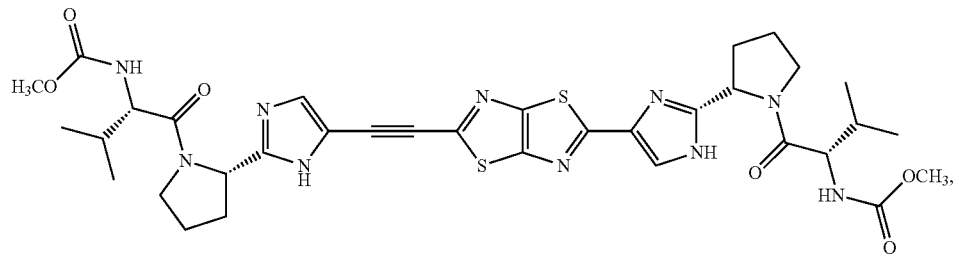
A91
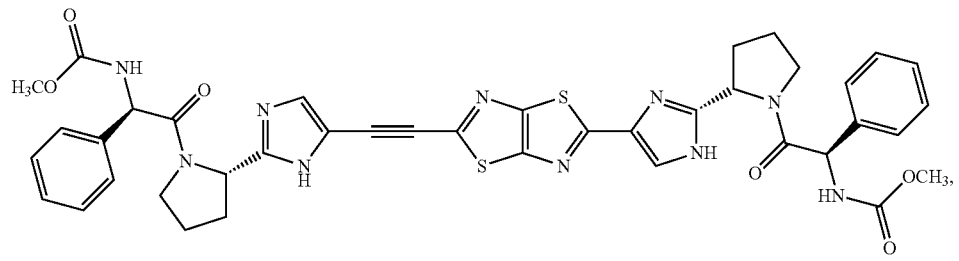
A92
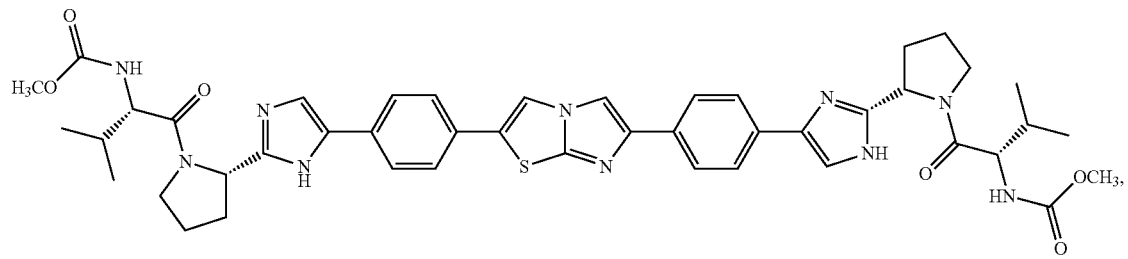
A93
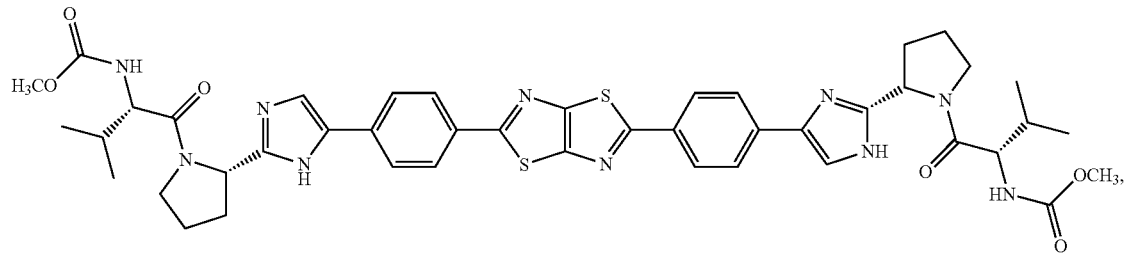
A94
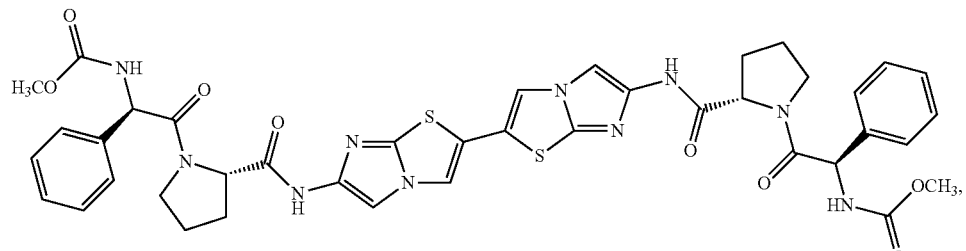
A95
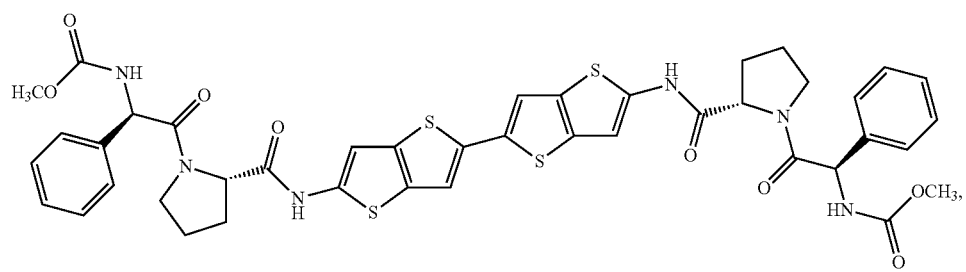
A96

-continued
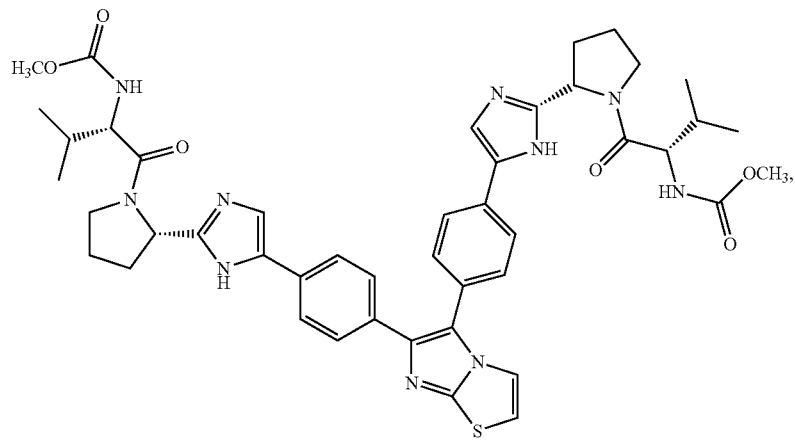
A97
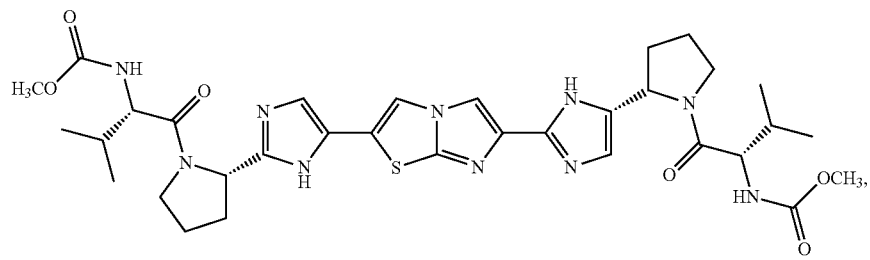
A98
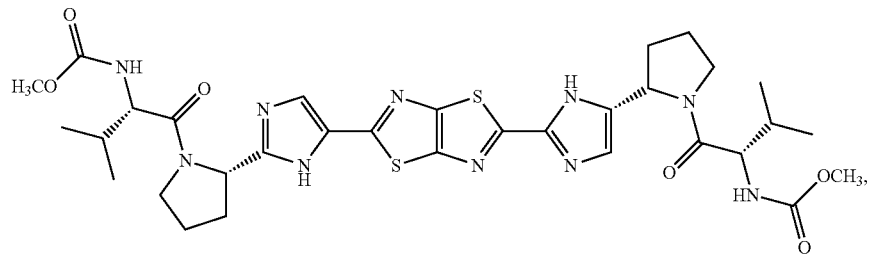
A99
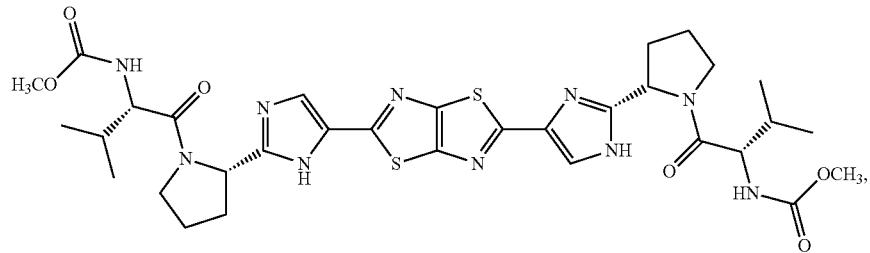
A100
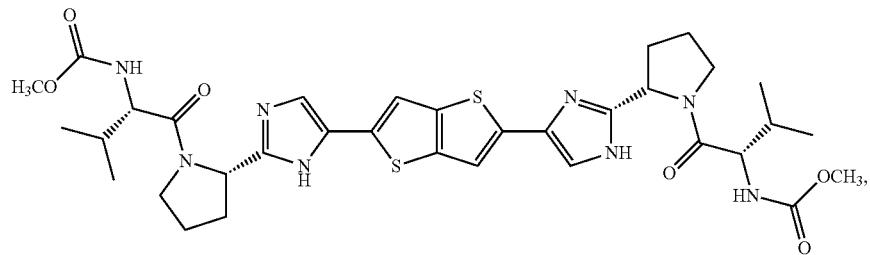
A101

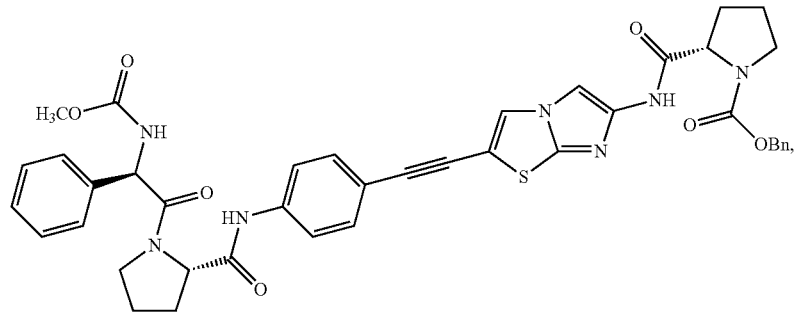
A102
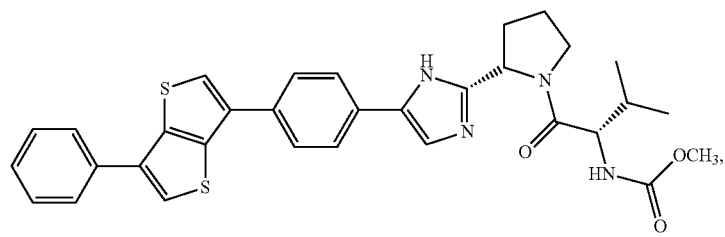
A103
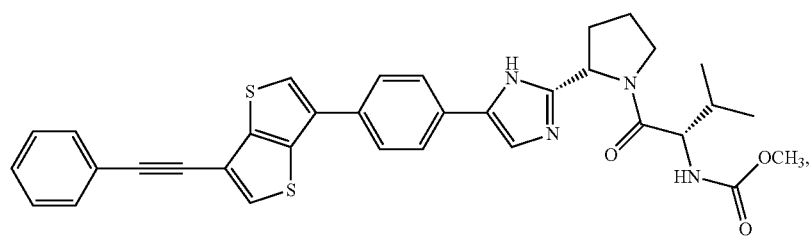
A104
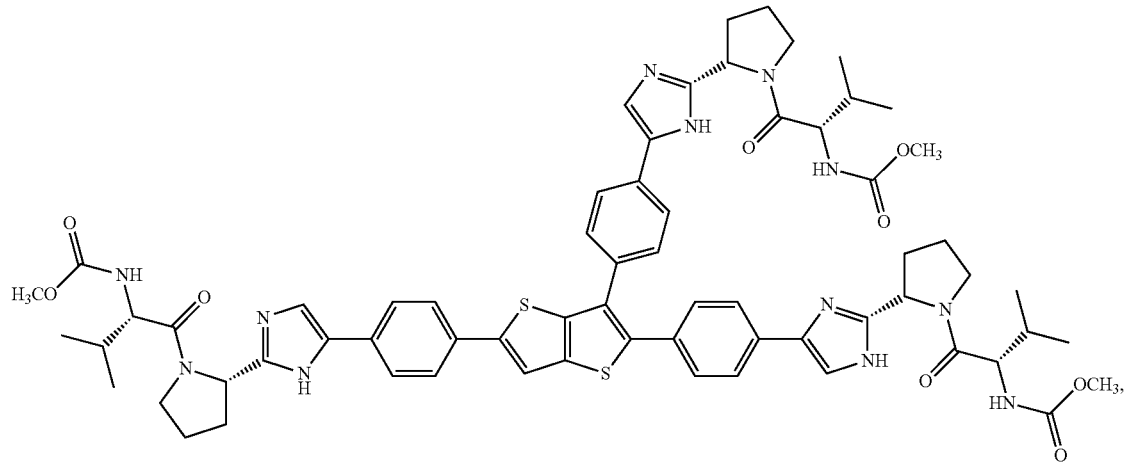
A105
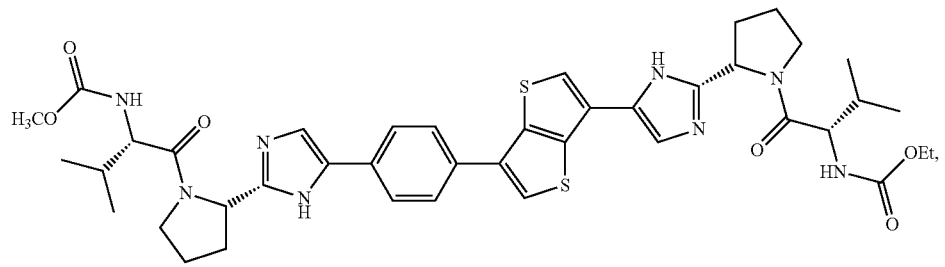
A106

-continued
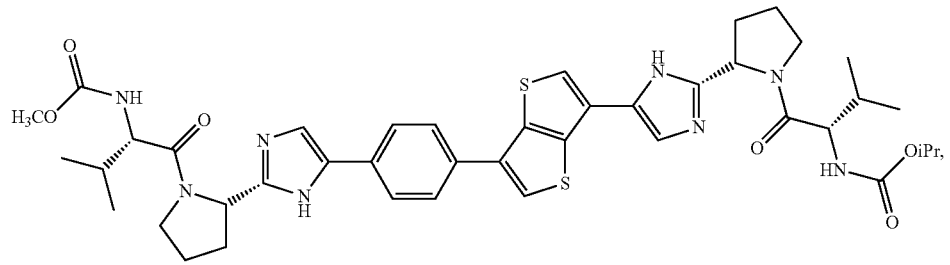
A107
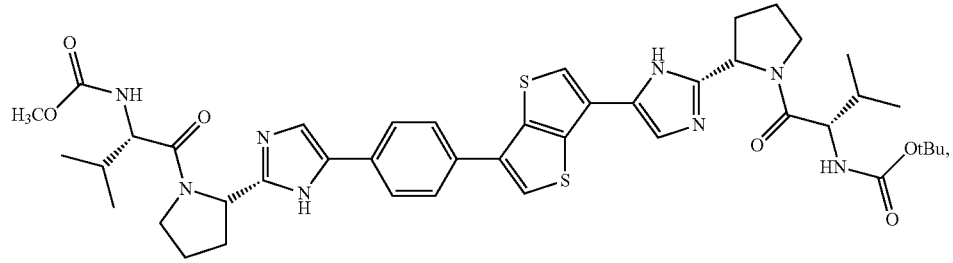
A108
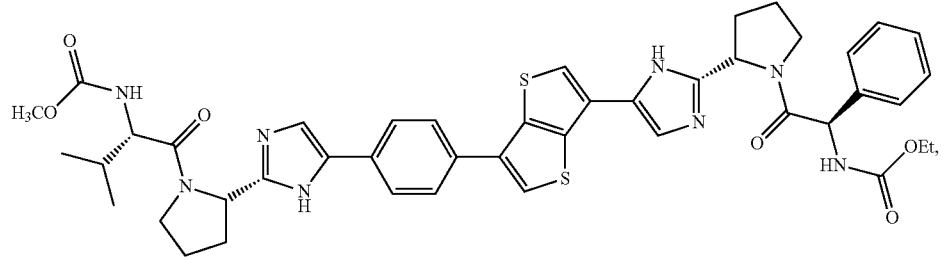
A109
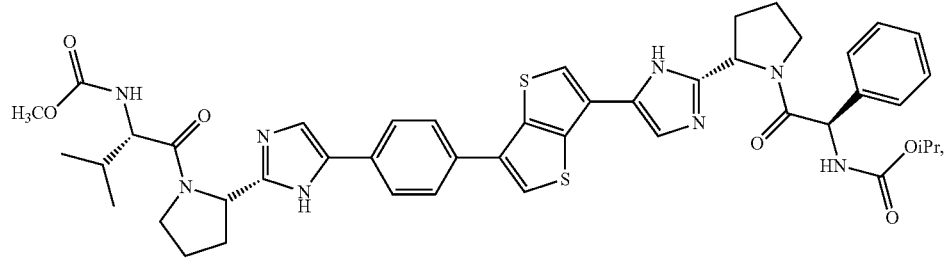
A110
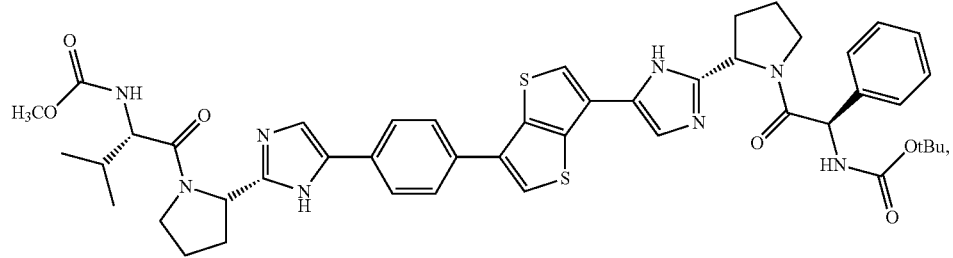
A111
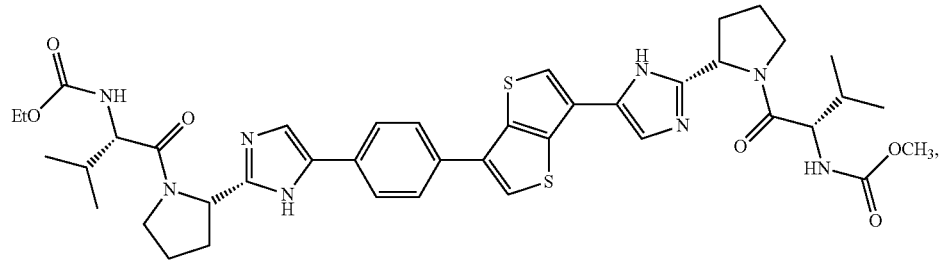
A112

-continued
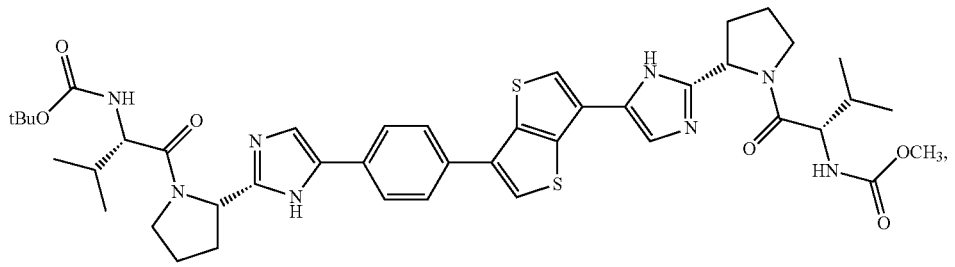
A113
A114
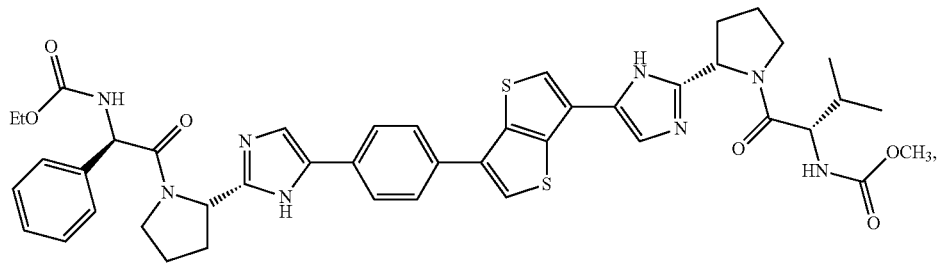
A115
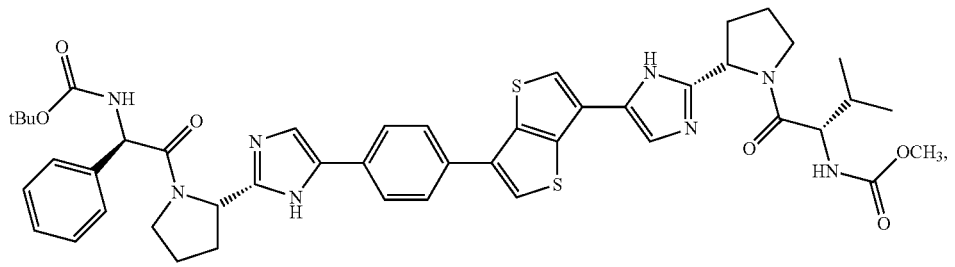
A116
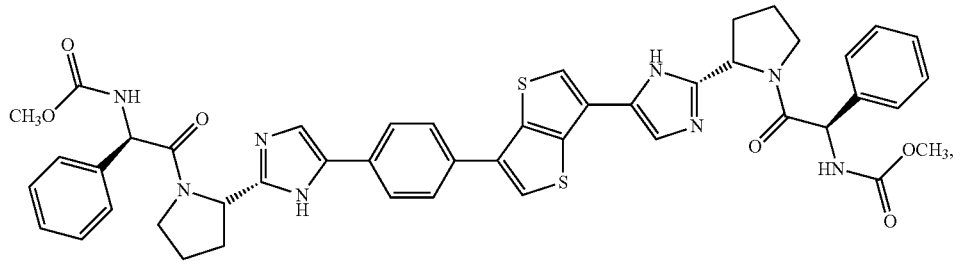
A117
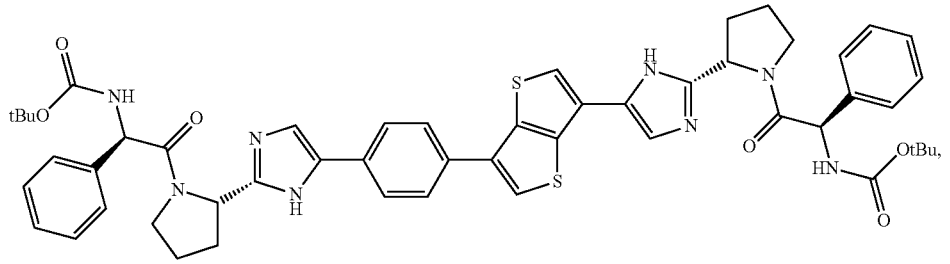
A118

-continued
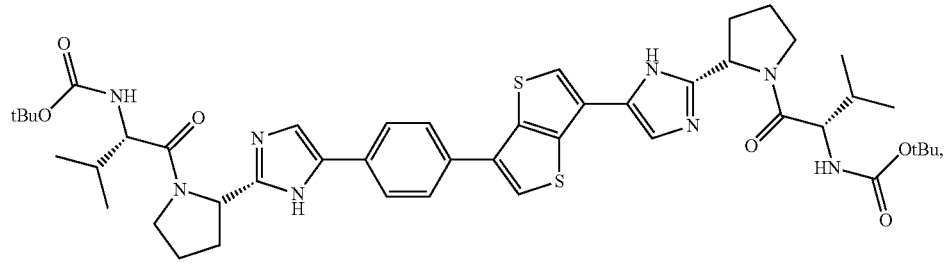
A119
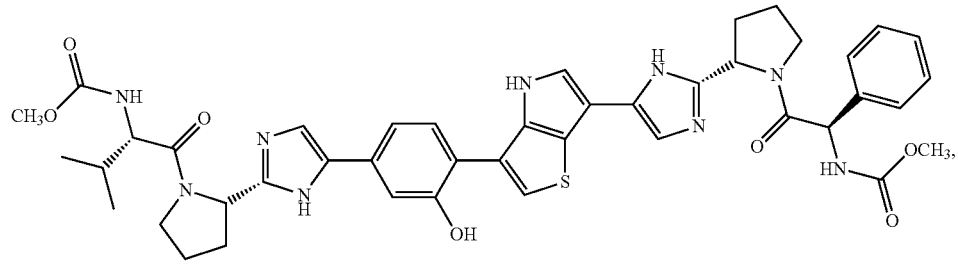
A120
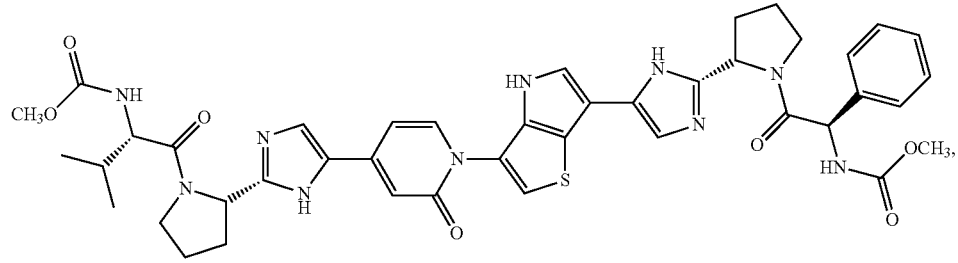
A121
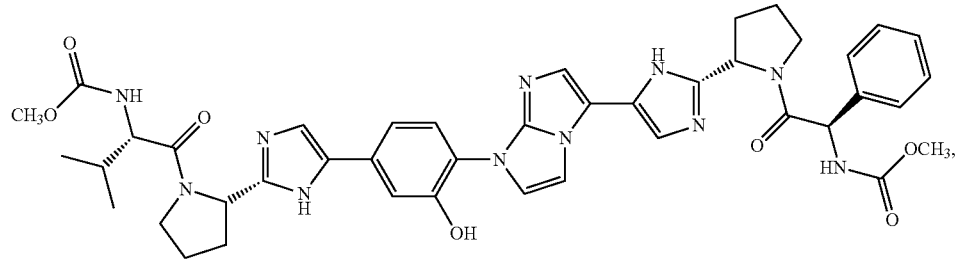
A122
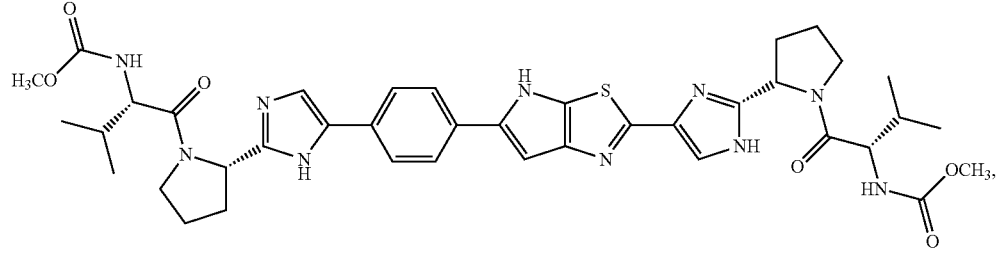
A123
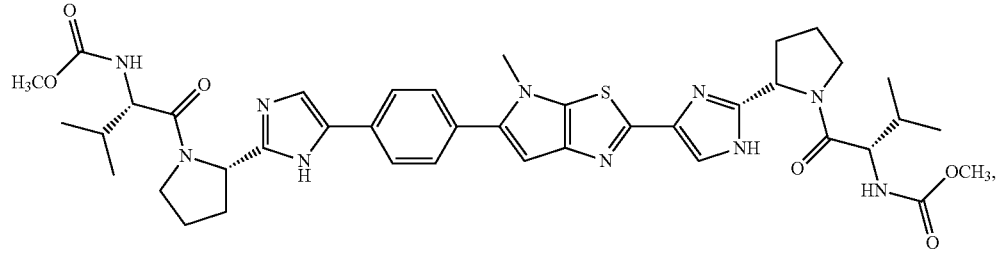
A124

-continued
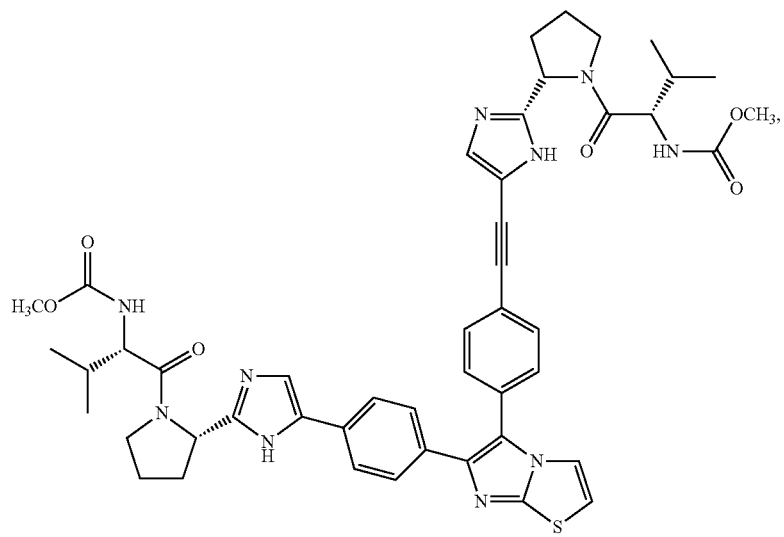
A125
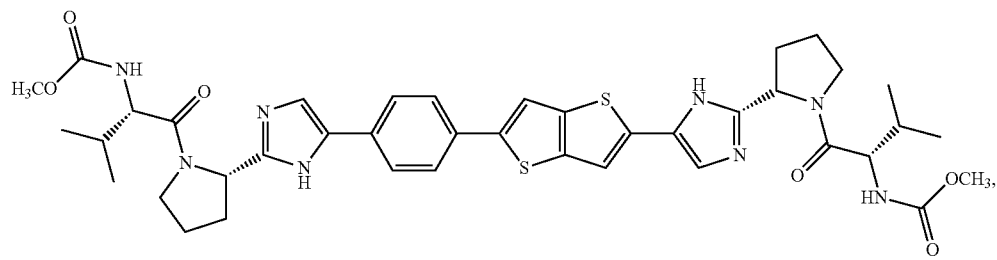
A126
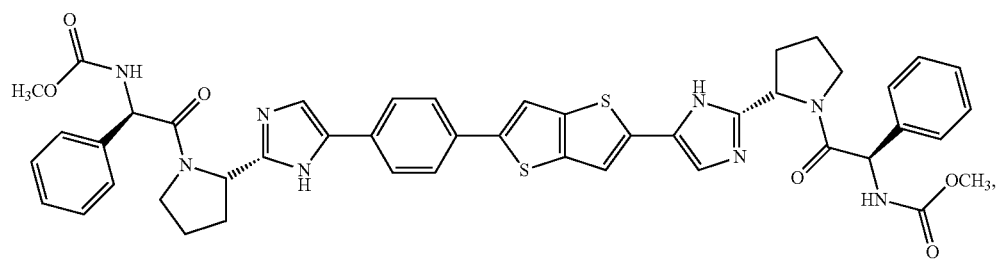
A127
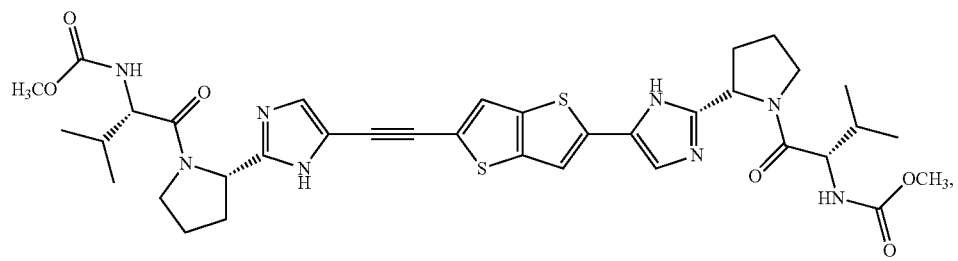
A128
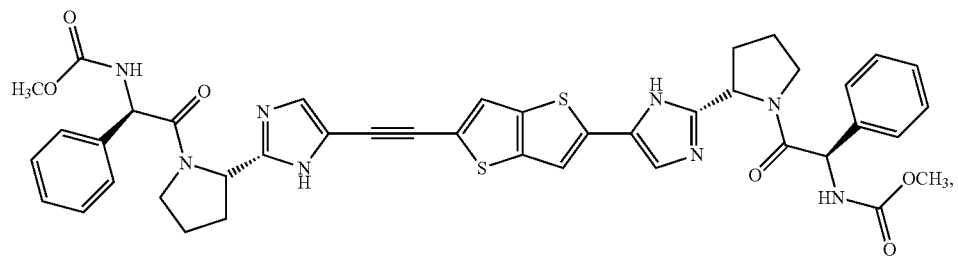
A129

-continued
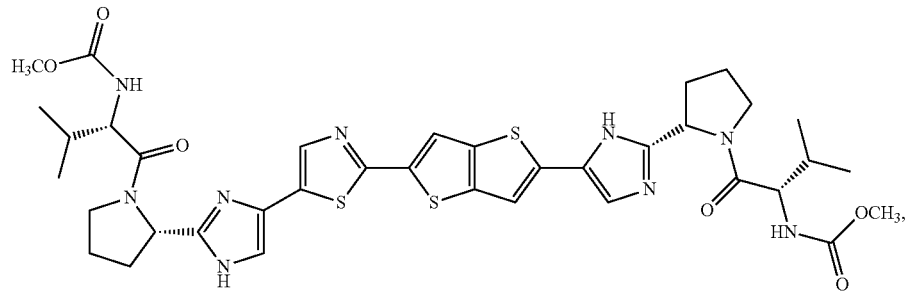
A130
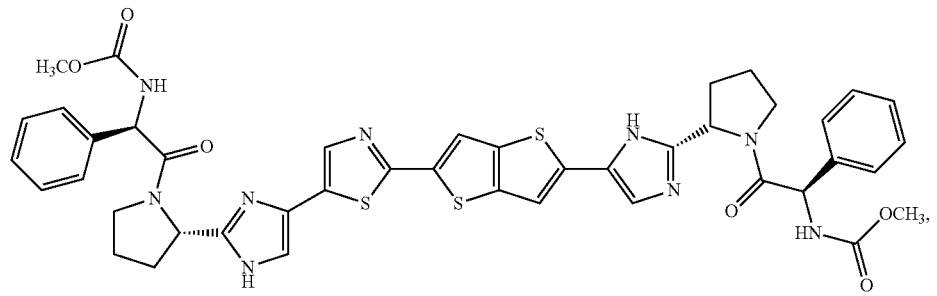
A131
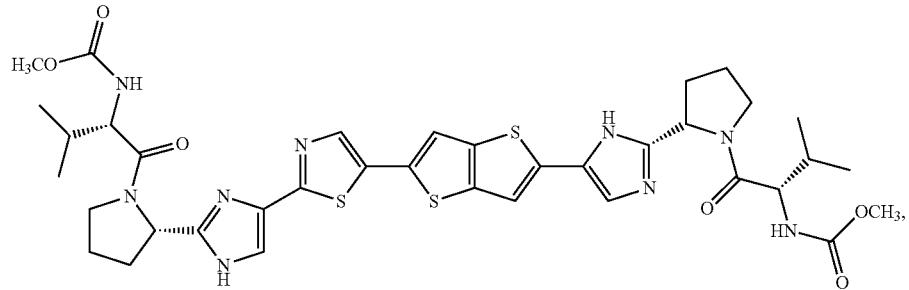
A132
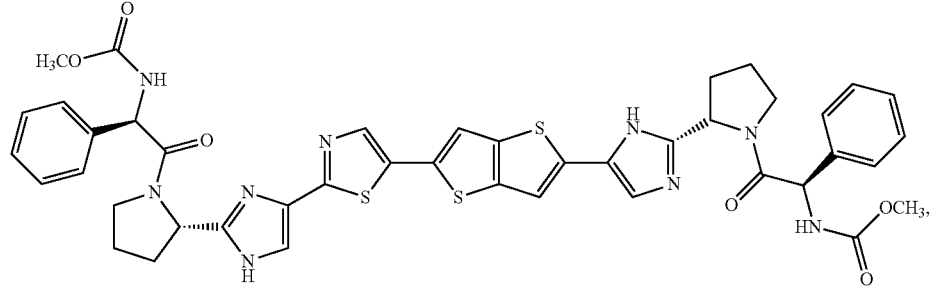
A133
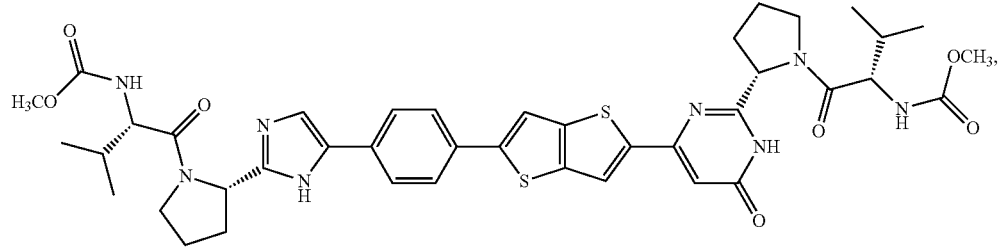
A134

-continued
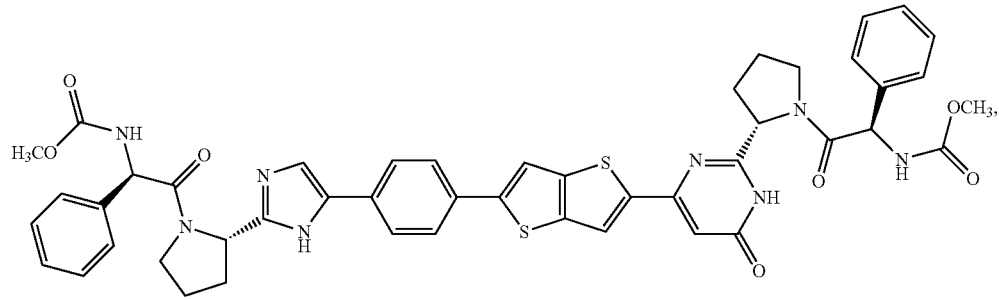
A135
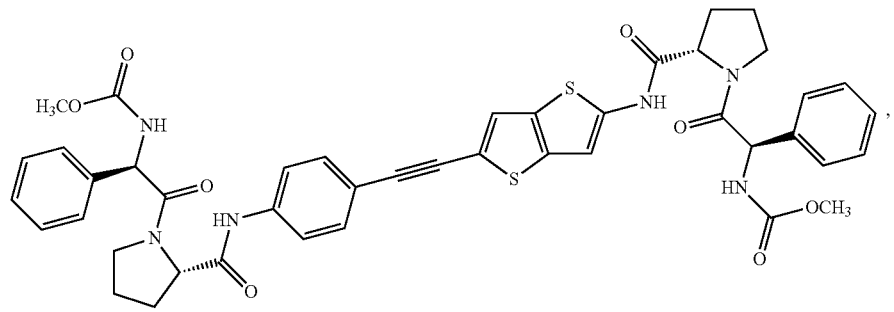
A136
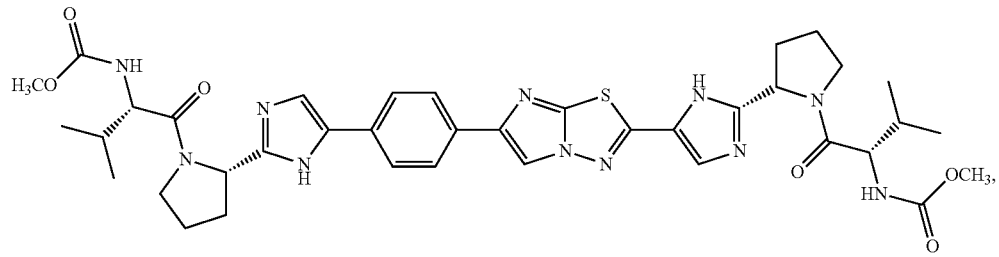
A137
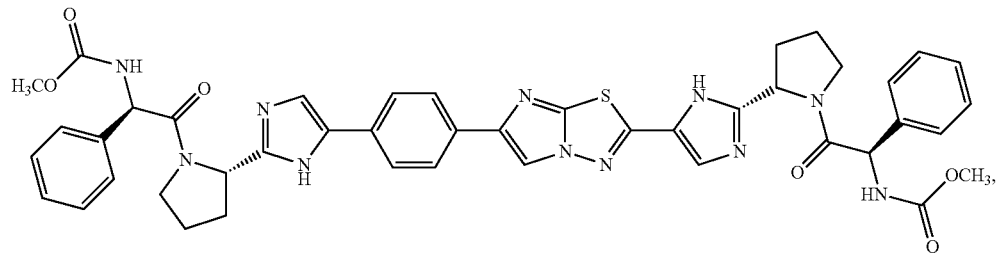
A138
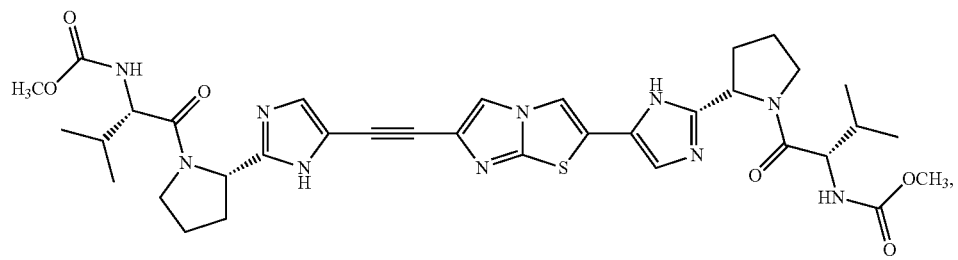
A139

-continued
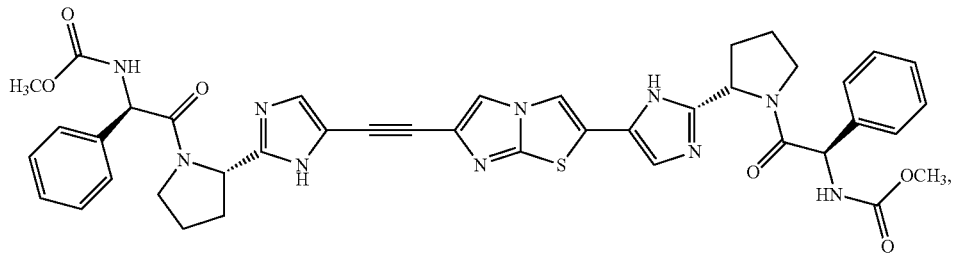
A140
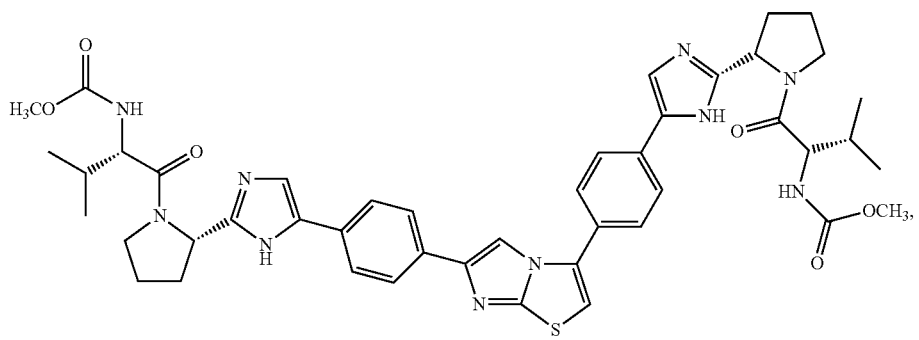
A141
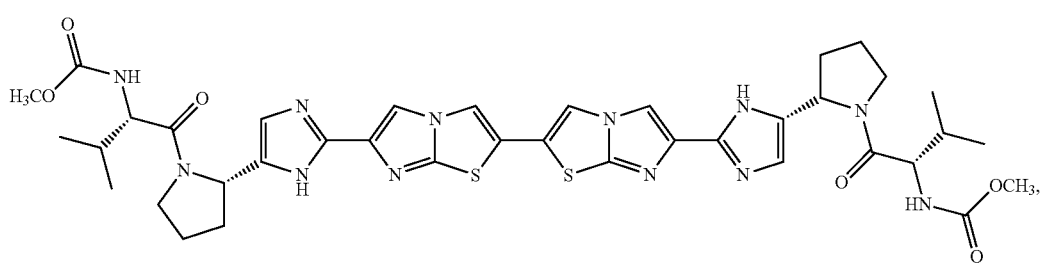
A142
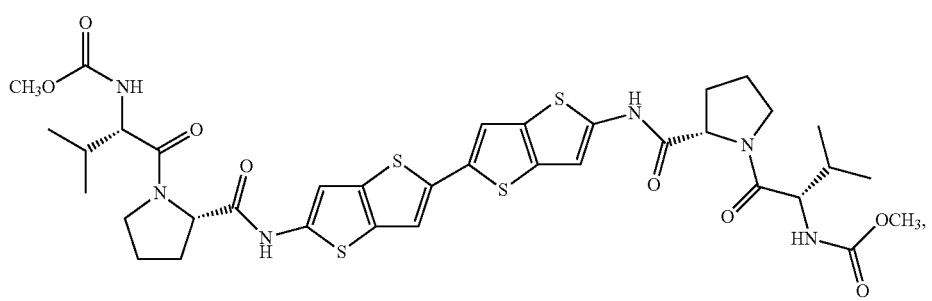
A143
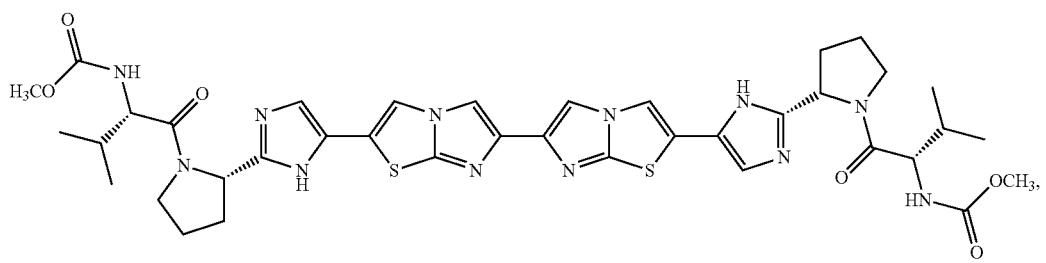
A144

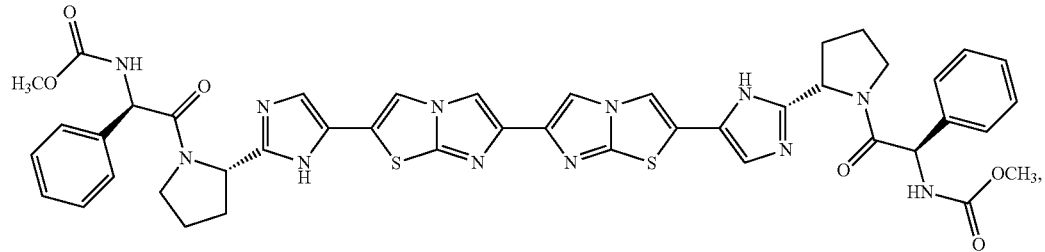
A145
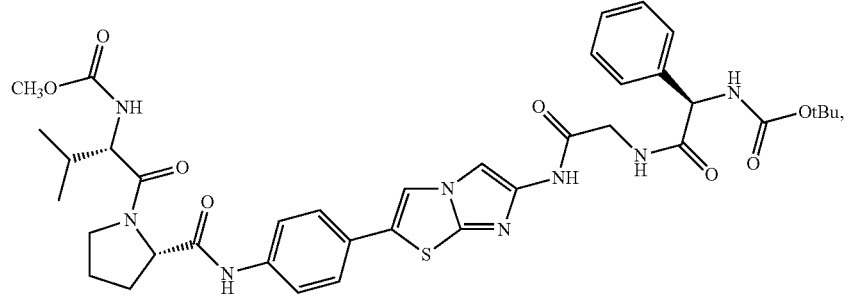
A146
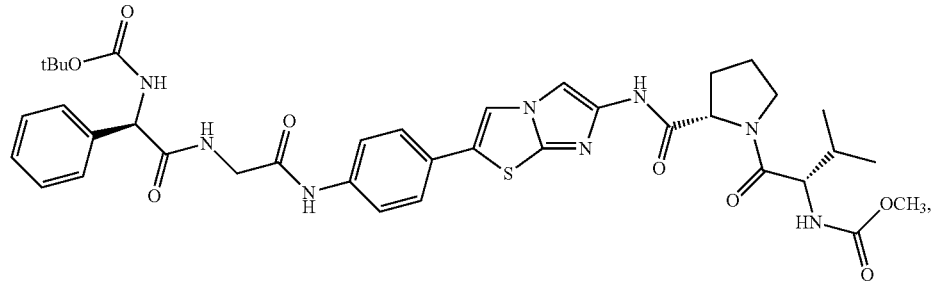
A147
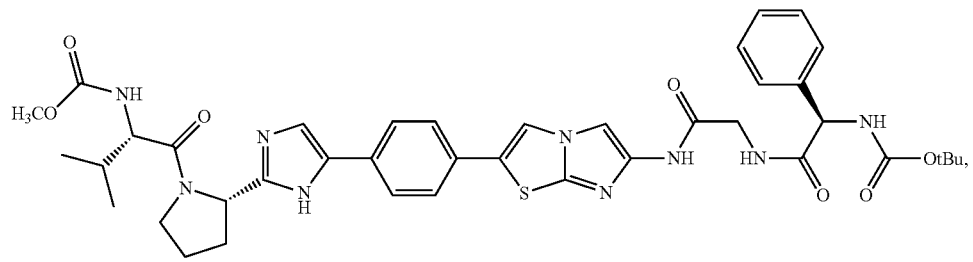
A148
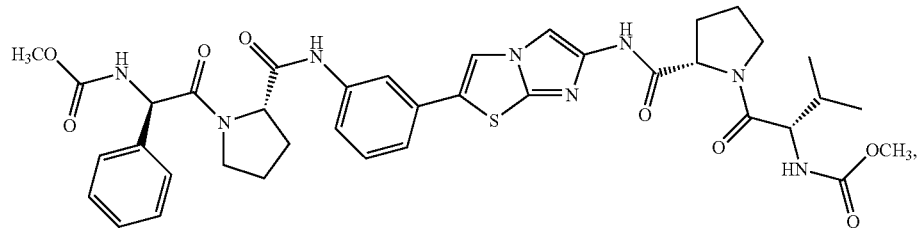
A149
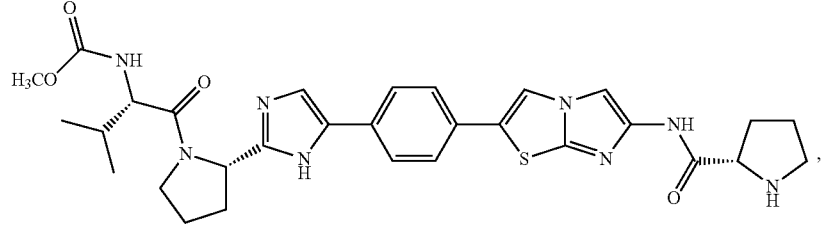
A150

-continued
A151
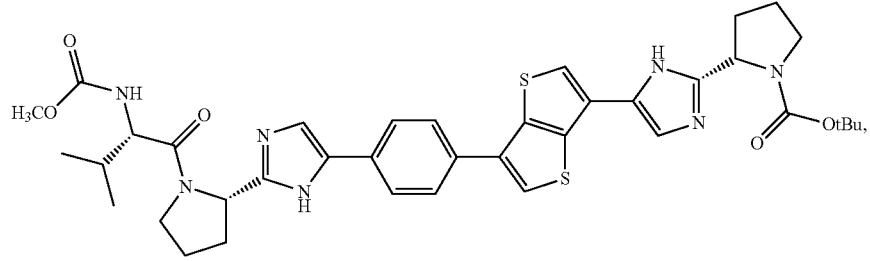
A152
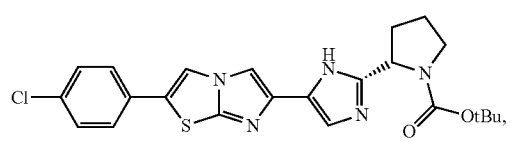
A153
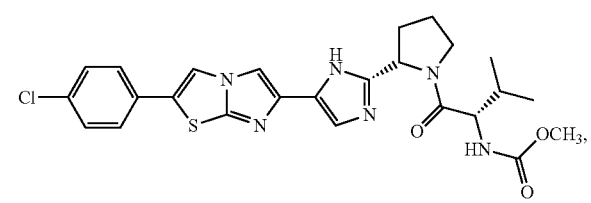
A154
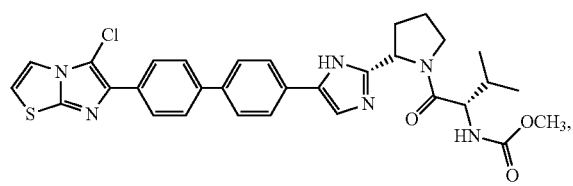
A155
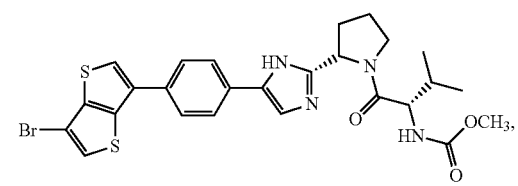
A156
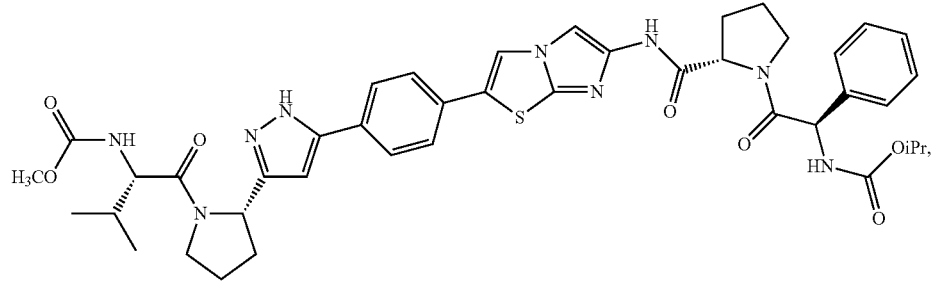
A157
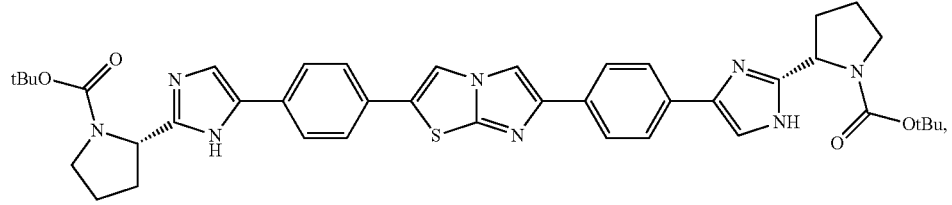
A158
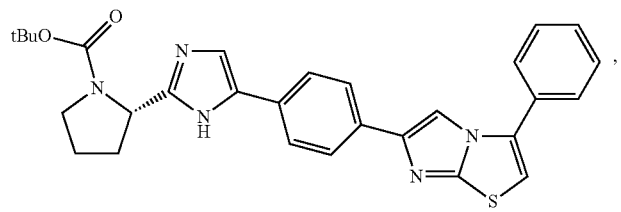

-continued
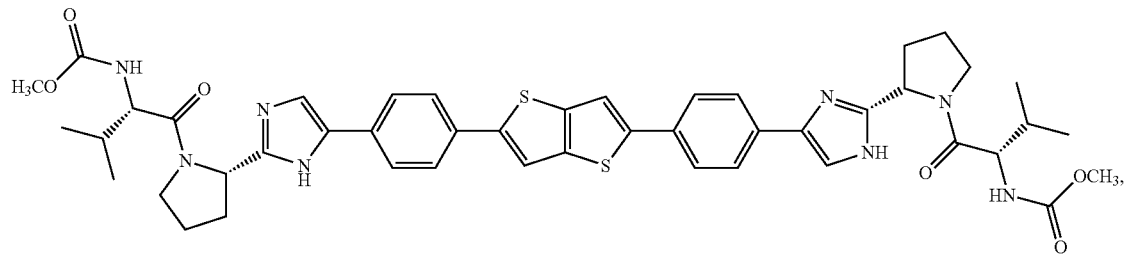
A159
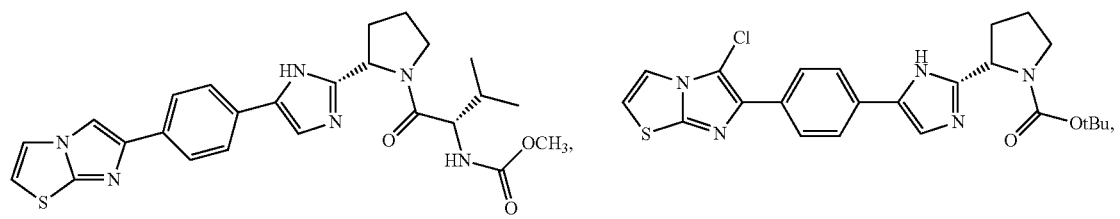
A160
A161
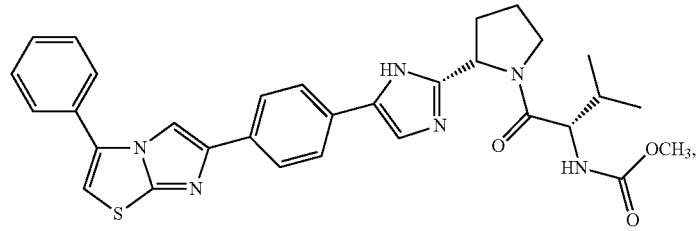
A162
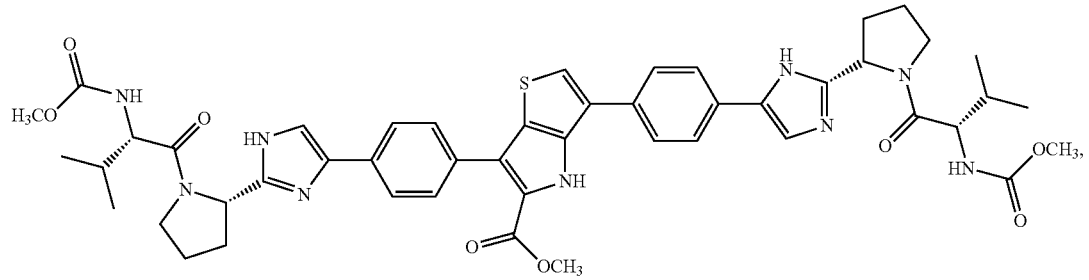
A163
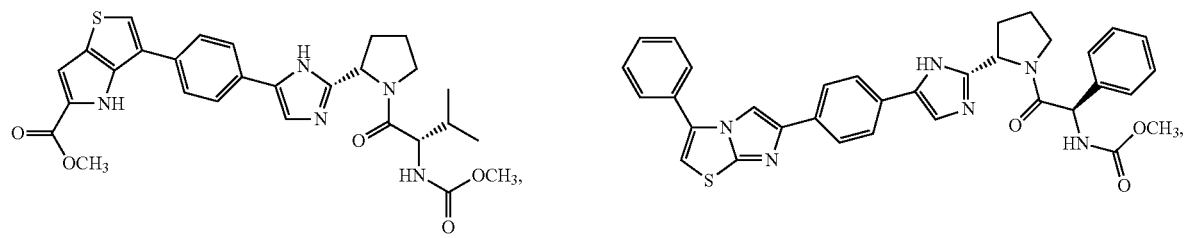
A164
A165
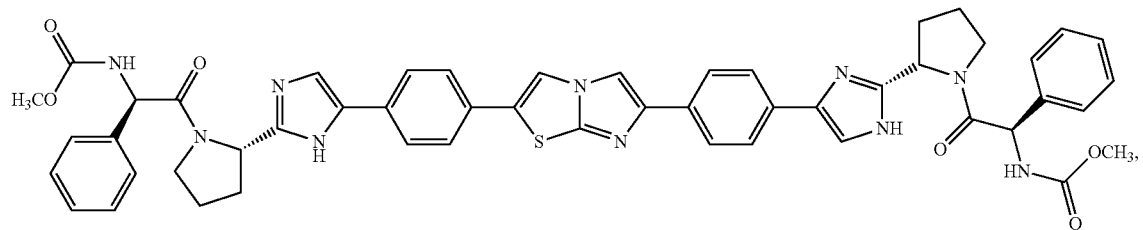
A166

A167
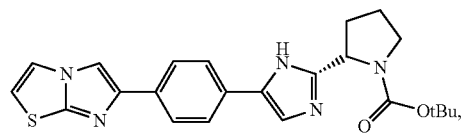
A168
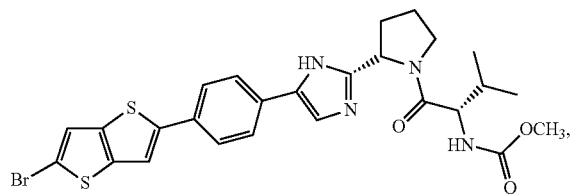
A169
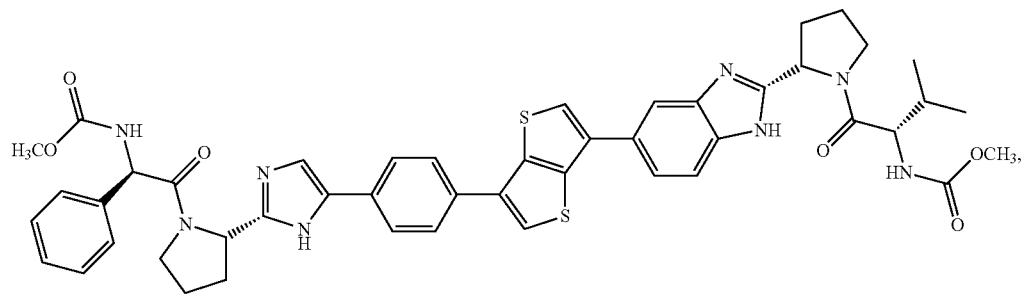
A170
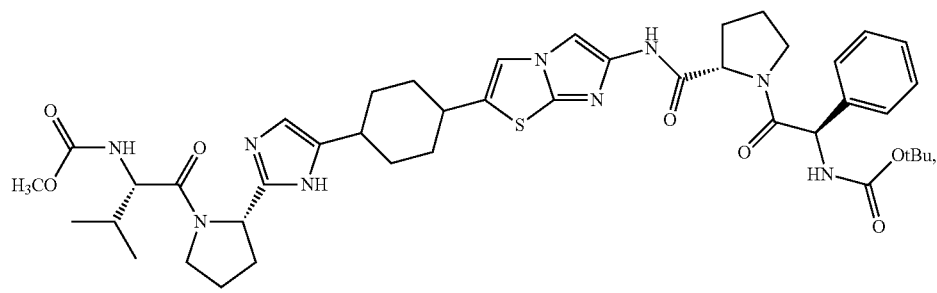
A171
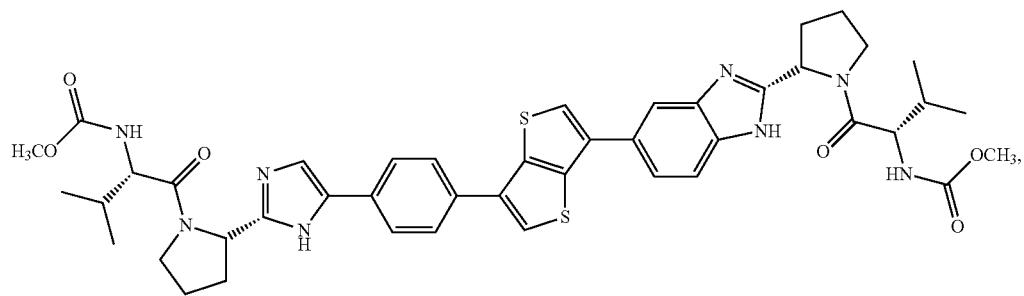
A172
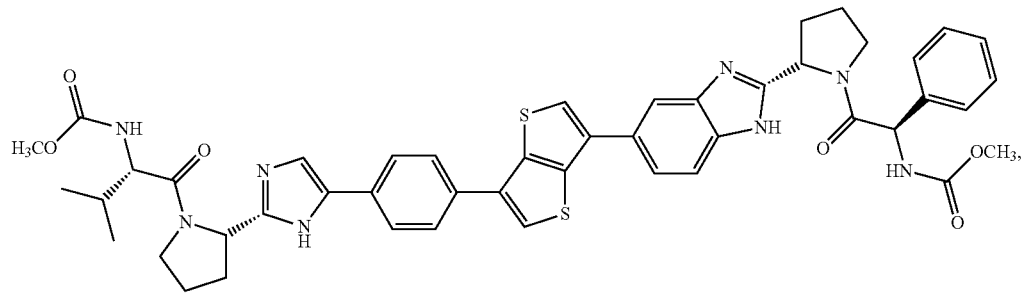

-continued
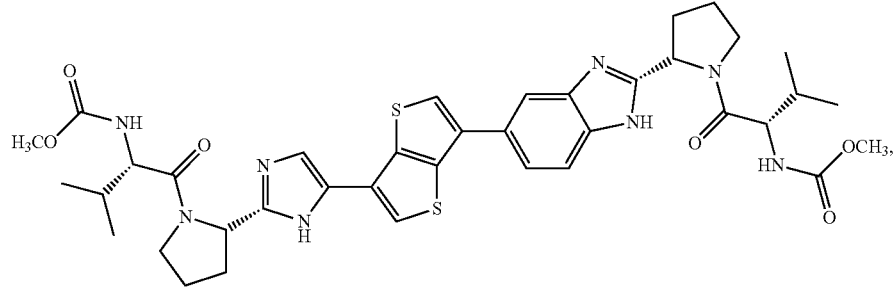
A173
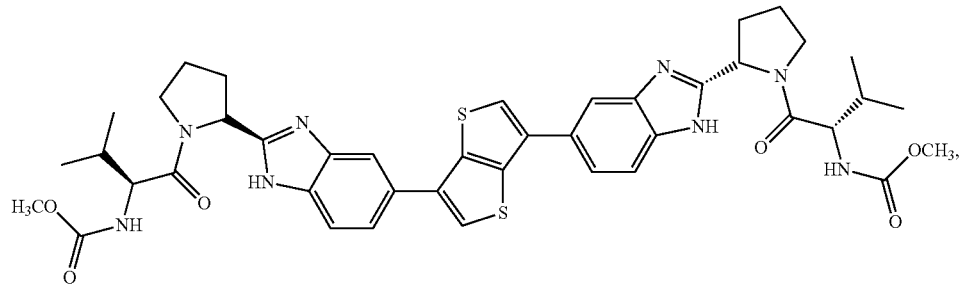
A174
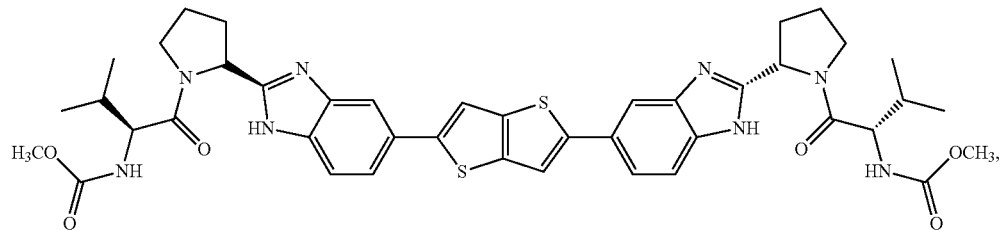
A175
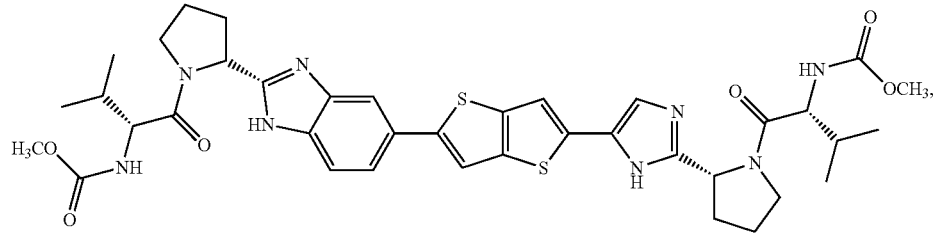
A176
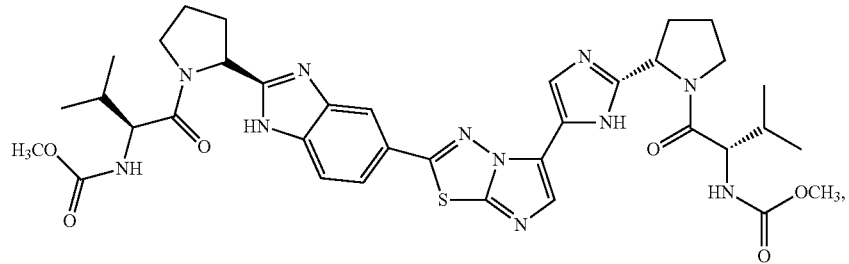
A177
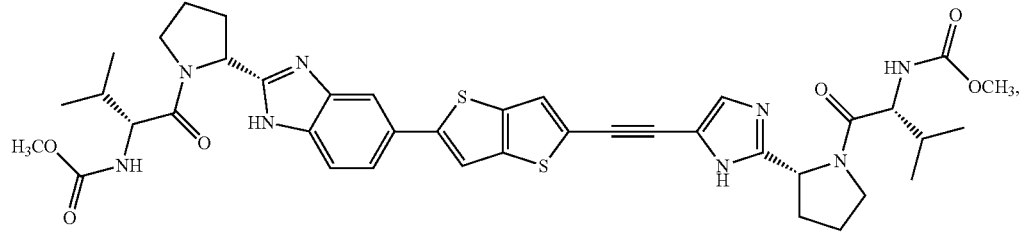
A178

-continued
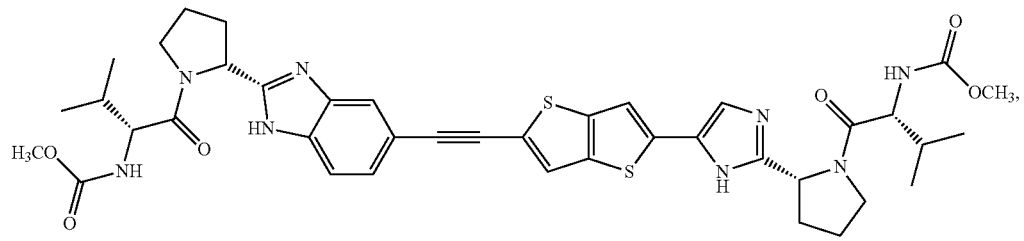
A179
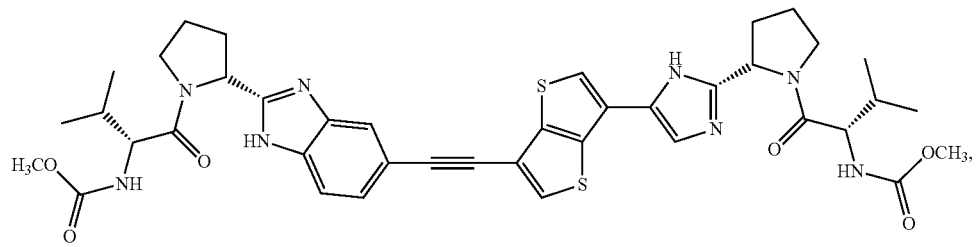
A180
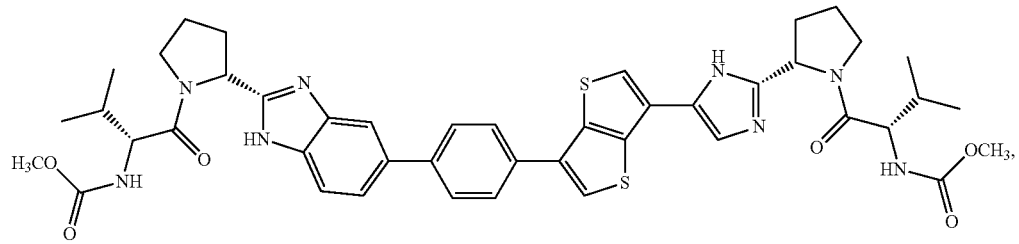
A181
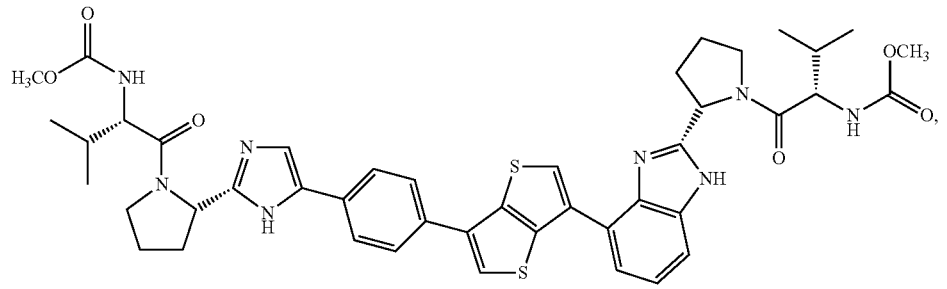
A182
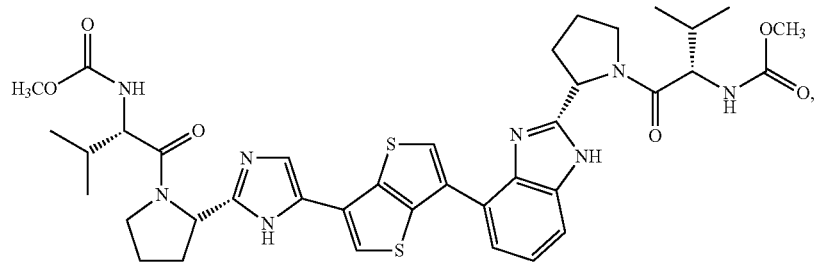
A183
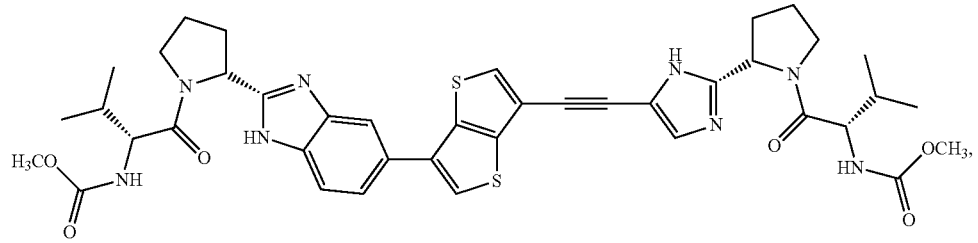
A184

A185
A186
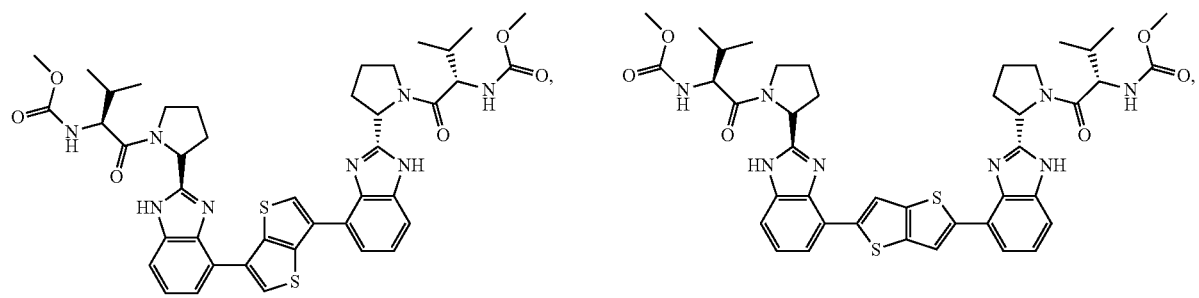
A187
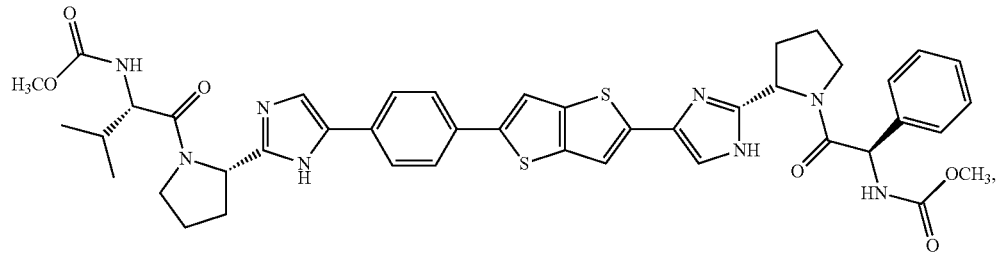
A188
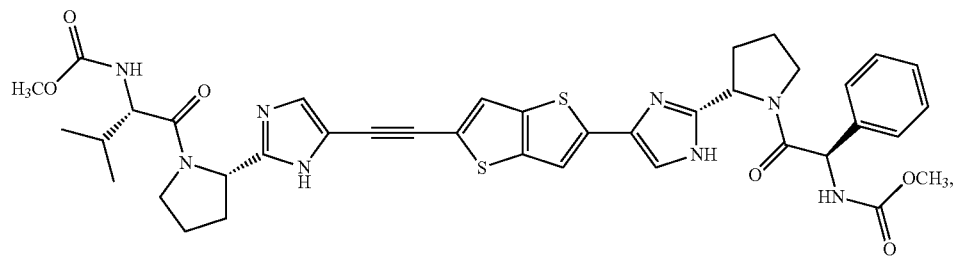
A189
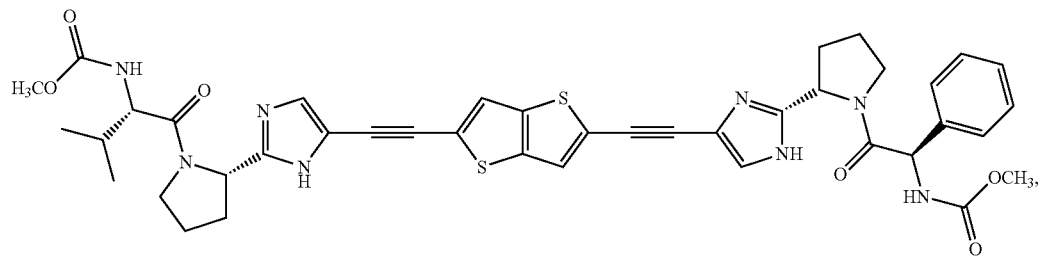
A190
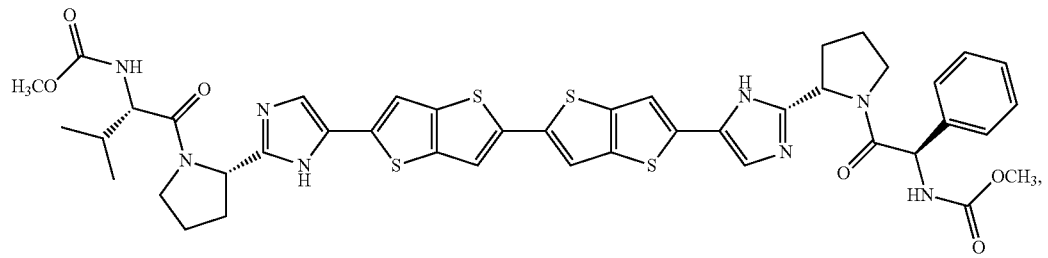
A191
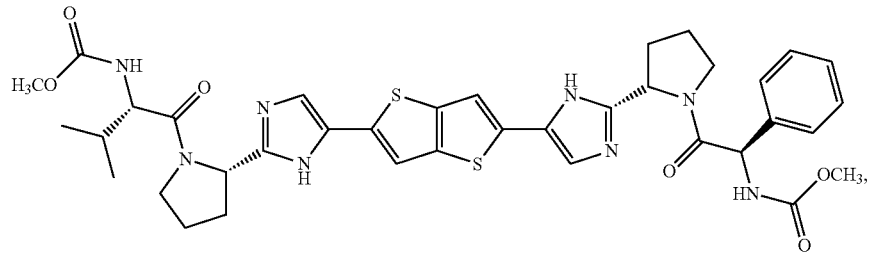

-continued
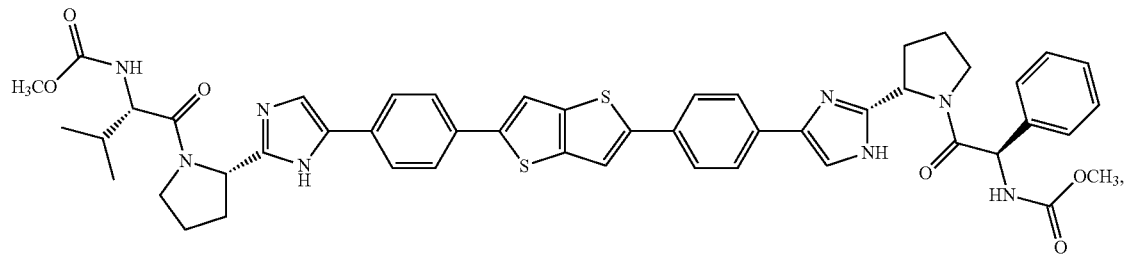
A192
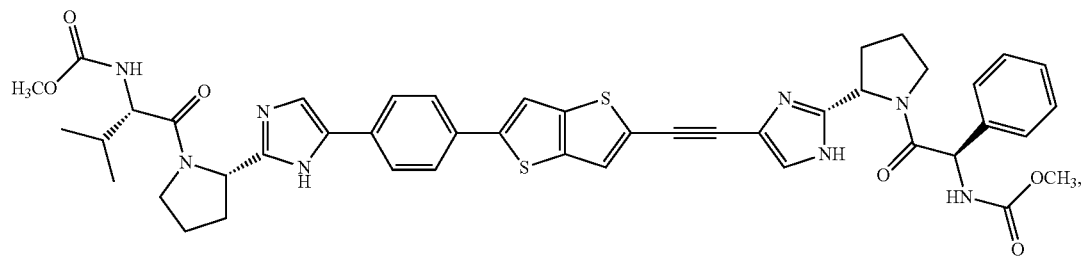
A193
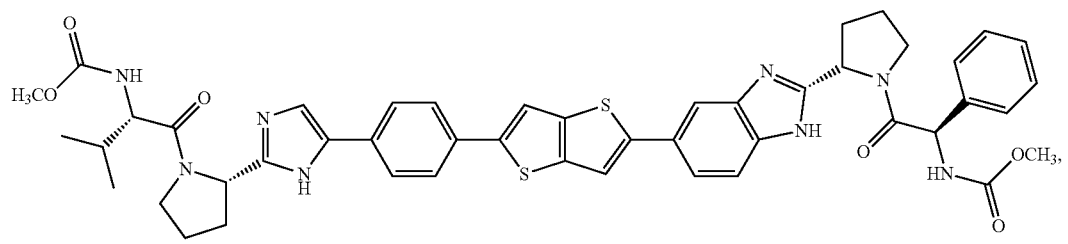
A194
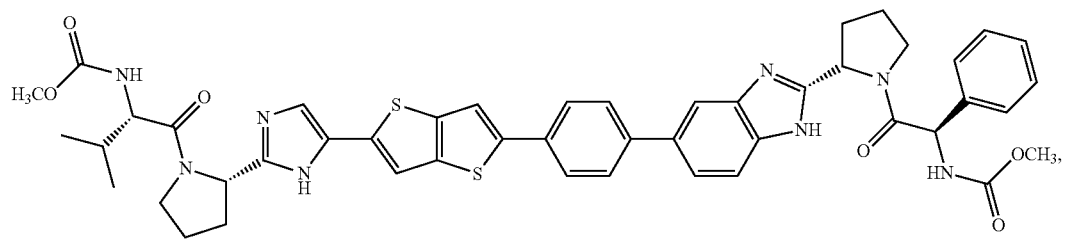
A195
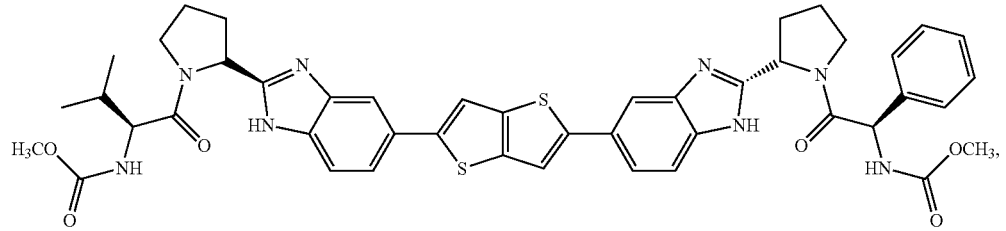
A196
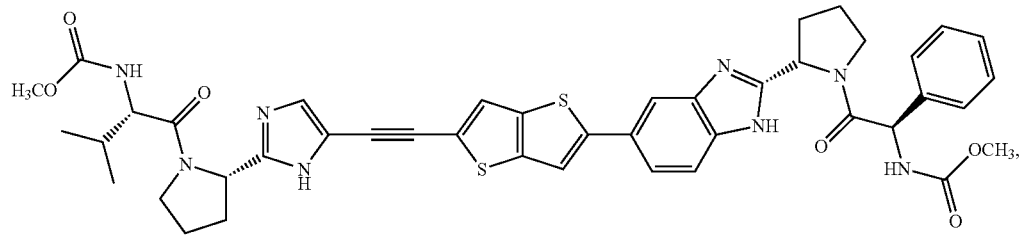
A197

-continued
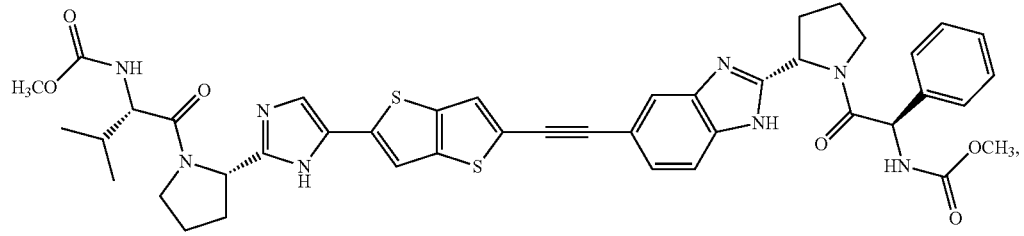
A198
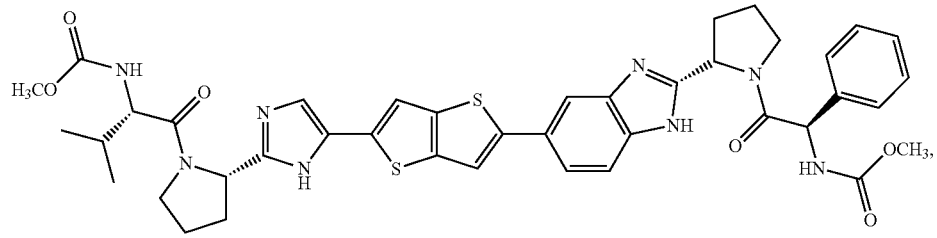
A199
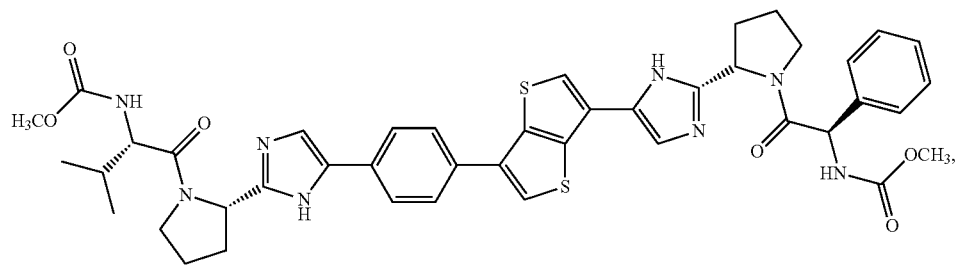
A200
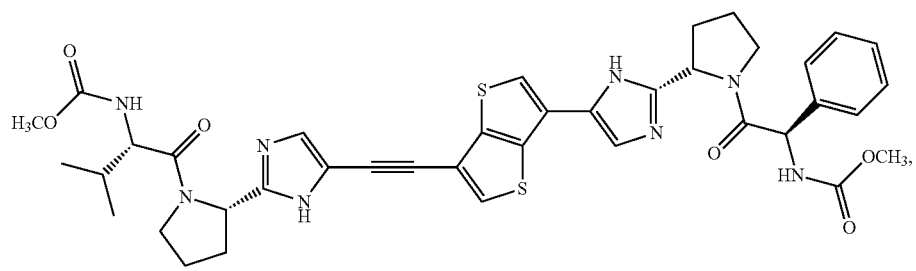
A201
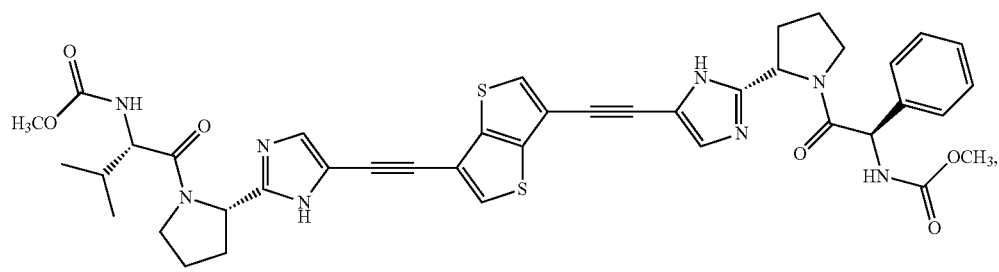
A202
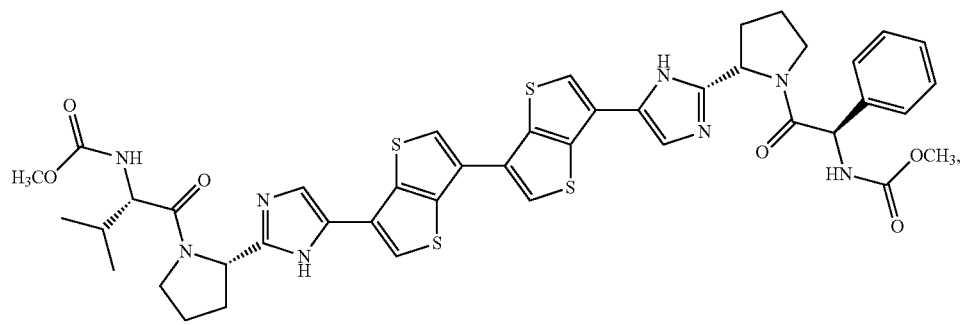
A203

-continued
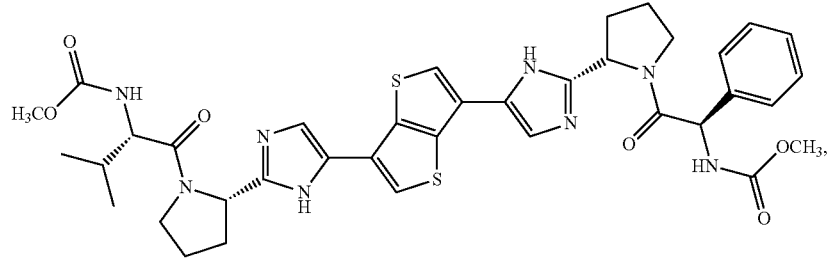
A204
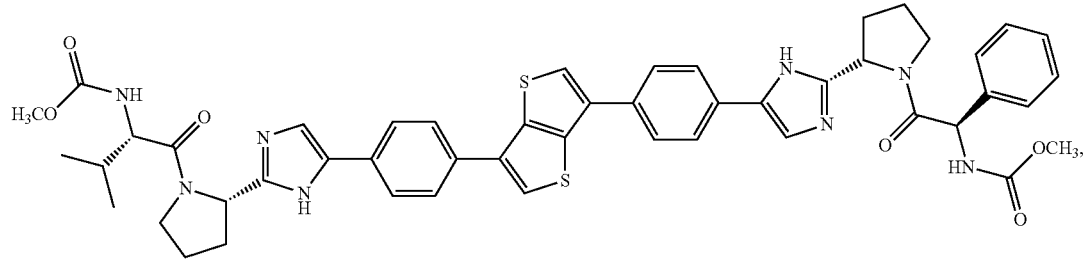
A205
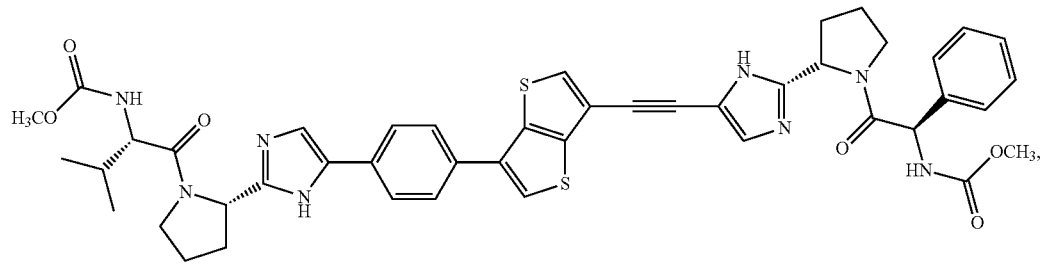
A206
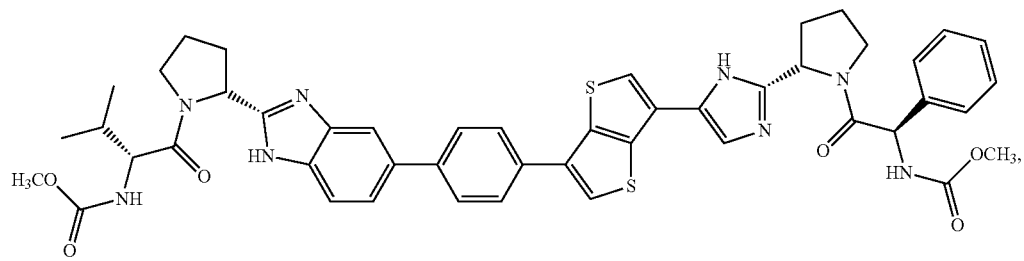
A207
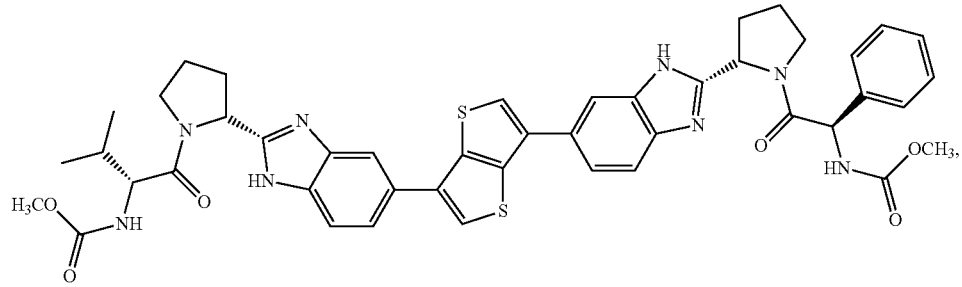
A208
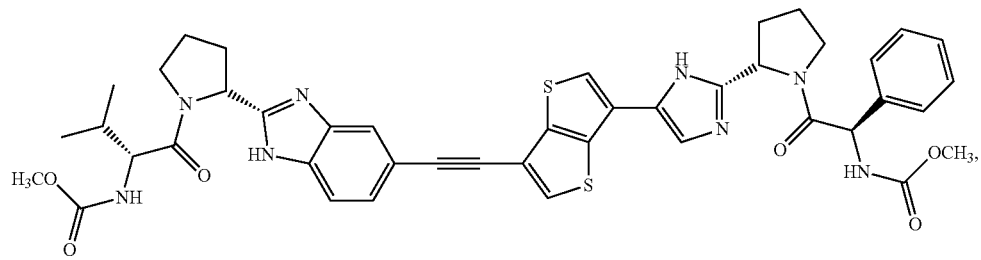
A209

-continued
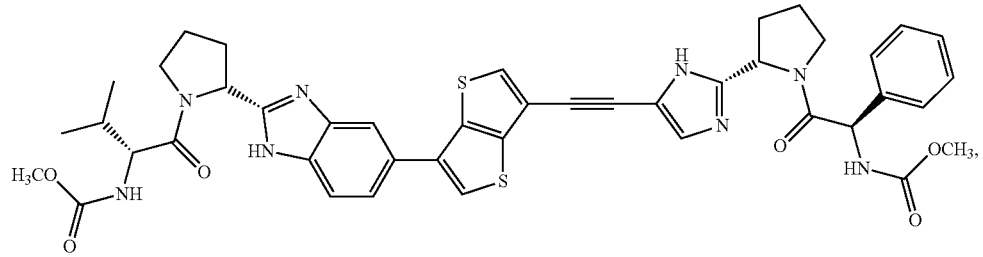
A210
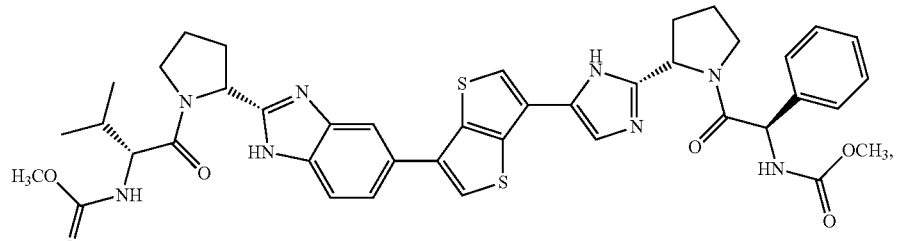
A211
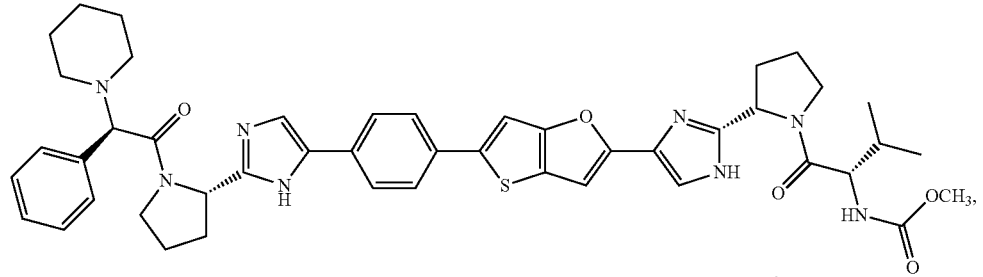
A212
A213
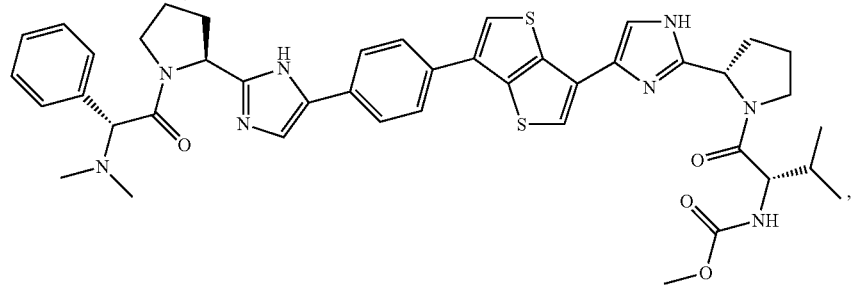
A214
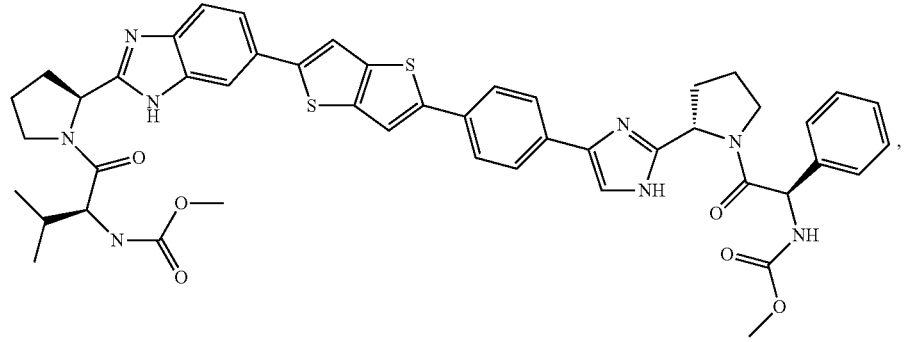
A215

-continued

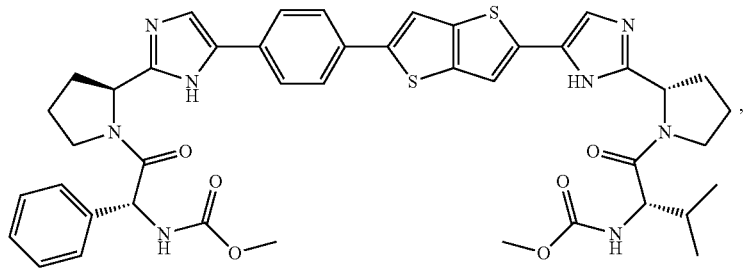

A216

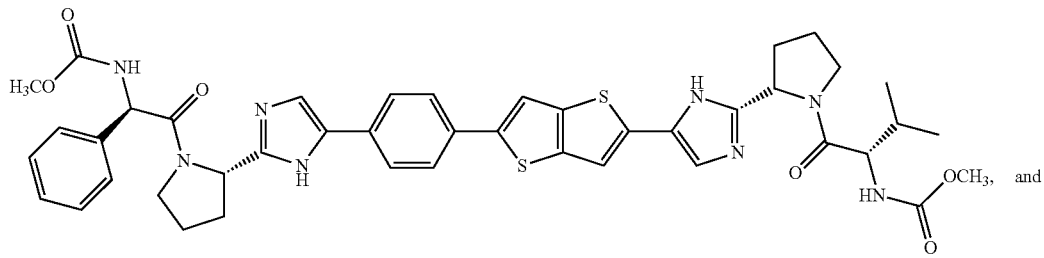

A217

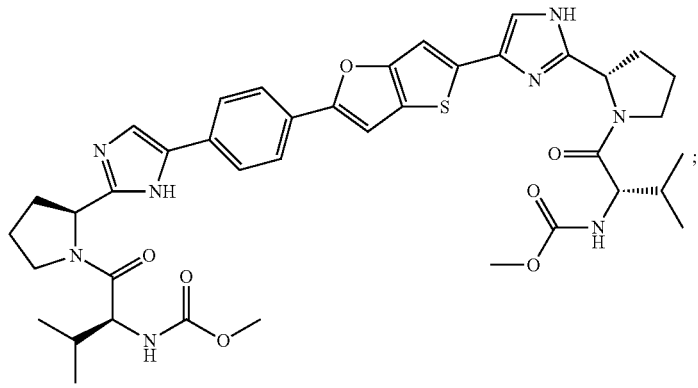

A218 and isotopic variants thereof; and pharmaceutically acceptable salts, solvates, and prodrugs thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

For example, the heterocyclic moieties,

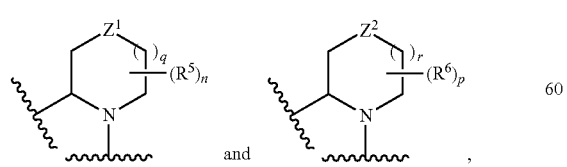

each contain at least one chiral center as indicated by star symbols. As result, the heterocyclic moiety may exist in at least two different stereoisomeric forms as shown below.

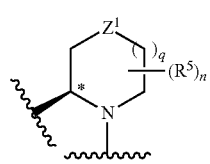 (i)

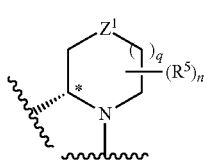 (ii)

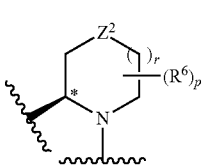 (iii)

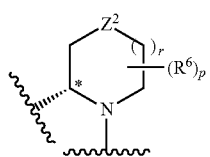

(iv)

In certain embodiments, the heterocyclic moiety

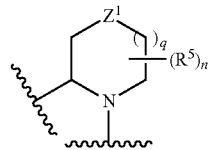

is in configuration (i) or (ii). In certain embodiments, the heterocyclic moiety

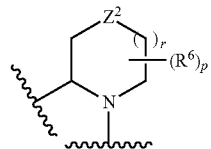

is in configuration (iii) or (iv).

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt. See, Berge et al., *J. Pharm. Sci.* 1977, 66, 1-19; and *Handbook of Pharmaceutical Salts, Properties, and Use*; Stahl and Wermuth, Ed.; Wiley-VCH and VHCA: Zurich, Switzerland, 2002.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, IA, or IB and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, Harper, *Progress in Drug Research* 1962, 4, 221-294; Morozowich et al. in *Design of Biopharmaceutical Properties through Prodrugs and Analogs*; Roche Ed., APHA Acad. Pharm. Sci.: 1977; Gangwar et al., *Des. Biopharm. Prop. Prodrugs Analogs*, 1977, 409-421; Bundgaard, *Arch. Pharm. Chem.* 1979, 86, 1-39; Farquhar et al., *J. Pharm. Sci.* 1983, 72, 324-325; Wernuth in *Drug Design: Fact or Fantasy*; Jolles et al. Eds.; Academic Press: London, 1984; pp 47-72; *Design of Prodrugs; Bundgaard et al. Eds.; Elsevier:* 1985; Fleisher et al., *Methods Enzymol.* 1985, 112, 360-381; Stella et al., *Drugs* 1985, 29, 455-473; *Bioreversible Carriers in Drug in Drug Design, Theory and Application*; Roche Ed.; APHA Acad. Pharm. Sci.: 1987; Bundgaard, *Controlled Drug Delivery* 1987, 17, 179-96; Waller et al., *Br. J. Clin. Pharmac.* 1989, 28, 497-507; Balant et al., *Eur. J. Drug Metab. Pharmacokinet.* 1990, 15, 143-53; Freeman et al., *J. Chem. Soc., Chem. Commun.* 1991, 875-877; Bundgaard, *Adv. Drug Delivery Rev.* 1992, 8, 1-38; Nathwani and Wood, *Drugs* 1993, 45, 866-94; Friis and Bundgaard, *Eur. J. Pharm. Sci.* 1996, 4, 49-59; Fleisher et al., *Adv. Drug Delivery Rev.* 1996, 19, 115-130; Sinhababu and Thakker, *Adv. Drug Delivery Rev.* 1996, 19, 241-273; Taylor, *Adv. Drug Delivery Rev.* 1996, 19, 131-148; Gaignault et al., *Pract. Med. Chem.* 1996, 671-696; Browne, *Clin. Neuropharmacol.* 1997, 20, 1-12; Valentino and Borchardt, *Drug Discovery Today* 1997, 2, 148-155; Pauletti et al., *Adv. Drug. Delivery Rev.* 1997, 27, 235-256; Mizen et al., *Pharm. Biotech.* 1998, 11, 345-365; Wiebe and Knaus, *Adv. Drug Delivery Rev.* 1999, 39, 63-80; Tan et al., *Adv. Drug Delivery Rev.* 1999, 39, 117-151; Balimane and Sinko, *Adv. Drug Delivery Rev.* 1999, 39, 183-209; Wang et al., *Curr. Pharm. Design* 1999, 5, 265-287; Han et al., *AAPS Pharmsci.* 2000, 2, 1-11; Asgharnejad in *Transport Processes in Pharmaceutical Systems*; Amidon et al., Eds.; Marcell Dekker: 2000; pp 185-218; Sinha et al., *Pharm. Res.* 2001, 18, 557-564; Anand et al., *Expert Opin. Biol. Ther.* 2002, 2, 607-620; Rao, *Resonace* 2003, 19-27; Sloan et al., *Med. Res. Rev.* 2003, 23, 763-793; Patterson et al., *Curr. Pharm. Des.* 2003, 9, 2131-2154; Hu, *IDrugs* 2004, 7, 736-742; Robinson et al., *Proc. Natl. Acad. Sci. U.S.A.* 2004, 101, 14527-14532; Erion et al., *J. Pharmacol. Exp. Ther.* 2005, 312, 554-560; Fang et al., *Curr. Drug Discov. Technol.* 2006, 3, 211-224; Stanczak et al., *Pharmacol. Rep.* 2006, 58, 599-613; Sloan et al., *Pharm. Res.* 2006, 23, 2729-2747; Stella et al., *Adv. Drug Deliv. Rev.* 2007, 59, 677-694; Gomes et al., *Molecules* 2007, 12, 2484-2506; Krafz et al., *ChemMedChem* 2008, 3, 20-53; Rautio et al., *AAPS J.* 2008, 10, 92-102; Rautio et al., *Nat. Rev. Drug. Discov.* 2008, 7, 255-270; Pavan et al., *Molecules*, 2008, 13, 1035-1065; Sandros et al., *Molecules* 2008, 13, 1156-1178; Singh et al., *Curr. Med. Chem.* 2008, 15, 1802-1826; Onishi et al., *Molecules*, 2008, 13, 2136-2155; Huttunen et al., *Curr. Med. Chem.* 2008, 15, 2346-2365; and Serafin et al., *Mini Rev. Med. Chem.* 2009, 9, 481-497.

Methods of Synthesis

The compounds provided herein can be prepared, isolated, or obtained by any method known to one of skill in the art. For an example, a compound of Formula II can be prepared as shown in Scheme I, wherein (a) $G^1$ is a leaving group, and $G^2$ is boronic acid (—B(OH)$_2$), boronate ester, or organotin; or (b) $G^1$ is boronic acid, boronate ester, or organotin, and $G^2$ is a leaving group. Examples of suitable leaving groups include, but are not limited to chloro, bromo, iodo, and triflate. Examples of suitable boronate esters and organiotins include, but are not limited to, 4,4,5,5-tetramethyl-[1,3,2]dioxaborolan-2-yl and —SnBu$_3$. Compounds of Formulae I-1 and I-2 are coupled together in the presence of a catalyst via the Stille or Suzuki reaction to form a compound of Formula II.

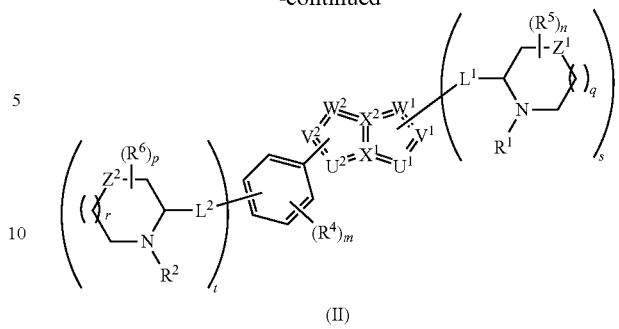

(II)

A compound of Formula XVI can be prepared as shown in Scheme II, wherein $G^1$ and $G^2$ are each as defined herein. Compounds of Formulae I-2 and II-1 are coupled together in the present of a catalyst via the Stille or Suzuki reaction to form a compound of Formula XVI.

The starting materials, compounds I-1, I-2, and II-1, used in the synthesis of the compounds provided herein are either commercially available or can be prepared by a method known to one of skill in the art. For example, compounds I-1, I-2, and II-1 can be prepared according to the methods described in U.S. Pat. Appl. Publ. Nos. 2009/0202478 and 2009/0202483; and International Pat. Appl. Nos. WO 2008/144380 and WO 2009/102694, the disclosure of each of which is incorporated herein by reference in its entirety.

Scheme II

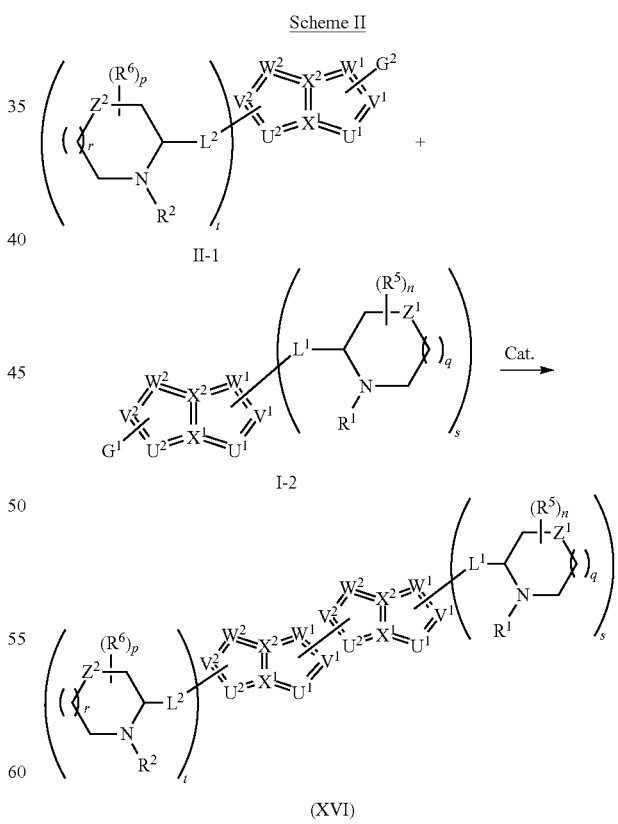

(XVI)

Pharmaceutical Compositions

Provided herein are pharmaceutical compositions comprising a compound provided herein, e.g., a compound of Formula I, IA, or IB, as an active ingredient, including a Scheme I

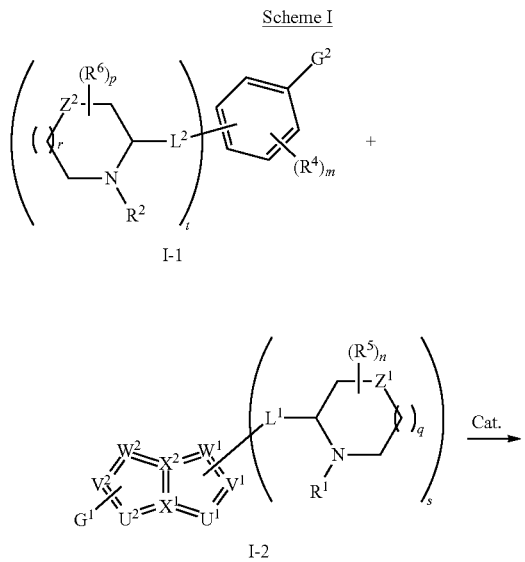

single enantiomer, a racemic mixture, a mixture of diastereomers, or an isotopic variant thereof; or a pharmaceutically acceptable salt, solvate, or prodrug thereof; or a pharmaceutically acceptable salt, solvate, hydrate, or prodrug; in combination with a pharmaceutically acceptable vehicle, carrier, diluent, or excipient, or a mixture thereof.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose, or other mono- or di-saccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate.

The compound provided herein may be administered alone, or in combination with one or more other compounds provided herein. The pharmaceutical compositions that comprise a compound provided herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

In one embodiment, the pharmaceutical compositions are provided in a dosage form for oral administration, which comprise a compound provided herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof; and one or more pharmaceutically acceptable excipients or carriers.

In another embodiment, the pharmaceutical compositions are provided in a dosage form for parenteral administration, which comprise a compound provided herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof; and one or more pharmaceutically acceptable excipients or carriers.

In yet another embodiment, the pharmaceutical compositions are provided in a dosage form for topical administration, which comprise a compound provided herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydro alcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-(3-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stiffing.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid; Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient (s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology*, 2nd ed.; Rathbone et al., Eds.; Marcel Dekker AG: 2005; Maroni et al., *Expert. Opin. Drug Deliv.* 2005, 2, 855-871; Shi et al., *Expert Opin. Drug Deliv.* 2005, 2, 1039-1058; *Polymers in Drug Delivery*; Ijeoma et al., Eds.; CRC Press LLC: Boca Raton, Fla., 2006; Badawy et al., *J. Pharm. Sci.* 2007, 9, 948-959; *Modified-Release Drug Delivery Technology*, supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS PharmSciTech.* 2008, 9, 635-638; Chrzanowski, *AAPS PharmSciTech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

1. Matrix Controlled Release Devices

The pharmaceutical compositions provided herein in a modified release dosage form can be fabricated using a matrix controlled release device known to those skilled in the art. See, Takada et al. in *Encyclopedia of Controlled Drug Delivery*; Mathiowitz Ed.; Wiley: 1999; Vol 2.

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; and Verma et al., *J. Controlled Release* 2002, 79, 7-27.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and International Pat. Appl. Publ. No. WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Ghebre-Sellassie Ed.; Marcel Dekker: 1994; and *Pharmaceutical Pelletization Technology*; Ghebre-Sellassie Ed.; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

Methods of Use

In one embodiment, provided herein are methods for treating or preventing a hepatitis C viral infection in a subject, which comprises administering to a subject a therapeutically effective amount of a compound provided herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof. In one embodiment, the subject is a mammal. In another embodiment, the subject is a human.

As used herein, the term "hepatitis C virus" or "HCV" refers to a viral species or a genetic variation thereof, a pathogenic strain of which causes hepatitis C. Examples of HCV include, but are not limited to, HCV genotypes 1, 2, 3, 4, and 5, and subtype 1a, 1b, 1c, 2a, 2b, 2c, 3a, and 3b.

In one embodiment, the hepatitis C viral infection is caused by HCV genotype 1. In certain embodiments, the hepatitis C viral infection is caused by HCV subtype 1a. In certain embodiments, the hepatitis C viral infection is caused by HCV subtype 1b. In certain embodiments, the hepatitis C viral infection is caused by HCV subtype 1c. In another embodiment, the hepatitis C viral infection is caused by HCV genotype 2. In certain embodiments, the hepatitis C viral infection is caused by HCV subtype 2a. In certain embodiments, the hepatitis C viral infection is caused by HCV subtype 2b. In certain embodiments, the hepatitis C viral infection is caused by HCV subtype 2c. In yet another embodiment, the hepatitis C viral infection is caused by HCV genotype 3. In certain embodiments, the hepatitis C viral infection is caused by HCV subtype 3a. In certain embodiments, the hepatitis C viral infection is caused by HCV subtype 3b. In yet another embodiment, the hepatitis C viral infection is caused by HCV genotype 4. In yet another embodiment, the hepatitis C viral infection is caused by HCV genotype 5. In yet another embodiment, the hepatitis C viral infection is caused by HCV genotype 6.

In another embodiment, provided herein is a method for inhibiting replication of a virus in a host, which comprises contacting the host with a therapeutically effective amount of a compound provided herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof. In one embodiment, the host is a cell. In another embodiment, the host is a human cell. In yet another embodiment, the host is a mammal. In still another embodiment, the host is human.

In one embodiment, the virus is a hepatitis C virus. In another embodiment, the virus is HCV genotype 1. In certain embodiments, the virus is HCV subtype 1a. In yet certain embodiments, the virus is HCV subtype 1b. In certain embodiments, the virus is HCV subtype 1c. In another embodiment, the virus is HCV genotype 2. In certain embodiments, the virus is HCV subtype 2a. In certain embodiments, the virus is HCV subtype 2b. In certain embodiments, the virus is HCV subtype 2c. In yet another embodiment, the virus is HCV genotype 3. In certain embodiments, the virus is HCV subtype 3a. In certain embodiments, the virus is HCV subtype 3b. In yet another embodiment, the virus is HCV genotype 4. In yet another embodiment, the virus is HCV genotype 5. In yet another embodiment, the virus is HCV genotype 6.

In certain embodiments, administration of a therapeutically effective amount of a compound provided herein (e.g., a compound of Formula I, IA, or IB, including a single enantiomer, a racemic mixture, a mixture of diastereomers, or an isotopic variant thereof; or a pharmaceutically acceptable salt, solvate, or prodrug thereof) results in a 10%, 20%, 30%, 40%, 50%, 60%, 70%, 80%, 90%, 95%, 99% or more reduction in the replication of the virus relative to a subject without administration of the compound, as determined at 1 day, 2 days, 3 days, 4 days, 5 days, 10 days, 15 days, or 30 days after the administration by a method known in the art, e.g., determination of viral titer.

In certain embodiments, administration of a therapeutically effective amount of a compound provided herein (e.g., a compound of Formula I, IA, or IB, including a single enantiomer, a racemic mixture, a mixture of diastereomers, or an isotopic variant thereof; or a pharmaceutically acceptable salt, solvate, or prodrug thereof) results in a 1, 2, 3, 4, 5, 10, 15, 20, 25, 50, 75, 100-fold or more reduction in the replication of the virus relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein (e.g., a compound of Formula I, IA, or IB, including a single enantiomer, a racemic mixture, a mixture of diastereomers, or an isotopic variant thereof; or a pharmaceutically acceptable salt, solvate, or prodrug thereof) results in a 10%, 20%, 30%, 40%, 50%, 60%, 70%, 80%, 90%, 95%, 99% or more reduction in the viral titer relative to a subject without administration of the compound, as determined at 1 day, 2 days, 3 days, 4 days, 5 days, 10 days, 15 days, or 30 days after the administration by a method known in the art.

In certain embodiments, administration of a therapeutically effective amount of a compound provided herein (e.g., a compound of Formula I, IA, or IB, including a single enantiomer, a racemic mixture, a mixture of diastereomers, or an isotopic variant thereof; or a pharmaceutically acceptable salt, solvate, or prodrug thereof) results in a 1, 2, 3, 4, 5, 10, 15, 20, 25, 50, 75, 100 or more fold reduction in the viral titer relative to a subject without administration of the compound, as determined at 1 day, 2 days, 3 days, 4 days, 5 days, 10 days, 15 days, or 30 days after the administration by a method known in the art.

In yet another embodiment, provided herein is a method for inhibiting the replication of an HCV virus, which comprises contacting the virus with a therapeutically effective amount of a compound provided herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof.

In one embodiment, the HCV is genotype 1. In certain embodiments, the HCV is subtype 1a. In certain embodiments, the HCV is subtype 1b. In certain embodiments, the HCV is subtype 1c. In another embodiment, the HCV is genotype 2. In certain embodiments, the HCV is subtype 2a. In certain embodiments, the HCV is subtype 2b. In certain embodiments, the HCV is subtype 2c. In yet another embodiment, the HCV is genotype 3. In certain embodiments, the HCV is subtype 3a. In certain embodiments, the HCV is subtype 3b. In yet another embodiment, the HCV is genotype 4. In yet another embodiment, the HCV is genotype 5. In yet another embodiment, the HCV is genotype 6.

In certain embodiments, the contacting of the virus with a therapeutically effective amount of a compound provided herein (e.g., a compound of Formula I, IA, or IB, including a single enantiomer, a racemic mixture, a mixture of diastereomers, or an isotopic variant thereof; or a pharmaceutically acceptable salt, solvate, or prodrug thereof) results in a 10%, 20%, 30%, 40%, 50%, 60%, 70%, 80%, 90%, 95%, 99% or more reduction in the virus titer relative to the virus without such contact, as determined at 1 day, 2 days, 3 days, 4 days, 5 days, 10 days, 15 days, or 30 days after the initial contact, by a method known in the art.

In certain embodiments, the contacting of the virus with a therapeutically effective amount of a compound provided herein (e.g., a compound of Formula I, IA, or IB, including a single enantiomer, a racemic mixture, a mixture of diastereomers, or an isotopic variant thereof; or a pharmaceutically acceptable salt, solvate, or prodrug thereof) results in a 1, 2, 3, 4, 5, 10, 15, 20, 25, 50, 75, 100 or more fold reduction in the viral titer relative to the virus without such contact, as determined at 1 day, 2 days, 3 days, 4 days, 5 days, 10 days, 15 days, or 30 days after the initial contact, by a method known in the art.

In still another embodiment, provided herein is a method for treating, preventing, or ameliorating one or more symptoms of a liver disease or disorder associated with an HCV infection, comprising administering to a subject a therapeutically effective amount of the compound provided herein, e.g., a compound of Formula I, IA, or IB, including a single enantiomer, a racemic mixture, a mixture of diastereomers, or an isotopic variant thereof; or a pharmaceutically acceptable salt, solvate, or prodrug thereof. Non-limiting examples of diseases associated with HCV infection include chronic hepatitis, cirrhosis, hepatocarcinoma, or extra hepatic manifestation.

In one embodiment, the hepatitis C viral infection is caused by HCV genotype 1. In certain embodiments, the hepatitis C viral infection is caused by HCV subtype 1a. In certain embodiments, the hepatitis C viral infection is caused by HCV subtype 1b. In certain embodiments, the hepatitis C viral infection is caused by HCV subtype 1c. In another embodiment, the hepatitis C viral infection is caused by HCV genotype 2. In certain embodiments, the hepatitis C viral infection is caused by HCV subtype 2a. In certain embodiments, the hepatitis C viral infection is caused by HCV subtype 2b. In certain embodiments, the hepatitis C viral infection is caused by HCV subtype 2c. In yet another embodiment, the hepatitis C viral infection is caused by HCV genotype 3. In certain embodiments, the hepatitis C viral infection is caused by HCV subtype 3a. In certain embodiments, the hepatitis C viral infection is caused by HCV subtype 3b. In yet another embodiment, the hepatitis C viral infection is caused by HCV genotype 4. In yet another embodiment, the hepatitis C viral infection is caused by HCV genotype 5. In yet another embodiment, the hepatitis C viral infection is caused by HCV genotype 6.

Depending on the condition, disorder, or disease, to be treated and the subject's condition, a compound provided herein may be administered by oral, parenteral (e.g., intramuscular, intraperitoneal, intravenous, intracerebroventricular (ICV), intracistemal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from about 0.1 to about 1,000 milligram, from about 0.1 to about 500 milligrams, or from 0.5 about to about 100 milligram active ingredient(s) per dosage unit, and if the condition of the patient requires, the dose can, by way of alternative, be administered as a continuous infusion.

In certain embodiments, an appropriate dosage level is about 0.01 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to about 100 mg/kg per day, about 0.05 to about 50 mg/kg per day, or about 0.1 to about 10 mg/kg per day. Within this range the dosage may be about 0.01 to about 0.1, about 0.1 to about 1.0, about 1.0 to about 10, or about 10 to about 50 mg/kg per day.
Combination Therapy The compounds provided herein may also be combined or used in combination with other therapeutic agents useful in the treatment and/or prevention of an HCV infection.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

As used herein, the term "synergistic" includes a combination of a compound provided herein and another therapy (e.g., a prophylactic or therapeutic agent) which has been or is currently being used to prevent, treat, or manage a condition, disorder, or disease, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a condition, disorder, or disease. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, treatment, or management of a condition, disorder, or disease). In addition, a synergistic effect can result in improved efficacy of agents in the prevention, treatment, or management of a condition, disorder, or disease. Finally, a synergistic effect of a combination of therapies (e.g., a combination of prophylactic or therapeutic agents) may avoid or reduce adverse or unwanted side effects associated with the use of either therapy alone.

The compound provided herein can be administered in combination or alternation with another therapeutic agent, such as an anti-HCV agent. In combination therapy, effective dosages of two or more agents are administered together, whereas in alternation or sequential-step therapy, an effective dosage of each agent is administered serially or sequentially. The dosages given will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

It has been recognized that drug-resistant variants of HCV can emerge after prolonged treatment with an antiviral agent. Drug resistance most typically occurs due to the mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameters of the drug can be altered by such combination or alternation therapy. In general, combination therapy is typically preferred over alternation therapy because it induces multiple simultaneous stresses on the virus.

In certain embodiments, the pharmaceutical compositions provided herein further comprise a second antiviral agent as described herein. In certain embodiments, the compound provided herein is combined with one or more agents selected from the group consisting of an interferon, ribavirin, amantadine, an interleukin, a NS3 protease inhibitor, a cysteine protease inhibitor, a phenanthrenequinone, a thiazolidine, a benzanilide, a helicase inhibitor, a polymerase inhibitor, a nucleotide analogue, a gliotoxin, a cerulenin, an antisense phosphorothioate oligodeoxynucleotide, an inhibitor of IRES-dependent translation, and a ribozyme. In one embodiment, the second antiviral agent is an interferon. In another embodiment, the interferon is selected from the group consisting of pegylated interferon alpha 2a, interferon alfacon-1, natural interferon, ALBUFERON®, interferon beta-1a, omega interferon, interferon alpha, interferon gamma, interferon tau, interferon delta, and interferon gamma-1b.

In certain embodiments, the compound provided herein is combined with a HCV protease inhibitor, including, but not limited to, BI 201335 (Boehringer Ingelheim); TMC 435 or TMC 435350 (Medivir/Tibotec); ITMN 191/R7227 (InterMune); MK 7009 (Merck); SCH 5034/SCH 503034/Boceprevir and SCH 900518/narlaprevir (Schering); VX950/telaprevir (Vertex); substrate-based NS3 protease inhibitors as disclosed in DE 19914474, WO 98/17679, WO 98/22496, WO 99/07734, and Attwood et al., *Antiviral Chemistry and Chemotherapy* 1999, 10, 259-273; non-substrate-based NS3 protease inhibitors, including 2,4,6-trihydroxy-3-nitro-benzamide derivatives (Sudo et al., *Biochem. Biophys. Res. Commun.* 1997, 238, 643-647), a phenanthrenequinone (Chu et al., *Tetrahedron Letters* 1996, 37, 7229-7232), RD3-4082, RD3-4078, SCH 68631, and SCH 351633 (Chu et al., *Bioorganic and Medicinal Chemistry Letters* 1999, 9, 1949-1952); and Eglin C, a potent serine protease inhibitor (Qasim et al., *Biochemistry* 1997, 36, 1598-1607).

Other suitable protease inhibitors for the treatment of HCV include those disclosed in, for example, U.S. Pat. No. 6,004,933, which discloses a class of cysteine protease inhibitors of HCV endopeptidase 2.

Additional hepatitis C virus NS3 protease inhibitors include those disclosed in, for example, Llinas-Brunet et al., *Bioorg. Med. Chem. Lett.* 1998, 8, 1713-1718; Steinkühler et al., *Biochemistry* 1998, 37, 8899-8905; U.S. Pat. Nos. 5,538,865; 5,990,276; 6,143,715; 6,265,380; 6,323,180; 6,329,379; 6,410,531; 6,420,380; 6,534,523; 6,608,027; 6,642,204; 6,653,295; 6,727,366; 6,838,475; 6,846,802; 6,867,185; 6,869,964; 6,872,805; 6,878,722; 6,908,901; 6,911,428; 6,995,174; 7,012,066; 7,041,698; 7,091,184; 7,169,760; 7,176,208; 7,208,600; and 7,491,794; U.S. Pat. Appl. Publ. Nos.: 2002/0016294, 2002/0016442; 2002/0032175; 2002/0037998; 2004/0229777; 2005/0090450; 2005/0153877; 2005/176648; 2006/0046956; 2007/0021330; 2007/0021351; 2007/0049536; 2007/0054842; 2007/0060510; 2007/0060565; 2007/0072809; 2007/0078081; 2007/0078122; 2007/0093414; 2007/0093430; 2007/0099825; 2007/0099929; 2007/0105781, 2008/0152622, 2009/0035271, 2009/0035272, 2009/0047244, 2009/0111969, 2009/0111982, 2009/0123425, 2009/0130059, 2009/0148407, 2009/0156800, 2009/0169510, 2009/0175822, 2009/0180981, and 2009/0202480; U.S. patent application Ser. No. 12/365,127; and International Pat. Appl. Publ. Nos.: WO 98/17679; WO 98/22496; WO 99/07734; WO 00/09543; WO 00/59929; WO 02/08187; WO 02/08251; WO 02/08256; WO 02/08198; WO 02/48116; WO 02/48157; WO 02/48172; WO 02/60926; WO 03/53349; WO 03/64416; WO 03/64455; WO 03/64456; WO 03/66103; WO 03/99274; WO 03/99316; WO 2004/032827; WO 2004/043339; WO 2005/037214; WO 2005/037860; WO 2006/000085; WO 2006/119061; WO 2006/122188; WO 2007/001406; WO 2007/014925; WO 2007/014926; WO 2007/015824; WO 2007/056120; WO 2008/019289; WO 2008/021960; WO 2008/022006; WO 2008/086161; WO 2009/053828; WO 2009/058856; WO 2009/073713; WO 2009/073780; WO 2009/080542; WO 2009/082701, WO 2009/082697, and WO 2009/085978; the disclosure of each of which is incorporated herein by reference in its entirety.

Other protease inhibitors include thiazolidine derivatives, such as RD-1-6250, RD4 6205, and RD4 6193, which show relevant inhibition in a reverse-phase HPLC assay with an NS3/4A fusion protein and NS5A/5B substrate (Sudo et al., *Antiviral Research* 1996, 32, 9-18); and thiazolidines and benzanilides identified in Kakiuchi et al., *FEBS Lett.* 1998, 421, 217-220; and Takeshita et al., *Analytical Biochemistry* 1997, 247, 242-246.

Suitable helicase inhibitors include, but are not limited to, those disclosed in U.S. Pat. No. 5,633,358; and International Pat. Appl. Publ. No. WO 97/36554.

Suitable nucleotide polymerase inhibitors include, but are not limited to, gliotoxin (Ferrari et al., *Journal of Virology* 1999, 73, 1649-1654) and cerulenin (Lohmann et al., *Virology* 1998, 249, 108-118).

Suitable interfering RNA (iRNA) based antivirals include, but are not limited to, short interfering RNA (siRNA) based antivirals, such as Sirna-034 and those described in International Pat. Appl. Publ. Nos. WO/03/070750 and WO 2005/012525, and U.S. Pat. Appl. Publ. No. 2004/0209831.

Suitable antisense phosphorothioate oligodeoxynucleotides (S-ODN) complementary to sequence stretches in the 5' non-coding region (NCR) of HCV virus include, but are not limited to those described in Alt et al., *Hepatology* 1995, 22, 707-717, and nucleotides 326-348 comprising the 3' end of the NCR and nucleotides 371-388 located in the core coding region of HCV RNA (Alt et al., *Archives of Virology* 1997, 142, 589-599; and Galderisi et al., *Journal of Cellular Physiology* 1999, 181, 251-257);

Suitable inhibitors of IRES-dependent translation include, but are not limited to, those described in Japanese Pat. Appl. Publ. Nos.: JP 08268890 and JP 10101591.

Suitable ribozymes include those disclosed in, for example, U.S. Pat. Nos. 6,043,077; 5,869,253; and 5,610,054.

Suitable nucleoside analogs include, but are not limited to, the compounds described in U.S. Pat. Nos. 6,660,721; 6,777,395; 6,784,166; 6,846,810; 6,927,291; 7,094,770; 7,105,499; 7,125,855; and 7,202,224; U.S. Pat. Appl. Publ. Nos. 2004/0121980; 2005/0009737; 2005/0038240; and 2006/0040890; and International Pat. Appl. Publ. Nos: WO 99/43691; WO 01/32153; WO 01/60315; WO 01/79246; WO 01/90121, WO 01/92282, WO 02/18404; WO 02/32920, WO 02/48165, WO 02/057425; WO 02/057287; WO 2004/002422, WO 2004/002999, and WO 2004/003000.

Other miscellaneous compounds that can be used as second agents include, for example, 1-amino-alkylcyclohexanes (U.S. Pat. No. 6,034,134), alkyl lipids (U.S. Pat. No. 5,922,757), vitamin E and other antioxidants (U.S. Pat. No. 5,922,757), squalene, amantadine, bile acids (U.S. Pat. No. 5,846,964), N-(phosphonacetyl)-L-aspartic acid (U.S. Pat. No. 5,830,905), benzenedicarboxamides (U.S. Pat. No. 5,633,388), polyadenylic acid derivatives (U.S. Pat. No. 5,496,546), 2',3'-dideoxyinosine (U.S. Pat. No. 5,026,687), benzimidazoles (U.S. Pat. No. 5,891,874), plant extracts (U.S. Pat. Nos. 5,725,859; 5,837,257; and 6,056,961), and piperidines (U.S. Pat. No. 5,830,905).

In certain embodiments, one or more compounds provided herein are administered in combination or alternation with an anti-hepatitis C virus interferon, including, but not limited to, INTRON® A (interferon alfa-2b), PEGASYS® (Peginterferon alfa-2a) ROFERON® A (recombinant interferon alfa-2a), INFERGEN® (interferon alfacon-1), and PEG-INTRON® (pegylated interferon alfa-2b). In one embodiment, the anti-hepatitis C virus interferon is INFERGEN®, IL-29 (PEG-Interferon lambda), R7025 (Maxy-alpha), BELEROFON®, oral interferon alpha, BLX-883 (LOCTERON®), omega interferon, MULTIFERON®, medusa interferon, ALBUFERON®, or REBIF®.

In certain embodiments, one or more compounds provided herein are administered in combination or alternation with an anti-hepatitis C virus polymerase inhibitor, such as ribavirin, viramidine, NM 283 (valopicitabine), PSI-6130, R1626, HCV-796, R7128, and those as disclosed in U.S. Pat. Appl. Publ. Nos. 2009/0081158 and 2009/0238790, the disclosure of each of which is incorporated herein by reference in its entirety.

In certain embodiments, the one or more compounds provided herein are administered in combination with ribavirin and an anti-hepatitis C virus interferon, such as INTRON® A (interferon alfa-2b), PEGASYS® (Peginterferon alfa-2a), ROFERON® A (recombinant interferon alfa-2a), INFERGEN® (interferon alfacon-1), and PEG-INTRON® (pegylated interferon alfa-2b), In certain embodiments, one or more compounds provided herein are administered in combination or alternation with an anti-hepatitis C virus protease inhibitor, such as ITMN-191, SCH 503034, VX950 (telaprevir), and TMC 435.

In certain embodiments, one or more compounds provided herein are administered in combination or alternation with an anti-hepatitis C virus vaccine, including, but not limited to, TG4040, PEVIPRO™, CGI-5005, HCV/MF59, GV1001, IC41, and INNO0101 (E1).

In certain embodiments, one or more compounds provided herein are administered in combination or alternation with an anti-hepatitis C virus monoclonal antibody, such as AB68 and XTL-6865 (formerly HepX-C); or an anti-hepatitis C virus polyclonal antibody, such as cicavir.

In certain embodiments, one or more compounds provided herein are administered in combination or alternation with an anti-hepatitis C virus immunomodulator, such as ZADAXIN® (thymalfasin), NOV-205, and oglufanide.

In certain embodiments, one or more compounds provided herein are administered in combination or alternation with NEXAVAR®, doxorubicin, PI-88, amantadine, JBK-122, VGX-410C, MX-3253 (celgosivir), SUVUS® (BIVN-401 or virostat), PF-03491390 (formerly IDN-6556), G126270, UT-231B, DEBIO-025, EMZ702, ACH-0137171, MitoQ, ANA975, AVI-4065, bavituximab (tarvacin), ALINIA® (nitrazoxanide), and PYN17.

The compounds provided herein can also be administered in combination with other classes of compounds, including, but not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54)

other miscellaneous agents, such as, hydroxyurea, procarbazine, mitotane, hexamethylmelamine, and gold compounds.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer, a racemic mixture, a mixture of diastereomers, or an isotopic variant thereof; or a pharmaceutically acceptable salt, solvate, or prodrug thereof.

In certain embodiments, the kit includes a container comprising a dosage form of the compound provided herein, including a single enantiomer, a racemic mixture, a mixture of diastereomers, or an isotopic variant thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); L (liter); mM (millimolar); µM (micromolar); Hz (Hertz); MHz (megahertz); mmol (millimoles); eq. (equivalent); hr or hrs (hours); min (minutes); MS (mass spectrometry); NMR (nuclear magnetic resonance); ESI (electrospray ionization); HPLC, (high-performance liquid chromatography or high pressure liquid chromatography); ACN, (acetonitrile); $CDCl_3$ (deuterated chloroform); DCM (dichloromethane); DMF (N,N-dimethylformamide); DMSO (dimethylsulfoxide); DMSO-$d_6$ (deuterated dimethylsulfoxide); EtOAc (ethyl acetate); $Et_2O$ (diethyl ether); EtOH (ethanol); MeOH (methanol); PE (petroleum ether); THF (tetrahydrofuran); DIPEA (N,N-diisopropylethylamine); TEA (triethylamine); TFA (trifluoroacetic acid); BOP (benzotriazole-1-yl-oxytris-(dimethylamino)-phosphonium hexafluorophosphate); HATU, (2-(7-aza-1H-benzotriazole-1-yl)-1,1,3,3-tetramethyluronium hexafluorophosphate); TBTU (O-(benzotriazol-1-yl)-N,N,N',N'-tetramethyluronium tetrafluoroborate); DIPC (1,3-diisopropylcarbodiimide); Me (methyl); Et (ethyl); iPr, (isopropyl); tBu (tert-butyl); Boc (tert-butoxylcarbony); Bn (benzyl); Ph (phenyl); AcO (acetate); $PdCl_2$(dppf) ((1,1'-bis(diphenylphosphino)ferrocene)dichloropalladium(II)); and Pd118 (1,1'-bis(di-tert-butylphosphino)ferrocene palladium (II) dichloride).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies herein are intended to exemplify the applicable chemistry through the use of specific examples and are not indicative of the scope of the disclosure.

Example 1A

HCV Replicon Assay

General procedure: Huh-7 cells containing HCV Coni subgenomic replicon (GS4.1 cells) were grown in Dulbecco's Modified Eagle Medium (DMEM) supplemented with 10% fetal bovine serum (FBS), 2 mM L-glutamine, 110 mg/L sodium pyruvate, 1× non-essential amino acids, 100 U/mL penicillin-streptomycin, and 0.5 mg/mL G418 (Invitrogen). For dose-response testing, the cells were seeded in 96-well plates at $7.5 \times 10^3$ cells/well in a volume of 50 µL, and incubated at 37° C./5% $CO_2$. Three hours after plating, 50 µL of ten 2-fold serial dilutions of compounds (highest concentration, 75 µM) were added, and cell cultures were incubated at 37° C./5% $CO_2$ in the presence of 0.5% DMSO. Alternatively, compounds were tested at a single concentration of 15 µM. In all cases, Huh-7 cells lacking the HCV replicon served as negative control. The cells were incubated in the presence of compounds for 72 hrs after which they were monitored for expression of the NS5A protein by enzyme-linked immunosorbent assay (ELISA). For this, the plates were then fixed for 1 min with acetone/methanol (1:1, v/v), washed twice with phosphate-buffered saline (PBS), 0.1% Tween 20, blocked for 1 hr at room temperature with TNE buffer containing 10% FBS and then incubated for 2 hr at 37° C. with the anti-NS5A mouse monoclonal antibody A-236 (ViroGen) diluted in the same buffer. After washing three times with PBS, 0.1% Tween 20, the cells were incubated 1 hr at 37° C. with anti-mouse immunoglobulin G-peroxidase conjugate in TNE, 10% FBS. After washing as described above, the reaction was developed with O-phenylenediamine (Zymed). The reaction was stopped after 30 min with 2 N $H_2SO_4$, and absorbance was read at 492 nm using Sunrise Tecan spectrophotometer. $EC_{50}$ values were determined from the % inhibition versus concentration data using a sigmoidal non-linear regression analysis based on four parameters with Tecan Magellan software. When screening at a single concentration, the results were expressed as % inhibition at 15 µM.

For cytotoxicity evaluation, GS4.1 cells were treated with compounds as described above and cellular viability was monitored using the Cell Titer 96 $AQ_{ueous}$ One Solution Cell Proliferation Assay (Promega). $CC_{50}$ values were determined from the % cytotoxicity versus concentration data with Tecan Magellan software as described above.

The biological results are summarized in Table 1A, wherein A represents a value smaller than 1 µM, B represents a value between 1 µM to 10 µM, C represents a value between 10 µM to 75 µM, D represents a value greater than 75 µM, A' represents a value smaller than 1 nM, B' represents a value between 1 nM to 10 nM, C' represents a value between 10 nM to 100 nM, and D' represents a value greater than 100 nM.

TABLE 1A

| Cmpd # | $EC_{50}$ | $CC_{50}$ |
|---|---|---|
| A1 | A' | D |
| A2 | B' | C |
| A7 | A' | D |
| A15 | A' | C |
| A22 | D' | D |
| A23 | D' | C |
| A27 | C' | D |
| A29 | D' | C |
| A30 | A' | D |
| A31 | C' | D |
| A32 | A' | D |
| A33 | A' | D |
| A34 | B' | C |
| A49 | A' | D |
| A55 | A' | C |
| A56 | A' | D |
| A57 | A' | D |
| A60 | A' | D |
| A76 | A' | D |
| A77 | A' | D |
| A78 | A' | D |
| A79 | A' | D |
| A80 | A' | D |
| A82 | A' | C |
| A84 | A' | D |
| A86 | A' | C |
| A87 | A' | D |
| A93 | A' | D |
| A103 | B' | C |
| A105 | C' | C |
| A111 | A' | D |
| A126 | A' | D |
| A130 | A' | D |
| A147 | C' | D |
| A148 | B' | D |
| A149 | C' | C |
| A150 | C' | C |
| A151 | A' | C |
| A152 | D' | C |
| A153 | C' | C |
| A154 | C' | C |
| A155 | C' | C |
| A156 | A' | D |
| A157 | C' | D |
| A158 | D' | C |
| A159 | A' | D |
| A160 | C' | D |
| A161 | D' | D |
| A162 | B' | C |
| A163 | A' | D |
| A164 | C' | C |
| A167 | D' | |
| A168 | C' | C |

Example 1B

Generation of HCV NS5A-Intergenotypic Stable Cell Lines for Genotypes 1a, 2a, 3a, and 4a The nucleotide sequences of the NS5A region of genotype 2a (GenBank Accession # AB047639), genotype 3a (GenBank Accession # D17763), and genotype 4a (GenBank Accession # DQ418788) were synthesized by an outside vendor. The NS5A region of each of these genotypes included the first 11 amino acids of the protease recognition sequence of genotype 1b, as well as the last 10 amino acids of genotype 1b. The NS5A gene cassettes were excised with site specific restriction endonucleases and ligated into a ZS11-luciferase genotype 1b backbone (backbone contains the genotype 1b NS3 protease, NS4a, NS4b, and NS5b coding regions) with similarly cut restriction enzyme sites. Thus, the newly constructed plasmid contains a genotype 2a-, 3a- or 4a-specific NS5A gene within the 1b-replicon.

To generate the 1a-H77 NS5a intergenotypic plasmid, dual cut sites were inserted into the ZS11-luciferase genotype 1b backbone that would bracket the NS5a region almost in its entirety. Using PCR and 1a-H77 specific primers also containing the corresponding restriction enzyme sites, the NS5a gene was amplified from the 1a-H77 replicon. The ZS11-luciferase genotype 1b backbone and the genotype 1a NS5a PCR products were restriction enzyme digested and then ligated using standard molecular cloning techniques. The newly constructed plasmid contains the genotype 1a-specific NS5a gene where as the backbone remains 1b as described herein.

These new intergenotypic plasmids were used to establish stable cell lines. RNA was generated from the NS5A intergenotypic plasmids and used in conjunction with a lipofectin reagent to transfect a cured Huh7 cell line. Transfected cells were selected for with G418. After selection has occurred the stable cell lines were propagated, tested for luciferase activity, and RT-PCR with genotype specific primers (either 1a, 2a, 3a, or 4a). Stable cell lines containing the intergenotypic replicon were then fully sequenced and analysed for proper expression of NS3, NS5A and NS5B proteins.

Drug titration analysis was performed using the luciferase replicon assay described herein.

Genotype 2a Infectious Virus Assay

The genotype 2a infectious virus assay measures the ability of a test compound to inhibit HCV replication in cell culture after 5 days of treatment at the time of HCV genotype 2a virus infection of a permissive human hepatoma cell line (HPC cells). The inhibition of HCV replication was measured by quantification of HCV core protein expression by an enzyme-linked immunosorbent assay (ELISA). Briefly, HPC cells were grown in DMEM containing glucose, L-glutamine and sodium pyruvate, 10% FBS, 100 IU/mL penicillin, 100 µg/mL streptomycin, 2 mM GlutaMAX, and non-essential amino acids. GlutaMAX was obtained from Invitrogen, Corp.; all other media reagents were obtained from Mediatech, Inc. For dose-response testing, ninety-six-well plates were seeded with HPC cells at a density of $2.5 \times 10^3$ cells/well in a volume of 50 µL, and incubated at 37° C./5% $CO_2$. Three hours after plating, 50 µL of ten 5-fold serial dilutions of compound and 100 µL of genotype 2a virus were added, and cell cultures were incubated at 37° C./5% $CO_2$. In all cases, mock infected HPC cells served as negative control. At 16 hours post treatment and infection, the virus inoculum was removed by aspiration. The cultures were treated at the same final concentrations of drug diluted in media and incubated for 4 additional days at 37° C./5% $CO_2$. Subsequently, the core ELISA was performed as follows. The plates were fixed for 90 seconds with acetone/methanol (1:1, v/v), washed three times with KPL wash solution (KPL, Inc.), blocked for 1 hr at room temperature with TNE buffer containing 10% FBS and then incubated for 2 hr at 37° C. with the anti-HCV core mouse monoclonal antibody (Thermo Scientific) diluted in the same buffer. After washing three times with KPL wash solution, the cells were incubated for 1 hr at 37° C. with an anti-mouse immunoglobulin G-peroxidase conjugate in TNE/10% FBS. After washing as described above, the reaction was developed with O-phenylenediamine (Invitrogen). The reaction was stopped after 30 min with 2 N $H_2SO_4$, and absorbance was read at 490 nm in a Victor³V 1420 multilabel counter (Perkin Elmer) and $EC_{50}$ concentrations were determined using Microsoft Excel and XLfit 4.1 software.

For cytotoxicity evaluation, HPC cells were treated with compounds as described above in the absence of the genotype 2a virus and cellular viability was monitored using the Cell Titer 96 AQueous One Solution Cell Proliferation Assay (Promega). Plates were then read at 490 nm in a Victor³V 1420 multilabel counter (Perkin Elmer) and $CC_{50}$ concentrations were determined using Microsoft Excel and XLfit 4.1 software.

Luciferase Replicon Assay

The HCV luciferase replicon assay measures the ability of a test compound to inhibit HCV replication in cell culture after 3 days of treatment in a human hepatoma cell line (Huh-7) bearing a HCV replicon containing a luciferase-neomycin phosphotransferase fusion gene. The inhibition of HCV replication was measured by quantification of luciferase protein expression. Briefly, Huh-7 cells containing either the HCV genotype 1a H77 strain or genotype 1b Cont strain subgenomic luciferase replicon (H1a-luc or Zluc, respectively) were grown in DMEM containing glucose, L-glutamine and sodium pyruvate, 10% fetal bovine serum (FBS), 100 IU/mL penicillin, 100 μg/mL streptomycin, 2 mM GlutaMAX, non-essential amino acids and 0.25 (H1a-luc) or 0.5 (Zluc) mg/mL G418. GlutaMAX was obtained from Invitrogen, Corp.; all other media reagents were obtained from Mediatech, Inc. For dose-response testing, the cells were seeded in 96-well plates at $1 \times 10^4$ (H1a-luc) or $7.5 \times 10^3$ (Zluc) cells/well in a volume of 50 μL, and incubated at 37° C./5% $CO_2$. Three hours after plating, 50 μL of ten 5-fold serial dilutions of compound were added, and cell cultures were incubated at 37° C./5% $CO_2$ for 72 hours. In all cases, Huh-7 cells lacking the HCV replicon served as negative control. To assess luciferase expression, the media/compound was removed from the plates and ONE-glo Luciferase assay reagent (Promega) was added to each well. The assay plates were shaken for 3 minutes at room temperature and luciferase activity for each well was measured with a 1 sec read time on the Victor³V multilabel counter using a 700 nm cut-off filter (Perkin Elmer). $EC_{50}$ values were calculated from dose response curves from the resulting best-fit equations determined by Microsoft Excel and XLfit 4.1 software.

For cytotoxicity evaluation, H1a-luc or Zluc cells were treated with compounds as described above and cellular viability was monitored using the Cell Titer 96 AQueous One Solution Cell Proliferation Assay (Promega). Plates were then read at 490 nm in a Victor³V 1420 multilabel counter (Perkin Elmer) and $CC_{50}$ concentrations were determined using Microsoft Excel and XLfit 4.1 software.

The biological results are summarized in Table 1B, wherein A" represents a value smaller than 100 pM, A' represents a value between 100 pM to 1 nM, B' represents a value between 1 nM to 10 nM, C' represents a value between 10 nM to 100 nM, and D' represents a value greater than 100 nM.

| Compound | Structure | $EC_{50}$ 1b | 2a | 3a | 4a | 1a | $CC_{50}$ |
|---|---|---|---|---|---|---|---|
| A15 | 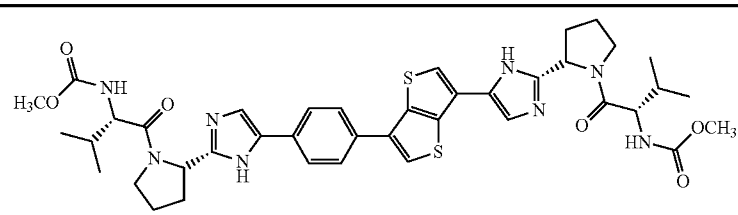 | A" | A" | A' | A" | A" | C |
| A200 | 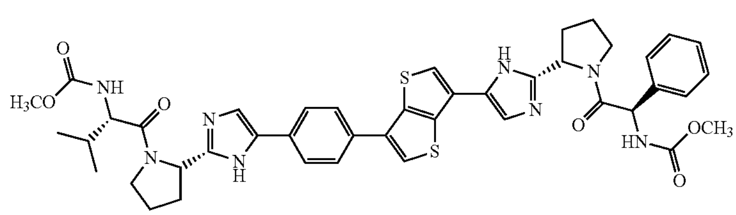 | A" | A" | A" | A" | A' | D |
| A111 | 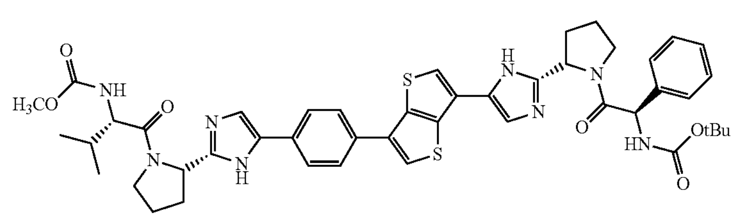 | A" | A" | A" | A" | A' | D |

-continued

| Compound | Structure | EC₅₀ 1b | 2a | 3a | 4a | 1a | CC₅₀ |
|---|---|---|---|---|---|---|---|
| A86 | 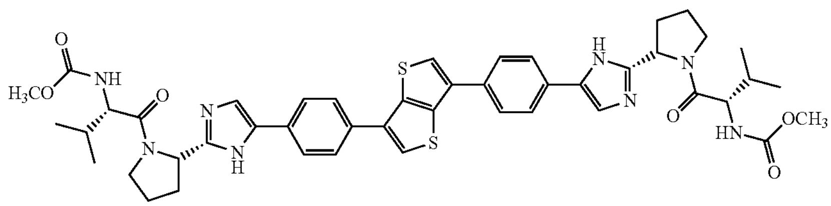 | A" | B' | B' | A" | A' | C |
| A169 | 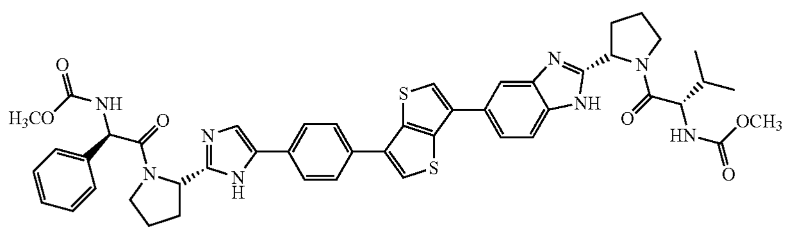 | A" | A" | A" | A" | A" | D |
| A171 | 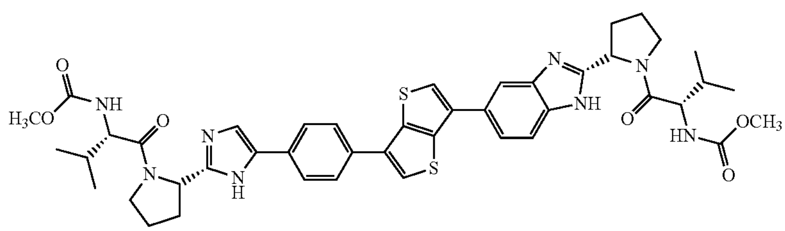 | A" | A' | B' | A" | A" | D |
| A172 | 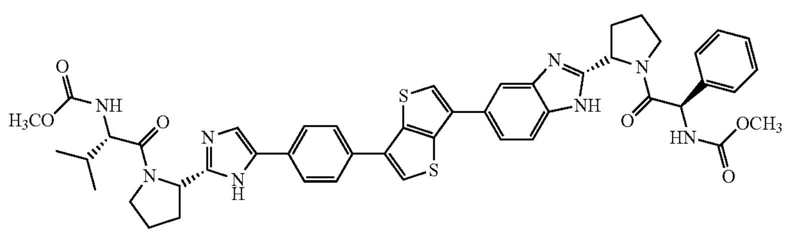 | A" | A" | A" | A" | A" | D |
| A114 | 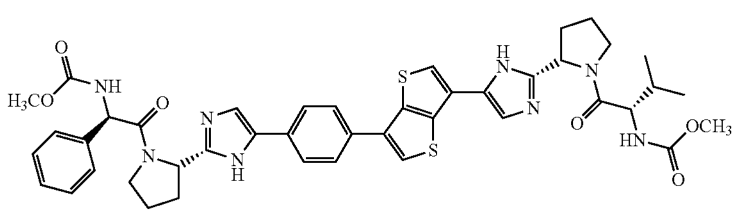 | A" | A" | A" | A" | A' | B |
| A206 | 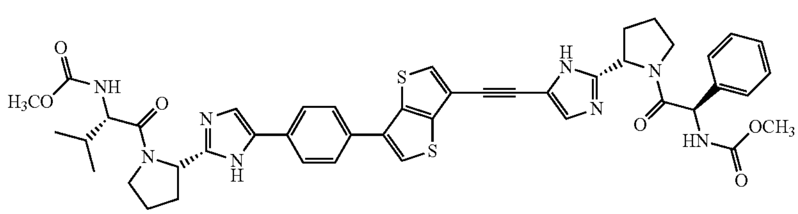 | A" | A" | A" | A" | ? | D |
| A208 | 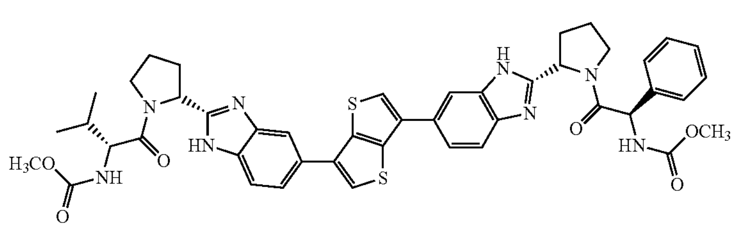 | A" | A" | A" | A" | A" | D |

-continued

| Compound | Structure | EC₅₀ | | | | | CC₅₀ |
|---|---|---|---|---|---|---|---|
| | | 1b | 2a | 3a | 4a | 1a | |
| A101 | 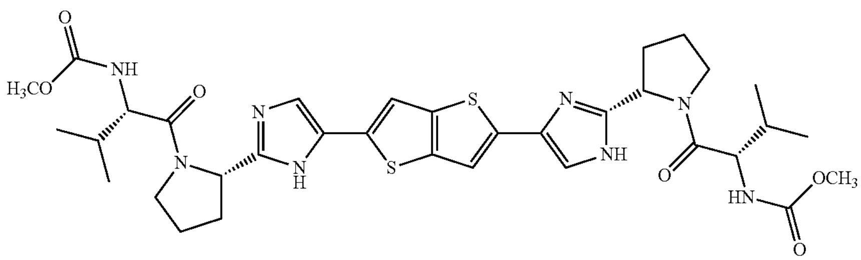 | A" | B' | B' | B' | C" | D |
| A126 | 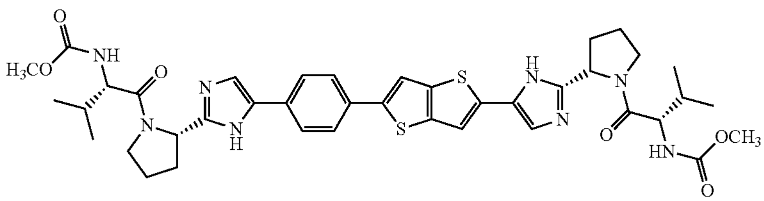 | A" | A' | B' | A" | A" | D |
| A212 | 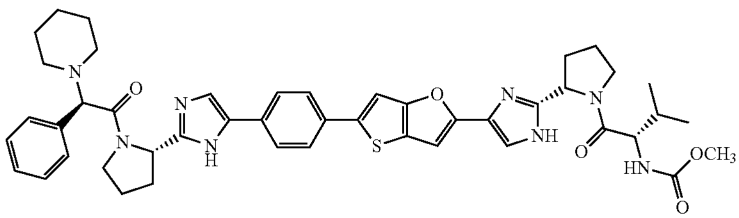 | A" | A" | A" | A" | A" | C |
| A213 | 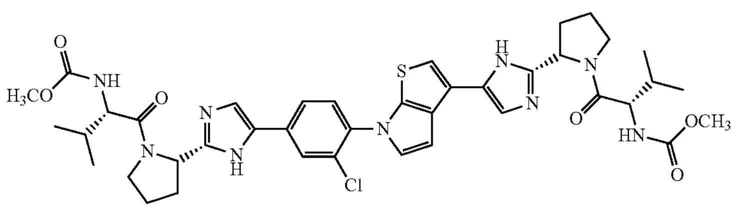 | A" | | | | A' | C |
| A114 | 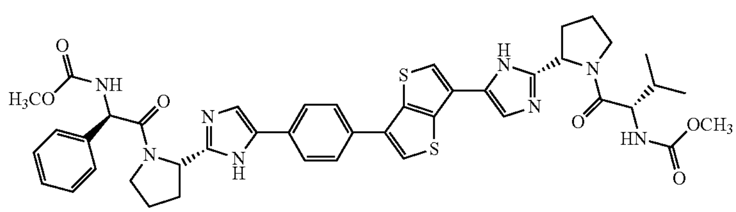 | A" | A" | A" | A" | A" | C |
| A169 | 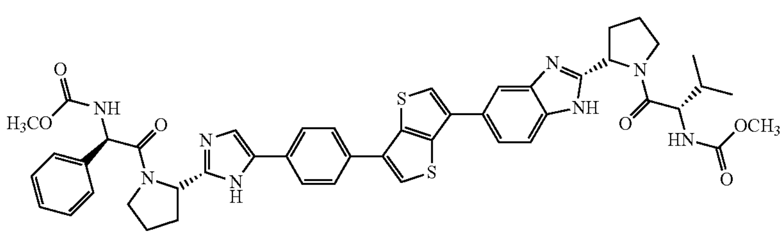 | A" | A" | A" | A" | A" | D |

-continued

| Compound | Structure | EC₅₀ | | | | | CC₅₀ |
|---|---|---|---|---|---|---|---|
| | | 1b | 2a | 3a | 4a | 1a | |
| A173 | 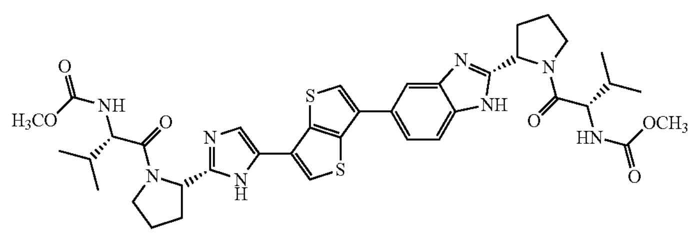 | A″ | B′ | B′ | B′ | C″ | C |
| A176 | 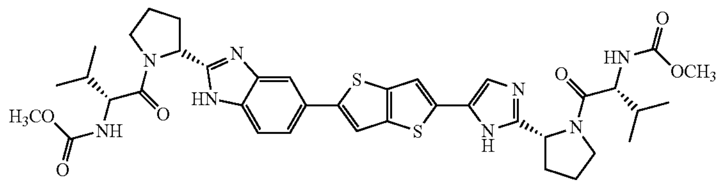 | A″ | A′ | A′ | A′ | A′ | C |
| A194 | 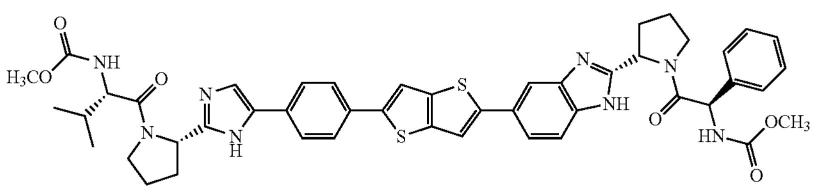 | A″ | B′ | A′ | A″ | A′ | D |
| A215 | 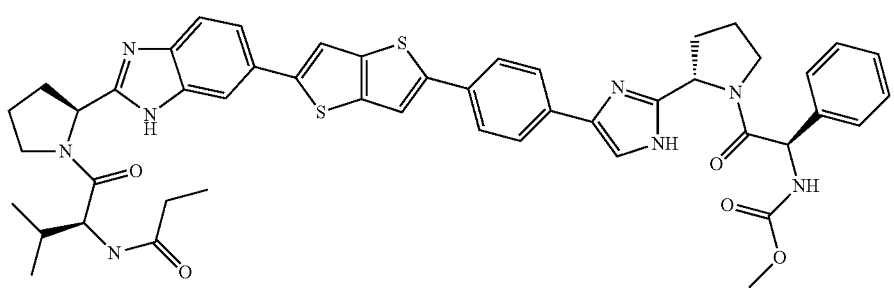 [SMILES: CCC(=O)N[C@H](C(=O)N1CCC[C@H]1c1nc2ccc(-c3cc4sc(-c5ccc(-c6c[nH]c([C@@H]7CCCN7C(=O)[C@H](NC(=O)OC)c7ccccc7)n6)cc5)cc4s3)cc2[nH]1)C(C)C] | A″ | A″ | A″ | A″ | A″ | D |
| A217 | 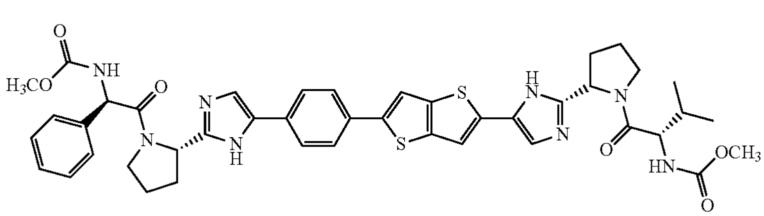 | A″ | A″ | A″ | A″ | A″ | D |

Example 2

Synthesis of (S)-2-methoxycarbonylamino-3-methyl butyric acid 1

L-Valine (S) (0.213 mol) was dissolved in anhydrous tetrahydrofuran (645 mL) with $NaHCO_3$ (0.640 mol) in water (645 mL). Methylchloroformate (0.235 mol) was added and the reaction mixture was stirred at room temperature overnight. The mixture was acidified to pH 3 with 1N HCl. The aqueous layer was extracted with EtOAc. The organic layers were dried over $MgSO_4$, filtered, and concentrated under reduced pressure to give compound 1 as a white solid in 98% yield. $^1$H NMR (DMSO-$d_6$, 400 MHz) δ (ppm) 0.93 (d, J=7.00 Hz, 3H), 1.00 (d, J=7.00 Hz, 3H), 2.23 (m, 1H), 3.70 (s, 3H), 4.33 (m, 1H), 5.26 (brs, 1H), 8.50 (brs, 1H); and MS (ESI, EI$^+$) m/z=176 (MH$^+$).

Example 3

Synthesis of Proline Derivatives 3a and 3b

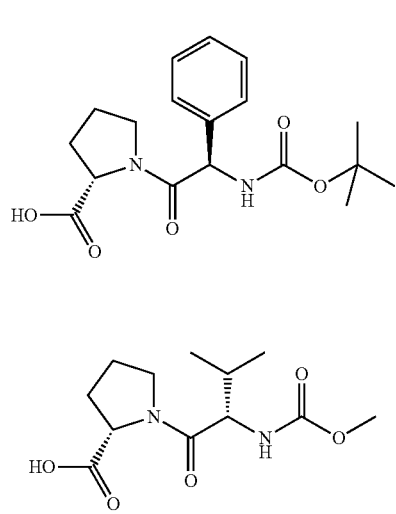

Compounds 3a and 3b were synthesized as shown in Scheme 1.

Preparation of (S,R)-1-(2-tert-butoxycarbonylamino-2-phenylacetyl)-pyrrolidine-2-carboxylic acid benzyl ester 2a. To a solution of Boc-D-α-phenylglycine (2 mmol), L-proline benzyl ester hydrochloride (2.2 mmol), and DIPEA (5 mmol) in dry dichloromethane (10 mL) was added TBTU (2.2 mmol). The reaction mixture was stirred at room temperature overnight. The mixture was concentrated under vacuum and the residue was passed through a SCX-2 column and further chromatographed to yield compound 2a. $^1$H NMR (CDCl$_3$, 400 MHz) δ (ppm) 1.40 (s, 9H), 1.76-1.82 (m, 1H), 1.92-2.07 (m, 3H), 3.09-3.15 (m, 1H), 3.70-3.77 (m, 1H), 4.47-4.51 (m, 1H), 5.16 (d, J=12.35 Hz, 1H), 5.23 (d, J=12.35 Hz, 1H), 5.43 (d, J=7.20 Hz, 1H), 6.12 (d, J=7.20 Hz, 1H), 7.27-7.41 (m, 10H); and MS (ESI, EI$^+$) m/z=439 (MH$^+$).

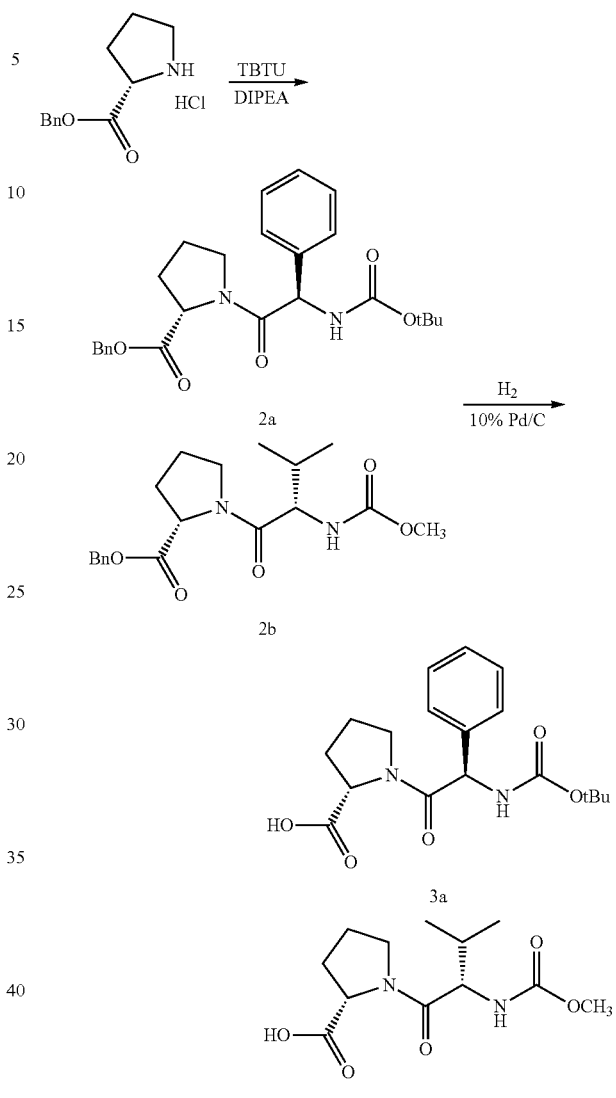

Scheme 1

Preparation of (S,S)-1-(2-methoxycarbonylamino-3-methyl-butyryl)-pyrrolidine-2-carboxylic acid benzyl ester 2b. Compound 2b was synthesized from compound 1 (2 mmol) and L-proline benzyl ester hydrochloride (2.2 mmol), following the procedure as described for compound 2a.

Preparation of (S,R)-1-(2-tert-butoxycarbonylamino-2-phenylacetyl)-pyrrolidine-2-carboxylic acid 3a. A mixture of compound 2a (2 mmol) and Pd/C (20 w %) in ethanol (30 mL) was hydrogenated for 3 hrs at atmospheric pressure. The reaction mixture was filtered off and concentrated in vacuo. The crude was taken in toluene and concentrated again, and then in Et$_2$O/petroleum ether and concentrated once more to give compound 3a as a glassy solid in 62% yield over two steps. MS (ESI, EI$^-$) m/z=347 (MH$^-$).

Preparation of (S,S)-1-(2(S)-methoxycarbonylamino-3-methyl-butyryl)-pyrrolidine-2-(S)-carboxylic acid 3b. Compound 3b was synthesized from compound 2b (2 mmol), following the procedure as described for compound 3a to give compound 3b as an oil in 55% yield over two steps. $^1$H NMR (CDCl$_3$, 400 MHz) δ (ppm) 0.96 (d, J=6.77 Hz, 3H), 1.00 (d, J=6.77 Hz, 3H), 1.99-2.29 (m, 5H), 3.67 (s, 3H), 3.81-3.87

(m, 1H), 4.28-4.32 (m, 1H), 4.58-4.61 (m, 1H), 5.51-5.53 (m, 1H); and MS (ESI, EI⁺) m/z=274.2 (MH⁺).

Example 4

Synthesis of (S,S)-[2-methyl-1-(2-{5-[4-(4,4,5,5-tetramethyl-[1,3,2]dioxaborolan-2-yl)phenyl]-imidazol-2-yl}-pyrrolidine-1-carbonyl)-propyl]-carbamic acid methyl ester 8

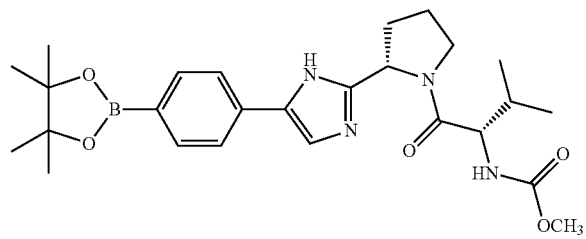

Compound 8 was synthesized as shown in Scheme 2.

Scheme 2

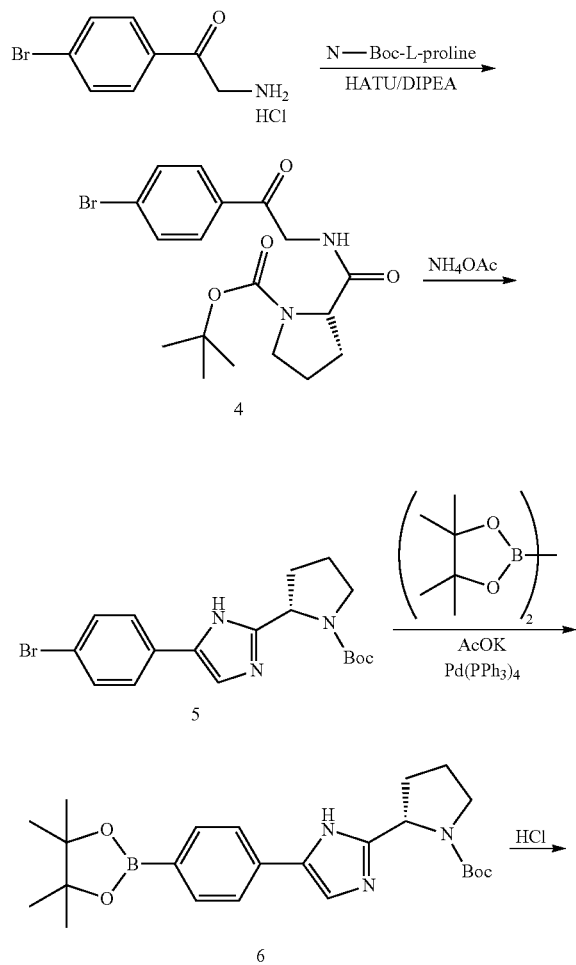

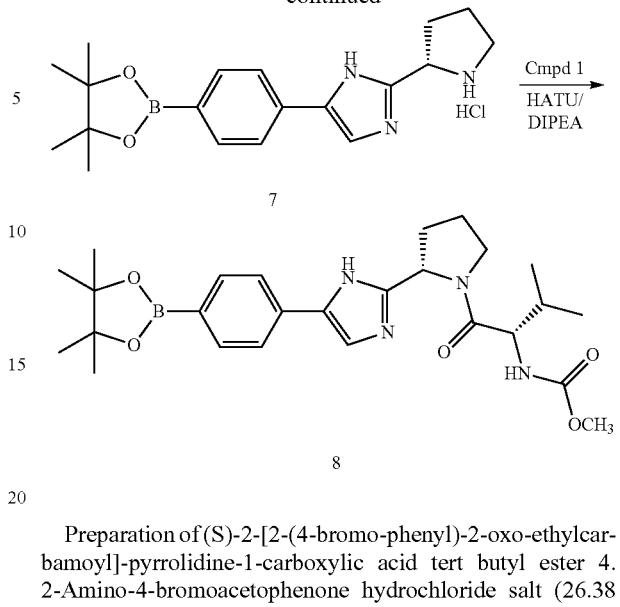

Preparation of (S)-2-[2-(4-bromo-phenyl)-2-oxo-ethylcarbamoyl]-pyrrolidine-1-carboxylic acid tert butyl ester 4. 2-Amino-4-bromoacetophenone hydrochloride salt (26.38 mmol) and N-Boc-L-proline (26.91 mmol) were dissolved in anhydrous dimethylformamide. HATU (28.49 mmol) was added, followed by DIPEA (83.89 mmol). The reaction mixture was stirred at room temperature for 16 hrs. The mixture was then concentrated under vacuum, diluted with EtOAc (250 mL) and water (180 mL). The organic layer was separated, washed sequentially with water (180 mL) and brine (180 mL), dried over $Na_2SO_4$, and concentrated in vacuo. The residue was purified by silica gel chromatography (PE/EtOAc) to give compound 4 as a beige compound in 83% yield. ¹H NMR (DMSO-$d_6$, 400 MHz) δ (ppm) 1.32 (s, 9H), 1.80 (m, 3H), 2.09 (m, 1H), 3.35 (m, 1H), 4.14 (m, 1H), 4.55 (m, 2H), 7.74 (d, J=7.90 Hz, 2H), 7.91 (d, J=7.90 Hz, 2H), 8.20 (brs, 1H).

Preparation of (S)-2-[5-(4-bromophenyl)-imidazol-2-yl]-pyrrolidine-1-carboxylic acid tert-butyl ester 5. Compound 4 (19.16 mmol) and NH₄OAc (95.75 mmol) were mixed together in xylene (96 mL). The reaction mixture was stirred at 140° C. for 2 hrs. The reaction mixture was then cooled down to room temperature and concentrated under vacuum. The residue was diluted with EtOAc (20 mL) and water (20 mL). A saturated NaHCO₃ solution was added. The organic layers were separated, washed sequentially with water (180 mL) and brine (180 mL), dried over $Na_2SO_4$, and concentrated in vacuo. The residue was purified by silica gel chromatography (PE/EtOAc) to give compound 5 as an orange solid in 76% yield. ¹H NMR (DMSO-$d_6$, 400 MHz) δ (ppm) 1.38 (s, 9H), 1.84-2.31 (m, 4H), 3.29 (s, 2H), 3.51 (brs, 1H), 4.75 (m, 1H), 7.74 (d, J=7.90 Hz, 2H), 7.91 (d, J=7.90 Hz, 2H), 12.18 (brs, 1H).

Preparation of (S) 2-{5-[4-(4,4,5,5-tetramethyl-[1,3,2]-dioxaboran-2-yl)-phenyl]-imidazol-2-yl}-pyrrolidine-1-carboxylic acid tert butyl ester 6. Compound 5 (5.94 mmol), bis(pinacolato)diboron (11.89 mmol), potassium acetate (14.87 mmol), and tetrakis triphenylphosphine palladium (0.24 mmol) were stirred in dry degassed dioxane (60 mL) in a pressure reactor at 90° C. under nitrogen for 16 hrs. The mixture was concentrated in vacuo. The crude material was dissolved in dichloromethan (100 mL), and washed sequentially with water (50 mL) and saturated sodium bicarbonate solution (10 mL). The dried organic layers were concentrated in vacuo and the residue was purified by silica gel chromatography (DCM/MeOH) to give compound 6 as a yellow solid in 92% yield. $^1$H NMR (DMSO-$d_6$, 400 MHz) δ (ppm) 1.20 (m, 21H), 1.77-2.30 (m, 4H), 3.52 (brs, 1H), 4.70-4.80 (m, 1H), 7.60-7.75 (m, 5H), 11.87 (s, 1H); and MS (ESI, EI$^+$) m/z=440 (MH$^+$).

Preparation of (S)-2-{5-[4-(4,4,5,5-tetramethyl-[1,3,2]-dioxaboran-2-yl)-phenyl]-imidazol-2-yl}-pyrrolidine hydrochloride salt 7. Compound 6 (27.3 mol) was dissolved in dioxane (20 mL) and a solution of HCl (4N) in dioxane (55 mL) was added. The reaction mixture was stirred at room temperature for 1 hr and concentrated under vacuum to give compound 7 as a white solid in a quantitative yield. $^1$H NMR (DMSO-$d_6$, 400 MHz) δ (ppm) 1.20 (m, 12H), 1.77-2.30 (m, 4H), 3.52 (brs, 1H), 4.70-4.80 (m, 1H), 7.60-7.75 (m, 5H), 11.87 (s, 1H).

Preparation of (S,S)-[2-methyl-1-(2-{5-[4-(4,4,5,5-tetramethyl-[1,3,2]dioxaborolan-2-yl)phenyl]-imidazol-2-yl}-pyrrolidine-1-carbonyl)-propyl]-carbamic acid methyl ester 8. Compound 7 (30.04 mmol) was dissolved in anhydrous dimethylformamide (200 mL) with DIPEA (19 mL) and HATU (31.41 mmol). The reaction mixture was stirred at room temperature for 30 min. Compound 1 (27.3 mmol) was then added and the mixture was stirred at room temperature for additional 2 hrs. Water and EtOAc were added. The organic layers were separated, dried over MgSO$_4$, filtered, and concentrated under vacuum. The residue was purified by silica gel chromatography (PE/EtOAc) to give compound 8 as a beige solid in 70% yield. MS (ESI, EI$^+$) m/z=497 (MH$^+$).

Example 5

Synthesis of Compounds A1 and A2

Compounds A1 and A2 were synthesized as shown in Scheme 3.

Preparation of 2-bromoimidazo[2,1-b]thiazole-6-carbonyl azide 9. Thionyl chloride (0.33 mol) was added to 2-bromoimidazo[2,1-b]thiazole-6-carboxylic acid (13.1 mmol). The reaction mixture was stirred at 85° C. during 3 hrs. The mixture was then concentrated under vacuum and the residue was taken in acetone (40 mL). The sodium azide (14.4 mmol) in water (5.2 mL) was added in one portion at 0° C. and the mixture was stirred at 0-10° C. for 45 min. Water was added, and the solid filtered off and washed with water and then with a mixture of water/acetone (50/50). The solid was dried in vacuo to give compound 9 as a beige solid in 80% yield. $^1$H NMR (DMSO-$d_6$, 400 MHz) δ (ppm) 8.27 (s, 1H), 8.49 (s, 1H); and MS (ESI, EI$^+$) m/z=272.05-274.07 (MH$^+$).

Scheme 3

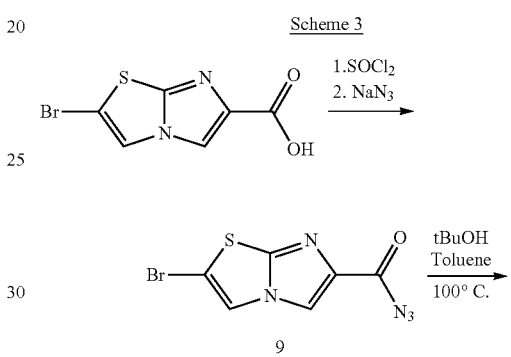

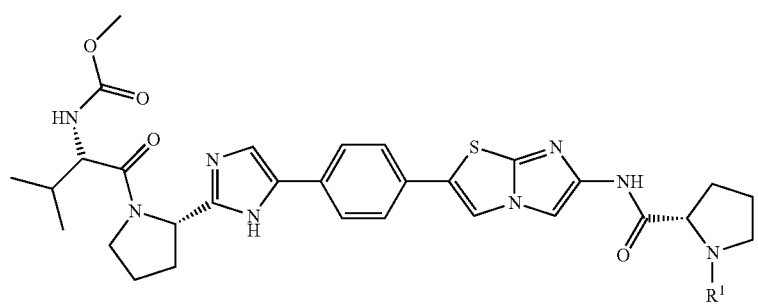

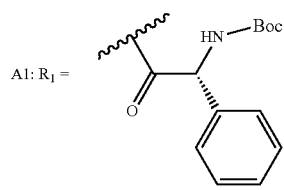

A1: $R_1$ =

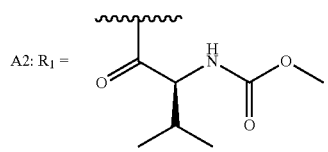

A2: $R_1$ =

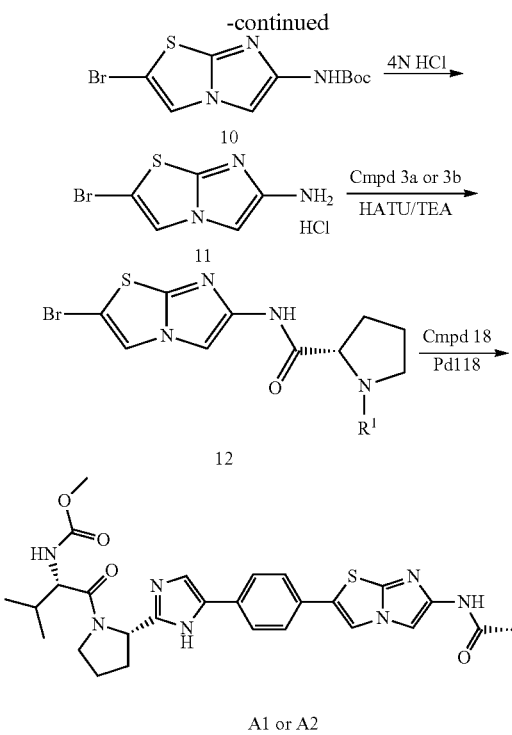

Preparation of (2-bromo-imidazo[2,1-b]thiazol-6-yl)-carbamic acid tert-butyl ester 10. A mixture of compound 9 (12.86 mmol) in a mixture of toluene and tent-butanol (v/v; 1/1; 42 mL) in a microwaves reactor was heated at 100° C. under microwaves irradiations for 45 min. The reaction mixture was concentrated under vacuum and the residue was purified by chromatography on a silica gel column (petroleum ether/ethyl acetate) to give compound 10 as a beige solid in 23%. $^1$H NMR (CDCl$_3$, 400 MHz) δ (ppm) 1.52 (s, 9H), 7.17 (brs, 1H), 7.43 (s, 1H), 7.57 (brs, 1H); and MS (ESI, EI$^+$) m/z=318-320 (MH$^+$).

Preparation of 2-bromo-imidazo[2,1-b]thiazol-6-ylamine hydrochloride 11. To a solution of 4M HCl in dioxane (2 mL) was added compound 10 (0.13 mmol). The reaction mixture was stirred at room temperature for 4 hrs. The mixture was concentrated under vacuum and the solid was dried in vacuo to give compound 11 as a white solid in quantitative yield. $^1$H NMR (CDCl$_3$, 400 MHz) δ (ppm) 5.26 (s, 2H), 8.20 (s, 1H), 9.92 (brs, 1H), 10.05 (brs, 1H); and MS (ESI, EI$^+$) m/z=218.02-220.03 (MH$^+$).

Preparation of (S,R)-{2-[2-(2-bromo-imidazo[2,1-b]thiazol-6-ylcarbamoyl)-pyrrolidin-1-yl]-2-oxo-1-phenyl-ethyl}-carbamic acid tert-butyl ester 12a. To a mixture of compound 11 (0.137 mmol), compound 3a (0.206 mmol), and HATU (0.206 mmol) in dimethylformamide (1.5 mL) was added TEA (0.55 mmol) dropwise. The reaction mixture was stirred at 40° C. for 4 hrs. The solvent was removed under reduced pressure and the residue dissolved in a mixture of dichloromethane/methanol (9/1). This mixture was passed through a SCX-2 column and the column was washed three times with the same eluent. The filtrate was concentrated and the residue was purified by chromatography on a silica gel column to give compound 12a as a yellow orange solid in 18% yield. MS (ESI, EI$^+$) m/z=548.24-550.20 (MH$^+$).

Preparation of (S,S)-{1-[2-(2-bromo-imidazo[2,1-b]thiazol-6-ylcarbamoyl)-pyrrolidine-1-carbonyl]-2-methyl-propyl}-carbamic acid methyl ester 12b. Compound 12b was synthesized from compound 11 (0.33 mmol) and compound 3b (0.495 mmol), following the procedure as described for compound 12a, to give compound 12b as a yellow oil in 44% yield. $^1$H NMR (DMSO-d$_6$, 400 MHz) δ (ppm) 0.93 (dd, 6H), 1.70-2.00 (m, 4H), 2.01-2.10 (m, 1H), 3.51 (s, 3H), 3.59 (m, 1H), 3.82 (m, 1H), 4.00 (t, 1H), 4.51 (dd, 1H), 7.34 (d, 1H), 7.80 (s, 1H), 8.15 (s, 1H), 10.64 (s, 1H); MS (ESI, EI$^+$) m/z=472-474 (MH$^+$).

Preparation of (S,S,S,R)-[1-(2-{5-[4-(6-{[1-(2-tert-butoxycarbonylamino-2-phenyl-acetyl)-pyrrolidine-2-carbonyl]-amino}imidazo[2,1-b]thiazol-2-yl)-phenyl]-1H-imidazol-2-yl}pyrrolidine-1-carbonyl)-2-methyl-propyl]-carbamic acid methyl ester A1. Compound 12a (0.091 mmol), compound 8 (0.182 mmol), and 1,1'-bis(di-tert-butylphosphino)ferrocene palladium dichloride (0.03 mmol) were added to a solution of dioxane (0.7 mL) and 1M NaHCO$_3$ in water (0.273 mmol). The reaction mixture was irradiated at 120° C. for 30 min. The mixture was diluted in ethyl acetate and washed sequentially with water and brine. The organic layer was dried, filtered, and concentrated under reduced pressure. The residue was purified by semi-preparative HPLC to give compound A1 as a white solid in 17% yield. $^1$H NMR (CDCl$_3$, 400 MHz) δ (ppm) 0.87-0.90 (m, 6H), 1.03-1.09 (m, 1H), 1.41 (s, 9H), 1.79-1.91 (m, 3H), 1.92-2.15 (m, 4H), 2.16-2.27 (m, 1H), 2.29-2.45 (m, 2H), 3.03-3.23 (m, 2H), 3.70 (s, 3H), 3.72-3.88 (m, 2H), 4.31-4.36 (m, 1H), 4.71-4.75 (m, 1H), 5.21-5.28 (m, 1H), 6-6.04 (m, 1H), 7.31-7.50 (m, 8H), 7.53-7.61 (m, 1H), 7.75-7.85 (m, 3H), 9.64 (s, 1H), 10.43 (brs, 1H); MS (ESI, EI$^+$) m/z=838.61 (MH$^+$).

Preparation of (S,S,S,S)-(1-{2-[2-(4-{2-[1-(2-methoxycarbonylamino-3-methyl-butyryl)-pyrrolidin-2-yl]-3H-imidazol-4-yl}-phenyl)-imidazo[2,1-b]thiazol-6-ylcarbamoyl]-pyrrolidine-1-carbonyl}-2-methyl-propyl)-carbamic acid methyl ester A2. Compound A2 was synthesized from compound 12b (0.072 mmol) and compound 8 (0.094 mmol), following the procedure as described for compound A1, to give compound A2 as a white solid. $^1$H NMR (DMSO-d$_6$, 400 MHz) δ (ppm) 0.85-0.95 (m, 12H), 1.76-2.03 (m, 7H), 2.06-2.18 (m, 3H), 3.51 (s, 6H), 3.58-3.65 (m, 1H), 3.67-3.86 (m, 3H), 3.99-4.03 (m, 1H), 4.21-4.31 (m, 1H), 4.53-4.57 (m, 1H), 5.04-5.08 (m, 1H), 7.28-7.37 (m, 1H), 7.52-7.71 (m, 3H), 7.76-7.84 (m, 3H), 8.35 (s, 1H), 8.53 (s, 1H), 10.64 (s, 1H), 11.81 (s, 1H); MS (ESI, EI$^+$) m/z=762.21 (MH$^+$).

Example 6

Synthesis of (S,R)-{2-oxo-1-phenyl-2-[3-(2-phenyl-imidazo[2,1-b]thiazol-6-ylcarbamoyl)-morpholin-4-yl]-ethyl}-carbamic acid tert-butyl ester A22

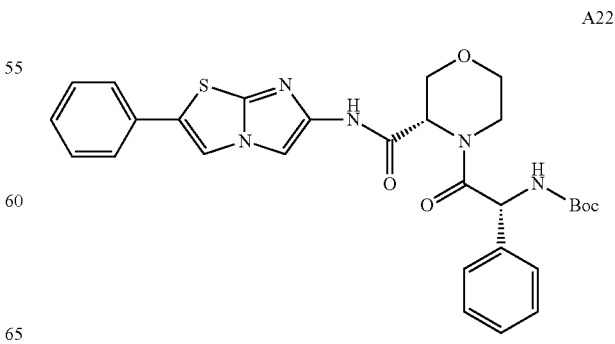

Compound A22 was synthesized as shown in Scheme 4.

Preparation of (S)-3-(2-bromo-imidazo[2,1-b]thiazol-6-ylcarbamoyl)-morpholine-4-carboxylic acid tert-butyl ester 14. Compound 14 was synthesized from compound 11 (0.286 mmol) and the (S)-4-morpholine-3-carboxylic acid (0.043 mmol), following the procedure as described for compound 12a to give compound 14 as a yellow oil in 54% yield. MS (ESI, EI$^+$) m/z=431.30-433.25 (MH$^+$).

Preparation of (S)-3-(2-phenyl-imidazo[2,1-b]thiazol-6-ylcarbamoyl)-morpholine-4-carboxylic acid tert-butyl ester 15. Compound 15 was synthesized from compound 14 (0.155 mmol) and phenylboronic acid (0.492 mmol), following the procedure as described for compound A1 to give compound 15 as a yellow gum in 38% yield. MS (ESI, EI$^+$) m/z=429 (MH$^+$).

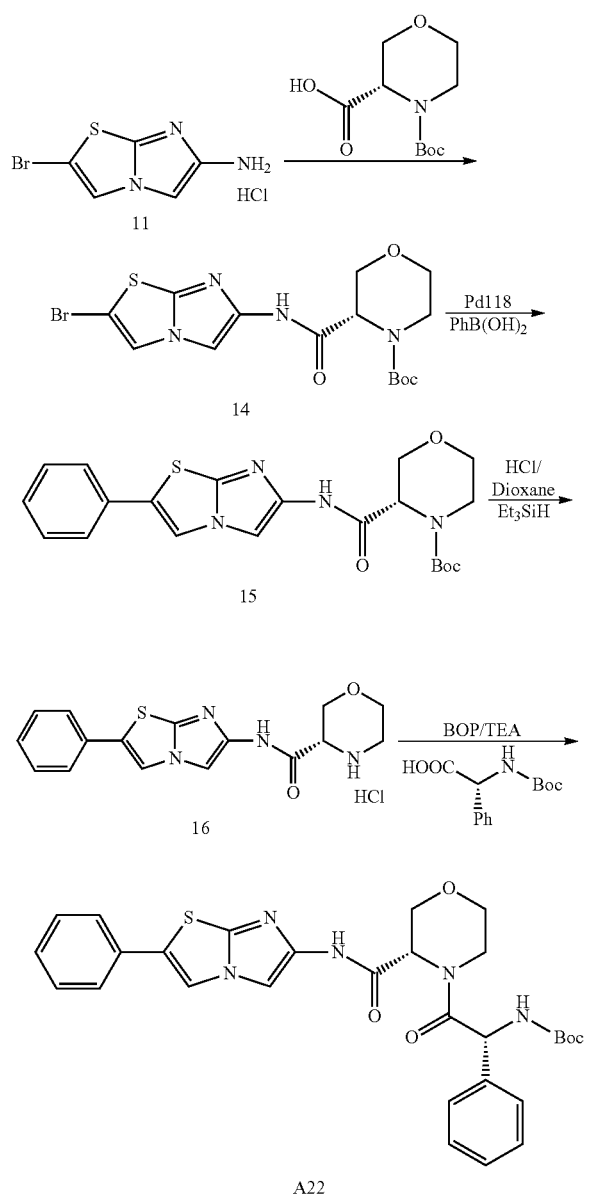

Preparation of (S)-morpholine-3-carboxylic acid (2-phenyl-imidazo[2,1-b]thiazol-6-yl)-amide, hydrochloride 16. Compound 15 (0.06 mmol) was added to a mixture of tetrahydrofuran (0.7 mL) and 4M HCl in dioxane (0.7 mL). Et$_3$SiH (0.408 mmol) was added and the reaction mixture was stirred at room temperature for 4 hrs. The reaction mixture was concentrated under reduced pressure to give compound 16 as an orange solid in quantitative yield. MS (ESI, EI$^+$) m/z=329.19 (MH$^+$).

Preparation of (S,R)-{2-oxo-1-phenyl-2-[3-(2-phenyl-imidazo[2,1-b]thiazol-6-ylcarbamoyl)-morpholin-4-yl]-ethyl}-carbamic acid tert-butyl ester A22. Compound 16 (0.063 mmol), Boc-D-α-phenylglycine (0.126 mmol), and BOP (0.126) were added to dichloromethane (1.9 mL). Triethylamine (3.15 mmol) was added dropwise and the reaction mixture was stirred at room temperature overnight. The mixture was diluted in dichloromethane, washed sequentially with saturated solution of NaHCO$_3$, water, and brine. The organic layers were gathered, dried, filtered, and concentrated under reduced pressure. The residue was purified by semi-preparative HPLC to give compound A22 as a white solid in 6% yield. $^1$H NMR (CDCl$_3$, 400 MHz) δ (ppm) 1.41 (s, 2H), 1.44 (s, 7H), 1.83-2.09 (m, 1H), 2.64-3.90 (m, 4H), 4.33-4.68 (m, 1H), 5.19-6.09 (m, 2H), 7.29-7.45 (m, 9H), 7.50-7.582 (m, 2H), 7.60-7.64 (m, 1H); MS (ESI, EI$^+$) m/z=562.29 (MH$^+$).

Example 7

Synthesis of (S,R)-{2-oxo-1-phenyl-2-[2-(2-phenyl-ethynyl-imidazo[2,1-b]thiazol-6-ylcarbamoyl)-pyrrolidin-1-yl]-ethyl}-carbamic acid tert-butyl ester compound A23

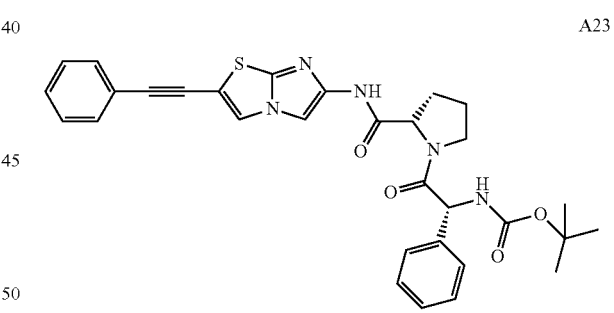

In a microwaves reactor were added compound 12a (0.091 mmol), phenylacetylene (0.182 mmol), copper iodide (0.005 mmol), and 1,1'-bis(di-tert-BP)ferrocene palladium dichloride (0.0091 mmol) in dimethylformamide (0.5 mL), followed by 1,1,3,3-tetramethylguanidine (0.182 mmol). The reaction mixture was irradiated at 80° C. for 30 min. The reaction mixture was then diluted in ethyl acetate and washed sequentially with water and brine. The organic layer was dried, filtered, and concentrated under reduced pressure. The residue was purified by semi-preparative HPLC to give compound A23 as an off-white solid in 52% yield. $^1$H NMR (CDCl$_3$, 400 MHz) δ (ppm) 1.39 (s, 9H), 1.83-2.11 (m, 4H), 3.10-3.27 (m, 1H), 3.74-3.86 (m, 1H), 5.43-5.48 (m, 1H), 5.98-6.02 (m, 1H), 7.31-7.44 (m, 10H), 7.49-7.52 (m, 2H), 9.88 (brs, 1H); and MS (ESI, EI$^+$) m/z=570.35 (MH$^+$).

Example 8

Synthesis of (S,R)-{2-oxo-1-phenyl-2-[2-(2-phenyl-imidazo[2,1-b]thiazol-6-ylcarbamoyl)-pyrrolidin-1-yl]-ethyl}-carbamic acid tert-butyl ester A24

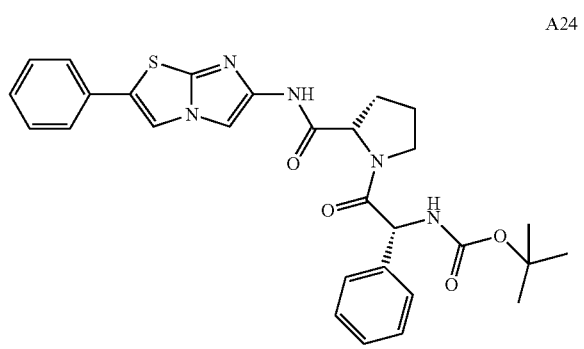

A24

Compound A24 was synthesized from compound 12a (0.053 mmol) and phenylboronic acid (0.16 mmol), following the procedure as described for compound A1, to give compound A24 as a white solid in 6% yield. $^1$H NMR (CDCl$_3$, 400 MHz) δ (ppm) 1.40 (s, 9H), 1.82-1.91 (m, 1H), 2.01-2.13 (m, 1H), 2.35-2.42 (m, 1H), 3.13-3.21 (m, 1H), 3.77-3.84 (m, 1H), 4.70-4.72 (m, 1H), 5.46 (d, J=7.08 Hz, 1H), 6.04 (d, J=7.08 Hz, 1H), 7.31-7.46 (m, 11H), 7.63 (s, 1H), 7.89 (s, 1H), 9.88 (brs, 1H); and MS (ESI, EI$^+$) m/z=546.23 (MH$^+$).

Example 9

Synthesis of Compound A26

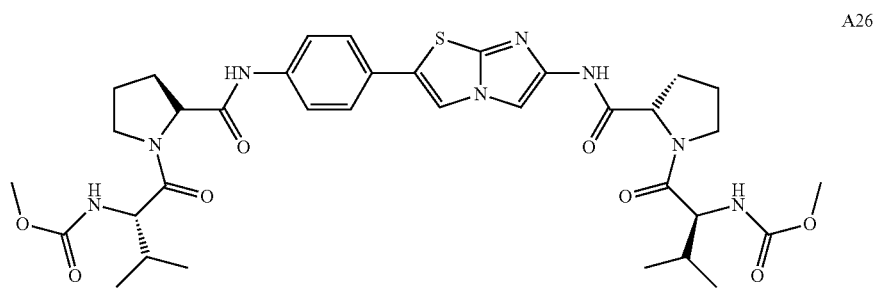

A26

Compound A26 was synthesized as shown in Scheme 5.
Preparation of (S,S)-(1-{2-[2-(4-amino-phenyl)-imidazo[2,1-b]thiazol-6-ylcarbamoyl]-pyrrolidine-1-carbonyl}-2-methyl-propyl)-carbamic acid methyl ester A25. Compound A25 was synthesized from 12b (0.318 mmol) and 4-aminophenylboronic acid (0.477 mmol), following the procedure as described for compound A1, to give compound A25 as a white solid in 29%. MS (ESI, EI$^+$) m/z=485.15 (MH$^+$).

Scheme 5

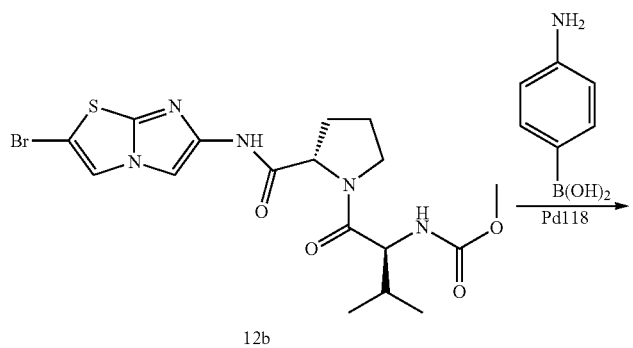

12b

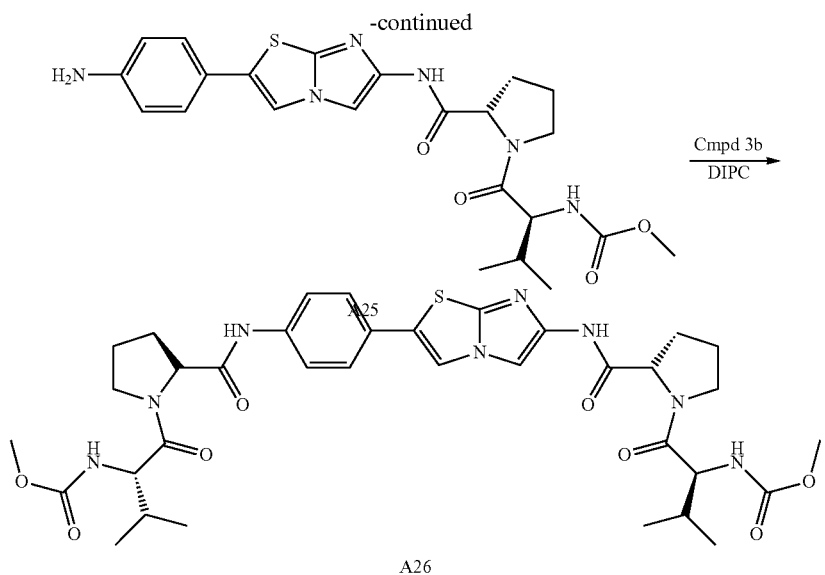

A26

Preparation of (S,S,S,S)-(1-{2-[4-(6-{[1-(2-methoxycarbonylamino-3-methyl-butyryl)-pyrrolidine-2-carbonyl]-amino}-imidazo[2,1-b]thiazol-2-yl)-phenylcarbamoyl]-pyrrolidine-1-carbonyl}-2-methyl-propyl)-carbamic acid methyl ester A26. To a solution of compound A25 (0.091 mmol) and compound 3b (0.109 mmol) in tetrahydrofuran (1 mL) was added 1,3-diisopropylcarbodiimide (0.146 mmol). The reaction mixture was stirred at room temperature during 3 days. The mixture was filtered through an isolute SPE SCX-2 column and after different washings with dichloromethane and dichloromethane/methanol, the expected compound was removed with NH$_3$/methanol. The filtrate was evaporated under reduced pressure and purified by preparative HPLC to give compound A26 as a white solid in 21% yield. $^1$H NMR (CDCl$_3$, 400 MHz) δ (ppm) 0.88 (d, J=6.56 Hz, 6H), 0.94 (d, J=6.56 Hz, 6H), 1.81-2.02 (m, 8H), 2.08-2.19 (m, 2H), 3.52 (s, 6H), 3.58-3.66 (m, 2H), 3.79-3.84 (m, 2H), 3.99-4.05 (m, 2H), 4.43-4.46 (m, 1H), 4.52-4.55 (m, 1H), 7.32 (d, J=8.15 Hz, 2H), 7.53 (d, J=8.55 Hz, 2H), 7.66 (d, J=8.55 Hz, 2H), 7.77 (s, 1H), 8.26 (s, 1H), 10.21 (s, 1H), 10.61 (s, 1H); and MS (ESI, EI$^+$) m/z=739.30 (MH$^+$).

Example 10

Synthesis of (S,S) [2-(4-{2-[1-(2-methoxycarbonylamino-3-methyl-butyryl)-pyrrolidin-2-yl]-3H-imidazol-4-yl}-phenyl)-imidazo[2,1-b]thiazol-6-yl]-carbamic acid tert-butyl ester A35

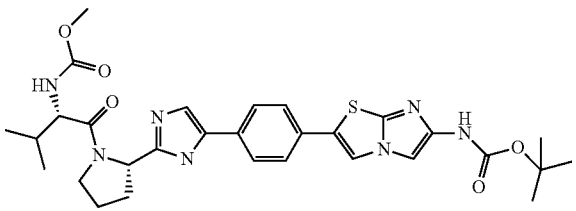

A35

Compound A35 was synthesized from compound 10 (0.126 mmol) and compound 8 (0.164 mmol), following the procedure as described for compound A1, as a white lyophilized solid in 22% yield. MS (ESI, EI$^+$) m/z=608.35 (MH$^+$).

Example 11

Synthesis of (S,S,S)-2-[2-(4-{2-[1-(2-methoxycarbonylamino-3-methyl-butyryl)-pyrrolidin-2-yl]-3H-imidazol-4-yl}-phenyl)-imidazo[2,1-b]thiazol-6-ylcarbamoyl]-pyrrolidine-1-carboxylic acid tert-butyl ester A36

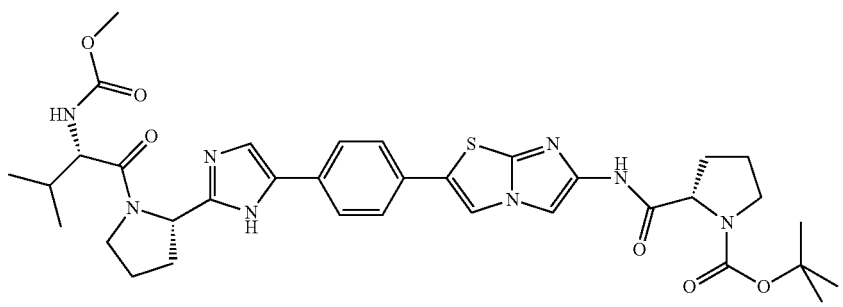

A36

To a solution of HCl in dioxane (4M, 0.1 mL) was added compound A35 (0.023 mmol) and the reaction mixture was stirred at room temperature for 3 hrs. The mixture was concentrated under reduced pressure. To the residue dissolved in dimethylformamide (0.230 mL) was added under nitrogen N-Boc-proline (0.035 mmol), HATU (0.035 mmol), and triethylamine (0.092 mmol). The reaction mixture was stirred at room temperature overnight. The mixture was diluted in ethyl acetate and washed sequentially with saturated $NaHCO_3$, HCl (1N), and water. The organic layer was dried, filtered, and concentrated under reduced pressure. The residue was purified by semi-preparative HPLC to give compound A38 as a white lyophilized solid in 16% yield. $^1$H NMR (DMSO-$d_6$, 400 MHz) δ (ppm) 0.82 (d, 3H), 0.88 (d, 3H), 1.24 (s, 6H), 1.38 (s, 3H), 1.70-2.00 (m, 6H), 2.10 (m, 3H), 3.31 (m, 1H), 3.41 (m, 1H), 3.52 (s, 3H), 3.79 (m, 2H), 4.00 (m, 1H), 4.28 (m, 1H), 5.08 (m, 1H), 7.29 (m, 1H), 7.52 (m, 3H), 7.81 (m, 2H), 8.36 (s, 1H), 10.61 (s, 1H), 10.66 (s, 1H), 11.84 (s, 1H); MS (ESI, EI$^+$) m/z=705.38 (MH$^+$).

Example 12

Synthesis of (S,S)-[4-(6-{[1-(2-tert-butoxycarbonylamino-2-phenyl-acetyl)-pyrrolidine-2-carbonyl]-amino}-imidazo[2,1-b]thiazol-2-yl)-phenyl]-carbamic acid tert-butyl ester A37

Compound A37 was synthesized as shown in Scheme 6.

Preparation of (S,S)-1-(2-tert-butoxycarbonylamino-2-phenyl-acetyl)-pyrrolidine-2-carboxylic acid benzyl ester 21. Compound 21 was synthesized from Boc-L-phenylglycine and L-proline benzyl ester hydrochloride, following the procedure as described for compound 2a, as a white crystallized solid. MS (ESI, EI$^+$) m/z=439 (MH$^+$).

Preparation of (S,S)-1-(2-tert-butoxycarbonylamino-2-phenyl-acetyl)-pyrrolidine-2-carboxylic acid 22. Compound 22 was synthesized from compound 21, following the procedure as described for compound 3a, as a foam. MS (ESI, EI$^-$) m/z=347 (MH$^-$).

Preparation of (S,S) {2-[2-(2-bromo-imidazo[2,1-b]thiazol-6-ylcarbamoyl)-pyrrolidin-1-yl]-2-oxo-1-phenyl-ethyl}-carbamic acid tert-butyl ester 23. Compound 23 was synthesized from compound 11 (0.471 mmol) and compound 22 (0.707 mmol), following the procedure as described for compound 12a. The reaction mixture was stirred at room temperature overnight. The solvent was removed under reduced pressure and the residue was dissolved in ethyl acetate before washing sequentially with $Na_2CO_3$, HCl (0.5N), and brine. The organic layers were dried, filtered, and concentrated under reduced pressure. The crude was purified by chromatography on a silica gel column to give compound 23 as a yellow solid in 45% yield. MS (ESI, EI$^+$) m/z=548.07-550.02 (MH$^+$).

A37

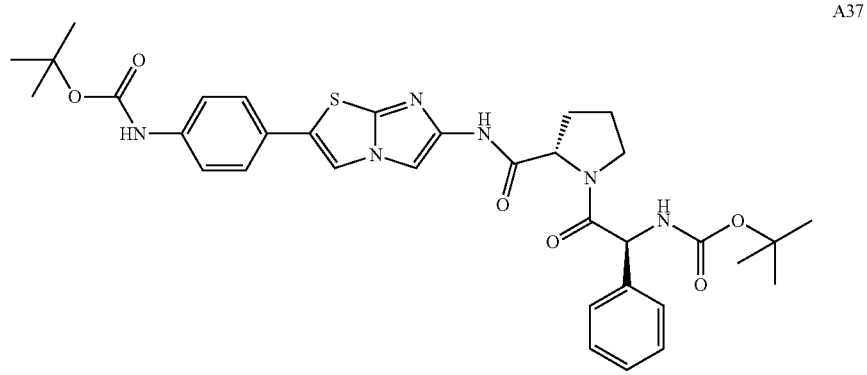 [SMILES: CC(C)(C)OC(=O)Nc1ccc(-c2cn3cc(NC(=O)[C@@H]4CCCN4C(=O)[C@@H](NC(=O)OC(C)(C)C)c4ccccc4)nc3s2)cc1]

Scheme 6

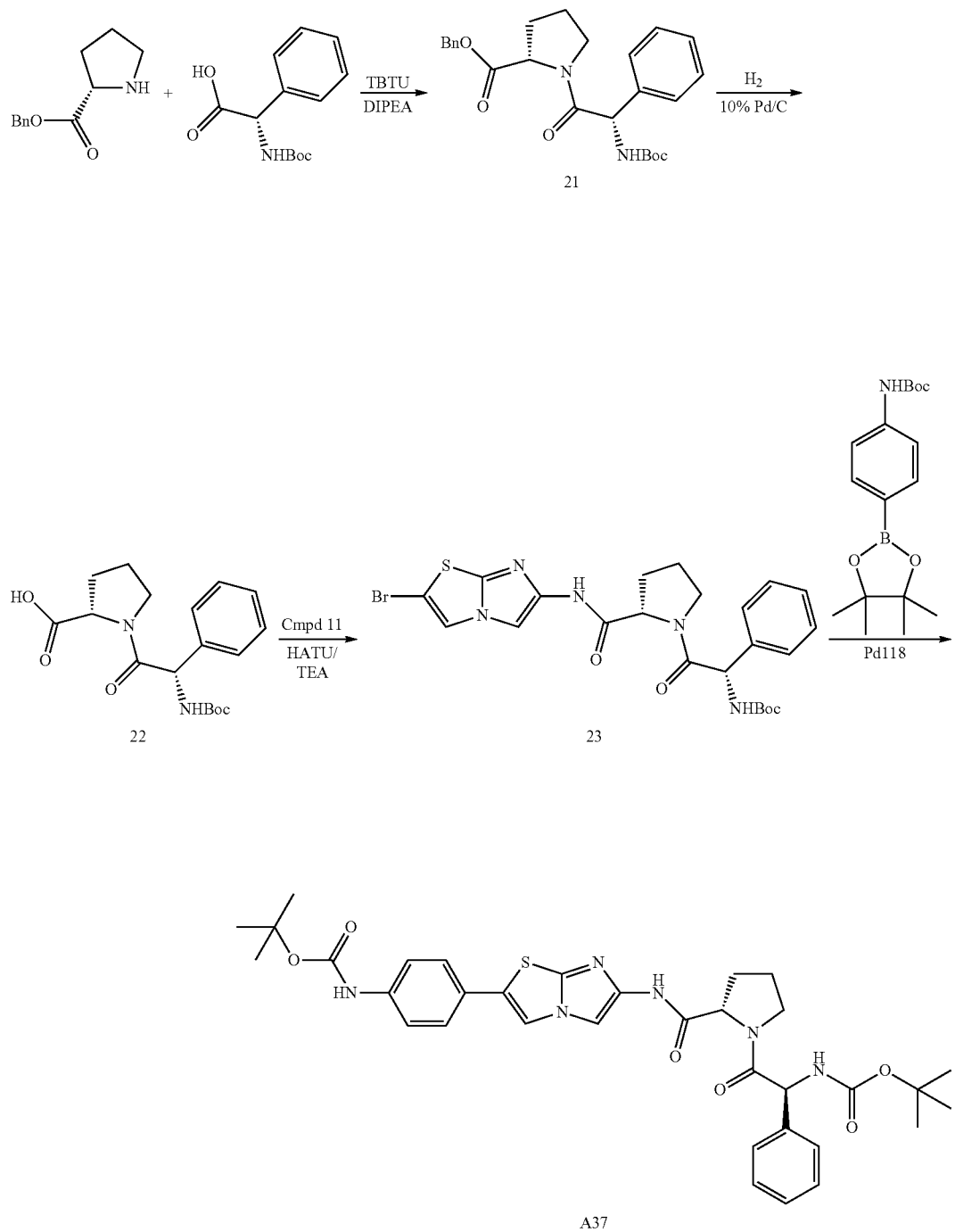

Preparation of (S,S)-[4-(6-{[1-(2-tert-butoxycarbonylamino-2-phenyl-acetyl)-pyrrolidine-2-carbonyl]-amino}-imidazo[2,1-b]thiazol-2-yl)-phenyl]-carbamic acid tert-butyl ester A37. Compound A37 was synthesized from compound 23 (0.100 mmol) and 4-(Boc-amino)benzeneboronic acid pinacol ester (0.150 mmol), following the procedure as described for compound A1, as a white lyophilized powder in 5% yield. MS (ESI, EI$^+$) m/z=661.27 (MH$^+$).

Example 13

Synthesis of (S,S,S,S)-[1-(2-{5-[4-(6-{[1-(2-tert-butoxycarbonylamino-2-phenyl-acetyl)-pyrrolidin-2-carbonyl]-amino}-imidazo[2,1-b]thiazol-2-yl)-phenyl]-1H-imidazol-2-yl}pyrrolidine-1-carbonyl)-2-methyl-propyl]-carbamic acid methyl ester A38

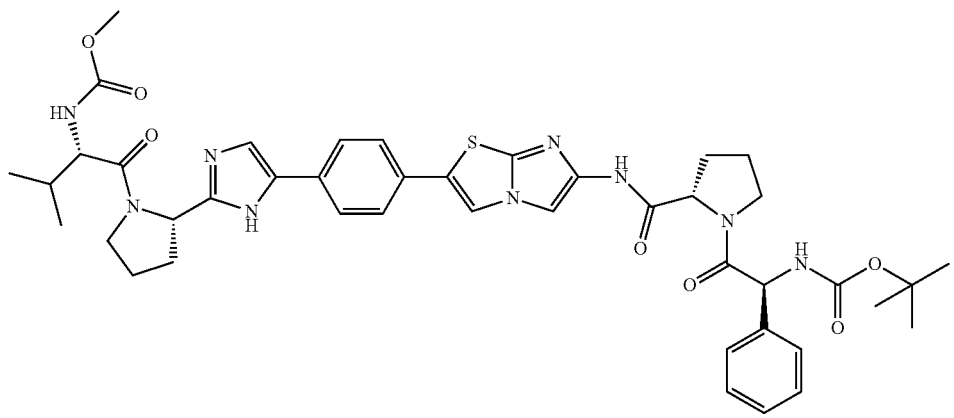

Compound A38 was synthesized from compound 23 (0.091 mmol) and compound 8 (0.137 mmol), following the procedure as described for compound A1 (reaction time=1 hr), as a white lyophilized powder in 10% yield. MS (ESI, EI$^+$) m/z=838.39 (MH$^+$).

Example 14

Synthesis of (S,S,S)-[1-(2-{5-[4-(6-{[1-(2-tert-butoxycarbonylamino-acetyl)-pyrrolidin-2-carbonyl]-amino}-imidazo[2,1-b]thiazol-2-yl)-phenyl]-1H-imidazol-2-yl}-pyrrolidine-1-carbonyl)-2-methyl-propyl]-carbamic acid methyl ester A39

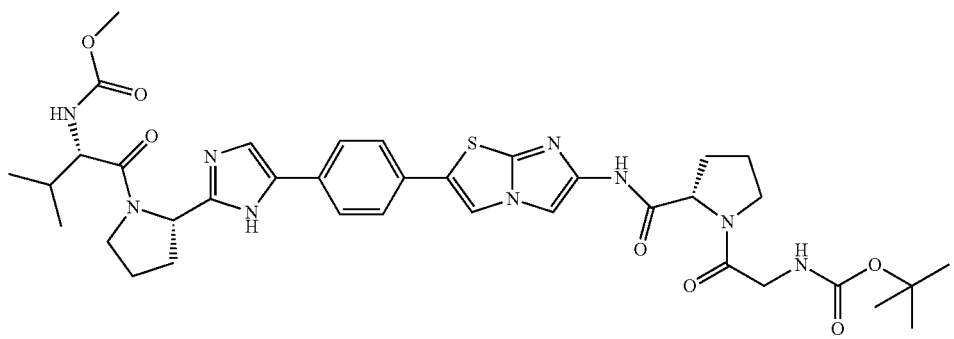

Compound A39 was synthesized as shown in Scheme 7.

Preparation of (S)-1-(2-tert-butoxycarbonylamino-acetyl)-pyrrolidine-2-carboxylic acid benzyl ester 26. Compound 26 was synthesized from N-Boc-glycine and L-proline benzyl ester hydrochloride, following the procedure as described for compound 2a, as a white crystallized solid. MS (ESI, EI$^+$) m/z=363 (MH$^+$).

Scheme 7

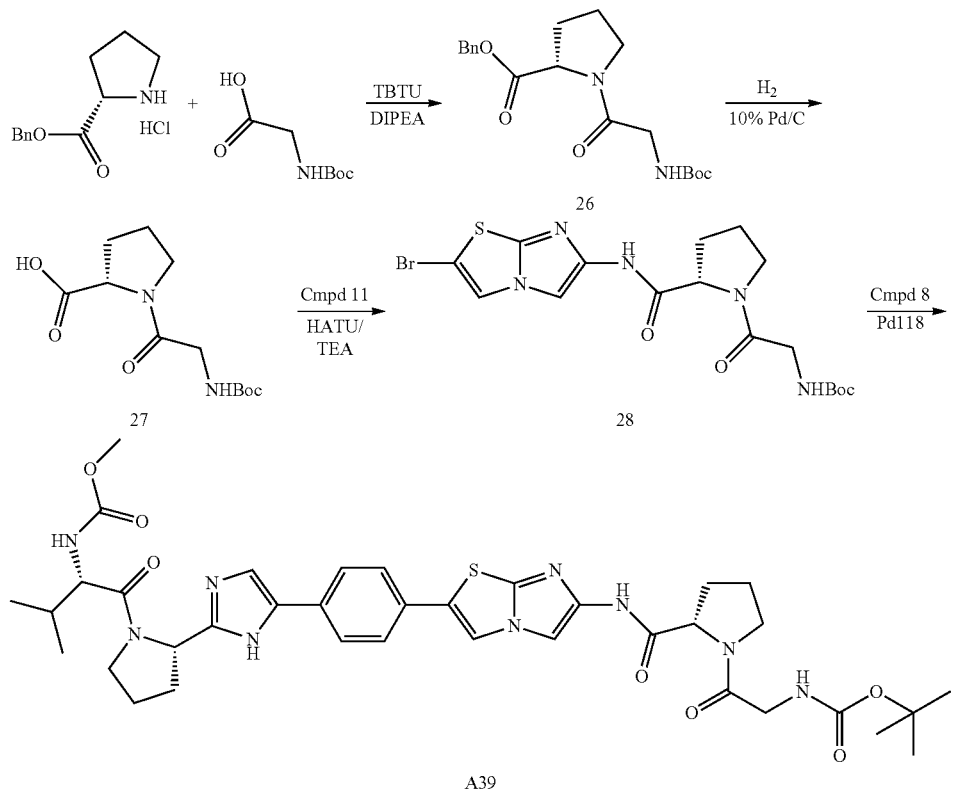

Preparation of (S)-1-(2-tert-butoxycarbonylamino-acetyl)-pyrrolidine-2-carboxylic acid 27. Compound 27 was synthesized from compound 26, following the procedure as described for compound 3a, as a white solid. MS (ESI, EI⁻) m/z=271 (MIT).

Preparation of (S)-{2-[2-(2-bromo-imidazo[2,1-b]thiazol-6-ylcarbamoyl)-pyrrolidin-1-yl]-2-oxo-ethyl}-carbamic acid tert-butyl ester 28. Compound 28 was synthesized from compound 11 (0.471 mmol) and compound 27 (0.707 mmol), following the procedure as described for compound 23, as an off-white solid in 46% yield. MS (ESI, EI⁺) m/z=471.99-474.01 (MH⁺).

Preparation of (S,S,S)-[1-(2-{5-[4-(6-[1-(2-tert-butoxycarbonylamino-acetyl)-pyrrolidin-2-carbonyl]-amino}-imidazo[2,1-b]thiazol-2-yl)-phenyl]-1H-imidazol-2-yl}-pyrrolidine-1-carbonyl)-2-methyl-propyl]-carbamic acid methyl ester A39. Compound A39 was synthesized from compound 28 (0.106 mmol) and compound 8 (0.159 mmol), following the procedure as described for compound A1 (reaction time=2.5 hrs), as a white lyophilized powder in 8% yield. MS (ESI, EI⁺) m/z=762.27 (MH⁺).

Example 15

Synthesis of (S,S,S,R)-[1-(2-{5-[4-(6-{[1-(2-methoxycarbonylamino-2-phenyl-acetyl)-pyrrolidin-2-carbonyl]-amino}-imidazo[2,1-b]thiazol-2-yl)-phenyl]-1H-imidazol-2-yl}-pyrrolidine-1-carbonyl)-2-methyl-propyl]-carbamic acid methyl ester A30

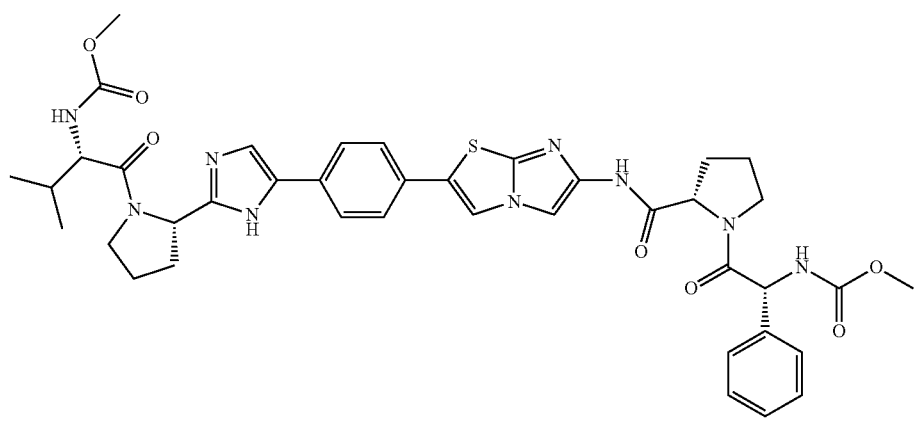

A30

Compound A30 was synthesized as shown in Scheme 8.

Preparation of (R)-methoxycarbonylamino-phenyl-acetic acid 31. D-(−)-α-Phenylglycine (0.165 mmol) was dissolved in tetrahydrofuran (500 mL), followed by the addition of NaHCO₃ (0.496 mmol) in water (500 mL), and then the addition of methylchloroformate (0.182 mmol) at room temperature. The reaction mixture was stirred at room temperature overnight. The mixture was acidified to pH=3 with HCl (1N) and the volatile was concentrated in vacuo. The aqueous layer was extracted with ethyl acetate and the organic layer was dried over MgSO₄, filtered, and concentrated in vacuo to give compound 31 as a pale yellow solid in 80% yield. MS (ESI, EI⁺) m/z=209 (MH⁺).

Preparation of (S,R)-1-(2-metoxycarbonylamino-2-phenyl-acetyl)-pyrrolidine-2-carboxylic acid benzyl ester 32. Compound 32 was synthesized from compound 31 and L-proline benzyl ester hydrochloride, following the procedure as described for compound 2a, as a white crystallized solid. MS (ESI, EI⁺) m/z=397 (MH⁺).

Preparation of (S,R)-1-(2-tert-butoxycarbonylamino-2-phenyl-acetyl)-pyrrolidine-2-carboxylic acid 33. Compound 33 was synthesized from compound 32, following the procedure as described for compound 3a, as a white solid. MS (ESI, EI⁻) m/z=305 (MH⁻).

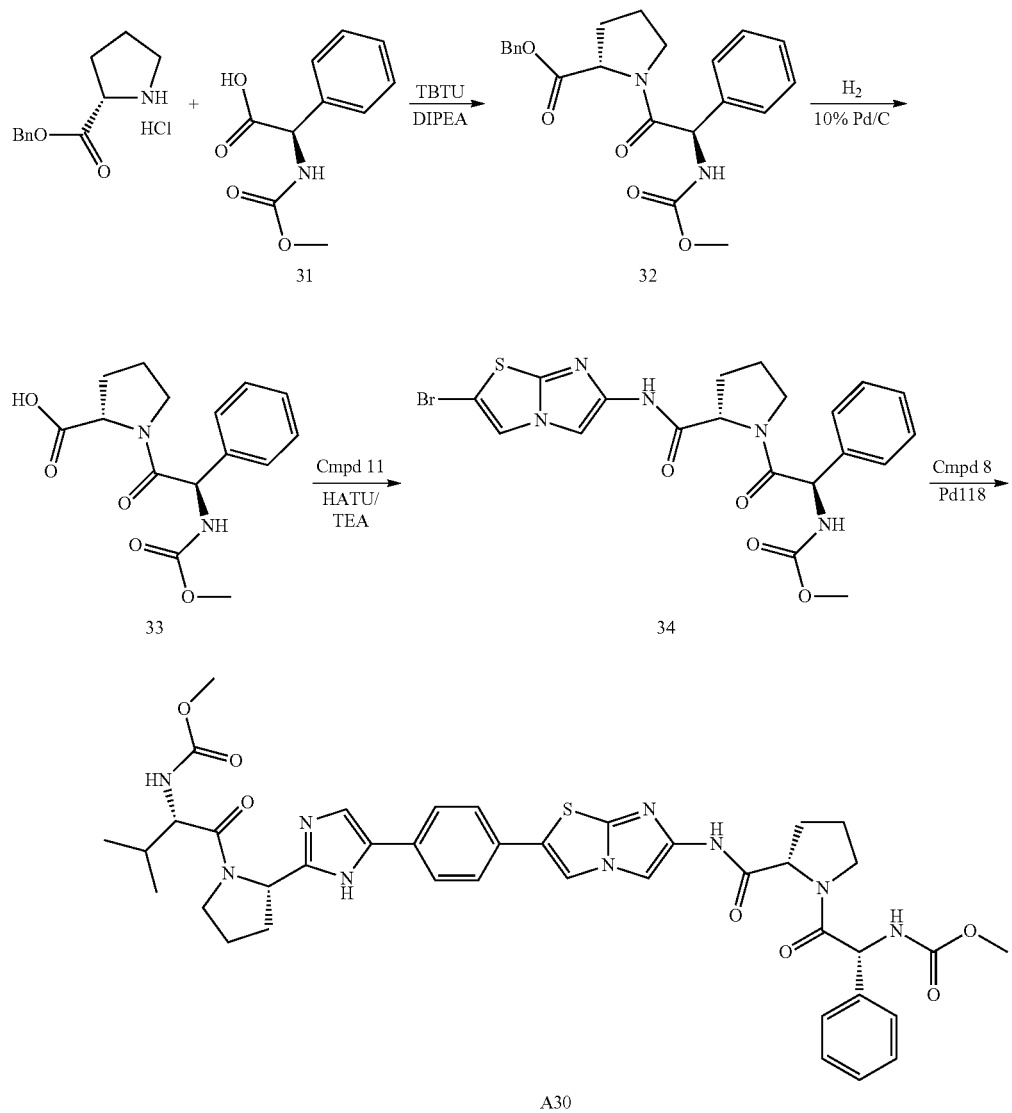

A30

Preparation of (S,R)-{2-[2-(2-bromo-imidazo[2,1-b]thiazol-6-ylcarbamoyl)-pyrrolidin-1-yl]-2-oxo-1-phenyl-ethyl}-carbamic acid methyl ester 34. Compound 34 was synthesized from compound 11 (0.471 mmol) and compound 33 (0.707 mmol), following the procedure as described for compound 23, as a yellow solid in 44% yield. MS (ESI, EI⁺) m/z=505.93-507.95 (MH⁺).

Preparation of (S,S,S,R)-[1-(2-{5-[4-(6-{[1-(2-methoxycarbonylamino-2-phenyl-acetyl)-pyrrolidin-2-carbonyl]-amino}-imidazo[2,1-b]thiazol-2-yl)-phenyl]-1H-imidazol-2-yl}-pyrrolidine-1-carbonyl)-2-methyl-propyl]-carbamic acid methyl ester A30. Compound A30 was synthesized from compound 34 (0.098 mmol) and compound 8 (0.127 mmol), following the procedure as described for compound A1, as a white lyophilized powder. MS (ESI, EI⁺) m/z=796.24 (MH⁺).

Example 16
Synthesis of (S,S,S,R)-1-(2-{5-[4-(6-{[1-(2-ethoxy-carbonylamino-2-phenylacetyl)-pyrrolidine-2-carbonyl]-amino}imidazo[2,1-b]thiazol-2-yl)-phenyl]-1H-imidazol-2-yl}pyrrolidine-1-carbonyl)-2-methyl-propyl]-carbamic acid methyl ester A55
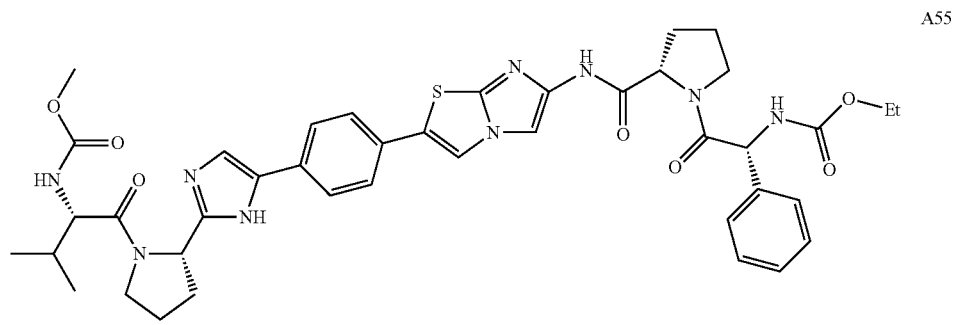 [SMILES: CCOC(=O)N[C@@H](C(=O)N1CCC[C@H]1C(=O)Nc1cn2cc(-c3ccc(-c4cnc([C@@H]5CCCN5C(=O)[C@@H](NC(=O)OC)C(C)C)[nH]4)cc3)sc2n1)c1ccccc1]
Compound A55 was synthesized as shown in Scheme 9.
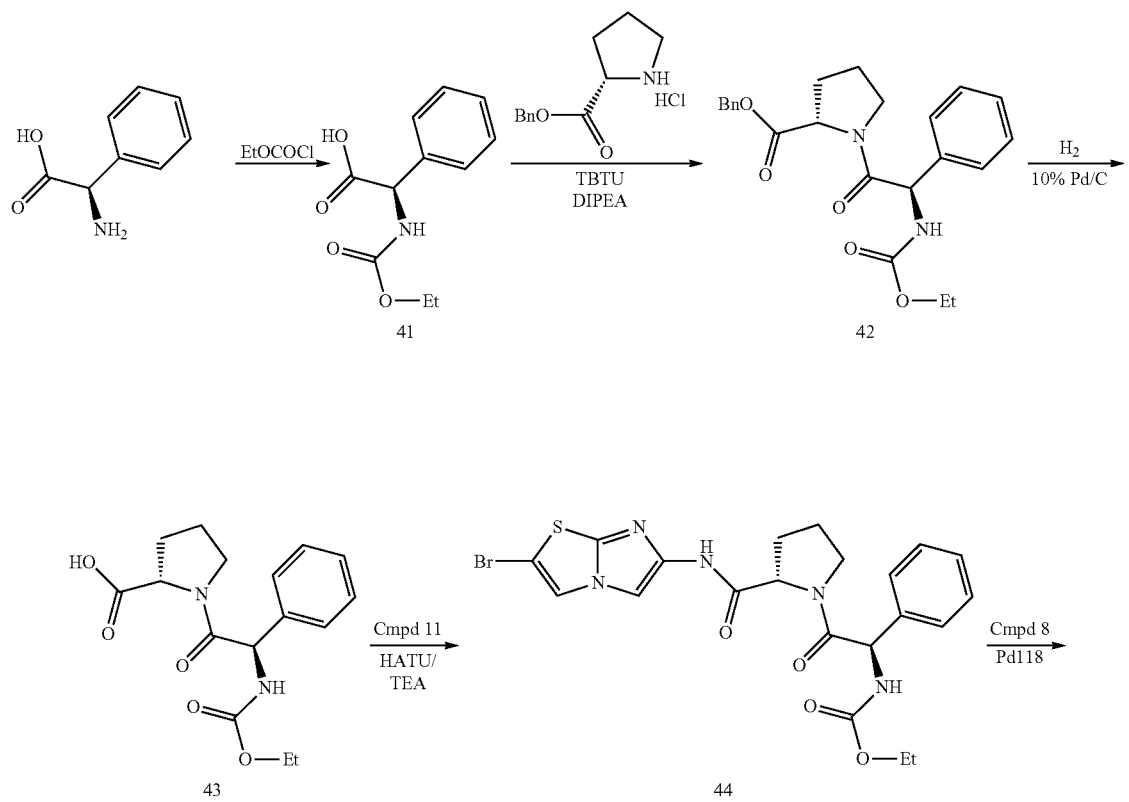

-continued

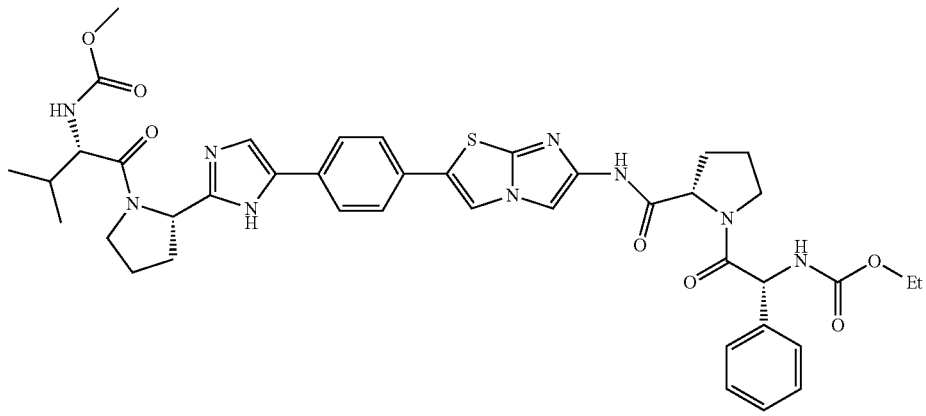

A55

Preparation of (R)-2-(ethoxycarbonylamino)-2-phenylacetic acid 41. D-Phenylglycine (R) (85.2 mmol) was dissolved in anhydrous THF (260 mL) with NaHCO$_3$ (256 mmol) in water (260 mL). Ethylchloroformate (0.235 mol) was added. After stirred at room temperature overnight, the reaction mixture was acidified to pH 3 with 1N HCl. The aqueous layer was extracted with EtOAc. The organic layers were dried over MgSO$_4$, filtered, and concentrated under reduced pressure to give (R)-2-(ethoxycarbonylamino)-2-phenylacetic acid 41 as a white solid in 82% yield. MS (ESI, EI$^+$) m/z=224.2 (MH$^+$).

Preparation of (S,R)-1-(2-ethoxycarbonylamino-2-phenylacetyl)-pyrrolidine-2-carboxylic acid benzyl ester 42. Compound 42 was synthesized from compound 41 (2 mmol) and L-proline benzyl ester hydrochloride (2.2 mmol), following the procedure as described for compound 2a.

Preparation of (S,R)-1-(2-tert-butoxycarbonylamino-2-phenylacetyl)-pyrrolidine-2-carboxylic acid 43. Compound 43 was synthesized from compound 42 (2 mmol), following the procedure as described for the compound 3a, to give compound 43 as a foam in 63% yield over last two steps. MS (ESI, EI$^+$) m/z=321.2 (MH$^+$).

Preparation of (S,R)-{2-[2-(2-bromo-imidazo[2,1-b]thiazol-6-ylcarbamoyl)-pyrrolidin-1-yl]-2-oxo-1-phenylethyl}-carbamic acid ethyl ester 44. Compound 44 was synthesized from compounds 43 (0.377 mmol) and 11 (0.565 mmol), following the procedure as described for compound 12a, at room temperature overnight, to give compound 44 as a yellow oil in 66% yield. $^1$H NMR (DMSO-d$_6$, 400 MHz) δ (ppm) 1.10 (t, 3H), 1.80 (m, 2H), 1.95 (m, 2H), 3.10 (m, 1H), 3.81 (m, 1H), 3.99 (m, 2H), 4.40 (m, 1H), 5.42 (m, 1H), 7.31 (m, 5H), 7.50 (d, 1H), 7.81 (s, 1H), 8.16 (s, 1H), 10.61 (s, 1H); MS (ESI, EI$^+$) m/z=520-522 (MH$^+$).

Preparation of (S,S,S,R)-[1-(2-{5-[4-(6-{[1-(2-ethoxycarbonylamino-2-phenylacetyl)-pyrrolidine-2-carbonyl]-amino}imidazo[2,1-b]thiazol-2-yl)-phenyl]-1H-imidazol-2-yl}pyrrolidine-1-carbonyl)-2-methyl-propyl]-carbamic acid methyl ester A55. Compound A55 was synthesized from compounds 44 (0.125 mmol) and 8 (0.187 mmol), following the procedure as described for compound A1, to give compound A55 as a lyophilized white solid in 11% yield. MS (ESI, EI$^+$) m/z=810.2 (MH$^+$).

Example 17

Synthesis of ((S)-1-{(S)-2-[2-(3-{[(S)-1-((R)-2-tert-butoxycarbonylamino-2-phenylacetyl)-pyrrolidine-2-carbonyl]-amino}-phenyl)-imidazo[2,1-b]thiazol-6-ylcarbamoyl]-pyrrolidine-1-carbonyl}-2-methyl-propyl)-carbamic acid methyl ester A58

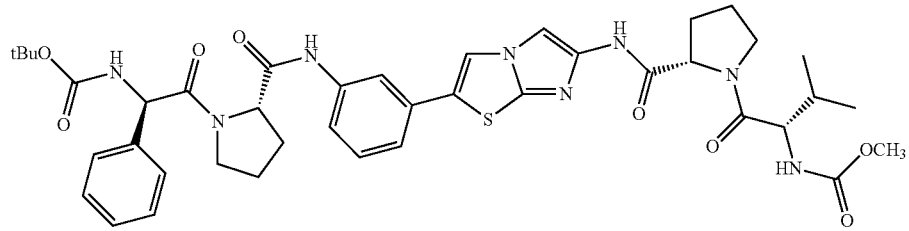

A58

Compound A58 was synthesized as shown in Scheme 10.

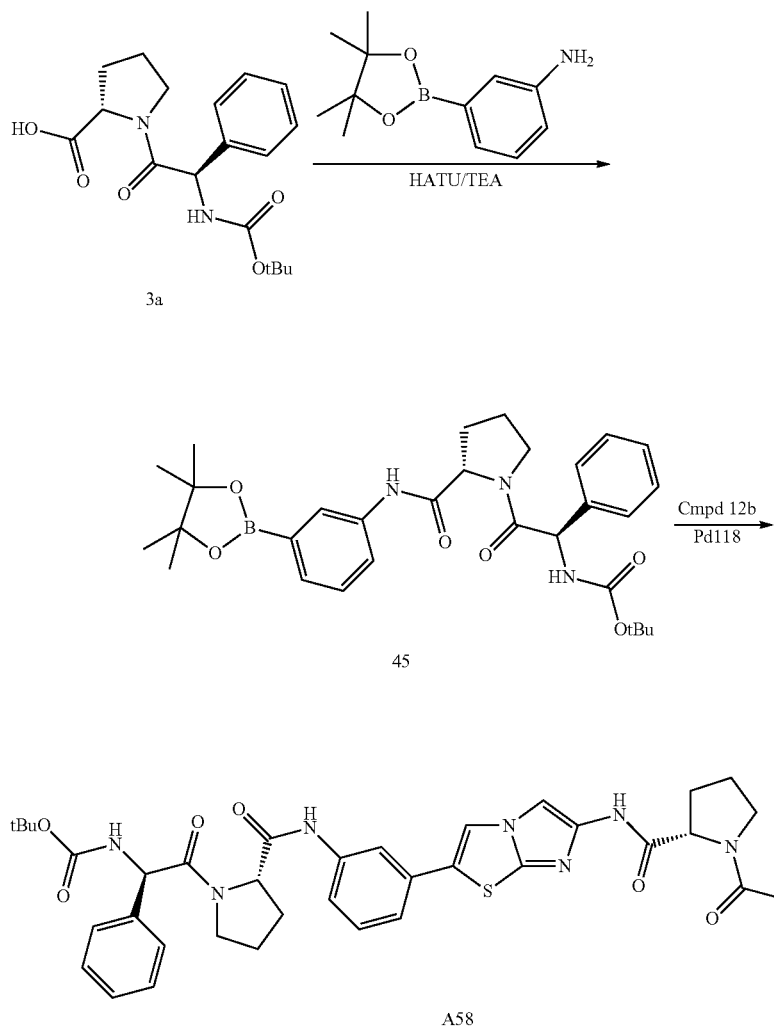

Preparation of ((R)-2-oxo-1-phenyl-2-{(S)-2-[3-(4,4,5,5-tetramethyl-[1,3,2]dioxaborolan-2-yl)-phenylcarbamoyl]-pyrrolidin-1-yl}-ethyl)-carbamic acid tert-butyl ester 45. Compound 45 was synthesized from 3-aminophenylboronic, pinacol ester (0.474 mmol) and compound 3a (0.43 mmol), following the procedure as described for compound 12a. The reaction mixture was stirred at room temperature overnight. The solvent was removed under reduced pressure. The resulting residue was dissolved in ethyl acetate and washed sequentially with $Na_2CO_3$, 0.5N HCl, and brine. The organic layers were dried, filtered, and concentrated under reduced pressure. The crude was purified by chromatography on a silica gel column to give compound 45 as a brown solid in 83% yield. MS (ESI, EI$^+$) m/z=550.02 (MH$^+$).

Preparation of ((S)-1-{(S)-2-[2-(3-{[(S)-1-((R)-2-tert-butoxycarbonylamino-2-phenylacetyl)-pyrrolidine-2-carbonyl]-amino}-phenyl)-imidazo[2,1-b]thiazol-6-ylcarbamoyl]-pyrrolidine-1-carbonyl}-2-methyl-propyl)-carbamic acid methyl ester A58. Compound A58 was synthesized from intermediate 12b (0.076 mmol) and intermediate 23 (0.164 mmol) following the procedure as described for the compound A1 to give compound A58 as a lyophilized white solid in 5% yield. $^1$H NMR (CDCl$_3$, 400 MHz) δ (ppm) 0.95 (d, J=6.78 Hz, 3H), 1 (d, J=6.78 Hz, 3H), 1.36 (s, 9H), 1.79-2.22 (m, 7H), 2.42-2.54 (m, 2H), 3.20-3.27 (m, 1H), 3.68 (s, 3H), 3.77-3.87 (m, 2H), 4.33-4.38 (m, 1H), 4.79-4.81 (m, 1H), 5.39 (d, J=6.74 Hz, 1H), 5.48 (d, J=9.07 Hz, 1H), 5.57 (d, J=6.74 Hz, 1H), 7.17 (d, J=7.65 Hz, 1H), 7.26 (s, 1H), 7.29-7.33 (m, 1H), 7.36-7.44 (m, 6H), 7.49-7.54 (m, 1H), 7.60 (s, 1H), 7.77 (s, 1H), 7.96 (brs, 1H), 9.27 (s, 1H), 9.50 (s, 1H); MS (ESI, EI$^+$) m/z=815.2 (MH$^+$).

Example 18

Synthesis of [(S)-1-((S)-2-{4-[4-(6-{2-[(S)-1(S)-2-methoxycarbonylamino-3-methyl-butyryl)-pyrrolidin-2-yl]-3H-imidazol-4-yl}-thieno[3,2-h]thiophen-3-yl)-phenyl]-1H-imidazol-2-yl}-pyrrolidine-1-carbonyl)-2-methyl-propyl]-carbamic acid methyl ester A15

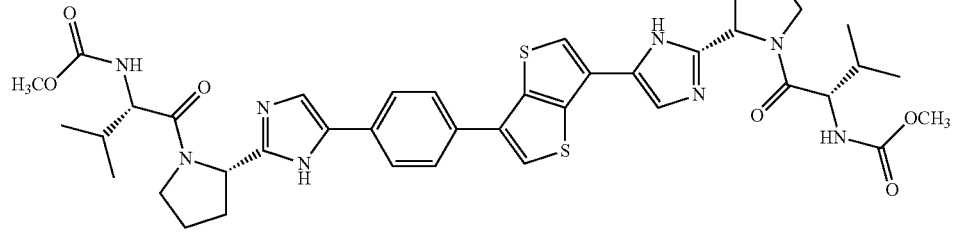

Compound A15 was synthesized as shown in Scheme 11.

Preparation of (S) 2-(1H-imidazol-2-yl)-pyrrolidine-1-carboxylic acid tert-butyl ester 46. N-(tert-Butoxycarbonyl)-L-prolinal (123.86 mmol) was carefully dissolved in 7N $NH_3$—$CH_3OH$ (180 mL) cooled with an ice bath and with vigorous stiffing. To the resultant ice-cooled mixture was added glyoxal (40 wt % solution in water) (619 mmol) dropwise. The mixture was stirred at room temperature for 4 days and then concentrated in vacuo to remove most of methanol. The mixture was extracted with ethyl acetate and the organic layer was filtered to remove the insoluble material in suspension. The organic layer was washed with brine, dried, and concentrated in vacuo. The crude was purified by silica cake to give compound 46 as a yellowish solid in 80% yield. MS (ESI, EI$^+$) m/z=238.21 (MH$^+$).

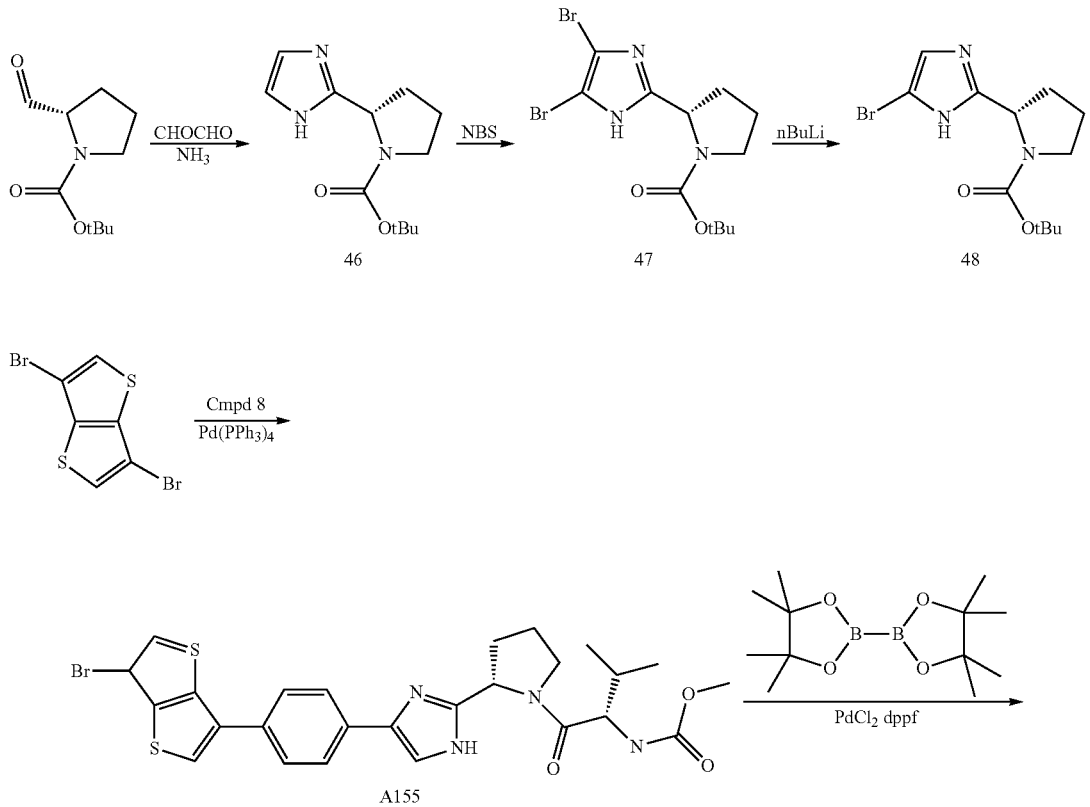

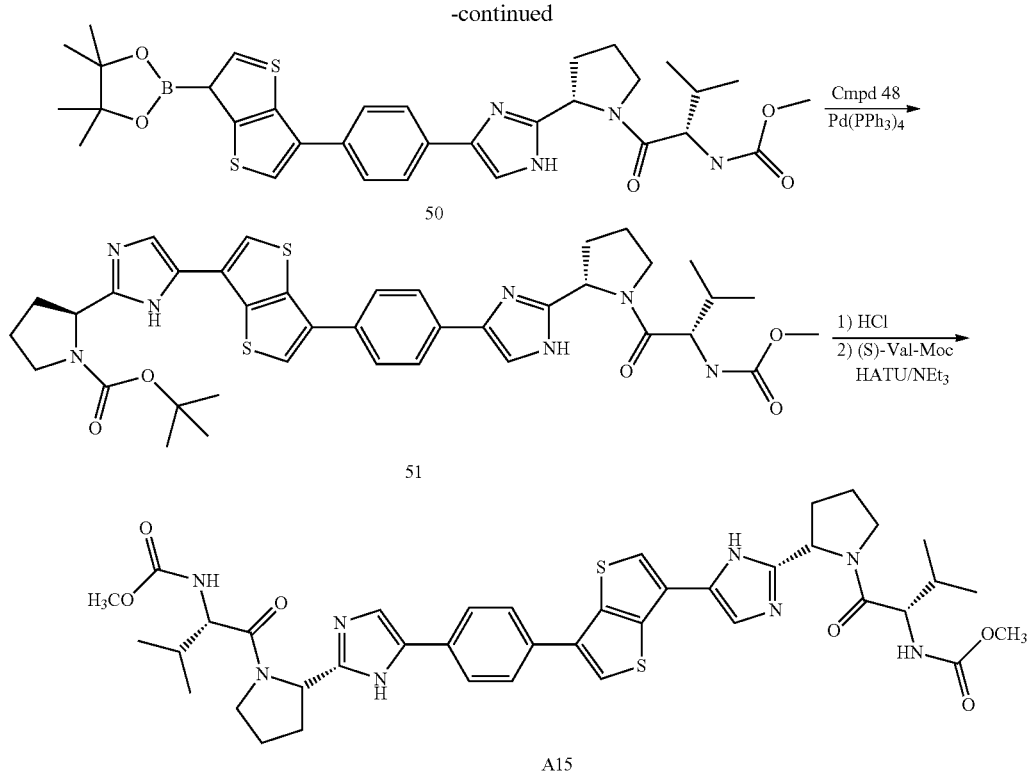

Preparation of (S) 2-(4,5-dibromo-1H-imidazol-2-yl)-pyrrolidine-1-carboxylic acid tert-butyl ester 47. N-Bromosuccinimide (210.7 mmol) was added portionwise to an ice-cooled solution of compound 46 (100.3 mmol) in dry dichloromethane (350 mL). The reaction mixture was stirred at 0° C. for 2 hrs, and then washed with water (4×100 mL). The combined aqueous layers were extracted with ethyl acetate. The organic extract was washed with water (2×30 mL). Combined organic layers were concentrated in vacuo to give crude compound 47 as slightly purple foam. MS (ESI, EI$^+$) m/z=394.09-396.05-398.05 (MH$^+$).

Preparation of (S) 2-(4-bromo-1H-imidazol-2-yl)-pyrrolidine-1-carboxylic acid tert-butyl ester 48. To a solution of intermediate 47 (75.93 mmol) in dry tetrahydrofuran (300 mL) at −78° C. under nitrogen was added n-butyllithium 2.5M solution in hexane (275 mmol). After completion of addition, the mixture was stirred under nitrogen between −70° C. and −80° C. for 30 min, and then allowed to warm up to −60° C. The reaction was carefully quenched with methanol (20 mL), maintaining the temperature below −40° C. The reaction mixture was then allowed to reach to 0° C., and water (100 mL) and ethyl acetate (100 mL) were added. The layers were separated and the organic was washed sequentially with a diluted HCl solution and brine. After evaporation in vacuo of the organic layer, the residue was purified by silica gel chromatography (eluent: DCM to DCM/methanol (1%)) to give compound 48 as a white foam in 52% yield. $^1$H NMR (DMSO-d$_6$, 400 MHz) δ (ppm) 1.16-1.37 (2s, 9H), 1.78-1.94 (m, 3H), 2.08-2.21 (m, 1H), 3.26-3.34 (m, 1H), 3.42-3.50 (m, 1H), 4.63-4.74 (m, 1H), 7.07-7.10 (m, 1H), 12.09-12.13 (m, 1H); MS (ESI, EI$^+$) m/z=316.23-318.24 (MH$^+$).

Preparation of [(S)-1-((S)-2-{4-[4-(6-bromo-thieno[3,2-b]thiophen-3-yl)-phenyl]-1H-imidazol-2-yl}-pyrrolidine-1-carbonyl)-2-methyl-propyl]-carbamic acid methyl ester A155. To a degassed mixture of 3,6-dibromo-thieno[3,2-b]thiophene (0.335 mmol), compound 8 (0.335 mmol), and sodium carbonate (1.34 mmol) in a mixture of DMF and water (10 mL/1 mL) was added Pd(PPh$_3$)$_4$ (0.335 mmol). The reaction mixture was heated for 1 hr at 80° C. Ethyl acetate and water were then added and the mixture was vigorously stirred for 10 min. The layers were partitioned into a phase separator. The organic layer was separated, dried over Na$_2$SO$_4$, filtered, and concentrated in vacuo. The residue was purified by silica gel chromatography (eluent: DCM to DCM/MeOH 9/1) to give compound A155 as a green gum in 74% yield. $^1$H NMR (DMSO-d$_6$, 400 MHz) δ (ppm) 0.85 (d, J=6.61 Hz, 3H), 0.90 (d, J=6.61 Hz, 3H), 1.92-2.19 (m, 5H), 3.53 (s, 3H), 3.77-3.84 (m, 2H), 4.06 (t, J=8.34 Hz, 1H), 5.07-5.09 (m, 1H), 7.28 (d, J=8.32 Hz, 1H), 7.54 (d, J=1.97 Hz, 1H), 7.70-7.76 (m, 2H), 7.84-7.93 (m, 3H), 8.08-8.14 (m, 1H), 11.81 (s, 1H); MS (ESI, EI$^+$) m/z=587-589 (MH$^+$).

Preparation of {(S)-2-methyl-1-[(S)-2-(4-{6-[6-(4,4,5,5-tetramethyl-[1,3,2]dioxaborolan-2-yl)-thieno[3,2-h]thiophen-3-yl]-phenyl}-1H-imidazol-2-yl)-pyrrolidine-1-carbonyl]-propyl}-carbamic acid methyl ester 50. To a degassed mixture of intermediate A155 (0.248 mmol), bis(pinacolato)diboron (0.372 mmol), and potassium acetate (0.745 mmol) in dry dioxane (1.5 mL) was added PdCl$_2$(dppf)

(0.0161 mmol). The reaction mixture was stirred at 90° C. overnight. The reaction mixture was partitioned between ethyl acetate and water. Organic layers were washed with brine, dried over Na$_2$SO$_4$, filtered, and concentrated under reduced pressure. The residue was purified by silica gel chromatography (eluent: DCM to DCM/MeOH 9/1) to afford compound 50 as a yellow gum in 48% yield. MS (ESI, EI$^+$) m/z=635 (MH$^+$).

Preparation of (S)-2-{5-[6-(4-{2-[(S)-4-((S)-2-methoxycarbonylamino-3-methyl-butyryl)-pyrrolidin-2-yl]-1H-imidazol-4-yl}-phenyl)-thieno[3,2-b]thiophen-3-yl]-1H-imidazol-2-yl}-pyrrolidine-1-carboxylic acid tert-butyl ester 51. To a degassed mixture of compounds 48 (1.10 mmol), 50 (1.10 mmol), and sodium carbonate (4.42 mmol) in a mixture of DMF and water (33 mL/3 mL) was added Pd(PPh$_3$)$_4$ (0.11 mmol). The reaction mixture was heated at 80° C. for 2 hrs. Ethyl acetate and water were added. The dried organic layers were evaporated in vacuo and the residue was purified by silica gel chromatography (eluent: DCM first; then DCM/MeOH 9/1) to give compound 51 as a beige solid in 59% yield. MS (ESI, EI$^+$) m/z=744 (MH$^+$).

Preparation of [(S)-1-((S)-2-{4-[4-(6-{2-[(S)-1-((S)-2-methoxycarbonylamino-3-methyl-butyryl)-pyrrolidin-2-yl]-3H-imidazol-4-yl}-thieno[3,2-b]thiophen-3-yl)-phenyl]-1H-imidazol-2-yl}-pyrrolidine-1-carbonyl)-2-methyl-propyl]-carbamic acid methyl ester A15. To a mixture of compound 51 (0.336 mmol) in dioxane (5 mL) was added 4N HCl in dioxane (5 mL). The mixture was stirred at room temperature overnight. The mixture was evaporated in vacuo and the residue was used directly for the next step without further purification. (MS (ESI, EI$^+$) m/z=644 (MH$^+$)). To a mixture of the intermediate, compound 3b (0.0854 mmol), and HATU (0.0854 mmol) in dry DMF (1 mL) under nitrogen was added dropwise triethylamine (0.465 mmol). The mixture was stirred at room temperature overnight. The solvent was removed under reduced pressure and the residue was dissolved in methanol. The mixture was eluted through a SCX-2 column. The filtrate was concentrated and the residue was purified by semi-preparative HPLC to give compound A15 as a white solid in 23% yield. $^1$H NMR (DMSO-d$_6$, 400 MHz) δ (ppm) 0.80-0.90 (m, 12H), 1.88-2.19 (m, 10H), 3.53 (s, 6H), 3.77-3.86 (4H), 4.03-4.08 (m, 2H), 5.07-5.13 (m, 2H), 7.29 (d, 2H), 7.45 (s, 1H), 7.51-7.56 (m, 1H), 7.72-7.89 (m, 5H), 7.99-8.03 (m, 1H), 11.76-11.83 (m, 1H), 11.91 (brs, 1H); MS (ESI, EI$^+$) m/z=801 (MH$^+$).

Example 19

Synthesis of [(S)-1-((S)-2-{4-[4-(6-{2-[(S)-1-((S)-2-methoxycarbonylamino-3-methyl-butyryl)-pyrrolidin-2-yl]-3H-imidazol-4-ylethynyl}-thieno[3,2-b]thiophen-3-yl)-phenyl]-1H-imidazol-2-yl}-pyrrolidine-1-carbonyl)-2-methyl-propyl]-carbamic acid methyl ester A84

A84

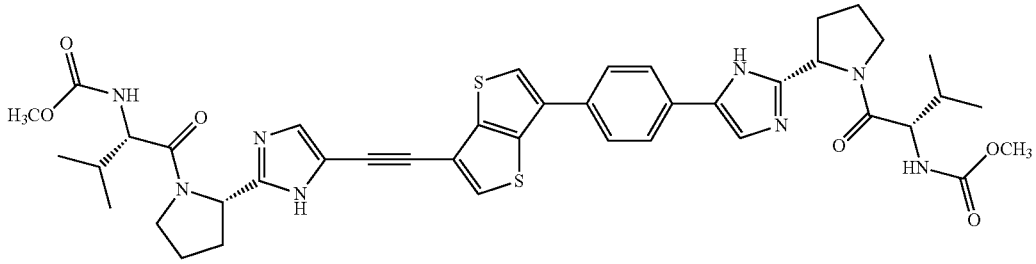

Compound A84 was synthesized as shown in Scheme 12.

Preparation of 5-bromo-2-((S)-1-tert-butoxycarbonyl-pyrrolidin-2-yl)-imidazole-1-carboxylic acid tert-butyl ester 52. To a stirred solution of compound 48 (6.32 mmol) in DCM (14 mL) was added (Boc)$_2$O (6.95 mmol), triethylamine (6.95 mmol), and DMAP (0.316 mmol). The reaction mixture was stirred overnight at room temperature. Dichloromethane and water were added to the reaction mixture. Organic layers were separated, dried over Na$_2$SO$_4$, filtered, and evaporated under reduced pressure. The residue was purified by silica gel chromatography (eluent: PE/AcOEt, 0% to 40%) to afford compound 52 in quantitative yield. $^1$H NMR (DMSO-d$_6$, 400 MHz) δ (ppm) 1.13 (s, 6H), 1.36 (s, 3H), 1.56 (d, J=4.59 Hz, 9H), 1.79-1.95 (m, 3H), 2.13-2.29 (m, 1H), 3.27-3.32 (m, 1H), 3.47-3.53 (m, 1H), 5.28-5.33 (m, 1H), 7.61 (s, 1H); MS (ESI, EI$^+$) m/z=416-418 (MH$^+$).

Preparation of 2(S)-2-(5-trimethylsilanylethynyl-1H-imidazol-2-yl)-pyrrolidine-1-carboxylic acid tert-butyl ester 53. To a degassed mixture of compound 52 (3.43 mmol) in DMF (15 mL) was successively added CuI (0.173 mmol), Pd118 (0.345 mmol), trimethylsilylacetylene (10.69 mmol), and 1,1',3,3'-tetramethylguanidine (7.33 mmol). The reaction mixture was irradiated in a microwave reactor at 90° C. for 30 min. Dichloromethane and water were added. Organic layers were separated, washed with brine, dried over Na$_2$SO$_4$, filtered, and evaporated under reduced pressure. The residue was purified by silica gel chromatography (eluent: PE/Et$_2$O, 10% to 100%) to afford compound 53 in 68% yield. MS (ESI, EI$^+$) m/z=334 (MH$^+$).

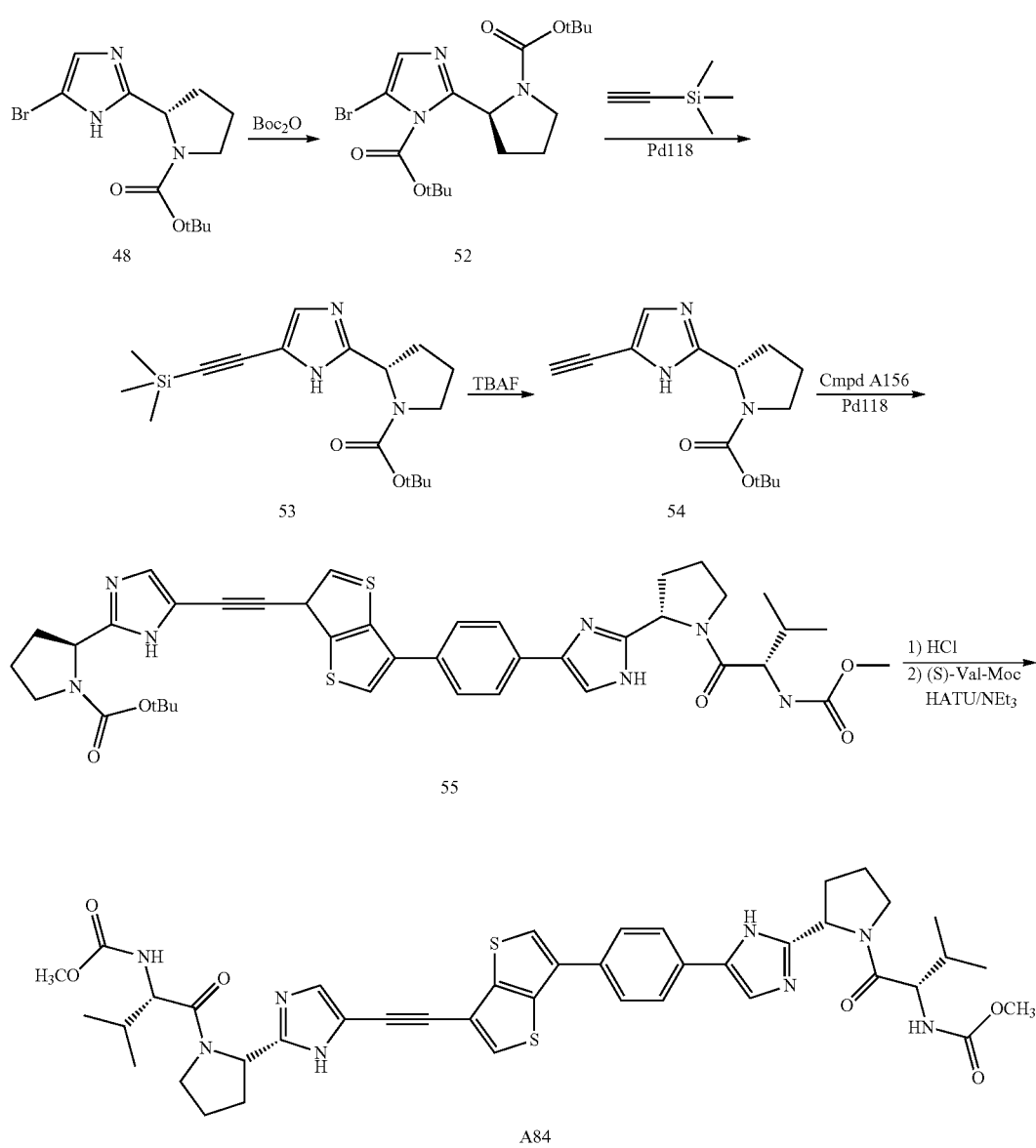

Scheme 12

Preparation of (S)-2-(5-ethynyl-1H-imidazol-2-yl)-pyrrolidine-1-carboxylic acid tert-butyl ester 54. To a mixture of compound 53 (4.6 mmol) in THF (50 mL) was added dropwise TBAF in THF (7 mmol). The reaction mixture was stirred for 1 hr and then concentrated under reduced pressure. The residue was purified by silica gel chromatography (eluent: PE/Et$_2$O, 20% to 100%) to give compound 54 as a beige precipitate in quantitative yield. $^1$H NMR (DMSO-d$_6$, 400 MHz) δ (ppm) 1.10 (s, 6H), 1.37 (s, 3H), 1.80-2.00 (m, 3H), 2.05-2.25 (m, 1H), 3.27-3.31 (m, 1H), 3.42-3.51 (m, 1H), 3.85 (brs, 1H), 4.64-4.76 (m, 1H), 7.35 (brs, 1H), 12.00 (brs, 1H); MS (ESI, EI$^+$) m/z=262 (MH$^+$).

Preparation of (S)-2-{5-[6-(4-{2-[(S)-1-((S)-2-methoxycarbonylamino-3-methyl-butyryl)-pyrrolidin-2-yl]-1H-imidazol-4-yl}-phenyl)-thieno[3,2-h]thiophen-3-ylethynyl]-1H-imidazol-2-yl}-pyrrolidine-1-carboxylic acid tert-butyl ester 55. To a degassed mixture of compound A155 (0.17 mmol) in DMF (3 mL) was successively added CuI (0.008 mmol), Pd118 (0.017 mmol), compound 54 (0.19 mmol), and 1,1',3,3'-tetramethylguanidine (0.19 mmol). The reaction mixture was irradiated in a microwave reactor at 90° C. for 30 min. Dichloromethane and water were added. Organic layers were separated, washed with brine, dried over Na$_2$SO$_4$, filtered, and evaporated under reduced pressure. The residue was purified by silica gel chromatography (eluent: DCM to DCM/MeOH 5%) to afford compound 55 in 47% yield. MS (ESI, EI$^+$) m/z=768.2 (MH$^+$).

Preparation of [(S)-1-((S)-2-{4-[4-(6-{2-[(S)-1-((S)-2-methoxycarbonylamino-3-methyl-butyryl)-pyrrolidin-2-yl]-3H-imidazol-4-ylethynyl}-thieno[3,2-h]thiophen-3-yl)-phenyl]-1H-imidazol-2-yl}-pyrrolidine-1-carbonyl)-2-methyl-propyl]-carbamic acid methyl ester A84. Compound A84 was prepared from compound 55 (0.081 mmol), following the procedure as described for compound A15, to give compound A84 as a white solid in 18% yield. MS (ESI, EI$^+$) m/z=825.7 (MH$^+$).

Example 20

Synthesis of [[(S)-1-((S)-2-{5-[4-(5-{2-[(S)-1-((S)-2-methoxycarbonylamino-3-methyl-butyryl)-pyrrolidin-2-yl]-3H-imidazol-4-yl}-thieno[3,2-b]thiophen-2-yl)-phenyl]-1H-imidazol-2-yl}-pyrrolidine-1-carbonyl)-2-methyl-propyl]-carbamic acid methyl ester A126

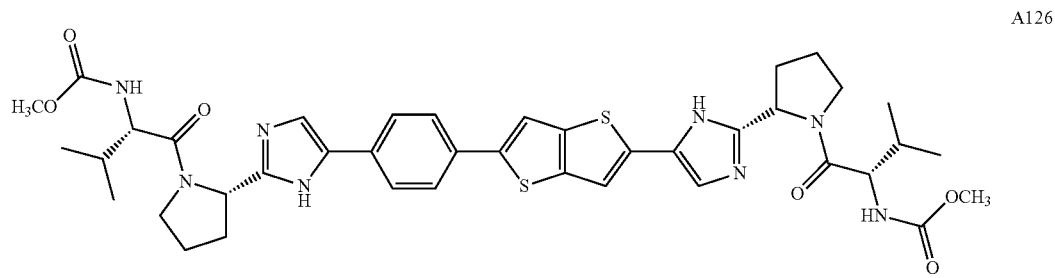

Compound A126 was synthesized as shown in Scheme 13.
Preparation of 2-((S)-1-tert-butoxycarbonyl-pyrrolidin-2-yl)-5-tributylstannanyl-imidazole-1-carboxylic acid tert-butyl ester 61. To a stirred solution of compound 52 (2.24 mmol) in dry toluene (15 mL) was added bis(tributyltin) (4.48 mmol) and Pd118 (0.22 mmol). The reaction mixture was irradiated in a microwave reactor at 100° C. for 4 hrs. Solvent was removed under reduced pressure and the residue was purified by silica gel chromatography (PE/EtOAc) to give compound 61 as a colorless oil in 60% yield. MS (ESI, EI$^+$) m/z=627 (MH$^+$).

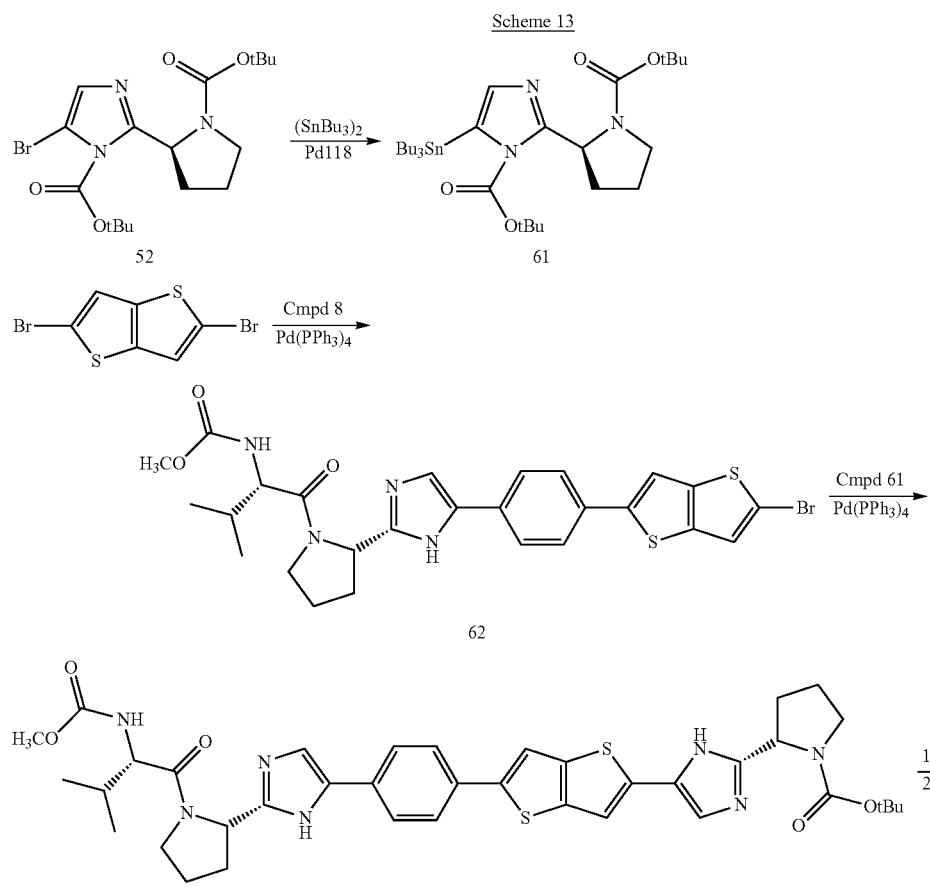

Scheme 13

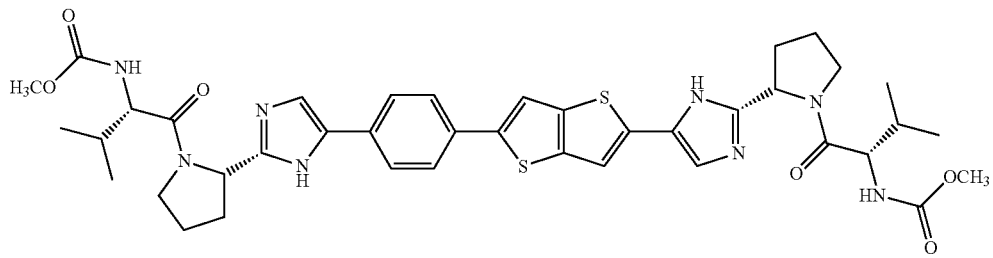

A126

Preparation of [(S)-1-((S)-2-{5-[4-(5-bromo-thieno[3,2-h]thiophen-2-yl)-phenyl]-1H-imidazol-2-yl}-pyrrolidine-1-carbonyl)-2-methyl-propyl]-carbamic acid methyl ester 62. Compound 62 was prepared from 2,5-dibromothieno[3,2-b]thiophene (1.678 mmol) and compound 8 (0.383 mmol), following the procedure as described for compound A1, to give compound 62 as a yellow solid in 15% yield. MS (ESI, EI⁺) m/z=587-589 (MH⁺).

Preparation of (S)-2-{5-[5-(4-{2-[(S)-1-((S)-2-methoxycarbonylamino-3-methyl-butyryl)-pyrrolidin-2-yl]-3H-imidazol-4-yl}-phenyl)-thieno[3,2-b]thiophen-2-yl]-1H-imidazol-2-yl}-pyrrolidine-1-carboxylic acid tert-butyl ester 63. A mixture of compound 62 (0.131 mmol), compound 61 (0.141 mmol), and Pd(PPh₃)₄ (0.017 mmol) was refluxed in dry toluene under nitrogen overnight. Solvent was removed under reduced pressure. The residue was purified by silica gel chromatography (eluent: DCM to DCM/MeOH 5%) to give compound 63 as an orange solid in 43% yield. MS (ESI, EI⁺) m/z=744.6 (MH⁺).

Preparation of [(S)-1-((S)-2-{5-[4-(5-{2-[(S)-1-((S)-2-methoxycarbonylamino-3-methyl-butyryl)-pyrrolidin-2-yl]-3H-imidazol-4-yl}-thieno[3,2-b]thiophen-2-yl)-phenyl]-1H-imidazol-2-yl}-pyrrolidine-1-carbonyl)-2-methyl-propyl]-carbamic acid methyl ester A126. Compound A126 was synthesized from compound 63 (0.0564 mmol), following the procedure as described for compound A15 to give compound A126 as a yellow solid in 8% yield. MS (ESI, EI⁺) m/z=801.6 (MH⁺).

Example 21

Synthesis of ((S)-1-{(S)-2-[5-(6-{2-[(S)-1-((S)-2-methoxycarbonylamino-3-methyl-butyryl)-pyrrolidin-2-yl]-3H-imidazol-4-yl}-thieno[3,2-b]thiophen-3-yl)-1H-imidazol-2-yl]-pyrrolidine-1-carbonyl}-2-methyl-propyl)-carbamic acid methyl ester A82

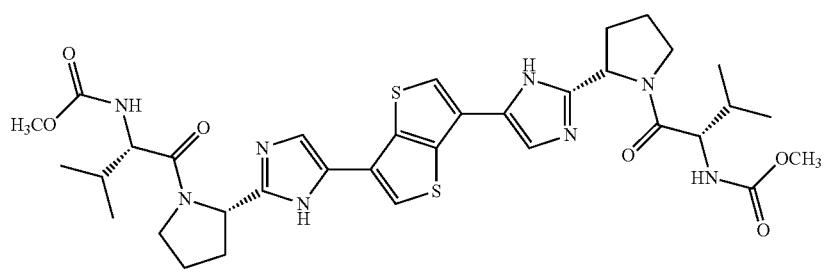

A82

Compound A82 was synthesized as shown in Scheme 14.

Scheme 14

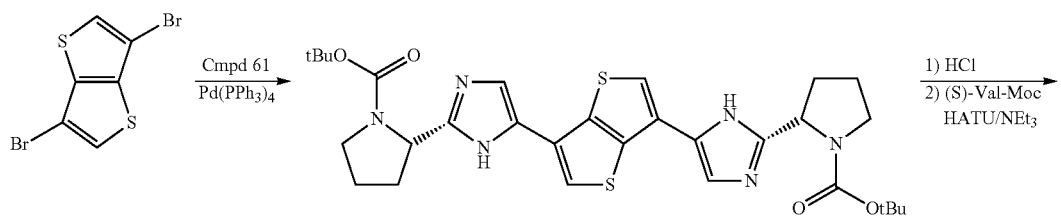

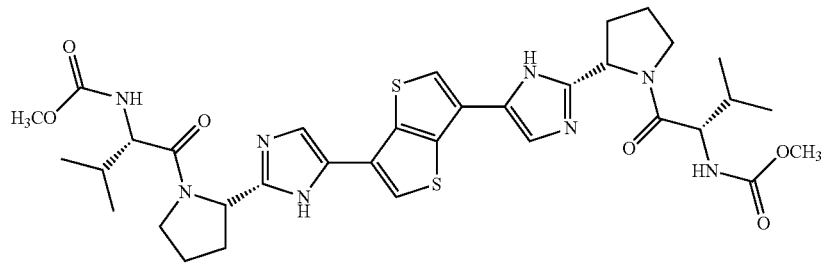

A82

Preparation of (2S,2'S)-tert-butyl 2,2'-(5,5'-(thieno[3,2-h]thiophene-3,6-diyl)bis(1H-imidazole-5,2-diyl))dipyrrolidine-1-carboxylate 65. Compound 65 was prepared from 3,6-dibromothieno[3,2-b]thiophene (0.168 mmol) with compound 61 (0.335 mmol), following the procedure as described for compound 63, to give compound 65 as a yellow solid in 48% yield. MS (ESI, EI+) m/z=611.4 (MH+).

Preparation of ((S)-1-{(S)-2-[5-(6-{2-[(S)-1-((S)-2-methoxycarbonylamino-3-methyl-butyryl)-pyrrolidin-2-yl]-3H-imidazol-4-yl}-thieno[3,2-b]thiophen-3-yl)-1H-imidazol-2-yl]-pyrrolidine-1-carbonyl}-2-methyl-propyl)-carbamic acid methyl ester A82. Compound A82 was prepared from compound 65 (0.09 mmol), following the procedure as described for compound A15, to give compound A82 as a white solid in 44% yield. $^1$H NMR (DMSO-$d_6$, 400 MHz) δ (ppm) 0.80-0.83 (m, 12H), 1.89-2.15 (m, 8H), 2.27-2.34 (m, 2H), 3.53 (s, 6H), 3.80-3.83 (m, 4H), 4.05 (t, J=8.41 Hz, 2H), 5.11 (dd, J=3.13 Hz and J=7.30 Hz, 2H), 7.28 (d, J=8.39 Hz, 2H), 7.37 (s, 2H), 7.67 (s, 2H), 11.80 (brs, 2H); MS (ESI, EI+) m/z=725.5 (MH+).

Example 22

Synthesis of ((S)-1-{(S)-2-[6-(5-{2-[(S)-1-((S)-2-Methoxycarbonylamino-3-methyl-butyryl)-pyrrolidin-2-yl]-1H-benzoimidazol-5-yl}-thieno[3,2-b]thiophen-2-yl)-1H-benzoimidazol-2-yl]-pyrrolidine-1-carbonyl}-2-methyl-propyl)-carbamic acid methyl ester A175

Compound A175 was synthesized as shown in Scheme 15.

Preparation of (S)-2-[5-(5-{2-[(S)-2-(1-tert-butoxycarbonyl)-pyrrolidin-2-yl]-1H-benzoimidazol-6-yl}-thieno[3,2-b]thiophen-2-yl)-1H-benzoimidazol-2-yl]-pyrrolidine-1-carboxylic acid tert-butyl ester 67. Compound 67 was prepared from 2,5-dibromothieno[3,2-b]thiophene (0.134 mmol) and (S)-2-[6-(4,4,5,5-tetramethyl-[1,3,2]dioxaborolan-2-yl)-1H-benzoimidazol-2-yl]-pyrrolidine-1-carboxylic acid tert-butyl ester 66 (0.288 mmol), following the procedure as described for compound A1, to give compound 67 as a yellow solid in 60% yield. MS (ESI, EI+) m/z=711.2 (MH+).

Preparation of ((S)-1-{(S)-2-[6-(5-{2-[(S)-1-((S)-2-Methoxycarbonylamino-3-methyl-butyryl)-pyrrolidin-2-yl]-1H-benzoimidazol-5-yl}-thieno[3,2-b]thiophen-2-yl)-1H-benzoimidazol-2-yl]-pyrrolidine-1-carbonyl}-2-methyl-propyl)-carbamic acid methyl ester A175. Compound A175 was prepared from compound 67, following the procedure as described for compound A15, to give compound A175 as a yellow solid in 32% yield. $^1$H NMR (DMSO-$d_6$, 400 MHz) δ (ppm) 0.82 (d, J=6.57 Hz, 6H), 0.85 (d, J=6.57 Hz, 6H), 1.89-2.09 (m, 6H), 2.18-2.28 (m, 4H), 3.54 (s, 6H), 3.80-3.86 (m, 4H), 4.07 (t, J=8.25 Hz, 2H), 5.15 (m, 2H), 7.3 (d, J=8.25 Hz, 2H), 7.45-7.60 (m, 4H), 7.70 (s, 1H), 7.80-7.83 (m, 3H); MS (ESI, EI+) m/z=825.5 (MH+).

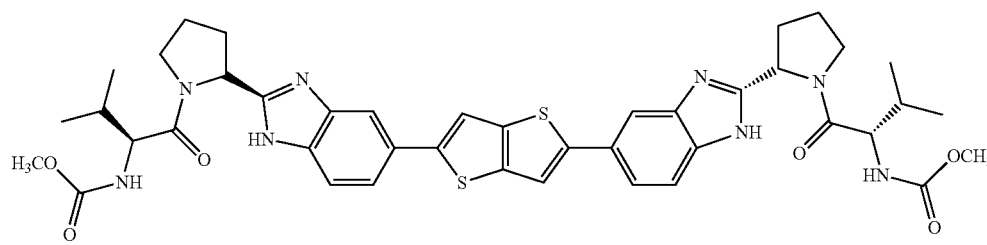

A175

Scheme 15
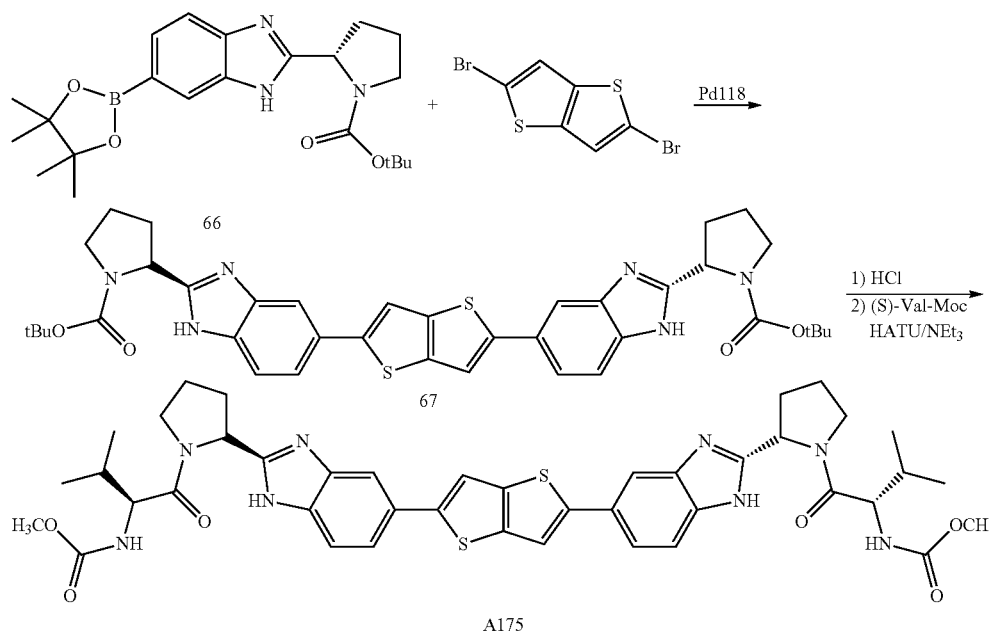
Example 23
Synthesis of [(S)-1-((S)-2-{4-[4-(6-{2-[(S)-1-((S)-2-methoxycarbonylamino-3-methyl-butyryl)-pyrrolidin-2-yl]-3H-benzoimidazol-5-yl}-thieno[3,2-b]thiophen-3-yl)-phenyl]-1H-imidazol-2-yl}-pyrrolidine-1-carbonyl)-2-methyl-propyl]-carbamic acid methyl ester A171
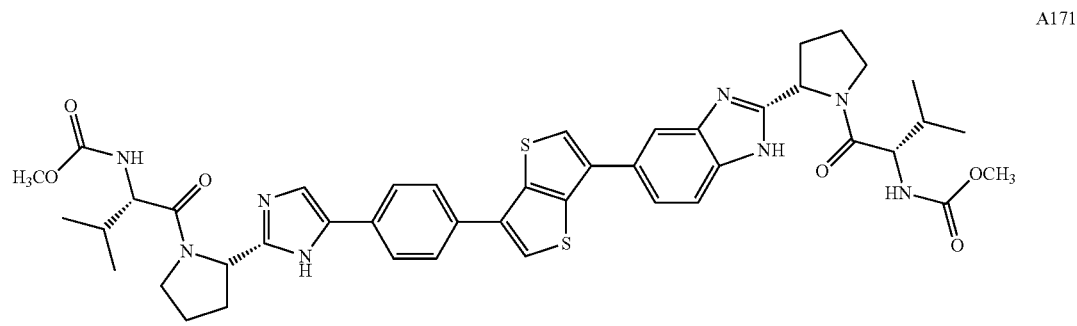
Compound A171 was synthesized as shown in Scheme 16.
Scheme 16
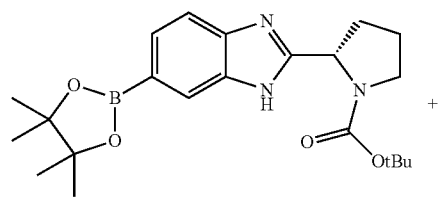

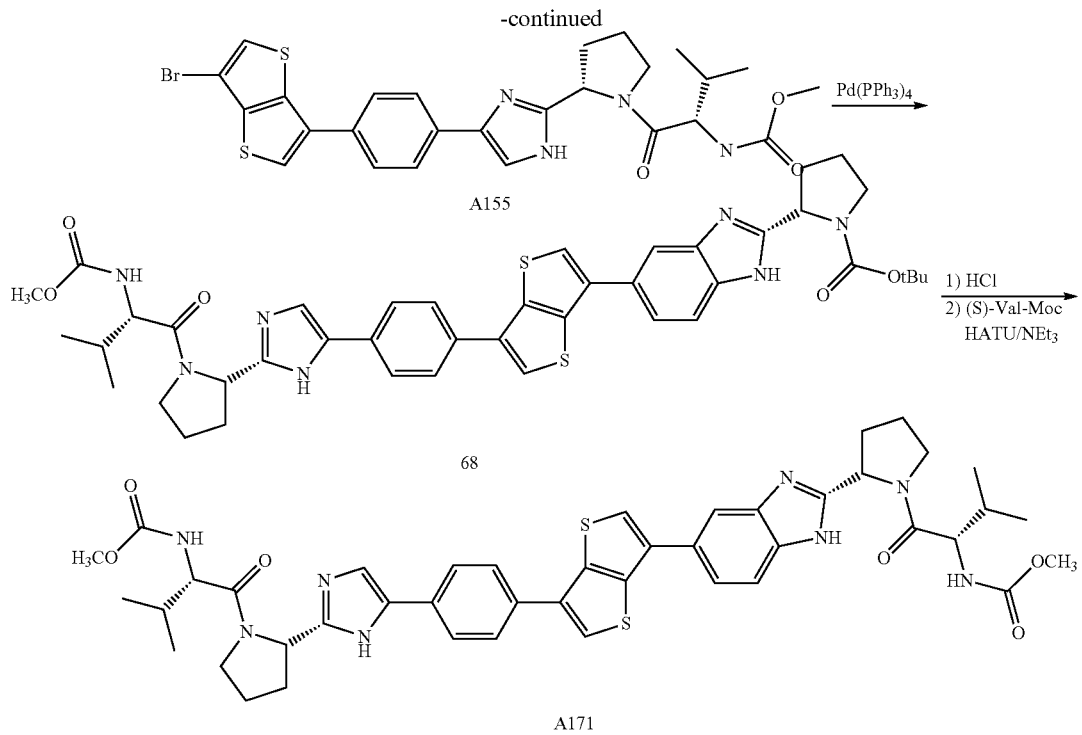

Preparation of (S)-2-{6-[6-(4-{2-[(S)-1-((S)-2-methoxy-carbonylamino-3-methyl-butyryl)-pyrrolidin-2-yl]-1H-imidazol-4-yl}-phenyl)-thieno[3,2-b]thiophen-3-yl]-1H-benzoimidazol-2-yl}-pyrrolidine-1-carboxylic acid tert-butyl ester 68. Compound 68 was prepared from compounds A155 (0.255 mmol) and 66, following the procedure as described for compound A155, to afford compound 68 as an ocre solid in 30% yield. $^1$H NMR (DMSO-$d_6$, 400 MHz) δ (ppm) 0.86 (d, J=6.71 Hz, 3H), 0.91 (d, J=6.71 Hz, 6H), 1.1 (s, 6H), 1.40 (s, 3H), 1.86-2.06 (m, 6H), 2.12-2.20 (m, 2H), 2.26-2.38 (m, 1H), 3.40-3.45 (m, 1H), 3.54 (s, 3H), 3.58-3.66 (m, 1H), 3.80-3.83 (m, 1H), 4.07 (t, J=8.28 Hz, 2H), 4.93-5.01 (m, 1H), 5.08-5.11 (m, 1H), 7.29 (d, J=8.19 Hz, 1H), 7.55-7.69 (m, 3H), 7.78 (d, J=8.32 Hz, 2H), 7.87 (d, J=8.23 Hz, 2H), 7.98-8.02 (m, 1H), 8.06 (m, 1H), 11.82 (s, 1H), 12.38-12.46 (m, 1H); MS (ESI, EI$^+$) m/z=794.2 (MH$^+$).

[(S)-1-((S)-2-{4-[4-(6-{2-[(S)-1-((S)-2-methoxycarbonylamino-3-methyl-butyryl)-pyrrolidin-2-yl]-3H-benzoimidazol-5-yl}-thieno[3,2-b]thiophen-3-yl)-phenyl]-1H-imidazol-2-yl}-pyrrolidine-1-carbonyl)-2-methyl-propyl]-carbamic acid methyl ester A171. Compound A171 was prepared from compound 68 (0.0503 mmol), following the procedure as described for compound A15, to afford compound A171 as a white solid in 16% yield. $^1$H NMR (CD$_3$OD, 400 MHz) δ (ppm) 0.89-1.01 (m, 12H), 2.05-2.45 (m, 12H), 3.55 (s, 6H), 3.90-4.13 (m, 4H), 4.24-4.29 (m, 2H), 5.18-5.21 (m, 1H), 5.29-5.32 (m, 1H), 7.36 (s, 1H), 7.63-8.00 (m, 11H); MS (ESI, EI$^+$) m/z=851.2 (MH$^+$).

Example 24

Synthesis of {(S)-1-[(S)-2-(5-{4-[3-(4-{2-[(S)-1-((S)-2-methoxycarbonylamino-3-methyl-butyryl)-pyrrolidin-2-yl]-1H-imidazol-4-yl}-phenyl)-4H-thieno[3,2-b]pyrrol-6-yl]-phenyl}-1H-imidazol-2-yl)-pyrrolidine-1-carbonyl]-2-methyl-propyl-carbamic acid methyl ester-5-carboxylic acid methyl ester A163

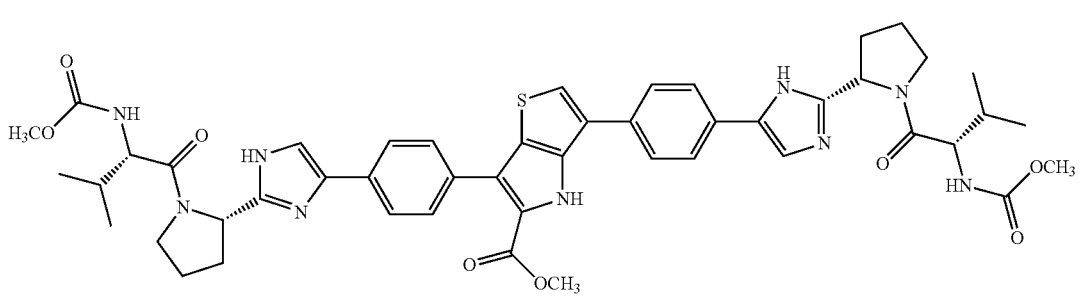

Compound A163 was synthesized as shown in Scheme 17.

Scheme 17

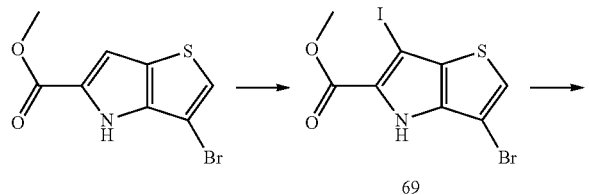

69

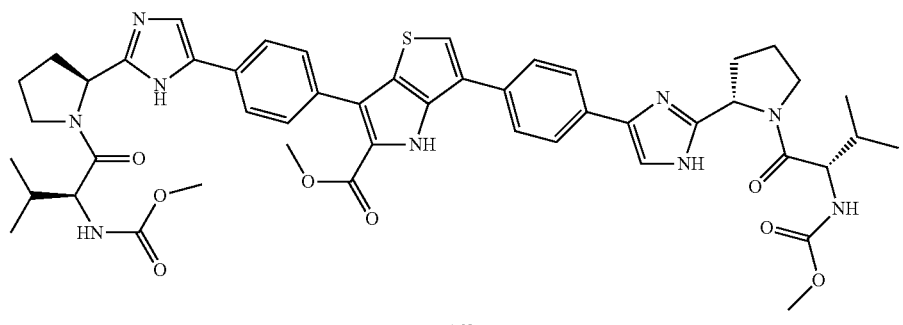

A163

Preparation of 3-bromo-6-iodo-4H-thieno[3,2-b]pyrrole-5-carboxylic acid methyl ester 69. To a solution of N-chlorosuccinimide (12 mmol) in acetone (25 mL) was added dropwise a solution of sodium iodide (12 mmol) in acetone (80 mL). 3-Bromo-4H-thieno[3,2-b]pyrrole-5-carboxylic acid methyl ester (10 mmol) in acetone (80 mL) was then added portionwise into the reaction mixture. After 1 hr of stirring, the reaction was poured into a solution of $Na_2SO_3$ 10% and extracted with AcOEt. Organic phases were washed with brine, dried over $Na_2SO_4$, filtered, and evaporated. The residue was purified by silica gel chromatography to give compound 69 as a yellowish solid in 68% yield. $^1$H NMR (CDCl$_3$, 400 MHz) δ (ppm) 3.96 (s, 3H), 7.26 (s, 1H), 9.22 (s, 1H).

Preparation of {(S)-1-[(S)-2-(5-{4-[3-(4-{2-[(S)-1-((S)-2-methoxycarbonylamino-3-methyl-butyryl)-pyrrolidin-2-yl]-1H-imidazol-4-yl}-phenyl)-4H-thieno[3,2-b]pyrrol-6-yl]-phenyl}-1H-imidazol-2-yl)-pyrrolidine-1-carbonyl]-2-methyl-propyl-carbamic acid methyl ester-5-carboxylic acid methyl ester A163. Compound A163 was prepared from compound 69 (0.052 mmol) and compound 8 (0.105 mmol), following the procedure as described for compound A1, to afford compound A163 as a white solid in 22% yield. MS (ESI, EI$^+$) m/z=918.2 (MH$^+$).

Example 25

Synthesis of [(S)-1-((S)-2-{4-[4-(6-{2-[(S)-1-((R)-2-methoxycarbonylamino-2-phenyl-acetyl)-pyrrolidin-2-yl]-3H-imidazol-4-yl}-thieno[3,2-b]thiophen-3-yl)-phenyl]-1H-imidazol-2-yl}-pyrrolidine-1-carbonyl)-2-methyl-propyl]-carbamic acid methyl ester A200

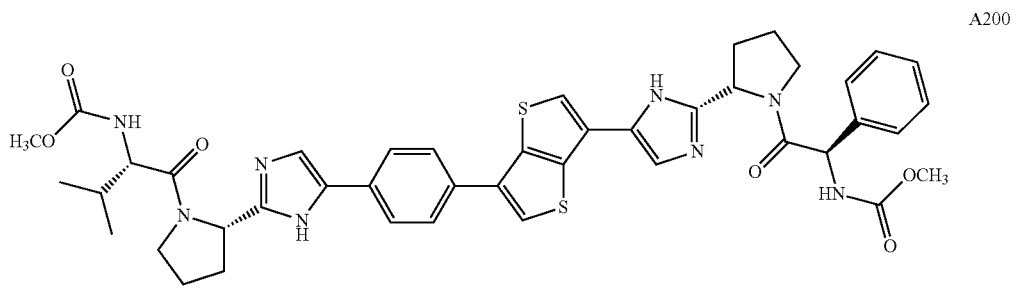

A200

Compound A200 was synthesized as shown in Scheme 18.

Preparation of {2-methyl-(S)-1-[2-(S)-(4-{4-[6-(2-(S)-pyrrolidin-2-yl-3H-imidazol-4-yl)-thieno[3,2-b]thiophen-3-yl]-phenyl}-1H-imidazol-2-yl)-pyrrolidine-1-carbonyl]-propyl}-carbamic acid methyl ester, hydrochloride salt 71. Compound 71 was synthesized from compound 51 (0.336 mmol), following the procedure as described for compound 3 to give compound 71 as a white solid in quantitative yield. MS (ESI, EI⁺) m/z=644 (MH⁺).

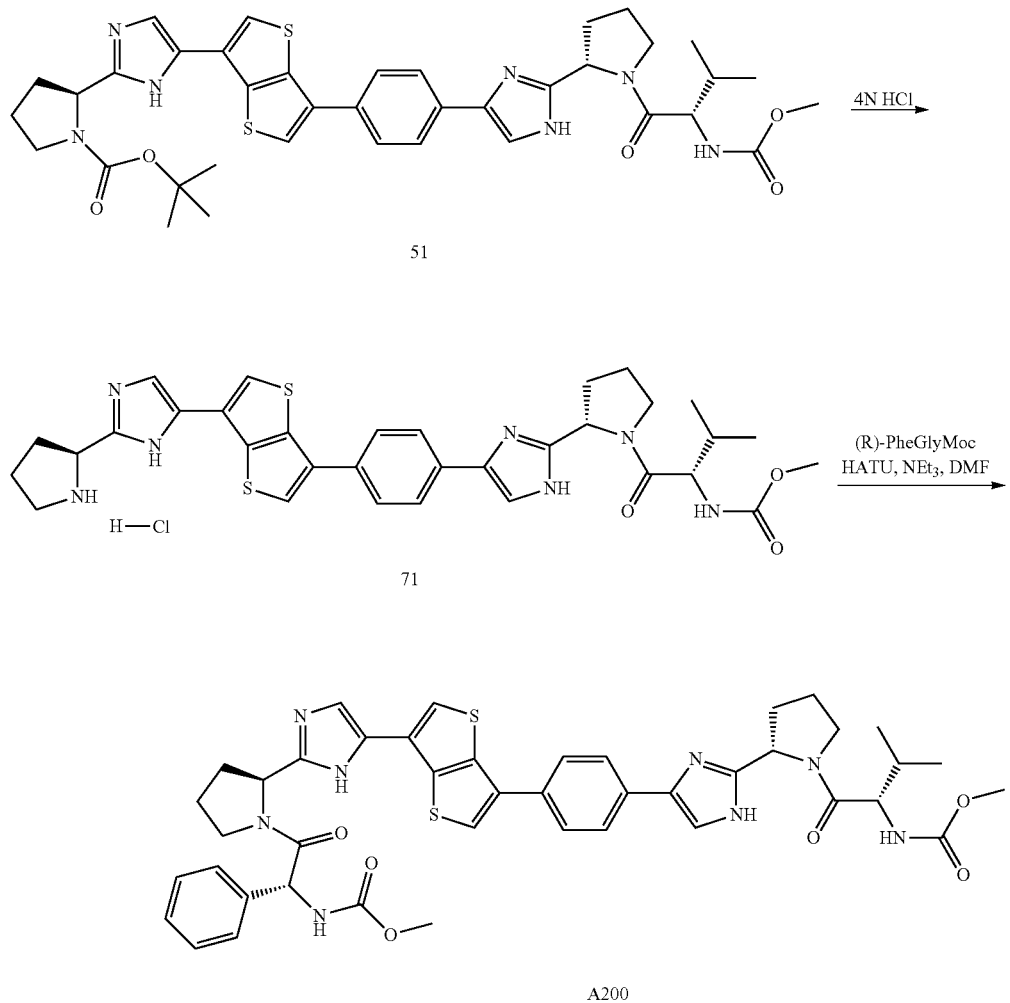

Preparation of [(S)-1-((S)-2-{4-[4-(6-{2-[(S)-1-((R)-2-methoxycarbonylamino-2-phenyl-acetyl)-pyrrolidin-2-yl]-3H-imidazol-4-yl}-thieno[3,2-b]thiophen-3-yl)-phenyl]-1H-imidazol-2-yl}-pyrrolidine-1-carbonyl)-2-methyl-propyl]-carbamic acid methyl ester A200. To a mixture of compound 71 (0.078 mmol), compound 33 (0.085 mmol), and HATU (0.085 mmol) in dimethylformamide (1 mL) was added Et₃N (0.465 mmol) dropwise. The reaction mixture was stirred at room temperature during 12 hrs. The solvent was removed under reduced pressure and the residue was dissolved in methanol. This mixture was eluted through a SCX-2 column. The filtrate was concentrated and the residue was purified by semi-preparative HPLC to give compound A200 as a white solid in 25% yield. ¹H NMR (DMSO-d₆, 400 MHz) δ (ppm) 0.85 (d, J=6.46 Hz, 3H), 0.91 (d, J=6.64 Hz, 3H), 1.84-2.20 (m, 8H), 3.11-3.22 (m, 1H), 3.35-3.38 (m, 1H), 3.51-3.54 (m, 6H), 3.77-3.92 (m, 2H), 4.04-4.09 (m, 1H), 5.06-5.11 (m, 2H), 5.48-5.52 (m, 1H), 6.88-8.40 (m, 13H), 11.80-11.87 (m, 1H); MS (ESI, EI⁺) m/z=835.4 (MH⁺).

Example 26

Synthesis of [(S)-1-((S)-2-{4-[4-(6-{(S)-2-[1-((R)-2-tert-butoxycarbonylamino-2-phenyl-acetyl)-pyrrolidin-2-yl]-3H-imidazol-4-yl}-thieno[3,2-b]thiophen-3-yl)-phenyl]-1H-imidazol-2-yl}-pyrrolidine-1-carbonyl)-2-methyl-propyl]-carbamic acid methyl ester A111

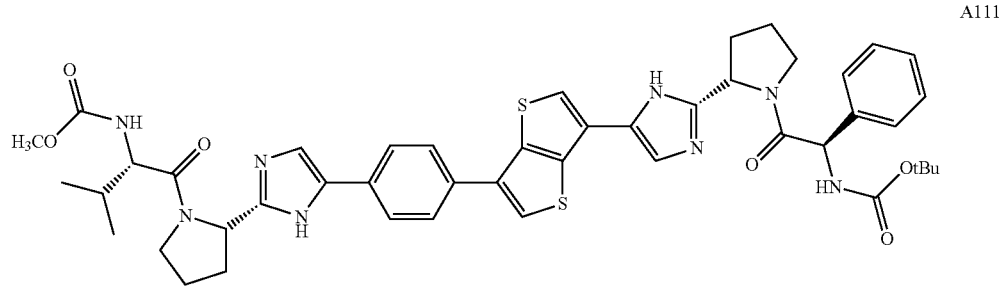

A111

Preparation of [(S)-1-((S)-2-{4-[4-(6-{(S)-2-[1-((R)-2-tert-butoxycarbonylamino-2-phenyl-acetyl)-pyrrolidin-2-yl]-3H-imidazol-4-yl}-thieno[3,2-b]thiophen-3-yl)-phenyl]-1H-imidazol-2-yl}-pyrrolidine-1-carbonyl)-2-methyl-propyl]-carbamic acid methyl ester A111. Compound A111 was synthesized from compound 71 (0.078 mmol) and (R)—N-Boc-phenylglycine (0.085 mmol), following the procedure as described for compound A200 to give compound A111 as a white solid in 24% yield. $^1$H NMR (DMSO-$d_6$, 400 MHz) δ (ppm) 0.85 (d, J=6.37 Hz, 3H), 0.91 (d, J=6.37 Hz, 3H), 1.34-1.38 (m, 9H), 1.84-2.20 (m, 8H), 3.12-3.18 (m, 1H), 3.53 (s, 3H), 3.77-3.91 (m, 2H), 4.04-4.09 (m, 1H), 5.06-5.11 (m, 2H), 5.42-5.45 (m, 1H), 6.90-8.40 (m, 13H), 11.79-11.82 (m, 1H); MS (ESI, EI$^+$) m/z=877.5 (MH$^+$).

Example 27

Synthesis of ((S)-1-{(S)-2-[5-(5-{2-[(S)-1-((S)-2-methoxycarbonylamino-3-methyl-butyryl)-pyrrolidin-2-yl]-3H-imidazol-4-yl}-thieno[3,2-b]thiophen-2-yl)-1H-imidazol-2-yl]-pyrrolidine-1-carbonyl}-2-methyl-propyl]-carbamic acid methyl ester A132

Compound A132 was synthesized as shown in Scheme 19.

Preparation of compound (S)-2-[5-(5-{2-[(S)-2-(1-tert-butoxycarbonyl)-pyrrolidin-2-yl]-3H-imidazol-4-yl}-thieno[3,2-b]thiophen-2-yl)-1H-imidazol-2-yl]-pyrrolidine-1-carboxylic acid tert-butyl ester 72. Compound 72 was synthesized from 2,5-dibromothieno[3,2-b]thiophene (0.168 mmol) and compound 61 (0.335 mmol), following the procedure as described for compound 63 to give compound 72 as a yellow solid in 50% yield. MS (ESI, EI$^+$) m/z=611.4 (MH$^+$).

Scheme 19

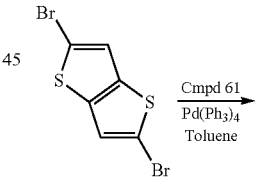

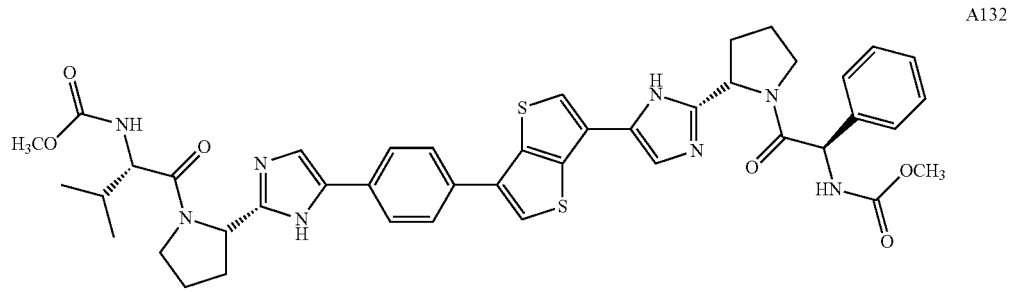

A132

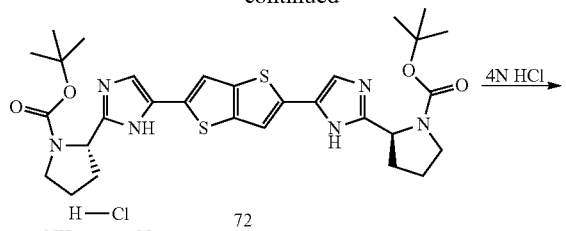

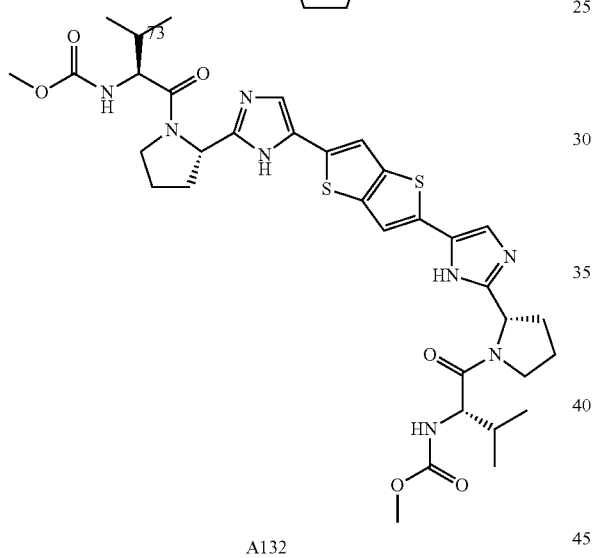

A132

Preparation of compound 73. To a solution of compound 72 (0.056 mmol) in methanol (2 mL) was added a solution of 4N HCl in dioxane (2 mL). The mixture was stirred at room temperature overnight and concentrated under reduced pressure to give compound 73 as a yellow solid in quantitative yield. MS (ESI, EI⁺) m/z=411.3 (MH⁺).

Preparation of ((S)-1-{(S)-2-[5-(5-{2-[(S)-1-((S)-2-methoxycarbonylamino-3-methyl-butyryl)-pyrrolidin-2-yl]-3H-imidazol-4-yl}-thieno[3,2-h]thiophen-2-yl)-1H-imidazol-2-yl]-pyrrolidine-1-carbonyl}-2-methyl-propyl]-carbamic acid methyl ester A132. A mixture of compound 73 (0.046 mmol), compound 1 (0.051 mmol), HATU (0.052 mmol) and DIPEA (0.230 mmol) in dry DMF (2 ml) was stirred at room temperature overnight. The mixture was scavenged onto SCX-2 cartridge and released. The filtrate was concentrated and the residue was purified by semi-preparative HPLC to give compound A132 as a yellow solid in 6% yield. MS (ESI, EI⁺) m/z=725.5 (MH⁺).

Example 28

Synthesis of ((S)-1-[(S)-2-(5-{4-[6-{4-{2-[(S)-1-((S)-2-methoxycarbonylamino-3-methyl-butyryl)-pyrrolidin-2-yl]-3H-imidazol-4-yl}-phenyl)-thieno[3,2-b]thiophen-3-yl]-phenyl}-1H-imidazol-2-yl)-pyrrolidine-1-carbonyl]-2-methyl-propyl}-carbamic acid methyl ester A86

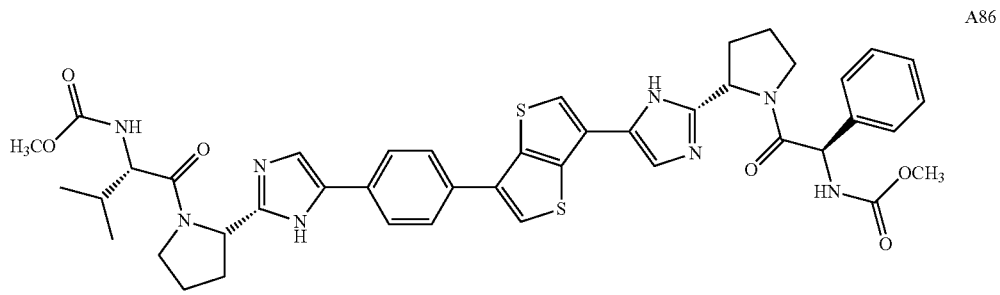

A86

Compound A86 was synthesized as shown in Scheme 20.

Preparation of ((S)-1-[(S)-2-(5-{4-[6-{4-{2-[(S)-1-((S)-2-methoxycarbonylamino-3-methyl-butyryl)-pyrrolidin-2-yl]-3H-imidazol-4-yl}-phenyl)-thieno[3,2-b]thiophen-3-yl]-phenyl}-1H-imidazol-2-yl)-pyrrolidine-1-carbonyl]-2-methyl-propyl}-carbamic acid methyl ester A86. Compound A26 was synthesized from 3,6-dibromothieno[3,2,b]thiophene (0.335 mmol) and compound 8 (0.738 mmol), following the procedure as described for compound A155. The residue was purified by semi-preparative HPLC to give compound A86 as a yellow solid in 28% yield. $^1$H NMR (CD$_3$OD, 400 MHz) δ (ppm) 0.92 (d, J=6.69 Hz, 6H), 0.97 (d, J=6.69 Hz, 6H), 1.01 (d, J=6.69 Hz, 2H), 2.01-2.13 (m, 4H), 2.20-2.40 (m, 6H), 3.67 (s, 6H), 3.87-3.93 (m, 2H), 3.99-4.04 (m, 2H), 4.25 (d, J=7.42 Hz, 2H), 5.18-5.21 (m, 2H), 7.37 (s, 2H), 7.79-7.86 (m, 10H); MS (ESI, EI$^+$) m/z=877.5 (MH$^+$).

carboxylic acid tert-butyl ester 76. Compound 76 was synthesized from 3,6-dibromothieno[3,2,b]thiophene (6.71 mmol) and compound 61 (6.71 mmol), following the procedure as described for compound 63 to give compound 76 as a yellow crystal. MS (ESI, EI$^+$) m/z=554-556 (MH$^+$).

Preparation of 4-(6-bromo-thieno[3,2-b]thiophen-3-yl)-2-(S)-pyrrolidin-2-yl-1H-imidazole, hydrochloride salt compound 77. Compound 77 was synthesized from compound 76 (1.29 mmol), following the procedure as described for compound 11 to give compound 77 in quantitative yield. MS (ESI, EI$^+$) m/z=354.1/356.13 (MH$^+$).

Preparation of ((S)-1-{(S)-2-[4-(6-bromo-thieno[3,2-b]thiophen-3-yl)-1H-imidazol-2-yl]-pyrrolidine-1-carbonyl}-2-methyl-propyl)-carbamic acid methyl ester 78. Compound 78 was synthesized from compound 77 (1.56 mmol) and compound 1 (1.64 mmol), following the procedure as

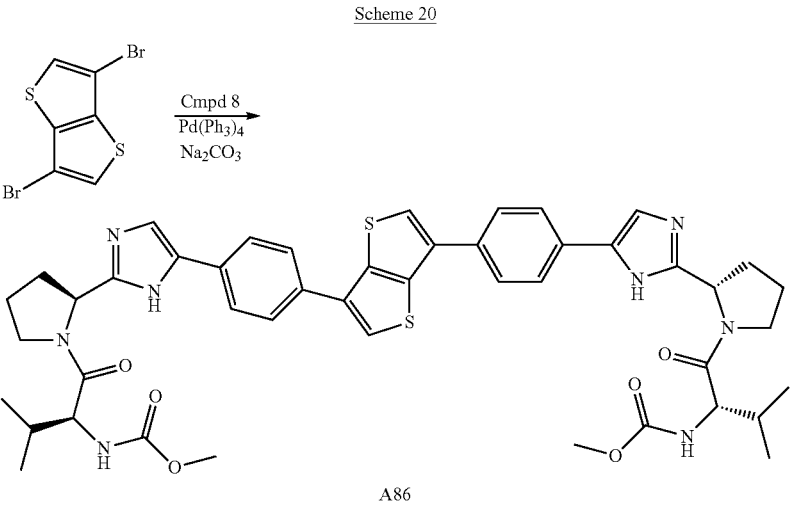

Scheme 20

A86

Example 29

Synthesis of [(S)-1-((S)-2-{4-[6-(4-{(S)-2-[1-(R)-2-dimethylamino-2-phenyl-acetyl)-pyrrolidin-2-yl]-3H-imidazol-4-yl}-phenyl)-thieno[3,2-b]thiophen-3-yl]-1H-imidazol-2-yl}-pyrrolidine-1-carbonyl)-2-methyl-propyl]-carbamic acid methyl ester A214 described for compound 23 to give compound 78 in 82% yield. MS (ESI, EI$^+$) m/z=513.2/515 (MH$^+$).

Preparation of (S)-2-{(5-[4-(6-{(S)-2-[1-((S)-2-methoxycarbonylamino-3-methyl-butyryl)-pyrrolidin-2-yl]-1H-imidazol-4-yl}-thieno[3,2-b]thiophen-3-yl)-phenyl]-1H-imidazol-2-yl}-pyrrolidine-1-carboxylic acid tert-butyl ester 79. Compound 79 was synthesized from compound 78 (0.896

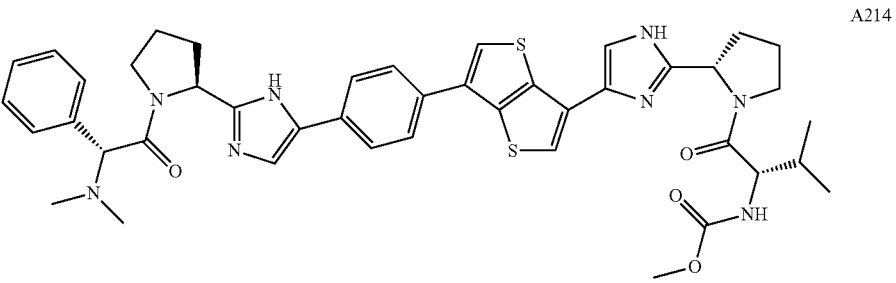 [SMILES: COC(=O)N[C@H](C(=O)N1CCC[C@H]1c1nc(-c2csc3c(-c4ccc(-c5cnc([C@@H]6CCCN6C(=O)[C@@H](c6ccccc6)N(C)C)[nH]5)cc4)csc23)c[nH]1)C(C)C]

A214

Compound A214 was synthesized as shown in Scheme 21.

Preparation of 4-(6-bromo-thieno[3,2-b]thiophen-3-yl)-2-(S)-(1-tert-butoxycarbonyl-pyrrolidin-2-yl)-imidazole-1- mmol) and compound 6 (0.941 mmol), following the procedure as described for compound A1 to give compound 79 in quantitative yield. MS (ESI, EI$^+$) m/z=745.4 (MH$^+$).

Scheme 21

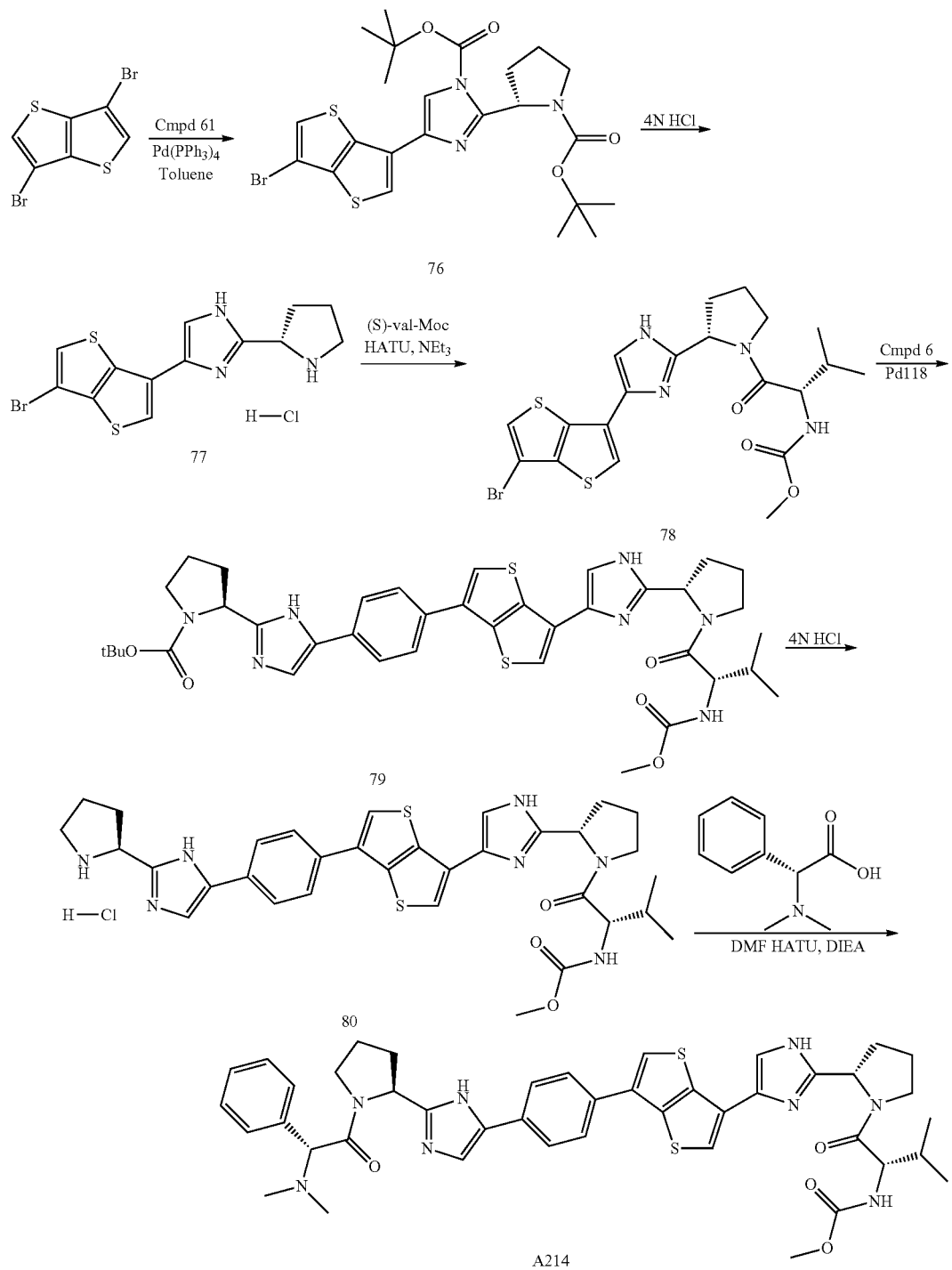

Preparation of {2-methyl-(S)-1-[(S)-2-(4-{6-[4-((S)-2-pyrrolidin-2-yl-3H-imidazol-4-yl)-phenyl]-thieno[3,2-b]thiophen-3-yl}-1H-imidazol-2-yl)-pyrrolidine-1-carbonyl]-propyl}-carbamic acid methyl ester, hydrochloride salt 80. Compound 80 was synthesized from compound 79 (1.36 mmol), following the procedure as described for compound 11 to give compound 80 in quantitative yield. MS (ESI, EI+) m/z=645.2 (MH+).

Preparation of [(S)-1-((S)-2-{4-[6-(4-{(S)-2-[1-(R)-2-dimethylamino-2-phenyl-acetyl)-pyrrolidin-2-yl]-3H-imidazol-4-yl}-phenyl)-thieno[3,2-b]thiophen-3-yl]-1H-imidazol-2-yl}-pyrrolidine-1-carbonyl)-2-methyl-propyl]-carbamic acid methyl ester A214. To a mixture of compound 80 (0.22 mmol), (R)—N,N-dimethylphenyl glycine (0.24 mmol), and HATU (0.24 mmol) in dimethylformamide (1.5 mL) was added DIEA (1.32 mmol) dropwise. The reaction mixture was stirred at room temperature for 1.5 hrs. The solvent was removed under reduced pressure and the residue was dissolved in dichloromethane (5 mL). This mixture was eluted through a SCX-2 column and the column was washed with CH₃OH/NH₃. The filtrate was concentrated and the residue was purified by chromatography on a silica gel column to give compound A214 as a white powder in 41% yield. MS (ESI, EI⁺) m/z=806.2 (MH⁺).

Example 30

Synthesis of [(S)-1-((S)-2-{4-[6-(4-{(S)-2-[1-(R)-2-dimethylamino-2-phenyl-acetyl)-pyrrolidin-2-yl]-3H-imidazol-4-yl}-phenyl)-thieno[3,2-b]thiophen-3-yl]-1H-imidazol-2-yl}-pyrrolidine-1-carbonyl)-2-methyl-propyl]-carbamic acid methyl ester A114

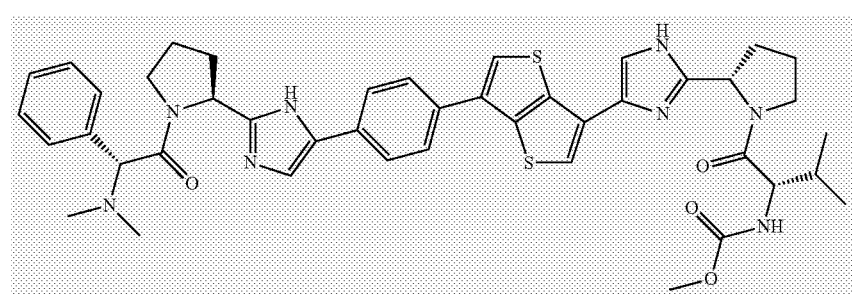

A114

Preparation of [(S)-1-((S)-2-{4-[6-(4-{(S)-2-[1-(R)-2-methoxycarbonylamino-2-phenyl-acetyl)-pyrrolidin-2-yl]-3H-imidazol-4-yl}-phenyl)-thieno[3,2-b]thiophen-3-yl]-1H-imidazol-2-yl}-pyrrolidine-1-carbonyl)-2-methyl-propyl]-carbamic acid methyl ester A114. To a mixture of compound 80 (0.133 mmol), compound 31 (0.133 mmol), and HATU (0.173 mmol) in dry DCM (2 mL) under nitrogen was added dropwise triethylamine (0.664 mmol). The mixture was stirred at 0° C. during 1 hr. The solvent was removed under reduced pressure and the residue was dissolved in methanol. This mixture was eluted through a SCX-2 column and washed with a solution of 7N NH₃ in CH₃OH. The filtrate was concentrated and the residue was purified two times by silica gel chromatography to give compound A114 as a white solid in 27% yield. ¹H NMR (DMSO-d₆, 400 MHz) δ (ppm) 0.81-0.86 (m, 6H), 1.83-2.19 (m, 8H), 2.28-2.38 (m, 1H), 3.10-3.21 (m, 1H), 3.52-3.55 (m, 6H), 3.80-3.90 (m, 2H), 4.05 (t, J=8.53 Hz, 1H), 5.06-5.19 (m, 2H), 5.41-5.53 (m, 1H), 6.92-7.15 (m, 1H), 7.28-7.47 (m, 6H), 7.54-7.68 (m, 1H), 7.75-7.91 (m, 5H), 8-8.03 (m, 1H), 11.76-12.21 (m, 2H); MS (ESI, EI⁺) m/z=835.3 (MH⁺).

Example 31

Synthesis of Compound 83

Compound 83 was synthesized as shown in Scheme 22.

Scheme 22

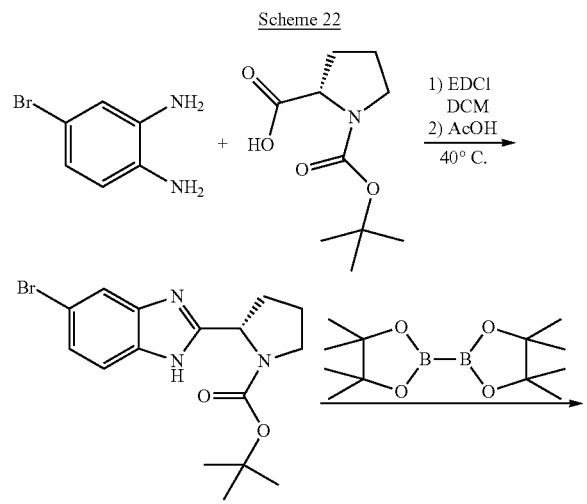

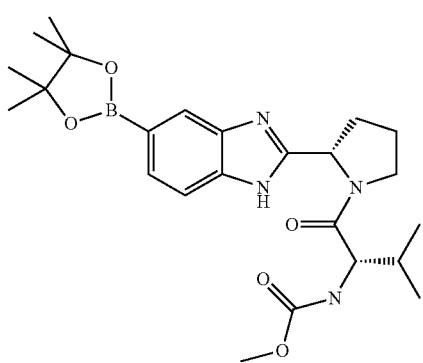

-continued

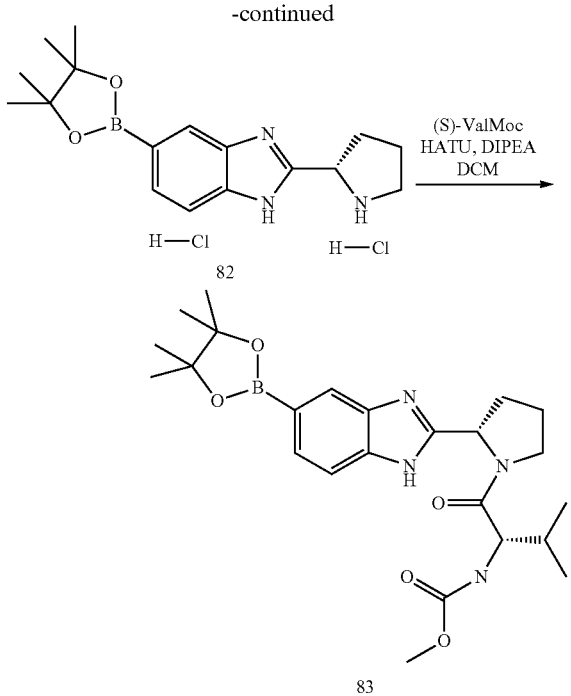

Preparation of compound 81. To a solution of Boc-Pro-OH (10.68 mmol) in DCM were added EDCI (11.73 mmol) and 4-bromo-1,2-diaminobenzene (10.69 mmol). The reaction was completed after 2 hrs at room temperature. Dichloromethane (30 mL) was added and the mixture was washed with water. The aqueous phase was extracted with dichloromethane and the combined organics were evaporated in vacuo. The crude was chromatographed to give a mixture of bis-acylated analogues. This mixture was heated in acetic acid (14 mL) at 40° C. for 2 hrs. Once cooled, saturated $Na_2CO_3$ solution was carefully added to adjust the mixture to pH ~8. The mixture was extracted with ethyl acetate and the organic layers were washed with saturated $NaHCO_3$ solution and water, dried over $Na_2SO_4$, and decolourized with activate charcoal. The mixture was filtered and concentrated in vacuo. The residue was purified by silica gel chromatography (eluent: DCM to DCM/MeOH 2%) to give compound 81 as an white solid in 6% yield. MS (ESI, EI$^+$) m/z=368 (MH$^+$).

Preparation of compound 66. To a mixture degazed of compound 81 (2.73 mmol), bispinacolatodiboron (3.82 mmol), KOAc (6 mmol), and tricyclobenzylphosphine (0.55 mmol) in DME (18 mL) was added $Pd_2(dba)_3$ (0.79 mmol).

The reaction mixture was irradiated at 150° C. during 1 hr. The solvent was removed in vacuo and the residue diluted with dichloromethane to filter salt. After concentrated in vacuo, the crude was purified by silica gel chromatography (eluent: DCM to DCM/MeOH 4%) to give compound 66 in a 59% yield. MS (ESI, EI$^+$) m/z=414.2 (MH$^+$).

Preparation of compound 82. Compound 82 was synthesized from compound 66 (2.42 mmol), following the procedure as described for compound 7 to give compound 82 as a white solid in quantitative yield. MS (ESI, EI$^+$) m/z=314.42 (MH$^+$).

Preparation of compound 83. To a mixture of compound 82 (2.48 mmol), compound 1 (2.60 mmol), and HATU (2.60 mmol) in dry dichloromethane (25 mL) was added DIPEA (12.40 mmol) dropwise. The mixture was stirred at room temperature for 2 hrs. Saturated $NH_4Cl$ solution was added and the reaction mixture was stirred vigorously during 15 min. The layers were separated and the organic layer was dried on $Na_2SO_4$, filtered, and concentrated in vacuo. The residue was purified by silica gel chromatography (eluent: DCM to DCM/MeOH 4%) to give compound 83 as a white foam. MS (ESI, EI$^+$) m/z=471.45 (MH$^+$).

Example 32

Synthesis of [(S)-1-((S)-2-{5-[4-(6-{(S)-2-[1-((R)-2-Methoxycarbonylamino-2-phenyl-acetyl)-pyrrolidin-2-yl]-3H-benzoimidazol-5-yl}-thieno[3,2-b]thiophen-3-yl)-phenyl]-1H-imidazol-2-yl}-pyrrolidine-1-carbonyl)-2-methyl-propyl]-carbamic acid methyl ester A172

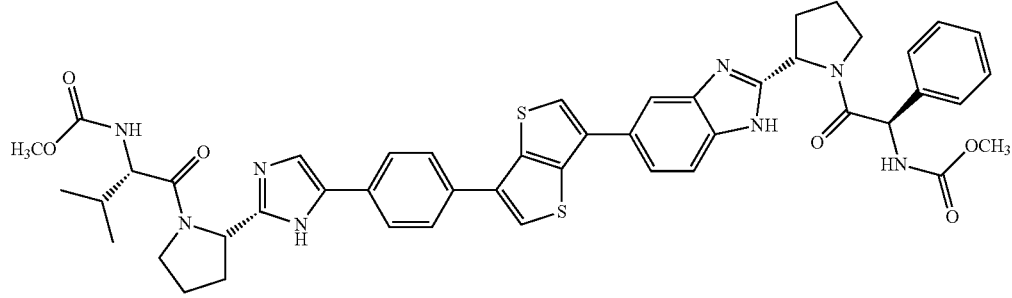

A172

Compound 172 was synthesized as shown in Scheme 23.

Preparation of {2-methyl-(S)-1-[2-(S)-(5-{4-[6-((S)-2-pyrrolidin-2-yl-3H-benzoimidazol-5-yl)-thieno[3,2-b]thiophen-3-yl]-phenyl}-1H-imidazol-2-yl)-pyrrolidine-1-carbonyl]-propyl}-carbamic acid methyl ester, hydrochloride salt E47. Compound 68 (0.189 mmol) was dissolved in methanol (3.8 mL) and 4N HCl in dioxane (3.8 mL) was added. The mixture was stirred 1 hr at room temperature before concentration under reduced pressure. The residue was precipitated in diethyl ether to give compound E47 as a beige solid in 97% yield. $^1$H NMR (DMSO-d$_6$, 400 MHz) δ (ppm) 0.76 (d, 3H), 0.83 (d, 3H), 2.07-2.20 (m, 8H), 2.36 (m, 4H), 3.10-3.43 (m, 2H), 3.82 (m, 1H), 4.04 (m, 1H), 4.12 (t, 1H), 5.08 (m, 1H), 5.22 (t, 1H), 7.26 (d, 1H), 7.83 (m, 2H), 7.94 (m, 2H), 8.08-8.15 (m, 3H), 8.17 (m, 2H), 8.25 (s, 1H), 8.75 (s, 1H), 10.66 (s, 1H), 14.94 (s, 1H), 15.51 (s, 1H); MS (ESI, EI$^+$) m/z=694.2 (MH$^+$).

Preparation of [(S)-1-((S)-2-{5-[4-(6-{(S)-2-[1-((R)-2-methoxycarbonylamino-2-phenyl-acetyl)-pyrrolidin-2-yl]-3H-benzoimidazol-5-yl}-thieno[3,2-b]thiophen-3-yl)-phenyl]-1H-imidazol-2-yl}-pyrrolidine-1-carbonyl)-2-methyl-propyl]-carbamic acid methyl ester A172. Intermediate E47 (0.178 mmol) was dissolved in DMF (3.6 mL) and the mixture was cooled down to −10° C. TEA (1.246 mmol), intermediate 31 (0.187 mmol), and HATU (0.231 mmol) were added and the mixture was stirred at −10° C. during 30 min. Ethyl acetate was added and the mixture was washed with water. The organic layer was dried over Na$_2$SO$_4$, filtered, and concentrated under reduced pressure. The residue was filtered on a SCX-2 column and the filtrate was purified by silica gel chromatography (eluent: DCM to DCM/MeOH 5%) and RP18 (H$_2$O to ACN/H$_2$O 60%) to give compound A172 as a white solid in 41% yield. $^1$H NMR (DMSO-d$_6$, 400 MHz) δ (ppm) 0.86 (d, 3H), 0.91 (d, 3H), 1.85-2.15 (m, 8H), 3.19 (m, 1H), 3.53 (s, 6H), 3.81 (m, 2H), 3.94 (m, 1H), 4.05 (m, 1H), 5.08 (m, 1H), 5.17 (m, 1H), 5.23 (m, 1H), 6.82 (m, 1H), 7.26-7.46 (m, 6H), 7.52-7.72 (m, 4H), 7.73-7.91 (m, 4H), 7.93-8.12 (m, 3H), 11.83 (s, 1H), 12.29 (s, 1H); MS (ESI, EI$^+$) m/z=886.2 (MH$^+$).

Scheme 23

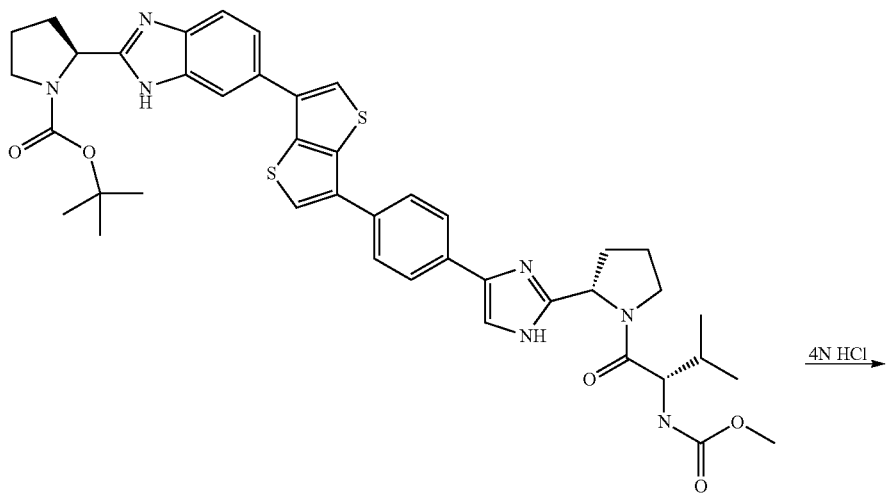

68

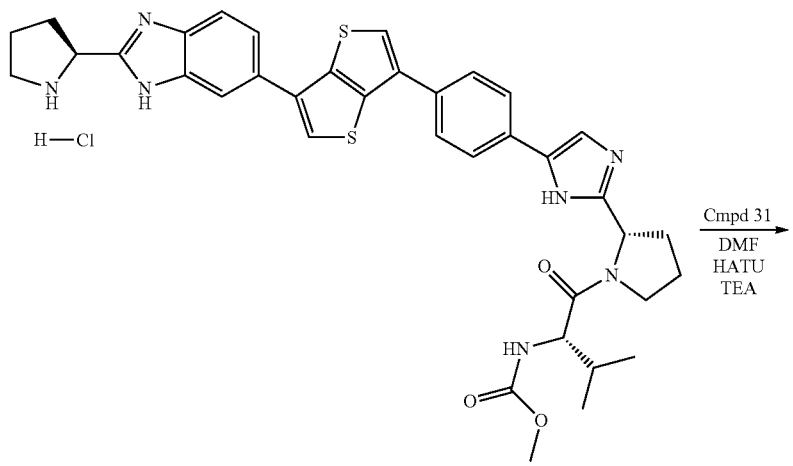

E47

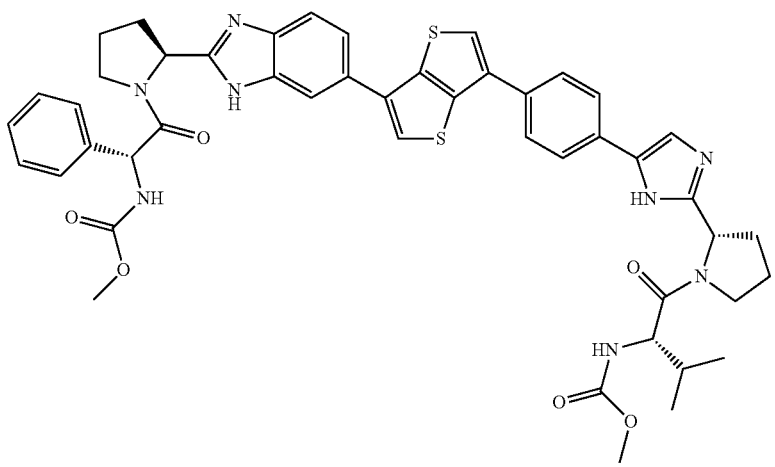
A172
Example 33
Synthesis of [(S)-1-((S)-2-{6-[6-(4-{(S)-2-[1-((R)-2-methoxycarbonylamino-2-phenyl-acetyl)-pyrrolidin-2-yl]-3H-imidazol-4-yl}-phenyl)-thieno[3,2-b]thiophen-3-yl]-1H-benzoimidazol-2-yl}-pyrrolidine-1-carbonyl)-2-methyl-propyl]-carbamic acid methyl ester A169
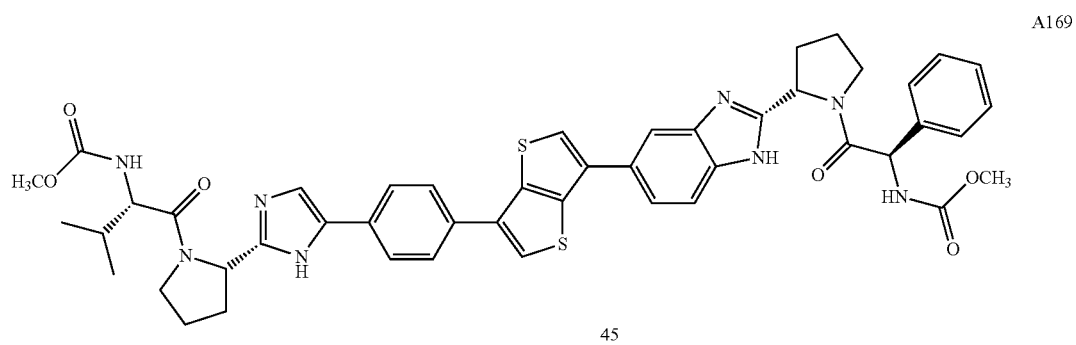
A169
Compound 169 was synthesized as shown in Scheme 24.
Scheme 24
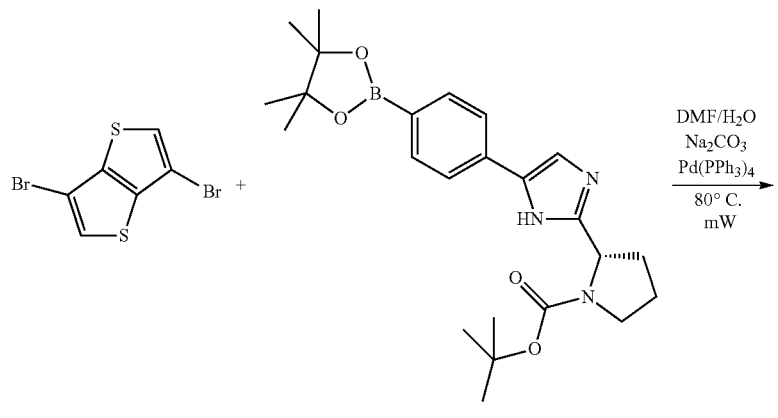

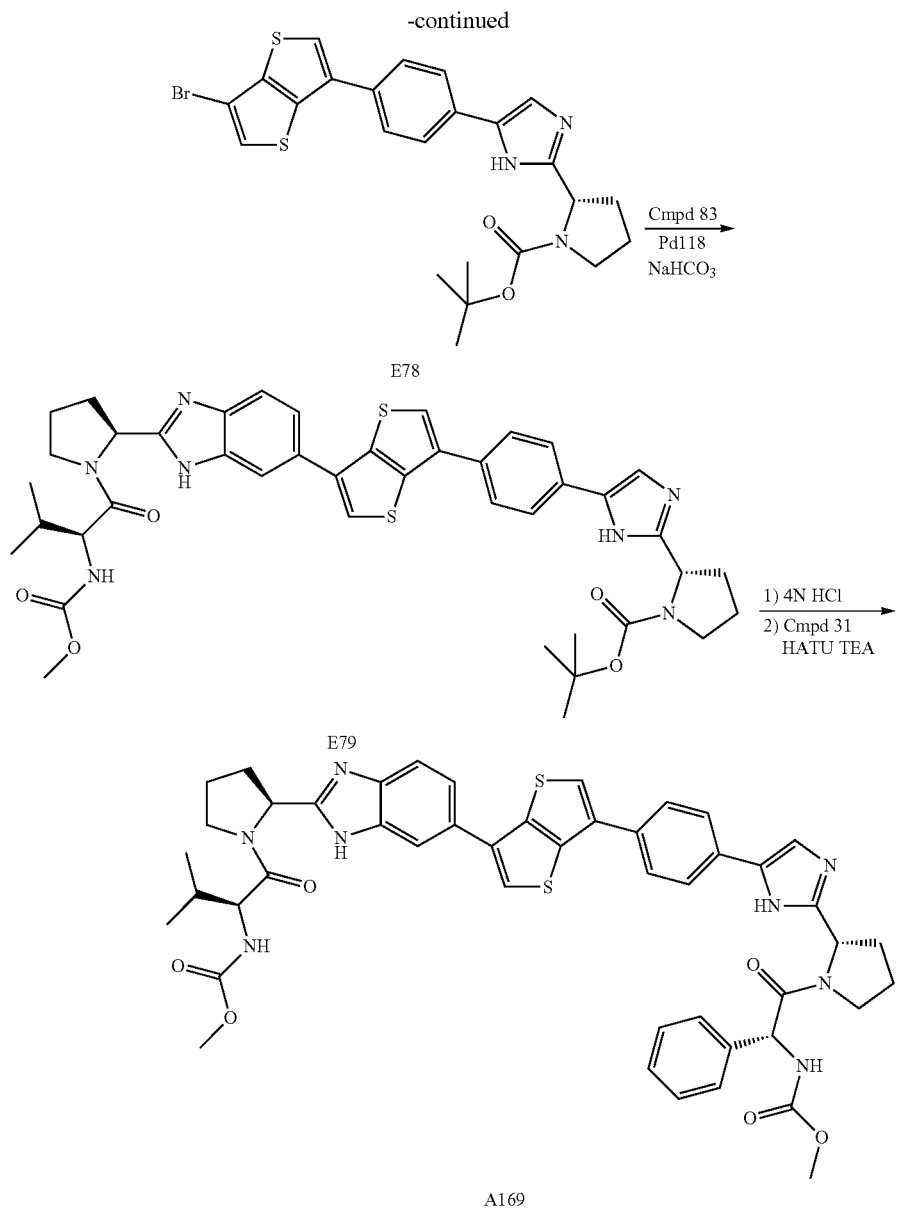

Preparation of (S)-2-{5-[4-(6-bromo-thieno[3,2-b]thiophen-3-yl)-phenyl]-1H-imidazol-2-yl}-pyrrolidine-1-carboxylic acid tert-butyl ester E78. To a mixture of DMF and water (20 mL/2.5 mL) were added Pd(PPh$_3$)$_4$ (0.1 mmol), 3,6-dibromo-thieno[3,2-b]thiophene (1.01 mmol), intermediate 6 (1.1 mmol), and sodium carbonate (4.04 mmol). The reaction mixture was degassed and irradiated for 1 hr at 80° C. Ethyl acetate was added and the organic layer was washed with water. The organic layer was dried over Na$_2$SO$_4$, filtered, and evaporated in vacuo. The residue was purified by silica gel chromatography (eluent: DCM-DCM/MeOH 98/2) to give intermediate E78 as a green gum in 41% yield. MS (ESI, EI$^+$) m/z=532.19-530.31 (MH$^+$).

Preparation of (S)-2-{5-[4-(6-{(S)-2-[1-((S)-2-methoxycarbonylamino-3-methyl-butyryl)-pyrrolidin-2-yl]-3H-benzoimidazol-5-yl}-thieno[3,2-h]thiophen-3-yl)-phenyl]-1H-imidazol-2-yl}-pyrrolidine-1-carboxylic acid tert-butyl ester E79. Compound 78 (0.198 mmol), intermediate 83 (0.228 mmol), and 1,1'-bis(di-tert-BP)ferrocene palladium dichloride (0.03 mmol) were added to a solution of dioxane (4 mL) and 1M NaHCO$_3$ in water (0.594 mmol). The reaction mixture was irradiated at 90° C. for 1 hr. The mixture was diluted in dichloromethane and washed with water. The two layers were separated and the organic layer was concentrated under reduced pressure. The residue was purified by silica gel chromatography (eluent: DCM-DCM/MeOH 95/5) to give intermediate E79 as a brown foam in 70% yield. $^1$H NMR (CDCl$_3$, 400 MHz) δ (ppm) 0.90-0.91 (m, 6H), 1.51 (s, 9H), 1.67-2.40 (m, 10H), 3.07-3.1 (m, 2H), 3.45-3.50 (m, 1H), 3.72 (s, 3H), 3.90 (m, 1H), 4.37 (m, 1H), 5.00-5.01 (m, 1H), 5.45-5.48 (m, 2H), 7.26-8.12 (m, 10H), 10.67 (m, 1H); MS (ESI, EI$^-$) m/z=792.79 (MH$^-$).

Preparation of [(S)-1-((S)-2-{6-[6-(4-{(S)-2-[1-((R)-2-methoxycarbonylamino-2-phenyl-acetyl)-pyrrolidin-2-yl]-3H-imidazol-4-yl}-phenyl)-thieno[3,2-b]thiophen-3-yl]-1H-benzoimidazol-2-yl}-pyrrolidine-1-carbonyl)-2-methyl-propyl]-carbamic acid methyl ester A169. Intermediate E79 (0.132 mmol) was dissolved in methanol (2.6 mL) and 4N HCl in dioxane (2.64 mL) was added. The mixture was stirred 1 hr at room temperature before concentration under reduced pressure. The residue was dissolved in DMF (2.6 mL) and the mixture was cooled down to −10° C. TEA (0.924 mmol), intermediate 31 (0.139 mmol), and HATU (0.172 mmol) were added and the mixture was stirred at −10° C. for 1 hr. Ethyl acetate was added and the mixture was washed with water. The organic layer was dried over $Na_2SO_4$, filtered, and concentrated under reduced pressure. The residue was filtered on a SCX-2 column and purified by silica gel chromatography (eluent: DCM-DCM/MeOH 97/3) to give compound A169 as a beige solid in 74% yield. $^1$H NMR (CDCl$_3$, 400 MHz) δ (ppm) 0.89-0.91 (m, 6H), 1.40-2.42 (m, 8H), 3.08-3.24 (m, 3H), 3.67 (m, 3H), 3.71 (m, 4H), 3.88-3.89 (m, 1H), 4.34-4.38 (m, 1H), 5.30-5.32 (m, 1H), 5.42-5.45 (m, 3H), 6.03-6.04 (m, 1H), 7.26-8.14 (m, 16H), 10.65 (m, 1H); MS (ESI, EI$^+$) m/z=885.8 (MH$^+$).

Example 34

Synthesis of (S)-1-{(S)-2-[6-(6-{2-[(S)-1-((R)-2-Methoxycarbonylamino-2-phenyl-acetyl)-pyrrolidin-2-yl]-3H-benzoimidazol-5-yl}-thieno[3,2-b]thiophen-3-yl)-1H-benzoimidazol-2-yl]-pyrrolidine-1-carbonyl}-2-methyl-propyl)-carbamic acid methyl ester A208

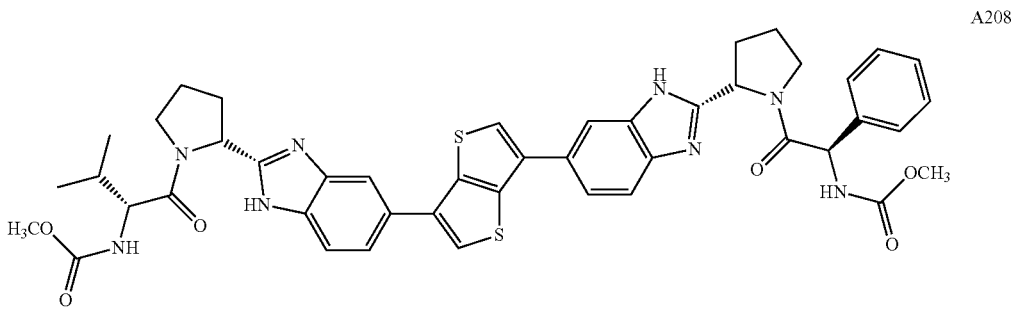

A208

Compound 208 was synthesized as shown in Scheme 25.

Preparation of (S)-2-[6-(6-bromo-thieno[3,2-b]thiophen-3-yl)-1H-benzoimidazol-2-yl]-pyrrolidine-1-carboxylic acid tert-butyl ester E52. Intermediate 52 was synthesized from 3,6-dibromothieno[3,2,b]thiophene (1.20 mmol) and the intermediate 66 (1.20 mmol) following the procedure as described for compound A155 (in this case, the mixture was stirred at 105° C. for 2 hrs) to give intermediate E52 as a brown gum in 53% yield. MS (ESI, EI$^+$) m/z=506 (MH$^+$).

Preparation of (S)-2-[6-(6-{2-((S)-1-((S)-2-methoxycarbonylamino-3-methyl-butyryl)-pyrrolidin-2-yl]-3H-benzoimidazol-5-yl}-thieno[3,2-b]thiophen-3-yl)-1H-benzoimidazol-2-yl]-pyrrolidine-1-carboxylic acid tert-butyl ester E53. Intermediate E53 was synthesized from intermediate E52 (0.159 mmol) and intermediate 83 (0.167 mmol) following the procedure as described for compound A1. The crude was purified by silica gel chromatography (eluent: DCM to DCM/MeOH 50%) to give intermediate E53 in 77% yield. MS (ESI, EI$^+$) m/z=768 (MH$^+$).

Scheme 25

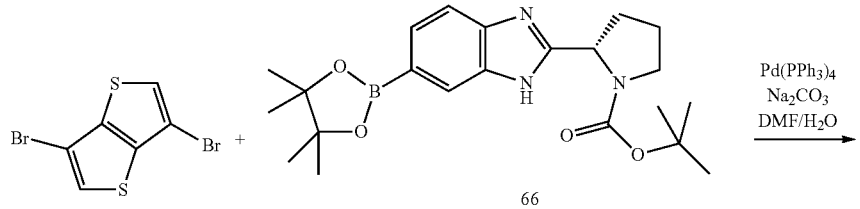

66

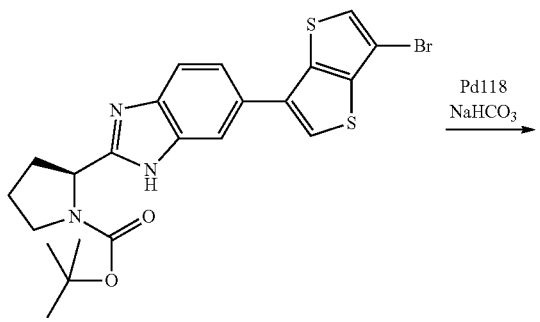

E52

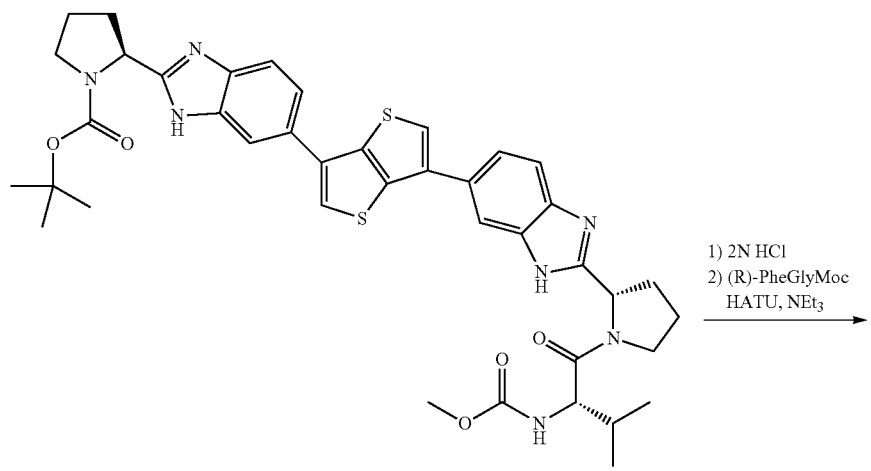

E53

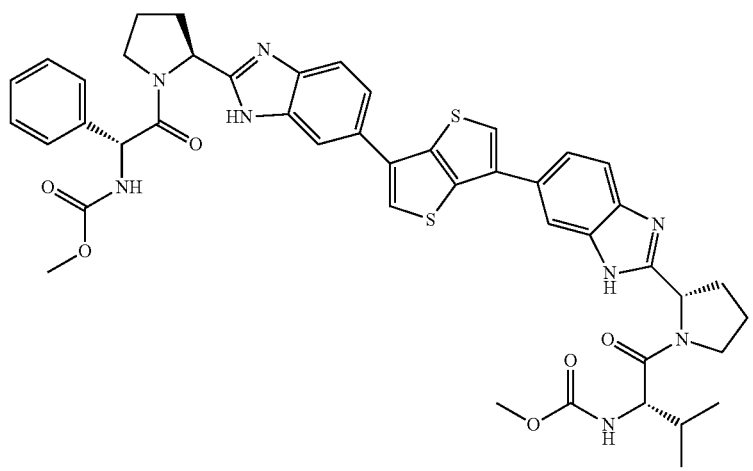

A208

Preparation of (S)-1-{(S)-2-[6-(6-{2-[(S)-1-((R)-2-methoxycarbonylamino-2-phenyl-acetyl)-pyrrolidin-2-yl]-3H-benzoimidazol-5-yl}-thieno[3,2-b]thiophen-3-yl)-1H-benzoimidazol-2-yl]-pyrrolidine-1-carbonyl}-2-methyl-propyl)-carbamic acid methyl ester A208. Compound A208 was synthesized from intermediate E53 (0.121 mmol) and intermediate 31 (0.1273 mmol), following the procedure as described for compound A15 (in this case, coupling was at 0° C.) to give compound A208 as a yellow lyophilized solid. MS (ESI, EI$^+$) m/z=860.2 (MH$^+$).

Example 35
Synthesis of (S)-1-{(S)-2-[6-(6-{2-[(S)-1-((R)-2-Methoxycarbonylamino-2-phenyl-acetyl)-pyrrolidin-2-yl]-3H-imidazol-4-ylethynyl}-thieno[3,2-b]thiophen-3-yl)-1H-benzoimidazol-2-yl]-pyrrolidine-1-carbonyl}-2-methyl-propyl)-carbamic acid methyl ester A206
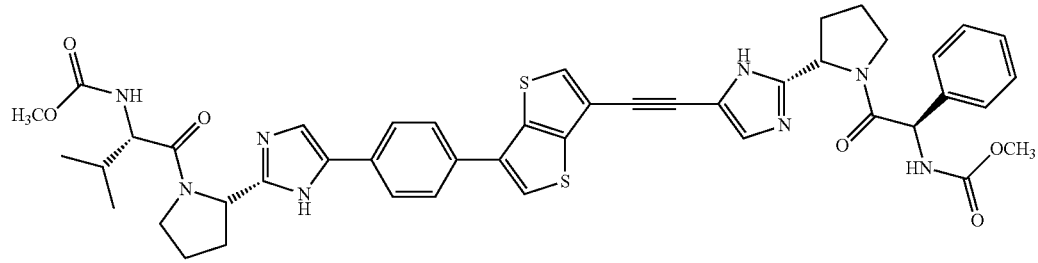
Compound 206 was synthesized as shown in Scheme 26.
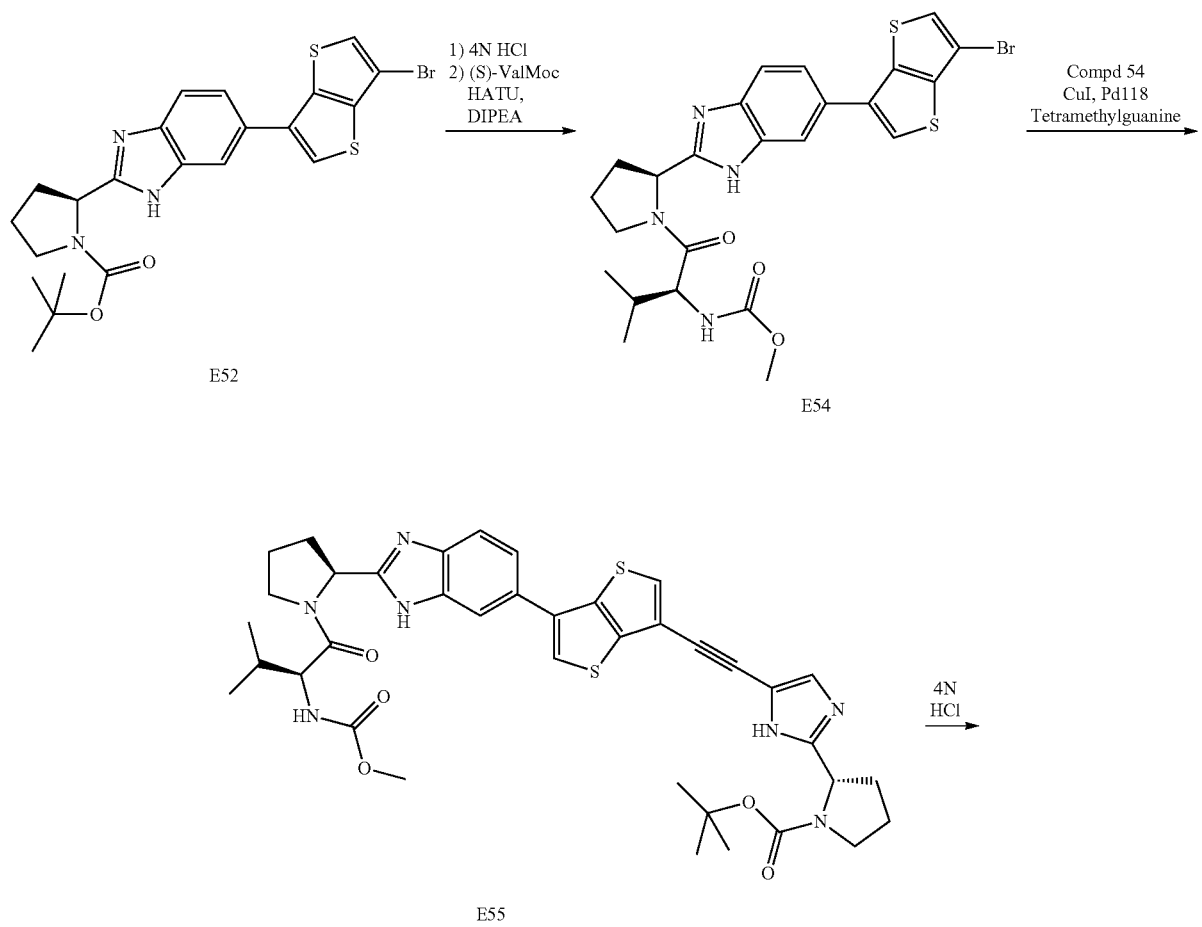

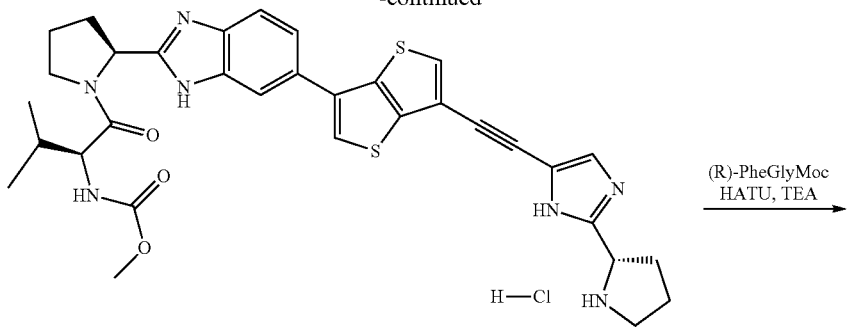

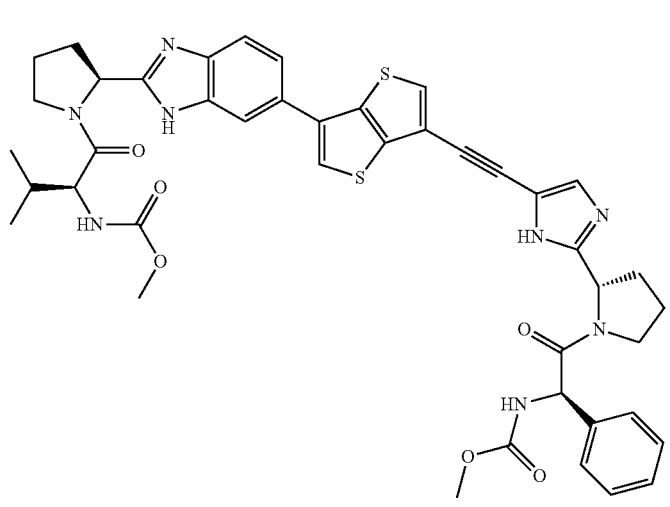

Preparation of ((S)-1-{(S)-2-[6-(6-bromo-thieno[3,2-b]thiophen-3-yl)-1H-benzoimidazol-2-yl]-pyrrolidine-1-carbonyl}-2-methyl-propyl)-carbamic acid methyl ester E54. Compound E52 (0.562 mmol) was solubilized in dioxane (7 mL) and 4N HCl in dioxane (5 mL) was added dropwise. The mixture was stirred at room temperature overnight. The reaction mixture was evaporated in vacuo and the residue was used directly for the next step (MS (ESI, EI$^+$) m/z=435 (MH$^+$)). To a mixture of the residue, intermediate 1 (0.590 mmol), and HATU (0.590 mmol) in dry DMF (10 mL/mmol) under nitrogen was added dropwise triethylamine (1.7 mmol). The mixture was stirred at room temperature for 1 hr. The solvent was removed under reduced pressure and the residue dissolved in methanol. This mixture was eluted through a SCX-2 column and the product was released with a solution of CH$_3$OH/NH$_3$. The filtrate was concentrated and the residue was purified by silica gel chromatography (eluent: DCM to DCM/MeOH 4%) to give intermediate E54 in quantitative yield. MS (ESI, EI$^+$) m/z=561 (MH$^+$).

Preparation of (S)-2-[5-(6-{(S)-2-[1-((S)-2-methoxycarbonylamino-3-methyl-butyryl)-pyrrolidin-2-yl]-3H-benzoimidazol-5-yl}-thieno[3,2-h]thiophen-3-ylethynyl)-1H-imidazol-2-yl]-pyrrolidine-1-carboxylic acid tert-butyl ester E55. Intermediate E55 was synthesized from intermediate E54 (0.125 mmol) and intermediate 54 (0.250 mmol), following the procedure as described for intermediate 55. The mixture was diluted with ethyl acetate and washed with a saturated NH$_4$Cl solution. The organic layer was dried over Na$_2$SO$_4$, filtered and concentrated under diminished pressure. The residue was purified by silica gel chromatography (eluent: DCM to DCM/AcOEt 60%) to give intermediate E55 in 54% yield. MS (ESI, EI$^+$) m/z=742.5 (MH$^+$).

Preparation of [2-methyl-(S)-1-((S)-2-{6-[6-((S)-2-pyrrolidin-2-yl-3H-imidazol-4-ylethynyl)-thieno[3,2-b]thiophen-3-yl]-1H-benzoimidazol-2-yl}-pyrrolidine-1-carbonyl)-propyl]-carbamic acid methyl ester, hydrochloride salt E56. Compound E56 was synthesized from intermediate E55 (0.067 mmol) following the procedure as described for intermediate E47 to give intermediate E56 in quantitative yield. MS (ESI, EI$^+$) m/z=642.37 (MH$^+$).

Preparation of (S)-1-{(S)-2-[6-(6-{2-[(S)-1-((R)-2-methoxycarbonylamino-2-phenyl-acetyl)-pyrrolidin-2-yl]-3H-imidazol-4-ylethynyl}-thieno[3,2-h]thiophen-3-yl)-1H-benzoimidazol-2-yl]-pyrrolidine-1-carbonyl}-2-methyl-propyl)-carbamic acid methyl ester A206. Compound A206 was synthesized from intermediate E56 (0.067 mmol), following the procedure as described for intermediate 12a (at room temperature) to give compound A206 as a white lyophilised powder in 82% yield. $^1$H NMR (DMSO-d$_6$, 400 MHz) δ (ppm) 0.82 (d, J=6.53 Hz, 3H), 0.86 (d, J=6.53 Hz, 3H), 1.87-2.10 (m, 7H), 2.19-2.28 (m, 2H), 3.53-3.55 (m, 6H), 3.81-3.88 (m, 2H), 3.95-4.01 (m, 1H), 4.08 (t, J=8.35 Hz, 1H), 4.83 (s, 1H), 4.98-5 (m, 1H), 5.17-5.20 (m, 1H), 5.46-5.48 (m, 1H), 7.14-7.22 (m, 1H), 7.28-7.42 (m, 6H), 7.52-7.66 (m, 4H), 8-8.06 (m, 2H), 12.01 (s, 1H); MS (ESI, EI$^+$) m/z=833.6 (MH$^+$).

Example 36

Synthesis of [(S)-1-((S)-2-{6-[5-(4-{(S)-2-[1-((R)-2-methoxycarbonylamino-2-phenyl-acetyl)-pyrrolidin-2-yl]-1H-imidazol-4-yl}-phenyl)-thieno[3,2-b]thiophen-2-yl)-1H-benzoimidazol-2-yl}-pyrrolidine-1-carbonyl)-2-methyl-propyl]-carbamic acid methyl ester A215

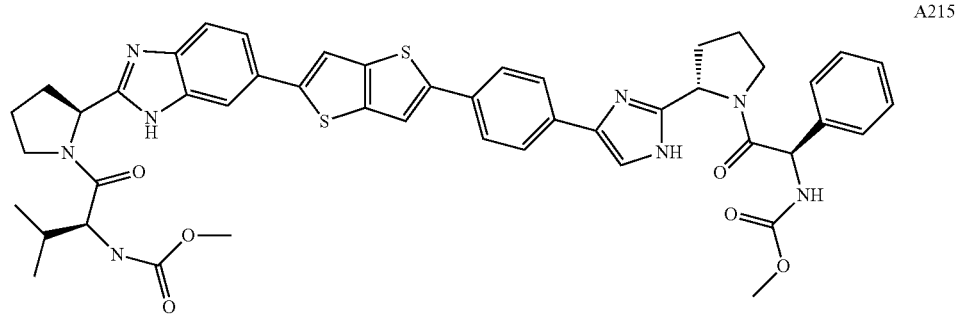 [SMILES: COC(=O)N[C@H](C(=O)N1CCC[C@H]1c1nc2ccc(-c3cc4sc(-c5ccc(-c6c[nH]c([C@@H]7CCCN7C(=O)[C@H](NC(=O)OC)c7ccccc7)n6)cc5)cc4s3)cc2[nH]1)C(C)C]

A215

Compound A215 was synthesized as shown in 27.

Preparation of (S)-2-[6-(5-bromo-thieno[3,2-b]thiophen-2-yl)-1H-benzoimidazol-2-yl]-pyrrolidine-1-carboxylic acid tert-butyl ester E64. In a round bottom flask were added intermediate 66 (2.42 mmol) and 3,6-dibromo-thieno[3,2-b]thiophene (7.26 mmol). The system was purged and anhydrous dioxane (36 mL) was added. Then, NaHCO$_3$ 1M (7.26 mmol) and Pd118 (0.242 mmol) were added. The reaction mixture was stirred under reflux (110° C.) for 1.5 hrs. The reaction mixture was cooled down to room temperature and DCM was added. The mixture was washed with water and the organic layer dried, filtered, and concentrated under reduced pressure. The residue was purified by silica gel chromatography (eluent: DCM to DCM/MeOH 2%) to give intermediate E64 as a yellow foam in 19% yield. MS (ESI, EI$^+$) m/z=505.8 (MH$^+$).

Preparation of 6-(5-bromo-thieno[3,2-b]thiophen-2-yl)-(S)-2-pyrrolidin-2-yl-1H-benzoimidazole, hydrochloride E65. Intermediate E65 was synthesized from intermediate E64 (0.198 mmol), following the procedure as described for intermediate E47 (without purification) to give intermediate E65 as a yellow solid in quantitative yield. MS (ESI, EI$^+$) m/z=405.8 (MH$^+$).

Scheme 27

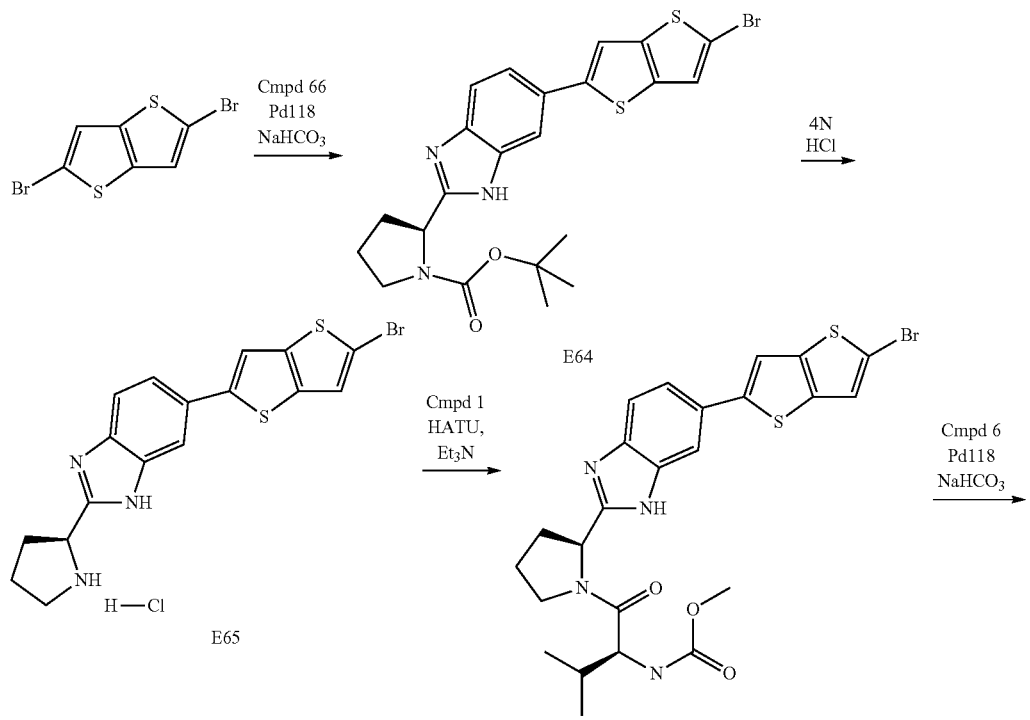

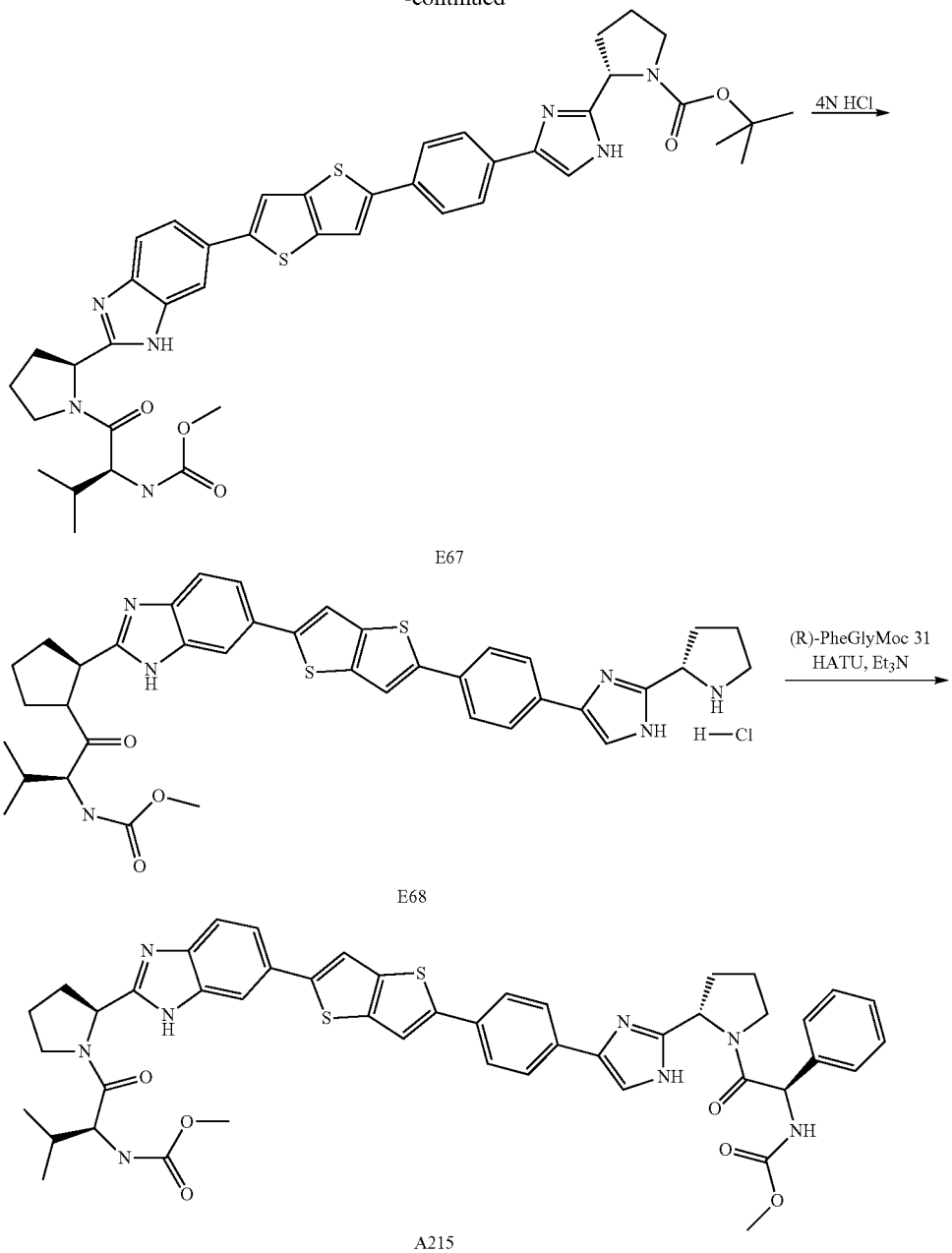

Preparation of ((S)-1-{(S)-2-[6-(5-bromo-thieno[3,2-b]thiophen-2-yl)-1H-benzoimidazol-2-yl]-pyrrolidine-1-carbonyl}-2-methyl-propyl)-carbamic acid methyl ester E66. Intermediate E65 (0.198 mmol) was dissolved in anhydrous DCM (5 mL). The intermediate 1 (0.198 mmol) was added, followed by HATU (0.257 mmol) and Et₃N (0.792 mmol). The reaction mixture was stirred at room temperature for 45 min. DCM was added and the mixture was washed with water. The organic layer was dried over Na₂SO₄, filtered, and concentrated under reduced pressure. The residue was purified by silica gel chromatography (eluent: DCM to DCM/MeOH 2%) to give intermediate E66 in quantitative yield. MS (ESI, EI⁺) m/z=562.7 (MH⁺).

Preparation of (S)-2-{4-[4-(5-{(S)-2-[1-((S)-2-methoxycarbonylamino-3-methyl-butyryl)-pyrrolidin-2-yl]-3H-benzoimidazol-5-yl}-thieno[3,2-b]thiophen-2-yl)-phenyl]-1H-imidazol-2-yl}-pyrrolidine-1-carboxylic acid tert-butyl ester E67. Intermediate E67 was synthesized from intermediate E66 (0.196 mmol), following the procedure as described for the compound A1 (110° C. for 35 min). The residue was purified by silica gel chromatography (eluent: DCM to DCM/MeOH 4%) to give intermediate E67 as a yellow solid in 46% yield. MS (ESI, EI⁺) m/z=794.2 (MH⁺).

Preparation of {2-methyl-(S)-1-[(S)-2-(6-{5-[4-((S)-2-pyrrolidin-2-yl-1H-imidazol-4-yl)-phenyl]-thieno[3,2-b]thiophen-2-yl}-1H-benzoimidazol-2-yl)-pyrrolidine-1-carbonyl]-propyl}-carbamic acid methyl ester, hydrochloride E68. Intermediate E68 was synthesized from intermediate E67 (0.086 mmol), following the procedure as described for intermediate E47 (without purification) to give intermediate E68 as an orange solid in quantitative yield. MS (ESI, EI⁺) m/z=694.14 (MH⁺).

Preparation of [(S)-1-((S)-2-{6-[5-(4-{(S)-2-[1-((R)-2-methoxycarbonylamino-2-phenyl-acetyl)-pyrrolidin-2-yl]-1H-imidazol-4-yl}-phenyl)-thieno[3,2-b]thiophen-2-yl)-1H-benzoimidazol-2-yl}-pyrrolidine-1-carbonyl)-2-methyl-propyl]-carbamic acid methyl ester A215. Compound A215 was synthesized from intermediate E68 (0.086 mmol) following the procedure as described for compound A114 to give compound A215 as a yellow solid in 48% yield. $^1$H NMR (DMSO-d$_6$, 400 MHz) δ (ppm) 0.82 (d, J=6.70 Hz, 3H), 0.86 (d, J=6.70 Hz, 3H), 1.82-2.10 (m, 7H), 2.16-2.28 (m, 2H), 3.10-3.16 (m, 1H), 3.52-3.55 (m, 6H), 3.80-3.90 (m, 3H), 4.07 (t, J=8.38 Hz, 1H), 5.04-5.19 (m, 2H), 5.37-5.53 (m, 1H), 6.91-7.1 (m, 1H), 7.30-7.88 (m, 15H), 11.77-1.95 (m, 1H), 12.29 (brs, 1H); MS (ESI, EI$^+$) m/z=885.3 (MH$^+$).

Example 37

Synthesis of [(S)-1-((S)-2-{4-[4-(5-{(S)-2-[1-((R)-2-methoxycarbonylamino-2-phenyl-acetyl)-pyrrolidin-2-yl]-3H-benzoimidazol-5-yl}-thieno[3,2-h]thiophen-2-yl)-phenyl]-1H-imidazol-2-yl}-pyrrolidine-1-carbonyl)-2-methyl-propyl]-carbamic acid methyl ester A194

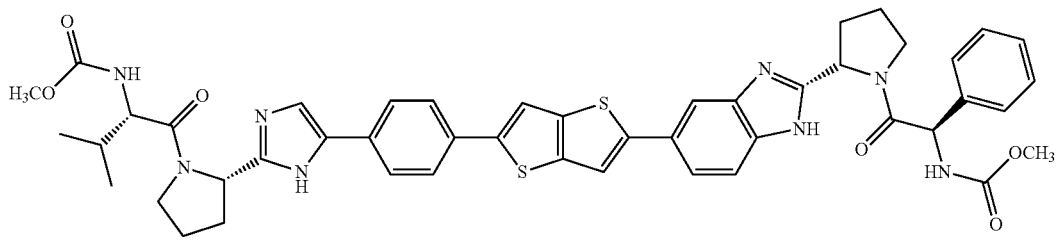

Compound A194 was synthesized as shown in Scheme 28.

Scheme 28

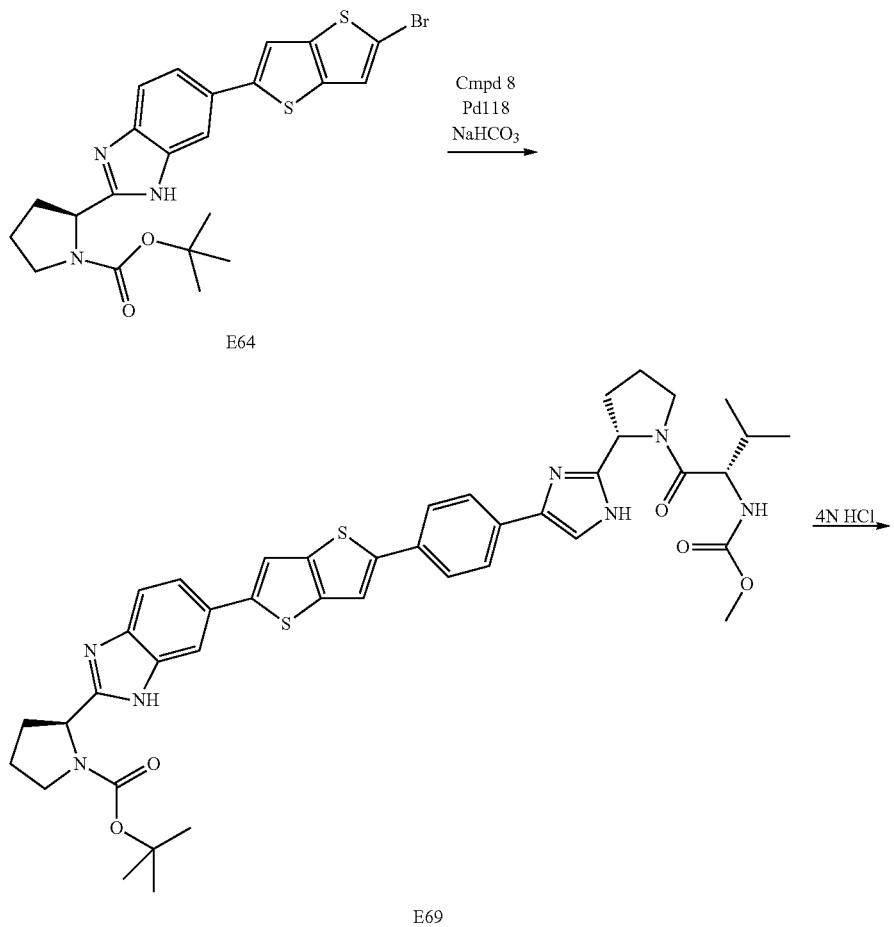

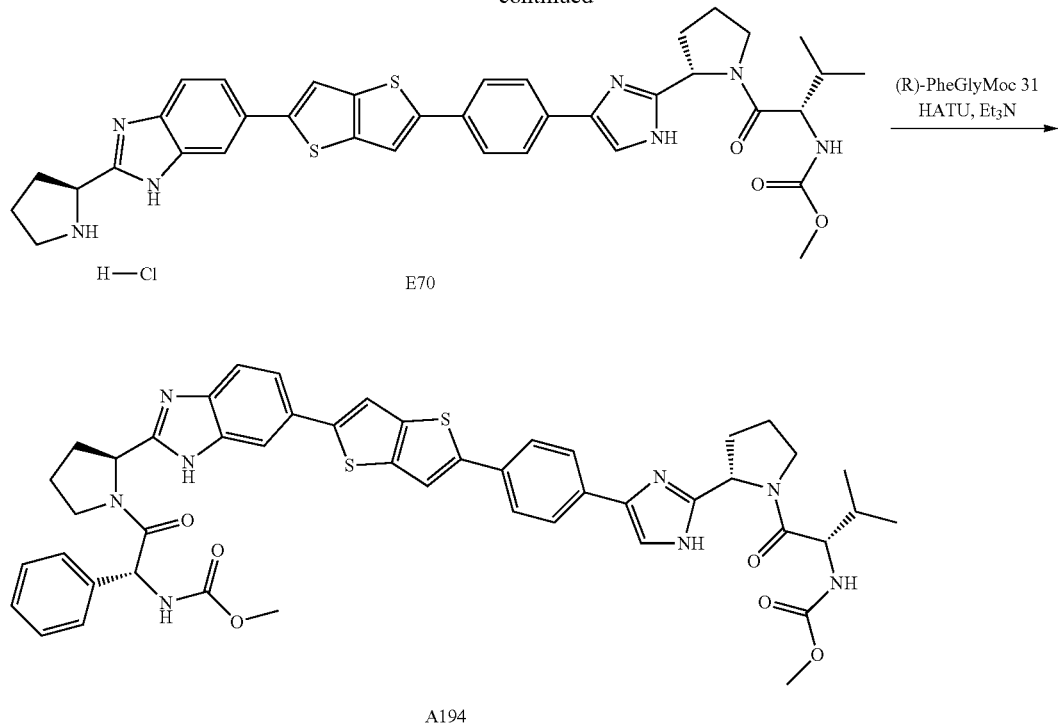

Preparation of (S)-2-{6-[5-(4-{(S)-2-[1-((S)-2-methoxycarbonylamino-3-methyl-butyryl)-pyrrolidin-2-yl]-1H-imidazol-4-yl}-phenyl)-thieno[3,2-b]thiophen-2-yl]-1H-benzoimidazol-2-yl}-pyrrolidine-1-carboxylic acid tert-butyl ester E69. Intermediate E69 was synthesized from intermediate E64 (0.198 mmol) and intermediate 8 (0.218 mmol) following the procedure as described for the compound A1 (110° C.). The crude was purified by silica gel chromatography (eluent: DCM to DCM/MeOH 40%) to give intermediate E69 in 80%. MS (ESI, EI+) m/z=794.2 (MH+).

Preparation of {2-methyl-(S)-1-[2-(4-{4-[5-((S)-2-pyrrolidin-2-yl-3H-benzoimidazol-5-yl)-thieno[3,2-b]thiophen-2-yl]-phenyl}-1H-imidazol-2-yl)-pyrrolidine-1-carbonyl]-propyl}-carbamic acid methyl ester, hydrochloride E70. Intermediate E70 was synthesized from intermediate E69 (0.159 mmol) following the procedure as described for intermediate E47 (without purification) to give intermediate E70 in quantitative yield. MS (ESI, EI+) m/z=694.14 (MH+).

Preparation of [(S)-1-((S)-2-{4-[4-(5-{(S)-2-[1-((R)-2-methoxycarbonylamino-2-phenyl-acetyl)-pyrrolidin-2-yl]-3H-benzoimidazol-5-yl}-thieno[3,2-h]thiophen-2-yl)-phenyl]-1H-imidazol-2-yl}-pyrrolidine-1-carbonyl)-2-methyl-propyl]-carbamic acid methyl ester A194. Compound A194 was synthesized from intermediate E70 (0.198 mmol) following the procedure as described for compound A114 to give compound A194 as a yellow lyophilized powder. $^1$H NMR (DMSO-d$_6$, 400 MHz) δ (ppm) 0.85 (d, J=6.52 Hz, 3H), 0.90 (d, J=6.52 Hz, 3H), 1.85-2.32 (m, 9H), 3.16-3.25 (m, 1H), 3.52-3.554 (m, 6H), 3.77-3.85 (m, 2H), 3.90-3.96 (m, 1H), 4.04-4.08 (m, 1H), 5.06-5.09 (m, 1H), 5.15-5.24 (m, 1H), 5.51-5.62 (m, 1H), 6.80-6.93 (m, 1H), 7.27-7.42 (m, 4H), 7.53-7.94 (m, 10H), 11.81 (m, 1H), 12.19-12.38 (m, 1H); MS (ESI, EI+) m/z=885.4 (MH+).

Example 38

Synthesis of ((S)-1-{(S)-2-[5-(5-{(S)-2-[1-((S)-2-methoxycarbonylamino-3-methyl-butyryl)-pyrrolidin-2-yl]-3H-benzoimidazol-5-yl}-thieno[3,2-b]thiophen-2-yl)-1H-imidazol-2-yl]-pyrrolidine-1-carbonyl}-2-methyl-propyl)-carbamic acid methyl ester A176

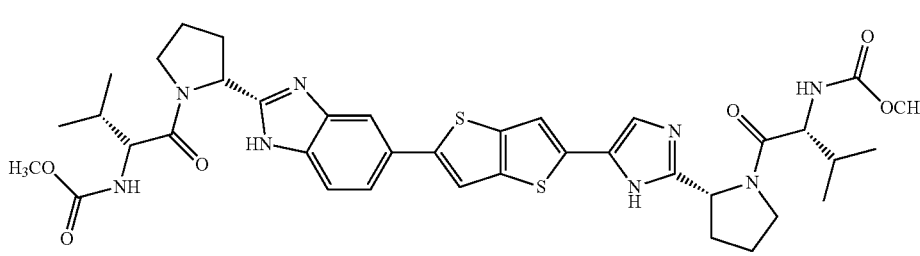

Compound A176 was synthesized as shown in Scheme 29.

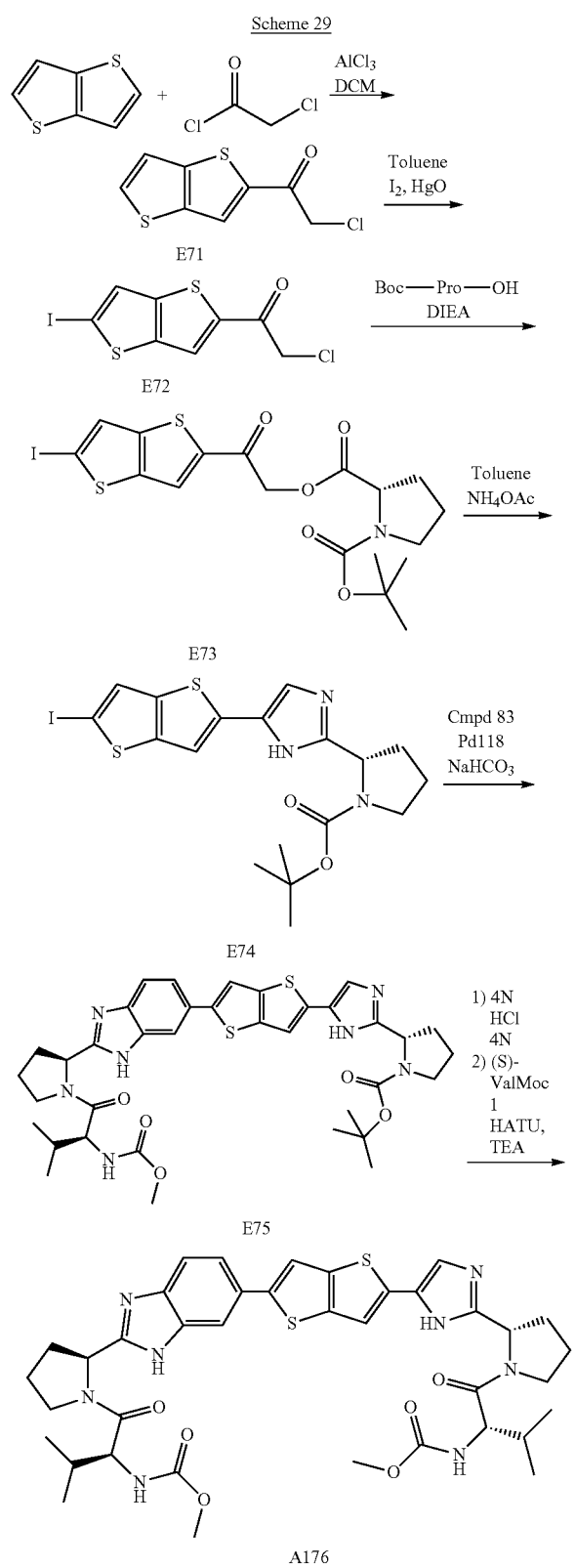

Scheme 29

Preparation of 2-chloro-1-thieno[3,2-b]thiophen-2-yl-ethanone E71. Thieno[3,2-b]-thiophene (38.5 mmol) was solubilized in anhydrous DCM (77 mL) and the chloroacetylchloride (39.66 mmol) was added. The reaction mixture was cooled down to 0° C. and AlCl$_3$ (43.12 mmol) solubilized in DCM (385 mL) was added slowly. The mixture was stirred at room temperature during 5 hrs. The reaction mixture was cooled again to 0° C. and water and 2N HCl were added until pH=1. The organic layer was dried over Na$_2$SO$_4$, filtered, and concentrated under reduced pressure. The residue was purified by silica gel chromatography to give intermediate E71 as a yellow solid in 43% yield. MS (ESI, EI$^+$) m/z=216.8 (MH$^+$).

Preparation of 2-chloro-1-(5-iodo-thieno[3,2-b]thiophen-2-yl)-ethanone E72. To a solution of intermediate E71 (17.53 mmol) in toluene (160 mL) were added HgO (89.40 mmol) and I$_2$ (85.90 mmol). The reaction mixture was stirred at 70° C. for 5 hrs. AcOEt was added and the reaction mixture was filtered on celite. The filtrate was washed with water, dried over Na$_2$SO$_4$, and concentrated under reduced pressure. The residue was triturated in DCM/Et$_2$O to give intermediate E72 as a yellow solid in 37% yield. MS (ESI, EI$^+$) m/z=343 (MH$^+$).

Preparation of intermediate E73. Intermediate E72 (7.59 mmol) was solubilized in acetonitrile (75 mL). BocPro-OH (7.97 mmol) was added, followed by DIEA (7.97 mmol). The reaction mixture was stirred at room temperature overnight and heated to 50° C. for 10 hrs. The solvent was removed. DCM was added and the mixture was washed with water. The organic layer was dried and concentrated under reduced pressure. The residue was purified by silica gel chromatography (eluent: DCM to DCM/MeOH 2%) to give intermediate E73 as a pale yellow foam in 59% yield. MS (ESI, EI$^-$) m/z=520.20 (MH$^-$).

Preparation of (S)-2-[5-(5-iodo-thieno[3,2-b]thiophene-2-yl)-1H-imidazol-2-yl]-pyrrolidine-1-carboxylic acid tert-butyl ester E74. Intermediate E73 (4.47 mmol) was dissolved in toluene (45 mL). NH$_4$OAc (89.4 mmol) was added and the reaction mixture was heated to reflux for 5 hrs. The solvent was removed and DCM added. The mixture was washed with water. The organic layer was dried, filtered, and concentrated under reduced pressure. The residue was purified by silica gel chromatography (eluent: DCM to DCM/MeOH 2%) to give intermediate E74 as a pale brown foam in 71% yield. MS (ESI, Er) m/z=502.16 (MH$^+$).

Preparation of (S)-2-[5-(5-{(S)-2-[1-((S)-2-methoxycarbonylamino-3-methyl-butyryl)-pyrrolidin-2-yl]-3H-benzoimidazol-5-yl}-thieno[3,2-b]thiophen-2-yl)-1H-imidazol-2-yl]-pyrrolidine-1-carboxylic acid tert-butyl ester E75. Intermediate E75 was synthesized from intermediate E74 (0.200 mmol) following the procedure as described for the compound A1 to give intermediate E75 in 49% yield. MS (ESI, EI$^+$) m/z=718 (MH$^+$).

Preparation of ((S)-1-{(S)-2-[5-(5-{(S)-2-[1-((S)-2-methoxycarbonylamino-3-methyl-butyryl)-pyrrolidin-2-yl]-3H-benzoimidazol-5-yl}-thieno[3,2-h]thiophen-2-yl)-1H-imidazol-2-yl]-pyrrolidine-1-carbonyl}-2-methyl-propyl)-carbamic acid methyl ester A176. Compound A176 was synthesized from intermediate E75 and intermediate 31 (0.056 mmol) following the procedure as described for the compound A15 (in this case, coupling was at 0° C.) to give compound A176 as a yellow lyophilized powder in 32% yield. $^1$H NMR (DMSO-d$_6$, 400 MHz) δ (ppm) 0.81-0.91 (m, 12H), 1.90-2.28 (m, 10H), 3.528 (s, 3H), 3.533 (s, 3H), 3.76-3.86 (m, 4H), 4.03-4.09 (m, 2H), 5.02-5.05 (m, 1H), 5.16-

5.18 (m, 1H), 7.27-7.31 (m, 2H), 7.42-7.54 (m, 4H), 7.66-7.81 (m, 2H), 11.88 (s, 1H), 12.26 (brs, 1H); MS (ESI, EI⁺) m/z=775.4 (MH⁺).

Example 39

Synthesis of [(S)-1-((S)-2-{5-[5-{(S)-2-[1-((R)-2-methoxycarbonylamino-2-phenyl-acetyl)-pyrrolidin-2-yl]-3H-imidazol-4-yl}-phenyl)-thieno[3,2-b]thiophen-2-yl]-1H-imidazol-2-yl}-pyrrolidine-1-carbonyl)-2-methyl-propyl]-carbamic acid methyl ester A216

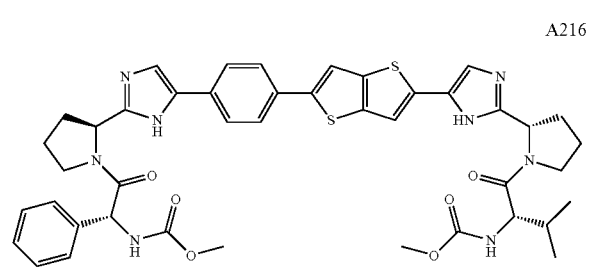 [SMILES: COC(=O)N[C@H](C(=O)N1CCC[C@H]1c1ncc(-c2cc3sc(-c4ccc(-c5cnc([C@@H]6CCCN6C(=O)[C@H](NC(=O)OC)c6ccccc6)[nH]5)cc4)cc3s2)[nH]1)C(C)C]

Compound A216 was synthesized as shown in Scheme 30.

Preparation of ((S)-1-{(S)-2-[5-(5-iodo-thieno[3,2-b]thiophen-2-yl)-1H-imidazol-2-yl]-pyrrolidine-1-carbonyl}-2-methyl-propyl)-carbamic acid methyl ester E76. Intermediate E76 was synthesized from intermediate E74 (0.997 mmol) and intermediate 1 (1.047 mmol) following the procedure as described for compound A15. The reaction mixture was diluted in ethyl acetate and washed with a solution of water with 0.5% HCO₂H. The organic layer was washed with brine and concentrated under reduced pressure. The residue was purified by silica gel chromatography to give intermediate E76 as an orange oil in 94% yield. MS (ESI, EI⁺) m/z=559 (MH⁺).

Preparation of (S)-2-{5-[4-(5-{(S)-2-[1-((S)-2-methoxycarbonylamino-3-methyl-butyryl)-pyrrolidin-2-yl]-3H-imidazol-4-yl}-thieno[3,2-b]thiophen-2-yl)-phenyl]-1H-imidazol-2-yl}-pyrrolidine-1-carboxylic acid tert-butyl ester E77. Intermediate E77 was synthesized from intermediate E76 (0.269 mmol) and intermediate 6 (0.295 mmol) following the procedure as described for compound A1 (90° C. for 40 min). The residue was purified by silica gel chromatography (eluent: DCM to DCM/MeOH 5%) to give intermediate E77 in 30% yield. MS (ESI, EI⁺) m/z=744.4 (MH⁺).

Preparation of [(S)-1-((S)-2-{5-[5-{(S)-2-[1-((R)-2-methoxycarbonylamino-2-phenyl-acetyl)-pyrrolidin-2-yl]-3H-imidazol-4-yl}-phenyl)-thieno[3,2-b]thiophen-2-yl]-1H-imidazol-2-yl}-pyrrolidine-1-carbonyl)-2-methyl-propyl]-

Scheme 30

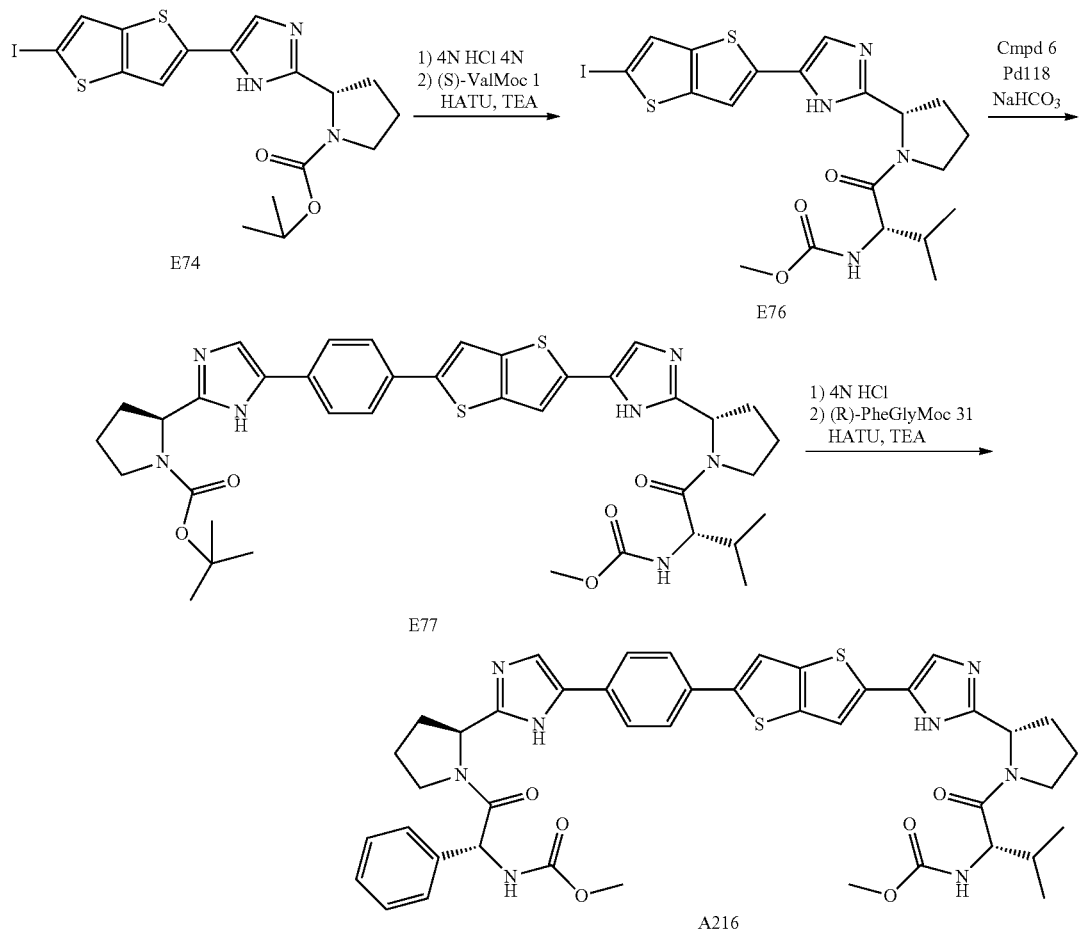

carbamic acid methyl ester A216. Compound A216 was synthesized from intermediate E77 (0.078 mmol) and intermediate 31 (0.078 mmol) following the procedure as described for compound A15 (in this case, coupling was at 0° C. and purification by silica gel chromatography) to give compound A216 as a yellow lyophilized solid in 17% yield. $^1$H NMR (CDCl$_3$, 400 MHz) δ (ppm) 0.88-0.91 (m, 6H), 1.89-2.12 (m, 5H), 2.17-2.23 (m, 2H), 2.30-2.39 (m, 1H), 2.90-3.11 (m, 2H), 3.17-3.26 (m, 2H), 3.61-3.73 (m, 6H), 3.74-3.87 (m, 2H), 4.31-4.36 (m, 1H), 5.22-5.30 (m, 2H), 5.37-5.43 (m, 2H), 5.97-6.02 (m, 1H), 7.13 (s, 1H), 7.36-7.46 (m, 7H), 7.56-7.82 (m, 4H), 10.41 (brs, 1H), 10.59-10.81 (m, 1H); MS (ESI, EI$^+$) m/z=835.4 (MH$^+$).

Example 40

Synthesis of ((S)-1-{(S)-2-[6-(6-{(S)-2-[1-((S)-2-methoxycarbonylamino-3-methyl-butyryl)-pyrrolidin-2-yl]-1H-imidazol-4-yl}-thieno[3,2-b]thiophen-3-yl)-1H-benzoimidazol-2-yl]-pyrrolidine-1-carbonyl}-2-methyl-propyl)-carbamic acid methyl ester A173 for compound A1. The crude was purified by silica gel chromatography (eluent: petroleum ether to petroleum ether/AcOEt 100%) to give intermediate E63 in 61%. MS (ESI, EI$^+$) m/z=661 (MH$^+$).

Preparation of ((S)-1-{(S)-2-[6-(6-{(S)-2-[1-((S)-2-methoxycarbonylamino-3-methyl-butyryl)-pyrrolidin-2-yl]-1H-imidazol-4-yl}-thieno[3,2-b]thiophen-3-yl)-1H-benzoimidazol-2-yl]-pyrrolidine-1-carbonyl}-2-methyl-propyl)-carbamic acid methyl ester A173. Compound A173 was synthesized from intermediate E63 (0.061 mmol) following the procedure as described for compound A15 to give compound A173 as a white lyophilized solid in 39% yield. $^1$H NMR (DMSO-d$_6$, 400 MHz) δ (ppm) 0.81-0.92 (m, 12H), 1.87-2.11 (m, 6H), 2.19-2.27 (m, 2H), 2.29-2.39 (m, 2H), 3.53 (s, 6H), 3.81-3.87 (m, 4H), 4.03-4.09 (m, 2H), 5.10-5.14 (m, 1H), 5.17-5.20 (m, 1H), 7.33 (dd, J=4.03 Hz and J=8.22 Hz, 2H), 7.44 (s, 1H), 7.53-7.64 (m, 2H), 7.73 (s, 1H), 7.79-7.85 (m, 1H), 7.89-7.95 (m, 1H), 11.93 (s, 1H), 12.29-12.34 (m, 1H); MS (ESI, EI$^+$) m/z=775 (MH$^+$).

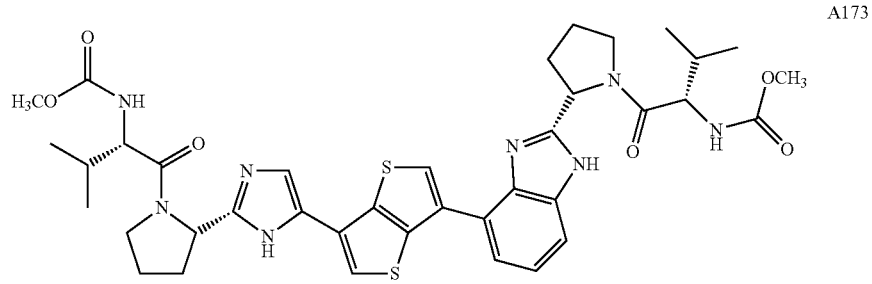

A173

Preparation of (S)-2-[4-(6-bromo-thieno[3,2,b]thiophen-3-yl)-1H-imidazol-2-yl]-pyrrolidine-1-carboxylic acid tert-butyl ester, hydrochloride E62. Intermediate E62 was synthesized from 3,6-dibromothieno[3,2,b]thiophene (0.336 mmol) and intermediate 61 (0.336 mmol) following the procedure as described for intermediate 63 (chromatography: eluent: petroleum ether to petroleum ether/AcOEt 80%) to give intermediate E62 in 50% yield. MS (ESI, EI$^+$) m/z=454 (MH$^+$).

Preparation of compound E63. Intermediate E63 was synthesized from intermediate E62 (0.199 mmol) and intermediate 66 (0.220 mmol) following the procedure as described Example 41

Synthesis of [(S)-1-((S)-2-{5-[4-(5-{2-[(S)-1-((S)-2-Methoxycarbonylamino-3-methyl-butyryl)-pyrrolidin-2-yl]-3H-imidazol-4-yl}-thieno[3,2-b]thiophen-2-yl)-phenyl]-1H-imidazol-2-yl}-pyrrolidine-1-carbonyl)-2-methyl-propyl]-carbamic acid methyl ester A126

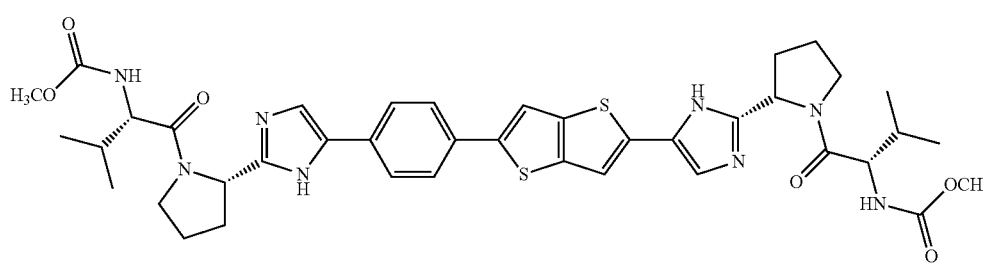

A126

Compound A126 was synthesized as shown in Scheme 31.

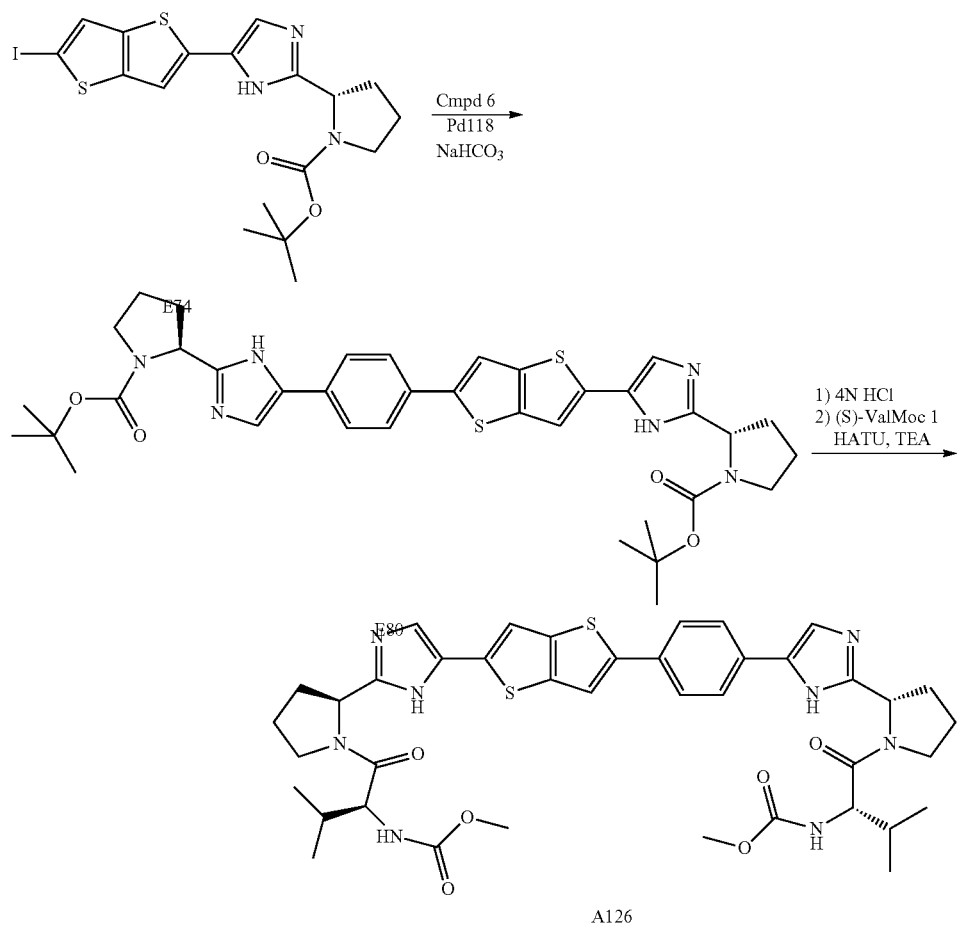

Preparation of compound E80. Intermediate E80 was synthesized from intermediate E74 (0.598 mmol) and intermediate 6 (0.658 mmol) following the procedure as described for the intermediate E77. After the chromatography, the compound was triturated in Et₂O to give intermediate E80 as a beige solid in 33% yield. MS (ESI, EI⁺) m/z=687.1 (MH⁺).

Preparation of [(S)-1-((S)-2-{5-[4-(5-{2-[(S)-1-((S)-2-Methoxycarbonylamino-3-methyl-butyryl)-pyrrolidin-2-yl]-3H-imidazol-4-yl}-thieno[3,2-b]thiophen-2-yl)-phenyl]-1H-imidazol-2-yl}-pyrrolidine-1-carbonyl)-2-methyl-propyl]-carbamic acid methyl ester A126. Compound A126 was synthesized from intermediate E80 (0.197 mmol) and intermediate 1 (0.414 mmol) following the procedure as described for the compound A15 (in this case, coupling was at 0° C. and silica gel chromatography after the passage on SCX-2 column) to give compound A126 as a yellow solid in 42% yield. ¹H NMR (DMSO-d₆, 400 MHz) δ (ppm) 0.84 (d, J=6.61 Hz, 6H), 0.90 (d, J=6.61 Hz, 6H), 1.90-2.01 (m, 6H), 2.08-2.18 (m, 4H), 3.26-3.30 (m, 1H), 3.39-3.43 (m, 1H), 3.53-3.55 (m, 6H), 3.76-3.83 (m, 3H), 4.05 (t, J=8.24 Hz, 2H), 5.02-5.08 (m, 2H), 7.25-7.29 (m, 2H), 7.42 (d, J=1.84 Hz, 1H), 7.48-7.49 (m, 1H), 7.51 (d, J=1.84 Hz, 1H), 7.59-7.70 (m, 2H), 7.73-7.81 (m, 2H), 11.78 (s, 1H), 11.88 (s, 1H); MS (ESI, EI⁺) m/z=801.1 (MH⁺).

Example 42

Synthesis of (S,S,S,S)-[1-(2-{5-[4-[5-{2-[1-(2-methoxycarbonylamino-2-methyl-butyryl)-pyrrolidin-2-yl]-1H-imidazol-4-yl}-thieno[3,2-b]furan-2-yl)-phenyl]-1H-imidazol-2-yl}-pyrrolidine-1-carbonyl)-2-methyl-propyl]-carbamic acid methyl ester A218

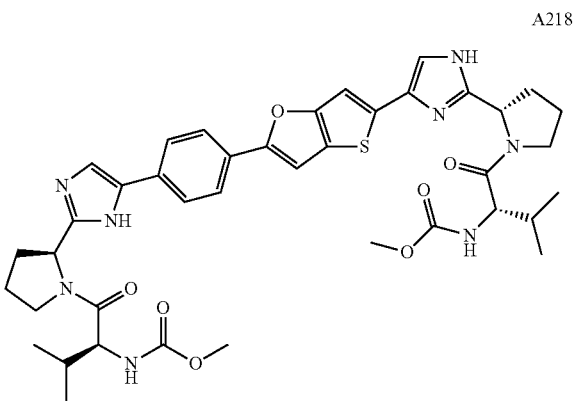 [SMILES: COC(=O)N[C@H](C(=O)N1CCC[C@H]1c1nc(-c2cc3oc(-c4ccc(-c5cnc([C@@H]6CCCN6C(=O)[C@@H](NC(=O)OC)C(C)C)[nH]5)cc4)cc3s2)c[nH]1)C(C)C]

Compound A218 was synthesized as shown in Scheme 32.

Preparation of 4-(2-bromo-thieno[3,2-b]furan-5-yl)-(S)-2-(1-tert-butoxycarbonyl-pyrrolidin-2-yl)-imidazole-1-carboxylic acid tert-butyl ester E81. Intermediate E81 was synthesized from 2,5-dibromo-thieno[3,2-b]furan (8.9 mmol) (Roowin) and intermediate 61 (9.35 mmol) following the procedure as described for the intermediate 63 (reaction time=6 hours and chromatography eluent: petroleum ether/AcOEt) to give intermediate E81 in 16% yield. MS (ESI, EI+) m/z=539 (MH+).

Preparation of (S)-2-(1-tert-butoxycarbonyl-pyrrolidin-2-yl)-4-[(S)-2-(4-{2-[1-((S)-2-methoxycarbonylamino-3-methyl-butyryl)-pyrrolidin-2-yl]-3H-imidazol-4-yl}-phenyl)-thieno[3,2-b]furan-5-yl]-imidazole-1-carboxylic acid tert-butyl ester E82. Intermediate E82 was synthesized from intermediate E81 (0.948 mmol) following the procedure as described for compound A1 (100° C.—20 minutes without silica gel chromatography) to give intermediate E82. MS (ESI, EI+) m/z=828.2 (MH+).

Preparation of (S,S,S)-{2-methyl-1-[2-(5-{4-[5-(2-pyrrolidin-2-yl-1H-imidazol-4-yl)-thieno[3,2-b]furan-2-yl]-phenyl}-1H-imidazol-2-yl)-pyrrolidine-1-carbonyl]-propyl}-carbamic acid methyl ester, hydrochloride E83. Intermediate E83 was synthesized from intermediate E82 following the procedure as described for intermediate 11 (reaction time=30 minutes) to give intermediate E83. MS (ESI, EI+) m/z=628 (MH+).

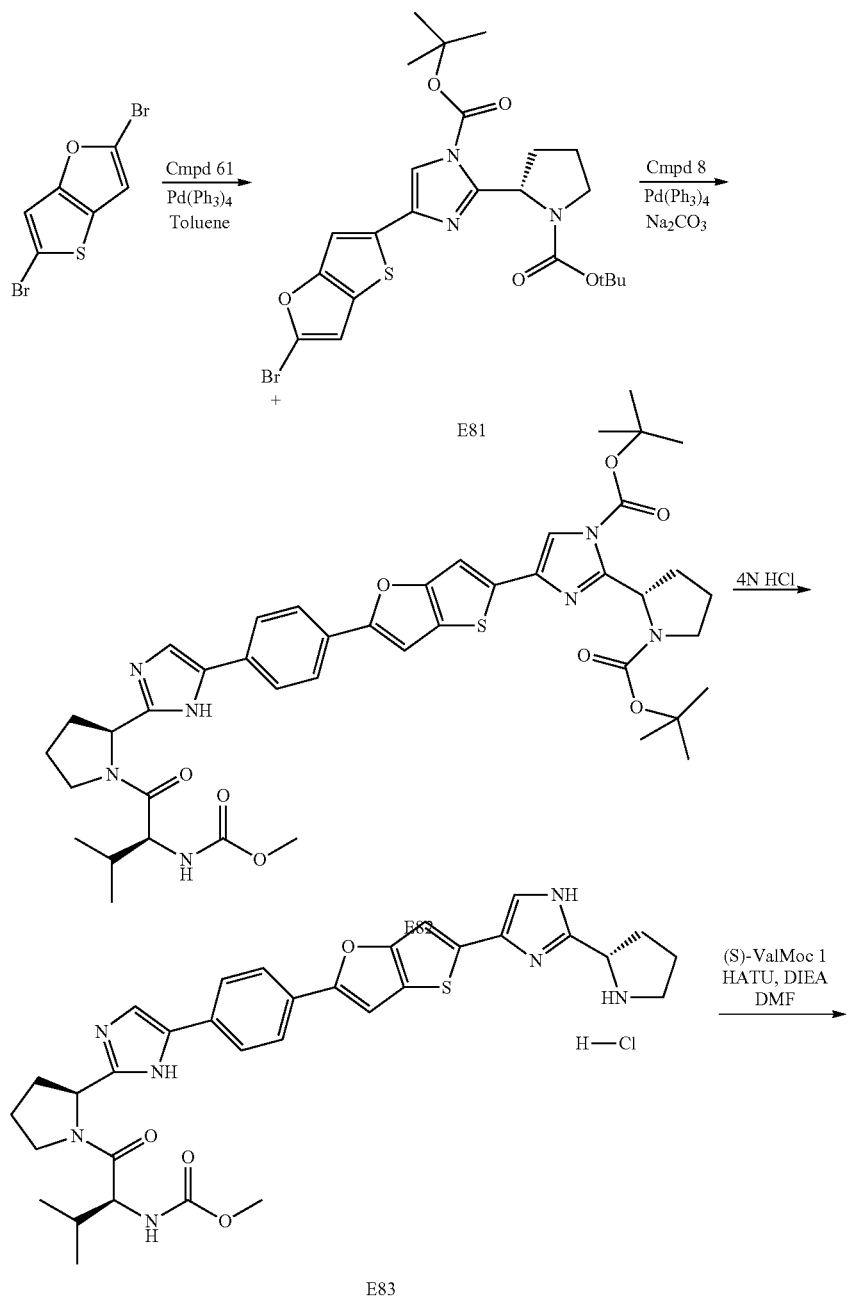

-continued

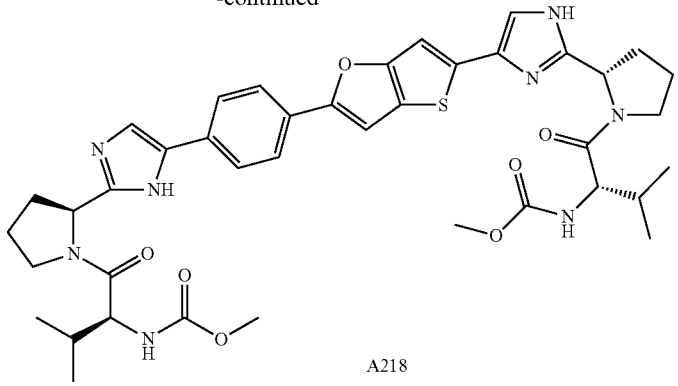

A218

Preparation of (S,S,S,S)-[1-(2-{5-[4-[5-{2-[1-(2-methoxycarbonylamino-2-methyl-butyryl)-pyrrolidin-2-yl]-1H-imidazol-4-yl}-thieno[3,2-b]furan-2-yl)-phenyl]-1H-imidazol-2-yl}-pyrrolidine-1-carbonyl)-2-methyl-propyl]-carbamic acid methyl ester A218. Compound A218 was synthesized from intermediate E83 following the procedure as described for compound A214 to give compound A218 as a pale yellow lyophilized solid in 1% (over 3 steps). MS (ESI, EI+) m/z=785.4 (MH+).

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A compound of Formula IIIB:

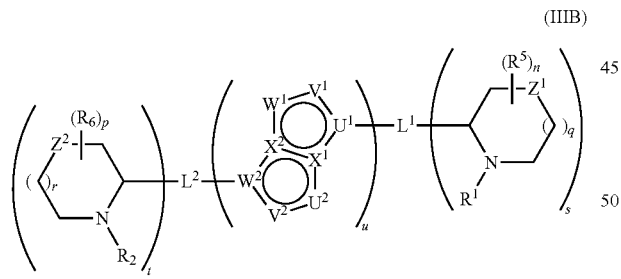

(IIIB)

or a single enantiomer, a racemic mixture, a mixture of diastereomers, or an isotopic variant thereof; or a pharmaceutically acceptable salt, solvate, or prodrug thereof;
wherein:
$U^1$, $W^2$, $X^1$, and $X^2$ are each C;
$U^2$ and $W^1$ are each S;
$V^1$ and $V^2$ are each independently $CR^{3a}$;
$R^1$ and $R^2$ are each independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(NR$^{1b}$R$^{1c}$)R$^{1a}$, —C(O)CH(R$^{1c}$)C(O)$R^{1b}$)R$^{1a}$, —C(O)CH(N(R$^{1c}$)C(O)OR$^{1b}$)R$^{1a}$, —C(O)CH(N(R$^{1c}$)C(O)NR$^{1b}$R$^{1d}$)R$^{1a}$, —C(O)OR$^{1a}$, —C(O)NR$^{1b}$R$^{1c}$, —C(NR$^{1a}$)NR$^{1b}$R$^{1c}$, —P(O)(OR$^{1a}$)R$^{1d}$, —CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; or two $R^5$ or two $R^6$ that are attached to the same ring are linked together to form a bond, —O—, —NR$^7$—, —S—, $C_{1-6}$ alkylene, $C_{1-6}$ heteroalkylene, $C_{2-6}$ alkenylene, or $C_{2-6}$ heteroalkenylene;

$L^1$ and $L^2$ are each independently selected from:
a bond,

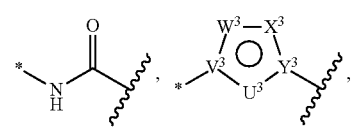

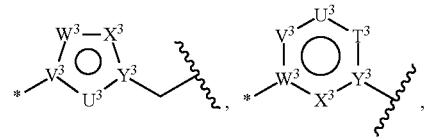

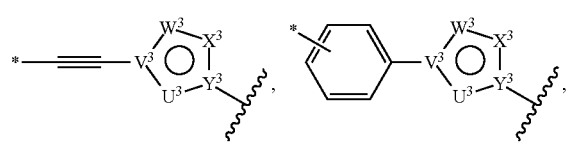

-continued

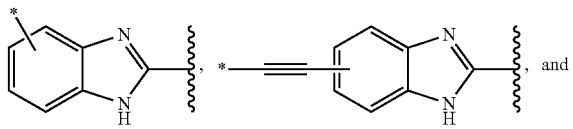

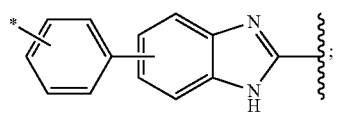

wherein each moiety is optionally substituted with one, two, three, or four $R^3$; the star (*) on each moiety represents the point of attachment thought which the moiety is connected to $U^1$ or $W^2$ of

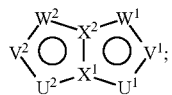

and the zigzag line (⌇) on each moiety represents the point of attachment through which the moiety is connected to

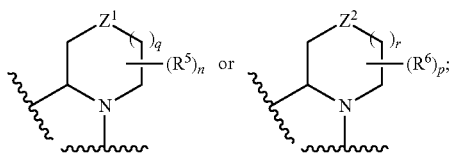

and wherein $T^3$ is a bond, C, N, O, S, $CR^{3a}$, or $NR^{3a}$; $U^3$, $V^3$, $W^3$, and $X^3$ are each independently C, N, O, S, $CR^{3a}$, or $NR^{3a}$; and $Y^3$ is C or N;

$Z^1$ and $Z^2$ are each a bond;

each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;

n is an integer of 2, 3, 4, 5, 6, or 7;
p is an integer of 0, 1, 2, 3, 4, 5, 6, or 7;
q and r are each independently an integer of 1, 2, 3, or 4; and
s, t, and u are each an integer of 1; and
wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more substituents Q, where each Q is independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^f$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —S$R^e$, —S(O)$R^e$, —S(O)$_2 R^e$, —S(O)N$R^f R^g$, and —S(O)$_2$N$R^f R^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

2. The compound of claim 1, having the structure of Formula IIIBa:

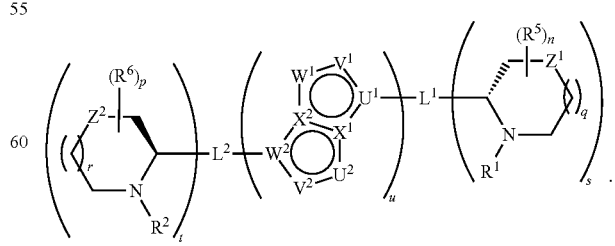

3. The compound of claim 2, having the structure of Formula IIIBd:

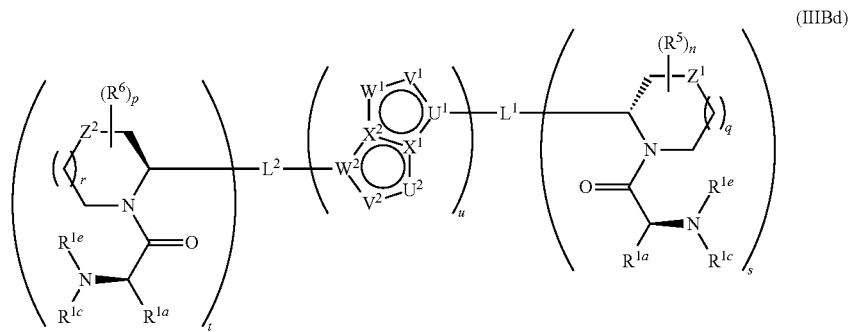

(IIIBd)

wherein each $R^{1e}$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents Q; or (c) —C(O)$R^{1b}$, C(O)OR$^{1b}$, or —C(O)NR$^{1b}$R$^{1d}$.

4. The compound of claim 1, having the structure of Formula IC:

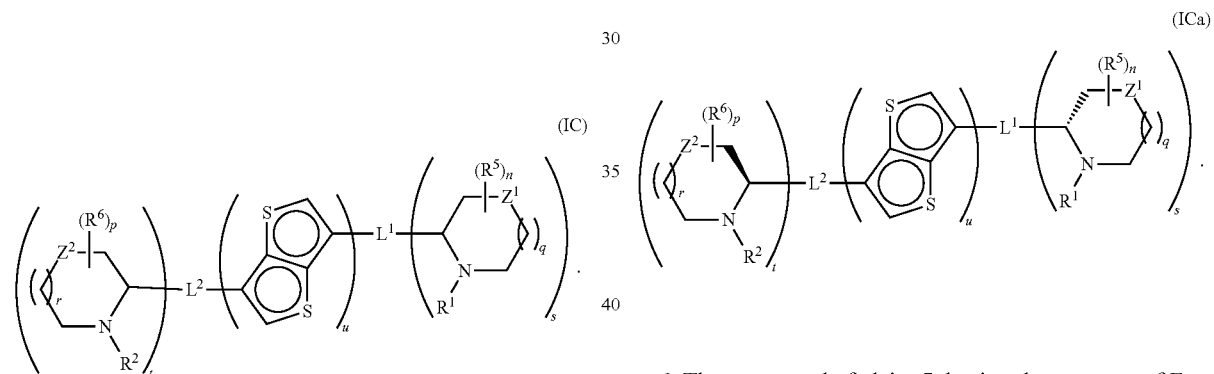

(IC)

5. The compound of claim 4, having the structure of Formula ICa:

(ICa)

6. The compound of claim 5, having the structure of Formula ICd:

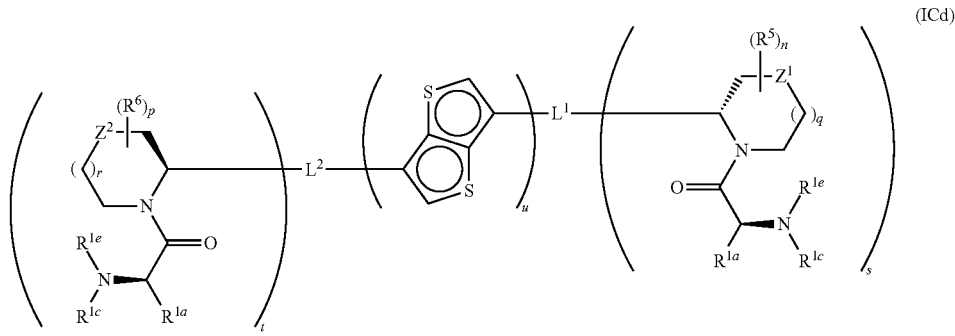

(ICd)

wherein each $R^{1e}$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents Q; or (c) —C(O)$R^{1b}$, —C(O)O$R^{1b}$, or —C(O)N$R^{1b}R^{1d}$.

7. The compound of claim 1, wherein $L^1$ and $L^2$ are each independently selected from the group consisting of:

a bond,

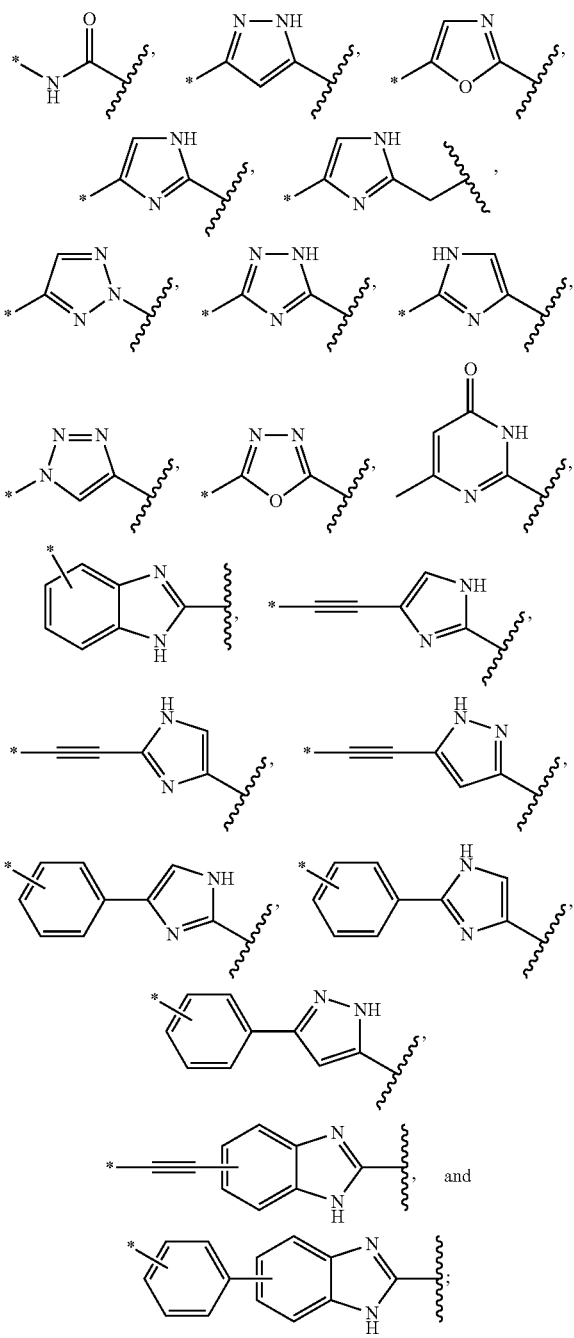

wherein each moiety is optionally substituted with one, two, three, or four $R^3$; the star (*) on each moiety represents the point of attachment through which the moiety is connected to $U^1$ or $W^2$ of

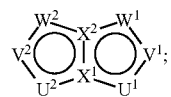

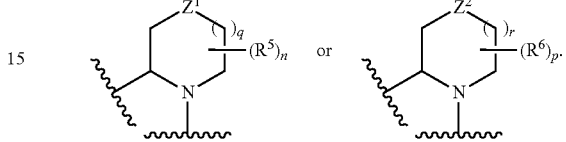

and the zigzag line ($\xi$) on each moiety represents the point of attachment through which the moiety is connected to 8. The compound of claim 7, wherein $L^1$ and $L^2$ are each independently selected from the group consisting of:

a bond,

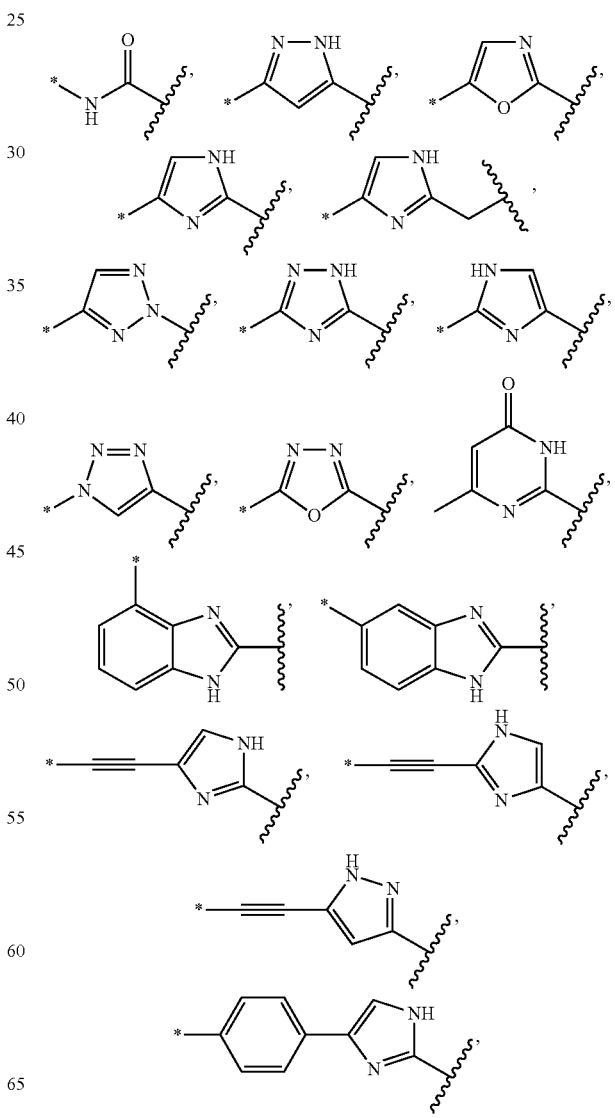

381
-continued

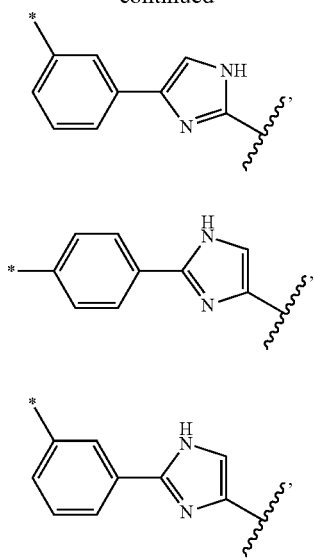

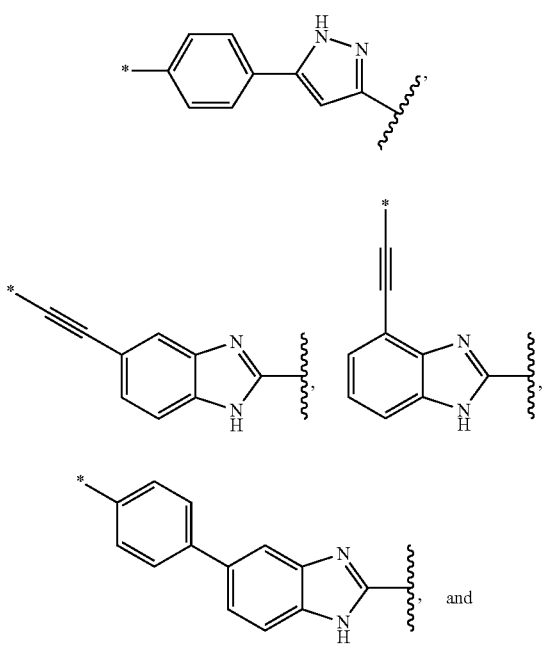

382
-continued

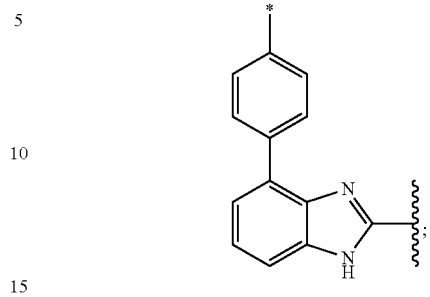

wherein each moiety is optionally substituted with one, two, three, or four $R^3$.

9. A compound of Formula IIC:

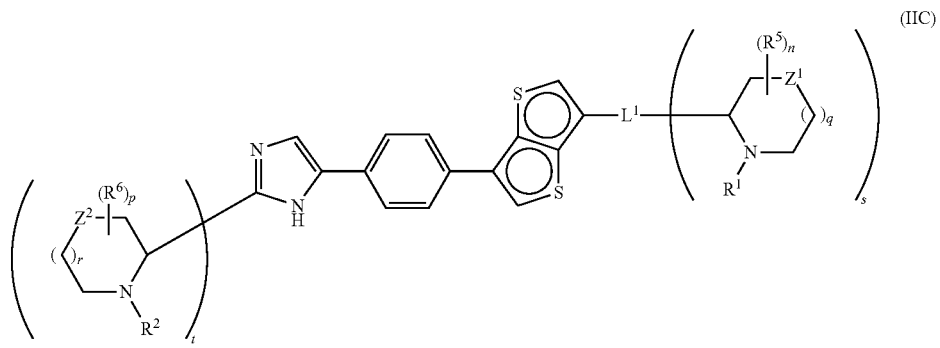

(IIC)

or a single enantiomer, a racemic mixture, a mixture of diastereomers, or an isotopic variant thereof; or a pharmaceutically acceptable salt, solvate, or prodrug thereof;
wherein:
$R^1$ and $R^2$ are each independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, —C(O)CH(N($R^{1c}$)C(O)N$R^{1b}R^{1d}$)$R^{1a}$, —C(O)O$R^{1a}$, —C(O)N$R^{1b}R^{1c}$, —C(N$R^{1a}$)N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;
each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or two R⁵ or two R⁶ that are attached to the same ring are linked together to form a bond, —O—, —NR⁷—, —S—C$_{1-6}$ alkylene, C$_{1-6}$ heteroalkylene, C$_{2-6}$ alkenylene, or C$_{2-6}$ heteroalkenylene;

L¹ is independently selected from:

a bond,

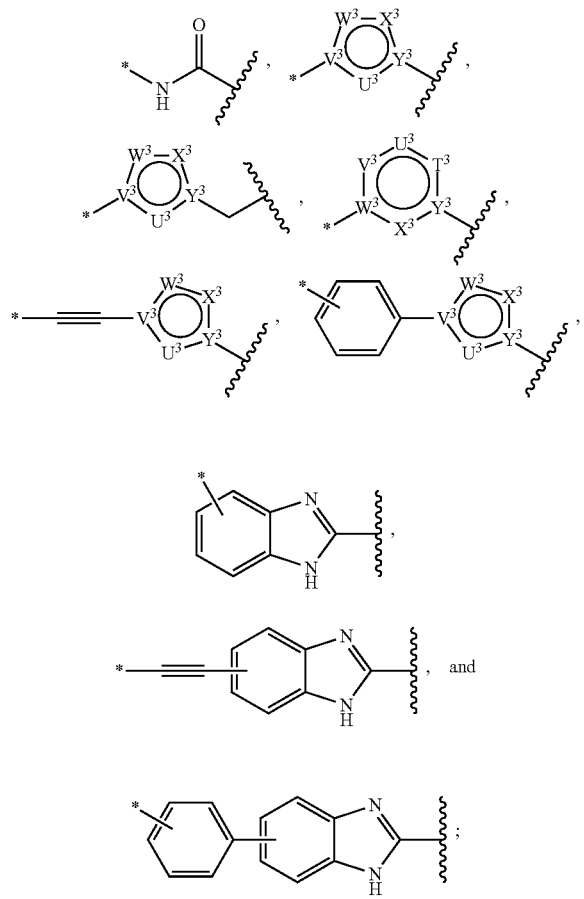

wherein each moiety is optionally substituted with one, two, three, or four R³; the star (*) on each moiety represents the point of attachment thought which the moiety is connected to the thieno[3,2-b]thienyl moiety; and the zigzag line ( ) on each moiety represents the point of attachment through which the moiety is connected to

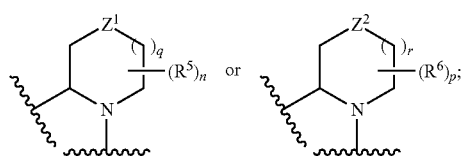

and wherein T³ is a bond, C, N, O, S, CR$^{3a}$, or NR$^{3a}$; U³, V³, W³, and X³ are each independently C, N, O, S, CR$^{3a}$, or NR$^{3a}$; and Y³ is C or N;

Z¹ and Z² are each a bond;

each R$^{1a}$, R$^{1b}$R$^{1c}$, and R$^{1d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

n and p are each independently an integer of 0, 1, 2, 3, 4, 5, 6, or 7;

q and r are each independently an integer of 1, 2, 3, or 4; and s and t are each an integer of 1;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more substituents Q, where each Q is independently selected from (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$;

wherein each Q$^a$ is independently selected from the group consisting of (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

10. The compound of claim 9, having the structure of Formula IICa:

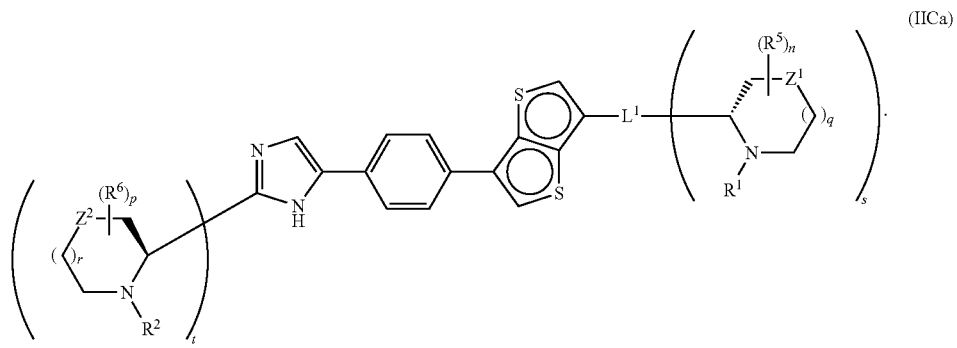

11. The compound of claim 9, having the structure of Formula IICd:

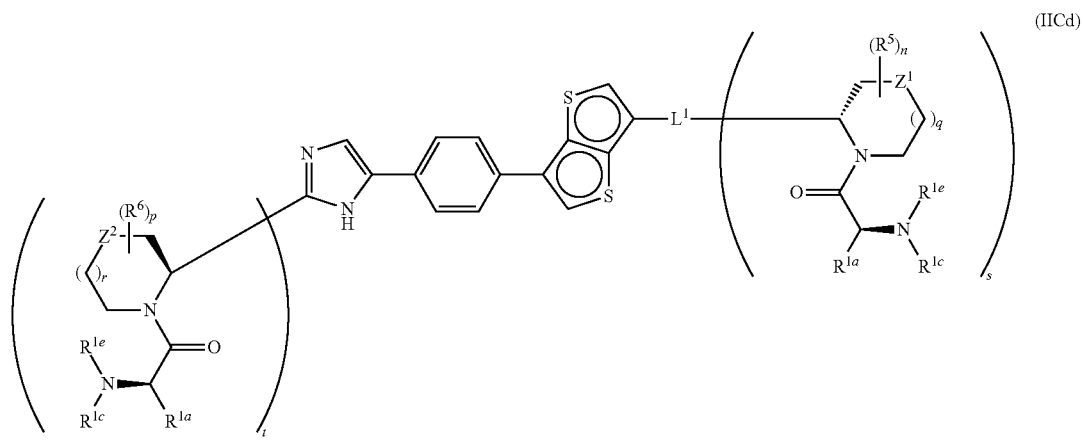

wherein each $R^{1e}$ is independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents Q; or (c) —C(O)$R^{1b}$, —C(O)O$R^{1b}$, or —C(O)N$R^{1b}R^{1d}$.

12. The compound of claim 9, wherein $R^1$ is —C(O)$R^{1a}$, —C(O)CH(N$R^{1b}R^{1c}$)$R^{1a}$, —C(O)CH[N(C(O)$R^{1b}$)$R^{1c}$]$R^{1a}$, —C(O)CH[N(C(O)O$R^{1b}$)$R^{1c}$]$R^{1a}$, or —C(O)CH[N(C(O)N$R^{1d}R^{1b}$)$R^{1c}$]$R^{1a}$.

13. The compound of claim 12, wherein $R^1$ is —C(O)CH[N(C(O)O$R^{1b}$)$R^{1c}$]$R^{1a}$.

14. The compound of claim 9, wherein $R^2$ is —C(O)$R^{1a}$, —C(O)CH(N$R^{1b}R^{1c}$)$R^{1a}$, —C(O)CH[N(C(O)$R^{1b}$)$R^{1c}$]$R^{1a}$, —C(O)CH[N(C(O)O$R^{1b}$)$R^{1c}$]$R^{1a}$, or —C(O)CH[N(C(O)N$R^{1d}R^{1b}$)$R^{1c}$]$R^{1a}$.

15. The compound of claim 14, wherein $R^2$ is —C(O)CH[N(C(O)O$R^{1b}$)$R^{1c}$]$R^{1a}$.

16. The compound of claim 11, wherein each $R^{1e}$ is independently hydrogen or —C(O)O$R^{1b}$.

17. The compound of claim 11, wherein each $R^{1a}$ is independently hydrogen, methyl, isopropyl, 2-methylpropyl, 1-methylpropyl, 2-methylthioethyl, phenyl, benzyl, 3-indolylmethyl, hydroxymethyl, 1-hydroxyethyl, sulfhydrylmethyl, 4-hydroxybenzyl, aminocarbonylmethyl, 2-(aminocarbonyl)ethyl, carboxymethyl, 2-carboxyethyl, 4-aminobutyl, 3-guanidinopropyl, or 5-imidazolylmethyl.

18. The compound of claim 16, wherein $R^{1b}$ is methyl, ethyl, propyl, or butyl.

19. The compound of claim 11, wherein $R^{1c}$ is hydrogen.

20. The compound of claim 1, wherein each $R^{3a}$ is independently hydrogen, oxo, chloro, fluoro, nitro, amino, hydroxy, methyl, trifluoromethyl, cyclohexyl, phenyl, methoxy, or methoxycarbonyl.

21. The compound of claim 1, wherein each $R^3$ is independently oxo, chloro, fluoro, nitro, amino, hydroxy, methyl, trifluoromethyl, cyclohexyl, phenyl, methoxy, or methoxycarbonyl.

22. The compound of claim 9, wherein n is 0.

23. The compound of claim 1, wherein two $R^5$ groups are linked together to form $C_{1-6}$ alkylene, optionally substituted with one or more substituents Q.

24. The compound of claim 1, wherein two $R^5$ groups are linked together to form methylene or ethylene.

25. The compound of claim 1, wherein q is 1 or 2.

26. The compound of claim 9, wherein the moiety

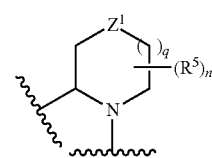

has the structure of:

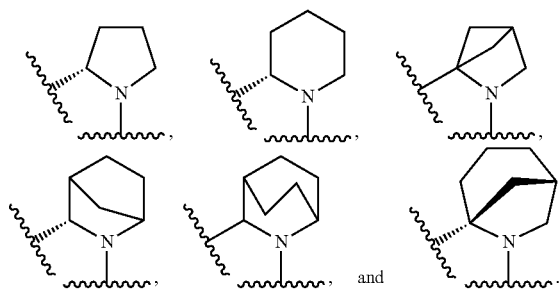

27. The compound of claim 9, wherein p is 0.

28. A compound of Formula IIIB:

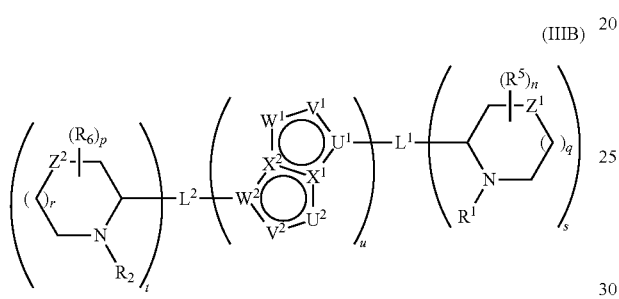
(IIIB)

or a single enantiomer, a racemic mixture, a mixture of diastereomers, or an isotopic variant thereof; or a pharmaceutically acceptable salt, solvate, or prodrug thereof;
wherein:

$U^1$, $W^2$, $X^1$, and $X^2$ are each C;
$U^2$ and $W^1$ are each S;
$V^1$ and $V^2$ are each independently $CR^{3a}$;
$R^1$ and $R^2$ are each independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, —C(O)CH(N($R^{1c}$)C(O)N$R^{1b}R^{1d}$)$R^{1a}$, —C(O)O$R^{1a}$, —C(O)N$R^{1b}R^{1c}$, —C(N$R^{1a}$)N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$;
each $R^{3a}$ is independently hydrogen or $R^3$;
each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; or
two $R^5$ or two $R^6$ that are attached to the same ring are linked together to form a bond, —O—, —N$R^7$—, —S—, $C_{1-6}$ alkylene, $C_{1-6}$ heteroalkylene, $C_{2-6}$ alkenylene, or $C_{2-6}$ heteroalkenylene;

$L^1$ and $L^2$ are each independently selected from:
a bond,

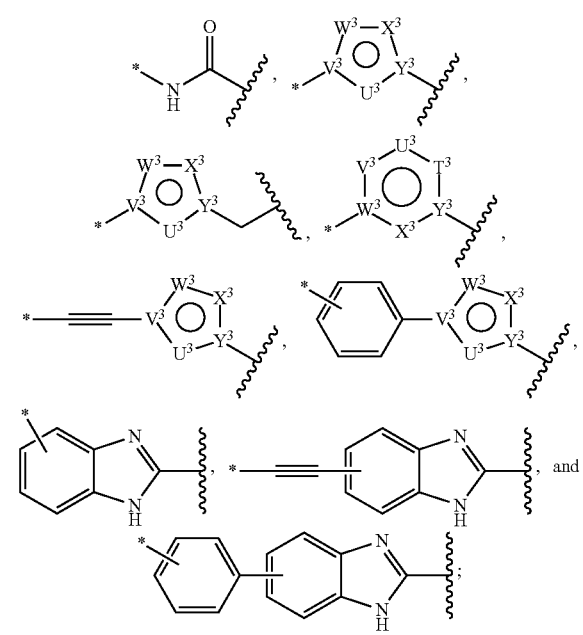

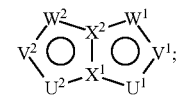

wherein each moiety is optionally substituted with one, two, three, or four $R^3$; the star (*) on each moiety represents the point of attachment thought which the moiety is connected to $U^1$ or $W^2$ of

and the zigzag line on each moiety represents the point of attachment through which the moiety is connected to

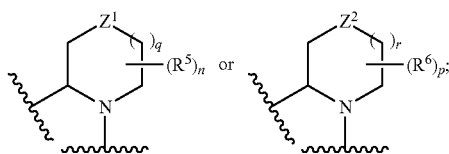

and wherein $T^3$ is a bond, C, N, O, S, $CR^{3a}$, or $NR^{3a}$; $U^3$, $V^3$, $W^3$, and $X^3$ are each independently C, N, O, S, $CR^{3a}$, or $NR^{3a}$; and $Y^3$ is C or N;
$Z^1$ and $Z^2$ are each a bond;
each $R^{1a}$, $R^{1b}$, $R^{1c}$, and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or $R^{1a}$ and $R^{1c}$ together with the C and N atoms to which they are attached form heterocyclyl; or $R^{1b}$ and $R^{1c}$ together with the N atom to which they are attached form heterocyclyl;
n is an integer of 0, 1, 2, 3, 4, 5, 6, or 7;
p is an integer of 2, 3, 4, 5, 6, or 7;
q and r are each independently an integer of 1, 2, 3, or 4; and
s, t, and u are each an integer of 1;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more substituents Q, where each Q is independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or in $R^f$ and $R^g$ to ether with the N atom to which they are attached form heterocyclyl.

29. The compound of claim 28, wherein two $R^6$ groups are linked together to form $C_{1-6}$ alkylene, optionally substituted with one or more substituents Q.

30. The compound of claim 29, wherein two $R^6$ groups are linked together to form methylene or ethylene.

31. The compound of claim 28, wherein r is 1 or 2.

32. The compound of claim 9, wherein the moiety

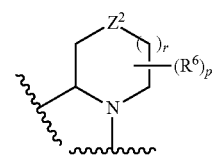

has the structure of:

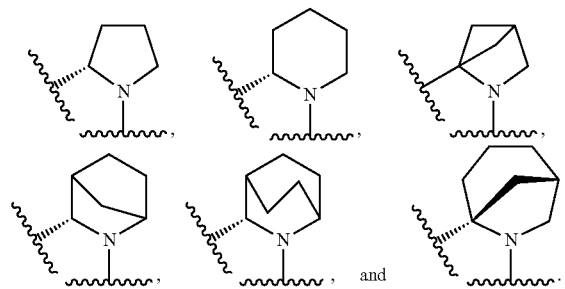

33. The compound of claim 9, selected from the group consisting of:

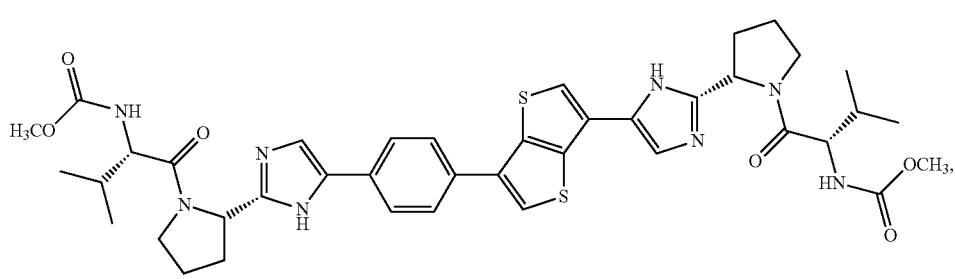

A15

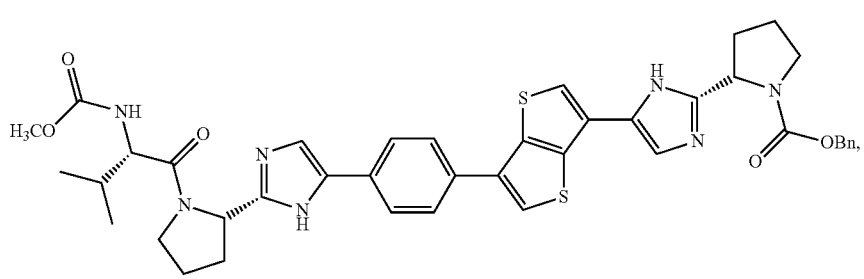

A49

-continued
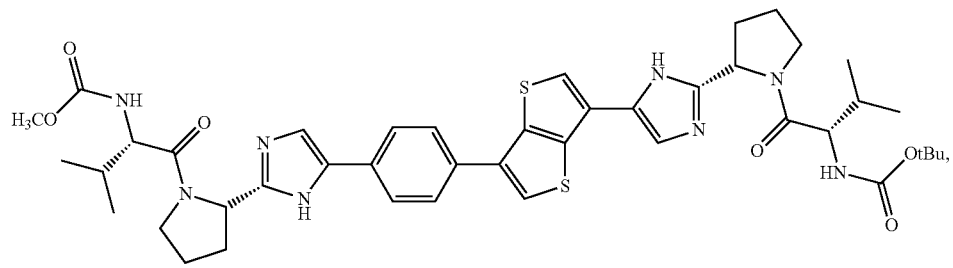
A76
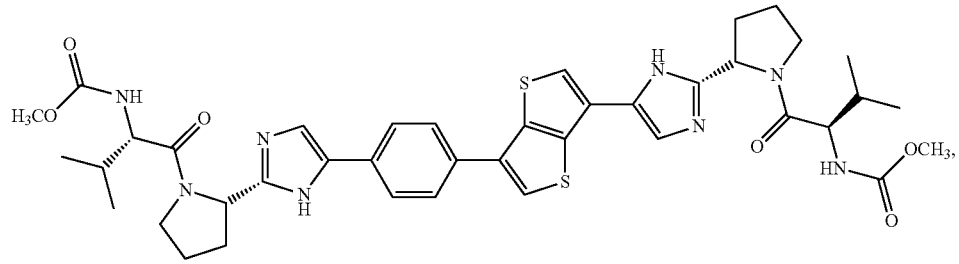
A77
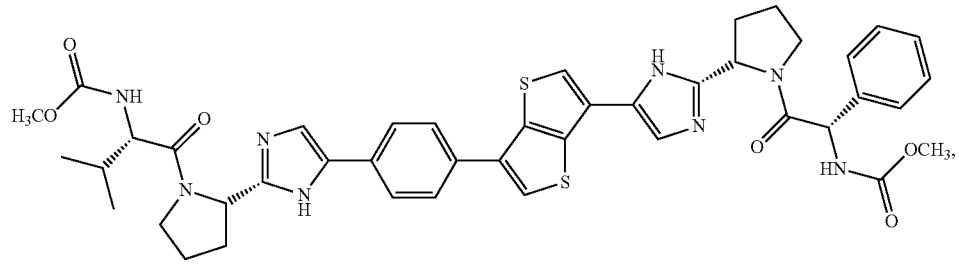
A78
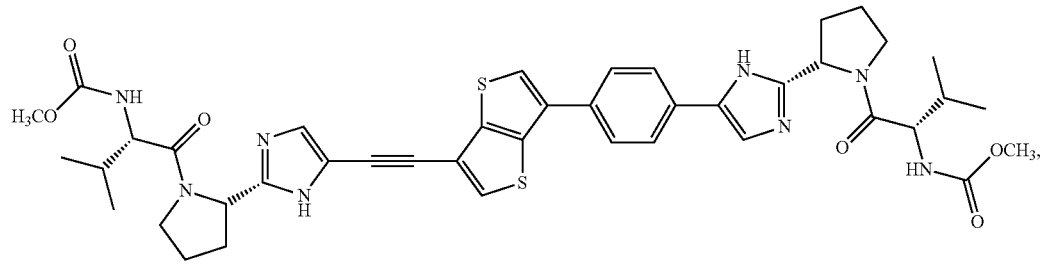
A84
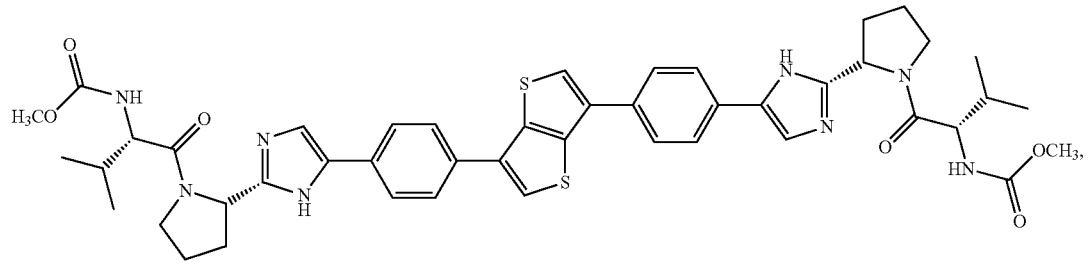
A86
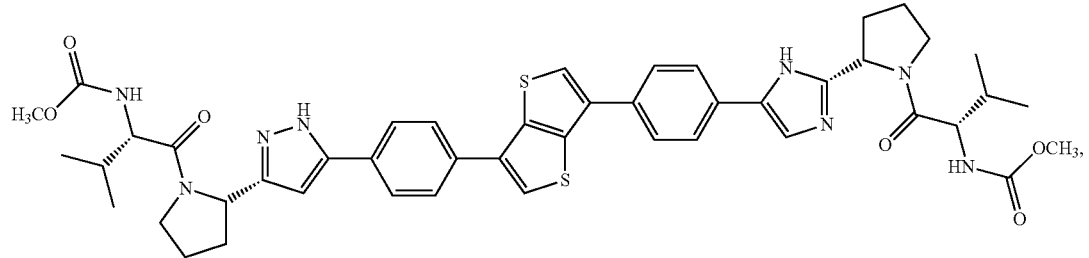
A87

-continued
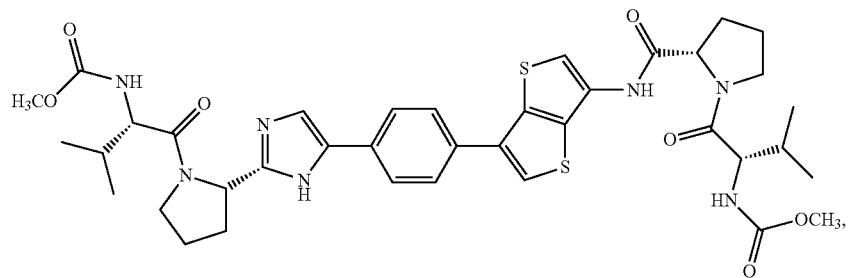 A88
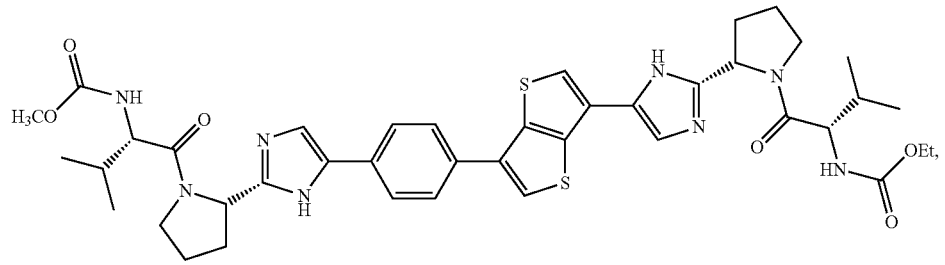 A106
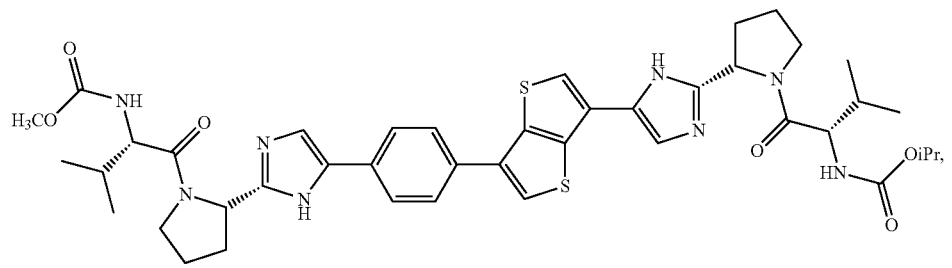 A107
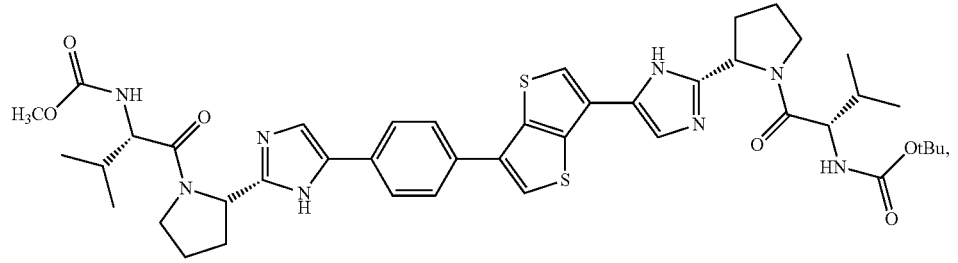 A108
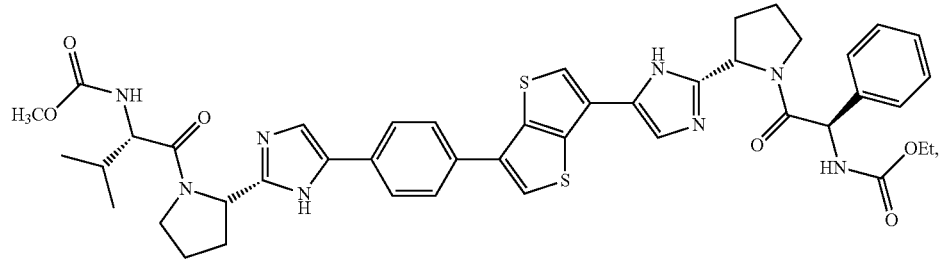 A109
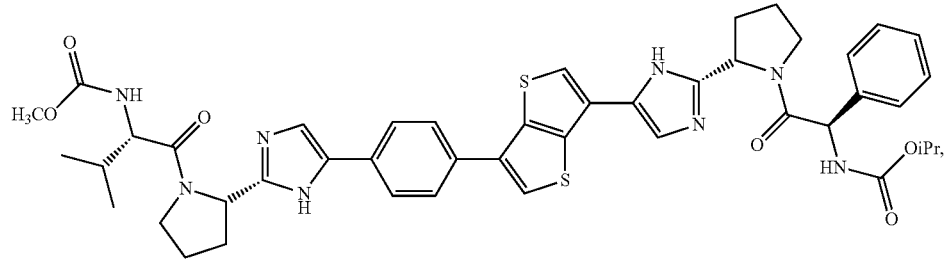 A110

-continued
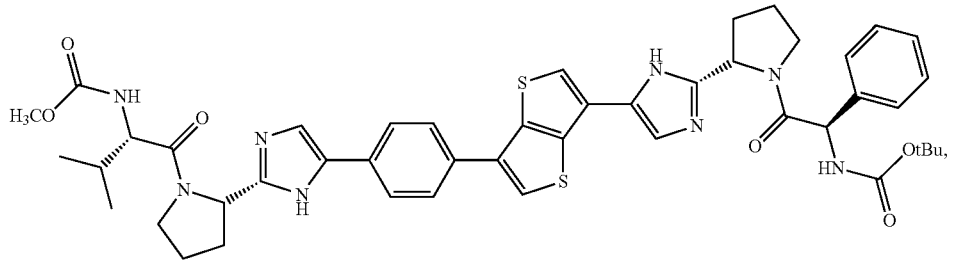
A111
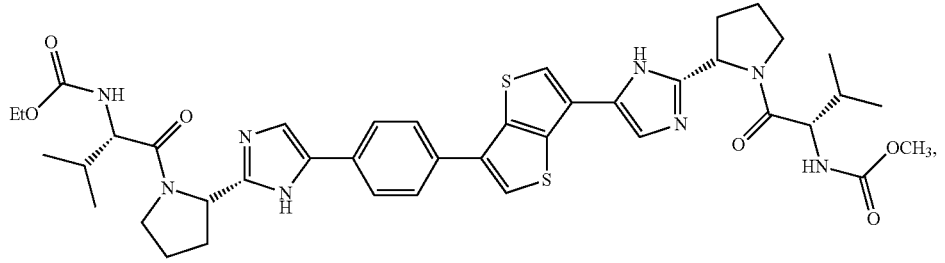
A112
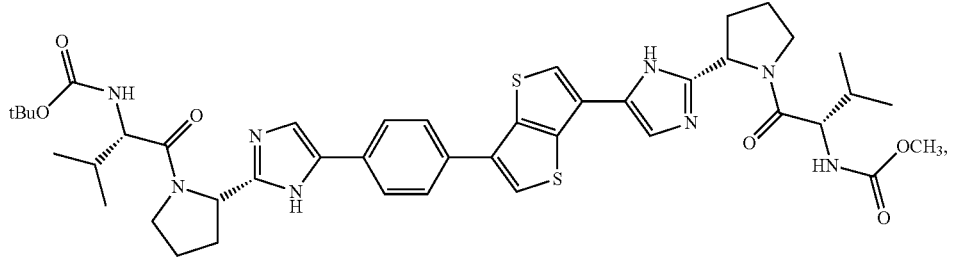
A113
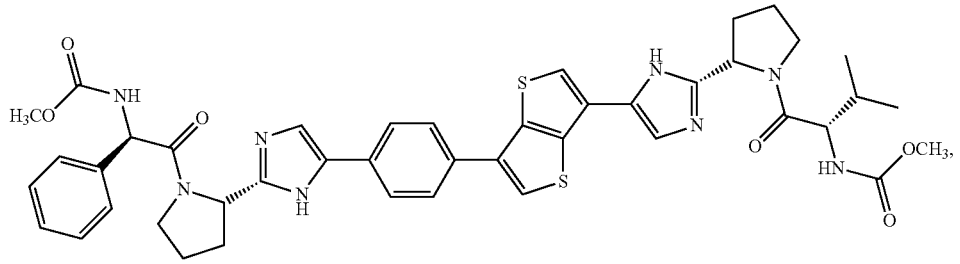
A114
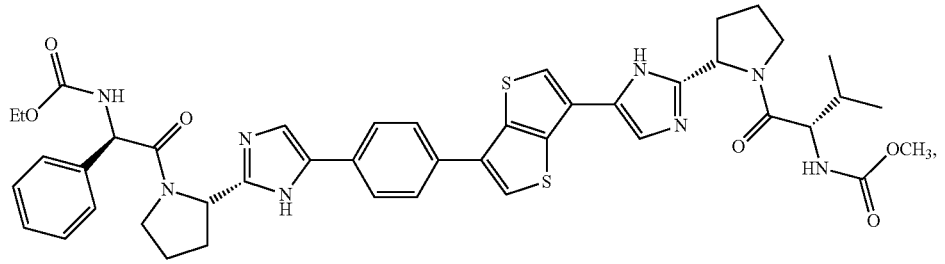
A115
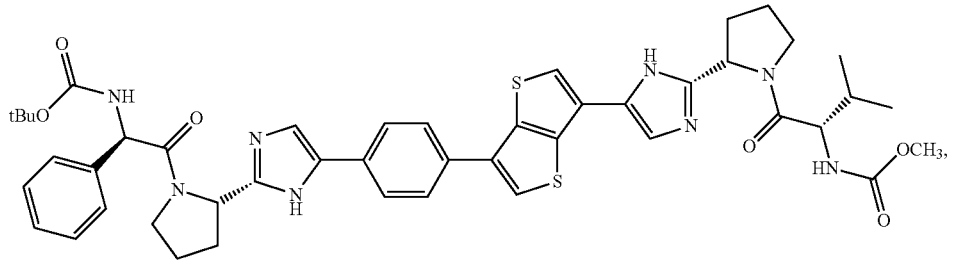
A116

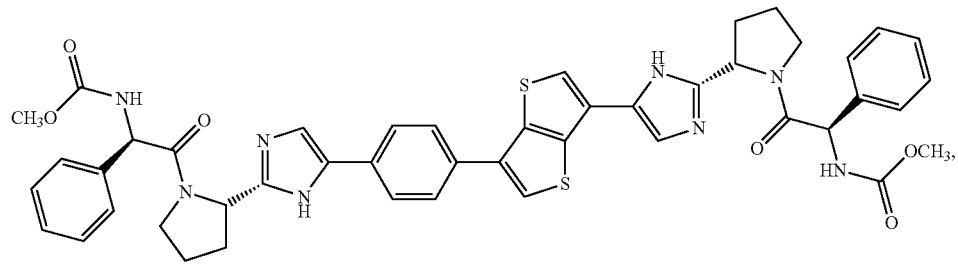
A117
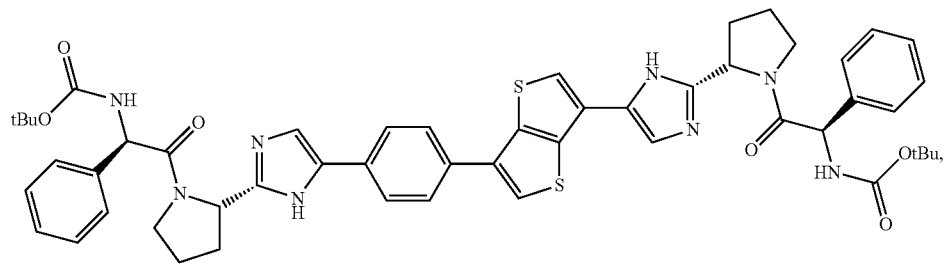
A118
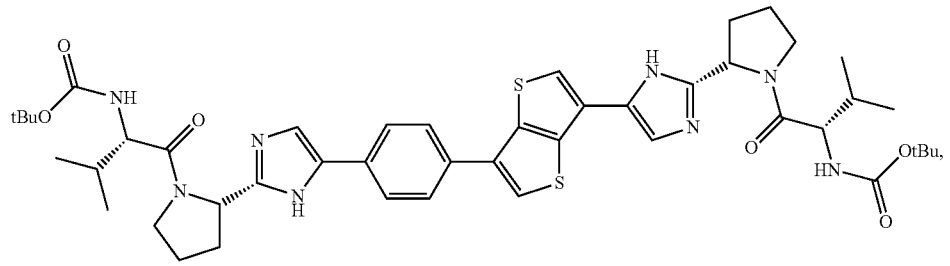
A119
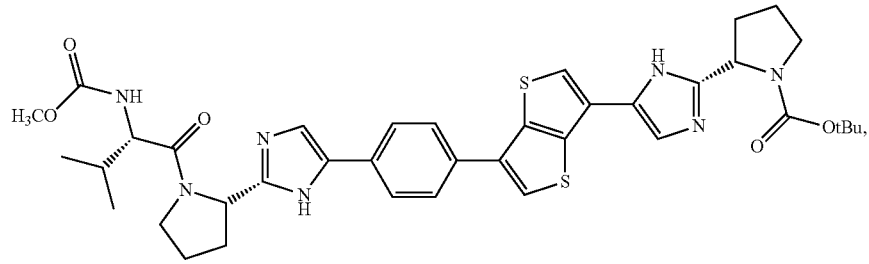
A151
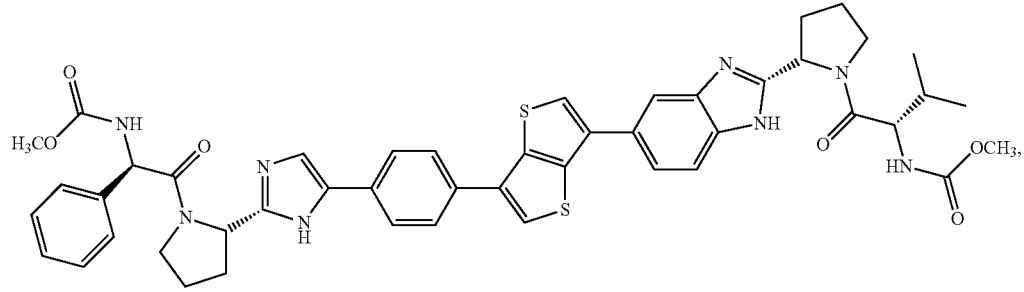
A169

-continued
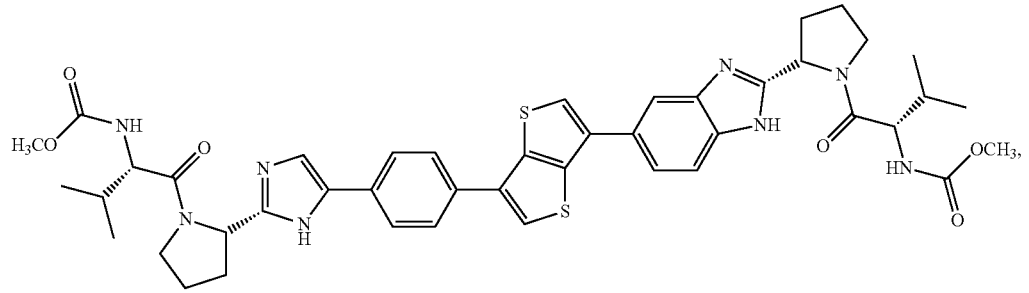
A171
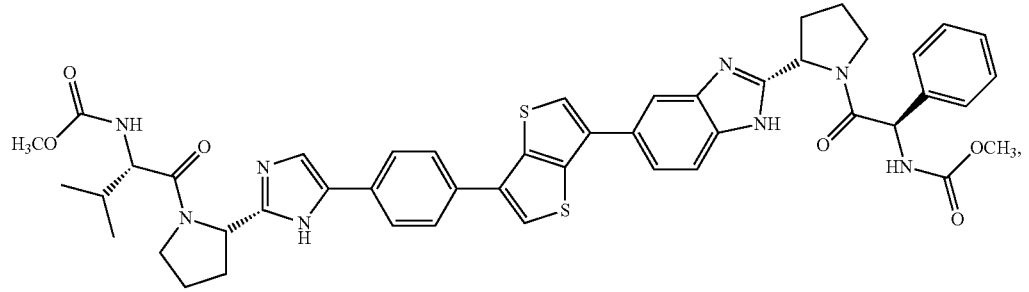
A172
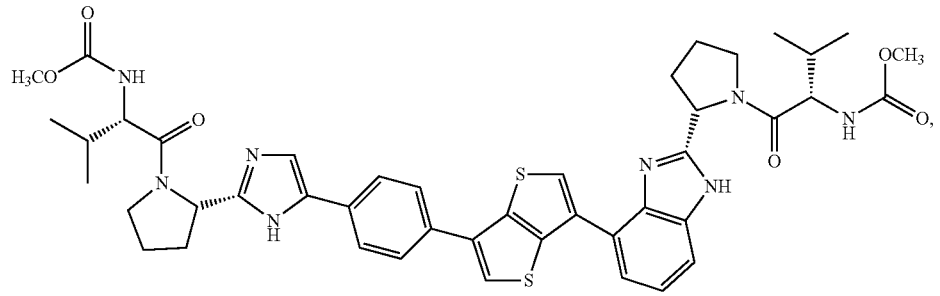
A182
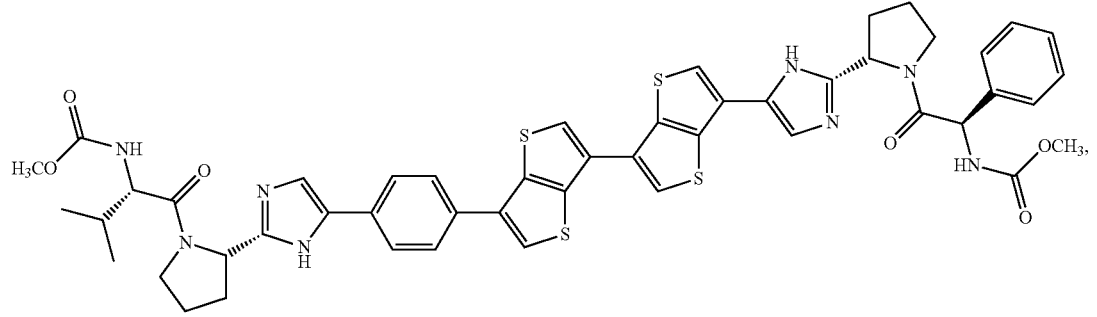
A200
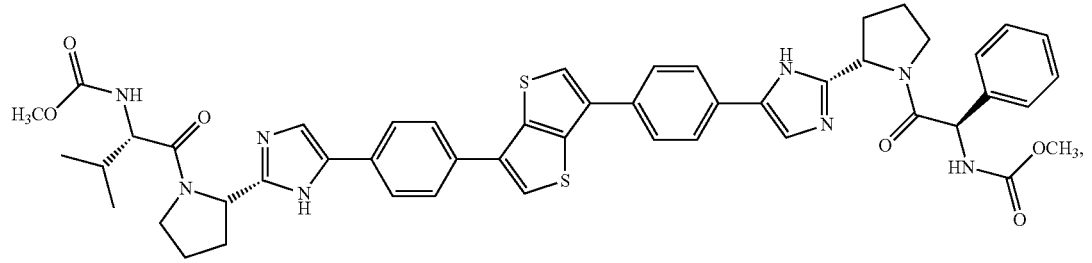
A205

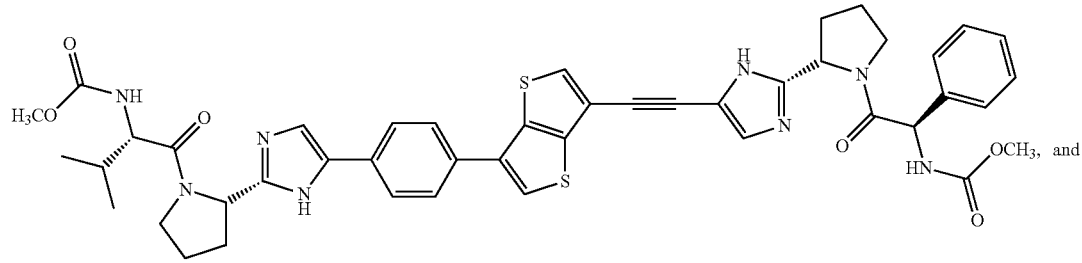

A206

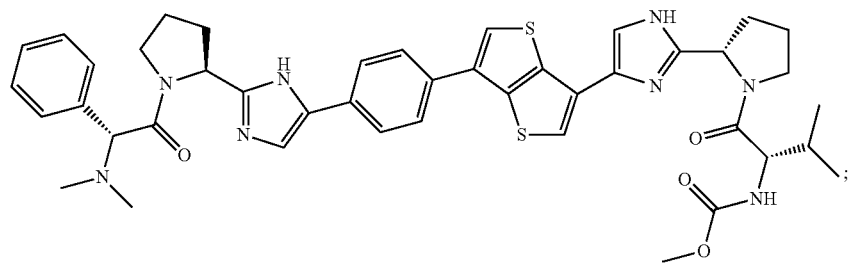

A214 and isotopic variants thereof; and pharmaceutically acceptable salts, and prodrugs thereof.

34. A pharmaceutical composition comprising the compound of claim 9 and one or more pharmaceutically acceptable carriers.

35. The pharmaceutical composition of claim 34, further comprising an antiviral agent.

36. The pharmaceutical composition of claim 35, wherein the antiviral agent is selected from the group consisting of an interferon, ribavirin, an interleukin, an NS3 protease inhibitor, a cysteine protease inhibitor, a phenathrenequinone, a thiazolidine, a benzanilide, a helicase inhibitor, a polymerase inhibitor, a nucleotide analogue, a liotoxin, acerulenin, an antisense phosphorothioate oligodeoxynucleotide, an inhibitor of IRES-dependent translation, and a ribozyme.

37. The pharmaceutical composition of claim 36, wherein the antiviral agent is an interferon.

38. The pharmaceutical composition of claim 37, wherein the interferon is selected from the group consisting of pegylated interferon alpha 2a, interferon alfahcon-1, natural interferon, albuferon, interferon beta-1a, omega interferon, interferon alpha, interferon gamma, interferon tau, interferon delta, and interferon gamma-1b.

39. The pharmaceutical composition of claim 34, wherein the composition is formulated for single dose administration.

40. The pharmaceutical composition of claim 34, wherein the composition is formulated as oral, parenteral, or intravenous dosage form.

41. The pharmaceutical composition of claim 40, wherein the oral dosage form is a tablet or capsule.

42. The pharmaceutical composition of claim 34, wherein the compound is administered in a dose of about 0.5 milligram to about 1,000 milligram daily.

43. The compound of claim 9, wherein $L^1$ is independently selected from the group consisting of:

a bond,

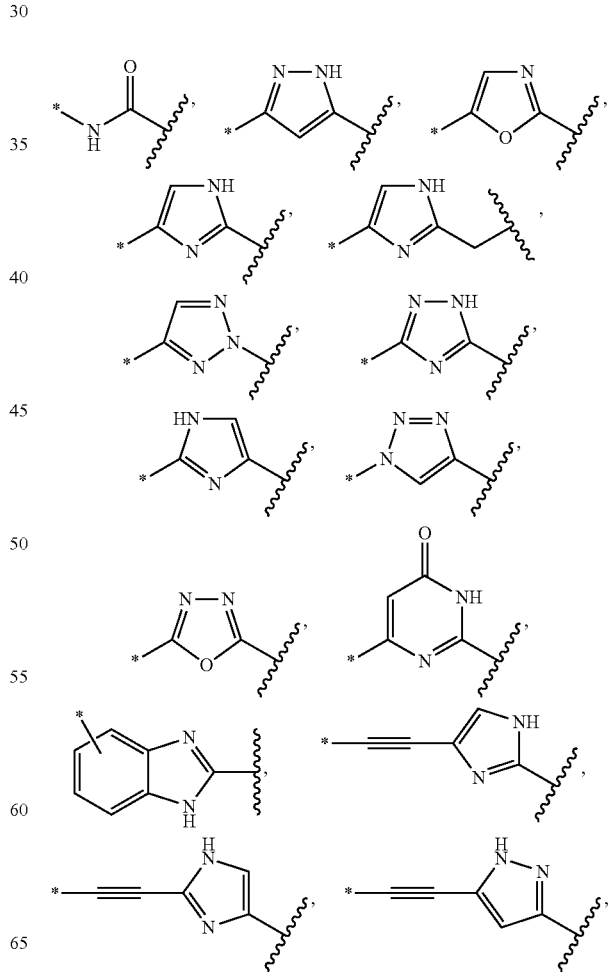

-continued

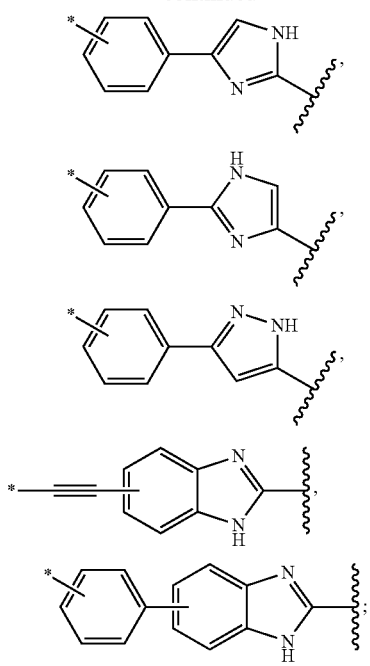

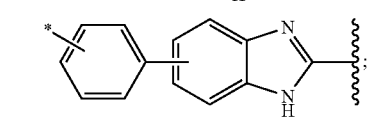

wherein each moiety is optionally substituted with one, two, three, or four $R^3$; the star (*) on each moiety represents the point of attachment through which the moiety is connected to $U^1$ or $W^2$ of

and the zigzag line ( ) on each moiety represents the point of attachment through which the moiety is connected to

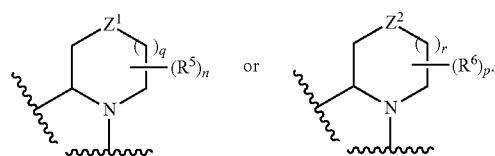

44. The compound of claim 9, wherein $L^1$ is independently selected from the group consisting of:

a bond,

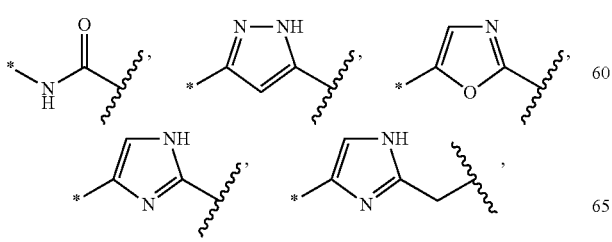

-continued

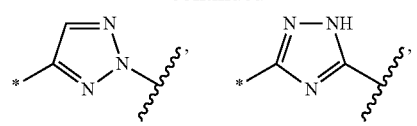

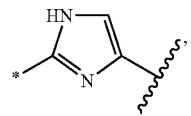

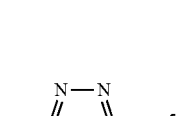

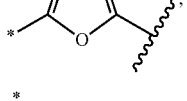

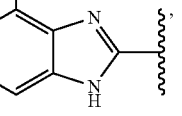

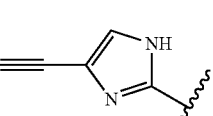

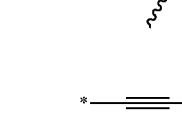

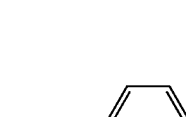

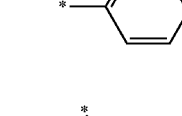

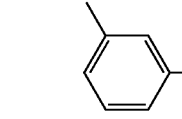

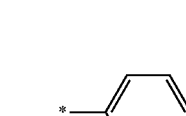

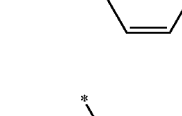

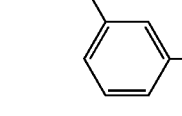

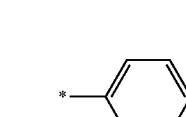

-continued

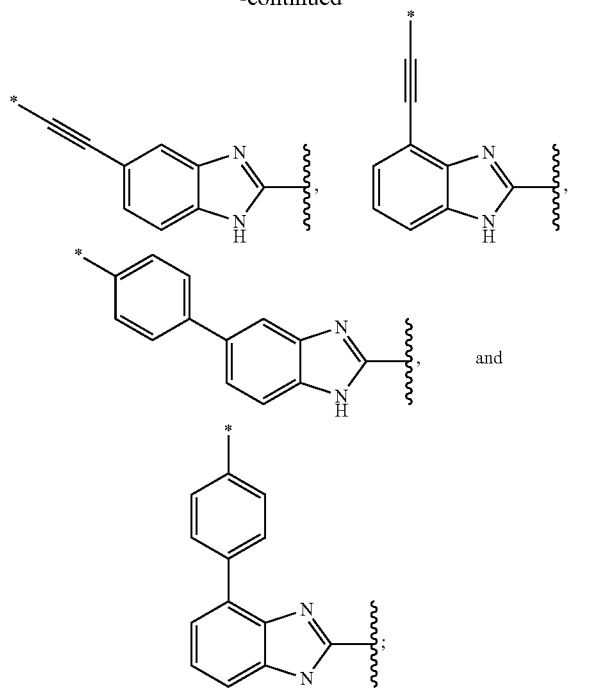

wherein each moiety is optionally substituted with one, two, three, or four R³.

45. The compound of claim 9, wherein n is an integer of 2 or more.

46. The compound of claim 45, wherein two R⁵ groups are linked together to form $C_{1-6}$ alkylene, optionally substituted with one or more substituents Q.

47. The compound of claim 45, wherein two R⁵ groups are linked together to form methylene or ethylene.

48. The compound of claim 9, wherein q is 1 or 2.

49. The compound of claim 9, wherein p is an integer of 2 or more.

50. The compound of claim 49, wherein two R⁶ groups are linked together to form $C_{1-6}$ alkylene, optionally substituted with one or more substituents Q.

51. The compound of claim 49, wherein two R⁶ groups are linked together to form methylene or ethylene.

52. The compound of claim 9, wherein r is 1 or 2.

53. A compound of Formula IIIB:

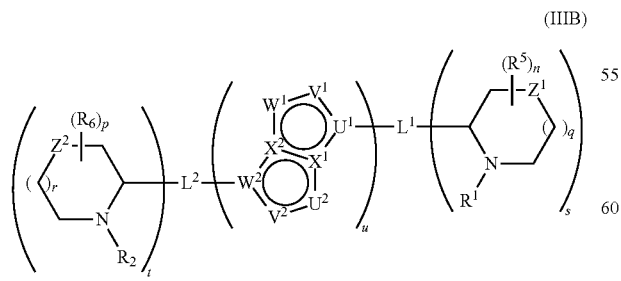

(IIIB)

or a single enantiomer, a racemic mixture, a mixture of diastereomers, or an isotopic variant thereof; or a pharmaceutically acceptable salt, solvate, or prodrug thereof;

wherein:

$U^1$, $W^2$, $X^1$, and $X^2$ are each C;

$U^2$ and $W^1$ are each S;

$V^1$ and $V^2$ are each independently $CR^{3a}$;

$R^1$ and $R^2$ are each independently (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N($R^{1c}$)C(O)O$R^{1b}$)$R^{1a}$, —C(O)CH(N($R^{1c}$)C(O)NR$^{1b}R^{1d}$)$R^{1a}$, —C(O)O$R^{1a}$, —C(O)NR$^{1b}R^{1c}$, —C(N$R^{1a}$)NR$^{1b}R^{1c}$, —P(O)(O$R^{1a}$)$R^{1d}$, —CH₂P(O)(O$R^{1a}$)$R^{1d}$, —S(O)$R^{1a}$, —S(O)₂$R^{1a}$, —S(O)NR$^{1b}R^{1c}$, or —S(O)₂NR$^{1b}R^{1c}$;

each $R^{3a}$ is independently hydrogen or $R^3$;

each $R^3$, $R^5$, and $R^6$ is independently (a) cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}R^{1c}$, —C(N$R^{1a}$)NR$^{1b}R^{1c}$, —O$R^{1a}$, —OC(O)$R^{1a}$, —OC(O)O$R^{1a}$, —OC(O)NR$^{1b}R^{1c}$, —OC(=N$R^{1a}$)NR$^{1b}R^{1c}$, —OS(O)$R^{1a}$, —OS(O)₂$R^{1a}$, —OS(O)NR$^{1b}R^{1c}$, —OS(O)₂NR$^{1b}R^{1c}$, —NR$^{1b}R^{1c}$, —NR$^{1a}$C(O)$R^{1d}$, —NR$^{1a}$C(O)O$R^{1d}$, —NR$^{1a}$C(O)NR$^{1b}R^{1c}$, —NR$^{1a}$C(=N$R^{1d}$)NR$^{1b}R^{1c}$, —NR$^{1a}$S(O)$R^{1d}$, —NR$^{1a}$S(O)₂$R^{1d}$, —NR$^{1a}$S(O)NR$^{1b}R^{1c}$, —NR$^{1a}$S(O)₂NR$^{1b}R^{1c}$, —S$R^{1a}$, —S(O)$R^{1a}$, —S(O)₂$R^{1a}$, —S(O)NR$^{1b}R^{1c}$, or —S(O)₂NR$^{1b}R^{1c}$; or two R⁵ or two R⁶ that are attached to the same ring are linked together to form a bond, —O—, —NR⁷—, —S—, $C_{1-6}$ alkylene, $C_{1-6}$ heteroalkylene, $C_{2-6}$ alkenylene, or $C_{2-6}$ heteroalkenylene;

$L^1$ and $L^2$ are each independently selected from:

a bond,

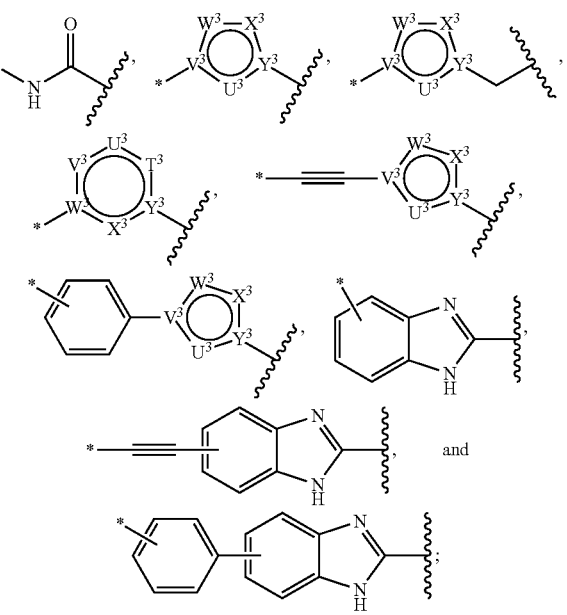

wherein each moiety is optionally substituted with one, two, three, or four R³; the star (*) on each moiety represents the point of attachment thought which the moiety is connected to $U^1$ or $W^2$ of

and the zigzag line ( ⌇ ) on each moiety represents the point of attachment through which the moiety is connected to

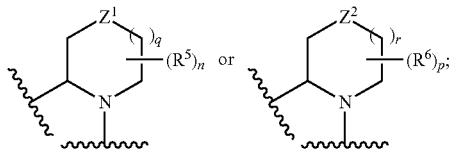

and wherein $T^3$ is a bond, C, N, O, S, $CR^{3a}$, or $NR^{3a}$; $U^3$, $V^3$, $W^3$, and $X^3$ are each independently C, N, O, S, $CR^{3a}$, or $NR^{3a}$; and $Y^3$ is C or N;

$Z^1$ and $Z^2$ are each a bond;

$R^{1a}$ and $R^{1c}$ together with the C and N atoms to which they are attached form pyrrolidinyl;

each $R^{1b}$ and $R^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

n and p are each independently an integer of 0, 1, 2, 3, 4, 5, 6, or 7;

q and r are each independently an integer of 1, 2, 3, or 4; and s, t, and u are each an integer of 1;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more substituents Q, where each Q is independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heterocyclyl, optionally substituted with one or more, in one embodiment, one, two, three, or four, substituents $Q^a$;

wherein each $Q^a$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^f$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

\* \* \* \* \*